US011390680B2

(12) United States Patent
Monroe et al.

(10) Patent No.: US 11,390,680 B2
(45) Date of Patent: Jul. 19, 2022

(54) ANTI-SIGLEC-7 ANTIBODIES AND METHODS OF USE THEREOF

(71) Applicant: Alector LLC, South San Francisco, CA (US)

(72) Inventors: Kate Monroe, Berkeley, CA (US); Helen Lam, Union City, CA (US); Arnon Rosenthal, Woodside, CA (US); Seung-Joo Lee, Benicia, CA (US); Francesca Avogadri-Connors, San Mateo, CA (US); William Monteith, San Francisco, CA (US)

(73) Assignee: Alector LLC, South San Francisco, CA (US)

( * ) Notice: Subject to any disclaimer, the term of this patent is extended or adjusted under 35 U.S.C. 154(b) by 0 days.

(21) Appl. No.: 16/792,040

(22) Filed: Feb. 14, 2020

(65) Prior Publication Data

US 2020/0277374 A1 Sep. 3, 2020

Related U.S. Application Data

(62) Division of application No. 15/756,043, filed as application No. PCT/US2016/049032 on Aug. 26, 2016, now Pat. No. 10,590,198.

(60) Provisional application No. 62/265,742, filed on Dec. 10, 2015, provisional application No. 62/211,656, filed on Aug. 28, 2015.

(51) Int. Cl.
| | | |
|---|---|---|
| *C07K 16/28* | (2006.01) | |
| *A61K 39/395* | (2006.01) | |
| *A61K 45/06* | (2006.01) | |
| *A61K 39/00* | (2006.01) | |
| *A61P 37/02* | (2006.01) | |
| *A61P 25/00* | (2006.01) | |
| *A61P 35/00* | (2006.01) | |

(52) U.S. Cl.
CPC .... *C07K 16/2803* (2013.01); *A61K 39/39558* (2013.01); *A61K 45/06* (2013.01); *A61K 2039/505* (2013.01); *A61P 25/00* (2018.01); *A61P 35/00* (2018.01); *A61P 37/02* (2018.01); *C07K 2317/24* (2013.01); *C07K 2317/30* (2013.01); *C07K 2317/76* (2013.01)

(58) Field of Classification Search
CPC ................ C07K 16/18; C07K 16/2803; C07K 2317/24; C07K 2317/30; C07K 2317/34; C07K 2317/76; C07K 2317/77; A61K 39/39558; A61K 45/06; A61K 2039/505; A61P 37/02; A61P 25/00; A61P 35/00
See application file for complete search history.

(56) References Cited

U.S. PATENT DOCUMENTS

| | | |
|---|---|---|
| 4,469,863 A | 9/1984 | Ts'o et al. |
| 4,657,760 A | 4/1987 | Kung et al. |
| 4,676,980 A | 6/1987 | Segal et al. |
| 4,816,567 A | 3/1989 | Cabilly et al. |
| 5,206,344 A | 4/1993 | Katre et al. |
| 5,225,212 A | 7/1993 | Martin et al. |
| 5,229,275 A | 7/1993 | Goroff et al. |
| 5,536,821 A | 7/1996 | Agrawal et al. |
| 5,541,306 A | 7/1996 | Agrawal et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,573,905 A | 11/1996 | Lerner et al. |
| 5,587,458 A | 12/1996 | King et al. |
| 5,591,669 A | 1/1997 | Krimpenfort et al. |
| 5,614,622 A | 3/1997 | Iyer et al. |
| 5,625,126 A | 4/1997 | Lonberg et al. |
| 5,633,425 A | 5/1997 | Lonberg et al. |
| 5,637,683 A | 6/1997 | Usher et al. |
| 5,637,684 A | 6/1997 | Cook et al. |
| 5,641,870 A | 6/1997 | Rinderknecht et al. |
| 5,648,237 A | 7/1997 | Carter et al. |
| 5,661,016 A | 8/1997 | Lonberg et al. |
| 5,700,922 A | 12/1997 | Cook |
| 5,717,083 A | 2/1998 | Cook et al. |
| 5,719,262 A | 2/1998 | Buchardt et al. |
| 5,731,168 A | 3/1998 | Carter et al. |
| 5,739,277 A | 4/1998 | Presta et al. |

(Continued)

FOREIGN PATENT DOCUMENTS

| | | |
|---|---|---|
| CN | 106831989 A | 6/2017 |
| EP | 0308936 B1 | 7/1994 |

(Continued)

OTHER PUBLICATIONS

Scott CJ et al. Immunocolloidal targeting of the endocytic Siglec-7 receptor using peripheral attachment of Siglec-7 antibodies to poly(lactid-co-glycolide) nanoparticles. Pharm. Res. 2007, 25(1), 135-146. (Year: 2007).*
UniProtKB—Q9Y286 (SIGL7_HUMAN), Sialic acid-binding Ig-like lectin Y (SIGLEC7). Retrieved from www.uniprot.org/uniprot/Q9Y286 on Oct. 22, 2021, 13 pages. (Year: 2021).*
Alegre, M.-L et al. (Jun. 1, 1994). "A Non-Activating "Humanized" Anti-cd3 Monoclonal Antibody Retains Immunosuppressive Properties in Vivo," Transplantation 57(11):1537-1543.

(Continued)

*Primary Examiner* — Kimberly Ballard
(74) *Attorney, Agent, or Firm* — Morrison & Foerster LLP

(57) ABSTRACT

The present disclosure is generally directed to compositions that include antibodies, e.g., monoclonal, chimeric, humanized antibodies, antibody fragments, etc., that specifically bind on or more epitopes within a Siglec-7 protein, e.g., human Siglec-7 or a mammalian Siglec-7, and use of such compositions in preventing, reducing risk, or treating an individual in need thereof.

30 Claims, 60 Drawing Sheets

Specification includes a Sequence Listing.

(56) References Cited

U.S. PATENT DOCUMENTS

| | | | |
|---|---|---|---|
| 5,739,308 | A | 4/1998 | Kandimalla et al. |
| 5,739,314 | A | 4/1998 | Roy et al. |
| 5,773,601 | A | 6/1998 | Agrawal |
| 5,789,199 | A | 8/1998 | Joly et al. |
| 5,840,523 | A | 11/1998 | Simmons et al. |
| 5,869,046 | A | 2/1999 | Presta et al. |
| 5,886,165 | A | 3/1999 | Kandimalla et al. |
| 5,929,226 | A | 7/1999 | Padmapriya et al. |
| 5,955,599 | A | 9/1999 | Iyer et al. |
| 5,959,177 | A | 9/1999 | Hein et al. |
| 5,962,674 | A | 10/1999 | Iyer et al. |
| 5,977,296 | A | 11/1999 | Nielsen et al. |
| 6,040,498 | A | 3/2000 | Stomp et al. |
| 6,075,181 | A | 6/2000 | Kucherlapati et al. |
| 6,117,992 | A | 9/2000 | Iyer |
| 6,140,482 | A | 10/2000 | Iyer et al. |
| 6,150,584 | A | 11/2000 | Kucherlapati et al. |
| 6,417,429 | B1 | 7/2002 | Hein et al. |
| 6,420,548 | B1 | 7/2002 | Vezina et al. |
| 6,455,308 | B1 | 9/2002 | Freier |
| 6,982,321 | B2 | 1/2006 | Winter |
| 7,034,121 | B2* | 4/2006 | Carreno ............. A61K 47/6849 530/387.3 |
| 7,087,409 | B2 | 8/2006 | Barbas, III et al. |
| 7,125,978 | B1 | 10/2006 | Vézina et al. |
| 8,148,498 | B2* | 4/2012 | Chedid .................. C07K 16/18 530/387.3 |
| 8,614,299 | B2 | 12/2013 | Baurin et al. |
| 8,796,427 | B2* | 8/2014 | Spee ........................ A61P 37/00 530/388.22 |
| 9,732,160 | B2* | 8/2017 | Rohlff ..................... C07K 16/40 |
| 9,879,083 | B2* | 1/2018 | Okamura ........... A61K 39/3955 |
| 10,047,167 | B2* | 8/2018 | Demarest ............... C07K 16/00 |
| 10,227,408 | B2* | 3/2019 | White ...................... C07K 7/06 |
| 10,590,198 | B2 | 3/2020 | Monroe et al. |
| 2007/0148167 | A1 | 6/2007 | Strohl |
| 2009/0181855 | A1 | 7/2009 | Vasquez et al. |
| 2010/0056386 | A1 | 3/2010 | Vasquez et al. |
| 2010/0280227 | A1 | 11/2010 | Ambrose et al. |
| 2017/0306014 | A1* | 10/2017 | Cornen ............. C07K 16/2803 |
| 2018/0244770 | A1 | 8/2018 | Monroe et al. |
| 2021/0246204 | A1 | 8/2021 | Culp et al. |

FOREIGN PATENT DOCUMENTS

| | | |
|---|---|---|
| EP | 0404097 B1 | 9/1996 |
| JP | 2003517482 A | 5/2003 |
| WO | WO-1987/04462 A1 | 7/1987 |
| WO | WO-1991/00360 A1 | 1/1991 |
| WO | WO-1991/10741 A1 | 7/1991 |
| WO | WO-1992/00373 A1 | 1/1992 |
| WO | WO-1993/08829 A1 | 5/1993 |
| WO | WO-1993/11161 A1 | 6/1993 |
| WO | WO-1993/16185 A2 | 8/1993 |
| WO | WO-1994/04690 A1 | 3/1994 |
| WO | WO-1996/27011 A1 | 9/1996 |
| WO | WO-1996/33735 A1 | 10/1996 |
| WO | WO-1996/34096 A1 | 10/1996 |
| WO | WO-1997/11971 A1 | 4/1997 |
| WO | WO-1997/17852 A1 | 5/1997 |
| WO | WO-1998/24893 A2 | 6/1998 |
| WO | WO-1999/32619 A1 | 7/1999 |
| WO | WO-1999/58572 A1 | 11/1999 |
| WO | WO-2000/44895 A1 | 8/2000 |
| WO | WO-2000/56746 A2 | 9/2000 |
| WO | WO-2000/75372 A1 | 12/2000 |
| WO | WO-2001/14398 A1 | 3/2001 |
| WO | WO-2001/29058 A1 | 4/2001 |
| WO | WO-2001/36646 A1 | 5/2001 |
| WO | WO-2001/44808 A2 | 6/2001 |
| WO | WO-2001/44808 A3 | 6/2001 |
| WO | WO-2001/90193 A1 | 11/2001 |
| WO | WO-2004/042072 A2 | 5/2004 |
| WO | WO-2005/026209 A2 | 3/2005 |
| WO | WO-2007/106585 A1 | 9/2007 |
| WO | WO-2008/079246 A2 | 7/2008 |
| WO | WO-2009/036379 A2 | 3/2009 |
| WO | WO-2010/105256 A1 | 9/2010 |
| WO | WO-2011/038301 A2 | 3/2011 |
| WO | WO-2012/009568 A2 | 1/2012 |
| WO | WO-2012045752 A1 | 4/2012 |
| WO | WO-2015/023752 A1 | 2/2015 |
| WO | WO-2015/089449 A2 | 6/2015 |
| WO | WO-2016038064 A1 | 3/2016 |
| WO | WO-2017040301 A1 | 3/2017 |
| WO | WO-2018006034 A1 | 1/2018 |
| WO | WO-2019140273 A1 | 7/2019 |

OTHER PUBLICATIONS

Almagro, J.C. et al. (2008). "Humanization of Antibodies," Frontiers in Bio-Science 13:1619-1633.

Alphey, M.S. et al. (Jan. 31, 2003). "High Resolution Crystal Structures of Siglec-7," The Journal of Biological Chemistry 278(5):3372-3377.

Al-Shawi, R. et al. (2008). "Neurotoxic and Neurotrophic Roles of proNGF and the Receptor Sortilin in the Adult and Ageing Nervous System," European Journal of Neuroscience 27:2103-2114.

Angal, S. et al. (1993). "A Single Amino Acid Substitution Abolishes the Heterogeneity of Chimeric Mouse/Human (IgG4) Antibody," Molecular Immunology 30(1):105-108.

Angata, T. et al. (Apr. 2000). "Siglec-7: A Sialic Acid-Binding Lectin of the Immunoglobulin Superfamily," Glycobiology 10(4):431-438.

Ariga, T. et al. (Mar. 11, 2008). "Role of Ganglioside Metabolism in the Pathogenesis of Alzheimer's Disease—A Review," J. Lipid Res. 49:1157-1175.

Armour, K.L. et al. (1999). "Recombinant Human IgG Molecules Lacking FcGamma Receptor I Binding and Monocyte Triggering Activities," Eur. J. Immunol. 29:2613-2624.

Armour, K.L. et al. (2003). "Differential Binding To Human Fcyriia and Fcyriib Receptors by Human IgG Wildtype and Mutant Antibodies," Molecular Immunology 40:585-593.

Armour, K.L. et al. (Jun. 25-28, 2000). "Mutant IgG Lacking FcyRIII Binding and ADCC Activities," The Haematology Journal, poster Session 1, Presented at the 5th Annual Meeting of the European Haematology Association, Birmingham, UK, 1 (Suppl. 1):27, 2 pages.

Arnett, M.G. et al. (Dec. 5, 2007). "pro-NGF, Sortilin, and p75NTR: Potential Mediators of Injury-Induced Apoptosis in the Mouse Dorsal Root Ganglion," Brain Research 1183:32-42, 18 pages.

Asquith, D.L. et al. (2009). "Animal Models of Rheumatoid Arthritis," Eur. J. Immunol. 39:2040-2044.

Attrill, H. et al. (Oct. 27, 2006; e-published on Aug. 8, 2006). "Siglec-7 Undergoes a Major Conformational Change When Complexed with the α(2,8)-Disialylganglioside GT1b," J. Biol. Chem. 281:32774-32783.

Avril, T. et al. (Dec. 1, 2004). "The Membrane-Proximal Immunoreceptor Tyrosine-Based Inhibitory Motif is Critical for the Inhibitory Signaling Mediated by Siglecs-7 and -9, CD33-Related Siglecs Expressed on Human Monocytes and NK Cells," J Immunol. 173(11):6841-6849.

Baca, M. et al. (1997). "Antibody Humanization Using Monovalent Phage Display," The Journal of Biological Chemistry 272(16):10678-10684.

Barbas III, C.F. et al. (Apr. 1994). "In Vitro Evolution of a Neutralizing Human Antibody to Human Immunodeficiency Virus Type 1 to Enhance Affinity and Broaden Strain Cross-Reactivity," Proc Nat. Acad. Sci. USA 91:3809-3813.

Bartholomaeus, P. et al. (2014). "Cell Contact-Dependent Priming and Fc Interaction with CD32+ Immune Cells Contribute to the TGN1412-Triggered Cytokine Response," The Journal of Immunology 192:2091-2098.

Bax, M. et al. (Dec. 15, 2007). "Dendritic Cell Maturation Results in Pronounced Changes in Glycan Expression Affecting Recognition by Siglecs and Galectins," J. Immunol. 179(12):8216-8224.

(56) References Cited

OTHER PUBLICATIONS

Beattie, M.S. et al. (Oct. 24, 2002). "ProNGF Induces p75-Mediated Death of Oligodendrocytes following Spinal Cord Injury," Neuron 36(3):375-386.
Boerner, P. et al. (1991). "Production Of Antigen-Specific Human Monoclonal Antibodies From In Vitro-Primed Human Splenocytes," Journal of Immunology 147(1):86-95.
Bolt, S. et al. (1993). "Generation of a Humanized, Non-Mitogenic Cd3 Monoclonal Antibody Which Retains In Vitro Immunosuppressive Properties," European Journal Immunol. 23:403-411.
Brehm, M.A. et al. (Apr. 2010). "Humanized Mouse Models to Study Human Diseases," Curr Opin Endocrinol Diabetes Obes. 17(2):120-125.
Brennan, M. et al. (Jul. 5, 1985). "Preparation of Bispecific Antibodies by Chemical Recombination of Monoclonal Immunoglobulin G1 Fragments," Science 229:81-83.
Bruggemann, M. et al. (1993). "Designer Mice: The Production of Human Antibody Repertoires in Transgenic Animals," Year in Immunol. 7:33-40.
Calligé, M. et al. (Jun. 2005). "CSN5/Jab1 is Involved in Ligand-Dependent Degradation of Estrogen Receptor α by the Proteasome," Mol. Cell Biol. 25(11):4349-4358.
Cantoni, C. et al. (Mar. 2015). "Trem2 Regulates Microglial Cell Activation in Response to Demyelination In Vivo," Acta Neuropathol, 129(3):429-447, thirty three pages.
Canziani, G.A. et al. (2004). "Kinetic Screening of Antibodies From Crude Hybridoma Samples Using Biacore," Analytical Biochemistry 325:301-307.
Cao, X. et al. (Sep. 2011). "Macrophage Polarization in the Maculae of Age-Related Macular Degeneration: A Pilot Study," Pathology International 61(9):528-535, fourteen pages.
Capel, P.J.A. et al. (1994). "Heterogeneity of Human IgG Fc Receptors," Immunomethods 4:25-34.
Carter, P. et al. (Feb. 1992). "High Level *Escherichia coli* Expression and Production of a Bivalent Humanized Antibody Fragment," Bio/technology 10:163-167.
Carter, P. et al. (May 1992). "Humanization of an Anti-p185HER2 Antibody for Human Cancer Therapy," Proc. Natl. Acad. Sci. USA 89:4285-4289.
Chang et al. (2002). "Retinal Degeneration Mutants in the Mouse," Vision Research 42:517-525.
Chothia, C. et al. (1987). "Canonical Structures for the Hypervariable Regions of Immunoglobulins," J. Mol. Biol, 196:901-917.
Chu, S.Y. et al. (2008; e-pub. Aug. 8, 2008). "Inhibition of B cell Receptor-Mediated Activation of Primary Human B Cells by Coengagement of CD19 and FcγRIIb with Fe-Engineered Antibodies," Molecular Immunology 45:3926-3933.
Clackson, T. et al. (1991). "Making Antibody Fragments Using Phage Display Libraries," Nature 352(15):624-628.
Cole, M.S. et al. (Aug. 27, 1999). "HuM291, A Humanized Anti-Cd3 Antibody is Immunosuppressive to T Cells While Exhibiting Reduced Mitogenicity in Vitro," Transplantation 68(4):563-571.
Correale, C. et al. (Feb. 2013). "Bacterial Sensor Triggering Receptor Expressed on Myeloid Cells-2 Regulates the Mucosal Inflammatory Response," Gastroenterology 144(2):346-356.
Crocker, P.R. et al. (Apr. 2007). "Siglecs and their Roles in the Immune System," Nat Rev Immunol. 7(4):255-266.
Crocker, P.R. et al. (Apr. 2012; e-published on Feb. 21, 2012). "CD33-related Siglecs as Potential Modulators of Inflammatory Responses," Ann. NY Acad. Sci. 1253:102-111.
Crocker, P.R. et al. (Jul. 1999). "Molecular Analysis of Sialoside Binding to Sialoadhesin by NMR and Site-Directed Mutagenesis," Biochem J. 341 (Pt. 2):355-361.
Crocker, P.R. et al. (Jun. 1, 2001). "Siglecs, Sialic Acids and Innate Immunity," Trends Immunol. 22(6):337-342.
Cruts, M. et al. (2008, e-pub. Mar. 6, 2008). "Loss of Progranulin Function in Frontotemporal Lobar Degeneration," Trends Genetics 24(4):186-194.

Cunningham, B.C. et al. (Jun. 2, 1989). "High-Resolution Epitope Mapping of hGH-Receptor Interactions By Alanine-Scanning Mutagenesis," Science 244:1081-1085.
Daëron, M. (1997). "FC Receptor Biology," Annu. Rev. Immunol. 15:203-234.
Dall' Acqua, W.F. et al. (Aug. 18, 2006). "Properties of Human IgG1s Engineered for Enhanced Binding to the Neonatal Fc Receptor (FcRn)," The Journal of Biological Chemistry 281 (33) :23514-23524.
Daneman, R. et al. (Oct. 29, 2010). "The Mouse Blood-Brain Barrier Transcriptome A New Resource for Understanding the Development and Function of Brain Endothelial Cells," PLoS One 5(10):e13741, sixteen pages.
Davis, P.M. et al. (2007). "Abatacept Binds to the Fc Receptor Cd64 But Does Not Mediate Complement-Dependent Cytotoxicity or Antibody-Dependent Cellular Cytotoxicity," The Journal of Rheumatology 34(11):2204-2210.
De Haas, M. et al. (1995). "Fcγ Receptors of Phagocytes," J. Lab. Clin. Med. 126(4):330-341.
Ducry, L. et al. (Jan. 2010; e-published on Sep. 21, 2009). "Antibody-Drug Conjugates: Linking Cytotoxic Payloads to Monoclonal Antibodies," Bioconjugate Chemistry 21(1):5-13.
Edwards, B.M. et al. (2003). "The Remarkable Flexibility of the Human Antibody Repertoire; Isolation of Over One Thousand Different Antibodies to a Single Protein, BLyS," J. Mol. Biol. 334:103-118.
El-Danaf, R.N. et al. (Feb. 11, 2015). "Characteristic Patterns of Dendritic Remodeling in Early-Stage Glaucoma: Evidence from Genetically Identified Retinal Ganglion Cell Types," The Journal of Neuroscience 35(6):2329-2343.
Estep, P. et al. (Mar.-Apr. 2013). "High Throughput Solution-Based Measurement of Antibody-Antigen Affinity and Epitope Binning," mAbs. 5(2):270-278.
Etemad, S. et al. (2012). "A Novel In Vitro Human Microglia Model: Characterization of Human Monocyte-Derived Microglia," Journal of Neuroscience Methods 209:79-89.
Fahnestock, M. et al. (2001). "The Precursor Pro-Nerve Growth Factor Is the Predominant Form of Nerve Growth Factor in Brain and Is Increased in Alzheimer's Disease," Molecular and Cellular Neuroscience 18:210-220.
Falco, M. et al. (1999; e-pub. Sep. 20, 1999). "Identification and Molecular Cloning of p75/AIRM1, A Novel Member of the Sialoadhesin Family That Functions as an Inhibitory Receptor in Human Natural Killer Cells," J. Exp. Med. 190(6):793-802.
Fan, Y.-J. (2008). "Differential effects of Pro-BDNF on Sensory Neurons after Sciatic Nerve Transection in Neonatal Rats," European Journal of Neuroscience 27:2380-2390.
Fasen, K. et al. (Feb. 2008; e-published on Dec. 19, 2007). "Ligand Binding Induces Cbl-Dependent EphB1 Receptor Degradation Through the Lysosomal Pathway," Traffic 9(2):251-266.
Feldhaus, M.J. et al. (2004, e-pub. May 31, 2004)."Yeast Display of Antibody Fragments: A Discovery and Characterization Platform," Journal of Immunological Methods 290:69-80.
Fellouse, F.A. et al. (Aug. 24, 2004). "Synthetic Antibodies from a Four-Amino-Acid Code: A Dominant Role for Tyrosine in Antigen Recognition," PNAS 101(34):12467-12472.
Fishwild, D.M. et al. (Jul. 1996). "High-Avidity Human IggK Monoclonal Antibodies from a Novel Strain of Minilocus Transgenic Mice," Nature Biotechnology 14:845-851.
Gabathuler, R. (2010, e-pub. Aug. 5, 2009). "Approaches to Transport Therapeutic Drugs across the Blood-Brain Barrier to Treat Brain Diseases," Neurobiology of Disease 37:48-57.
Gawish, R. et al. (Apr. 2015; e.pub Dec. 4, 2014). "Triggering Receptor Expressed on Myeloid cells-2 Fine-Tunes Inflammatory Responses in Murine Gram-Negative Sepsis," The FASEB Journal 29(4):1247-1257.
Gerngross, T.U. (Nov. 2004, e-pub. Nov. 4, 2004). "Advances in the Production of Human Therapeutic Proteins in Yeasts and Filamentous Fungi," Nature Biotechnology 22(11 ):1409-1414.
Gieseke, F. et al. (2012). "Siglec-7 Tetramers Characterize B-Cell Subpopulations and Leukemic Blasts," Eur. J. Immunology 42:2176-2186.

(56) References Cited

OTHER PUBLICATIONS

Graham, F.L. et al. (1977). "Characteristics of a Human Cell Line Transformed by DNA from Human Adenovirus Type 5," Journal of General Virology 36:59-72.
Griffiths, A.D. et al. (1993). "Human Anti-Self Antibodies with High Specificity from Phage Display Libraries," The EMBO Journal 12(2):725-734.
Gruber, M. et al. (1994). "Efficient Tumor Cell Lysis Mediated by a Bispecific Single Chain Antibody Expressed in *Escherichia coli*," The Journal of Immunology 152(11):5368-5374.
Gupta, N. et al. (2003). "Activated Microglia in Human Retinitis Pigmentosa, Late-Onset Retinal Degeneration, and Age-Related Macular Degeneration," Experimental Eye Research 76(4):463-471.
Hamers-Casterman, C. et al. (Jun. 3, 1993). "Naturally Occurring Antibodies Devoid of Light Chains," Nature 363:446-448.
Harrington, A.W. et al. (Apr. 20, 2004). "Secreted proNGF is a Pathophysiological Death-Inducing Ligand After Adult CNS Injury," Proc. Natl. Acad. Sci USA 101(16):6226-6230.
Harris, W.J. (Nov. 1, 1995). "Therapeutic Monoclonals—Production of Humanized Monoclonal Antibodies for In Vivo Imaging and Therapy," Biochem. Soc. Transactions 23(4):1035-1038.
Hawkins, R.E. et al. (1992). "Selection of Phage Antibodies by Binding Affinity Mimicking Affinity Maturation," Journal of Molecular Biology 226:889-896.
Hezareh, M. et al. (Dec. 2001). "Effector Function Activities of a Panel of Mutants of a Broadly Neutralizing Antibody against Human Immunodeficiency Virus Type 1," Journal of Virology vol. 75(24): 12161-12168.
Holliger, P. et al. (Jul. 1993). ""Diabodies": Small Bivalent and Bispecific Antibody Fragments," Proceedings of the National Academy of Sciences 90:6444-6448.
Hongo, J.S. et al. (1995). "Development and Characterization of Murine Monoclonal Antibodies to the Latency-Associated Peptide of Transforming Growth Factor ß1," Hybridoma 14(3):253-260.
Hoogenboom, H.R. et al. (1992). "By-Passing Immunisation. Human Antibodies from Synthetic Repertoires of Germline Hh Gene Segments Rearranged in Vitro," Journal of Molecular Biology 227:381-388.
Hudak, J.E. et al. (Jan. 2014; e-pub. Nov. 24, 2013). "Glycocalyx Engineering Reveals a Siglec-Based Mechanism For NK Cell Immunoevasion," Nat Chem Biol. 10(1):69-75, 22 pages.
Humphrey, M.B. et al. (2006). "TREM2, a DAP12-Associated Receptor, Regulates Osteoclast Differentiation and Function," J Bone Miner Res. 21(2):237-245.
Hurle, M.R. et al. (Aug. 1994)."Protein Engineering Techniques for Antibody Humanization," Current Opinion in Biotechnology 5:428-433.
Hutchins, J.T. et al. (Dec. 1995). "Improved Biodistribution, Tumor Targeting, and Reduced Immunogenicity in Mice with a Gamma 4 Variant of Campath-IH," Proc. Natl. Acad. Sci. 92:11980-11984.
Hutton, M. et al. (Jun. 18, 1998). "Association of Missense and 5'-Splice-Site Mutations in Tau with the Inherited Dementia FTDP-17," Nature 393:702-705.
Ikehara, Y. et al. (Oct. 8, 2004; e-pub. Aug. 3, 2004). "Negative Regulation of T Cell Receptor Signaling by Siglec-7 (p70/AIRM) and Siglec-9," J. Biol. Chem. 279(41):43117-43125.
Ito, M. et al. (2008). "NOD/Shi-scid IL2rynull (NOG) Mice More Appropriate for Humanized Mouse Models," Curr Top Microbiol Immunol. 324:53-76.
Ito, R. et al. (May 2012; e-published on Feb. 13, 2012). "Current Advances in Humanized Mouse Models," Cellular & Molecular Immunology 9(3):208-214.
Jackson, J.R. et al. (Apr. 1, 1995). "In Vitro Antibody Maturation. Improvement of a High Affinity, Neutralizing Antibody against IL-1 Beta," The Journal of Immunology 157(7):3310-3319.
Jakobovits, A. et al. (Mar. 18, 1993) "Germ-line Transmission and Expression of a Human-derived Yeast Artificial Chromosome," Nature 362:255-258.
Jakobovits, A. et al. (Mar. 1993). "Analysis of Homozygous Mutant Chimeric Mice Deletion of the Immunoglobulin Heavy-chain Joining Region Blocks B-Cell Development and Antibody Production," Proceedings of the National Academy of Sciences 90:2551-2555.
Jandus, C. et al. (Apr. 2014). "Interactions Between Siglec-7/9 Receptors and Ligands Influence NK Cell-Dependent Tumor Immunosurveillance," J. Clinical Invest. 124(4):1810-1820.
Jansen, P. et al. (Nov. 2007, e-pub. Oct. 14, 2007). "Roles for the Pro-Neurotrophin Receptor Sortilin in Neuronal Development, Aging and Brain Injury," Nature Neuroscience 10(11):1449-1457.
Johnson, K.S. et al. (Aug. 1993). "Human antibody engineering: Current Opinion in Structural Biology," Current Opinion in Structural Biology 3(4):564-571.
Jones, P.T. et al. (May 29, 1986). "Replacing the Complementarity-Determining Regions in a Human Antibody with Those from a Mouse," Nature 321:522-525.
Kawasaki, N. et al. (Aug. 15, 2014; e-published on Jul. 7, 2014). "Targeted Delivery of Mycobacterial Antigens to Human Dendritic Cells via Siglec-7 Induces Robust T Cell Activation," The Journal of Immunology 193(4):1560-1566.
Kelm, S. et al. (1994). "Sialoadhesin, Myelin-Associated Glycoprotein and CD22 Define a New Family of Sialic Acid-Dependent Adhesion Molecules of the Immunoglobulin Superfamily," Current Biology 4(11):965-972.
Kelm, S. et al. (Jan. 1, 1996). "The Sialoadhesins—A Family of Sialic Acid-Dependent Cellular Recognition Molecules Within the Immunoglobulin Superfamily", Glycoconjugate Journal 13(6):913-926.
Kniep, B. et al. (Sep. 15, 1993). "CDw60 Glycolipid Antigens of Human Leukocytes: Structural Characterization and Cellular Distribution," Blood 82(6):1776-1786.
Koga, T. et al. (Apr. 15, 2004). "Costimulatory Signals Mediated by the ITAM Motif Cooperate with RANKL for Bone Homeostasis," Nature 428:758-763.
Köhler, G et al. (Aug. 7, 1975). "Continuous Cultures of Fused Cells Secreting Antibody of Predefined Specificity," Nature 256:495-497.
Kostelny, S.A. et al. (Mar. 1, 1992). "Formation of a Bispecific Antibody by the Use of Leucine Zippers," The Journal of Immunology 148(5):1547-1553.
Kozbor, D. et al. (Dec. 1984). "A Human Hybrid Myeloma for Production of Human Monoclonal Antibodies," The Journal of Immunology 133(6):3001-3005.
Laird, A.S. et al. (Oct. 13, 2010). "Progranulin is Neurotrophic in Vivo and Protects against a Mutant TDP-43 Induced Axonopathy," PLOS One 5(10):e13368, seven pages.
Langer, R. (Sep. 28, 1990). "New Methods of Drug Delivery," Science 249(4976):1527-1533.
Lartigue, J.D. (Jul. 5, 2012). "Antibody-Drug Conjugates: Guided Missiles Deployed Against Cancerous Cells," OncLive located at <https://www.onclive.com/printer?url=/publications/oncology-live/2012/june-2012/antibody-drug-conjugates-guided-missiles-deployed-against-cancerous-cells>, last visited on Nov. 27, 2018, four pages.
Lazar, G.A. et al. (Mar. 14, 2006). "Engineered Antibody Fc variants with Enhanced Effector Function," PNAS 103(11):4005-4010.
Lee, C.V. et al. (2004). "Bivalent Antibody Phage Display Mimics Natural Immunoglobulin," Journal of Immunological Methods 284(1-2):119-132.
Lee, C.V. et al. (2004). "High-affinity Human Antibodies from Phage-displayed Synthetic Fab Libraries with a Single Framework Scaffold," Journal of Molecular Biology 340:1073-1093.
Li, H. et al. (Feb. 2006). "Optimization of Humanized IgGs in Glycoengineered Pichia Pastoris," Nature Biotechnology 24(2):210-215.
Li, J. et al. (Mar. 7, 2006). "Human Antibodies for Immunotherapy Development Generated via a Human B Cell Hybridoma Technology," PNAS 103(10):3557-3562.
Lightle, S. et al. (Mar. 24, 2010; e-published on Jan. 29, 2010). "Mutations Within a Human Lgg2 Antibody Form Distinct and Homogeneous Disulfide Isomers but do not Affect Fc Gamma Receptor or C1q Binding," Protein Science 19:753-762.

(56) References Cited

OTHER PUBLICATIONS

Lipovsek, D. et al. (2004, e-pub. May 31, 2004). "In-vitro protein evolution by ribosome display and mRNA display," Journal of Immunological Methods 290:51-67.
Lloyd, C. et al. (2009; e-pub. Oct. 29, 2008). "Modelling the Human Immune Response: Performance of a 10I I Human Antibody Repertoire Against a Broad Panel of Therapeutically Relevant Antigens," Protein Eng. Design & Select 22(3):159-168.
Lock, K. et al. (Jan. 2004). "Expression of CD33-Related Siglecs on Human Mononuclear Phagocytes, Monocyte-Derived Dendritic Cells and Plasmacytoid Dendritic Cells," Immunobiology 209(1-2):199-207.
Lonberg, N. et al. (1995). "Human Antibodies from Transgenic Mice," International Reviews of Immunology. 13:65-93.
Lonberg, N. et al. (Apr. 28, 1994). "Antigen-Specific Human Antibodies from Mice Comprising Four Distinct Genetic Modifications," Nature 368:856-859.
Low, D. et al. (2013). "Animal Models of Ulcerative Colitis and their Application in Drug Research," Drug Design, Development and Therapy 7:1341-1357.
Lütje, S. et al. (Feb. 19, 2014). "Anti-CEA Antibody Fragments Labeled with [18F]AlF for PET Imaging of CEA-Expressing Tumors," Bioconjugate Chemistry 25(2):335-341.
MacAuley, M.S. et al. (Jan. 2014). "Glyco-Engineering 'Super-Self'," Nat. Chem. Biol. 10(1):7-8.
MacAuley, M.S. et al. (Oct. 2014; e-published on Sep. 19, 2014). "Siglec Regulation of Immune Cell Function in Disease," Nature Reviews Immunology 14(10):653-666, twenty nine pages.
Marks, J.D. et al. (1991). "By-passing immunization: Human antibodies from V-gene libraries displayed on phage," Journal of Molecular Biology 222(3): 581-597.
Marks, J.D. et al. (Jul. 1992)."By-Passing Immunization: Building High Affinity Human Antibodies By Chain Shuffling," Bio/Technology 10:779-782.
Martens, L.H. et al. (Nov. 2012). "Progranulin Deficiency Promotes Neuroinflammation and Neuron Loss Following Toxin-Induced Injury," The Journal of Clinical Investigation 122(11):3955-3959.
Mather, J.P. (1980). "Establishment and Characterization of Two Distinct Mouse Testicular Epithelial Cell Lines," Biology of Reproduction 23:243-252.
Mather, J.P. et al. (1982). "Culture of Testicular Cells in Hormone-Supplemented Serum-Free Medium," Annals of the New York Academy of Sciences, Testicular Cell Culture 383:44-68.
May, A.P. et al. (Apr. 1998). "Crystal Structure of the N-Terminal Domain of Sialoadhesin in Complex with 3' Sialyllactose at 1.85 Å Resolution," Molecular Cell 1(5):719-728.
McCafferty, J. et al. (Dec. 6, 1990). "Phage Antibodies: Filamentous Phage Displaying Antibody Variable Domains," Nature 348:552-554.
McEarchern, J.A. et al. (Feb. 1, 2007, e-pub. Oct. 12, 2006). "Engineered Anti-CD70 Antibody with Multiple Effector Functions Exhibits in Vitro and in Vivo Antitumor Activities," Blood 109(3):1185-1192.
McMillan, S.J. et al. (Aug. 11, 2008; e-published on Jan. 17, 2008). "CD33-related Sialic-Acid-Binding Immunoglobulin-Like Lectins in Health and Disease," Carbohydrate Research 343(12):2050-2056.
McMillan, S.J. et al. (Mar. 14, 2013; e-pub. Jan. 11, 2013). "Siglec-E is a Negative Regulator of Acute Pulmonary Neutrophil Inflammation and Suppresses CD11b ß2-Integrin-Dependent Signaling," Blood 121 (11):2084-2094.
Melchior, B. et al. (Jul. 12, 2010). "Dual Induction of TREM2 and Tolerance-Related Transcript, Tmem176b, in amyloid transgenic Mice: Implications for Vaccine-Based therapies for Alzheimer's Disease," ASN Neuro 2(3) e0037:157-170.
Milstein, C. et al. (Oct. 6, 1983). "Hybrid Hybridomas and their use in Immunohistochemistry," Nature 305:537-540.
Mizoguchi, A. (2012). "Animal Models of Inflammatory Bowel Disease," Progress in Molecular Biology and Translational Science 105:263-320, fifty eight pages.
Monsonego-Oran, E. et al. (Sep. 25, 2002; e-published on Aug. 28, 2002). "FGF Receptors Ubiquitylation: Dependence on Tyrosine Kinase Activity and Role in Down regulation," FEBS Letters 528(1-3):83-89.
Morimoto, K. et al. (1992). "Single-Step Purification of F(ab')2 Fragments of Mouse Monoclonal Antibodies (Immunoglobulins G1) by Hydrophobic Interaction High Performance Liquid Chromatography Using TSKgel Phenyl-5PW," Journal of Biochemical and Biophysical Methods 24:107-117.
Morrison, S.L. (Apr. 28, 1994). "Success in Specification," Nature 368:812-813.
Morrison, S.L. et al. (Nov. 1984). "Chimeric Human Antibody Molecules: Mouse Antigen-binding Domains with Human Constant Region Domains," Proc. Nat'l Acad. Sci 81:6851-6855.
Munson, P.J. et al. (1980). "Ligand: A Versatile Computerized Approach for Characterization of Ligand-binding Systems," Analytical Biochemistry 107:220-239.
Nakamura, K. et al. (2007)."Intracellular Sortilin Expression Pattern Regulates proNGF-Induced Naturally Occurring Cell Death during Development," Cell Death and Differentiation 14:1552-1554.
Neary, D. et al. (Dec. 1998). "Frontotemporal Lobar Degeneration: A Consensus on Clinical Diagnostic Criteria," Neurology 51:1546-1554.
Neuberger, M. (Jul. 1996). "Generating high-avidity human Mabs in mice," Nature Biotechnology 14:826, one page.
Neumann, M. et al. (Oct. 2007). "TDP-43 Proteinopathy in Frontotemporal Lobar Degeneration and Amyotrophic Lateral Sclerosis," Arch Neurol. 64(10):1388-1394.
Nicoll, G. et al. (2003). "Ganglioside GD3 Expression on Target Cells Can Modulate NK Cell Cytotoxicity Via Siglec-7-Dependent and -Independent Mechanisms," Eur. J. Immunol. 33(6):1 642-1648.
Nicoll, G. et al. (Nov. 26, 1999). "Identification and Characterization of a Novel Siglec, Siglec-7, Expressed by Human Natural Killer Cells and Monocytes," The Journal of Biological Chemistry 274(48):34089-34095.
Novack, D.V. et al. (2008). "The Osteoclast: Friend or Foe?," Annu. Rev. Pathol. Mech. Dis. 3:457-484.
Nykjaer, A. et al. (2005, e-pub. Jan. 26, 2005). "p75NTR—Live or Let Die," Current Opinion in Neurobiology 15:49-57.
Nykjaer, A. et al. (Feb. 26, 2004). "Sortilin is Essential for proNGF Induced Neuronal Cell Death," Nature 427:843-848.
Oganesyan, V. et al. (2008). "Structural characterization of a Human Fc Fragment Engineered for Lack of Effector Functions," Acta Crystallography 64:700-704.
Ohgidani, M. et al. (May 14, 2014). "Direct induction of ramified microglia-like cells from human monocytes: Dynamic microglial dysfunction in Nasu-Hakola disease," Scientific Reports 4(Article No. 4957):1-7.
Orr, S.J. et al. (Feb. 9, 2007). "SOCS3 Targets Siglec 7 for Proteasomal Degradation and Blocks Siglec 7-mediated Responses," Journal of Biological Chemistry 282(6):3418-3422.
Otero, K. et al. (2012; e-published on Feb. 6, 2012). "TREM2 and ß-Catenin Regulate Bone Homeostasis by Controlling the Rate of Osteoclastogenesis," J Immunol188:2612-2621.
Park, M. et al. (Jan. 2015). "Triggering Receptor Expressed on Myeloid Cells 2 (TREM2) Promotes Adipogenesis and Diet-Induced Obesity," Diabetes 64:117-127.
Paul, S.P. et al. (Jul. 15, 2000). "Myeloid Specific Human CD33 is an Inhibitory Receptor With Differential ITIM Function in Recruiting the Phosphatases SHP-1 and SHP-2," Blood 96(2):483-490.
Peng, Q. et al. (May 18, 2010). "TREM2- and DAP12-Dependent Activation of PI3K Requires DAP10 and Is Inhibited by SHIP1," Science Signaling 3(122):ra38, pp. 1-15.
Pennesi, M.E. et al. (Aug. 2012). "Animal Models of Age Related Macular Degeneration," Molecular Aspects of Medicine 33(4):487-509, forty pages.
Peters, S.J. et al. (Jul. 13, 2012). "Engineering an Improved IgG4 Molecule with Reduced Disulfide Bond Heterogeneity and Increased Fab Domain Thermal Stability," The Journal of Biological Chemistry 287(29):24525-24533.
Pillai, S. et al. (2012; Jan. 3, 2012). "Siglecs and Immune Regulation," Annu. Rev. Immunol. 30:357-392.

(56) References Cited

OTHER PUBLICATIONS

Plückthun, A. (Dec. 1992). "Mono- and Bivalent Antibody Fragments Produced in *Escherichia coli*: Engineering, Folding and Antigen Binding," Immunological Reviews130:151-188.
Pollenz, R.S. et al. (Dec. 1, 2006, e-pub. Aug. 25, 2006). "Ligand-Dependent and -Independent Degradation of the Human Aryl Hydrocarbon Receptor (hAHR) in Cell Culture Models," Chemico-Biological Interactions 164(1-2):49-59.
Presta, L.G. (1992). "Antibody Engineering," Current Opinion in Structural Biology 2:593-596.
Presta, L.G. et al. (Sep. 1, 1993). "Humanization of an Antibody Directed Against IgE," The Journal of Immunology 151(5):2623-2632.
Product sheet for Human Siglec-7/CD328 Antibody, Monoclonal mouse IgG2B Clone #194212, R&D Systems, Catalog No. MAB1138, Feb. 7, 2018. (Year: 2018).
Provenzano, M.J. (2008). "p75NTR and Sortilin Increase After Facial Nerve Injury," Laryngoscope 118:87-93.
Ratnavalli, E. et al. (Jun. 2002). "The Prevalence of Frontotemporal Dementia," Neurology 58(1 of 2):1615-1621.
Ravetch, J.V. et al. (1991). "Fc Receptors," Annual Review Immunology 9:457-492.
Reddy, M.P. et al. (2000). "Elimination of Fc Receptor-Dependent Effector Functions of a Modified IgG4 Monoclonal Antibody to Human CD4," The Journal of Immunology 164:1925-1933.
Reverberi, R. et al. (2007). "Factors Affecting the Antigen-Antibody Reaction," Blood Transfus 5:227-240.
Riechmann, L. et al. (Mar. 24, 1988). "Reshaping Human Antibodies for Therapy," Nature 332:323-327.
Roberts, R.W. et al. (Nov. 1997). "RNA-Peptide Fusions for the In Vitro Selection of Peptides and Proteins," Proc. Natl. Acad. Sci. USA 94:12297-12302.
Rosok, M.J. et al. (Sep. 13, 1996). "Combinatorial Library Strategy for the Rapid Humanization of Anticarcinoma BR96 Fab," The Journal of Biological Chemistry 271(37):22611-22618.
Sazinsky, S.L. et al. (Dec. 23, 2008). "Aglycosylated Immunoglobulin G1 Variants Productively Engage Activating Fc Receptors," PNAS 105(51):20167-20172.
Schabbauer, G. et al. (Jul. 2010). "Myeloid PTEN Promotes Inflammation but Impairs Bactericidal Activities During Murine Pneumococcal Pneumonia," The Journal of Immunology 185(1):468-476.
Schaffitzel, C. et al. (1999). "Ribosome Display: An In Vitro Method for Selection and Evolution of Antibodies from Libraries," Journal of Immunological Methods 231:119-135.
Schier, R. et al. (1996). "Identification of Functional and Structural Amino-Acid Residues by Parsimonious Mutagenesis," Gene 169:147-155.
Schymick, J.C. et al. (2007). "Progranulin Mutations and Amyotrophic Lateral Sclerosis or Amyotrophic Lateral Sclerosis-Frontotemporal Dementia Phenotypes," Journal of Neurology, Neurosurgery and Psychiatry 78:754-756.
Seno, H. et al. (Jan. 6, 2009). "Efficient Colonic Mucosal Wound Repair Requires Trem2 Signaling," PNAS 106(1):256-261.
Shalaby, M.F et al. (Jan. 1992). "Development of Humanized Bispecitic Antibodies Reactive with Cytotoxic Lymphocytes and Tumor Cells Overexpressing the HER2 Protooncogene," The Journal of Experimental Medicine 175:217-225.
Sharif, O. et al. (Jun. 12, 2014). "The Triggering Receptor Expressed on Myeloid Cells 2 Inhibits Complement Component 1 q Effector Mechanisms and Exerts Detrimental Effects during Pneumococcal Pneumonia," PLoS Pathogen 10(6):e1004167, sixteen pages.
Sheriff, S. et al. (Sep. 1996). "Redefining the Minimal Antigen-binding Fragment," Nature Structural & Molecular Biology 3(9):733-736.
Shields, R.L. et al. (Mar. 2, 2001). "High Resolution Mapping of the Binding Site on Human IgG1 for FcγRI, FcγRII, FcγRIII, and FcRn and Design of IgG1 Variants with Improved Binding to the FcγR," The Journal of Biological Chemistry 276(9):6591-6604.
Sidhu, S.S. et al. (Apr. 2004). "Phage-displayed Antibody Libraries of Synthetic Heavy Chain Complementarity Determining Regions," Journal of Molecular Biology 338(2):299-310.
Sieber, M.W. et al. (Jan. 3, 2013). "Attenuated Inflammatory Response in Triggering Receptor Expressed on Myeloid Cells 2 (TREM2) Knock-Out Mice following Stroke," PLoS ONE 8(1):e52982, ten pages.
Sims, M.J. et al. (Aug. 15, 1993). "A Humanized CD18 Antibody Can Block Function Without Cell Destruction," The Journal of Immunology 151(4):2296-2308.
Siolas, D. et al. (Sep. 2013). "Patient-Derived Tumor Xenografts: Transforming Clinical Samples into Mouse Models," Cancer Research 73(17):5315-5319.
Skerra, A. (1993). "Bacterial Expression of Immunoglobulin Fragments," Current Opinion in Immunology 5:256-262.
Sollid, L.M. et al. (Sep. 2008). "Animal Models of Inflammatory Bowel Disease at the Dawn of the New Genetics Era," PLoS Med 5(9):1338-1342(e198).
Strohl, W.R. (2009; e-published on Nov. 4, 2009). "Optimization of Fc-mediated Effector Functions of Monoclonal Antibodies," Current Opinion in Biotechnology 20:685-691.
Sun, M. et al. (May 2013). "TREM-2 Promotes Host Resistance Against Pseudomonas aeruginosa Infection by Suppressing Corneal Inflammation via a PI3K/Akt Signaling Pathway," Investigative Ophthalmology & Visual Science 54(5):3451-3462.
Suresh, M.R. et al. (1986). "Bispecific Monoclonal Antibodies from Hybrid Hybridomas," Methods in Enzymology 121:210-228.
Svennerholm, L. (1964). "The Gangliosides," J. Lipid Res. 5:145-155.
Takahashi, K. et al. (Apr. 10, 2007). "TREM2-Transduced Myeloid Precursors Mediate Nervous Tissue Debris Clearance and Facilitate Recovery in an Animal Model of Multiple Sclerosis," Pios Med 4(4):e124, pp. 0675-0689.
Takahashi, K. et al. (Feb. 21, 2005). "Clearance of Apoptotic Neurons Without Inflammation by Microglial Triggering Receptor Expressed on Myeloid Cells-2," Journal of Experimental Medicine 201(4):647-657.
Tanaka, Y. et al. (2013). "Exacerbated Inflammatory Responses Related to Activated Microglia After Traumatic Brain Injury in Progranulin-Deficient Mice," Neuroscience 231:49-60.
Tavaré, R. et al. (Jan. 21, 2014). "Engineered Antibody Fragments for Immuno-PET Imaging of Endogenous CD8+ T Cells in Vivo," PNAS 111(3):1108-1113.
Teng, H.K. et al. (Jun. 1, 2005). "ProBDNF Induces Neuronal Apoptosis via Activation of a Receptor Complex of p75 NTR and Sortilin," The Journal of Neuroscience 25(22):5455-5463.
Traunecker, A. et al. (1991). "Bispecific Single Chain Molecules (Janusins) Target Cytotoxic Lymphocytes on HIV Infected Cells," The EMBO Journal 10(12):3655-3659.
Tutt, A. et al. (Jul. 1, 1991). "Trispecific F(ab')3 Derivatives that Use Cooperative Signaling Via the TCR/CD3 Complex and CD2 to Activate and Redirect Resting Cytotoxic T Cells1," The Journal of Immunology 147(1):60-69.
Ulyanova, T. et al. (1999). "The Sialoadhesin CD33 is a Myeloid-Specific Inhibitory Receptor," Eur J Immunol. 29:3440-3449.
Urlaub, G. et al. (Jul. 1980). "Isolation of Chinese Hamster Cell Mutants Deficient in Dihydrofolate Reductase Activity," Proc. Natl. Acad. Sci. 77(7):4216-4220.
Urmacher, C. et al. (Dec. 1989). "Tissue Distribution of GD3 Ganglioside Detected by Mouse Monoclonal Antibody R24," Am. J. Dermatopathol. 11 (6):577-581.
Vafa, O. et al. (2014; e-published on Jul. 17, 2013). "An Engineered Fc Variant of an IgG Eliminates All Immune Effector Functions Via Structural Perturbations," Methods 65:114-126.
Van Dijk, M.A et al. (2001)."Human Antibodies as Next Generation Therapeutics," Current Opinion in Chemical Biology 5:368-374.
Varchetta, S. et al. (Dec. 13, 2013). "Sialic Acid-Binding Ig-Like Lectin-7 Interacts with HIV-1 Gp120 and Facilitates Infection of CD4pos T Cells and Macrophages," Retrovirology 10(1):154, pp. 1-13.
Varchetta, S. et al. (Sep. 28, 2012). "Engagement of Siglec-7 Receptor Induces a Pro-Inflammatory Response Selectively in Monocytes," PLOS ONE 7(9):e45821, pp. 1-12.

(56) References Cited

OTHER PUBLICATIONS

Varki, A. et al. (Jan. 1, 2006; e-published on Jul. 13, 2005). "Siglecs—The Major Subfamily of I-Type Lectins," Glycobiology 16(1):1R-27R.
Vaswani, S.K. et al. (Aug. 1998). "Humanized Antibodies as Potential Therapeutic Drugs," Annals of Allergy, Asthma & Immunology 81:105-119.
Verhoeyen, M. et al. (1988). "Reshaping Human Antibodies: Grafting an Antilysozyme Activity," Science 239:1534-1536.
Vetrano, S. et al. (2008). "Unique Role of Junctional Adhesion Molecule-A in Maintaining Mucosal Homeostasis in Inflammatory Bowel Disease," Gastroenterology 135(1):173-184.
Vincent, K.J. et al. (Dec. 2012; e-pub. Nov. 1, 2012). "Current Strategies in Antibody Engineering: Fc Engineering and pH-dependent Antigen Binding, Bispecific Antibodies And Antibody Drug Conjugates," Biotechnol J. 7(12):1444-1450.
Vitale, C. et al. (Dec. 21, 1999). "Engagement of p75/AIRM1 or CD33 Inhibits the Proliferation of Normal or Leukemic Myeloid Cells," Proceedings of the National Academy of Sciences, USA 96(26):15091-15096.
Vitale, C. et al. (May 8, 2001). "Surface Expression and Function of P75/AIRM-1 or CD33 in Acute Myeloid Leukemias: Engagement of CD33 Induces Apoptosis of Leukemic Cells," Proc Natl Acad Sci USA 98(10):5764-5769.
Volosin, M. et al. (Jul. 19, 2006). "Interaction of Survival and Death Signaling in Basal Forebrain Neurons: Roles of Neurotrophins and Proneurotrophins," The Journal of Neuroscience 26(29):7756-7766.
Volosin, M. et al. (Sep. 24, 2008). "Induction of Proneurotrophins and Activation of P75ntr-Mediated Apoptosis Via Neurotrophin Receptor-Interacting Factor in Hippocampal Neurons After Seizures," The Journal of Neuroscience 28(39):9870-9879, twenty five pages.
Von Gunten, S. et al. (Nov. 2008). "Basic and Clinical Immunology of Siglecs," Ann. NY Acad. Sci. 1143:61-82, twenty five pages.
Wang, Y. et al. (Mar. 12, 2015; e-published on Feb. 26, 2015). "TREM2 Lipid Sensing Sustains the Microglial Response in an Alzheimer's Disease Model," Cell 160(6):1061-1071.
Waterhouse, P. et al. (1993). "Combinatorial Infection and In Vivo Recombination: A Strategy for Making Large Phage Antibody Repertoires," Nucleic Acids Research 21(9):2265-2266.
Wei, Y. et al. (2007). "Enhanced Protein Expressions of Sortilin and p75NTR in Retina of Rat Following Elevated Intraocular Pressure-Induced Retinal Ischemia," Neuroscience Letters 429(2-3):169-174.
White, A.L. et al. (Jan. 12, 2015). "Conformation of the Human Immunoglobulin G2 Hinge Imparts Superagonistic Properties to Immunostimulatory Anticancer Antibodies," Cancer Cell 27:138-148.
Wiehr, S. et al. (2014). "Pharmacokinetics and PET Imaging Properties of Two Recombinant Anti-PSMA Antibody Fragments in Comparison to their Parental Antibody," The Prostate 74(7):743-755.
Wilkinson, I.C. et al. (2013). "Monovalent IgG4 Molecules: Immunoglobulin Fc Mutations that Result in a Monomeric Structure," mAbs 5(3):406-417.
Williams, J.J.L. et al. (2012). "Unbiased identification of substrates for the Epac1-inducible E3 ubiquitin ligase component SOCS-3," Biochem. Soc. Trans. 40(part 1):215-218.
Wilson, N.S. et al. (Jan. 18, 2011). "An Fcγ Receptor-Dependent Mechanism Drives Antibody-Mediated Target-Receptor Signaling in Cancer Cells," Cancer Cell 19:101-113.
Xu, D. et al. (2000). "In Vitro Characterization of Five Humanized OKT3 Effector Function Variant Antibodies," Cellular Immunology 200(1):16-26.
Xu, J. et al. (Jul. 2000). "Diversity in the CDR3 Region of VH Is Sufficient for Most Antibody Specificities," Immunity 13:37-45.
Yamaji, T. et al. (Feb. 22, 2002). "A Small Region of the Natural Killer Cell Receptor, Siglec-7, Is Responsible for Its Preferred Binding to α2,8-Disialyl and Branched α2,6-Sialyl Residues," J. Biol. Chem. 277(8):6324-6332.
Yano, H. et al. (Nov. 25, 2009)."Proneurotrophin-3 Is a Neuronal Apoptotic Ligand Evidence for Retrograde-Directed Cell Killing," The Journal of Neuroscience 29(47):14790-14802.
Ye, J. et al. (Jul. 2013; e-pub. May 13, 2013). "IgBLAST: An Immunoglobulin Variable Domain Sequence Analysis Tool," Nucleic Acids Research 41:W34-W40.
Yelton, D.E. et al. (1995). "Affinity maturation of the BR96 anti-carcinoma antibody by codon-based mutagenesis," The Journal of Immunology 155:1994-2004.
Yin, F. et al. (Dec. 21, 2009). "Exaggerated Inflammation, Impaired Host Defense, and Neuropathology in Progranulin-Deficient Mice," J. Exp. Med. 207(1):117-128.
Zapata, G. et al. (1995). "Engineering Linear F(ab')2 Fragments for Efficient Production in *Escherichia coli* and Enhanced Antiproliferative Activity," Protein Engineering Designs and Selections 8(10):1057-1062.
Zhou, Q. et al. (Mar. 1, 2014). "Humanized NOD-SCID IL2rg-/- Mice as a Preclinical Model for Cancer Research and its Potential Use for Individualized Cancer Therapies," Cancer Letters 344(1):13-19.
Zhu, Y. et al. (Sep. 15, 2014, e-pub. Jul. 31, 2014). "CSF1/CSF1 R Blockade Reprograms Tumor-Infiltrating Macrophages and Improves Response to T Cell Checkpoint Immunotherapy in Pancreatic Cancer Models," Cancer Research 74(18):5057-5069.
International Preliminary Report on Patentability dated Mar. 15, 2018 for PCT Application No. PCT/US2016/049032 filed on Aug. 26, 2016, 14 pages.
International Search Report and Written Opinion dated Jan. 18, 2017 for PCT Application No. PCT/US2016/049032 filed on Aug. 26, 2016, 23 pages.
Singaporean Search Report and Written Opinion dated Dec. 13, 2018 for SG Application No. 11201801640W filed on Feb. 28, 2018, 13 pages.
Beckman Coulter, (2011). "IOTest Anti-p75 / AIRM1-PE: PN A22330," available online at www.bc-cytometry.com/PDF/DataSheet/A22330.pdf>, 2 pages.
Bio-Rad (2004). "Datasheet: MCA5782GA Product Details Mouse Anti Human SIGLEC-7," Available online at images.bio-rad-antibodies.com/datasheets/datasheet-MCA5782GA.pdf>, 3 pages.
Chinese Search Report dated Feb. 2, 2021 for CN Application No. 201680059071.6 filed on Aug. 26, 2016, 4 pages. English translation.
International Search Report and Written Opinion for International Patent Application No. PCT/US2019/035990, dated Oct. 2, 2019, 10 pages.

\* cited by examiner

| | | |
|---|---|---|
| Human Siglec-7 | --MLLLLLLLPLLWGHERVEGQKSNRKDYSLTMQSSVTVQEGMCVHVRCSFSYPVDSQTDS | 58 |
| Chimpanzee Siglec-7 | -MLLLLLLPPLLIWGRERVEGQKSNRKDYSLTMQSSVTVQEGMCVHVRCSFSYPVDSQTDS | 59 |
| Pygmy Chimpanzee Siglec-7 | -MLLLLLLPLLIWGRERVEGQKSNRKDYSLTMQSSVTVQEGMCVHVRCSFSYPVDSQTDS | 59 |
| Orangutan Siglec-7 | MLLILLLLFLPLLWGMERVEGQKMNRKDYSLMQSSVTVQCSFSYPVDSQTDS | 60 |
| Gorilla Siglec-7 | --MLLILLLLPLLIWGRENVEGQKSKRDYSLTMQSSVTVQEGMCVHVRCSFSYPVDSQTDS | 59 |
| Gibbon Siglec-7 | --MLLILLLLLRLLIWGRERVEGQKSNQKWYPLMWQSSVTVQEGLCVHVRCSFSYPVDSQTDS | 59 |
| | : ***** * *****************:: ;:. :* ************* | |
| Human Siglec-7 | DPVHGYWFRAGNDISWKAPVATNNPAWAVQEETRDRFHLLGDPQTKNCTLSIRDARMSDA | 118 |
| Chimpanzee Siglec-7 | DPVHGYWFWAENDISWKAPVATNNPARAVREETRDRFHLLGDPQTKNCTLSIRDARMSDA | 119 |
| Pygmy Chimpanzee Siglec-7 | DPVHGYWFRAENDISWKAPVATNNPARAVREETRDRFHLLGDPQTKNCTLSIRDARMSDA | 119 |
| Orangutan Siglec-7 | DPVHGYWFRAGDISWKAPVATNNPAQAVREETRDRFHLLGDPQTKNCTLSIRDARMSDA | 120 |
| Gorilla Siglec-7 | DPVHGYWFRAENDISWKAPVATNDPARAVRENTRDRFHLLGDPQTKNCTLSIRDARMSDA | 119 |
| Gibbon Siglec-7 | DPVHGYWFRAGDDISWKTPVATNRRARAVREETRDRFHLLGDPQTKNCTLSIRDARMSDA | 119 |
| | ***** :.:* *. .: ************************** | |
| Human Siglec-7 | GRYFFRMEKGNIKWNYKYDQLS--------------------------------- | 140 |
| Chimpanzee Siglec-7 | GRYFFRMEKGNIKWNYKHDQLSVNVTIASQAPLSRYHLEVLELVTVQEGXCVSVPGSVLXP | 179 |
| Pygmy Chimpanzee Siglec-7 | GRYFFRMEKGNIKWNYKYDQLS--------------------------------- | 141 |
| Orangutan Siglec-7 | GRYFFRMRGNIKWNYKYDRLSVNVTASQAPPSRYHLEVPESVTVQEGLCVSVPCSVLXP | 180 |
| Gorilla Siglec-7 | GRYFFRMERGMIKWNYKYDQLS--------------------------------- | 141 |
| Gibbon Siglec-7 | GTYFFRMERGKIKWMYKYHQLS--------------------------------- | 142 |
| | *.***: ****:*. :*:*: | |
| Human Siglec-7 | ------------------------------------------------------ | 140 |
| Chimpanzee Siglec-7 | YYNKTDSSPVHGCWFKKGINLQWMPVAINIPNGKVQETRGKFHLLGDLKTNMCSLSIRD | 239 |
| Pygmy Chimpanzee Siglec-7 | ------------------------------------------------------ | 141 |
| Orangutan Siglec-7 | YWWDSSPYHGCWFKEGINIQWMPVATHIPMKVEETRGRFBLLGDLKTNMCSLSIRD | 240 |
| Gorilla Siglec-7 | ------------------------------------------------------ | 141 |
| Gibbon Siglec-7 | ------------------------------------------------------ | 141 |
| Human Siglec-7 | --------------VNVTALTHRPNIIPGTLESGCFQNLICSVPW | 172 |
| Chimpanzee Siglec-7 | ARKGDLGNYYFQVERGQIRWNIKTKQLSVNVTALTHRPNIIPGTLESGCFQMLICSVPW | 299 |
| Pygmy Chimpanzee Siglec-7 | --------------VNVTALTHRPNIIPGTLESGCFQMLICSVPW | 173 |
| Orangutan Siglec-7 | ARKGDLGNYYFQVERGXIRWNYKMKQLSVNVTALTHRPNIIPSTLESGCFQNLICSVPW | 300 |
| Gorilla Siglec-7 | --------------VNVTALTHRPNIIPSTLESGCFQNLICSVPW | 173 |
| Gibbon Siglec-7 | --------------VNVTALTHRPNVIPGTLESGCFQMLICSTPW | 173 |
| | *:;. ****:.****:***: | |
| Human Siglec-7 | ACEGQGTPPMISWMGTSVS-PLHPSTTRSSVLTLIPQPQHHGTSLTCQVTLPGAGVTTNRT | 231 |
| Chimpanzee Siglec-7 | ACEGQGTPPMISWMGTSVS-PLHPSTTRSSVLTLIPQPQHHGTSLTCQVTLPGAGVTTNRE | 358 |
| Pygmy Chimpanzee Siglec-7 | ACEGQGTPPMISWMGTSVS-PLHPSTTRSSVLTLIPQPQHHGTSLTCQVTLPGAGVTTNRE | 232 |

FIG. 1A

```
Orangutan Siglec-7      ACEQGTPPHISWMGTSVSTBLHPSTTRSSVLTLIPQXEDHGTWFTLQYVLTPAYVTVCSI         360
Gorilla Siglec-7        ACEQGTPPHISWMGTSVS--PLHPSTTRSSVLTLIPQPQEHGTSLTCQVTLPGAGVTTWRT         232
Gibbon Siglec-7         ACEQGTPPHISWMGTSLS--PLRPSTTRSSVLTLIPQPQDHGTSLTCQVTLPGAGVTTWRT         232
                        ******************  * *********************  **** *******  .

Human Siglec-7          --IQLMVSYPPQNL---TVTVFQQEGTASTALGWSESSLSVLEGQSLRLVCAVDSNPPARLSW      288
Chimpanzee Siglec-7     --IQLMVSYPPQNL---TVTVFQQEGTASTALGWSSSLSVLEGQSLRLVCAVDSNPPARLSW      415
Pygmy Chimpanzee Siglec-7 --IQLMVSYPPQNL---TVTVFQQEGTASTALGNSSSLSVLEGQSLRLVCAVDSNPPARLSW    289
Orangutan Siglec-7      PQSHSVSFLPVSITLSLXPFMFFSTASTALGNSSSLSVLEGQSLRLVCAVDSNPPARLSW         420
Gorilla Siglec-7        --TQLMVSYPPQNL---TVTIFQGEGTASTALGNSSSLSVLEGQSLRLVCAVDSNPPARLSW      289
Gibbon Siglec-7         --TRLMVSYPPQNL---TVTVFQGEGTASTALGNSSSLSVLEGQSLRLVCAVDSNPPARLSW      289
                          *   ******    *** *  *************  *********************

Human Siglec-7          TWRSLTLYPSQPSNPIVLELQVHLGDEGEETCRAQNSLGSQVSLNLSLQRYTGKMRPV           348
Chimpanzee Siglec-7     TWRSLTLYPSQPSNPIVLELQVHLGDEGEETCRAQNSLGSQVSLNLSLQHETTGKMRPY           475
Pygmy Chimpanzee Siglec-7 TWRSLTLYPSQPSNPLVLELQVHLGDEGEPTCRAQMSLGSQVSLMLSLQHEYTGKMRPV         349
Orangutan Siglec-7      TWRSLTLYPSQPSNPIVLELQVHLGDEGECTCRAQNSLGSQVSLMLSLQHEYTGKMRPY           480
Gorilla Siglec-7        TWRSLTLYPSQPSNPLVLELQVHLGDEGEFTCRAQMSLGSQBVSLMLSLQHEYTGKMRPY         349
Gibbon Siglec-7         TWRSLTLYPSQPSMPLVLELRVHLGDHGEFTCRABMSLGSQHFSLMLSLQHEYTGKMRPY         349
                        **********  * ****  ****** ***      ***** *   ***   ****

Human Siglec-7          SGVLLGAVGGAGATALVFLSFCVIFIVVRSCKKSARPAADVGDIGMKDANTTRGSASQG         408
Chimpanzee Siglec-7     SGVLLGAVGGAGATALVFLSFCVIFIVVRSCKKSARPAADVGDTSMEDANTIRGSASQG         535
Pygmy Chimpanzee Siglec-7 SGVLLGAVGGAGATALVFLSFCVIFIVVRSCKKSARPAADVGDTGMEDANTIRGSASQG       409
Orangutan Siglec-7      SGVMLGAVGGAGATALVFLSFCVIFIVVRSCREKBARPAADVGDTGMEDANTVRGSASQG         540
Gorilla Siglec-7        SGVLLGAVGGAGATALVFLSFCVIFIVVRSCKKSARPAADVGDTGMEDANTIRGSASQG         409
Gibbon Siglec-7         SGVILGAVGGAGAGATALVFLSFCVIFIVVNSYRKSARPAAGVGDYGMEDAMAIRGSASQG       409
                        *** ************* ** *********** * *****  *** * ** *******

Human Siglec-7          WLTESWADDNPRHRGLAAHSSGEERETQYAPLSFHKGEPQDLSGQEATNNEYSEIKIPK--      467
Chimpanzee Siglec-7     TLTESWAYDNPRREGLAAPSSGEEREVQYAPLSFHKGEPQDLSGQEATMNEYSEIKIPK--      594
Pygmy Chimpanzee Siglec-7 TLTESWAYDNPRHKGLAAPSSGEEREVQYAPLSFHKGEPQDLSGQEATNNEYSEIKIPKX     469
Orangutan Siglec-7      TLTESWADDMPRHLGLAAPSGGEERETQYASLSFHKGEPQDLSRQEATNNEYSEIKIPK--      593
Gorilla Siglec-7        TLTESWADDNPRHYGLAAPSSGEEREVQYAPLSFHKGEPQDLSGQEATNNEYSEIKIPK--      468
Gibbon Siglec-7         TMIESWADDNPRHRGLAAPSSGEECEIQVASVSFHKYEPQDLSGQEATNNEVSETKIPK--      468
                        * ****  ****  **** * ***   *  ****  ********** ***   ****

Human Siglec-7          --------------------                                              467
Chimpanzee Siglec-7     --------------------                                              594
Pygmy Chimpanzee Siglec-7 EMAEZARACLRVNDPSSKCVRG                                           490
Orangutan Siglec-7      --------------------                                              599
Gorilla Siglec-7        --------------------                                              468
Gibbon Siglec-7         --------------------                                              468
```

FIG. 1A (Cont)

| Mutation | 4E3 Fab | 1085 MAb | 1085 Fab | 6-434 MAb | 52.7 MAb |
|---|---|---|---|---|---|
| M30A | 122.9 (79) | 89.9 (39) | 20.1 (12) | 84.8 (9) | 100.0 (6) |
| Q31A | 111.5 (46) | 104.0 (11) | 18.2 (13) | 100.8 (22) | 100.7 (42) |
| V44A | 115.0 (12) | 93.9 (27) | 13.3 (7) | 69.0 (43) | 89.3 (8) |
| M45A | 129.1 (25) | 37.3 (2) | 1.6 (3) | 111.0 (48) | 125.9 (92) |
| S47A | 103.4 (14) | 81.7 (5) | 1.5 (1) | 103.1 (17) | 117.9 (23) |
| F49A | 145.5 (28) | 158.7 (28) | 13.9 (9) | 112.9 (30) | 157.8 (13) |
| Y50A | 139.2 (77) | 108.5 (75) | 18.2 (3) | 97.9 (30) | 142.3 (26) |
| I72A | | 130.1 (80) | 92.8 (9) | 64.2 (11) | 100.7 (7) |
| W74A | 26.5 (12) | 101.0 (67) | 79.8 (30) | 74.9 (28) | 83.7 (25) |
| M81A | 25.7 (16) | 153.1 (23) | 137.7 (73) | 111.6 (20) | 5.6 (6) |
| T103A | 22.0 (13) | 96.3 (52) | 6.3 (4) | 77.5 (33) | 105.7 (39) |
| K104A | 138.9 (25) | 13.6 (1) | -2.0 (5) | 83.8 (7) | 115.1 (67) |
| T107A | 115.0 (80) | 83.8 (27) | 0.4 (10) | 66.8 (8) | 129.2 (9) |
| N124A | 124.2 (105) | 149.9 (22) | 81.1 (42) | 126.0 (40) | 115.2 (4) |
| M185A | 1.0 (4) | 29.1 (5) | -2.2 (8) | | |
| | 92.6 (62) | | | 69.3 (3) | 74.3 (9) |

Binding Reactivity (% WT)

FIG. 1F

```
Potential humanized sequence based on IMGT IGKV3-11*01 acceptor framework (AbM CDR definition)
IGKV3-11*01 EIVLTQSPATLSLSPGERATLSCRASQSVSSYLAWYQQKPGQAPRLLIYDASNRAT
            GIPARFSGSGSGTDFTLTISSLEPEDFAVYYCQQRSNWPP
Joining region IMGT J00242|IGKJ2*01|YTFGQGTKLEIK 10         20         30         40         50
seq          10         20         30         40         50
AbM       bbb  pp       bbb  b    b bi bi  i     ii ibbi  i
S7-4E3   QIVLTQSPAILSASPGEKVTMTC SAMSSFTYMY WYQQKPGSSPRLLIF DTSWLAS
            *                **  *                 **       *
3-11*01  EIVLTQSPATLSLSPGERATLSC RASQSVSSYLAWYQQKPGQAPRLLIY DASNRAT
h4E3-L1  EIVLTQSPATLSLSPGERATLSC SAMSSFTYMY WYQQKPGQAPRLLIY DTSWLAS
h4E3-L2  EIVLTQSPATLSLSPGERVTMSC SAMSSFTYMY WYQQKPGQAPRLLIY DTSWLAS
h4E3-L3  EIVLTQSPATLSLSPGERVTMSC SAMSSFTYMY WYQQKPGQAPRLLIY DTSWLAS
                         A                                  #                          S                  #

60         70         80         90        100
seq          60         70         80         90        100
AbM        b  b        bbb  b     ib bib   ibi ibi  i    b b b
S7-4E3   GVPIRFSGSGSGTSYSLTISRMEAEDTAAYYC QQWSSSPLT FGAGTKLELK
           *  *                ** *  ** *    * ##                *
3-11*01  GIPARFSGSGSGTDFTLTISSLEPEDFAVYYC QQRSNWPP  FGQGTKLEIK
h4E3-L1  GIPARFSGSGSGTDFTLTISSLEPEDFAVYYC QQWSSSPLT FGQGTKLEIK
h4E3-L2  GVPARFSGSGSGTDFTLTISSMEPEDFAVYYC QQWSSSPLT FGQGTKLEIK
h4E3-L3  GVPARFSGSGSGTDYTLTISSMEPEDFAVYYC QQWSSSPLT FGQGTKLEIK
                              T deamidation substitutions: Q/S/A/D
^ tryptophan oxidation substitutions: H/Y/F h4E3-L1 is a "CDR-swap" with no changes to human framework. Subsequent sequences alter framework
changes shown in red (compared to sequence above it).
```

FIG. 6B

Potential humanized sequence based on IMGT IGHV3-21*01 acceptor framework (AbM CDR definition)
IGHV3-21*01 EVQLVESGGGLVKPGGSLRLSCAASGFTFSSYSMNWVRQAPGKGLEWVSSISSSSSYIY
            YADSVKGRFTISRDNAKNSLYLQMNSLRAEDTAVYYCARX
Joining region  IMGT J00256|IGHJ4*01|YFDYWGQGTLVTVSS

```
                          10         20         30         40         50
seq                       10         20         30         40         50     a
AbM           b b b     b   b b b   b b b   b l i     l ibb b
S7-4E3        EVQLVESGGGLVKPGGSLRLSCAVS GFTFSNYDMS WVRQMPEKRLEWVA TISSGGGYTY
                                    *                   *       *       *
h4E3-B1       EVQLVESGGGLVKPGGSLRLSCAAS GFTFSSYSMN WVRQAPGKGLEWVS SISSSSSYIY
h4E3-B2       EVQLVESGGGLVKPGGSLRLSCAAS GFTFSNYDMS WVRQAPGKGLEWVS TISSGGGYTY
h4E3-B3       EVQLVESGGGLVKPGGSLRLSCAVS GFTFSNYDMS WVRQAPGKGLEWVA TISSGGGYTY 60         70         80  abc    90         100        110      120
seq             60         70         80         90                    110      i  b b b
AbM              i b     bbb b x   b   b b b        bibibb              i b b b
S7-4E3        YPDSVRGRFTISRDNAKNALVLQMSSLRSEDTALYYCTR HGYGNYDWYFDV WGAGATVTVSS
                *                                                         *
h4E3-B1       YADSVKGRFTISRDNAKNSLYLQMNSLRAEDTAVYYCAR HGYGNYDWYFDV WGQGTLVTVSS
h4E3-B2       YADSVKGRFTISRDNAKNSLYLQMNSLRAEDTAVYYCAR HGYGNYDWYFDV WGQGTLVTVSS
h4E3-B3       YADSVKGRFTISRDNAKNSLYLQMNSLRAEDTAVYYCTR HGYGNYDWYFDV WGQGTLVTVSS
              P
```

\# deamidation substitutions: Q/S/A/D
^ tryptophan oxidation substitutions: H/Y/F h4E3-B1 is a "CDR-swap" with no changes to human framework. Subsequent sequences alter framework changes shown in red (compared to sequence above it).

FIG. 6C

Potential humanized sequence based on IMGT IGKV1-39*01 acceptor framework (AbM CDR definition)
IGKV1-39*01 DIQMTQSPSSLSASVGDRVTITCRASQSISSYLNWYQQKPGKAPKLLIYAASSLQS
            GVPSRFSGSGSGTDFTLTISSLQPEDFATYYCQQSYSTPP
Joining region IMGT J00242|IGKJ2*01|YTFGQGTKLEIK

```
seq           10         20         30         40         50
AbM           10         20         30         40         50
          bbb    pp pp   bbb    b bbb bi bi 1   11 1bbi      i
S7-10B5.1 DVQMTQTTSSLSASLGDRVTITSC RASQSISSYLN WYQQRPGTVKLLIY YTSRLHS
              **                 *                  ***
1-39*01   DIQMTQSPSSLSASVGDRVTITC  RASQSISSYLN WYQQKPGKAPKLLIY AASSLQS
h10B5-L1  DIQMTQSPSSLSASVGDRVTITC  RASQDINTYLN WYQQKPGKAPKLLIY YTSRLHS
h10B5-L2  DIQMTQSPSSLSASVGDRVTITC  RASQDINTYLN WYQQKPGKAPKLLIY YTSRLHS
h10B5-L3  DVQMTQSPSSLSASVGDRVTITC  RASQDINTYLN WYQQKPGRAPKLLIY YTSRLHS
                                       #                  TV seq            60         70         80         90        100
AbM            60         70         80         90        100
            b      b      bbb    ib bib ibi ibi     i      b b b
S7-10B5.1 GVPSRFSGSGSGTDYSLTISMLEQEDIAYYC QQSMTLPWT FGQGTKLEIK
                            ** *   *  *  *           *
1-39*01   GVPSRFSGSGSGTDFTLTISSLQPEDFATYYC QQSYSTPP  FGQGTKLEIK
h10B5-L1  GVPSRFSGSGSGTDFTLTISSLQPEDFATYYC QQGMTLPWT FGQGTKLEIK
h10B5-L2  GVPSRFSGSGSGTDFTLTISSLQPEDFATYYC QQGMTLPWT FGQGTKLEIK
h10B5-L3  GVPSRFSGSGSGTDYTLTISSLQPEDFATYYC QQGMTLPWT FGQGTKLEIK
                         I    F                #
``` deamidation substitutions: Q/S/A/D h10B5-L1 is a "CDR-swap" with no changes to human framework. Subsequent sequences alter framework changes shown in red (compared to sequence above it).

FIG. 6D potential humanized sequence based on IMGT IGHV1-46*01 acceptor framework (AbM CDR definition)
IGHV1-46*01 QVQLVQSGAEVKKPGASVKVSCKASGYTFTSYYMHWVRQAPGQGLEWMGIINPSGGSTS
            YAQKFQGRVTMTRDTSTSTVYMELSSLRSEDTAVYYCAR
joining region IMGT J00256|IGHJ4*01|YFDYWGQGTLVTVSS

```
               seq                    10         20         30         40         50
               AbM                    10         20         30         40    50  a
                              bbb  b          bbbb bb  b  bli   i ibb  b
s7-10B5.1      QVHLQQSGPELVKPGASYKISCKAS CYAFTWCMMH WVRQRPGKGLDWIG RIFPGMGHTN
                *                 *                *                    *  *
1-46*01        QVQLVQSGAEVKPGASVKVSCKAS  GYTFTSYYMH WVRQAPGQGLEWMG IINPSGGSTS
h10B5-H1       QVQLVQSGAEVKPGASVKVSCKAS  GYAFTWCMMH WVRQAPGQGLEWMG RIFPGMGHTN
h10B5-H2       QVQLVQSGAEVKPGASVKVSCKAS  GYAFTWCMMH WVRQAPGQGLEWIG RIFPGMGHTN
h10B5-H3       QVQLVQSGAEVKPGASVKISCKAS  GYAFTWCMMH WVRQAPGQGLEWIG RIFPGMGHTN
h10B5-H4       QVQLVQSGAEVKPGASVKISCKAS  GYAFTWCMMH WVRQAPGQGLEWIG RIFPGMGHTN
                                  V                    #^            @   # seq      60         70         80         90        100        110
               AbM      60         70      80 abc       90                     110
                       i  b   bbbx    bbb      bibibb                       i  b b h
s7-10B5.1      YSGKFKDKATLTEDKSSSTAYMQLSSLRSEDSAVYFCAR DYSDYYFDY WGQGTLVTVSS
                **   ****  *  *****  **  *   ***   **      *                **
1-46*01        YAQKFQGRVTMTRDTSTSTVYMELSSLRSEDTAVYYCAR   DYSDYYFDY WGQGTLVTVSS
h10B5-H1       YAQKFQGRVTMTRDTSTSTVYMELSSLRSEDTAVYYCAR   DYSDYYFDY WGQGTLVTVSS
h10B5-H2       YAQKFQGRATLTEDTSTSTAYMELSSLRSEDTAVYYCAR   DYSDYYFDY WGQGTLVTVSS
h10B5-H3       YAQKFQGRATLTEDTSTSTAYMELSSLRSEDTAVYYCAR   DYSDYYFDY WGQGTLVTVSS
h10B5-H4       YAQKFQGRATLTEDKSTSTAYMELSSLRSEDTAVYYCAR   DYSDYYFDY WGQGTLVTVSS
                        S                            F
``` deamidation substitutions: Q/S/A
@ isoaspartate substitutions: Q/S/A
^ tryptophan oxidation substitutions: H/Y/F h10B5-H1 is a "CDR-swap" with no changes to human framework. Subsequent sequences alter framework changes shown in red (compared to sequence above it).

FIG. 6E

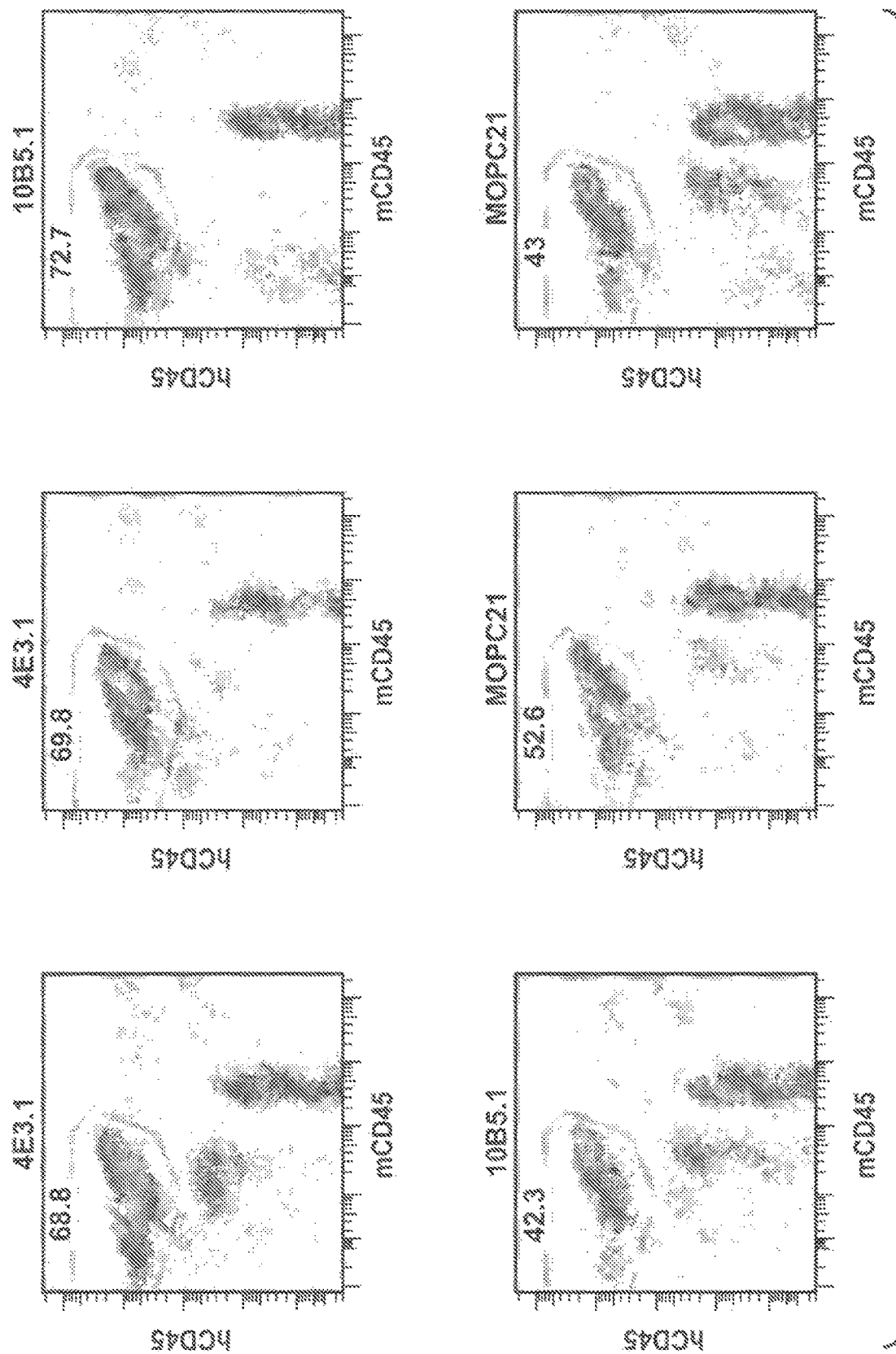

SEQUENCE LISTING

<160> NUMBER OF SEQ ID NOS: 537

<210> SEQ ID NO 1
<211> LENGTH: 467
<212> TYPE: PRT
<213> ORGANISM: Homo sapiens

<400> SEQUENCE: 1

```
Met Leu Leu Leu Leu Leu Leu Pro Leu Leu Trp Gly Arg Glu Arg Val
1               5                   10                  15

Glu Gly Gln Lys Ser Asn Arg Lys Asp Tyr Ser Leu Thr Met Gln Ser
            20                  25                  30

Ser Val Thr Val Gln Glu Gly Met Cys Val His Val Arg Cys Ser Phe
        35                  40                  45

Ser Tyr Pro Val Asp Ser Gln Thr Asp Ser Asp Pro Val His Gly Tyr
    50                  55                  60

Trp Phe Arg Ala Gly Asn Asp Ile Ser Trp Lys Ala Pro Val Ala Thr
65                  70                  75                  80

Asn Asn Pro Ala Trp Ala Val Gln Glu Glu Thr Arg Asp Arg Phe His
                85                  90                  95
```

Leu Leu Gly Asp Pro Gln Thr Lys Asn Cys Thr Leu Ser Ile Arg Asp
            100                 105                 110

Ala Arg Met Ser Asp Ala Gly Arg Tyr Phe Arg Met Glu Lys Gly
    115                 120                 125

Asn Ile Lys Trp Asn Tyr Lys Tyr Asp Gln Leu Ser Val Asn Val Thr
    130                 135                 140

Ala Leu Thr His Arg Pro Asn Ile Leu Ile Pro Gly Thr Leu Glu Ser
145                 150                 155                 160

Gly Cys Phe Gln Asn Leu Thr Cys Ser Val Pro Trp Ala Cys Glu Gln
                165                 170                 175

Gly Thr Pro Pro Met Ile Ser Trp Met Gly Thr Ser Val Ser Pro Leu
            180                 185                 190

His Pro Ser Thr Thr Arg Ser Ser Val Leu Thr Leu Ile Pro Gln Pro
            195                 200                 205

Gln His His Gly Thr Ser Leu Thr Cys Gln Val Thr Leu Pro Gly Ala
        210                 215                 220

Gly Val Thr Thr Asn Arg Thr Ile Gln Leu Asn Val Ser Tyr Pro Pro
225                 230                 235                 240

Gln Asn Leu Thr Val Thr Val Phe Gln Gly Glu Gly Thr Ala Ser Thr
                245                 250                 255

Ala Leu Gly Asn Ser Ser Ser Leu Ser Val Leu Glu Gly Gln Ser Leu
            260                 265                 270

Arg Leu Val Cys Ala Val Asp Ser Asn Pro Pro Ala Arg Leu Ser Trp
        275                 280                 285

Thr Trp Arg Ser Leu Thr Leu Tyr Pro Ser Gln Pro Ser Asn Pro Leu
290                 295                 300

Val Leu Glu Leu Gln Val His Leu Gly Asp Glu Gly Glu Phe Thr Cys
305                 310                 315                 320

Arg Ala Gln Asn Ser Leu Gly Ser Gln His Val Ser Leu Asn Leu Ser
                325                 330                 335

Leu Gln Gln Glu Tyr Thr Gly Lys Met Arg Pro Val Ser Gly Val Leu
            340                 345                 350

Leu Gly Ala Val Gly Gly Ala Gly Ala Thr Ala Leu Val Phe Leu Ser
        355                 360                 365

Phe Cys Val Ile Phe Ile Val Val Arg Ser Cys Arg Lys Lys Ser Ala
370                 375                 380

Arg Pro Ala Ala Asp Val Gly Asp Ile Gly Met Lys Asp Ala Asn Thr
385                 390                 395                 400

Ile Arg Gly Ser Ala Ser Gln Gly Asn Leu Thr Glu Ser Trp Ala Asp
                405                 410                 415

Asp Asn Pro Arg His His Gly Leu Ala Ala His Ser Ser Gly Glu Glu
            420                 425                 430

Arg Glu Ile Gln Tyr Ala Pro Leu Ser Phe His Lys Gly Glu Pro Gln
        435                 440                 445

Asp Leu Ser Gly Gln Glu Ala Thr Asn Asn Glu Tyr Ser Glu Ile Lys
    450                 455                 460

Ile Pro Lys
465

<210> SEQ ID NO 2
<211> LENGTH: 594
<212> TYPE: PRT
<213> ORGANISM: Pan troglodytes
<220> FEATURE:

```
<221> NAME/KEY: VARIANT
<222> LOCATION: 168, 178, 183
<223> OTHER INFORMATION: Xaa = Any Amino Acid

<400> SEQUENCE: 2

Met Leu Leu Leu Leu Leu Pro Pro Leu Leu Trp Gly Arg Glu Arg
1               5                   10                  15

Val Glu Gly Gln Lys Ser Asn Arg Lys Asp Tyr Ser Leu Thr Met Gln
                20                  25                  30

Ser Ser Val Thr Val Gln Glu Gly Met Cys Val His Val Arg Cys Ser
                35                  40                  45

Phe Ser Tyr Pro Val Asp Ser Gln Thr Asp Ser Asp Pro Val His Gly
50                  55                  60

Tyr Trp Phe Trp Ala Glu Asn Asp Ile Ser Trp Lys Ala Pro Val Ala
65                  70                  75                  80

Thr Asn Asn Pro Ala Arg Ala Val Arg Glu Glu Thr Arg Asp Arg Phe
                85                  90                  95

His Leu Leu Gly Asp Pro Gln Thr Lys Asn Cys Thr Leu Ser Ile Arg
                100                 105                 110

Asp Ala Arg Met Ser Asp Ala Gly Arg Tyr Phe Phe Arg Met Glu Lys
                115                 120                 125

Gly Asn Ile Lys Trp Asn Tyr Lys His Asp Gln Leu Ser Val Asn Val
130                 135                 140

Thr Ala Ser Gln Ala Pro Leu Ser Arg Tyr Arg Leu Glu Val Leu Glu
145                 150                 155                 160

Leu Val Thr Val Gln Glu Gly Xaa Cys Val Ser Val Pro Cys Ser Val
                165                 170                 175

Leu Xaa Pro Tyr Tyr Asn Xaa Thr Asp Ser Ser Pro Val His Gly Cys
                180                 185                 190

Trp Phe Lys Lys Gly Ile Asn Ile Gln Trp Asn Asn Pro Val Ala Thr
                195                 200                 205

Asn Ile Pro Asn Gly Lys Val Gln Glu Thr Arg Gly Arg Phe His Leu
210                 215                 220

Leu Gly Asp Leu Lys Thr Asn Asn Cys Ser Leu Ser Ile Arg Asp Ala
225                 230                 235                 240

Arg Lys Gly Asp Leu Gly Asn Tyr Tyr Phe Gln Val Glu Arg Gly Gln
                245                 250                 255

Ile Arg Trp Asn Tyr Lys Thr Lys Gln Leu Ser Val Asn Val Thr Ala
                260                 265                 270

Leu Thr His Arg Pro Asn Ile Leu Ile Pro Gly Thr Leu Glu Ser Gly
                275                 280                 285

Cys Phe Gln Asn Leu Thr Cys Ser Val Pro Trp Ala Cys Glu Gln Gly
                290                 295                 300

Thr Pro Pro Met Ile Ser Trp Met Gly Thr Ser Val Ser Pro Leu His
305                 310                 315                 320

Pro Ser Thr Thr Arg Ser Ser Val Leu Thr Leu Ile Pro Gln Pro Gln
                325                 330                 335

His His Gly Thr Ser Leu Thr Cys Gln Val Thr Leu Pro Gly Ala Gly
                340                 345                 350

Val Thr Thr Asn Arg Thr Ile Gln Leu Asn Val Ser Tyr Pro Pro Gln
                355                 360                 365

Asn Leu Thr Val Thr Val Phe Gln Gly Glu Gly Thr Ala Ser Thr Ala
370                 375                 380
```

```
Leu Gly Asn Ser Ser Leu Ser Val Leu Glu Gly Gln Ser Leu Arg
385                 390                 395                 400

Leu Val Cys Ala Val Asp Ser Asn Pro Pro Ala Arg Leu Ser Trp Thr
            405                 410                 415

Trp Arg Ser Leu Thr Leu Tyr Pro Ser Gln Pro Ser Asn Pro Leu Val
            420                 425                 430

Leu Glu Leu Gln Val His Leu Gly Asp Glu Gly Glu Phe Thr Cys Arg
            435                 440                 445

Ala Gln Asn Ser Leu Gly Ser Gln His Val Ser Leu Asn Leu Ser Leu
            450                 455                 460

Gln His Glu Tyr Thr Gly Lys Met Arg Pro Val Ser Gly Val Leu Leu
465                 470                 475                 480

Gly Ala Val Gly Gly Ala Gly Ala Thr Ala Leu Val Phe Leu Ser Phe
            485                 490                 495

Cys Val Ile Phe Ile Val Val Arg Ser Cys Arg Lys Lys Ser Ala Arg
            500                 505                 510

Pro Ala Ala Asp Val Gly Asp Thr Gly Met Glu Asp Ala Asn Thr Ile
            515                 520                 525

Arg Gly Ser Ala Ser Gln Gly Thr Leu Thr Glu Ser Trp Ala Tyr Asp
530                 535                 540

Asn Pro Arg His His Gly Leu Ala Ala Pro Ser Ser Gly Glu Glu Arg
545                 550                 555                 560

Glu Val Gln Tyr Ala Pro Leu Ser Phe His Lys Gly Glu Pro Gln Asp
            565                 570                 575

Leu Ser Gly Gln Glu Ala Thr Asn Asn Glu Tyr Ser Glu Ile Lys Ile
            580                 585                 590

Pro Lys

<210> SEQ ID NO 3
<211> LENGTH: 490
<212> TYPE: PRT
<213> ORGANISM: Pan paniscus
<220> FEATURE:
<221> NAME/KEY: VARIANT
<222> LOCATION: 465, 469
<223> OTHER INFORMATION: Xaa = Any Amino Acid

<400> SEQUENCE: 3

Met Leu Leu Leu Leu Leu Leu Pro Leu Leu Trp Gly Arg Glu Arg
1               5                   10                  15

Val Glu Gly Gln Lys Ser Asn Arg Lys Asp Tyr Ser Leu Thr Met Gln
            20                  25                  30

Ser Ser Val Thr Val Gln Glu Gly Met Cys Val His Val Arg Cys Ser
            35                  40                  45

Phe Ser Tyr Pro Val Asp Ser Gln Thr Asp Ser Asp Pro Val His Gly
            50                  55                  60

Tyr Trp Phe Arg Ala Glu Asn Asp Ile Ser Trp Lys Ala Pro Val Ala
65                  70                  75                  80

Thr Asn Asn Pro Ala Arg Ala Val Arg Glu Glu Thr Arg Asp Arg Phe
            85                  90                  95

His Leu Leu Gly Asp Pro Gln Thr Lys Asn Cys Thr Leu Ser Ile Arg
            100                 105                 110

Asp Ala Arg Met Ser Asp Ala Gly Arg Tyr Phe Phe Arg Met Glu Lys
            115                 120                 125
```

Gly Asn Ile Lys Trp Asn Tyr Lys Tyr Asp Gln Leu Ser Val Asn Val
            130                 135                 140

Thr Ala Leu Thr His Arg Pro Asn Ile Leu Ile Pro Gly Thr Leu Glu
145                 150                 155                 160

Ser Gly Cys Phe Gln Asn Leu Thr Cys Ser Val Pro Trp Ala Cys Glu
                165                 170                 175

Gln Gly Thr Pro Pro Met Ile Ser Trp Met Gly Thr Ser Val Ser Pro
            180                 185                 190

Leu His Pro Ser Thr Thr Arg Ser Ser Val Leu Thr Leu Ile Pro Gln
        195                 200                 205

Pro Gln His His Gly Thr Ser Leu Thr Cys Gln Val Thr Leu Pro Gly
210                 215                 220

Ala Gly Val Thr Thr Asn Arg Thr Ile Gln Leu Asn Val Ser Tyr Pro
225                 230                 235                 240

Pro Gln Asn Leu Thr Val Thr Val Phe Gln Gly Glu Gly Thr Ala Ser
                245                 250                 255

Thr Ala Leu Gly Asn Ser Ser Leu Ser Val Leu Glu Gly Gln Ser
            260                 265                 270

Leu Arg Leu Val Cys Ala Val Asp Ser Asn Pro Pro Ala Arg Leu Ser
        275                 280                 285

Trp Thr Trp Arg Ser Leu Thr Leu Tyr Pro Ser Gln Pro Ser Asn Pro
290                 295                 300

Leu Val Leu Glu Leu Gln Val His Leu Gly Asp Glu Gly Glu Phe Thr
305                 310                 315                 320

Cys Arg Ala Gln Asn Ser Leu Gly Ser Gln His Val Ser Leu Asn Leu
                325                 330                 335

Ser Leu Gln His Glu Tyr Thr Gly Lys Met Arg Pro Val Ser Gly Val
            340                 345                 350

Leu Leu Gly Ala Val Gly Gly Ala Gly Ala Thr Ala Leu Val Phe Leu
        355                 360                 365

Ser Phe Cys Val Ile Phe Ile Val Val Arg Ser Cys Arg Lys Lys Ser
370                 375                 380

Ala Arg Pro Ala Ala Asp Val Gly Asp Thr Gly Met Glu Asp Ala Asn
385                 390                 395                 400

Thr Ile Arg Gly Ser Ala Ser Gln Gly Thr Leu Thr Glu Ser Trp Ala
                405                 410                 415

Tyr Asp Asn Pro Arg His His Gly Leu Ala Ala Pro Ser Ser Gly Glu
            420                 425                 430

Glu Arg Glu Val Gln Tyr Ala Pro Leu Ser Phe His Lys Gly Glu Pro
        435                 440                 445

Gln Asp Leu Ser Gly Gln Glu Ala Thr Asn Asn Glu Tyr Ser Glu Ile
450                 455                 460

Xaa Ile Pro Lys Xaa Glu Asn Ala Glu Ala Arg Ala Cys Leu Arg Val
465                 470                 475                 480

His Asp Pro Ser Ser Lys Gly Val Arg Gly
                485                 490

<210> SEQ ID NO 4
<211> LENGTH: 599
<212> TYPE: PRT
<213> ORGANISM: Pongo abelii
<220> FEATURE:
<221> NAME/KEY: VARIANT
<222> LOCATION: 179, 257, 337, 378
<223> OTHER INFORMATION: Xaa = Any Amino Acid

<400> SEQUENCE: 4

| | | | | | | | | | | | | | | |
|---|---|---|---|---|---|---|---|---|---|---|---|---|---|---|
Met Leu Leu Leu Leu Leu Phe Leu Pro Leu Leu Trp Gly Arg Glu
1               5                   10                  15

Arg Val Glu Gly Gln Lys Asn Asn Arg Lys Asp Tyr Ser Leu Met Met
            20                  25                  30

Gln Ser Ser Val Thr Val Gln Glu Gly Leu Cys Val His Val Gln Cys
        35                  40                  45

Ser Phe Ser Tyr Pro Val Asp Ser Gln Thr Asp Ser Asp Pro Val His
    50                  55                  60

Gly Tyr Trp Phe Arg Ala Gly Asp Asp Ile Ser Trp Lys Ala Pro Val
65                  70                  75                  80

Ala Thr Asn Asn Pro Ala Gln Ala Val Arg Glu Glu Thr Arg Asp Arg
                85                  90                  95

Phe His Leu Leu Gly Asp Pro Gln Thr Lys Asn Cys Thr Leu Ser Ile
            100                 105                 110

Arg Asp Ala Arg Met Ser Asp Ala Gly Arg Tyr Phe Phe Arg Met Glu
        115                 120                 125

Arg Gly Asn Ile Lys Trp Asn Tyr Lys Tyr Asp Arg Leu Ser Val Asn
    130                 135                 140

Val Thr Ala Ser Gln Ala Pro Pro Ser Arg Tyr Arg Leu Glu Val Pro
145                 150                 155                 160

Glu Ser Val Thr Val Gln Glu Gly Leu Cys Val Ser Val Pro Cys Ser
                165                 170                 175

Val Leu Xaa Pro Tyr Tyr Asn Trp Thr Asp Ser Ser Pro Val His Gly
            180                 185                 190

Cys Trp Phe Lys Lys Gly Ile Asn Ile Gln Trp Asn Asn Pro Val Ala
        195                 200                 205

Thr Asn Ile Pro Asn Gly Lys Val Glu Glu Thr Arg Gly Arg Phe His
    210                 215                 220

Leu Leu Gly Asp Leu Lys Thr Asn Asn Cys Ser Leu Ser Ile Arg Asp
225                 230                 235                 240

Ala Arg Lys Gly Asp Leu Gly Asn Tyr Tyr Phe Gln Val Glu Arg Gly
                245                 250                 255

Xaa Ile Arg Trp Asn Tyr Lys Met Lys Gln Leu Ser Val Asn Val Thr
            260                 265                 270

Ala Leu Thr His Arg Pro Asn Ile Leu Ile Pro Gly Thr Leu Glu Ser
        275                 280                 285

Gly Cys Phe Gln Asn Leu Thr Cys Ser Val Pro Trp Ala Cys Glu Gln
    290                 295                 300

Gly Thr Pro Pro Met Ile Ser Trp Met Gly Thr Ser Val Ser Thr His
305                 310                 315                 320

Leu His Pro Ser Thr Thr Arg Ser Ser Val Leu Thr Leu Ile Pro Gln
                325                 330                 335

Xaa Glu Asp His Gly Thr Asn Phe Thr Leu Gln Tyr Val Leu Thr Pro
            340                 345                 350

Ala Tyr Val Thr Val Cys Ser Ile Pro Gln Ser His Ser Val Ser Phe
        355                 360                 365

Leu Pro Val Ser Ile Thr Leu Ser Leu Xaa Pro Phe Asn Phe Phe Ser
    370                 375                 380

Thr Ala Ser Thr Ala Leu Gly Asn Ser Ser Ser Leu Ser Val Leu Glu
385                 390                 395                 400

```
Gly Gln Ser Leu Arg Leu Val Cys Ala Val Asp Ser Asn Pro Pro Ala
                405                 410                 415

Arg Leu Ser Trp Thr Trp Arg Ser Leu Thr Leu Tyr Pro Ser Gln Pro
            420                 425                 430

Ser Asn Pro Leu Val Leu Glu Leu Arg Val His Leu Gly Asp Glu Gly
        435                 440                 445

Glu Cys Ile Cys Arg Ala Gln Asn Ser Leu Gly Ser Gln His Val Ser
    450                 455                 460

Leu Asn Leu Ser Leu Gln His Glu Tyr Thr Gly Lys Met Arg Pro Val
465                 470                 475                 480

Ser Gly Val Met Leu Gly Ala Val Gly Gly Ala Gly Ala Thr Ala Leu
                485                 490                 495

Val Phe Leu Ser Phe Cys Val Ile Phe Ile Val Val Arg Ser Cys Arg
            500                 505                 510

Lys Lys Ser Ala Arg Pro Ala Ala Asp Val Gly Asp Thr Gly Met Glu
        515                 520                 525

Asp Ala Asn Thr Val Arg Gly Ser Ala Ser Gln Gly Thr Leu Ile Glu
    530                 535                 540

Ser Trp Ala Asp Asp Asn Pro Arg His Leu Gly Leu Ala Ala Pro Ser
545                 550                 555                 560

Ser Gly Glu Glu Arg Glu Ile Gln Tyr Ala Ser Leu Ser Phe His Lys
                565                 570                 575

Gly Glu Pro Gln Asp Leu Ser Arg Gln Glu Ala Thr Asn Asn Glu Tyr
            580                 585                 590

Ser Glu Ile Lys Ile Pro Lys
        595

<210> SEQ ID NO 5
<211> LENGTH: 468
<212> TYPE: PRT
<213> ORGANISM: Gorilla gorilla gorilla

<400> SEQUENCE: 5

Met Leu Leu Leu Leu Leu Leu Pro Leu Leu Trp Gly Arg Glu Arg
1               5                   10                  15

Val Glu Gly Gln Lys Ser Lys Arg Lys Asp Tyr Ser Leu Thr Met Gln
                20                  25                  30

Ser Ser Val Thr Val Gln Glu Gly Met Cys Val His Val Arg Cys Ser
            35                  40                  45

Phe Ser Tyr Pro Val Asp Ser Gln Thr Asp Ser Asp Pro Val His Gly
        50                  55                  60

Tyr Trp Phe Arg Ala Glu Asn Asp Ile Ser Trp Lys Ala Pro Val Ala
65                  70                  75                  80

Thr Asn Asp Pro Ala Arg Ala Val Arg Glu Glu Thr Arg Asp Arg Phe
                85                  90                  95

His Leu Leu Gly Asp Pro Gln Thr Lys Asn Cys Thr Leu Ser Ile Arg
            100                 105                 110

Asp Ala Arg Met Ser Asp Ala Gly Arg Tyr Phe Phe Arg Met Glu Lys
        115                 120                 125

Gly Asn Ile Lys Trp Asn Tyr Lys Tyr Asp Gln Leu Ser Val Asn Val
    130                 135                 140

Thr Ala Leu Thr His Arg Pro Asn Ile Leu Ile Pro Ser Thr Leu Glu
145                 150                 155                 160
```

Ser Gly Cys Phe Gln Asn Leu Thr Cys Ser Val Pro Trp Ala Cys Glu
            165                 170                 175

Gln Gly Thr Pro Pro Met Ile Ser Trp Met Gly Thr Ser Val Ser Pro
        180                 185                 190

Leu His Pro Ser Thr Thr Arg Ser Ser Val Leu Thr Leu Ile Pro Gln
    195                 200                 205

Pro Gln His His Gly Thr Ser Leu Thr Cys Gln Val Thr Leu Pro Gly
210                 215                 220

Ala Gly Val Thr Thr Asn Arg Thr Ile Gln Leu Asn Val Ser Tyr Pro
225                 230                 235                 240

Pro Gln Asn Leu Thr Val Thr Ile Phe Gln Gly Glu Gly Thr Ala Ser
            245                 250                 255

Thr Ala Leu Gly Asn Ser Ser Ser Leu Ser Val Leu Glu Gly Gln Ser
        260                 265                 270

Leu Arg Leu Val Cys Ala Val Asp Ser Asn Pro Pro Ala Arg Leu Ser
    275                 280                 285

Trp Thr Trp Arg Ser Leu Thr Leu Tyr Pro Ser Gln Pro Ser Asn Pro
290                 295                 300

Leu Val Leu Glu Leu Gln Val His Leu Gly Asp Glu Gly Glu Phe Thr
305                 310                 315                 320

Cys Arg Ala Gln Asn Ser Leu Gly Ser Gln His Val Ser Leu Asn Leu
            325                 330                 335

Ser Leu Gln His Glu Tyr Thr Gly Lys Met Arg Pro Val Ser Gly Val
        340                 345                 350

Leu Leu Gly Ala Val Gly Gly Ala Gly Ala Thr Ala Leu Val Phe Leu
    355                 360                 365

Ser Phe Cys Val Ile Phe Ile Val Val Arg Ser Cys Arg Lys Lys Ser
370                 375                 380

Ala Arg Pro Ala Ala Asp Val Gly Asp Thr Gly Met Glu Asp Ala Asn
385                 390                 395                 400

Thr Ile Arg Gly Ser Ala Ser Gln Gly Thr Leu Thr Glu Ser Trp Ala
            405                 410                 415

Asp Asp Asn Pro Arg His Tyr Gly Leu Ala Ala Pro Ser Ser Gly Glu
        420                 425                 430

Glu Arg Glu Val Gln Tyr Ala Pro Leu Ser Phe His Lys Gly Glu Pro
    435                 440                 445

Gln Asp Leu Ser Gly Gln Glu Ala Thr Asn Asn Glu Tyr Ser Glu Ile
450                 455                 460

Lys Ile Pro Lys
465

<210> SEQ ID NO 6
<211> LENGTH: 468
<212> TYPE: PRT
<213> ORGANISM: Nomascus leucogenys

<400> SEQUENCE: 6

Met Leu Leu Leu Leu Leu Leu Leu Pro Leu Trp Gly Arg Glu Arg
1               5                   10                  15

Val Glu Gly Gln Lys Ser Asn Gln Lys Asn Tyr Pro Leu Met Met Gln
            20                  25                  30

Ser Ser Val Thr Val Gln Glu Gly Leu Cys Val His Val Arg Cys Ser
        35                  40                  45

```
Phe Ser Tyr Pro Val Asp Ser Gln Thr Asp Ser Asp Pro Val His Gly
 50                  55                  60

Tyr Trp Phe Arg Ala Gly Asp Asp Ile Ser Trp Lys Thr Pro Val Ala
 65                  70                  75                  80

Thr Asn Asn Arg Ala Arg Ala Val Arg Glu Glu Thr Arg Asp Arg Phe
                 85                  90                  95

His Leu Leu Gly Asp Pro Gln Thr Lys Asn Cys Thr Leu Ser Ile Arg
                100                 105                 110

Asp Ala Arg Met Ser Asp Ala Gly Thr Tyr Phe Tyr Arg Met Glu Arg
            115                 120                 125

Gly Lys Ile Lys Trp Asn Tyr Lys Tyr His Gln Leu Ser Val His Val
            130                 135                 140

Thr Ala Leu Thr His Arg Pro Asn Ile Val Ile Pro Gly Thr Leu Glu
145                 150                 155                 160

Ser Gly Cys Phe Gln Asn Leu Thr Cys Ser Val Pro Trp Ala Cys Glu
                165                 170                 175

Gln Gly Thr Pro Pro Met Ile Ser Trp Met Gly Thr Ser Leu Ser Pro
                180                 185                 190

Leu His Pro Ser Thr Arg Ser Ser Val Leu Thr Leu Ile Pro Gln
                195                 200                 205

Pro Gln Asp His Gly Thr Ser Leu Thr Cys Gln Val Thr Leu Pro Gly
210                 215                 220

Ala Gly Val Thr Thr Asn Arg Thr Ile Arg Leu Asn Val Ser Tyr Pro
225                 230                 235                 240

Pro Gln Asn Leu Thr Val Thr Val Phe Gln Gly Glu Gly Thr Ala Ser
                245                 250                 255

Thr Ala Leu Gly Asn Ser Ser Ser Leu Ser Val Leu Glu Gly Gln Ser
                260                 265                 270

Leu Arg Leu Val Cys Ala Val Asp Ser Asn Pro Pro Ala Arg Leu Ser
            275                 280                 285

Trp Thr Trp Arg Ser Leu Thr Leu Tyr Pro Ser Gln Pro Ser Asn Pro
            290                 295                 300

Leu Val Leu Glu Leu Arg Val His Leu Gly Asp Glu Gly Glu Phe Thr
305                 310                 315                 320

Cys Arg Ala Arg Asn Ser Leu Gly Ser Gln His Phe Ser Leu Asn Leu
                325                 330                 335

Ser Leu Gln His Glu Tyr Thr Gly Lys Met Arg Pro Val Ser Gly Val
                340                 345                 350

Thr Leu Gly Ala Val Gly Gly Ala Gly Ala Thr Ala Leu Val Phe Leu
            355                 360                 365

Ser Phe Cys Val Ile Phe Ile Val Val Arg Ser Tyr Arg Lys Lys Ser
            370                 375                 380

Ala Arg Pro Ala Ala Gly Val Gly Asp Thr Gly Met Glu Asp Ala Asn
385                 390                 395                 400

Ala Ile Arg Gly Ser Ala Ser Gln Gly Thr Met Ile Glu Ser Trp Ala
                405                 410                 415

Asp Asp Asn Pro Arg His His Gly Leu Ala Ala Pro Ser Ser Gly Glu
                420                 425                 430

Glu Gly Glu Ile Gln Tyr Ala Ser Val Ser Phe His Lys Val Glu Pro
            435                 440                 445

Gln Asp Leu Ser Gly Gln Glu Ala Thr Asn Asn Glu Tyr Ser Glu Ile
            450                 455                 460
```

Lys Ile Pro Lys
465

<210> SEQ ID NO 7
<211> LENGTH: 16
<212> TYPE: PRT
<213> ORGANISM: Artificial Sequence
<220> FEATURE:
<223> OTHER INFORMATION: Synthetic Construct

<400> SEQUENCE: 7

Arg Ser Ser Gln Ser Leu Val His Ser Thr Gly Asn Thr Tyr Leu His
1               5                   10                  15

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Arg Ala Ser Gln Ser Ile Ser Asp Tyr Leu His
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Ser Ala Asn Ser Ser Phe Ile Tyr Met Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Construct

<400> SEQUENCE: 10

Lys Ala Ser Asp His Ile Asn Asn Trp Leu Ala
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Synthetic Construct

<400> SEQUENCE: 11

Arg Ser Ser Gln Ser Leu Val His Ser Thr Gly Asn Thr Tyr Leu His
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic Construct

```
<400> SEQUENCE: 12

Arg Ser Ser Gln Ser Leu Val His Ser Thr Gly Asn Ile Tyr Leu His
1               5                   10                  15

<210> SEQ ID NO 13
<211> LENGTH: 11
<212> TYPE: PRT
<213> ORGANISM: Artificial Sequence
<220> FEATURE:
<223> OTHER INFORMATION: Synthetic Construct

<400> SEQUENCE: 13

Lys Ala Ser Gln Lys Val Gly Thr Asn Val Ala
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct

<400> SEQUENCE: 14

Ser Ala Asn Ser Ser Phe Thr Tyr Met Tyr
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct

<400> SEQUENCE: 15

Arg Ala Ser Gln Ser Ile Ser Glu Tyr Leu His
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic Construct

<400> SEQUENCE: 16

Leu Ala Ser Gln Thr Ile Gly Thr Trp Leu Ala
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Synthetic Construct

<400> SEQUENCE: 17

Arg Ser Ser Gln Ser Leu Val His Ser Thr Gly Asn Thr Tyr Leu His
1               5                   10                  15

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct
```

-continued

```
<400> SEQUENCE: 18

Arg Ala Ser Gln Asp Ile Ser Glx Tyr Leu Asn
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

Arg Ala Ser Gln Ser Ile Arg Glu Tyr Leu His
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Synthetic Construct

<400> SEQUENCE: 20

Lys Val Ser Asn Arg Phe Ser
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Tyr Ala Ser Gln Ser Ile Ser
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic Construct

<400> SEQUENCE: 22

Asp Thr Ser Asn Leu Ala Ser
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

Gly Ala Thr Ser Leu Glu Thr
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 24

Lys Val Ser Asn Arg Phe Cys
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Lys Val Ser Asn Arg Phe Glx
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic Construct

<400> SEQUENCE: 26

Ser Ala Ser Thr Arg His Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic Construct

<400> SEQUENCE: 27

Asp Thr Ser Asn Leu Ala Ser
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic Construct

<400> SEQUENCE: 28

Phe Ala Ser Gln Ser Ile Cys
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Construct

<400> SEQUENCE: 29

Ala Ala Thr Ser Leu Ala Asp
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 30

Lys Val Ser Asn Arg Phe Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic Construct

<400> SEQUENCE: 31

Leu Ser Ser Arg Leu His Ser
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic Construct

<400> SEQUENCE: 32

Phe Ala Ser Gln Ser Ile Cys
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

<400> SEQUENCE: 33

Ser Gln Asn Thr His Val Pro Tyr Thr
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Construct

<400> SEQUENCE: 34

Gln Lys Gly Leu Asn Phe Pro Leu Thr
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct

<400> SEQUENCE: 35

Gln Gln Trp Ser Ser Ser Pro Leu Thr
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Construct
```

<400> SEQUENCE: 36

His Gln Tyr Trp Asn Thr Pro Tyr Thr
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Construct

<400> SEQUENCE: 37

Ser Gln Asn Thr His Val Pro Tyr Thr
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Ser Gln Asn Thr His Val Pro Tyr Thr
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct

<400> SEQUENCE: 39

His Gln Gly Asn Ser Val Gln Tyr Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Construct

<400> SEQUENCE: 40

Gln Gln Trp Ser Ser Ser Pro Leu Thr
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Construct

<400> SEQUENCE: 41

Gln Asn Gly His Asn Phe Pro Tyr Thr
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 42

Gln Gln Leu Tyr Ser Thr Pro Tyr Thr
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Construct

<400> SEQUENCE: 43

Ser Gln Asn Thr His Val Pro Tyr Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44

Gln Gln Gly His Thr Gly Ala Trp Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

<400> SEQUENCE: 45

Gln Lys Ala His Asn Phe Pro Tyr Thr
1               5

<210> SEQ ID NO 46
<211> LENGTH: 10
<212> TYPE: PRT
<213> ORGANISM: Artificial Sequence
<220> FEATURE:
<223> OTHER INFORMATION: Synthetic Construct

<400> SEQUENCE: 46

Ser Glu Val Phe Pro Ile Thr Tyr Met Asn
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Synthetic Construct

<400> SEQUENCE: 47

Phe Asn Ile Lys Gly Ser Leu Leu His
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Construct
```

<400> SEQUENCE: 48

Phe Thr Phe Ser Asn Tyr Asp Met Ser
1               5

<210> SEQ ID NO 49
<211> LENGTH: 10
<212> TYPE: PRT
<213> ORGANISM: Artificial Sequence
<220> FEATURE:
<223> OTHER INFORMATION: Synthetic Construct

<400> SEQUENCE: 49

Ser Glu Val Phe Pro Ile Thr Tyr Met Asn
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Synthetic Construct

<400> SEQUENCE: 50

Tyr Ile Phe Thr Asp Tyr Gly Ile Thr
1               5

<210> SEQ ID NO 51
<211> LENGTH: 10
<212> TYPE: PRT
<213> ORGANISM: Artificial Sequence
<220> FEATURE:
<223> OTHER INFORMATION: Synthetic Construct

<400> SEQUENCE: 51

Ser Glu Val Phe Pro Ile Thr Tyr Met Asn
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Synthetic Construct

<400> SEQUENCE: 52

Tyr Thr Phe Thr Asn Tyr Trp Ile Asn
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic Construct

<400> SEQUENCE: 53

Phe Ile Phe Ser Asn Tyr Asp Met Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 54

Phe Thr Phe Ser Asn Tyr Ala Met Ser
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Construct

<400> SEQUENCE: 55

Phe Ser Leu Ser Asn Tyr Gly Val His
1               5

<210> SEQ ID NO 56
<211> LENGTH: 10
<212> TYPE: PRT
<213> ORGANISM: Artificial Sequence
<220> FEATURE:
<223> OTHER INFORMATION: Synthetic Construct

<400> SEQUENCE: 56

Ser Glu Val Phe Pro Ile Thr Tyr Met Asn
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Synthetic Construct

<400> SEQUENCE: 57

Tyr Ala Phe Thr Asn Cys Trp Met Asn
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Construct

<400> SEQUENCE: 58

Phe Thr Phe Ser Thr Tyr Ala Met Phe
1               5

<210> SEQ ID NO 59
<211> LENGTH: 14
<212> TYPE: PRT
<213> ORGANISM: Artificial Sequence
<220> FEATURE:
<223> OTHER INFORMATION: Synthetic Construct

<400> SEQUENCE: 59

Ile Gly Asp Ile Leu Pro Ser Ile Gly Arg Thr Met Tyr Gly
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Synthetic Construct
```

<400> SEQUENCE: 60

Ile Gly Trp Ile Asp Pro Glu Asp Gly Glu Thr Arg Phe Asp
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Synthetic Construct

<400> SEQUENCE: 61

Val Ala Thr Ile Ser Ser Gly Gly Asp Tyr Thr Tyr Tyr Pro
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Synthetic Construct

<400> SEQUENCE: 62

Ile Gly Asp Ile Leu Pro Ser Ile Gly Arg Thr Met Tyr Gly
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Synthetic Construct

<400> SEQUENCE: 63

Ile Gly Glu Ile Ser Pro Arg Ser Gly Glu Thr Tyr Phe Asn
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Synthetic Construct

<400> SEQUENCE: 64

Ile Gly Asp Ile Leu Pro Ser Ile Gly Arg Thr Met Tyr Gly
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Synthetic Construct

<400> SEQUENCE: 65

Ile Gly Asn Ile Tyr Ser Gly Ser Ser Arg Thr Asn Tyr Asn
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Synthetic Construct

```
<400> SEQUENCE: 66

Val Ala Thr Ile Ser Ser Gly Gly Gly Tyr Thr Tyr Tyr Pro
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Synthetic Construct

<400> SEQUENCE: 67

Val Ala Ser Ile Ser Ser Gly Gly Ser Tyr Asn Tyr Tyr Pro
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Synthetic Construct

<400> SEQUENCE: 68

Leu Gly Val Ile Trp Ala Gly Gly Ile Thr Asn Tyr Asn
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Synthetic Construct

<400> SEQUENCE: 69

Ile Gly Asp Ile Leu Pro Ser Ile Gly Arg Thr Met Tyr Gly
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Synthetic Construct

<400> SEQUENCE: 70

Ile Gly Arg Ile Phe Pro Gly Asn Gly His Thr Asn Tyr Ser
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Synthetic Construct

<400> SEQUENCE: 71

Val Ala Ser Ile Ser Ser Gly Gly Arg Tyr Thr Tyr Tyr Pro
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic Construct
```

<400> SEQUENCE: 72

Ala Arg Ser Glu Gly Tyr Leu Leu Ala Tyr
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Synthetic Construct

<400> SEQUENCE: 73

Ala Arg Thr Glu Tyr Ser Asn Pro Ala Trp Phe Ala Tyr
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Synthetic Construct

<400> SEQUENCE: 74

Ala Arg His Gly Tyr Gly Asn Tyr Asp Trp Tyr Phe Asp Val
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic Construct

<400> SEQUENCE: 75

Ala Arg Ser Glu Gly Tyr Leu Leu Ala Tyr
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Synthetic Construct

<400> SEQUENCE: 76

Ala Arg Glu Gly Asn Pro Phe Thr Tyr
1               5

<210> SEQ ID NO 77
<211> LENGTH: 10
<212> TYPE: PRT
<213> ORGANISM: Artificial Sequence
<220> FEATURE:
<223> OTHER INFORMATION: Synthetic Construct

<400> SEQUENCE: 77

Ala Arg Ser Glu Gly Tyr Leu Leu Ala Tyr
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Synthetic Construct

```
<400> SEQUENCE: 78

Ala Arg Glu Gly Leu Arg Ala Met Asp Tyr
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Synthetic Construct

<400> SEQUENCE: 79

Thr Arg His Gly Tyr Gly Asn Tyr Asp Trp Tyr Phe Asp Val
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Synthetic Construct

<400> SEQUENCE: 80

Ala Ser Gln Ser Tyr Gly Ser Ser Tyr Trp Tyr Phe Asp Val
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Synthetic Construct

<400> SEQUENCE: 81

Ala Lys Gln Gly Gly Thr Ser Phe Ser Tyr
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic Construct

<400> SEQUENCE: 82

Ala Arg Ser Glu Gly Tyr Leu Leu Ala Tyr
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Synthetic Construct

<400> SEQUENCE: 83

Ala Arg Asp Tyr Ser Asp Tyr Tyr Phe Asp Tyr
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Synthetic Construct
```

<400> SEQUENCE: 84

Val Arg His Ser Tyr Gly Ser Ser Tyr Trp Tyr Leu Asp Val
1               5                   10

<210> SEQ ID NO 85
<211> LENGTH: 23
<212> TYPE: PRT
<213> ORGANISM: Artificial Sequence
<220> FEATURE:
<223> OTHER INFORMATION: Synthetic Construct

<400> SEQUENCE: 85

Asp Val Glx Met Thr Gln Thr Pro Leu Ser Leu Pro Val Ser Leu Gly
1               5                   10                  15

Asp Gln Ala Ser Ile Ser Cys
            20

<210> SEQ ID NO 86
<211> LENGTH: 23
<212> TYPE: PRT
<213> ORGANISM: Artificial Sequence
<220> FEATURE:
<223> OTHER INFORMATION: Synthetic Construct

<400> SEQUENCE: 86

Asp Ile Gln Met Thr Gln Phe Pro Ala Thr Leu Ser Val Thr Pro Gly
1               5                   10                  15

Asp Arg Val Ser Leu Ser Cys
            20

<210> SEQ ID NO 87
<211> LENGTH: 21
<212> TYPE: PRT
<213> ORGANISM: Artificial Sequence
<220> FEATURE:
<223> OTHER INFORMATION: Synthetic Construct

<400> SEQUENCE: 87

Val Leu Thr Gln Ser Pro Ala Ile Met Ser Ala Ser Pro Gly Glu Lys
1               5                   10                  15

Val Thr Met Thr Cys
            20

<210> SEQ ID NO 88
<211> LENGTH: 23
<212> TYPE: PRT
<213> ORGANISM: Artificial Sequence
<220> FEATURE:
<223> OTHER INFORMATION: Synthetic Construct

<400> SEQUENCE: 88

Asp Ile Gln Met Thr Gln Ser Leu Ser Tyr Leu Ser Val Ser Leu Gly
1               5                   10                  15

Gly Arg Val Thr Ile Thr Cys
            20

<210> SEQ ID NO 89
<211> LENGTH: 23
<212> TYPE: PRT
<213> ORGANISM: Artificial Sequence
<220> FEATURE:
<223> OTHER INFORMATION: Synthetic Construct

<400> SEQUENCE: 89

Asp Val Glx Met Thr Gln Thr Pro Leu Ser Leu Pro Val Ser Leu Gly
1               5                   10                  15

Asp Gln Ala Ser Ile Ser Cys
            20

<210> SEQ ID NO 90
<211> LENGTH: 23
<212> TYPE: PRT
<213> ORGANISM: Artificial Sequence
<220> FEATURE:
<223> OTHER INFORMATION: Synthetic Construct

<400> SEQUENCE: 90

Asp Val Val Met Thr Gln Thr Pro Leu Ser Leu Pro Val Ser Leu Gly
1               5                   10                  15

Asp Gln Ala Ser Ile Ser Cys
            20

<210> SEQ ID NO 91
<211> LENGTH: 22
<212> TYPE: PRT
<213> ORGANISM: Artificial Sequence
<220> FEATURE:
<223> OTHER INFORMATION: Synthetic Construct

<400> SEQUENCE: 91

Asn Glx Met Thr Gln Phe Gln Lys Phe Met Ser Thr Ser Val Gly Asp
1               5                   10                  15

Arg Val Ser Leu Thr Cys
            20

<210> SEQ ID NO 92
<211> LENGTH: 25
<212> TYPE: PRT
<213> ORGANISM: Artificial Sequence
<220> FEATURE:
<223> OTHER INFORMATION: Synthetic Construct

<400> SEQUENCE: 92

Gly Glx Gln Asn Val Leu Thr Gln Ser Pro Ala Ile Leu Ser Ala Ser
1               5                   10                  15

Pro Gly Glu Lys Val Thr Met Thr Cys
            20                  25

<210> SEQ ID NO 93
<211> LENGTH: 23
<212> TYPE: PRT
<213> ORGANISM: Artificial Sequence
<220> FEATURE:
<223> OTHER INFORMATION: Synthetic Construct

<400> SEQUENCE: 93

Asp Ile Gln Met Thr Gln Glx Pro Ala Thr Leu Ser Val Thr Pro Gly
1               5                   10                  15

Asp Arg Val Ser Leu Ser Cys
            20

<210> SEQ ID NO 94
<211> LENGTH: 23
<212> TYPE: PRT
<213> ORGANISM: Artificial Sequence
<220> FEATURE:

```
<223> OTHER INFORMATION: Synthetic Construct

<400> SEQUENCE: 94

Asp Ile Gln Met Thr Gln Ser Pro Ala Ser Gln Ser Ala Ser Leu Gly
1               5                   10                  15

Glu Ser Val Thr Ile Thr Cys
            20

<210> SEQ ID NO 95
<211> LENGTH: 23
<212> TYPE: PRT
<213> ORGANISM: Artificial Sequence
<220> FEATURE:
<223> OTHER INFORMATION: Synthetic Construct

<400> SEQUENCE: 95

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 96
<211> LENGTH: 21
<212> TYPE: PRT
<213> ORGANISM: Artificial Sequence
<220> FEATURE:
<223> OTHER INFORMATION: Synthetic Construct

<400> SEQUENCE: 96

Glx Met Thr Gln Phe Thr Ser Ser Met Ser Gly Ser Glu Gly Asp Arg
1               5                   10                  15

Val Thr Ile Ser His
            20

<210> SEQ ID NO 97
<211> LENGTH: 23
<212> TYPE: PRT
<213> ORGANISM: Artificial Sequence
<220> FEATURE:
<223> OTHER INFORMATION: Synthetic Construct

<400> SEQUENCE: 97

Asp Ile Gln Met Thr Gln Phe Pro Ala Thr Leu Ser Gly Thr Pro Gly
1               5                   10                  15

Asp Arg Val Glx Leu Ser Arg
            20

<210> SEQ ID NO 98
<211> LENGTH: 15
<212> TYPE: PRT
<213> ORGANISM: Artificial Sequence
<220> FEATURE:
<223> OTHER INFORMATION: Synthetic Construct

<400> SEQUENCE: 98

Trp Tyr Leu Gln Lys Pro Gly Gln Ser Pro Lys Leu Leu Ile Tyr
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Synthetic Construct
```

-continued

```
<400> SEQUENCE: 99

Trp Tyr Gln His Lys Ser His Glu Ser Pro Arg Leu Leu Ile Lys
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Synthetic Construct

<400> SEQUENCE: 100

Trp Tyr Gln Gln Lys Pro Gly Ser Ser Pro Arg Leu Leu Ile Phe
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Synthetic Construct

<400> SEQUENCE: 101

Trp Tyr Gln Gln Lys Pro Gly Asn Ala Pro Arg Leu Leu Ile Ser
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Synthetic Construct

<400> SEQUENCE: 102

Trp Tyr Leu Gln Lys Pro Gly Gln Ser Pro Lys Leu Leu Ile Tyr
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Synthetic Construct

<400> SEQUENCE: 103

Trp Tyr Leu Gln Lys Pro Gly Gln Ser Pro Lys Leu Leu Ile Tyr
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Synthetic Construct

<400> SEQUENCE: 104

Gly Phe Gln Gln Lys Pro Gly His Ser Pro Lys Ala Gly Ile Tyr
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Synthetic Construct
```

```
<400> SEQUENCE: 105

Trp Tyr Gln Gln Lys Pro Gly Ser Ser Pro Arg Leu Leu Ile Phe
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Synthetic Construct

<400> SEQUENCE: 106

Trp Tyr His Gln Lys Ser His Glu Ser Pro Arg Leu Leu Ile Lys
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Synthetic Construct

<400> SEQUENCE: 107

Trp Tyr Gln Gln Lys Pro Gly Lys Ser Pro Gln Leu Leu Ile Tyr
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Synthetic Construct

<400> SEQUENCE: 108

Trp Tyr Leu Gln Lys Pro Gly Gln Ser Pro Lys Leu Leu Ile Tyr
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Synthetic Construct

<400> SEQUENCE: 109

Trp Tyr Glu Gln Lys Ala Asp Gly Thr Ala Asn Leu Ile Ile Tyr
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Synthetic Construct

<400> SEQUENCE: 110

Trp Tyr Gln Gln Lys Ser His Glu Ser Pro Arg Leu Glx Ile Lys
1               5                   10                  15

<210> SEQ ID NO 111
<211> LENGTH: 32
<212> TYPE: PRT
<213> ORGANISM: Artificial Sequence
<220> FEATURE:
<223> OTHER INFORMATION: Synthetic Construct
```

-continued

<400> SEQUENCE: 111

Gly Val Pro Asp Arg Phe Ser Gly Ser Gly Ala Gly Thr Asp Phe Thr
1               5                   10                  15

Leu Lys Ile Ser Arg Val Glu Ala Glu Asp Leu Gly Val Tyr Phe Cys
            20                  25                  30

<210> SEQ ID NO 112
<211> LENGTH: 32
<212> TYPE: PRT
<213> ORGANISM: Artificial Sequence
<220> FEATURE:
<223> OTHER INFORMATION: Synthetic Construct

<400> SEQUENCE: 112

Gly Ile Pro Ser Arg Phe Ser Gly Ser Gly Ser Gly Trp Asp Phe Thr
1               5                   10                  15

Leu Ser Ile Asn Ser Val Glu Pro Glu Asp Val Gly Ile Tyr Tyr Cys
            20                  25                  30

<210> SEQ ID NO 113
<211> LENGTH: 32
<212> TYPE: PRT
<213> ORGANISM: Artificial Sequence
<220> FEATURE:
<223> OTHER INFORMATION: Synthetic Construct

<400> SEQUENCE: 113

Gly Val Pro Ile Arg Phe Ser Gly Ser Gly Ser Gly Thr Ser Tyr Ser
1               5                   10                  15

Leu Thr Ile Ser Arg Met Glu Ala Glu Asp Thr Ala Thr Tyr Tyr Cys
            20                  25                  30

<210> SEQ ID NO 114
<211> LENGTH: 32
<212> TYPE: PRT
<213> ORGANISM: Artificial Sequence
<220> FEATURE:
<223> OTHER INFORMATION: Synthetic Construct

<400> SEQUENCE: 114

Gly Phe Pro Ser Arg Phe Ser Gly Ser Gly Ser Gly Lys Asp Tyr Thr
1               5                   10                  15

Leu Ser Ile Thr Ser Leu Gln Thr Glu Asp Val Ala Thr Tyr Tyr Cys
            20                  25                  30

<210> SEQ ID NO 115
<211> LENGTH: 32
<212> TYPE: PRT
<213> ORGANISM: Artificial Sequence
<220> FEATURE:
<223> OTHER INFORMATION: Synthetic Construct

<400> SEQUENCE: 115

Gly Val Pro Asp Arg Phe Ser Gly Ser Gly Ala Gly Thr Asp Phe Thr
1               5                   10                  15

Leu Lys Ile Ser Arg Val Glu Ala Glu Asp Leu Gly Val Tyr Phe Cys
            20                  25                  30

<210> SEQ ID NO 116
<211> LENGTH: 32
<212> TYPE: PRT
<213> ORGANISM: Artificial Sequence
<220> FEATURE:
<223> OTHER INFORMATION: Synthetic Construct

<400> SEQUENCE: 116

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Phe Cys
            20                  25                  30

<210> SEQ ID NO 117
<211> LENGTH: 32
<212> TYPE: PRT
<213> ORGANISM: Artificial Sequence
<220> FEATURE:
<223> OTHER INFORMATION: Synthetic Construct

<400> SEQUENCE: 117

Gly Val Gln Asp Arg Phe Thr Ala Arg Gly Leu Gly Ser Asp Phe Ile
1               5                   10                  15

Leu Pro Ile Thr Thr Glx Gln Leu Glu Asp Leu Ala Glu Tyr Glx Cys
            20                  25                  30

<210> SEQ ID NO 118
<211> LENGTH: 32
<212> TYPE: PRT
<213> ORGANISM: Artificial Sequence
<220> FEATURE:
<223> OTHER INFORMATION: Synthetic Construct

<400> SEQUENCE: 118

Gly Val Pro Ile Arg Phe Ser Gly Ser Gly Ser Gly Thr Ser Tyr Ser
1               5                   10                  15

Leu Thr Ile Ser Arg Met Glu Ala Glu Asp Thr Ala Thr Tyr Tyr Cys
            20                  25                  30

<210> SEQ ID NO 119
<211> LENGTH: 32
<212> TYPE: PRT
<213> ORGANISM: Artificial Sequence
<220> FEATURE:
<223> OTHER INFORMATION: Synthetic Construct

<400> SEQUENCE: 119

Gly Ile Pro Ser Arg Phe Ser Gly Ser Gly Ser Gly Ser Asp Phe Thr
1               5                   10                  15

Leu Thr Ile Asn Ser Val Glu Pro Glu Asp Val Gly Val Tyr Tyr Cys
            20                  25                  30

<210> SEQ ID NO 120
<211> LENGTH: 32
<212> TYPE: PRT
<213> ORGANISM: Artificial Sequence
<220> FEATURE:
<223> OTHER INFORMATION: Synthetic Construct

<400> SEQUENCE: 120

Gly Val Pro Ser Arg Phe Ser Gly Ser Gly Ser Gly Thr Lys Phe Ser
1               5                   10                  15

Phe Lys Ile Ser Ser Leu Gln Ala Glu Asp Phe Val Ser Tyr Tyr Cys
            20                  25                  30

<210> SEQ ID NO 121
<211> LENGTH: 32
<212> TYPE: PRT
<213> ORGANISM: Artificial Sequence
<220> FEATURE:

```
<223> OTHER INFORMATION: Synthetic Construct

<400> SEQUENCE: 121

Gly Val Pro Asp Arg Phe Ser Gly Ser Gly Ala Gly Thr Asp Phe Thr
1               5                   10                  15

Leu Lys Ile Ser Arg Val Glu Ala Glu Asp Leu Gly Val Tyr Phe Cys
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: Synthetic Construct

<400> SEQUENCE: 122

Gly Glx Pro Ser Arg Leu Ser Gly Glx Gly Trp Val Thr Asp Tyr Phe
1               5                   10                  15

Leu Pro Ile His Thr Ser Glu Gln Glu Asp Arg Gly Ser Tyr Phe Cys
            20                  25                  30

<210> SEQ ID NO 123
<211> LENGTH: 32
<212> TYPE: PRT
<213> ORGANISM: Artificial Sequence
<220> FEATURE:
<223> OTHER INFORMATION: Synthetic Construct

<400> SEQUENCE: 123

Gly Ile Pro Ser Arg Phe Ser Gly Ser Gly Ser Gly Ser Asp Phe Thr
1               5                   10                  15

Leu Ser Ile Asn Thr Val Glu Pro Glu Asp Val Gly Val Tyr Tyr Cys
            20                  25                  30

<210> SEQ ID NO 124
<211> LENGTH: 10
<212> TYPE: PRT
<213> ORGANISM: Artificial Sequence
<220> FEATURE:
<223> OTHER INFORMATION: Synthetic Construct

<400> SEQUENCE: 124

Phe Gly Gly Gly Thr Lys Leu Glu Ile Lys
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Synthetic Construct

<400> SEQUENCE: 125

Phe Gly Gly Gly Thr Lys Leu Glu Met Lys
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Synthetic Construct
```

<400> SEQUENCE: 126

Phe Gly Gly Gly Thr Lys Leu Glu Leu Lys
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Synthetic Construct

<400> SEQUENCE: 127

Phe Gly Gly Gly Thr Arg Leu Glu Ile Lys
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Synthetic Construct

<400> SEQUENCE: 128

Phe Gly Gly Gly Thr Lys Leu Glu Ile Lys
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Synthetic Construct

<400> SEQUENCE: 129

Phe Gly Gly Gly Thr Lys Leu Glu Ile Lys
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Synthetic Construct

<400> SEQUENCE: 130

Phe Gly Gly Gly Thr Lys Leu Glu Ile Lys
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Synthetic Construct

<400> SEQUENCE: 131

Phe Gly Ala Gly Thr Lys Leu Glu Leu Lys
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Synthetic Construct

```
<400> SEQUENCE: 132

Phe Gly Gly Gly Thr Lys Leu Glu Ile Lys
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Synthetic Construct

<400> SEQUENCE: 133

Phe Gly Gly Gly Thr Lys Leu Glu Ile Lys
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Synthetic Construct

<400> SEQUENCE: 134

Phe Gly Gly Gly Thr Lys Leu Glu Ile Lys
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Synthetic Construct

<400> SEQUENCE: 135

Phe Gly Gly Gly Thr Lys Leu Glu Ile Lys
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Synthetic Construct

<400> SEQUENCE: 136

Phe Gly Gly Gly Thr Lys Leu Glu Ile Lys
1               5                   10

<210> SEQ ID NO 137
<211> LENGTH: 26
<212> TYPE: PRT
<213> ORGANISM: Artificial Sequence
<220> FEATURE:
<223> OTHER INFORMATION: Synthetic Construct

<400> SEQUENCE: 137

Gln Val Gln Leu Gln Gln Ser Gly Ser Glu Leu Arg Ser Pro Gly Ser
1               5                   10                  15

Ser Val Lys Leu Ser Cys Lys Asp Phe Asp
            20                  25

<210> SEQ ID NO 138
<211> LENGTH: 26
<212> TYPE: PRT
<213> ORGANISM: Artificial Sequence
<220> FEATURE:
```

<223> OTHER INFORMATION: Synthetic Construct

<400> SEQUENCE: 138

Gln Val Gln Leu Gln Gln Ser Gly Ala Glu Leu Val Arg Pro Gly Ala
1               5                   10                  15

Ser Val Lys Leu Ser Cys Ser Ala Ser Gly
            20                  25

<210> SEQ ID NO 139
<211> LENGTH: 26
<212> TYPE: PRT
<213> ORGANISM: Artificial Sequence
<220> FEATURE:
<223> OTHER INFORMATION: Synthetic Construct

<400> SEQUENCE: 139

Glu Val Lys Leu Val Glu Ser Gly Gly Thr Leu Val Lys Pro Gly Gly
1               5                   10                  15

Ser Leu Lys Ile Ser Cys Ala Ala Ser Gly
            20                  25

<210> SEQ ID NO 140
<211> LENGTH: 26
<212> TYPE: PRT
<213> ORGANISM: Artificial Sequence
<220> FEATURE:
<223> OTHER INFORMATION: Synthetic Construct

<400> SEQUENCE: 140

Gln Val Gln Leu Gln Gln Ser Gly Ser Glu Leu Arg Ser Pro Gly Ser
1               5                   10                  15

Ser Val Lys Leu Ser Cys Lys Asp Phe Asp
            20                  25

<210> SEQ ID NO 141
<211> LENGTH: 26
<212> TYPE: PRT
<213> ORGANISM: Artificial Sequence
<220> FEATURE:
<223> OTHER INFORMATION: Synthetic Construct

<400> SEQUENCE: 141

Gln Val Gln Leu Gln Gln Ser Gly Ala Glu Leu Ala Arg Pro Gly Ala
1               5                   10                  15

Ser Val Lys Leu Ser Cys Lys Ala Ser Gly
            20                  25

<210> SEQ ID NO 142
<211> LENGTH: 26
<212> TYPE: PRT
<213> ORGANISM: Artificial Sequence
<220> FEATURE:
<223> OTHER INFORMATION: Synthetic Construct

<400> SEQUENCE: 142

Gln Val Gln Leu Gln Gln Ser Gly Ser Glu Leu Arg Ser Pro Gly Ser
1               5                   10                  15

Ser Val Lys Leu Ser Cys Lys Asp Phe Asp
            20                  25

<210> SEQ ID NO 143
<211> LENGTH: 26
<212> TYPE: PRT
<213> ORGANISM: Artificial Sequence
<220> FEATURE:
<223> OTHER INFORMATION: Synthetic Construct

<400> SEQUENCE: 143

Gln Val Gln Leu Gln Gln Ser Gly Ala Glu Leu Val Lys Pro Gly Ala
1               5                   10                  15

Ser Val Lys Leu Ser Cys Lys Thr Ser Gly
            20                  25

<210> SEQ ID NO 144
<211> LENGTH: 26
<212> TYPE: PRT
<213> ORGANISM: Artificial Sequence
<220> FEATURE:
<223> OTHER INFORMATION: Synthetic Construct

<400> SEQUENCE: 144

Glu Val Lys Leu Ala Asp Ser Gly Gly Ala Leu Val Asn Pro Gly Gly
1               5                   10                  15

Ser Leu Lys Ile Ser Cys Ala Val Ser Gly
            20                  25

<210> SEQ ID NO 145
<211> LENGTH: 23
<212> TYPE: PRT
<213> ORGANISM: Artificial Sequence
<220> FEATURE:
<223> OTHER INFORMATION: Synthetic Construct

<400> SEQUENCE: 145

Leu Val Glx Ser Gly Gly Ala Leu Val Lys Pro Gly Gly Ser Leu Lys
1               5                   10                  15

Leu Ser Cys Ala Ala Ser Gly
            20

<210> SEQ ID NO 146
<211> LENGTH: 26
<212> TYPE: PRT
<213> ORGANISM: Artificial Sequence
<220> FEATURE:
<223> OTHER INFORMATION: Synthetic Construct

<400> SEQUENCE: 146

Gln Val Gln Leu Lys Gln Ser Gly Pro Val Leu Val Ala Pro Ser Gln
1               5                   10                  15

Ser Leu Ser Ile Thr Cys Thr Val Ser Gly
            20                  25

<210> SEQ ID NO 147
<211> LENGTH: 26
<212> TYPE: PRT
<213> ORGANISM: Artificial Sequence
<220> FEATURE:
<223> OTHER INFORMATION: Synthetic Construct

<400> SEQUENCE: 147

Gln Val Gln Leu Gln Gln Ser Gly Ser Glu Leu Arg Ser Pro Gly Ser
1               5                   10                  15

Ser Val Lys Leu Ser Cys Lys Asp Phe Asp
            20                  25

<210> SEQ ID NO 148
<211> LENGTH: 26
<212> TYPE: PRT

```
<213> ORGANISM: Artificial Sequence
<220> FEATURE:
<223> OTHER INFORMATION: Synthetic Construct

<400> SEQUENCE: 148

Gln Val Gln Leu Gln Gln Ser Gly Pro Glu Leu Val Lys Pro Gly Ala
1               5                   10                  15

Ser Val Lys Ile Ser Cys Lys Ala Ser Gly
            20                  25

<210> SEQ ID NO 149
<211> LENGTH: 26
<212> TYPE: PRT
<213> ORGANISM: Artificial Sequence
<220> FEATURE:
<223> OTHER INFORMATION: Synthetic Construct

<400> SEQUENCE: 149

Glu Val Lys Leu Val Glu Phe Gly Gly Ala Leu Val Lys Pro Gly Gly
1               5                   10                  15

Ser Leu Lys Leu Ser Cys Ala Ala Leu Gly
            20                  25

<210> SEQ ID NO 150
<211> LENGTH: 12
<212> TYPE: PRT
<213> ORGANISM: Artificial Sequence
<220> FEATURE:
<223> OTHER INFORMATION: Synthetic Construct

<400> SEQUENCE: 150

Trp Val Arg Gln Lys Pro Gly His Gly Phe Glu Trp
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Synthetic Construct

<400> SEQUENCE: 151

Trp Ile Lys Gln Arg Pro Leu Gln Gly Leu Glu Trp
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Synthetic Construct

<400> SEQUENCE: 152

Trp Val Arg Gln Asn Pro Glu Lys Arg Leu Glu Trp
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Synthetic Construct

<400> SEQUENCE: 153

Trp Val Arg Gln Lys Pro Gly His Gly Phe Glu Trp
1               5                   10
```

<210> SEQ ID NO 154
<211> LENGTH: 12
<212> TYPE: PRT
<213> ORGANISM: Artificial Sequence
<220> FEATURE:
<223> OTHER INFORMATION: Synthetic Construct

<400> SEQUENCE: 154

Trp Val Lys Gln Arg Thr Gly Gln Gly Leu Glu Trp
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Synthetic Construct

<400> SEQUENCE: 155

Trp Val Arg Gln Lys Pro Gly His Gly Phe Glu Trp
1               5                   10

<210> SEQ ID NO 156
<211> LENGTH: 12
<212> TYPE: PRT
<213> ORGANISM: Artificial Sequence
<220> FEATURE:
<223> OTHER INFORMATION: Synthetic Construct

<400> SEQUENCE: 156

Trp Val Lys Gln Arg Pro Gly Gln Gly Leu Glu Trp
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Synthetic Construct

<400> SEQUENCE: 157

Trp Val Arg Gln Asn Pro Glu Lys Arg Leu Glu Trp
1               5                   10

<210> SEQ ID NO 158
<211> LENGTH: 12
<212> TYPE: PRT
<213> ORGANISM: Artificial Sequence
<220> FEATURE:
<223> OTHER INFORMATION: Synthetic Construct

<400> SEQUENCE: 158

Trp Val Arg Gln Thr Pro Glu Lys Arg Leu Glu Trp
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Synthetic Construct

<400> SEQUENCE: 159

Trp Val Arg Gln Phe Pro Gly Lys Gly Leu Glu Trp
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Synthetic Construct

<400> SEQUENCE: 160

Trp Val Arg Gln Lys Pro Gly His Gly Phe Glu Trp
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Synthetic Construct

<400> SEQUENCE: 161

Trp Val Arg Gln Arg Pro Gly Lys Gly Leu Asp Trp
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Synthetic Construct

<400> SEQUENCE: 162

Arg Val Arg Gln Thr Pro Glu Lys Arg Glu Glu Gly
1               5                   10

<210> SEQ ID NO 163
<211> LENGTH: 35
<212> TYPE: PRT
<213> ORGANISM: Artificial Sequence
<220> FEATURE:
<223> OTHER INFORMATION: Synthetic Construct

<400> SEQUENCE: 163

Glu Lys Phe Glu Asp Lys Ala Thr Leu Asp Ala Asp Thr Val Ser Asn
1               5                   10                  15

Thr Ala Tyr Leu Glu Leu Asn Ser Leu Thr Ser Glu Asp Ser Ala Ile
            20                  25                  30

Tyr Tyr Cys
        35

<210> SEQ ID NO 164
<211> LENGTH: 35
<212> TYPE: PRT
<213> ORGANISM: Artificial Sequence
<220> FEATURE:
<223> OTHER INFORMATION: Synthetic Construct

<400> SEQUENCE: 164

Pro Lys Phe Gln Asp Lys Ala Phe Leu Thr Ala Asp Thr Ser Ser Thr
1               5                   10                  15

Thr Ala Tyr Leu Gln Leu Ser Ser Leu Thr Ser Glu Asp Thr Ala Ile
            20                  25                  30

Tyr Tyr Cys
        35

<210> SEQ ID NO 165

```
<211> LENGTH: 35
<212> TYPE: PRT
<213> ORGANISM: Artificial Sequence
<220> FEATURE:
<223> OTHER INFORMATION: Synthetic Construct

<400> SEQUENCE: 165

Asp Ile Phe Lys Gly Arg Phe Thr Ile Ser Arg Asp Asp Ala Lys Asn
1               5                   10                  15

Ala Leu Tyr Leu Gln Met Ser Ser Leu Arg Ser Glu Asp Thr Ala Leu
            20                  25                  30

Tyr Tyr Cys
        35

<210> SEQ ID NO 166
<211> LENGTH: 35
<212> TYPE: PRT
<213> ORGANISM: Artificial Sequence
<220> FEATURE:
<223> OTHER INFORMATION: Synthetic Construct

<400> SEQUENCE: 166

Glu Lys Phe Glu Asp Lys Ala Thr Leu Asp Ala Asp Thr Val Ser Asn
1               5                   10                  15

Thr Ala Tyr Leu Glu Leu Asn Ser Leu Thr Ser Glu Asp Ser Ala Ile
            20                  25                  30

Tyr Tyr Cys
        35

<210> SEQ ID NO 167
<211> LENGTH: 35
<212> TYPE: PRT
<213> ORGANISM: Artificial Sequence
<220> FEATURE:
<223> OTHER INFORMATION: Synthetic Construct

<400> SEQUENCE: 167

Glu Asn Tyr Arg Val Lys Ala Thr Leu Thr Ala Asp Lys Ser Ser Ser
1               5                   10                  15

Thr Ala Tyr Met Gln Leu Phe Ser Leu Thr Ser Glu Asp Ser Ala Val
            20                  25                  30

Tyr Phe Cys
        35

<210> SEQ ID NO 168
<211> LENGTH: 35
<212> TYPE: PRT
<213> ORGANISM: Artificial Sequence
<220> FEATURE:
<223> OTHER INFORMATION: Synthetic Construct

<400> SEQUENCE: 168

Glu Lys Phe Glu Asp Lys Ala Thr Leu Asp Ala Asp Thr Val Ser Asn
1               5                   10                  15

Thr Ala Tyr Leu Glu Leu Asn Ser Leu Thr Ser Glu Asp Ser Ala Ile
            20                  25                  30

Tyr Tyr Cys
        35

<210> SEQ ID NO 169
<211> LENGTH: 35
<212> TYPE: PRT
<213> ORGANISM: Artificial Sequence
```

<220> FEATURE:
<223> OTHER INFORMATION: Synthetic Construct

<400> SEQUENCE: 169

Glu Lys Phe Lys Ser Lys Ala Thr Leu Thr Val Asp Thr Ser Ser
1               5                   10                  15

Thr Ala Tyr Met Gln Leu Ser Ser Leu Thr Ser Asp Asp Ser Ala Val
                20                  25                  30

Tyr Tyr Cys
        35

<210> SEQ ID NO 170
<211> LENGTH: 35
<212> TYPE: PRT
<213> ORGANISM: Artificial Sequence
<220> FEATURE:
<223> OTHER INFORMATION: Synthetic Construct

<400> SEQUENCE: 170

Asp Ser Val Lys Gly Arg Phe Thr Ile Ser Arg Asp Asn Ala Lys Asn
1               5                   10                  15

Ala Leu Tyr Leu Gln Met Ser Ser Leu Arg Ser Glu Asp Thr Ala Leu
                20                  25                  30

Tyr Tyr Cys
        35

<210> SEQ ID NO 171
<211> LENGTH: 35
<212> TYPE: PRT
<213> ORGANISM: Artificial Sequence
<220> FEATURE:
<223> OTHER INFORMATION: Synthetic Construct

<400> SEQUENCE: 171

Asp Ser Val Lys Gly Arg Phe Thr Ile Ser Arg Asp Asn Ala Arg Asn
1               5                   10                  15

Thr Leu Tyr Leu Gln Met Ser Ser Leu Arg Ser Lys Asp Thr Ala Met
                20                  25                  30

Tyr Tyr Cys
        35

<210> SEQ ID NO 172
<211> LENGTH: 35
<212> TYPE: PRT
<213> ORGANISM: Artificial Sequence
<220> FEATURE:
<223> OTHER INFORMATION: Synthetic Construct

<400> SEQUENCE: 172

Ser Val Leu Met Ser Arg Leu Ser Ile Ser Lys Asp Asn Ser Lys Ser
1               5                   10                  15

Gln Val Phe Leu Lys Met Asn Ser Leu Gln Thr Asp Asp Thr Ala Met
                20                  25                  30

Tyr Tyr Cys
        35

<210> SEQ ID NO 173
<211> LENGTH: 35
<212> TYPE: PRT
<213> ORGANISM: Artificial Sequence
<220> FEATURE:
<223> OTHER INFORMATION: Synthetic Construct

<400> SEQUENCE: 173

Glu Lys Phe Glu Asp Lys Ala Thr Leu Asp Ala Asp Thr Val Ser Asn
1               5                   10                  15

Thr Ala Tyr Leu Glu Leu Asn Ser Leu Thr Ser Glu Asp Ser Ala Ile
            20                  25                  30

Tyr Tyr Cys
        35

<210> SEQ ID NO 174
<211> LENGTH: 35
<212> TYPE: PRT
<213> ORGANISM: Artificial Sequence
<220> FEATURE:
<223> OTHER INFORMATION: Synthetic Construct

<400> SEQUENCE: 174

Gly Lys Phe Lys Asp Lys Ala Thr Leu Thr Glu Asp Lys Ser Ser Ser
1               5                   10                  15

Thr Ala Tyr Met Gln Leu Ser Ser Leu Thr Ser Glu Asp Ser Ala Val
            20                  25                  30

Tyr Phe Cys
        35

<210> SEQ ID NO 175
<211> LENGTH: 35
<212> TYPE: PRT
<213> ORGANISM: Artificial Sequence
<220> FEATURE:
<223> OTHER INFORMATION: Synthetic Construct

<400> SEQUENCE: 175

Asp Ser Ala Lys Asp Arg His Pro Ile Phe Arg Asp Asn Ala Arg Asn
1               5                   10                  15

Thr Leu Tyr Leu Gln Met Ser Ser Leu Arg Ser Lys Asp Thr Ala Met
            20                  25                  30

Tyr Tyr Cys
        35

<210> SEQ ID NO 176
<211> LENGTH: 11
<212> TYPE: PRT
<213> ORGANISM: Artificial Sequence
<220> FEATURE:
<223> OTHER INFORMATION: Synthetic Construct

<400> SEQUENCE: 176

Trp Gly Gln Gly Thr Leu Val Thr Val Ser Ala
1               5                   10

<210> SEQ ID NO 177
<211> LENGTH: 11
<212> TYPE: PRT
<213> ORGANISM: Artificial Sequence
<220> FEATURE:
<223> OTHER INFORMATION: Synthetic Construct

<400> SEQUENCE: 177

Trp Gly Gln Gly Thr Leu Val Thr Val Ser Ala
1               5                   10

<210> SEQ ID NO 178
<211> LENGTH: 11
<212> TYPE: PRT

```
<213> ORGANISM: Artificial Sequence
<220> FEATURE:
<223> OTHER INFORMATION: Synthetic Construct

<400> SEQUENCE: 178

Trp Gly Ala Gly Ala Thr Val Thr Val Ser Ser
1               5                   10

<210> SEQ ID NO 179
<211> LENGTH: 11
<212> TYPE: PRT
<213> ORGANISM: Artificial Sequence
<220> FEATURE:
<223> OTHER INFORMATION: Synthetic Construct

<400> SEQUENCE: 179

Trp Gly Gln Gly Thr Leu Val Thr Val Ser Ala
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Synthetic Construct

<400> SEQUENCE: 180

Trp Gly His Gly Thr Leu Val Thr Val Ser Ala
1               5                   10

<210> SEQ ID NO 181
<211> LENGTH: 11
<212> TYPE: PRT
<213> ORGANISM: Artificial Sequence
<220> FEATURE:
<223> OTHER INFORMATION: Synthetic Construct

<400> SEQUENCE: 181

Trp Gly Gln Gly Thr Leu Val Thr Val Ser Ala
1               5                   10

<210> SEQ ID NO 182
<211> LENGTH: 11
<212> TYPE: PRT
<213> ORGANISM: Artificial Sequence
<220> FEATURE:
<223> OTHER INFORMATION: Synthetic Construct

<400> SEQUENCE: 182

Trp Gly Gln Gly Thr Ser Val Thr Val Ser Ser
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Synthetic Construct

<400> SEQUENCE: 183

Trp Gly Ala Gly Ala Thr Val Thr Val Ser Ser
1               5                   10

<210> SEQ ID NO 184
<211> LENGTH: 11
<212> TYPE: PRT
<213> ORGANISM: Artificial Sequence
```

```
<220> FEATURE:
<223> OTHER INFORMATION: Synthetic Construct

<400> SEQUENCE: 184

Trp Gly Ala Gly Thr Thr Val Thr Val Ser Ser
1               5                   10

<210> SEQ ID NO 185
<211> LENGTH: 11
<212> TYPE: PRT
<213> ORGANISM: Artificial Sequence
<220> FEATURE:
<223> OTHER INFORMATION: Synthetic Construct

<400> SEQUENCE: 185

Trp Gly Gln Gly Thr Leu Val Thr Val Ser Ala
1               5                   10

<210> SEQ ID NO 186
<211> LENGTH: 11
<212> TYPE: PRT
<213> ORGANISM: Artificial Sequence
<220> FEATURE:
<223> OTHER INFORMATION: Synthetic Construct

<400> SEQUENCE: 186

Trp Gly Gln Gly Thr Leu Val Thr Val Ser Ala
1               5                   10

<210> SEQ ID NO 187
<211> LENGTH: 11
<212> TYPE: PRT
<213> ORGANISM: Artificial Sequence
<220> FEATURE:
<223> OTHER INFORMATION: Synthetic Construct

<400> SEQUENCE: 187

Trp Gly Gln Gly Thr Thr Leu Thr Val Ser Ser
1               5                   10

<210> SEQ ID NO 188
<211> LENGTH: 11
<212> TYPE: PRT
<213> ORGANISM: Artificial Sequence
<220> FEATURE:
<223> OTHER INFORMATION: Synthetic Construct

<400> SEQUENCE: 188

Trp Gly Ala Gly Thr Thr Val Thr Val Ser Ser
1               5                   10

<210> SEQ ID NO 189
<211> LENGTH: 112
<212> TYPE: PRT
<213> ORGANISM: Artificial Sequence
<220> FEATURE:
<223> OTHER INFORMATION: Synthetic Construct

<400> SEQUENCE: 189

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Thr Gly Asn Thr Tyr Leu His Trp Phe Gln Gln Arg Pro Gly Gln Ser
        35                  40                  45
```

```
Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Tyr Thr Phe Gly Gln Gly Thr Lys Val Glu Ile Lys
            100                 105                 110
```

<210> SEQ ID NO 190
<211> LENGTH: 112
<212> TYPE: PRT
<213> ORGANISM: Artificial Sequence
<220> FEATURE:
<223> OTHER INFORMATION: Synthetic Construct

<400> SEQUENCE: 190

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Thr Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Tyr Thr Phe Gly Gln Gly Thr Lys Val Glu Ile Lys
            100                 105                 110
```

<210> SEQ ID NO 191
<211> LENGTH: 112
<212> TYPE: PRT
<213> ORGANISM: Artificial Sequence
<220> FEATURE:
<223> OTHER INFORMATION: Synthetic Construct

<400> SEQUENCE: 191

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Val His Ser
                20                  25                  30

Thr Gly Asn Thr Tyr Leu His Trp Tyr Gln Gln Lys Pro Gly Gln Pro
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Ser Gln Asn
                85                  90                  95

Thr His Val Pro Tyr Thr Phe Gly Gln Gly Thr Lys Val Glu Ile Lys
            100                 105                 110
```

<210> SEQ ID NO 192
<211> LENGTH: 112
<212> TYPE: PRT
<213> ORGANISM: Artificial Sequence
<220> FEATURE:
<223> OTHER INFORMATION: Synthetic Construct

<400> SEQUENCE: 192

Glu Ile Val Leu Thr Gln Ser Pro Ala Thr Leu Ser Leu Ser Pro Gly
1               5                   10                  15

Glu Arg Ala Thr Leu Ser Cys Arg Ser Ser Gln Ser Leu Val His Ser
            20                  25                  30

Thr Gly Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Ile Pro
    50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 193
<211> LENGTH: 112
<212> TYPE: PRT
<213> ORGANISM: Artificial Sequence
<220> FEATURE:
<223> OTHER INFORMATION: Synthetic Construct

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Thr Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 194
<211> LENGTH: 112
<212> TYPE: PRT
<213> ORGANISM: Artificial Sequence
<220> FEATURE:
<223> OTHER INFORMATION: Synthetic Construct

<400> SEQUENCE: 194

Glu Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Ser
            20                  25                  30

Thr Gly Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Ile Pro
    50                  55                  60

```
Ala Arg Phe Ser Gly Ser Gly Ser Gly Thr Glu Phe Thr Leu Thr Ile
 65                  70                  75                  80

Ser Ser Leu Gln Ser Glu Asp Phe Ala Val Tyr Tyr Cys Ser Gln Asn
                 85                  90                  95

Thr His Val Pro Tyr Thr Phe Gly Gln Gly Thr Lys Val Glu Ile Lys
            100                 105                 110
```

<210> SEQ ID NO 195
<211> LENGTH: 112
<212> TYPE: PRT
<213> ORGANISM: Artificial Sequence
<220> FEATURE:
<223> OTHER INFORMATION: Synthetic Construct

<400> SEQUENCE: 195

```
Asp Ile Gln Met Thr Gln Ser Pro Ser Thr Leu Ser Ala Ser Val Gly
  1               5                  10                  15

Asp Arg Val Thr Ile Thr Cys Arg Ser Gln Ser Leu Val His Ser
                 20                  25                  30

Thr Gly Asn Thr Tyr Leu His Trp Tyr Gln Gln Lys Pro Gly Lys Ala
                 35                  40                  45

Pro Lys Leu Leu Ile Tyr Lys Val Ser Asn Arg Phe Ser Gly Val Pro
 50                  55                  60

Ser Arg Phe Ser Gly Ser Gly Ser Gly Thr Glu Phe Thr Leu Thr Ile
 65                  70                  75                  80

Ser Ser Leu Gln Pro Asp Asp Phe Ala Thr Tyr Tyr Cys Ser Gln Asn
                 85                  90                  95

Thr His Val Pro Tyr Thr Phe Gly Gln Gly Thr Lys Val Glu Ile Lys
            100                 105                 110
```

<210> SEQ ID NO 196
<211> LENGTH: 112
<212> TYPE: PRT
<213> ORGANISM: Artificial Sequence
<220> FEATURE:
<223> OTHER INFORMATION: Synthetic Construct

<400> SEQUENCE: 196

```
Asp Ile Gln Leu Thr Gln Ser Pro Ser Phe Leu Ser Ala Ser Val Gly
  1               5                  10                  15

Asp Arg Val Thr Ile Thr Cys Arg Ser Gln Ser Leu Val His Ser
                 20                  25                  30

Thr Gly Asn Thr Tyr Leu His Trp Tyr Gln Gln Lys Pro Gly Lys Ala
                 35                  40                  45

Pro Lys Leu Leu Ile Tyr Lys Val Ser Asn Arg Phe Ser Gly Val Pro
 50                  55                  60

Ser Arg Phe Ser Gly Ser Gly Ser Gly Thr Glu Phe Thr Leu Thr Ile
 65                  70                  75                  80

Ser Ser Leu Gln Pro Glu Asp Phe Ala Thr Tyr Tyr Cys Ser Gln Asn
                 85                  90                  95

Thr His Val Pro Tyr Thr Phe Gly Gln Gly Thr Lys Val Glu Ile Lys
            100                 105                 110
```

<210> SEQ ID NO 197
<211> LENGTH: 112
<212> TYPE: PRT
<213> ORGANISM: Artificial Sequence
<220> FEATURE:
<223> OTHER INFORMATION: Synthetic Construct

```
<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Thr Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 198
<211> LENGTH: 112
<212> TYPE: PRT
<213> ORGANISM: Artificial Sequence
<220> FEATURE:
<223> OTHER INFORMATION: Synthetic Construct

<400> SEQUENCE: 198

Glu Ile Val Leu Thr Gln Ser Pro Gly Thr Leu Ser Leu Ser Pro Gly
1               5                   10                  15

Glu Arg Ala Thr Leu Ser Cys Arg Ser Ser Gln Ser Leu Val His Ser
            20                  25                  30

Thr Gly Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 199
<211> LENGTH: 107
<212> TYPE: PRT
<213> ORGANISM: Artificial Sequence
<220> FEATURE:
<223> OTHER INFORMATION: Synthetic Construct

<400> SEQUENCE: 199

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Tyr
            20                  25                  30

Leu His Trp Tyr Gln Gln Lys Pro Gly Lys Ala Pro Lys Leu Leu Ile
        35                  40                  45

Tyr Tyr Ala Ser Gln Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Lys Gly Leu Asn Phe Pro Leu
                85                  90                  95

Thr Phe Gly Gln Gly Thr Lys Val Glu Ile Lys
            100                 105

<210> SEQ ID NO 200
<211> LENGTH: 107
<212> TYPE: PRT
<213> ORGANISM: Artificial Sequence
<220> FEATURE:
<223> OTHER INFORMATION: Synthetic Construct

<400> SEQUENCE: 200

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asp Tyr
            20                  25                  30

Leu His Trp Tyr Gln Gln Lys Pro Gly Lys Ala Pro Lys Leu Leu Ile
        35                  40                  45

Tyr Tyr Ala Ser Gln Ser Ile Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Lys Gly Leu Asn Phe Pro Leu
                85                  90                  95

Thr Phe Gly Gln Gly Thr Lys Val Glu Ile Lys
            100                 105

<210> SEQ ID NO 201
<211> LENGTH: 107
<212> TYPE: PRT
<213> ORGANISM: Artificial Sequence
<220> FEATURE:
<223> OTHER INFORMATION: Synthetic Construct

<400> SEQUENCE: 201

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Ser Ile Ser Asp Tyr
            20                  25                  30

Leu His Trp Tyr Gln Gln Lys Pro Gly Lys Ala Pro Lys Leu Leu Ile
        35                  40                  45

Tyr Tyr Ala Ser Gln Ser Ile Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Lys Gly Leu Asn Phe Pro Leu
                85                  90                  95

Thr Phe Gly Gln Gly Thr Lys Val Glu Ile Lys
            100                 105

<210> SEQ ID NO 202
<211> LENGTH: 107
<212> TYPE: PRT
<213> ORGANISM: Artificial Sequence
<220> FEATURE:
<223> OTHER INFORMATION: Synthetic Construct -continued

<400> SEQUENCE: 202

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp Tyr
            20                  25                  30

Leu His Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Lys Gly Leu Asn Phe Pro Leu
                85                  90                  95

Thr Phe Gly Gln Gly Thr Lys Val Glu Ile Lys
            100                 105

<210> SEQ ID NO 203
<211> LENGTH: 107
<212> TYPE: PRT
<213> ORGANISM: Artificial Sequence
<220> FEATURE:
<223> OTHER INFORMATION: Synthetic Construct

<400> SEQUENCE: 203

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Tyr
            20                  25                  30

Leu His Trp Tyr Gln Gln Lys Pro Gly Lys Ala Pro Lys Leu Leu Ile
        35                  40                  45

Tyr Tyr Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Lys Gly Leu Asn Phe Pro Leu
                85                  90                  95

Thr Phe Gly Gln Gly Thr Lys Val Glu Ile Lys
            100                 105

<210> SEQ ID NO 204
<211> LENGTH: 107
<212> TYPE: PRT
<213> ORGANISM: Artificial Sequence
<220> FEATURE:
<223> OTHER INFORMATION: Synthetic Construct

<400> SEQUENCE: 204

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asp Tyr
            20                  25                  30

Leu His Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Lys Gly Leu Asn Phe Pro Leu
                85                  90                  95

Thr Phe Gly Gln Gly Thr Lys Val Glu Ile Lys
           100                 105

<210> SEQ ID NO 205
<211> LENGTH: 107
<212> TYPE: PRT
<213> ORGANISM: Artificial Sequence
<220> FEATURE:
<223> OTHER INFORMATION: Synthetic Construct

<400> SEQUENCE: 205

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Asp Tyr
                20                  25                  30

Leu His Trp Tyr Gln Gln Lys Pro Gly Gln Ala Pro Arg Leu Leu Ile
            35                  40                  45

Tyr Tyr Ala Ser Gln Ser Ile Ser Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Lys Gly Leu Asn Phe Pro Leu
                85                  90                  95

Thr Phe Gly Gln Gly Thr Lys Val Glu Ile Lys
           100                 105

<210> SEQ ID NO 206
<211> LENGTH: 107
<212> TYPE: PRT
<213> ORGANISM: Artificial Sequence
<220> FEATURE:
<223> OTHER INFORMATION: Synthetic Construct

<400> SEQUENCE: 206

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Ser Ile Ser Asp Tyr
                20                  25                  30

Leu His Trp Tyr Leu Gln Lys Pro Gly Gln Ser Pro Gln Leu Leu Ile
            35                  40                  45

Tyr Tyr Ala Ser Gln Ser Ile Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Lys Gly Leu Asn Phe Pro Leu
                85                  90                  95

Thr Phe Gly Gln Gly Thr Lys Val Glu Ile Lys
           100                 105

<210> SEQ ID NO 207
<211> LENGTH: 107
<212> TYPE: PRT
<213> ORGANISM: Artificial Sequence
<220> FEATURE:
<223> OTHER INFORMATION: Synthetic Construct

<400> SEQUENCE: 207

Asp Val Val Met Thr Gln Ser Pro Leu Ser Leu Pro Val Thr Leu Gly
1               5                   10                  15

Gln Pro Ala Ser Ile Ser Cys Arg Ala Ser Gln Ser Ile Ser Asp Tyr
            20                  25                  30

Leu His Trp Phe Gln Gln Arg Pro Gly Gln Ser Pro Arg Arg Leu Ile
        35                  40                  45

Tyr Tyr Ala Ser Gln Ser Ile Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Lys Gly Leu Asn Phe Pro Leu
                85                  90                  95

Thr Phe Gly Gln Gly Thr Lys Val Glu Ile Lys
            100                 105

<210> SEQ ID NO 208
<211> LENGTH: 107
<212> TYPE: PRT
<213> ORGANISM: Artificial Sequence
<220> FEATURE:
<223> OTHER INFORMATION: Synthetic Construct

<400> SEQUENCE: 208

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Ile Ser Asp Tyr
            20                  25                  30

Leu His Trp Tyr Gln Gln Lys Pro Gly Gln Pro Pro Lys Leu Leu Ile
        35                  40                  45

Tyr Tyr Ala Ser Gln Ser Ile Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Lys Gly Leu Asn Phe Pro Leu
                85                  90                  95

Thr Phe Gly Gln Gly Thr Lys Val Glu Ile Lys
            100                 105

<210> SEQ ID NO 209
<211> LENGTH: 106
<212> TYPE: PRT
<213> ORGANISM: Artificial Sequence
<220> FEATURE:
<223> OTHER INFORMATION: Synthetic Construct

<400> SEQUENCE: 209

Glu Ile Val Leu Thr Gln Ser Pro Ala Thr Leu Ser Leu Ser Pro Gly
1               5                   10                  15

Glu Arg Ala Thr Leu Ser Cys Ser Ala Asn Ser Ser Phe Ile Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

```
Asp Phe Ala Val Tyr Tyr Cys Gln Gln Trp Ser Ser Pro Leu Thr
                85                  90                  95

Phe Gly Gln Gly Thr Lys Val Glu Ile Lys
            100                 105

<210> SEQ ID NO 210
<211> LENGTH: 106
<212> TYPE: PRT
<213> ORGANISM: Artificial Sequence
<220> FEATURE:
<223> OTHER INFORMATION: Synthetic Construct

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Ser Ala Asn Ser Ser Phe Ile Tyr Met
                20                  25                  30

Tyr Trp Tyr Gln Gln Lys Pro Gly Lys Ala Pro Lys Leu Leu Ile Tyr
            35                  40                  45

Asp Thr Ser Asn Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Pro Leu Thr
                85                  90                  95

Phe Gly Gln Gly Thr Lys Val Glu Ile Lys
            100                 105

<210> SEQ ID NO 211
<211> LENGTH: 106
<212> TYPE: PRT
<213> ORGANISM: Artificial Sequence
<220> FEATURE:
<223> OTHER INFORMATION: Synthetic Construct

<400> SEQUENCE: 211

Asp Ile Gln Met Thr Gln Ser Pro Ser Thr Leu Ser Ala Ser Val Gly
1               5                   10                  15

Asp Arg Val Thr Ile Thr Cys Ser Ala Asn Ser Ser Phe Ile Tyr Met
                20                  25                  30

Tyr Trp Tyr Gln Gln Lys Pro Gly Lys Ala Pro Lys Leu Leu Ile Tyr
            35                  40                  45

Asp Thr Ser Asn Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Gln Gln Trp Ser Ser Pro Leu Thr
                85                  90                  95

Phe Gly Gln Gly Thr Lys Val Glu Ile Lys
            100                 105

<210> SEQ ID NO 212
<211> LENGTH: 106
<212> TYPE: PRT
<213> ORGANISM: Artificial Sequence
<220> FEATURE:
<223> OTHER INFORMATION: Synthetic Construct
```

<400> SEQUENCE: 212

Asp Ile Gln Met Thr Gln Ser Pro Ser Ser Leu Ser Ala Ser Val Gly
1               5                   10                  15

Asp Arg Val Thr Ile Thr Cys Ser Ala Asn Ser Ser Phe Ile Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Ser Pro Leu Thr
                85                  90                  95

Phe Gly Gln Gly Thr Lys Val Glu Ile Lys
            100                 105

<210> SEQ ID NO 213
<211> LENGTH: 106
<212> TYPE: PRT
<213> ORGANISM: Artificial Sequence
<220> FEATURE:
<223> OTHER INFORMATION: Synthetic Construct

<400> SEQUENCE: 213

Asp Ile Gln Leu Thr Gln Ser Pro Ser Phe Leu Ser Ala Ser Val Gly
1               5                   10                  15

Asp Arg Val Thr Ile Thr Cys Ser Ala Asn Ser Ser Phe Ile Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Ser Pro Leu Thr
                85                  90                  95

Phe Gly Gln Gly Thr Lys Val Glu Ile Lys
            100                 105

<210> SEQ ID NO 214
<211> LENGTH: 106
<212> TYPE: PRT
<213> ORGANISM: Artificial Sequence
<220> FEATURE:
<223> OTHER INFORMATION: Synthetic Construct

<400> SEQUENCE: 214

Glu Ile Val Met Thr Gln Ser Pro Ala Thr Leu Ser Val Ser Pro Gly
1               5                   10                  15

Glu Arg Ala Thr Leu Ser Cys Ser Ala Asn Ser Ser Phe Ile Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Ala Arg Phe Ser Gly Ser
    50                  55                  60

Gly Ser Gly Thr Glu Phe Thr Leu Thr Ile Ser Ser Leu Gln Ser Glu
65                  70                  75                  80

Asp Phe Ala Val Tyr Tyr Cys Gln Gln Trp Ser Ser Pro Leu Thr
                85                  90                  95

Phe Gly Gln Gly Thr Lys Val Glu Ile Lys
            100                 105

<210> SEQ ID NO 215
<211> LENGTH: 106
<212> TYPE: PRT
<213> ORGANISM: Artificial Sequence
<220> FEATURE:
<223> OTHER INFORMATION: Synthetic Construct

<400> SEQUENCE: 215

Glu Ile Val Leu Thr Gln Ser Pro Gly Thr Leu Ser Leu Ser Pro Gly
1               5                   10                  15

Glu Arg Ala Thr Leu Ser Cys Ser Ala Asn Ser Ser Phe Ile Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Ser Pro Leu Thr
                85                  90                  95

Phe Gly Gln Gly Thr Lys Val Glu Ile Lys
            100                 105

<210> SEQ ID NO 216
<211> LENGTH: 106
<212> TYPE: PRT
<213> ORGANISM: Artificial Sequence
<220> FEATURE:
<223> OTHER INFORMATION: Synthetic Construct

<400> SEQUENCE: 216

Asp Ile Val Met Thr Gln Ser Pro Leu Ser Leu Pro Val Thr Pro Gly
1               5                   10                  15

Glu Pro Ala Ser Ile Ser Cys Ser Ala Asn Ser Ser Phe Ile Tyr Met
            20                  25                  30

Tyr Trp Tyr Leu Gln Lys Pro Gly Gln Ser Pro Gln Leu Leu Ile Tyr
        35                  40                  45

Asp Thr Ser Asn Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys Gln Gln Trp Ser Ser Pro Leu Thr
                85                  90                  95

Phe Gly Gln Gly Thr Lys Val Glu Ile Lys
            100                 105

<210> SEQ ID NO 217
<211> LENGTH: 106
<212> TYPE: PRT
<213> ORGANISM: Artificial Sequence
<220> FEATURE:
<223> OTHER INFORMATION: Synthetic Construct

```
<400> SEQUENCE: 217

Asp Val Val Met Thr Gln Ser Pro Leu Ser Leu Pro Val Thr Leu Gly
1               5                   10                  15

Gln Pro Ala Ser Ile Ser Cys Ser Ala Asn Ser Ser Phe Ile Tyr Met
            20                  25                  30

Tyr Trp Phe Gln Gln Arg Pro Gly Gln Ser Pro Arg Arg Leu Ile Tyr
        35                  40                  45

Asp Thr Ser Asn Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys Gln Gln Trp Ser Ser Ser Pro Leu Thr
                85                  90                  95

Phe Gly Gln Gly Thr Lys Val Glu Ile Lys
            100                 105

<210> SEQ ID NO 218
<211> LENGTH: 106
<212> TYPE: PRT
<213> ORGANISM: Artificial Sequence
<220> FEATURE:
<223> OTHER INFORMATION: Synthetic Construct

<400> SEQUENCE: 218

Asp Ile Val Met Thr Gln Ser Pro Asp Ser Leu Ala Val Ser Leu Gly
1               5                   10                  15

Glu Arg Ala Thr Ile Asn Cys Ser Ala Asn Ser Ser Phe Ile Tyr Met
            20                  25                  30

Tyr Trp Tyr Gln Gln Lys Pro Gly Gln Pro Pro Lys Leu Leu Ile Tyr
        35                  40                  45

Asp Thr Ser Asn Leu Ala Ser Gly Val Pro Asp Arg Phe Ser Gly Ser
    50                  55                  60

Gly Ser Gly Thr Asp Phe Thr Leu Thr Ile Ser Ser Leu Gln Ala Glu
65                  70                  75                  80

Asp Val Ala Val Tyr Tyr Cys Gln Gln Trp Ser Ser Ser Pro Leu Thr
                85                  90                  95

Phe Gly Gln Gly Thr Lys Val Glu Ile Lys
            100                 105

<210> SEQ ID NO 219
<211> LENGTH: 107
<212> TYPE: PRT
<213> ORGANISM: Artificial Sequence
<220> FEATURE:
<223> OTHER INFORMATION: Synthetic Construct

<400> SEQUENCE: 219

Asp Ile Gln Met Thr Gln Ser Pro Ser Thr Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

Asp Asp Phe Ala Thr Tyr Tyr Cys His Gln Tyr Trp Asn Thr Pro Tyr
                85                  90                  95

Thr Phe Gly Gln Gly Thr Lys Val Glu Ile Lys
            100                 105

<210> SEQ ID NO 220
<211> LENGTH: 107
<212> TYPE: PRT
<213> ORGANISM: Artificial Sequence
<220> FEATURE:
<223> OTHER INFORMATION: Synthetic Construct

<400> SEQUENCE: 220

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys His Gln Tyr Trp Asn Thr Pro Tyr
                85                  90                  95

Thr Phe Gly Gln Gly Thr Lys Val Glu Ile Lys
            100                 105

<210> SEQ ID NO 221
<211> LENGTH: 107
<212> TYPE: PRT
<213> ORGANISM: Artificial Sequence
<220> FEATURE:
<223> OTHER INFORMATION: Synthetic Construct

<400> SEQUENCE: 221

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Trp Asn Thr Pro Tyr
                85                  90                  95

Thr Phe Gly Gln Gly Thr Lys Val Glu Ile Lys
            100                 105

<210> SEQ ID NO 222
<211> LENGTH: 107
<212> TYPE: PRT
<213> ORGANISM: Artificial Sequence
<220> FEATURE:
<223> OTHER INFORMATION: Synthetic Construct

<400> SEQUENCE: 222

Asp Ile Gln Leu Thr Gln Ser Pro Ser Phe Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys His Gln Tyr Trp Asn Thr Pro Tyr
                85                  90                  95

Thr Phe Gly Gln Gly Thr Lys Val Glu Ile Lys
            100                 105

<210> SEQ ID NO 223
<211> LENGTH: 107
<212> TYPE: PRT
<213> ORGANISM: Artificial Sequence
<220> FEATURE:
<223> OTHER INFORMATION: Synthetic Construct

<400> SEQUENCE: 223

Glu Ile Val Met Thr Gln Ser Pro Ala Thr Leu Ser Val Ser Pro Gly
1               5                   10                  15

Glu Arg Ala Thr Leu Ser Cys Lys Ala Ser Asp His Ile Asn Asn Trp
            20                  25                  30

Leu Ala Trp Tyr Gln Gln Lys Pro Gly Gln Ala Pro Arg Leu Leu Ile
        35                  40                  45

Tyr Gly Ala Thr Ser Leu Glu Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys His Gln Tyr Trp Asn Thr Pro Tyr
                85                  90                  95

Thr Phe Gly Gln Gly Thr Lys Val Glu Ile Lys
            100                 105

<210> SEQ ID NO 224
<211> LENGTH: 107
<212> TYPE: PRT
<213> ORGANISM: Artificial Sequence
<220> FEATURE:
<223> OTHER INFORMATION: Synthetic Construct

<400> SEQUENCE: 224

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Asp His Ile Asn Asn Trp
            20                  25                  30

Leu Ala Trp Tyr Gln Gln Lys Pro Gly Gln Ala Pro Arg Leu Leu Ile
        35                  40                  45

Tyr Gly Ala Thr Ser Leu Glu Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

```
Glu Asp Phe Ala Val Tyr Tyr Cys His Gln Tyr Trp Asn Thr Pro Tyr
                85                  90                  95

Thr Phe Gly Gln Gly Thr Lys Val Glu Ile Lys
            100                 105
```

<210> SEQ ID NO 225
<211> LENGTH: 107
<212> TYPE: PRT
<213> ORGANISM: Artificial Sequence
<220> FEATURE:
<223> OTHER INFORMATION: Synthetic Construct

<400> SEQUENCE: 225

```
Glu Ile Val Leu Thr Gln Ser Pro Gly Thr Leu Ser Leu Ser Pro Gly
1               5                   10                  15

Glu Arg Ala Thr Leu Ser Cys Lys Ala Ser Asp His Ile Asn Asn Trp
            20                  25                  30

Leu Ala Trp Tyr Gln Gln Lys Pro Gly Gln Ala Pro Arg Leu Leu Ile
        35                  40                  45

Tyr Gly Ala Thr Ser Leu Glu Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys His Gln Tyr Trp Asn Thr Pro Tyr
                85                  90                  95

Thr Phe Gly Gln Gly Thr Lys Val Glu Ile Lys
            100                 105
```

<210> SEQ ID NO 226
<211> LENGTH: 107
<212> TYPE: PRT
<213> ORGANISM: Artificial Sequence
<220> FEATURE:
<223> OTHER INFORMATION: Synthetic Construct

<400> SEQUENCE: 226

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Asp His Ile Asn Asn Trp
            20                  25                  30

Leu Ala Trp Tyr Gln Gln Lys Pro Gly Gln Pro Pro Lys Leu Leu Ile
        35                  40                  45

Tyr Gly Ala Thr Ser Leu Glu Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln Tyr Trp Asn Thr Pro Tyr
                85                  90                  95

Thr Phe Gly Gln Gly Thr Lys Val Glu Ile Lys
            100                 105
```

<210> SEQ ID NO 227
<211> LENGTH: 107
<212> TYPE: PRT
<213> ORGANISM: Artificial Sequence
<220> FEATURE:
<223> OTHER INFORMATION: Synthetic Construct

<400> SEQUENCE: 227

Asp Val Val Met Thr Gln Ser Pro Leu Ser Leu Pro Val Thr Leu Gly
1               5                   10                  15

Gln Pro Ala Ser Ile Ser Cys Lys Ala Ser Asp His Ile Asn Asn Trp
            20                  25                  30

Leu Ala Trp Phe Gln Gln Arg Pro Gly Gln Ser Pro Arg Arg Leu Ile
        35                  40                  45

Tyr Gly Ala Thr Ser Leu Glu Thr Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys His Gln Tyr Trp Asn Thr Pro Tyr
                85                  90                  95

Thr Phe Gly Gln Gly Thr Lys Val Glu Ile Lys
            100                 105

<210> SEQ ID NO 228
<211> LENGTH: 107
<212> TYPE: PRT
<213> ORGANISM: Artificial Sequence
<220> FEATURE:
<223> OTHER INFORMATION: Synthetic Construct

<400> SEQUENCE: 228

Asp Ile Val Met Thr Gln Ser Pro Leu Ser Leu Pro Val Thr Pro Gly
1               5                   10                  15

Glu Pro Ala Ser Ile Ser Cys Lys Ala Ser Asp His Ile Asn Asn Trp
            20                  25                  30

Leu Ala Trp Tyr Leu Gln Lys Pro Gly Gln Ser Pro Gln Leu Leu Ile
        35                  40                  45

Tyr Gly Ala Thr Ser Leu Glu Thr Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys His Gln Tyr Trp Asn Thr Pro Tyr
                85                  90                  95

Thr Phe Gly Gln Gly Thr Lys Val Glu Ile Lys
            100                 105

<210> SEQ ID NO 229
<211> LENGTH: 112
<212> TYPE: PRT
<213> ORGANISM: Artificial Sequence
<220> FEATURE:
<223> OTHER INFORMATION: Synthetic Construct

<400> SEQUENCE: 229

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Thr Gly Asn Thr Tyr Leu His Trp Phe Gln Gln Arg Pro Gly Gln Ser
        35                  40                  45

Pro Arg Arg Leu Ile Tyr Lys Val Ser Asn Arg Phe Cys Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
            85                  90                  95

Thr His Val Pro Tyr Thr Phe Gly Gln Gly Thr Lys Val Glu Ile Lys
            100                 105                 110

<210> SEQ ID NO 230
<211> LENGTH: 112
<212> TYPE: PRT
<213> ORGANISM: Artificial Sequence
<220> FEATURE:
<223> OTHER INFORMATION: Synthetic Construct

<400> SEQUENCE: 230

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Cys Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
            85                  90                  95

Thr His Val Pro Tyr Thr Phe Gly Gln Gly Thr Lys Val Glu Ile Lys
            100                 105                 110

<210> SEQ ID NO 231
<211> LENGTH: 112
<212> TYPE: PRT
<213> ORGANISM: Artificial Sequence
<220> FEATURE:
<223> OTHER INFORMATION: Synthetic Construct

<400> SEQUENCE: 231

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Val His Ser
            20                  25                  30

Thr Gly Asn Thr Tyr Leu His Trp Tyr Gln Gln Lys Pro Gly Gln Pro
            35                  40                  45

Pro Lys Leu Leu Ile Tyr Lys Val Ser Asn Arg Phe Cys Gly Val Pro
        50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Ser Gln Asn
            85                  90                  95

Thr His Val Pro Tyr Thr Phe Gly Gln Gly Thr Lys Val Glu Ile Lys
            100                 105                 110

<210> SEQ ID NO 232
<211> LENGTH: 112
<212> TYPE: PRT
<213> ORGANISM: Artificial Sequence
<220> FEATURE:
<223> OTHER INFORMATION: Synthetic Construct

<400> SEQUENCE: 232

Glu Ile Val Leu Thr Gln Ser Pro Ala Thr Leu Ser Leu Ser Pro Gly
1               5                   10                  15

Glu Arg Ala Thr Leu Ser Cys Arg Ser Ser Gln Ser Leu Val His Ser
            20                  25                  30

Thr Gly Asn Thr Tyr Leu His Trp Tyr Gln Gln Lys Pro Gly Gln Ala
        35                  40                  45

Pro Arg Leu Leu Ile Tyr Lys Val Ser Asn Arg Phe Cys Gly Ile Pro
    50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 233
<211> LENGTH: 112
<212> TYPE: PRT
<213> ORGANISM: Artificial Sequence
<220> FEATURE:
<223> OTHER INFORMATION: Synthetic Construct

<400> SEQUENCE: 233

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Thr Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Cys Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 234
<211> LENGTH: 112
<212> TYPE: PRT
<213> ORGANISM: Artificial Sequence
<220> FEATURE:
<223> OTHER INFORMATION: Synthetic Construct

<400> SEQUENCE: 234

Glu Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Ser
            20                  25                  30

Thr Gly Asn Thr Tyr Leu His Trp Tyr Gln Gln Lys Pro Gly Gln Ala
        35                  40                  45

Pro Arg Leu Leu Ile Tyr Lys Val Ser Asn Arg Phe Cys Gly Ile Pro
    50                  55                  60

Ala Arg Phe Ser Gly Ser Gly Ser Gly Thr Glu Phe Thr Leu Thr Ile
65                  70                  75                  80

Ser Ser Leu Gln Ser Glu Asp Phe Ala Val Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 235
<211> LENGTH: 112
<212> TYPE: PRT
<213> ORGANISM: Artificial Sequence
<220> FEATURE:
<223> OTHER INFORMATION: Synthetic Construct

<400> SEQUENCE: 235

Glu Ile Val Leu Thr Gln Ser Pro Gly Thr Leu Ser Leu Ser Pro Gly
1               5                   10                  15

Glu Arg Ala Thr Leu Ser Cys Arg Ser Ser Gln Ser Leu Val His Ser
            20                  25                  30

Thr Gly Asn Thr Tyr Leu His Trp Tyr Gln Gln Lys Pro Gly Gln Ala
        35                  40                  45

Pro Arg Leu Leu Ile Tyr Lys Val Ser Asn Arg Phe Cys Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 236
<211> LENGTH: 112
<212> TYPE: PRT
<213> ORGANISM: Artificial Sequence
<220> FEATURE:
<223> OTHER INFORMATION: Synthetic Construct

<400> SEQUENCE: 236

Asp Ile Gln Leu Thr Gln Ser Pro Ser Phe Leu Ser Ala Ser Val Gly
1               5                   10                  15

Asp Arg Val Thr Ile Thr Cys Arg Ser Ser Gln Ser Leu Val His Ser
            20                  25                  30

Thr Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Cys Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Glu Asp Phe Ala Thr Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 237
<211> LENGTH: 112
<212> TYPE: PRT
<213> ORGANISM: Artificial Sequence
<220> FEATURE:
<223> OTHER INFORMATION: Synthetic Construct

<400> SEQUENCE: 237

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Thr Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Cys Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 238
<211> LENGTH: 112
<212> TYPE: PRT
<213> ORGANISM: Artificial Sequence
<220> FEATURE:
<223> OTHER INFORMATION: Synthetic Construct

<400> SEQUENCE: 238

Asp Ile Gln Met Thr Gln Ser Pro Ser Thr Leu Ser Ala Ser Val Gly
1               5                   10                  15

Asp Arg Val Thr Ile Thr Cys Arg Ser Ser Gln Ser Leu Val His Ser
            20                  25                  30

Thr Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Cys Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 239
<211> LENGTH: 112
<212> TYPE: PRT
<213> ORGANISM: Artificial Sequence
<220> FEATURE:
<223> OTHER INFORMATION: Synthetic Construct

<400> SEQUENCE: 239

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Thr Gly Asn Ile Tyr Leu His Trp Phe Gln Gln Arg Pro Gly Gln Ser
        35                  40                  45

Pro Arg Arg Leu Ile Tyr Lys Val Ser Asn Arg Phe Glx Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Ser Gln Asn
            85                  90                  95

Thr His Val Pro Tyr Thr Phe Gly Gln Gly Thr Lys Val Glu Ile Lys
            100                 105                 110
```

<210> SEQ ID NO 240
<211> LENGTH: 112
<212> TYPE: PRT
<213> ORGANISM: Artificial Sequence
<220> FEATURE:
<223> OTHER INFORMATION: Synthetic Construct

<400> SEQUENCE: 240

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Thr Gly Asn Ile Tyr Leu His Trp Tyr Leu Gln Lys Pro Gly Gln Ser
        35                  40                  45

Pro Gln Leu Leu Ile Tyr Lys Val Ser Asn Arg Phe Glx Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
            85                  90                  95

Thr His Val Pro Tyr Thr Phe Gly Gln Gly Thr Lys Val Glu Ile Lys
            100                 105                 110
```

<210> SEQ ID NO 241
<211> LENGTH: 112
<212> TYPE: PRT
<213> ORGANISM: Artificial Sequence
<220> FEATURE:
<223> OTHER INFORMATION: Synthetic Construct

<400> SEQUENCE: 241

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Val His Ser
            20                  25                  30

Thr Gly Asn Ile Tyr Leu His Trp Tyr Gln Gln Lys Pro Gly Gln Pro
        35                  40                  45

Pro Lys Leu Leu Ile Tyr Lys Val Ser Asn Arg Phe Glx Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Ser Gln Asn
            85                  90                  95

Thr His Val Pro Tyr Thr Phe Gly Gln Gly Thr Lys Val Glu Ile Lys
            100                 105                 110
```

<210> SEQ ID NO 242
<211> LENGTH: 112
<212> TYPE: PRT
<213> ORGANISM: Artificial Sequence
<220> FEATURE:
<223> OTHER INFORMATION: Synthetic Construct

<400> SEQUENCE: 242

Glu Ile Val Leu Thr Gln Ser Pro Ala Thr Leu Ser Leu Ser Pro Gly
1               5                  10                  15

Glu Arg Ala Thr Leu Ser Cys Arg Ser Ser Gln Ser Leu Val His Ser
            20                  25                  30

Thr Gly Asn Ile Tyr Leu His Trp Tyr Gln Gln Lys Pro Gly Gln Ala
        35                  40                  45

Pro Arg Leu Leu Ile Tyr Lys Val Ser Asn Arg Phe Glx Gly Ile Pro
    50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 243
<211> LENGTH: 112
<212> TYPE: PRT
<213> ORGANISM: Artificial Sequence
<220> FEATURE:
<223> OTHER INFORMATION: Synthetic Construct

<400> SEQUENCE: 243

Asp Ile Gln Met Thr Gln Ser Pro Ser Ser Leu Ser Ala Ser Val Gly
1               5                  10                  15

Asp Arg Val Thr Ile Thr Cys Arg Ser Ser Gln Ser Leu Val His Ser
            20                  25                  30

Thr Gly Asn Ile Tyr Leu His Trp Tyr Gln Gln Lys Pro Gly Lys Ala
        35                  40                  45

Pro Lys Leu Leu Ile Tyr Lys Val Ser Asn Arg Phe Glx Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 244
<211> LENGTH: 112
<212> TYPE: PRT
<213> ORGANISM: Artificial Sequence
<220> FEATURE:
<223> OTHER INFORMATION: Synthetic Construct

<400> SEQUENCE: 244

Glu Ile Val Met Thr Gln Ser Pro Ala Thr Leu Ser Val Ser Pro Gly
1               5                  10                  15

Glu Arg Ala Thr Leu Ser Cys Arg Ser Ser Gln Ser Leu Val His Ser
            20                  25                  30

Thr Gly Asn Ile Tyr Leu His Trp Tyr Gln Gln Lys Pro Gly Gln Ala
        35                  40                  45

Pro Arg Leu Leu Ile Tyr Lys Val Ser Asn Arg Phe Glx Gly Ile Pro
    50                  55                  60

Ala Arg Phe Ser Gly Ser Gly Ser Gly Thr Glu Phe Thr Leu Thr Ile
65                  70                  75                  80

Ser Ser Leu Gln Ser Glu Asp Phe Ala Val Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 245
<211> LENGTH: 112
<212> TYPE: PRT
<213> ORGANISM: Artificial Sequence
<220> FEATURE:
<223> OTHER INFORMATION: Synthetic Construct

<400> SEQUENCE: 245

Glu Ile Val Leu Thr Gln Ser Pro Gly Thr Leu Ser Leu Ser Pro Gly
1               5                   10                  15

Glu Arg Ala Thr Leu Ser Cys Arg Ser Ser Gln Ser Leu Val His Ser
            20                  25                  30

Thr Gly Asn Ile Tyr Leu His Trp Tyr Gln Gln Lys Pro Gly Gln Ala
        35                  40                  45

Pro Arg Leu Leu Ile Tyr Lys Val Ser Asn Arg Phe Glx Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 246
<211> LENGTH: 112
<212> TYPE: PRT
<213> ORGANISM: Artificial Sequence
<220> FEATURE:
<223> OTHER INFORMATION: Synthetic Construct

<400> SEQUENCE: 246

Asp Ile Gln Met Thr Gln Ser Pro Ser Thr Leu Ser Ala Ser Val Gly
1               5                   10                  15

Asp Arg Val Thr Ile Thr Cys Arg Ser Ser Gln Ser Leu Val His Ser
            20                  25                  30

Thr Gly Asn Ile Tyr Leu His Trp Tyr Gln Gln Lys Pro Gly Lys Ala
        35                  40                  45

Pro Lys Leu Leu Ile Tyr Lys Val Ser Asn Arg Phe Glx Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 247
<211> LENGTH: 112
<212> TYPE: PRT
<213> ORGANISM: Artificial Sequence
<220> FEATURE:
<223> OTHER INFORMATION: Synthetic Construct

<400> SEQUENCE: 247

Asp Ile Gln Leu Thr Gln Ser Pro Ser Phe Leu Ser Ala Ser Val Gly
1               5                   10                  15

Asp Arg Val Thr Ile Thr Cys Arg Ser Ser Gln Ser Leu Val His Ser
            20                  25                  30

Thr Gly Asn Ile Tyr Leu His Trp Tyr Gln Gln Lys Pro Gly Lys Ala
        35                  40                  45

Pro Lys Leu Leu Ile Tyr Lys Val Ser Asn Arg Phe Glx Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Glu Asp Phe Ala Thr Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 248
<211> LENGTH: 112
<212> TYPE: PRT
<213> ORGANISM: Artificial Sequence
<220> FEATURE:
<223> OTHER INFORMATION: Synthetic Construct

<400> SEQUENCE: 248

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Thr Gly Asn Ile Tyr Leu His Trp Tyr Gln Gln Lys Pro Gly Lys Ala
        35                  40                  45

Pro Lys Leu Leu Ile Tyr Lys Val Ser Asn Arg Phe Glx Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 249
<211> LENGTH: 107
<212> TYPE: PRT
<213> ORGANISM: Artificial Sequence
<220> FEATURE:
<223> OTHER INFORMATION: Synthetic Construct

<400> SEQUENCE: 249

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Lys Val Gly Thr Asn
            20                  25                  30

Val Ala Trp Tyr Gln Gln Lys Pro Gly Gln Ala Pro Arg Leu Leu Ile
        35                  40                  45

Tyr Ser Ala Ser Thr Arg His Arg Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys His Gln Gly Asn Ser Val Gln Tyr
                85                  90                  95

Thr Phe Gly Gln Gly Thr Lys Val Glu Ile Lys
            100                 105

<210> SEQ ID NO 250
<211> LENGTH: 107
<212> TYPE: PRT
<213> ORGANISM: Artificial Sequence
<220> FEATURE:
<223> OTHER INFORMATION: Synthetic Construct

<400> SEQUENCE: 250

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Lys Val Gly Thr Asn
            20                  25                  30

Val Ala Trp Tyr Gln Gln Lys Pro Gly Gln Ala Pro Arg Leu Leu Ile
        35                  40                  45

Tyr Ser Ala Ser Thr Arg His Arg Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys His Gln Gly Asn Ser Val Gln Tyr
                85                  90                  95

Thr Phe Gly Gln Gly Thr Lys Val Glu Ile Lys
            100                 105

<210> SEQ ID NO 251
<211> LENGTH: 107
<212> TYPE: PRT
<213> ORGANISM: Artificial Sequence
<220> FEATURE:
<223> OTHER INFORMATION: Synthetic Construct

<400> SEQUENCE: 251

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Lys Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Thr Arg His Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys His Gln Gly Asn Ser Val Gln Tyr
                85                  90                  95

Thr Phe Gly Gln Gly Thr Lys Val Glu Ile Lys
            100                 105

<210> SEQ ID NO 252
<211> LENGTH: 107
<212> TYPE: PRT
<213> ORGANISM: Artificial Sequence
<220> FEATURE:
<223> OTHER INFORMATION: Synthetic Construct

<400> SEQUENCE: 252

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Lys Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Thr Arg His Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys His Gln Gly Asn Ser Val Gln Tyr
                85                  90                  95

Thr Phe Gly Gln Gly Thr Lys Val Glu Ile Lys
            100                 105

<210> SEQ ID NO 253
<211> LENGTH: 107
<212> TYPE: PRT
<213> ORGANISM: Artificial Sequence
<220> FEATURE:
<223> OTHER INFORMATION: Synthetic Construct

<400> SEQUENCE: 253

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Lys Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Thr Arg His Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Gly Asn Ser Val Gln Tyr
                85                  90                  95

Thr Phe Gly Gln Gly Thr Lys Val Glu Ile Lys
            100                 105

<210> SEQ ID NO 254
<211> LENGTH: 107
<212> TYPE: PRT
<213> ORGANISM: Artificial Sequence
<220> FEATURE:
<223> OTHER INFORMATION: Synthetic Construct

<400> SEQUENCE: 254

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Lys Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Thr Arg His Arg Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys His Gln Gly Asn Ser Val Gln Tyr
            85                  90                  95

Thr Phe Gly Gln Gly Thr Lys Val Glu Ile Lys
            100                 105

<210> SEQ ID NO 255
<211> LENGTH: 107
<212> TYPE: PRT
<213> ORGANISM: Artificial Sequence
<220> FEATURE:
<223> OTHER INFORMATION: Synthetic Construct

<400> SEQUENCE: 255

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Lys Val Gly Thr Asn
            20                  25                  30

Val Ala Trp Tyr Gln Gln Lys Pro Gly Gln Ala Pro Arg Leu Leu Ile
        35                  40                  45

Tyr Ser Ala Ser Thr Arg His Arg Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys His Gln Gly Asn Ser Val Gln Tyr
            85                  90                  95

Thr Phe Gly Gln Gly Thr Lys Val Glu Ile Lys
            100                 105

<210> SEQ ID NO 256
<211> LENGTH: 107
<212> TYPE: PRT
<213> ORGANISM: Artificial Sequence
<220> FEATURE:
<223> OTHER INFORMATION: Synthetic Construct

<400> SEQUENCE: 256

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Lys Val Gly Thr Asn
            20                  25                  30

Val Ala Trp Tyr Gln Gln Lys Pro Gly Gln Pro Pro Lys Leu Leu Ile
        35                  40                  45

Tyr Ser Ala Ser Thr Arg His Arg Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln Gly Asn Ser Val Gln Tyr
            85                  90                  95

Thr Phe Gly Gln Gly Thr Lys Val Glu Ile Lys
            100                 105

<210> SEQ ID NO 257
<211> LENGTH: 107
<212> TYPE: PRT
<213> ORGANISM: Artificial Sequence
<220> FEATURE:
<223> OTHER INFORMATION: Synthetic Construct

<400> SEQUENCE: 257

Asp Ile Val Met Thr Gln Ser Pro Leu Ser Leu Pro Val Thr Pro Gly
1               5                   10                  15

Glu Pro Ala Ser Ile Ser Cys Lys Ala Ser Gln Lys Val Gly Thr Asn
            20                  25                  30

Val Ala Trp Tyr Leu Gln Lys Pro Gly Gln Ser Pro Gln Leu Leu Ile
        35                  40                  45

Tyr Ser Ala Ser Thr Arg His Arg Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys His Gln Gly Asn Ser Val Gln Tyr
                85                  90                  95

Thr Phe Gly Gln Gly Thr Lys Val Glu Ile Lys
            100                 105

<210> SEQ ID NO 258
<211> LENGTH: 107
<212> TYPE: PRT
<213> ORGANISM: Artificial Sequence
<220> FEATURE:
<223> OTHER INFORMATION: Synthetic Construct

<400> SEQUENCE: 258

Asp Val Val Met Thr Gln Ser Pro Leu Ser Leu Pro Val Thr Leu Gly
1               5                   10                  15

Gln Pro Ala Ser Ile Ser Cys Lys Ala Ser Gln Lys Val Gly Thr Asn
            20                  25                  30

Val Ala Trp Phe Gln Gln Arg Pro Gly Gln Ser Pro Arg Arg Leu Ile
        35                  40                  45

Tyr Ser Ala Ser Thr Arg His Arg Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys His Gln Gly Asn Ser Val Gln Tyr
                85                  90                  95

Thr Phe Gly Gln Gly Thr Lys Val Glu Ile Lys
            100                 105

<210> SEQ ID NO 259
<211> LENGTH: 106
<212> TYPE: PRT
<213> ORGANISM: Artificial Sequence
<220> FEATURE:
<223> OTHER INFORMATION: Synthetic Construct

<400> SEQUENCE: 259

Glu Ile Val Leu Thr Gln Ser Pro Ala Thr Leu Ser Leu Ser Pro Gly
1               5                   10                  15

Glu Arg Ala Thr Leu Ser Cys Ser Ala Asn Ser Ser Phe Thr Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

```
Asp Phe Ala Val Tyr Tyr Cys Gln Gln Trp Ser Ser Pro Leu Thr
                85                  90                  95

Phe Gly Gln Gly Thr Lys Val Glu Ile Lys
            100                 105

<210> SEQ ID NO 260
<211> LENGTH: 106
<212> TYPE: PRT
<213> ORGANISM: Artificial Sequence
<220> FEATURE:
<223> OTHER INFORMATION: Synthetic Construct

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Ser Ala Asn Ser Ser Phe Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Pro Leu Thr
                85                  90                  95

Phe Gly Gln Gly Thr Lys Val Glu Ile Lys
            100                 105

<210> SEQ ID NO 261
<211> LENGTH: 106
<212> TYPE: PRT
<213> ORGANISM: Artificial Sequence
<220> FEATURE:
<223> OTHER INFORMATION: Synthetic Construct

<400> SEQUENCE: 261

Asp Ile Gln Met Thr Gln Ser Pro Ser Ser Leu Ser Ala Ser Val Gly
1               5                   10                  15

Asp Arg Val Thr Ile Thr Cys Ser Ala Asn Ser Ser Phe Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Pro Leu Thr
                85                  90                  95

Phe Gly Gln Gly Thr Lys Val Glu Ile Lys
            100                 105

<210> SEQ ID NO 262
<211> LENGTH: 106
<212> TYPE: PRT
<213> ORGANISM: Artificial Sequence
<220> FEATURE:
<223> OTHER INFORMATION: Synthetic Construct
```

<400> SEQUENCE: 262

Asp Ile Gln Met Thr Gln Ser Pro Ser Thr Leu Ser Ala Ser Val Gly
1               5                   10                  15

Asp Arg Val Thr Ile Thr Cys Ser Ala Asn Ser Ser Phe Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Gln Gln Trp Ser Ser Ser Pro Leu Thr
                85                  90                  95

Phe Gly Gln Gly Thr Lys Val Glu Ile Lys
            100                 105

<210> SEQ ID NO 263
<211> LENGTH: 106
<212> TYPE: PRT
<213> ORGANISM: Artificial Sequence
<220> FEATURE:
<223> OTHER INFORMATION: Synthetic Construct

<400> SEQUENCE: 263

Asp Ile Gln Leu Thr Gln Ser Pro Ser Phe Leu Ser Ala Ser Val Gly
1               5                   10                  15

Asp Arg Val Thr Ile Thr Cys Ser Ala Asn Ser Ser Phe Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Ser Pro Leu Thr
                85                  90                  95

Phe Gly Gln Gly Thr Lys Val Glu Ile Lys
            100                 105

<210> SEQ ID NO 264
<211> LENGTH: 106
<212> TYPE: PRT
<213> ORGANISM: Artificial Sequence
<220> FEATURE:
<223> OTHER INFORMATION: Synthetic Construct

<400> SEQUENCE: 264

Glu Ile Val Met Thr Gln Ser Pro Ala Thr Leu Ser Val Ser Pro Gly
1               5                   10                  15

Glu Arg Ala Thr Leu Ser Cys Ser Ala Asn Ser Ser Phe Thr Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Ala Arg Phe Ser Gly Ser
    50                  55                  60

Gly Ser Gly Thr Glu Phe Thr Leu Thr Ile Ser Ser Leu Gln Ser Glu
65                  70                  75                  80

```
Asp Phe Ala Val Tyr Tyr Cys Gln Gln Trp Ser Ser Pro Leu Thr
                85                  90                  95

Phe Gly Gln Gly Thr Lys Val Glu Ile Lys
            100                 105

<210> SEQ ID NO 265
<211> LENGTH: 106
<212> TYPE: PRT
<213> ORGANISM: Artificial Sequence
<220> FEATURE:
<223> OTHER INFORMATION: Synthetic Construct

<400> SEQUENCE: 265

Glu Ile Val Leu Thr Gln Ser Pro Gly Thr Leu Ser Leu Ser Pro Gly
1               5                   10                  15

Glu Arg Ala Thr Leu Ser Cys Ser Ala Asn Ser Ser Phe Thr Tyr Met
                20                  25                  30

Tyr Trp Tyr Gln Gln Lys Pro Gly Gln Ala Pro Arg Leu Leu Ile Tyr
            35                  40                  45

Asp Thr Ser Asn Leu Ala Ser Gly Ile Pro Asp Arg Phe Ser Gly Ser
        50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Ser Pro Leu Thr
                85                  90                  95

Phe Gly Gln Gly Thr Lys Val Glu Ile Lys
            100                 105

<210> SEQ ID NO 266
<211> LENGTH: 106
<212> TYPE: PRT
<213> ORGANISM: Artificial Sequence
<220> FEATURE:
<223> OTHER INFORMATION: Synthetic Construct

<400> SEQUENCE: 266

Asp Ile Val Met Thr Gln Ser Pro Leu Ser Leu Pro Val Thr Pro Gly
1               5                   10                  15

Glu Pro Ala Ser Ile Ser Cys Ser Ala Asn Ser Ser Phe Thr Tyr Met
                20                  25                  30

Tyr Trp Tyr Leu Gln Lys Pro Gly Gln Ser Pro Gln Leu Leu Ile Tyr
            35                  40                  45

Asp Thr Ser Asn Leu Ala Ser Gly Val Pro Asp Arg Phe Ser Gly Ser
        50                  55                  60

Gly Ser Gly Thr Asp Phe Thr Leu Lys Ile Ser Arg Val Glu Ala Glu
65                  70                  75                  80

Asp Val Gly Val Tyr Tyr Cys Gln Gln Trp Ser Ser Pro Leu Thr
                85                  90                  95

Phe Gly Gln Gly Thr Lys Val Glu Ile Lys
            100                 105

<210> SEQ ID NO 267
<211> LENGTH: 106
<212> TYPE: PRT
<213> ORGANISM: Artificial Sequence
<220> FEATURE:
<223> OTHER INFORMATION: Synthetic Construct
```

<400> SEQUENCE: 267

Asp Val Val Met Thr Gln Ser Pro Leu Ser Leu Pro Val Thr Leu Gly
1               5                   10                  15

Gln Pro Ala Ser Ile Ser Cys Ser Ala Asn Ser Ser Phe Thr Tyr Met
            20                  25                  30

Tyr Trp Phe Gln Gln Arg Pro Gly Gln Ser Pro Arg Arg Leu Ile Tyr
        35                  40                  45

Asp Thr Ser Asn Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys Gln Gln Trp Ser Ser Ser Pro Leu Thr
                85                  90                  95

Phe Gly Gln Gly Thr Lys Val Glu Ile Lys
            100                 105

<210> SEQ ID NO 268
<211> LENGTH: 106
<212> TYPE: PRT
<213> ORGANISM: Artificial Sequence
<220> FEATURE:
<223> OTHER INFORMATION: Synthetic Construct

<400> SEQUENCE: 268

Asp Ile Val Met Thr Gln Ser Pro Asp Ser Leu Ala Val Ser Leu Gly
1               5                   10                  15

Glu Arg Ala Thr Ile Asn Cys Ser Ala Asn Ser Ser Phe Thr Tyr Met
            20                  25                  30

Tyr Trp Tyr Gln Gln Lys Pro Gly Gln Pro Pro Lys Leu Leu Ile Tyr
        35                  40                  45

Asp Thr Ser Asn Leu Ala Ser Gly Val Pro Asp Arg Phe Ser Gly Ser
    50                  55                  60

Gly Ser Gly Thr Asp Phe Thr Leu Thr Ile Ser Ser Leu Gln Ala Glu
65                  70                  75                  80

Asp Val Ala Val Tyr Tyr Cys Gln Gln Trp Ser Ser Ser Pro Leu Thr
                85                  90                  95

Phe Gly Gln Gly Thr Lys Val Glu Ile Lys
            100                 105

<210> SEQ ID NO 269
<211> LENGTH: 107
<212> TYPE: PRT
<213> ORGANISM: Artificial Sequence
<220> FEATURE:
<223> OTHER INFORMATION: Synthetic Construct

<400> SEQUENCE: 269

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Glu Tyr
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Cys Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Asn Gly His Asn Phe Pro Tyr
                85                  90                  95

Thr Phe Gly Gln Gly Thr Lys Val Glu Ile Lys
            100                 105

<210> SEQ ID NO 270
<211> LENGTH: 107
<212> TYPE: PRT
<213> ORGANISM: Artificial Sequence
<220> FEATURE:
<223> OTHER INFORMATION: Synthetic Construct

<400> SEQUENCE: 270

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Ser Ile Ser Glu Tyr
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Cys Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Asn Gly His Asn Phe Pro Tyr
                85                  90                  95

Thr Phe Gly Gln Gly Thr Lys Val Glu Ile Lys
            100                 105

<210> SEQ ID NO 271
<211> LENGTH: 107
<212> TYPE: PRT
<213> ORGANISM: Artificial Sequence
<220> FEATURE:
<223> OTHER INFORMATION: Synthetic Construct

<400> SEQUENCE: 271

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Glu Tyr
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Cys Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Asn Gly His Asn Phe Pro Tyr
                85                  90                  95

Thr Phe Gly Gln Gly Thr Lys Val Glu Ile Lys
            100                 105

<210> SEQ ID NO 272
<211> LENGTH: 107
<212> TYPE: PRT
<213> ORGANISM: Artificial Sequence
<220> FEATURE:
<223> OTHER INFORMATION: Synthetic Construct
```

<400> SEQUENCE: 272

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Glu Tyr
            20                  25                  30

Leu His Trp Tyr Gln Gln Lys Pro Gly Gln Ala Pro Arg Leu Leu Ile
        35                  40                  45

Tyr Phe Ala Ser Gln Ser Ile Cys Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Asn Phe Pro Tyr
                85                  90                  95

Thr Phe Gly Gln Gly Thr Lys Val Glu Ile Lys
            100                 105

<210> SEQ ID NO 273
<211> LENGTH: 107
<212> TYPE: PRT
<213> ORGANISM: Artificial Sequence
<220> FEATURE:
<223> OTHER INFORMATION: Synthetic Construct

<400> SEQUENCE: 273

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Glu Tyr
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Cys Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Asn Gly His Asn Phe Pro Tyr
                85                  90                  95

Thr Phe Gly Gln Gly Thr Lys Val Glu Ile Lys
            100                 105

<210> SEQ ID NO 274
<211> LENGTH: 107
<212> TYPE: PRT
<213> ORGANISM: Artificial Sequence
<220> FEATURE:
<223> OTHER INFORMATION: Synthetic Construct

<400> SEQUENCE: 274

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Glu Tyr
            20                  25                  30

Leu His Trp Tyr Gln Gln Lys Pro Gly Gln Ala Pro Arg Leu Leu Ile
        35                  40                  45

Tyr Phe Ala Ser Gln Ser Ile Cys Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Asn Gly His Asn Phe Pro Tyr
                85                  90                  95

Thr Phe Gly Gln Gly Thr Lys Val Glu Ile Lys
                100                 105

<210> SEQ ID NO 275
<211> LENGTH: 107
<212> TYPE: PRT
<213> ORGANISM: Artificial Sequence
<220> FEATURE:
<223> OTHER INFORMATION: Synthetic Construct

<400> SEQUENCE: 275

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Glu Tyr
                20                  25                  30

Leu His Trp Tyr Gln Gln Lys Pro Gly Gln Ala Pro Arg Leu Leu Ile
            35                  40                  45

Tyr Phe Ala Ser Gln Ser Ile Cys Gly Ile Pro Asp Arg Phe Ser Gly
    50                  55                  60

Ser Gly Ser Gly Thr Asp Phe Thr Leu Thr Ile Ser Arg Leu Glu Pro
65              70                  75                  80

Glu Asp Phe Ala Val Tyr Tyr Cys Gln Asn Gly His Asn Phe Pro Tyr
                85                  90                  95

Thr Phe Gly Gln Gly Thr Lys Val Glu Ile Lys
                100                 105

<210> SEQ ID NO 276
<211> LENGTH: 107
<212> TYPE: PRT
<213> ORGANISM: Artificial Sequence
<220> FEATURE:
<223> OTHER INFORMATION: Synthetic Construct

<400> SEQUENCE: 276

Asp Val Val Met Thr Gln Ser Pro Leu Ser Leu Pro Val Thr Leu Gly
1               5                   10                  15

Gln Pro Ala Ser Ile Ser Cys Arg Ala Ser Gln Ser Ile Ser Glu Tyr
                20                  25                  30

Leu His Trp Phe Gln Gln Arg Pro Gly Gln Ser Pro Arg Arg Leu Ile
            35                  40                  45

Tyr Phe Ala Ser Gln Ser Ile Cys Gly Val Pro Asp Arg Phe Ser Gly
    50                  55                  60

Ser Gly Ser Gly Thr Asp Phe Thr Leu Lys Ile Ser Arg Val Glu Ala
65              70                  75                  80

Glu Asp Val Gly Val Tyr Tyr Cys Gln Asn Gly His Asn Phe Pro Tyr
                85                  90                  95

Thr Phe Gly Gln Gly Thr Lys Val Glu Ile Lys
                100                 105

<210> SEQ ID NO 277
<211> LENGTH: 107
<212> TYPE: PRT
<213> ORGANISM: Artificial Sequence
<220> FEATURE:
<223> OTHER INFORMATION: Synthetic Construct

<400> SEQUENCE: 277

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Ser Ile Ser Glu Tyr
            20                  25                  30

Leu His Trp Tyr Leu Gln Lys Pro Gly Gln Ser Pro Gln Leu Leu Ile
        35                  40                  45

Tyr Phe Ala Ser Gln Ser Ile Cys Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Asn Gly His Asn Phe Pro Tyr
                85                  90                  95

Thr Phe Gly Gln Gly Thr Lys Val Glu Ile Lys
            100                 105

<210> SEQ ID NO 278
<211> LENGTH: 107
<212> TYPE: PRT
<213> ORGANISM: Artificial Sequence
<220> FEATURE:
<223> OTHER INFORMATION: Synthetic Construct

<400> SEQUENCE: 278

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Ile Ser Glu Tyr
            20                  25                  30

Leu His Trp Tyr Gln Gln Lys Pro Gly Gln Pro Pro Lys Leu Leu Ile
        35                  40                  45

Tyr Phe Ala Ser Gln Ser Ile Cys Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Asn Gly His Asn Phe Pro Tyr
                85                  90                  95

Thr Phe Gly Gln Gly Thr Lys Val Glu Ile Lys
            100                 105

<210> SEQ ID NO 279
<211> LENGTH: 107
<212> TYPE: PRT
<213> ORGANISM: Artificial Sequence
<220> FEATURE:
<223> OTHER INFORMATION: Synthetic Construct

<400> SEQUENCE: 279

Asp Ile Gln Met Thr Gln Ser Pro Ser Thr Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Leu Tyr Ser Thr Pro Tyr
                85                  90                  95

Thr Phe Gly Gln Gly Thr Lys Val Glu Ile Lys
            100                 105

<210> SEQ ID NO 280
<211> LENGTH: 107
<212> TYPE: PRT
<213> ORGANISM: Artificial Sequence
<220> FEATURE:
<223> OTHER INFORMATION: Synthetic Construct

<400> SEQUENCE: 280

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Ser Thr Pro Tyr
                85                  90                  95

Thr Phe Gly Gln Gly Thr Lys Val Glu Ile Lys
            100                 105

<210> SEQ ID NO 281
<211> LENGTH: 107
<212> TYPE: PRT
<213> ORGANISM: Artificial Sequence
<220> FEATURE:
<223> OTHER INFORMATION: Synthetic Construct

<400> SEQUENCE: 281

Asp Ile Gln Leu Thr Gln Ser Pro Ser Phe Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Tyr Ser Thr Pro Tyr
                85                  90                  95

Thr Phe Gly Gln Gly Thr Lys Val Glu Ile Lys
            100                 105

<210> SEQ ID NO 282
<211> LENGTH: 107
<212> TYPE: PRT
<213> ORGANISM: Artificial Sequence
<220> FEATURE:
<223> OTHER INFORMATION: Synthetic Construct

<400> SEQUENCE: 282

Glu Ile Val Met Thr Gln Ser Pro Ala Thr Leu Ser Val Ser Pro Gly
1               5                   10                  15

Glu Arg Ala Thr Leu Ser Cys Leu Ala Ser Gln Thr Ile Gly Thr Trp
            20                  25                  30

Leu Ala Trp Tyr Gln Gln Lys Pro Gly Gln Ala Pro Arg Leu Leu Ile
        35                  40                  45

Tyr Ala Ala Thr Ser Leu Ala Asp Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Tyr Ser Thr Pro Tyr
                85                  90                  95

Thr Phe Gly Gln Gly Thr Lys Val Glu Ile Lys
            100                 105

<210> SEQ ID NO 283
<211> LENGTH: 107
<212> TYPE: PRT
<213> ORGANISM: Artificial Sequence
<220> FEATURE:
<223> OTHER INFORMATION: Synthetic Construct

<400> SEQUENCE: 283

Glu Ile Val Leu Thr Gln Ser Pro Ala Thr Leu Ser Leu Ser Pro Gly
1               5                   10                  15

Glu Arg Ala Thr Leu Ser Cys Leu Ala Ser Gln Thr Ile Gly Thr Trp
            20                  25                  30

Leu Ala Trp Tyr Gln Gln Lys Pro Gly Gln Ala Pro Arg Leu Leu Ile
        35                  40                  45

Tyr Ala Ala Thr Ser Leu Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Leu Tyr Ser Thr Pro Tyr
                85                  90                  95

Thr Phe Gly Gln Gly Thr Lys Val Glu Ile Lys
            100                 105

<210> SEQ ID NO 284
<211> LENGTH: 107
<212> TYPE: PRT
<213> ORGANISM: Artificial Sequence
<220> FEATURE:
<223> OTHER INFORMATION: Synthetic Construct

<400> SEQUENCE: 284

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Leu Tyr Ser Thr Pro Tyr
            85                  90                  95

Thr Phe Gly Gln Gly Thr Lys Val Glu Ile Lys
            100                 105

<210> SEQ ID NO 285
<211> LENGTH: 107
<212> TYPE: PRT
<213> ORGANISM: Artificial Sequence
<220> FEATURE:
<223> OTHER INFORMATION: Synthetic Construct

<400> SEQUENCE: 285

Glu Ile Val Leu Thr Gln Ser Pro Gly Thr Leu Ser Leu Ser Pro Gly
1               5                   10                  15

Glu Arg Ala Thr Leu Ser Cys Leu Ala Ser Gln Thr Ile Gly Thr Trp
            20                  25                  30

Leu Ala Trp Tyr Gln Gln Lys Pro Gly Gln Ala Pro Arg Leu Leu Ile
            35                  40                  45

Tyr Ala Ala Thr Ser Leu Ala Asp Gly Ile Pro Asp Arg Phe Ser Gly
    50                  55                  60

Ser Gly Ser Gly Thr Asp Phe Thr Leu Thr Ile Ser Arg Leu Glu Pro
65              70                  75                  80

Glu Asp Phe Ala Val Tyr Tyr Cys Gln Gln Leu Tyr Ser Thr Pro Tyr
            85                  90                  95

Thr Phe Gly Gln Gly Thr Lys Val Glu Ile Lys
            100                 105

<210> SEQ ID NO 286
<211> LENGTH: 107
<212> TYPE: PRT
<213> ORGANISM: Artificial Sequence
<220> FEATURE:
<223> OTHER INFORMATION: Synthetic Construct

<400> SEQUENCE: 286

Asp Ile Val Met Thr Gln Ser Pro Leu Ser Leu Pro Val Thr Pro Gly
1               5                   10                  15

Glu Pro Ala Ser Ile Ser Cys Leu Ala Ser Gln Thr Ile Gly Thr Trp
            20                  25                  30

Leu Ala Trp Tyr Leu Gln Lys Pro Gly Gln Ser Pro Gln Leu Leu Ile
            35                  40                  45

Tyr Ala Ala Thr Ser Leu Ala Asp Gly Val Pro Asp Arg Phe Ser Gly
    50                  55                  60

Ser Gly Ser Gly Thr Asp Phe Thr Leu Lys Ile Ser Arg Val Glu Ala
65              70                  75                  80

Glu Asp Val Gly Val Tyr Tyr Cys Gln Gln Leu Tyr Ser Thr Pro Tyr
            85                  90                  95

Thr Phe Gly Gln Gly Thr Lys Val Glu Ile Lys
            100                 105

<210> SEQ ID NO 287
<211> LENGTH: 107
<212> TYPE: PRT
<213> ORGANISM: Artificial Sequence
<220> FEATURE:
<223> OTHER INFORMATION: Synthetic Construct

<400> SEQUENCE: 287

Asp Ile Val Met Thr Gln Ser Pro Asp Ser Leu Ala Val Ser Leu Gly
1               5                   10                  15

Glu Arg Ala Thr Ile Asn Cys Leu Ala Ser Gln Thr Ile Gly Thr Trp
            20                  25                  30

Leu Ala Trp Tyr Gln Gln Lys Pro Gly Gln Pro Pro Lys Leu Leu Ile
        35                  40                  45

Tyr Ala Ala Thr Ser Leu Ala Asp Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Leu Tyr Ser Thr Pro Tyr
                85                  90                  95

Thr Phe Gly Gln Gly Thr Lys Val Glu Ile Lys
            100                 105

<210> SEQ ID NO 288
<211> LENGTH: 107
<212> TYPE: PRT
<213> ORGANISM: Artificial Sequence
<220> FEATURE:
<223> OTHER INFORMATION: Synthetic Construct

<400> SEQUENCE: 288

Asp Val Val Met Thr Gln Ser Pro Leu Ser Leu Pro Val Thr Leu Gly
1               5                   10                  15

Gln Pro Ala Ser Ile Ser Cys Leu Ala Ser Gln Thr Ile Gly Thr Trp
            20                  25                  30

Leu Ala Trp Phe Gln Gln Arg Pro Gly Gln Ser Pro Arg Arg Leu Ile
        35                  40                  45

Tyr Ala Ala Thr Ser Leu Ala Asp Gly Val Pro Asp Arg Phe Ser Gly
50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln Leu Tyr Ser Thr Pro Tyr
                85                  90                  95

Thr Phe Gly Gln Gly Thr Lys Val Glu Ile Lys
            100                 105

<210> SEQ ID NO 289
<211> LENGTH: 112
<212> TYPE: PRT
<213> ORGANISM: Artificial Sequence
<220> FEATURE:
<223> OTHER INFORMATION: Synthetic Construct

<400> SEQUENCE: 289

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Thr Gly Asn Thr Tyr Leu His Trp Phe Gln Gln Arg Pro Gly Gln Ser
        35                  40                  45

Pro Arg Arg Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
            85                  90                  95

Thr His Val Pro Tyr Thr Phe Gly Gln Gly Thr Lys Val Glu Ile Lys
            100                 105                 110

<210> SEQ ID NO 290
<211> LENGTH: 112
<212> TYPE: PRT
<213> ORGANISM: Artificial Sequence
<220> FEATURE:
<223> OTHER INFORMATION: Synthetic Construct

<400> SEQUENCE: 290

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
            85                  90                  95

Thr His Val Pro Tyr Thr Phe Gly Gln Gly Thr Lys Val Glu Ile Lys
            100                 105                 110

<210> SEQ ID NO 291
<211> LENGTH: 112
<212> TYPE: PRT
<213> ORGANISM: Artificial Sequence
<220> FEATURE:
<223> OTHER INFORMATION: Synthetic Construct

<400> SEQUENCE: 291

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Val His Ser
            20                  25                  30

Thr Gly Asn Thr Tyr Leu His Trp Tyr Gln Gln Lys Pro Gly Gln Pro
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Ser Gln Asn
            85                  90                  95

Thr His Val Pro Tyr Thr Phe Gly Gln Gly Thr Lys Val Glu Ile Lys
            100                 105                 110

<210> SEQ ID NO 292
<211> LENGTH: 112
<212> TYPE: PRT
<213> ORGANISM: Artificial Sequence
<220> FEATURE:
<223> OTHER INFORMATION: Synthetic Construct

<400> SEQUENCE: 292

Glu Ile Val Leu Thr Gln Ser Pro Ala Thr Leu Ser Leu Ser Pro Gly
1               5                   10                  15

Glu Arg Ala Thr Leu Ser Cys Arg Ser Ser Gln Ser Leu Val His Ser
            20                  25                  30

Thr Gly Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Ile Pro
    50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 293
<211> LENGTH: 112
<212> TYPE: PRT
<213> ORGANISM: Artificial Sequence
<220> FEATURE:
<223> OTHER INFORMATION: Synthetic Construct

<400> SEQUENCE: 293

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Thr Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 294
<211> LENGTH: 112
<212> TYPE: PRT
<213> ORGANISM: Artificial Sequence
<220> FEATURE:
<223> OTHER INFORMATION: Synthetic Construct

<400> SEQUENCE: 294

Glu Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Ser
            20                  25                  30

Thr Gly Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Ile Pro
    50                  55                  60

Ala Arg Phe Ser Gly Ser Gly Ser Gly Thr Glu Phe Thr Leu Thr Ile
65                  70                  75                  80

Ser Ser Leu Gln Ser Glu Asp Phe Ala Val Tyr Tyr Cys Ser Gln Asn
            85                  90                  95

Thr His Val Pro Tyr Thr Phe Gly Gln Gly Thr Lys Val Glu Ile Lys
            100                 105                 110

<210> SEQ ID NO 295
<211> LENGTH: 112
<212> TYPE: PRT
<213> ORGANISM: Artificial Sequence
<220> FEATURE:
<223> OTHER INFORMATION: Synthetic Construct

<400> SEQUENCE: 295

Asp Ile Gln Met Thr Gln Ser Pro Ser Thr Leu Ser Ala Ser Val Gly
1               5                   10                  15

Asp Arg Val Thr Ile Thr Cys Arg Ser Ser Gln Ser Leu Val His Ser
            20                  25                  30

Thr Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Ser Gln Asn
            85                  90                  95

Thr His Val Pro Tyr Thr Phe Gly Gln Gly Thr Lys Val Glu Ile Lys
            100                 105                 110

<210> SEQ ID NO 296
<211> LENGTH: 112
<212> TYPE: PRT
<213> ORGANISM: Artificial Sequence
<220> FEATURE:
<223> OTHER INFORMATION: Synthetic Construct

<400> SEQUENCE: 296

Asp Ile Gln Leu Thr Gln Ser Pro Ser Phe Leu Ser Ala Ser Val Gly
1               5                   10                  15

Asp Arg Val Thr Ile Thr Cys Arg Ser Ser Gln Ser Leu Val His Ser
            20                  25                  30

Thr Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Glu Asp Phe Ala Thr Tyr Tyr Cys Ser Gln Asn
            85                  90                  95

Thr His Val Pro Tyr Thr Phe Gly Gln Gly Thr Lys Val Glu Ile Lys
            100                 105                 110

<210> SEQ ID NO 297
<211> LENGTH: 112
<212> TYPE: PRT
<213> ORGANISM: Artificial Sequence
<220> FEATURE:
<223> OTHER INFORMATION: Synthetic Construct

<400> SEQUENCE: 297

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Thr Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 298
<211> LENGTH: 112
<212> TYPE: PRT
<213> ORGANISM: Artificial Sequence
<220> FEATURE:
<223> OTHER INFORMATION: Synthetic Construct

<400> SEQUENCE: 298

Glu Ile Val Leu Thr Gln Ser Pro Gly Thr Leu Ser Leu Ser Pro Gly
1               5                   10                  15

Glu Arg Ala Thr Leu Ser Cys Arg Ser Ser Gln Ser Leu Val His Ser
            20                  25                  30

Thr Gly Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Ser Gln Asn
                85                  90                  95

Thr His Val Pro Tyr Thr Phe Gly Gln Gly Thr Lys Val Glu Ile Lys
            100                 105                 110

<210> SEQ ID NO 299
<211> LENGTH: 107
<212> TYPE: PRT
<213> ORGANISM: Artificial Sequence
<220> FEATURE:
<223> OTHER INFORMATION: Synthetic Construct

<400> SEQUENCE: 299

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Glx Tyr
            20                  25                  30

Leu Asn Trp Tyr Gln Gln Lys Pro Gly Lys Ala Pro Lys Leu Leu Ile
        35                  40                  45

Tyr Leu Ser Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Gly Ala Trp
                85                  90                  95

Thr Phe Gly Gln Gly Thr Lys Val Glu Ile Lys
            100                 105

<210> SEQ ID NO 300
<211> LENGTH: 107
<212> TYPE: PRT
<213> ORGANISM: Artificial Sequence
<220> FEATURE:
<223> OTHER INFORMATION: Synthetic Construct

<400> SEQUENCE: 300

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Glx Tyr
            20                  25                  30

Leu Asn Trp Tyr Gln Gln Lys Pro Gly Lys Ala Pro Lys Leu Leu Ile
        35                  40                  45

Tyr Leu Ser Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly His Thr Gly Ala Trp
                85                  90                  95

Thr Phe Gly Gln Gly Thr Lys Val Glu Ile Lys
            100                 105

<210> SEQ ID NO 301
<211> LENGTH: 107
<212> TYPE: PRT
<213> ORGANISM: Artificial Sequence
<220> FEATURE:
<223> OTHER INFORMATION: Synthetic Construct

<400> SEQUENCE: 301

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asp Ile Ser Glx Tyr
            20                  25                  30

Leu Asn Trp Tyr Gln Gln Lys Pro Gly Lys Ala Pro Lys Leu Leu Ile
        35                  40                  45

Tyr Leu Ser Ser Arg Leu His Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Gly His Thr Gly Ala Trp
                85                  90                  95

Thr Phe Gly Gln Gly Thr Lys Val Glu Ile Lys
            100                 105

<210> SEQ ID NO 302
<211> LENGTH: 107
<212> TYPE: PRT
<213> ORGANISM: Artificial Sequence
<220> FEATURE:
<223> OTHER INFORMATION: Synthetic Construct

<400> SEQUENCE: 302

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asp Ile Ser Glx Tyr
            20                  25                  30

Leu Asn Trp Tyr Gln Gln Lys Pro Gly Lys Ala Pro Lys Leu Leu Ile
        35                  40                  45

Tyr Leu Ser Ser Arg Leu His Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly His Thr Gly Ala Trp
                85                  90                  95

Thr Phe Gly Gln Gly Thr Lys Val Glu Ile Lys
            100                 105

<210> SEQ ID NO 303
<211> LENGTH: 107
<212> TYPE: PRT
<213> ORGANISM: Artificial Sequence
<220> FEATURE:
<223> OTHER INFORMATION: Synthetic Construct

<400> SEQUENCE: 303

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Glx Tyr
            20                  25                  30

Leu Asn Trp Tyr Gln Gln Lys Pro Gly Gln Ala Pro Arg Leu Leu Ile
        35                  40                  45

Tyr Leu Ser Ser Arg Leu His Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly His Thr Gly Ala Trp
                85                  90                  95

Thr Phe Gly Gln Gly Thr Lys Val Glu Ile Lys
            100                 105

<210> SEQ ID NO 304
<211> LENGTH: 107
<212> TYPE: PRT
<213> ORGANISM: Artificial Sequence
<220> FEATURE:
<223> OTHER INFORMATION: Synthetic Construct

<400> SEQUENCE: 304

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asp Ile Ser Glx Tyr
            20                  25                  30

Leu Asn Trp Tyr Gln Gln Lys Pro Gly Gln Ala Pro Arg Leu Leu Ile
        35                  40                  45

Tyr Leu Ser Ser Arg Leu His Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Gly His Thr Gly Ala Trp
            85                  90                  95

Thr Phe Gly Gln Gly Thr Lys Val Glu Ile Lys
            100                 105

<210> SEQ ID NO 305
<211> LENGTH: 107
<212> TYPE: PRT
<213> ORGANISM: Artificial Sequence
<220> FEATURE:
<223> OTHER INFORMATION: Synthetic Construct

<400> SEQUENCE: 305

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Asp Ile Ser Glx Tyr
            20                  25                  30

Leu Asn Trp Tyr Gln Gln Lys Pro Gly Gln Ala Pro Arg Leu Leu Ile
            35                  40                  45

Tyr Leu Ser Ser Arg Leu His Ser Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Gly His Thr Gly Ala Trp
            85                  90                  95

Thr Phe Gly Gln Gly Thr Lys Val Glu Ile Lys
            100                 105

<210> SEQ ID NO 306
<211> LENGTH: 107
<212> TYPE: PRT
<213> ORGANISM: Artificial Sequence
<220> FEATURE:
<223> OTHER INFORMATION: Synthetic Construct

<400> SEQUENCE: 306

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Asp Ile Ser Glx Tyr
            20                  25                  30

Leu Asn Trp Tyr Leu Gln Lys Pro Gly Gln Ser Pro Gln Leu Leu Ile
            35                  40                  45

Tyr Leu Ser Ser Arg Leu His Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln Gly His Thr Gly Ala Trp
            85                  90                  95

Thr Phe Gly Gln Gly Thr Lys Val Glu Ile Lys
            100                 105

<210> SEQ ID NO 307
<211> LENGTH: 107
<212> TYPE: PRT
<213> ORGANISM: Artificial Sequence
<220> FEATURE:
<223> OTHER INFORMATION: Synthetic Construct

<400> SEQUENCE: 307

Asp Val Val Met Thr Gln Ser Pro Leu Ser Leu Pro Val Thr Leu Gly
1               5                   10                  15

Gln Pro Ala Ser Ile Ser Cys Arg Ala Ser Gln Asp Ile Ser Glx Tyr
            20                  25                  30

Leu Asn Trp Phe Gln Gln Arg Pro Gly Gln Ser Pro Arg Arg Leu Ile
        35                  40                  45

Tyr Leu Ser Ser Arg Leu His Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln Gly His Thr Gly Ala Trp
                85                  90                  95

Thr Phe Gly Gln Gly Thr Lys Val Glu Ile Lys
                100                 105

<210> SEQ ID NO 308
<211> LENGTH: 107
<212> TYPE: PRT
<213> ORGANISM: Artificial Sequence
<220> FEATURE:
<223> OTHER INFORMATION: Synthetic Construct

<400> SEQUENCE: 308

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Asp Ile Ser Glx Tyr
            20                  25                  30

Leu Asn Trp Tyr Gln Gln Lys Pro Gly Gln Pro Pro Lys Leu Leu Ile
        35                  40                  45

Tyr Leu Ser Ser Arg Leu His Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Gly His Thr Gly Ala Trp
                85                  90                  95

Thr Phe Gly Gln Gly Thr Lys Val Glu Ile Lys
                100                 105

<210> SEQ ID NO 309
<211> LENGTH: 107
<212> TYPE: PRT
<213> ORGANISM: Artificial Sequence
<220> FEATURE:
<223> OTHER INFORMATION: Synthetic Construct

<400> SEQUENCE: 309

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Glu Tyr
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Cys Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Lys Ala His Asn Phe Pro Tyr
                85                  90                  95

Thr Phe Gly Gln Gly Thr Lys Val Glu Ile Lys
            100                 105

<210> SEQ ID NO 310
<211> LENGTH: 107
<212> TYPE: PRT
<213> ORGANISM: Artificial Sequence
<220> FEATURE:
<223> OTHER INFORMATION: Synthetic Construct

<400> SEQUENCE: 310

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Ser Ile Arg Glu Tyr
                20                  25                  30

Leu His Trp Tyr Gln Gln Lys Pro Gly Lys Ala Pro Lys Leu Leu Ile
            35                  40                  45

Tyr Phe Ala Ser Gln Ser Ile Cys Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Lys Ala His Asn Phe Pro Tyr
                85                  90                  95

Thr Phe Gly Gln Gly Thr Lys Val Glu Ile Lys
            100                 105

<210> SEQ ID NO 311
<211> LENGTH: 107
<212> TYPE: PRT
<213> ORGANISM: Artificial Sequence
<220> FEATURE:
<223> OTHER INFORMATION: Synthetic Construct

<400> SEQUENCE: 311

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Arg Glu Tyr
                20                  25                  30

Leu His Trp Tyr Gln Gln Lys Pro Gly Gln Ala Pro Arg Leu Leu Ile
            35                  40                  45

Tyr Phe Ala Ser Gln Ser Ile Cys Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Lys Ala His Asn Phe Pro Tyr
                85                  90                  95

Thr Phe Gly Gln Gly Thr Lys Val Glu Ile Lys
            100                 105

<210> SEQ ID NO 312
<211> LENGTH: 107
<212> TYPE: PRT
<213> ORGANISM: Artificial Sequence
<220> FEATURE:
<223> OTHER INFORMATION: Synthetic Construct

<400> SEQUENCE: 312

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Arg Glu Tyr
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Cys Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Lys Ala His Asn Phe Pro Tyr
                85                  90                  95

Thr Phe Gly Gln Gly Thr Lys Val Glu Ile Lys
            100                 105
```

<210> SEQ ID NO 313
<211> LENGTH: 107
<212> TYPE: PRT
<213> ORGANISM: Artificial Sequence
<220> FEATURE:
<223> OTHER INFORMATION: Synthetic Construct

<400> SEQUENCE: 313

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Arg Glu Tyr
            20                  25                  30

Leu His Trp Tyr Gln Gln Lys Pro Gly Gln Ala Pro Arg Leu Leu Ile
        35                  40                  45

Tyr Phe Ala Ser Gln Ser Ile Cys Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Lys Ala His Asn Phe Pro Tyr
                85                  90                  95

Thr Phe Gly Gln Gly Thr Lys Val Glu Ile Lys
            100                 105
```

<210> SEQ ID NO 314
<211> LENGTH: 107
<212> TYPE: PRT
<213> ORGANISM: Artificial Sequence
<220> FEATURE:
<223> OTHER INFORMATION: Synthetic Construct

<400> SEQUENCE: 314

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Glu Tyr
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Cys Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80
```

```
Glu Asp Ile Ala Thr Tyr Tyr Cys Gln Lys Ala His Asn Phe Pro Tyr
                85                  90                  95

Thr Phe Gly Gln Gly Thr Lys Val Glu Ile Lys
            100                 105
```

<210> SEQ ID NO 315
<211> LENGTH: 107
<212> TYPE: PRT
<213> ORGANISM: Artificial Sequence
<220> FEATURE:
<223> OTHER INFORMATION: Synthetic Construct

<400> SEQUENCE: 315

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Arg Glu Tyr
                20                  25                  30

Leu His Trp Tyr Gln Gln Lys Pro Gly Gln Ala Pro Arg Leu Leu Ile
            35                  40                  45

Tyr Phe Ala Ser Gln Ser Ile Cys Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Lys Ala His Asn Phe Pro Tyr
                85                  90                  95

Thr Phe Gly Gln Gly Thr Lys Val Glu Ile Lys
            100                 105
```

<210> SEQ ID NO 316
<211> LENGTH: 107
<212> TYPE: PRT
<213> ORGANISM: Artificial Sequence
<220> FEATURE:
<223> OTHER INFORMATION: Synthetic Construct

<400> SEQUENCE: 316

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Ile Arg Glu Tyr
                20                  25                  30

Leu His Trp Tyr Gln Gln Lys Pro Gly Gln Pro Pro Lys Leu Leu Ile
            35                  40                  45

Tyr Phe Ala Ser Gln Ser Ile Cys Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Lys Ala His Asn Phe Pro Tyr
                85                  90                  95

Thr Phe Gly Gln Gly Thr Lys Val Glu Ile Lys
            100                 105
```

<210> SEQ ID NO 317
<211> LENGTH: 107
<212> TYPE: PRT
<213> ORGANISM: Artificial Sequence
<220> FEATURE:
<223> OTHER INFORMATION: Synthetic Construct -continued

```
<400> SEQUENCE: 317

Asp Val Val Met Thr Gln Ser Pro Leu Ser Leu Pro Val Thr Leu Gly
1               5                   10                  15

Gln Pro Ala Ser Ile Ser Cys Arg Ala Ser Gln Ser Ile Arg Glu Tyr
            20                  25                  30

Leu His Trp Phe Gln Gln Arg Pro Gly Gln Ser Pro Arg Arg Leu Ile
        35                  40                  45

Tyr Phe Ala Ser Gln Ser Ile Cys Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Lys Ala His Asn Phe Pro Tyr
                85                  90                  95

Thr Phe Gly Gln Gly Thr Lys Val Glu Ile Lys
            100                 105

<210> SEQ ID NO 318
<211> LENGTH: 107
<212> TYPE: PRT
<213> ORGANISM: Artificial Sequence
<220> FEATURE:
<223> OTHER INFORMATION: Synthetic Construct

<400> SEQUENCE: 318

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Ser Ile Arg Glu Tyr
            20                  25                  30

Leu His Trp Tyr Leu Gln Lys Pro Gly Gln Ser Pro Gln Leu Leu Ile
        35                  40                  45

Tyr Phe Ala Ser Gln Ser Ile Cys Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Lys Ala His Asn Phe Pro Tyr
                85                  90                  95

Thr Phe Gly Gln Gly Thr Lys Val Glu Ile Lys
            100                 105

<210> SEQ ID NO 319
<211> LENGTH: 118
<212> TYPE: PRT
<213> ORGANISM: Artificial Sequence
<220> FEATURE:
<223> OTHER INFORMATION: Synthetic Construct

<400> SEQUENCE: 319

Gln Val Gln Leu Val Gln Ser Gly Ala Glu Val Lys Lys Pro Gly Ala
1               5                   10                  15

Ser Val Lys Val Ser Cys Lys Ala Ser Gly Ser Glu Val Phe Pro Ile
            20                  25                  30

Thr Tyr Met Asn Trp Val Arg Gln Ala Pro Gly Gln Gly Leu Glu Trp
        35                  40                  45

Ile Gly Asp Ile Leu Pro Ser Ile Gly Arg Thr Met Tyr Gly Gln Lys
    50                  55                  60

Phe Gln Gly Arg Val Thr Met Thr Arg Asp Thr Ser Thr Ser Thr Val
65                  70                  75                  80
```

```
Tyr Met Glu Leu Ser Ser Leu Arg Ser Glu Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 320
<211> LENGTH: 118
<212> TYPE: PRT
<213> ORGANISM: Artificial Sequence
<220> FEATURE:
<223> OTHER INFORMATION: Synthetic Construct

<400> SEQUENCE: 320

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Glu Val Phe Pro Ile
            20                  25                  30

Thr Tyr Met Asn Trp Val Arg Gln Ala Pro Gly Lys Gly Leu Glu Trp
        35                  40                  45

Ile Gly Asp Ile Leu Pro Ser Ile Gly Arg Thr Met Tyr Gly Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 321
<211> LENGTH: 118
<212> TYPE: PRT
<213> ORGANISM: Artificial Sequence
<220> FEATURE:
<223> OTHER INFORMATION: Synthetic Construct

<400> SEQUENCE: 321

Gln Val Gln Leu Val Gln Ser Gly Ala Glu Val Lys Lys Pro Gly Ser
1               5                   10                  15

Ser Val Lys Val Ser Cys Lys Ala Ser Gly Ser Glu Val Phe Pro Ile
            20                  25                  30

Thr Tyr Met Asn Trp Val Arg Gln Ala Pro Gly Gln Gly Leu Glu Trp
        35                  40                  45

Ile Gly Asp Ile Leu Pro Ser Ile Gly Arg Thr Met Tyr Gly Gln Lys
    50                  55                  60

Phe Gln Gly Arg Val Thr Ile Thr Ala Asp Glu Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115
```

```
<210> SEQ ID NO 322
<211> LENGTH: 118
<212> TYPE: PRT
<213> ORGANISM: Artificial Sequence
<220> FEATURE:
<223> OTHER INFORMATION: Synthetic Construct

<400> SEQUENCE: 322

Glu Val Gln Leu Val Gln Ser Gly Ala Glu Val Lys Lys Pro Gly Glu
1               5                   10                  15

Ser Leu Lys Ile Ser Cys Lys Gly Ser Gly Ser Glu Val Phe Pro Ile
                20                  25                  30

Thr Tyr Met Asn Trp Val Arg Gln Met Pro Gly Lys Gly Leu Glu Trp
        35                  40                  45

Ile Gly Asp Ile Leu Pro Ser Ile Gly Arg Thr Met Tyr Gly Pro Ser
    50                  55                  60

Phe Gln Gly Gln Val Thr Ile Ser Ala Asp Lys Ser Ile Ser Thr Ala
65                  70                  75                  80

Tyr Leu Gln Trp Ser Ser Leu Lys Ala Ser Asp Thr Ala Met Tyr Tyr
                85                  90                  95

Cys Ala Arg Ser Glu Gly Tyr Leu Leu Ala Tyr Trp Gly Gln Gly Thr
                100                 105                 110

Leu Val Thr Val Ser Ser
        115

<210> SEQ ID NO 323
<211> LENGTH: 118
<212> TYPE: PRT
<213> ORGANISM: Artificial Sequence
<220> FEATURE:
<223> OTHER INFORMATION: Synthetic Construct

<400> SEQUENCE: 323

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Glu Val Phe Pro Ile
                20                  25                  30

Thr Tyr Met Asn Trp Val Arg Gln Ala Pro Gly Lys Gly Leu Glu Trp
        35                  40                  45

Ile Gly Asp Ile Leu Pro Ser Ile Gly Arg Thr Met Tyr Gly Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Ser Glu Gly Tyr Leu Leu Ala Tyr Trp Gly Gln Gly Thr
                100                 105                 110

Leu Val Thr Val Ser Ser
        115

<210> SEQ ID NO 324
<211> LENGTH: 118
<212> TYPE: PRT
<213> ORGANISM: Artificial Sequence
<220> FEATURE:
<223> OTHER INFORMATION: Synthetic Construct

<400> SEQUENCE: 324

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Ser Glu Val Phe Pro Ile
            20                  25                  30

Thr Tyr Met Asn Trp Val Arg Gln Ala Pro Gly Lys Gly Leu Glu Trp
        35                  40                  45

Ile Gly Asp Ile Leu Pro Ser Ile Gly Arg Thr Met Tyr Gly Asp Ser
 50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 325
<211> LENGTH: 118
<212> TYPE: PRT
<213> ORGANISM: Artificial Sequence
<220> FEATURE:
<223> OTHER INFORMATION: Synthetic Construct

<400> SEQUENCE: 325

Gln Val Gln Leu Val Glu Ser Gly Gly Val Val Gln Pro Gly Arg
1               5                   10                  15

Ser Leu Arg Leu Ser Cys Ala Ala Ser Gly Ser Glu Val Phe Pro Ile
            20                  25                  30

Thr Tyr Met Asn Trp Val Arg Gln Ala Pro Gly Lys Gly Leu Glu Trp
        35                  40                  45

Ile Gly Asp Ile Leu Pro Ser Ile Gly Arg Thr Met Tyr Gly Asp Ser
 50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 326
<211> LENGTH: 118
<212> TYPE: PRT
<213> ORGANISM: Artificial Sequence
<220> FEATURE:
<223> OTHER INFORMATION: Synthetic Construct

<400> SEQUENCE: 326

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Glu Val Phe Pro Ile
            20                  25                  30

Thr Tyr Met Asn Trp Ile Arg Gln Pro Pro Gly Lys Gly Leu Glu Trp
        35                  40                  45

Ile Gly Asp Ile Leu Pro Ser Ile Gly Arg Thr Met Tyr Gly Pro Ser
 50                  55                  60
```

```
Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 327
<211> LENGTH: 118
<212> TYPE: PRT
<213> ORGANISM: Artificial Sequence
<220> FEATURE:
<223> OTHER INFORMATION: Synthetic Construct

<400> SEQUENCE: 327

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ser Glu Val Phe Pro Ile
            20                  25                  30

Thr Tyr Met Asn Trp Ile Arg Gln Pro Pro Gly Lys Gly Leu Glu Trp
        35                  40                  45

Ile Gly Asp Ile Leu Pro Ser Ile Gly Arg Thr Met Tyr Gly Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 328
<211> LENGTH: 118
<212> TYPE: PRT
<213> ORGANISM: Artificial Sequence
<220> FEATURE:
<223> OTHER INFORMATION: Synthetic Construct

<400> SEQUENCE: 328

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Glu Val Phe Pro Ile
            20                  25                  30

Thr Tyr Met Asn Trp Ile Arg Gln Pro Pro Gly Lys Gly Leu Glu Trp
        35                  40                  45

Ile Gly Asp Ile Leu Pro Ser Ile Gly Arg Thr Met Tyr Gly Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Glu Gly Tyr Leu Leu Ala Tyr Trp Gly Gln Gly Thr
            100                 105                 110
```

Leu Val Thr Val Ser Ser
        115

<210> SEQ ID NO 329
<211> LENGTH: 120
<212> TYPE: PRT
<213> ORGANISM: Artificial Sequence
<220> FEATURE:
<223> OTHER INFORMATION: Synthetic Construct

<400> SEQUENCE: 329

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Gly Ser
            20                  25                  30

Leu Leu His Trp Val Arg Gln Ala Pro Gly Gln Gly Leu Glu Trp Ile
        35                  40                  45

Gly Trp Ile Asp Pro Glu Asp Gly Glu Thr Arg Phe Asp Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Glu Tyr Ser Asn Pro Ala Trp Phe Ala Tyr Trp Gly Gln
            100                 105                 110

Gly Thr Leu Val Thr Val Ser Ser
        115                 120

<210> SEQ ID NO 330
<211> LENGTH: 120
<212> TYPE: PRT
<213> ORGANISM: Artificial Sequence
<220> FEATURE:
<223> OTHER INFORMATION: Synthetic Construct

<400> SEQUENCE: 330

Glu Val Gln Leu Val Gln Ser Gly Ala Glu Val Lys Lys Pro Gly Glu
1               5                   10                  15

Ser Leu Lys Ile Ser Cys Lys Gly Ser Gly Phe Asn Ile Lys Gly Ser
            20                  25                  30

Leu Leu His Trp Val Arg Gln Met Pro Gly Lys Gly Leu Glu Trp Ile
        35                  40                  45

Gly Trp Ile Asp Pro Glu Asp Gly Glu Thr Arg Phe Asp Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Thr Glu Tyr Ser Asn Pro Ala Trp Phe Ala Tyr Trp Gly Gln
            100                 105                 110

Gly Thr Leu Val Thr Val Ser Ser
        115                 120

<210> SEQ ID NO 331
<211> LENGTH: 120
<212> TYPE: PRT
<213> ORGANISM: Artificial Sequence
<220> FEATURE:
<223> OTHER INFORMATION: Synthetic Construct

<400> SEQUENCE: 331

Glu Val Gln Leu Leu Glu Ser Gly Gly Leu Val Gln Pro Gly Gly
1               5                   10                  15

Ser Leu Arg Leu Ser Cys Ala Ala Ser Gly Phe Asn Ile Lys Gly Ser
            20                  25                  30

Leu Leu His Trp Val Arg Gln Ala Pro Gly Lys Gly Leu Glu Trp Ile
        35                  40                  45

Gly Trp Ile Asp Pro Glu Asp Gly Glu Thr Arg Phe Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Glu Tyr Ser Asn Pro Ala Trp Phe Ala Tyr Trp Gly Gln
            100                 105                 110

Gly Thr Leu Val Thr Val Ser Ser
            115                 120

<210> SEQ ID NO 332
<211> LENGTH: 120
<212> TYPE: PRT
<213> ORGANISM: Artificial Sequence
<220> FEATURE:
<223> OTHER INFORMATION: Synthetic Construct

<400> SEQUENCE: 332

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Gly Ser
            20                  25                  30

Leu Leu His Trp Val Arg Gln Ala Pro Gly Gln Gly Leu Glu Trp Ile
        35                  40                  45

Gly Trp Ile Asp Pro Glu Asp Gly Glu Thr Arg Phe Asp Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Glu Tyr Ser Asn Pro Ala Trp Phe Ala Tyr Trp Gly Gln
            100                 105                 110

Gly Thr Leu Val Thr Val Ser Ser
            115                 120

<210> SEQ ID NO 333
<211> LENGTH: 120
<212> TYPE: PRT
<213> ORGANISM: Artificial Sequence
<220> FEATURE:
<223> OTHER INFORMATION: Synthetic Construct

<400> SEQUENCE: 333

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Ile Lys Gly Ser
            20                  25                  30

Leu Leu His Trp Val Arg Gln Ala Pro Gly Lys Gly Leu Glu Trp Ile
        35                  40                  45

```
Gly Trp Ile Asp Pro Glu Asp Gly Glu Thr Arg Phe Asp Asp Ser Val
        50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Thr Glu Tyr Ser Asn Pro Ala Trp Phe Ala Tyr Trp Gly Gln
                100                 105                 110

Gly Thr Leu Val Thr Val Ser Ser
            115                 120

<210> SEQ ID NO 334
<211> LENGTH: 120
<212> TYPE: PRT
<213> ORGANISM: Artificial Sequence
<220> FEATURE:
<223> OTHER INFORMATION: Synthetic Construct

<400> SEQUENCE: 334

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Gly Ser
                20                  25                  30

Leu Leu His Trp Val Arg Gln Ala Pro Gly Lys Gly Leu Glu Trp Ile
            35                  40                  45

Gly Trp Ile Asp Pro Glu Asp Gly Glu Thr Arg Phe Asp Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Thr Glu Tyr Ser Asn Pro Ala Trp Phe Ala Tyr Trp Gly Gln
                100                 105                 110

Gly Thr Leu Val Thr Val Ser Ser
            115                 120

<210> SEQ ID NO 335
<211> LENGTH: 120
<212> TYPE: PRT
<213> ORGANISM: Artificial Sequence
<220> FEATURE:
<223> OTHER INFORMATION: Synthetic Construct

<400> SEQUENCE: 335

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Gly Ser
                20                  25                  30

Leu Leu His Trp Val Arg Gln Ala Pro Gly Lys Gly Leu Glu Trp Ile
            35                  40                  45

Gly Trp Ile Asp Pro Glu Asp Gly Glu Thr Arg Phe Asp Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

```
Ala Arg Thr Glu Tyr Ser Asn Pro Ala Trp Phe Ala Tyr Trp Gly Gln
            100                 105                 110

Gly Thr Leu Val Thr Val Ser Ser
        115                 120

<210> SEQ ID NO 336
<211> LENGTH: 120
<212> TYPE: PRT
<213> ORGANISM: Artificial Sequence
<220> FEATURE:
<223> OTHER INFORMATION: Synthetic Construct

<400> SEQUENCE: 336

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Asn Ile Lys Gly Ser
            20                  25                  30

Leu Leu His Trp Ile Arg Gln Pro Pro Gly Lys Gly Leu Glu Trp Ile
        35                  40                  45

Gly Trp Ile Asp Pro Glu Asp Gly Glu Thr Arg Phe Asp Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Thr Glu Tyr Ser Asn Pro Ala Trp Phe Ala Tyr Trp Gly Gln
            100                 105                 110

Gly Thr Leu Val Thr Val Ser Ser
        115                 120

<210> SEQ ID NO 337
<211> LENGTH: 120
<212> TYPE: PRT
<213> ORGANISM: Artificial Sequence
<220> FEATURE:
<223> OTHER INFORMATION: Synthetic Construct

<400> SEQUENCE: 337

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Asn Ile Lys Gly Ser
            20                  25                  30

Leu Leu His Trp Val Arg Gln Ala Pro Gly Lys Gly Leu Glu Trp Ile
        35                  40                  45

Gly Trp Ile Asp Pro Glu Asp Gly Glu Thr Arg Phe Asp Ala Pro Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Arg Thr Glu Tyr Ser Asn Pro Ala Trp Phe Ala Tyr Trp Gly Gln
            100                 105                 110

Gly Thr Leu Val Thr Val Ser Ser
        115                 120

<210> SEQ ID NO 338
<211> LENGTH: 120
<212> TYPE: PRT
```

<213> ORGANISM: Artificial Sequence
<220> FEATURE:
<223> OTHER INFORMATION: Synthetic Construct

<400> SEQUENCE: 338

```
Gln Val Gln Leu Gln Glu Ser Gly Pro Gly Leu Val Lys Pro Ser Gln
1               5                   10                  15
Thr Leu Ser Leu Thr Cys Thr Val Ser Gly Phe Asn Ile Lys Gly Ser
            20                  25                  30
Leu Leu His Trp Ile Arg Gln Pro Pro Gly Lys Gly Leu Glu Trp Ile
        35                  40                  45
Gly Trp Ile Asp Pro Glu Asp Gly Glu Thr Arg Phe Asp Pro Ser Leu
    50                  55                  60
Lys Ser Arg Val Thr Ile Ser Val Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Thr Glu Tyr Ser Asn Pro Ala Trp Phe Ala Tyr Trp Gly Gln
            100                 105                 110
Gly Thr Leu Val Thr Val Ser Ser
        115                 120
```

<210> SEQ ID NO 339
<211> LENGTH: 121
<212> TYPE: PRT
<213> ORGANISM: Artificial Sequence
<220> FEATURE:
<223> OTHER INFORMATION: Synthetic Construct

<400> SEQUENCE: 339

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Asp Met Ser Trp Val Arg Gln Ala Pro Gly Lys Gly Leu Glu Trp Val
        35                  40                  45
Ala Thr Ile Ser Ser Gly Gly Asp Tyr Thr Tyr Tyr Pro Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg His Gly Tyr Gly Asn Tyr Asp Trp Tyr Phe Asp Val Trp Gly
            100                 105                 110
Gln Gly Thr Leu Val Thr Val Ser Ser
        115                 120
```

<210> SEQ ID NO 340
<211> LENGTH: 121
<212> TYPE: PRT
<213> ORGANISM: Artificial Sequence
<220> FEATURE:
<223> OTHER INFORMATION: Synthetic Construct

<400> SEQUENCE: 340

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
```

Asp Met Ser Trp Val Arg Gln Ala Pro Gly Lys Gly Leu Glu Trp Val
            35                  40                  45

Ala Thr Ile Ser Ser Gly Gly Asp Tyr Thr Tyr Tyr Pro Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Gly Tyr Gly Asn Tyr Asp Trp Tyr Phe Asp Val Trp Gly
            100                 105                 110

Gln Gly Thr Leu Val Thr Val Ser Ser
            115                 120

<210> SEQ ID NO 341
<211> LENGTH: 121
<212> TYPE: PRT
<213> ORGANISM: Artificial Sequence
<220> FEATURE:
<223> OTHER INFORMATION: Synthetic Construct

<400> SEQUENCE: 341

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
            35                  40                  45

Ala Thr Ile Ser Ser Gly Gly Asp Tyr Thr Tyr Tyr Pro Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Gly Tyr Gly Asn Tyr Asp Trp Tyr Phe Asp Val Trp Gly
            100                 105                 110

Gln Gly Thr Leu Val Thr Val Ser Ser
            115                 120

<210> SEQ ID NO 342
<211> LENGTH: 121
<212> TYPE: PRT
<213> ORGANISM: Artificial Sequence
<220> FEATURE:
<223> OTHER INFORMATION: Synthetic Construct

<400> SEQUENCE: 342

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
            35                  40                  45

Ala Thr Ile Ser Ser Gly Gly Asp Tyr Thr Tyr Tyr Pro Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 343
<211> LENGTH: 121
<212> TYPE: PRT
<213> ORGANISM: Artificial Sequence
<220> FEATURE:
<223> OTHER INFORMATION: Synthetic Construct

<400> SEQUENCE: 343

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Asn Tyr
            20                  25                  30

Asp Met Ser Trp Val Arg Gln Ala Pro Gly Gln Gly Leu Glu Trp Val
        35                  40                  45

Ala Thr Ile Ser Ser Gly Gly Asp Tyr Thr Tyr Tyr Pro Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 344
<211> LENGTH: 121
<212> TYPE: PRT
<213> ORGANISM: Artificial Sequence
<220> FEATURE:
<223> OTHER INFORMATION: Synthetic Construct

<400> SEQUENCE: 344

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Asn Tyr
            20                  25                  30

Asp Met Ser Trp Val Arg Gln Ala Pro Gly Gln Gly Leu Glu Trp Val
        35                  40                  45

Ala Thr Ile Ser Ser Gly Gly Asp Tyr Thr Tyr Tyr Pro Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Tyr Gly Asn Tyr Asp Trp Tyr Phe Asp Val Trp Gly
            100                 105                 110

Gln Gly Thr Leu Val Thr Val Ser Ser
        115                 120

```
<210> SEQ ID NO 345
<211> LENGTH: 121
<212> TYPE: PRT
<213> ORGANISM: Artificial Sequence
<220> FEATURE:
<223> OTHER INFORMATION: Synthetic Construct

<400> SEQUENCE: 345

Glu Val Gln Leu Val Gln Ser Gly Ala Glu Val Lys Pro Gly Glu
1               5                   10                  15

Ser Leu Lys Ile Ser Cys Lys Gly Ser Gly Phe Thr Phe Ser Asn Tyr
                20                  25                  30

Asp Met Ser Trp Val Arg Gln Met Pro Gly Lys Gly Leu Glu Trp Val
            35                  40                  45

Ala Thr Ile Ser Ser Gly Gly Asp Tyr Thr Tyr Tyr Pro Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 346
<211> LENGTH: 121
<212> TYPE: PRT
<213> ORGANISM: Artificial Sequence
<220> FEATURE:
<223> OTHER INFORMATION: Synthetic Construct

<400> SEQUENCE: 346

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Thr Phe Ser Asn Tyr
                20                  25                  30

Asp Met Ser Trp Ile Arg Gln Pro Pro Gly Lys Gly Leu Glu Trp Val
            35                  40                  45

Ala Thr Ile Ser Ser Gly Gly Asp Tyr Thr Tyr Tyr Pro Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 347
<211> LENGTH: 121
<212> TYPE: PRT
<213> ORGANISM: Artificial Sequence
<220> FEATURE:
<223> OTHER INFORMATION: Synthetic Construct

<400> SEQUENCE: 347

Glu Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
            35                  40                  45

Ala Thr Ile Ser Ser Gly Gly Asp Tyr Thr Tyr Tyr Pro Ala Pro Val
 50                  55                  60

Lys Gly Arg Phe Thr Ile Ser Arg Asp Asp Ser Lys Asn Thr Leu Tyr
 65                  70                  75                  80

Leu Gln Met Asn Ser Leu Lys Thr Glu Asp Thr Ala Val Tyr Tyr Cys
                85                  90                  95

Ala Arg His Gly Tyr Gly Asn Tyr Asp Trp Tyr Phe Asp Val Trp Gly
            100                 105                 110

Gln Gly Thr Leu Val Thr Val Ser Ser
            115                 120
```

<210> SEQ ID NO 348
<211> LENGTH: 121
<212> TYPE: PRT
<213> ORGANISM: Artificial Sequence
<220> FEATURE:
<223> OTHER INFORMATION: Synthetic Construct

<400> SEQUENCE: 348

```
Gln Leu Gln Leu Gln Glu Ser Gly Pro Gly Leu Val Lys Pro Ser Glu
 1               5                  10                  15

Thr Leu Ser Leu Thr Cys Thr Val Ser Gly Phe Thr Phe Ser Asn Tyr
            20                  25                  30

Asp Met Ser Trp Ile Arg Gln Pro Pro Gly Lys Gly Leu Glu Trp Val
            35                  40                  45

Ala Thr Ile Ser Ser Gly Gly Asp Tyr Thr Tyr Tyr Pro Pro Ser Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg His Gly Tyr Gly Asn Tyr Asp Trp Tyr Phe Asp Val Trp Gly
            100                 105                 110

Gln Gly Thr Leu Val Thr Val Ser Ser
            115                 120
```

<210> SEQ ID NO 349
<211> LENGTH: 118
<212> TYPE: PRT
<213> ORGANISM: Artificial Sequence
<220> FEATURE:
<223> OTHER INFORMATION: Synthetic Construct

<400> SEQUENCE: 349

```
Gln Val Gln Leu Val Gln Ser Gly Ala Glu Val Lys Lys Pro Gly Ala
 1               5                  10                  15

Ser Val Lys Val Ser Cys Lys Ala Ser Gly Ser Glu Val Phe Pro Ile
            20                  25                  30

Thr Tyr Met Asn Trp Val Arg Gln Ala Pro Gly Gln Gly Leu Glu Trp
            35                  40                  45

Ile Gly Asp Ile Leu Pro Ser Ile Gly Arg Thr Met Tyr Gly Gln Lys
 50                  55                  60
```

Phe Gln Gly Arg Val Thr Met Thr Arg Asp Thr Ser Thr Ser Thr Val
65                  70                  75                  80

Tyr Met Glu Leu Ser Ser Leu Arg Ser Glu Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 350
<211> LENGTH: 118
<212> TYPE: PRT
<213> ORGANISM: Artificial Sequence
<220> FEATURE:
<223> OTHER INFORMATION: Synthetic Construct

<400> SEQUENCE: 350

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Glu Val Phe Pro Ile
            20                  25                  30

Thr Tyr Met Asn Trp Val Arg Gln Ala Pro Gly Lys Gly Leu Glu Trp
        35                  40                  45

Ile Gly Asp Ile Leu Pro Ser Ile Gly Arg Thr Met Tyr Gly Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 351
<211> LENGTH: 118
<212> TYPE: PRT
<213> ORGANISM: Artificial Sequence
<220> FEATURE:
<223> OTHER INFORMATION: Synthetic Construct

<400> SEQUENCE: 351

Gln Val Gln Leu Val Gln Ser Gly Ala Glu Val Lys Lys Pro Gly Ser
1               5                   10                  15

Ser Val Lys Val Ser Cys Lys Ala Ser Gly Ser Glu Val Phe Pro Ile
            20                  25                  30

Thr Tyr Met Asn Trp Val Arg Gln Ala Pro Gly Gln Gly Leu Glu Trp
        35                  40                  45

Ile Gly Asp Ile Leu Pro Ser Ile Gly Arg Thr Met Tyr Gly Gln Lys
    50                  55                  60

Phe Gln Gly Arg Val Thr Ile Thr Ala Asp Glu Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 352
<211> LENGTH: 118
<212> TYPE: PRT
<213> ORGANISM: Artificial Sequence
<220> FEATURE:
<223> OTHER INFORMATION: Synthetic Construct

<400> SEQUENCE: 352

Glu Val Gln Leu Val Gln Ser Gly Ala Glu Val Lys Lys Pro Gly Glu
1               5                   10                  15

Ser Leu Lys Ile Ser Cys Lys Gly Ser Gly Ser Glu Val Phe Pro Ile
            20                  25                  30

Thr Tyr Met Asn Trp Val Arg Gln Met Pro Gly Lys Gly Leu Glu Trp
        35                  40                  45

Ile Gly Asp Ile Leu Pro Ser Ile Gly Arg Thr Met Tyr Gly Pro Ser
    50                  55                  60

Phe Gln Gly Gln Val Thr Ile Ser Ala Asp Lys Ser Ile Ser Thr Ala
65                  70                  75                  80

Tyr Leu Gln Trp Ser Ser Leu Lys Ala Ser Asp Thr Ala Met Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 353
<211> LENGTH: 118
<212> TYPE: PRT
<213> ORGANISM: Artificial Sequence
<220> FEATURE:
<223> OTHER INFORMATION: Synthetic Construct

<400> SEQUENCE: 353

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Glu Val Phe Pro Ile
            20                  25                  30

Thr Tyr Met Asn Trp Val Arg Gln Ala Pro Gly Lys Gly Leu Glu Trp
        35                  40                  45

Ile Gly Asp Ile Leu Pro Ser Ile Gly Arg Thr Met Tyr Gly Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 354
<211> LENGTH: 118
<212> TYPE: PRT
<213> ORGANISM: Artificial Sequence
<220> FEATURE:
<223> OTHER INFORMATION: Synthetic Construct

<400> SEQUENCE: 354

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Glu Val Phe Pro Ile
            20                  25                  30

Thr Tyr Met Asn Trp Val Arg Gln Ala Pro Gly Lys Gly Leu Glu Trp
        35                  40                  45

Ile Gly Asp Ile Leu Pro Ser Ile Gly Arg Thr Met Tyr Gly Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 355
<211> LENGTH: 118
<212> TYPE: PRT
<213> ORGANISM: Artificial Sequence
<220> FEATURE:
<223> OTHER INFORMATION: Synthetic Construct

<400> SEQUENCE: 355

Gln Val Gln Leu Val Glu Ser Gly Gly Gly Val Val Gln Pro Gly Arg
1               5                   10                  15

Ser Leu Arg Leu Ser Cys Ala Ala Ser Gly Ser Glu Val Phe Pro Ile
            20                  25                  30

Thr Tyr Met Asn Trp Val Arg Gln Ala Pro Gly Lys Gly Leu Glu Trp
        35                  40                  45

Ile Gly Asp Ile Leu Pro Ser Ile Gly Arg Thr Met Tyr Gly Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 356
<211> LENGTH: 118
<212> TYPE: PRT
<213> ORGANISM: Artificial Sequence
<220> FEATURE:
<223> OTHER INFORMATION: Synthetic Construct

<400> SEQUENCE: 356

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Glu Val Phe Pro Ile
            20                  25                  30

Thr Tyr Met Asn Trp Ile Arg Gln Pro Pro Gly Lys Gly Leu Glu Trp
        35                  40                  45

```
Ile Gly Asp Ile Leu Pro Ser Ile Gly Arg Thr Met Tyr Gly Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Glu Gly Tyr Leu Leu Ala Tyr Trp Gly Gln Gly Thr
                100                 105                 110

Leu Val Thr Val Ser Ser
        115

<210> SEQ ID NO 357
<211> LENGTH: 118
<212> TYPE: PRT
<213> ORGANISM: Artificial Sequence
<220> FEATURE:
<223> OTHER INFORMATION: Synthetic Construct

<400> SEQUENCE: 357

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ser Glu Val Phe Pro Ile
                20                  25                  30

Thr Tyr Met Asn Trp Ile Arg Gln Pro Pro Gly Lys Gly Leu Glu Trp
            35                  40                  45

Ile Gly Asp Ile Leu Pro Ser Ile Gly Arg Thr Met Tyr Gly Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Glu Gly Tyr Leu Leu Ala Tyr Trp Gly Gln Gly Thr
                100                 105                 110

Leu Val Thr Val Ser Ser
        115

<210> SEQ ID NO 358
<211> LENGTH: 118
<212> TYPE: PRT
<213> ORGANISM: Artificial Sequence
<220> FEATURE:
<223> OTHER INFORMATION: Synthetic Construct

<400> SEQUENCE: 358

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Glu Val Phe Pro Ile
                20                  25                  30

Thr Tyr Met Asn Trp Ile Arg Gln Pro Pro Gly Lys Gly Leu Glu Trp
            35                  40                  45

Ile Gly Asp Ile Leu Pro Ser Ile Gly Arg Thr Met Tyr Gly Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

-continued

Cys Ala Arg Ser Glu Gly Tyr Leu Leu Ala Tyr Trp Gly Gln Gly Thr
                100                 105                 110

Leu Val Thr Val Ser Ser
        115

<210> SEQ ID NO 359
<211> LENGTH: 116
<212> TYPE: PRT
<213> ORGANISM: Artificial Sequence
<220> FEATURE:
<223> OTHER INFORMATION: Synthetic Construct

<400> SEQUENCE: 359

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Thr Asp Tyr
                20                  25                  30

Gly Ile Thr Trp Val Arg Gln Met Pro Gly Lys Gly Leu Glu Trp Ile
                35                  40                  45

Gly Glu Ile Ser Pro Arg Ser Gly Glu Thr Tyr Phe Asn Pro Ser Phe
            50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Gly Asn Pro Phe Thr Tyr Trp Gly Gln Gly Thr Leu Val
                100                 105                 110

Thr Val Ser Ser
        115

<210> SEQ ID NO 360
<211> LENGTH: 116
<212> TYPE: PRT
<213> ORGANISM: Artificial Sequence
<220> FEATURE:
<223> OTHER INFORMATION: Synthetic Construct

<400> SEQUENCE: 360

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Tyr
                20                  25                  30

Gly Ile Thr Trp Val Arg Gln Ala Pro Gly Gln Gly Leu Glu Trp Ile
                35                  40                  45

Gly Glu Ile Ser Pro Arg Ser Gly Glu Thr Tyr Phe Asn Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Asn Pro Phe Thr Tyr Trp Gly Gln Gly Thr Leu Val
                100                 105                 110

Thr Val Ser Ser
        115

<210> SEQ ID NO 361
<211> LENGTH: 116
<212> TYPE: PRT

<213> ORGANISM: Artificial Sequence
<220> FEATURE:
<223> OTHER INFORMATION: Synthetic Construct

<400> SEQUENCE: 361

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ile Phe Thr Asp Tyr
            20                  25                  30

Gly Ile Thr Trp Val Arg Gln Ala Pro Gly Lys Gly Leu Glu Trp Ile
        35                  40                  45

Gly Glu Ile Ser Pro Arg Ser Gly Glu Thr Tyr Phe Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asn Pro Phe Thr Tyr Trp Gly Gln Gly Thr Leu Val
            100                 105                 110

Thr Val Ser Ser
        115

<210> SEQ ID NO 362
<211> LENGTH: 116
<212> TYPE: PRT
<213> ORGANISM: Artificial Sequence
<220> FEATURE:
<223> OTHER INFORMATION: Synthetic Construct

<400> SEQUENCE: 362

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Asp Tyr
            20                  25                  30

Gly Ile Thr Trp Val Arg Gln Ala Pro Gly Gln Gly Leu Glu Trp Ile
        35                  40                  45

Gly Glu Ile Ser Pro Arg Ser Gly Glu Thr Tyr Phe Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Asn Pro Phe Thr Tyr Trp Gly Gln Gly Thr Leu Val
            100                 105                 110

Thr Val Ser Ser
        115

<210> SEQ ID NO 363
<211> LENGTH: 116
<212> TYPE: PRT
<213> ORGANISM: Artificial Sequence
<220> FEATURE:
<223> OTHER INFORMATION: Synthetic Construct

<400> SEQUENCE: 363

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Phe Thr Asp Tyr
            20                  25                  30

Gly Ile Thr Trp Val Arg Gln Ala Pro Gly Lys Gly Leu Glu Trp Ile
            35                  40                  45

Gly Glu Ile Ser Pro Arg Ser Gly Glu Thr Tyr Phe Asn Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asn Pro Phe Thr Tyr Trp Gly Gln Gly Thr Leu Val
            100                 105                 110

Thr Val Ser Ser
        115

<210> SEQ ID NO 364
<211> LENGTH: 116
<212> TYPE: PRT
<213> ORGANISM: Artificial Sequence
<220> FEATURE:
<223> OTHER INFORMATION: Synthetic Construct

<400> SEQUENCE: 364

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Phe Thr Asp Tyr
            20                  25                  30

Gly Ile Thr Trp Val Arg Gln Ala Pro Gly Lys Gly Leu Glu Trp Ile
            35                  40                  45

Gly Glu Ile Ser Pro Arg Ser Gly Glu Thr Tyr Phe Asn Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asn Pro Phe Thr Tyr Trp Gly Gln Gly Thr Leu Val
            100                 105                 110

Thr Val Ser Ser
        115

<210> SEQ ID NO 365
<211> LENGTH: 116
<212> TYPE: PRT
<213> ORGANISM: Artificial Sequence
<220> FEATURE:
<223> OTHER INFORMATION: Synthetic Construct

<400> SEQUENCE: 365

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Ile Phe Thr Asp Tyr
            20                  25                  30

Gly Ile Thr Trp Val Arg Gln Ala Pro Gly Lys Gly Leu Glu Trp Ile
            35                  40                  45

Gly Glu Ile Ser Pro Arg Ser Gly Glu Thr Tyr Phe Asn Asp Ser Val
        50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Glu Gly Asn Pro Phe Thr Tyr Trp Gly Gln Gly Thr Leu Val
            100                 105                 110

Thr Val Ser Ser
        115

<210> SEQ ID NO 366
<211> LENGTH: 116
<212> TYPE: PRT
<213> ORGANISM: Artificial Sequence
<220> FEATURE:
<223> OTHER INFORMATION: Synthetic Construct

<400> SEQUENCE: 366

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ile Phe Thr Asp Tyr
            20                  25                  30

Gly Ile Thr Trp Ile Arg Gln Pro Pro Gly Lys Gly Leu Glu Trp Ile
        35                  40                  45

Gly Glu Ile Ser Pro Arg Ser Gly Glu Thr Tyr Phe Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Gly Asn Pro Phe Thr Tyr Trp Gly Gln Gly Thr Leu Val
            100                 105                 110

Thr Val Ser Ser
        115

<210> SEQ ID NO 367
<211> LENGTH: 116
<212> TYPE: PRT
<213> ORGANISM: Artificial Sequence
<220> FEATURE:
<223> OTHER INFORMATION: Synthetic Construct

<400> SEQUENCE: 367

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Ile Phe Thr Asp Tyr
            20                  25                  30

Gly Ile Thr Trp Val Arg Gln Ala Pro Gly Lys Gly Leu Glu Trp Ile
        35                  40                  45

Gly Glu Ile Ser Pro Arg Ser Gly Glu Thr Tyr Phe Asn Ala Pro Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Arg Glu Gly Asn Pro Phe Thr Tyr Trp Gly Gln Gly Thr Leu Val
            100                 105                 110

Thr Val Ser Ser
        115
```

```
<210> SEQ ID NO 368
<211> LENGTH: 116
<212> TYPE: PRT
<213> ORGANISM: Artificial Sequence
<220> FEATURE:
<223> OTHER INFORMATION: Synthetic Construct

<400> SEQUENCE: 368

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ile Phe Thr Asp Tyr
            20                  25                  30

Gly Ile Thr Trp Ile Arg Gln Pro Pro Gly Lys Gly Leu Glu Trp Ile
        35                  40                  45

Gly Glu Ile Ser Pro Arg Ser Gly Glu Thr Tyr Phe Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Gly Asn Pro Phe Thr Tyr Trp Gly Gln Gly Thr Leu Val
            100                 105                 110

Thr Val Ser Ser
        115

<210> SEQ ID NO 369
<211> LENGTH: 118
<212> TYPE: PRT
<213> ORGANISM: Artificial Sequence
<220> FEATURE:
<223> OTHER INFORMATION: Synthetic Construct

<400> SEQUENCE: 369

Gln Val Gln Leu Val Gln Ser Gly Ala Glu Val Lys Lys Pro Gly Ala
1               5                   10                  15

Ser Val Lys Val Ser Cys Lys Ala Ser Gly Ser Glu Val Phe Pro Ile
            20                  25                  30

Thr Tyr Met Asn Trp Val Arg Gln Ala Pro Gly Gln Gly Leu Glu Trp
        35                  40                  45

Ile Gly Asp Ile Leu Pro Ser Ile Gly Arg Thr Met Tyr Gly Gln Lys
    50                  55                  60

Phe Gln Gly Arg Val Thr Met Thr Arg Asp Thr Ser Thr Ser Thr Val
65                  70                  75                  80

Tyr Met Glu Leu Ser Ser Leu Arg Ser Glu Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 370
<211> LENGTH: 118
<212> TYPE: PRT
<213> ORGANISM: Artificial Sequence
<220> FEATURE:
<223> OTHER INFORMATION: Synthetic Construct

<400> SEQUENCE: 370

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Ser Glu Val Phe Pro Ile
            20                  25                  30

Thr Tyr Met Asn Trp Val Arg Gln Ala Pro Gly Lys Gly Leu Glu Trp
            35                  40                  45

Ile Gly Asp Ile Leu Pro Ser Ile Gly Arg Thr Met Tyr Gly Asp Ser
 50                  55                  60

Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Arg Ser Glu Gly Tyr Leu Leu Ala Tyr Trp Gly Gln Gly Thr
            100                 105                 110

Leu Val Thr Val Ser Ser
            115

<210> SEQ ID NO 371
<211> LENGTH: 118
<212> TYPE: PRT
<213> ORGANISM: Artificial Sequence
<220> FEATURE:
<223> OTHER INFORMATION: Synthetic Construct

<400> SEQUENCE: 371

Gln Val Gln Leu Val Gln Ser Gly Ala Glu Val Lys Lys Pro Gly Ser
 1               5                  10                  15

Ser Val Lys Val Ser Cys Lys Ala Ser Gly Ser Glu Val Phe Pro Ile
            20                  25                  30

Thr Tyr Met Asn Trp Val Arg Gln Ala Pro Gly Gln Gly Leu Glu Trp
            35                  40                  45

Ile Gly Asp Ile Leu Pro Ser Ile Gly Arg Thr Met Tyr Gly Gln Lys
 50                  55                  60

Phe Gln Gly Arg Val Thr Ile Thr Ala Asp Glu Ser Thr Ser Thr Ala
 65                  70                  75                  80

Tyr Met Glu Leu Ser Ser Leu Arg Ser Glu Asp Thr Ala Val Tyr Tyr
                 85                  90                  95

Cys Ala Arg Ser Glu Gly Tyr Leu Leu Ala Tyr Trp Gly Gln Gly Thr
            100                 105                 110

Leu Val Thr Val Ser Ser
            115

<210> SEQ ID NO 372
<211> LENGTH: 118
<212> TYPE: PRT
<213> ORGANISM: Artificial Sequence
<220> FEATURE:
<223> OTHER INFORMATION: Synthetic Construct

<400> SEQUENCE: 372

Glu Val Gln Leu Val Gln Ser Gly Ala Glu Val Lys Lys Pro Gly Glu
 1               5                  10                  15

Ser Leu Lys Ile Ser Cys Lys Gly Ser Gly Ser Glu Val Phe Pro Ile
            20                  25                  30

Thr Tyr Met Asn Trp Val Arg Gln Met Pro Gly Lys Gly Leu Glu Trp
            35                  40                  45

Ile Gly Asp Ile Leu Pro Ser Ile Gly Arg Thr Met Tyr Gly Pro Ser
 50                  55                  60
```

```
Phe Gln Gly Gln Val Thr Ile Ser Ala Asp Lys Ser Ile Ser Thr Ala
 65                  70                  75                  80

Tyr Leu Gln Trp Ser Ser Leu Lys Ala Ser Asp Thr Ala Met Tyr Tyr
                 85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 373
<211> LENGTH: 118
<212> TYPE: PRT
<213> ORGANISM: Artificial Sequence
<220> FEATURE:
<223> OTHER INFORMATION: Synthetic Construct

<400> SEQUENCE: 373

Glu Val Gln Leu Val Glu Ser Gly Gly Gly Leu Val Gln Pro Gly Gly
  1               5                  10                  15

Ser Leu Arg Leu Ser Cys Ala Ala Ser Gly Ser Glu Val Phe Pro Ile
             20                  25                  30

Thr Tyr Met Asn Trp Val Arg Gln Ala Pro Gly Lys Gly Leu Glu Trp
         35                  40                  45

Ile Gly Asp Ile Leu Pro Ser Ile Gly Arg Thr Met Tyr Gly Asp Ser
 50                  55                  60

Val Lys Gly Arg Phe Thr Ile Ser Arg Asp Asn Ala Lys Asn Ser Leu
 65                  70                  75                  80

Tyr Leu Gln Met Asn Ser Leu Arg Ala Glu Asp Thr Ala Val Tyr Tyr
                 85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 374
<211> LENGTH: 118
<212> TYPE: PRT
<213> ORGANISM: Artificial Sequence
<220> FEATURE:
<223> OTHER INFORMATION: Synthetic Construct

<400> SEQUENCE: 374

Glu Val Gln Leu Val Glu Ser Gly Gly Gly Leu Val Gln Pro Gly Gly
  1               5                  10                  15

Ser Leu Arg Leu Ser Cys Ala Ala Ser Gly Ser Glu Val Phe Pro Ile
             20                  25                  30

Thr Tyr Met Asn Trp Val Arg Gln Ala Pro Gly Lys Gly Leu Glu Trp
         35                  40                  45

Ile Gly Asp Ile Leu Pro Ser Ile Gly Arg Thr Met Tyr Gly Asp Ser
 50                  55                  60

Val Lys Gly Arg Phe Thr Ile Ser Arg Asp Asn Ala Lys Asn Ser Leu
 65                  70                  75                  80

Tyr Leu Gln Met Asn Ser Leu Arg Ala Glu Asp Thr Ala Val Tyr Tyr
                 85                  90                  95
```

```
Cys Ala Arg Ser Glu Gly Tyr Leu Leu Ala Tyr Trp Gly Gln Gly Thr
                100                 105                 110

Leu Val Thr Val Ser Ser
        115
```

<210> SEQ ID NO 375
<211> LENGTH: 118
<212> TYPE: PRT
<213> ORGANISM: Artificial Sequence
<220> FEATURE:
<223> OTHER INFORMATION: Synthetic Construct

<400> SEQUENCE: 375

```
Gln Val Gln Leu Val Glu Ser Gly Gly Gly Val Val Gln Pro Gly Arg
1               5                   10                  15

Ser Leu Arg Leu Ser Cys Ala Ala Ser Gly Ser Glu Val Phe Pro Ile
            20                  25                  30

Thr Tyr Met Asn Trp Val Arg Gln Ala Pro Gly Lys Gly Leu Glu Trp
        35                  40                  45

Ile Gly Asp Ile Leu Pro Ser Ile Gly Arg Thr Met Tyr Gly Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Ser Glu Gly Tyr Leu Leu Ala Tyr Trp Gly Gln Gly Thr
                100                 105                 110

Leu Val Thr Val Ser Ser
        115
```

<210> SEQ ID NO 376
<211> LENGTH: 118
<212> TYPE: PRT
<213> ORGANISM: Artificial Sequence
<220> FEATURE:
<223> OTHER INFORMATION: Synthetic Construct

<400> SEQUENCE: 376

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Glu Val Phe Pro Ile
            20                  25                  30

Thr Tyr Met Asn Trp Ile Arg Gln Pro Pro Gly Lys Gly Leu Glu Trp
        35                  40                  45

Ile Gly Asp Ile Leu Pro Ser Ile Gly Arg Thr Met Tyr Gly Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Glu Gly Tyr Leu Leu Ala Tyr Trp Gly Gln Gly Thr
                100                 105                 110

Leu Val Thr Val Ser Ser
        115
```

<210> SEQ ID NO 377
<211> LENGTH: 118
<212> TYPE: PRT

```
<213> ORGANISM: Artificial Sequence
<220> FEATURE:
<223> OTHER INFORMATION: Synthetic Construct

<400> SEQUENCE: 377

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ser Glu Val Phe Pro Ile
            20                  25                  30

Thr Tyr Met Asn Trp Ile Arg Gln Pro Pro Gly Lys Gly Leu Glu Trp
        35                  40                  45

Ile Gly Asp Ile Leu Pro Ser Ile Gly Arg Thr Met Tyr Gly Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Glu Gly Tyr Leu Leu Ala Tyr Trp Gly Gln Gly Thr
                100                 105                 110

Leu Val Thr Val Ser Ser
            115

<210> SEQ ID NO 378
<211> LENGTH: 118
<212> TYPE: PRT
<213> ORGANISM: Artificial Sequence
<220> FEATURE:
<223> OTHER INFORMATION: Synthetic Construct

<400> SEQUENCE: 378

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Glu Val Phe Pro Ile
            20                  25                  30

Thr Tyr Met Asn Trp Ile Arg Gln Pro Pro Gly Lys Gly Leu Glu Trp
        35                  40                  45

Ile Gly Asp Ile Leu Pro Ser Ile Gly Arg Thr Met Tyr Gly Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Glu Gly Tyr Leu Leu Ala Tyr Trp Gly Gln Gly Thr
                100                 105                 110

Leu Val Thr Val Ser Ser
            115

<210> SEQ ID NO 379
<211> LENGTH: 117
<212> TYPE: PRT
<213> ORGANISM: Artificial Sequence
<220> FEATURE:
<223> OTHER INFORMATION: Synthetic Construct

<400> SEQUENCE: 379

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn Tyr
            20                  25                  30
```

```
Trp Ile Asn Trp Val Arg Gln Met Pro Gly Lys Gly Leu Glu Trp Ile
            35                  40                  45

Gly Asn Ile Tyr Ser Gly Ser Ser Arg Thr Asn Tyr Asn Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Gly Leu Arg Ala Met Asp Tyr Trp Gly Gln Gly Thr Leu
                100                 105                 110

Val Thr Val Ser Ser
            115

<210> SEQ ID NO 380
<211> LENGTH: 117
<212> TYPE: PRT
<213> ORGANISM: Artificial Sequence
<220> FEATURE:
<223> OTHER INFORMATION: Synthetic Construct

<400> SEQUENCE: 380

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
                20                  25                  30

Trp Ile Asn Trp Val Arg Gln Ala Pro Gly Lys Gly Leu Glu Trp Ile
            35                  40                  45

Gly Asn Ile Tyr Ser Gly Ser Ser Arg Thr Asn Tyr Asn Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Arg Ala Met Asp Tyr Trp Gly Gln Gly Thr Leu
                100                 105                 110

Val Thr Val Ser Ser
            115

<210> SEQ ID NO 381
<211> LENGTH: 117
<212> TYPE: PRT
<213> ORGANISM: Artificial Sequence
<220> FEATURE:
<223> OTHER INFORMATION: Synthetic Construct

<400> SEQUENCE: 381

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Ile Asn Trp Val Arg Gln Ala Pro Gly Gln Gly Leu Glu Trp Ile
            35                  40                  45

Gly Asn Ile Tyr Ser Gly Ser Ser Arg Thr Asn Tyr Asn Gln Lys Phe
        50                  55                  60

Gln Gly Arg Val Thr Met Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Glu Gly Leu Arg Ala Met Asp Tyr Trp Gly Gln Gly Thr Leu
            100                 105                 110

Val Thr Val Ser Ser
        115

<210> SEQ ID NO 382
<211> LENGTH: 117
<212> TYPE: PRT
<213> ORGANISM: Artificial Sequence
<220> FEATURE:
<223> OTHER INFORMATION: Synthetic Construct

<400> SEQUENCE: 382

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Trp Ile Asn Trp Val Arg Gln Ala Pro Gly Lys Gly Leu Glu Trp Ile
        35                  40                  45

Gly Asn Ile Tyr Ser Gly Ser Ser Arg Thr Asn Tyr Asn Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Arg Ala Met Asp Tyr Trp Gly Gln Gly Thr Leu
            100                 105                 110

Val Thr Val Ser Ser
        115

<210> SEQ ID NO 383
<211> LENGTH: 117
<212> TYPE: PRT
<213> ORGANISM: Artificial Sequence
<220> FEATURE:
<223> OTHER INFORMATION: Synthetic Construct

<400> SEQUENCE: 383

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Ile Asn Trp Val Arg Gln Ala Pro Gly Gln Gly Leu Glu Trp Ile
        35                  40                  45

Gly Asn Ile Tyr Ser Gly Ser Ser Arg Thr Asn Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Leu Arg Ala Met Asp Tyr Trp Gly Gln Gly Thr Leu
            100                 105                 110

Val Thr Val Ser Ser
        115
```

```
<210> SEQ ID NO 384
<211> LENGTH: 117
<212> TYPE: PRT
<213> ORGANISM: Artificial Sequence
<220> FEATURE:
<223> OTHER INFORMATION: Synthetic Construct

<400> SEQUENCE: 384

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Thr Asn Tyr
                20                  25                  30

Trp Ile Asn Trp Val Arg Gln Ala Pro Gly Lys Gly Leu Glu Trp Ile
            35                  40                  45

Gly Asn Ile Tyr Ser Gly Ser Ser Arg Thr Asn Tyr Asn Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Arg Ala Met Asp Tyr Trp Gly Gln Gly Thr Leu
            100                 105                 110

Val Thr Val Ser Ser
        115

<210> SEQ ID NO 385
<211> LENGTH: 117
<212> TYPE: PRT
<213> ORGANISM: Artificial Sequence
<220> FEATURE:
<223> OTHER INFORMATION: Synthetic Construct

<400> SEQUENCE: 385

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
                20                  25                  30

Trp Ile Asn Trp Val Arg Gln Ala Pro Gly Lys Gly Leu Glu Trp Ile
            35                  40                  45

Gly Asn Ile Tyr Ser Gly Ser Ser Arg Thr Asn Tyr Asn Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Arg Ala Met Asp Tyr Trp Gly Gln Gly Thr Leu
            100                 105                 110

Val Thr Val Ser Ser
        115

<210> SEQ ID NO 386
<211> LENGTH: 117
<212> TYPE: PRT
<213> ORGANISM: Artificial Sequence
<220> FEATURE:
<223> OTHER INFORMATION: Synthetic Construct

<400> SEQUENCE: 386

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Tyr Thr Phe Thr Asn Tyr
            20                  25                  30

Trp Ile Asn Trp Ile Arg Gln Pro Gly Lys Gly Leu Glu Trp Ile
        35                  40                  45

Gly Asn Ile Tyr Ser Gly Ser Ser Arg Thr Asn Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Gly Leu Arg Ala Met Asp Tyr Trp Gly Gln Gly Thr Leu
            100                 105                 110

Val Thr Val Ser Ser
        115

<210> SEQ ID NO 387
<211> LENGTH: 117
<212> TYPE: PRT
<213> ORGANISM: Artificial Sequence
<220> FEATURE:
<223> OTHER INFORMATION: Synthetic Construct

<400> SEQUENCE: 387

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Asn Tyr
            20                  25                  30

Trp Ile Asn Trp Val Arg Gln Ala Pro Gly Lys Gly Leu Glu Trp Ile
        35                  40                  45

Gly Asn Ile Tyr Ser Gly Ser Ser Arg Thr Asn Tyr Asn Ala Pro Val
50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Arg Glu Gly Leu Arg Ala Met Asp Tyr Trp Gly Gln Gly Thr Leu
            100                 105                 110

Val Thr Val Ser Ser
        115

<210> SEQ ID NO 388
<211> LENGTH: 117
<212> TYPE: PRT
<213> ORGANISM: Artificial Sequence
<220> FEATURE:
<223> OTHER INFORMATION: Synthetic Construct

<400> SEQUENCE: 388

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Trp Ile Asn Trp Ile Arg Gln Pro Pro Gly Lys Gly Leu Glu Trp Ile
        35                  40                  45

Gly Asn Ile Tyr Ser Gly Ser Ser Arg Thr Asn Tyr Asn Pro Ser Leu
50                  55                  60
```

```
Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Gly Leu Arg Ala Met Asp Tyr Trp Gly Gln Gly Thr Leu
            100                 105                 110

Val Thr Val Ser Ser
        115

<210> SEQ ID NO 389
<211> LENGTH: 121
<212> TYPE: PRT
<213> ORGANISM: Artificial Sequence
<220> FEATURE:
<223> OTHER INFORMATION: Synthetic Construct

<400> SEQUENCE: 389

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Asn Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Gly Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 390
<211> LENGTH: 121
<212> TYPE: PRT
<213> ORGANISM: Artificial Sequence
<220> FEATURE:
<223> OTHER INFORMATION: Synthetic Construct

<400> SEQUENCE: 390

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Asn Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Gly Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg His Gly Tyr Gly Asn Tyr Asp Trp Tyr Phe Asp Val Trp Gly
            100                 105                 110
```

Gln Gly Thr Leu Val Thr Val Ser Ser
        115                 120

<210> SEQ ID NO 391
<211> LENGTH: 121
<212> TYPE: PRT
<213> ORGANISM: Artificial Sequence
<220> FEATURE:
<223> OTHER INFORMATION: Synthetic Construct

<400> SEQUENCE: 391

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Asn Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Gly Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 392
<211> LENGTH: 121
<212> TYPE: PRT
<213> ORGANISM: Artificial Sequence
<220> FEATURE:
<223> OTHER INFORMATION: Synthetic Construct

<400> SEQUENCE: 392

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Asn Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Gly Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 393
<211> LENGTH: 121
<212> TYPE: PRT
<213> ORGANISM: Artificial Sequence
<220> FEATURE:
<223> OTHER INFORMATION: Synthetic Construct

<400> SEQUENCE: 393

Gln Val Gln Leu Val Gln Ser Gly Ala Glu Val Lys Lys Pro Gly Ala
1               5                   10                  15

Ser Val Lys Val Ser Cys Lys Ala Ser Gly Phe Ile Phe Ser Asn Tyr
            20                  25                  30

Asp Met Ser Trp Val Arg Gln Ala Pro Gly Gln Gly Leu Glu Trp Val
        35                  40                  45

Ala Thr Ile Ser Ser Gly Gly Gly Tyr Thr Tyr Tyr Pro Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 394
<211> LENGTH: 121
<212> TYPE: PRT
<213> ORGANISM: Artificial Sequence
<220> FEATURE:
<223> OTHER INFORMATION: Synthetic Construct

<400> SEQUENCE: 394

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ile Phe Ser Asn Tyr
            20                  25                  30

Asp Met Ser Trp Val Arg Gln Ala Pro Gly Gln Gly Leu Glu Trp Val
        35                  40                  45

Ala Thr Ile Ser Ser Gly Gly Gly Tyr Thr Tyr Tyr Pro Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 395
<211> LENGTH: 121
<212> TYPE: PRT
<213> ORGANISM: Artificial Sequence
<220> FEATURE:
<223> OTHER INFORMATION: Synthetic Construct

<400> SEQUENCE: 395

Glu Val Gln Leu Val Gln Ser Gly Ala Glu Val Lys Lys Pro Gly Glu
1               5                   10                  15

Ser Leu Lys Ile Ser Cys Lys Gly Ser Gly Phe Ile Phe Ser Asn Tyr
            20                  25                  30

Asp Met Ser Trp Val Arg Gln Met Pro Gly Lys Gly Leu Glu Trp Val
        35                  40                  45

Ala Thr Ile Ser Ser Gly Gly Gly Tyr Thr Tyr Tyr Pro Pro Ser Phe
            50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Thr Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 396
<211> LENGTH: 121
<212> TYPE: PRT
<213> ORGANISM: Artificial Sequence
<220> FEATURE:
<223> OTHER INFORMATION: Synthetic Construct

<400> SEQUENCE: 396

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ile Phe Ser Asn Tyr
                20                  25                  30

Asp Met Ser Trp Ile Arg Gln Pro Pro Gly Lys Gly Leu Glu Trp Val
            35                  40                  45

Ala Thr Ile Ser Ser Gly Gly Gly Tyr Thr Tyr Tyr Pro Pro Ser Leu
        50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Thr Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 397
<211> LENGTH: 121
<212> TYPE: PRT
<213> ORGANISM: Artificial Sequence
<220> FEATURE:
<223> OTHER INFORMATION: Synthetic Construct

<400> SEQUENCE: 397

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Ile Phe Ser Asn Tyr
                20                  25                  30

Asp Met Ser Trp Val Arg Gln Ala Pro Gly Lys Gly Leu Glu Trp Val
            35                  40                  45

Ala Thr Ile Ser Ser Gly Gly Gly Tyr Thr Tyr Tyr Pro Ala Pro Val
        50                  55                  60

Lys Gly Arg Phe Thr Ile Ser Arg Asp Asp Ser Lys Asn Thr Leu Tyr
 65                  70                  75                  80

Leu Gln Met Asn Ser Leu Lys Thr Glu Asp Thr Ala Val Tyr Tyr Cys
                85                  90                  95

Thr Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 398
<211> LENGTH: 121
<212> TYPE: PRT
<213> ORGANISM: Artificial Sequence
<220> FEATURE:
<223> OTHER INFORMATION: Synthetic Construct

<400> SEQUENCE: 398

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ile Phe Ser Asn Tyr
            20                  25                  30

Asp Met Ser Trp Ile Arg Gln Pro Pro Gly Lys Gly Leu Glu Trp Val
        35                  40                  45

Ala Thr Ile Ser Ser Gly Gly Tyr Thr Tyr Tyr Pro Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Thr Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 399
<211> LENGTH: 121
<212> TYPE: PRT
<213> ORGANISM: Artificial Sequence
<220> FEATURE:
<223> OTHER INFORMATION: Synthetic Construct

<400> SEQUENCE: 399

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Ser Tyr Asn Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gln Ser Tyr Gly Ser Ser Tyr Trp Tyr Phe Asp Val Trp Gly
            100                 105                 110

Gln Gly Thr Leu Val Thr Val Ser Ser
        115                 120

<210> SEQ ID NO 400
<211> LENGTH: 121
<212> TYPE: PRT

<213> ORGANISM: Artificial Sequence
<220> FEATURE:
<223> OTHER INFORMATION: Synthetic Construct

<400> SEQUENCE: 400

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Ala Met Ser Trp Val Arg Gln Ala Pro Gly Lys Gly Leu Glu Trp Val
        35                  40                  45
Ala Ser Ile Ser Ser Gly Gly Ser Tyr Asn Tyr Tyr Pro Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ser Gln Ser Tyr Gly Ser Ser Tyr Trp Tyr Phe Asp Val Trp Gly
            100                 105                 110
Gln Gly Thr Leu Val Thr Val Ser Ser
        115                 120
```

<210> SEQ ID NO 401
<211> LENGTH: 121
<212> TYPE: PRT
<213> ORGANISM: Artificial Sequence
<220> FEATURE:
<223> OTHER INFORMATION: Synthetic Construct

<400> SEQUENCE: 401

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Asn Tyr
            20                  25                  30
Ala Met Ser Trp Val Arg Gln Ala Pro Gly Lys Gly Leu Glu Trp Val
        35                  40                  45
Ala Ser Ile Ser Ser Gly Gly Ser Tyr Asn Tyr Tyr Pro Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ser Gln Ser Tyr Gly Ser Ser Tyr Trp Tyr Phe Asp Val Trp Gly
            100                 105                 110
Gln Gly Thr Leu Val Thr Val Ser Ser
        115                 120
```

<210> SEQ ID NO 402
<211> LENGTH: 121
<212> TYPE: PRT
<213> ORGANISM: Artificial Sequence
<220> FEATURE:
<223> OTHER INFORMATION: Synthetic Construct

<400> SEQUENCE: 402

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
```

```
Ala Met Ser Trp Val Arg Gln Ala Pro Gly Lys Gly Leu Glu Trp Val
        35                  40                  45

Ala Ser Ile Ser Ser Gly Gly Ser Tyr Asn Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gln Ser Tyr Gly Ser Ser Tyr Trp Tyr Phe Asp Val Trp Gly
            100                 105                 110

Gln Gly Thr Leu Val Thr Val Ser Ser
        115                 120
```

<210> SEQ ID NO 403
<211> LENGTH: 121
<212> TYPE: PRT
<213> ORGANISM: Artificial Sequence
<220> FEATURE:
<223> OTHER INFORMATION: Synthetic Construct

<400> SEQUENCE: 403

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Asn Tyr
            20                  25                  30

Ala Met Ser Trp Val Arg Gln Ala Pro Gly Gln Gly Leu Glu Trp Val
        35                  40                  45

Ala Ser Ile Ser Ser Gly Gly Ser Tyr Asn Tyr Tyr Pro Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Gln Ser Tyr Gly Ser Ser Tyr Trp Tyr Phe Asp Val Trp Gly
            100                 105                 110

Gln Gly Thr Leu Val Thr Val Ser Ser
        115                 120
```

<210> SEQ ID NO 404
<211> LENGTH: 121
<212> TYPE: PRT
<213> ORGANISM: Artificial Sequence
<220> FEATURE:
<223> OTHER INFORMATION: Synthetic Construct

<400> SEQUENCE: 404

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Asn Tyr
            20                  25                  30

Ala Met Ser Trp Val Arg Gln Ala Pro Gly Gln Gly Leu Glu Trp Val
        35                  40                  45

Ala Ser Ile Ser Ser Gly Gly Ser Tyr Asn Tyr Tyr Pro Gln Lys Phe
    50                  55                  60

Gln Gly Arg Val Thr Met Thr Arg Asp Thr Ser Thr Ser Thr Val Tyr
65                  70                  75                  80
```

Met Glu Leu Ser Ser Leu Arg Ser Glu Asp Thr Ala Val Tyr Tyr Cys
                85                  90                  95

Ala Ser Gln Ser Tyr Gly Ser Ser Tyr Trp Tyr Phe Asp Val Trp Gly
            100                 105                 110

Gln Gly Thr Leu Val Thr Val Ser Ser
        115                 120

<210> SEQ ID NO 405
<211> LENGTH: 121
<212> TYPE: PRT
<213> ORGANISM: Artificial Sequence
<220> FEATURE:
<223> OTHER INFORMATION: Synthetic Construct

<400> SEQUENCE: 405

Glu Val Gln Leu Val Gln Ser Gly Ala Glu Val Lys Lys Pro Gly Glu
1               5                   10                  15

Ser Leu Lys Ile Ser Cys Lys Gly Ser Gly Phe Thr Phe Ser Asn Tyr
            20                  25                  30

Ala Met Ser Trp Val Arg Gln Met Pro Gly Lys Gly Leu Glu Trp Val
        35                  40                  45

Ala Ser Ile Ser Ser Gly Gly Ser Tyr Asn Tyr Tyr Pro Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Gln Ser Tyr Gly Ser Ser Tyr Trp Tyr Phe Asp Val Trp Gly
            100                 105                 110

Gln Gly Thr Leu Val Thr Val Ser Ser
        115                 120

<210> SEQ ID NO 406
<211> LENGTH: 121
<212> TYPE: PRT
<213> ORGANISM: Artificial Sequence
<220> FEATURE:
<223> OTHER INFORMATION: Synthetic Construct

<400> SEQUENCE: 406

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Thr Phe Ser Asn Tyr
            20                  25                  30

Ala Met Ser Trp Ile Arg Gln Pro Pro Gly Lys Gly Leu Glu Trp Val
        35                  40                  45

Ala Ser Ile Ser Ser Gly Gly Ser Tyr Asn Tyr Tyr Pro Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ser Gln Ser Tyr Gly Ser Ser Tyr Trp Tyr Phe Asp Val Trp Gly
            100                 105                 110

Gln Gly Thr Leu Val Thr Val Ser Ser
        115                 120

-continued

```
<210> SEQ ID NO 407
<211> LENGTH: 121
<212> TYPE: PRT
<213> ORGANISM: Artificial Sequence
<220> FEATURE:
<223> OTHER INFORMATION: Synthetic Construct

<400> SEQUENCE: 407

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Ser Tyr Asn Tyr Tyr Pro Ala Pro Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Ser Gln Ser Tyr Gly Ser Ser Tyr Trp Tyr Phe Asp Val Trp Gly
            100                 105                 110

Gln Gly Thr Leu Val Thr Val Ser Ser
        115                 120

<210> SEQ ID NO 408
<211> LENGTH: 121
<212> TYPE: PRT
<213> ORGANISM: Artificial Sequence
<220> FEATURE:
<223> OTHER INFORMATION: Synthetic Construct

<400> SEQUENCE: 408

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Thr Phe Ser Asn Tyr
            20                  25                  30

Ala Met Ser Trp Ile Arg Gln Pro Pro Gly Lys Gly Leu Glu Trp Val
        35                  40                  45

Ala Ser Ile Ser Ser Gly Gly Ser Tyr Asn Tyr Tyr Pro Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ser Gln Ser Tyr Gly Ser Ser Tyr Trp Tyr Phe Asp Val Trp Gly
            100                 105                 110

Gln Gly Thr Leu Val Thr Val Ser Ser
        115                 120

<210> SEQ ID NO 409
<211> LENGTH: 116
<212> TYPE: PRT
<213> ORGANISM: Artificial Sequence
<220> FEATURE:
<223> OTHER INFORMATION: Synthetic Construct

<400> SEQUENCE: 409

Gln Val Gln Leu Gln Glu Ser Gly Pro Gly Leu Val Lys Pro Ser Glu
1               5                   10                  15
```

-continued

```
Thr Leu Ser Leu Thr Cys Thr Val Ser Gly Phe Ser Leu Ser Asn Tyr
            20                  25                  30

Gly Val His Trp Ile Arg Gln Pro Gly Lys Gly Leu Glu Trp Leu
        35                  40                  45

Gly Val Ile Trp Ala Gly Gly Ile Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Gln Gly Gly Thr Ser Phe Ser Tyr Trp Gly Gln Gly Thr Leu Val
            100                 105                 110

Thr Val Ser Ser
        115

<210> SEQ ID NO 410
<211> LENGTH: 116
<212> TYPE: PRT
<213> ORGANISM: Artificial Sequence
<220> FEATURE:
<223> OTHER INFORMATION: Synthetic Construct

<400> SEQUENCE: 410

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Ser Asn Tyr
            20                  25                  30

Gly Val His Trp Val Arg Gln Ala Pro Gly Lys Gly Leu Glu Trp Leu
        35                  40                  45

Gly Val Ile Trp Ala Gly Gly Ile Thr Asn Tyr Asn Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gln Gly Gly Thr Ser Phe Ser Tyr Trp Gly Gln Gly Thr Leu Val
            100                 105                 110

Thr Val Ser Ser
        115

<210> SEQ ID NO 411
<211> LENGTH: 116
<212> TYPE: PRT
<213> ORGANISM: Artificial Sequence
<220> FEATURE:
<223> OTHER INFORMATION: Synthetic Construct

<400> SEQUENCE: 411

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Gly Val His Trp Val Arg Gln Ala Pro Gly Lys Gly Leu Glu Trp Leu
        35                  40                  45

Gly Val Ile Trp Ala Gly Gly Ile Thr Asn Tyr Asn Asp Ser Val Lys
50                  55                  60
```

```
Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Lys Gln Gly Gly Thr Ser Phe Ser Tyr Trp Gly Gln Gly Thr Leu Val
            100                 105                 110

Thr Val Ser Ser
        115

<210> SEQ ID NO 412
<211> LENGTH: 116
<212> TYPE: PRT
<213> ORGANISM: Artificial Sequence
<220> FEATURE:
<223> OTHER INFORMATION: Synthetic Construct

<400> SEQUENCE: 412

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Ser Asn Tyr
                20                  25                  30

Gly Val His Trp Val Arg Gln Ala Pro Gly Lys Gly Leu Glu Trp Leu
             35                  40                  45

Gly Val Ile Trp Ala Gly Gly Ile Thr Asn Tyr Asn Asp Ser Val Lys
     50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Lys Gln Gly Gly Thr Ser Phe Ser Tyr Trp Gly Gln Gly Thr Leu Val
            100                 105                 110

Thr Val Ser Ser
        115

<210> SEQ ID NO 413
<211> LENGTH: 116
<212> TYPE: PRT
<213> ORGANISM: Artificial Sequence
<220> FEATURE:
<223> OTHER INFORMATION: Synthetic Construct

<400> SEQUENCE: 413

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ser Leu Ser Asn Tyr
                20                  25                  30

Gly Val His Trp Val Arg Gln Ala Pro Gly Lys Gly Leu Glu Trp Leu
             35                  40                  45

Gly Val Ile Trp Ala Gly Gly Ile Thr Asn Tyr Asn Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Gln Gly Gly Thr Ser Phe Ser Tyr Trp Gly Gln Gly Thr Leu Val
            100                 105                 110
```

Thr Val Ser Ser
        115

<210> SEQ ID NO 414
<211> LENGTH: 116
<212> TYPE: PRT
<213> ORGANISM: Artificial Sequence
<220> FEATURE:
<223> OTHER INFORMATION: Synthetic Construct

<400> SEQUENCE: 414

Glu Val Gln Leu Val Gln Ser Gly Ala Glu Val Lys Lys Pro Gly Glu
1               5                   10                  15

Ser Leu Lys Ile Ser Cys Lys Gly Ser Gly Phe Ser Leu Ser Asn Tyr
            20                  25                  30

Gly Val His Trp Val Arg Gln Met Pro Gly Lys Gly Leu Glu Trp Leu
        35                  40                  45

Gly Val Ile Trp Ala Gly Gly Ile Thr Asn Tyr Asn Pro Ser Phe Gln
    50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Lys Gln Gly Gly Thr Ser Phe Ser Tyr Trp Gly Gln Gly Thr Leu Val
            100                 105                 110

Thr Val Ser Ser
        115

<210> SEQ ID NO 415
<211> LENGTH: 116
<212> TYPE: PRT
<213> ORGANISM: Artificial Sequence
<220> FEATURE:
<223> OTHER INFORMATION: Synthetic Construct

<400> SEQUENCE: 415

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Ser Asn Tyr
            20                  25                  30

Gly Val His Trp Val Arg Gln Ala Pro Gly Gln Gly Leu Glu Trp Leu
        35                  40                  45

Gly Val Ile Trp Ala Gly Gly Ile Thr Asn Tyr Asn Gln Lys Phe Gln
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Lys Gln Gly Gly Thr Ser Phe Ser Tyr Trp Gly Gln Gly Thr Leu Val
            100                 105                 110

Thr Val Ser Ser
        115

<210> SEQ ID NO 416
<211> LENGTH: 116
<212> TYPE: PRT
<213> ORGANISM: Artificial Sequence
<220> FEATURE:
<223> OTHER INFORMATION: Synthetic Construct

<400> SEQUENCE: 416

Gln Val Gln Leu Val Gln Ser Gly Ala Glu Val Lys Lys Pro Gly Ala
1               5                   10                  15

Ser Val Lys Val Ser Cys Lys Ala Ser Gly Phe Ser Leu Ser Asn Tyr
            20                  25                  30

Gly Val His Trp Val Arg Gln Ala Pro Gly Gln Gly Leu Glu Trp Leu
        35                  40                  45

Gly Val Ile Trp Ala Gly Gly Ile Thr Asn Tyr Asn Gln Lys Phe Gln
    50                  55                  60

Gly Arg Val Thr Met Thr Arg Asp Thr Ser Thr Ser Thr Val Tyr Met
65                  70                  75                  80

Glu Leu Ser Ser Leu Arg Ser Glu Asp Thr Ala Val Tyr Tyr Cys Ala
                85                  90                  95

Lys Gln Gly Gly Thr Ser Phe Ser Tyr Trp Gly Gln Gly Thr Leu Val
            100                 105                 110

Thr Val Ser Ser
        115

<210> SEQ ID NO 417
<211> LENGTH: 116
<212> TYPE: PRT
<213> ORGANISM: Artificial Sequence
<220> FEATURE:
<223> OTHER INFORMATION: Synthetic Construct

<400> SEQUENCE: 417

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Ser Asn Tyr
            20                  25                  30

Gly Val His Trp Ile Arg Gln Pro Pro Gly Lys Gly Leu Glu Trp Leu
        35                  40                  45

Gly Val Ile Trp Ala Gly Gly Ile Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Gln Gly Gly Thr Ser Phe Ser Tyr Trp Gly Gln Gly Thr Leu Val
            100                 105                 110

Thr Val Ser Ser
        115

<210> SEQ ID NO 418
<211> LENGTH: 116
<212> TYPE: PRT
<213> ORGANISM: Artificial Sequence
<220> FEATURE:
<223> OTHER INFORMATION: Synthetic Construct

<400> SEQUENCE: 418

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asn Tyr
            20                  25                  30

Gly Val His Trp Ile Arg Gln Pro Pro Gly Lys Gly Leu Glu Trp Leu
        35                  40                  45

```
Gly Val Ile Trp Ala Gly Ile Thr Asn Tyr Asn Pro Ser Leu Lys
            50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Lys Gln Gly Gly Thr Ser Phe Ser Tyr Trp Gly Gln Gly Thr Leu Val
                100                 105                 110

Thr Val Ser Ser
            115

<210> SEQ ID NO 419
<211> LENGTH: 118
<212> TYPE: PRT
<213> ORGANISM: Artificial Sequence
<220> FEATURE:
<223> OTHER INFORMATION: Synthetic Construct

<400> SEQUENCE: 419

Gln Val Gln Leu Val Gln Ser Gly Ala Glu Val Lys Lys Pro Gly Ala
 1               5                  10                  15

Ser Val Lys Val Ser Cys Lys Ala Ser Gly Ser Glu Val Phe Pro Ile
                 20                  25                  30

Thr Tyr Met Asn Trp Val Arg Gln Ala Pro Gly Gln Gly Leu Glu Trp
             35                  40                  45

Ile Gly Asp Ile Leu Pro Ser Ile Gly Arg Thr Met Tyr Gly Gln Lys
         50                  55                  60

Phe Gln Gly Arg Val Thr Met Thr Arg Asp Thr Ser Thr Ser Thr Val
 65                  70                  75                  80

Tyr Met Glu Leu Ser Ser Leu Arg Ser Glu Asp Thr Ala Val Tyr Tyr
                 85                  90                  95

Cys Ala Arg Ser Glu Gly Tyr Leu Leu Ala Tyr Trp Gly Gln Gly Thr
                100                 105                 110

Leu Val Thr Val Ser Ser
            115

<210> SEQ ID NO 420
<211> LENGTH: 118
<212> TYPE: PRT
<213> ORGANISM: Artificial Sequence
<220> FEATURE:
<223> OTHER INFORMATION: Synthetic Construct

<400> SEQUENCE: 420

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Ser Glu Val Phe Pro Ile
                 20                  25                  30

Thr Tyr Met Asn Trp Val Arg Gln Ala Pro Gly Lys Gly Leu Glu Trp
             35                  40                  45

Ile Gly Asp Ile Leu Pro Ser Ile Gly Arg Thr Met Tyr Gly Asp Ser
         50                  55                  60

Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95
```

```
Cys Ala Arg Ser Glu Gly Tyr Leu Leu Ala Tyr Trp Gly Gln Gly Thr
                100                 105                 110

Leu Val Thr Val Ser Ser
        115

<210> SEQ ID NO 421
<211> LENGTH: 118
<212> TYPE: PRT
<213> ORGANISM: Artificial Sequence
<220> FEATURE:
<223> OTHER INFORMATION: Synthetic Construct

<400> SEQUENCE: 421

Gln Val Gln Leu Val Gln Ser Gly Ala Glu Val Lys Lys Pro Gly Ser
1               5                   10                  15

Ser Val Lys Val Ser Cys Lys Ala Ser Gly Ser Glu Val Phe Pro Ile
                20                  25                  30

Thr Tyr Met Asn Trp Val Arg Gln Ala Pro Gly Gln Gly Leu Glu Trp
            35                  40                  45

Ile Gly Asp Ile Leu Pro Ser Ile Gly Arg Thr Met Tyr Gly Gln Lys
        50                  55                  60

Phe Gln Gly Arg Val Thr Ile Thr Ala Asp Glu Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Ser Glu Gly Tyr Leu Leu Ala Tyr Trp Gly Gln Gly Thr
                100                 105                 110

Leu Val Thr Val Ser Ser
        115

<210> SEQ ID NO 422
<211> LENGTH: 118
<212> TYPE: PRT
<213> ORGANISM: Artificial Sequence
<220> FEATURE:
<223> OTHER INFORMATION: Synthetic Construct

<400> SEQUENCE: 422

Glu Val Gln Leu Val Gln Ser Gly Ala Glu Val Lys Lys Pro Gly Glu
1               5                   10                  15

Ser Leu Lys Ile Ser Cys Lys Gly Ser Gly Ser Glu Val Phe Pro Ile
                20                  25                  30

Thr Tyr Met Asn Trp Val Arg Gln Met Pro Gly Lys Gly Leu Glu Trp
            35                  40                  45

Ile Gly Asp Ile Leu Pro Ser Ile Gly Arg Thr Met Tyr Gly Pro Ser
        50                  55                  60

Phe Gln Gly Gln Val Thr Ile Ser Ala Asp Lys Ser Ile Ser Thr Ala
65                  70                  75                  80

Tyr Leu Gln Trp Ser Ser Leu Lys Ala Ser Asp Thr Ala Met Tyr Tyr
                85                  90                  95

Cys Ala Arg Ser Glu Gly Tyr Leu Leu Ala Tyr Trp Gly Gln Gly Thr
                100                 105                 110

Leu Val Thr Val Ser Ser
        115

<210> SEQ ID NO 423
<211> LENGTH: 118
<212> TYPE: PRT
```

<213> ORGANISM: Artificial Sequence
<220> FEATURE:
<223> OTHER INFORMATION: Synthetic Construct

<400> SEQUENCE: 423

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Glu Val Phe Pro Ile
            20                  25                  30

Thr Tyr Met Asn Trp Val Arg Gln Ala Pro Gly Lys Gly Leu Glu Trp
        35                  40                  45

Ile Gly Asp Ile Leu Pro Ser Ile Gly Arg Thr Met Tyr Gly Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 424
<211> LENGTH: 118
<212> TYPE: PRT
<213> ORGANISM: Artificial Sequence
<220> FEATURE:
<223> OTHER INFORMATION: Synthetic Construct

<400> SEQUENCE: 424

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Glu Val Phe Pro Ile
            20                  25                  30

Thr Tyr Met Asn Trp Val Arg Gln Ala Pro Gly Lys Gly Leu Glu Trp
        35                  40                  45

Ile Gly Asp Ile Leu Pro Ser Ile Gly Arg Thr Met Tyr Gly Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 425
<211> LENGTH: 118
<212> TYPE: PRT
<213> ORGANISM: Artificial Sequence
<220> FEATURE:
<223> OTHER INFORMATION: Synthetic Construct

<400> SEQUENCE: 425

Gln Val Gln Leu Val Glu Ser Gly Gly Gly Val Val Gln Pro Gly Arg
1               5                   10                  15

Ser Leu Arg Leu Ser Cys Ala Ala Ser Gly Ser Glu Val Phe Pro Ile
            20                  25                  30

```
Thr Tyr Met Asn Trp Val Arg Gln Ala Pro Gly Lys Gly Leu Glu Trp
            35                  40                  45

Ile Gly Asp Ile Leu Pro Ser Ile Gly Arg Thr Met Tyr Gly Asp Ser
 50                  55                  60

Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                85                  90                  95

Cys Ala Arg Ser Glu Gly Tyr Leu Leu Ala Tyr Trp Gly Gln Gly Thr
                100                 105                 110

Leu Val Thr Val Ser Ser
        115

<210> SEQ ID NO 426
<211> LENGTH: 118
<212> TYPE: PRT
<213> ORGANISM: Artificial Sequence
<220> FEATURE:
<223> OTHER INFORMATION: Synthetic Construct

<400> SEQUENCE: 426

Gln Val Gln Leu Gln Glu Ser Gly Pro Gly Leu Val Lys Pro Ser Glu
 1               5                  10                  15

Thr Leu Ser Leu Thr Cys Thr Val Ser Gly Ser Glu Val Phe Pro Ile
             20                  25                  30

Thr Tyr Met Asn Trp Ile Arg Gln Pro Pro Gly Lys Gly Leu Glu Trp
            35                  40                  45

Ile Gly Asp Ile Leu Pro Ser Ile Gly Arg Thr Met Tyr Gly Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Ser Glu Gly Tyr Leu Leu Ala Tyr Trp Gly Gln Gly Thr
                100                 105                 110

Leu Val Thr Val Ser Ser
        115

<210> SEQ ID NO 427
<211> LENGTH: 118
<212> TYPE: PRT
<213> ORGANISM: Artificial Sequence
<220> FEATURE:
<223> OTHER INFORMATION: Synthetic Construct

<400> SEQUENCE: 427

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Ser Glu Val Phe Pro Ile
             20                  25                  30

Thr Tyr Met Asn Trp Ile Arg Gln Pro Pro Gly Lys Gly Leu Glu Trp
            35                  40                  45

Ile Gly Asp Ile Leu Pro Ser Ile Gly Arg Thr Met Tyr Gly Pro Ser
 50                  55                  60

Leu Lys Ser Arg Val Thr Ile Ser Val Asp Thr Ser Lys Asn Gln Phe
 65                  70                  75                  80
```

```
Ser Leu Lys Leu Ser Ser Val Thr Ala Ala Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 428
<211> LENGTH: 118
<212> TYPE: PRT
<213> ORGANISM: Artificial Sequence
<220> FEATURE:
<223> OTHER INFORMATION: Synthetic Construct

<400> SEQUENCE: 428

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Glu Val Phe Pro Ile
            20                  25                  30

Thr Tyr Met Asn Trp Ile Arg Gln Pro Pro Gly Lys Gly Leu Glu Trp
        35                  40                  45

Ile Gly Asp Ile Leu Pro Ser Ile Gly Arg Thr Met Tyr Gly Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ser
        115

<210> SEQ ID NO 429
<211> LENGTH: 118
<212> TYPE: PRT
<213> ORGANISM: Artificial Sequence
<220> FEATURE:
<223> OTHER INFORMATION: Synthetic Construct

<400> SEQUENCE: 429

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Thr Asn Cys
            20                  25                  30

Trp Met Asn Trp Val Arg Gln Met Pro Gly Lys Gly Leu Glu Trp Ile
        35                  40                  45

Gly Arg Ile Phe Pro Gly Asn Gly His Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Ser Asp Tyr Tyr Phe Asp Tyr Trp Gly Gln Gly Thr
            100                 105                 110

Leu Val Thr Val Ser Ser
        115
```

-continued

```
<210> SEQ ID NO 430
<211> LENGTH: 118
<212> TYPE: PRT
<213> ORGANISM: Artificial Sequence
<220> FEATURE:
<223> OTHER INFORMATION: Synthetic Construct

<400> SEQUENCE: 430

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Cys
                20                  25                  30

Trp Met Asn Trp Val Arg Gln Ala Pro Gly Gln Gly Leu Glu Trp Ile
            35                  40                  45

Gly Arg Ile Phe Pro Gly Asn Gly His Thr Asn Tyr Ser Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
                100                 105                 110

Leu Val Thr Val Ser Ser
        115

<210> SEQ ID NO 431
<211> LENGTH: 118
<212> TYPE: PRT
<213> ORGANISM: Artificial Sequence
<220> FEATURE:
<223> OTHER INFORMATION: Synthetic Construct

<400> SEQUENCE: 431

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Asn Cys
                20                  25                  30

Trp Met Asn Trp Val Arg Gln Ala Pro Gly Gln Gly Leu Glu Trp Ile
            35                  40                  45

Gly Arg Ile Phe Pro Gly Asn Gly His Thr Asn Tyr Ser Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
                100                 105                 110

Leu Val Thr Val Ser Ser
        115

<210> SEQ ID NO 432
<211> LENGTH: 118
<212> TYPE: PRT
<213> ORGANISM: Artificial Sequence
<220> FEATURE:
<223> OTHER INFORMATION: Synthetic Construct

<400> SEQUENCE: 432

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Tyr Ala Phe Thr Asn Cys
            20                  25                  30

Trp Met Asn Trp Val Arg Gln Ala Pro Gly Lys Gly Leu Glu Trp Ile
        35                  40                  45

Gly Arg Ile Phe Pro Gly Asn Gly His Thr Asn Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Ser Asp Tyr Tyr Phe Asp Tyr Trp Gly Gln Gly Thr
            100                 105                 110

Leu Val Thr Val Ser Ser
            115

<210> SEQ ID NO 433
<211> LENGTH: 118
<212> TYPE: PRT
<213> ORGANISM: Artificial Sequence
<220> FEATURE:
<223> OTHER INFORMATION: Synthetic Construct

<400> SEQUENCE: 433

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Cys
            20                  25                  30

Trp Met Asn Trp Val Arg Gln Ala Pro Gly Lys Gly Leu Glu Trp Ile
        35                  40                  45

Gly Arg Ile Phe Pro Gly Asn Gly His Thr Asn Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Ser Asp Tyr Tyr Phe Asp Tyr Trp Gly Gln Gly Thr
            100                 105                 110

Leu Val Thr Val Ser Ser
            115

<210> SEQ ID NO 434
<211> LENGTH: 118
<212> TYPE: PRT
<213> ORGANISM: Artificial Sequence
<220> FEATURE:
<223> OTHER INFORMATION: Synthetic Construct

<400> SEQUENCE: 434

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Cys
            20                  25                  30

Trp Met Asn Trp Val Arg Gln Ala Pro Gly Lys Gly Leu Glu Trp Ile
        35                  40                  45

Gly Arg Ile Phe Pro Gly Asn Gly His Thr Asn Tyr Ser Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Ser Asp Tyr Tyr Phe Asp Tyr Trp Gly Gln Gly Thr
            100                 105                 110

Leu Val Thr Val Ser Ser
            115

<210> SEQ ID NO 435
<211> LENGTH: 118
<212> TYPE: PRT
<213> ORGANISM: Artificial Sequence
<220> FEATURE:
<223> OTHER INFORMATION: Synthetic Construct

<400> SEQUENCE: 435

Gln Val Gln Leu Val Glu Ser Gly Gly Val Val Gln Pro Gly Arg
 1               5                  10                  15

Ser Leu Arg Leu Ser Cys Ala Ala Ser Gly Tyr Ala Phe Thr Asn Cys
                 20                  25                  30

Trp Met Asn Trp Val Arg Gln Ala Pro Gly Lys Gly Leu Glu Trp Ile
             35                  40                  45

Gly Arg Ile Phe Pro Gly Asn Gly His Thr Asn Tyr Ser Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Ser Asp Tyr Tyr Phe Asp Tyr Trp Gly Gln Gly Thr
            100                 105                 110

Leu Val Thr Val Ser Ser
            115

<210> SEQ ID NO 436
<211> LENGTH: 118
<212> TYPE: PRT
<213> ORGANISM: Artificial Sequence
<220> FEATURE:
<223> OTHER INFORMATION: Synthetic Construct

<400> SEQUENCE: 436

Gln Val Gln Leu Gln Glu Ser Gly Pro Gly Leu Val Lys Pro Ser Glu
 1               5                  10                  15

Thr Leu Ser Leu Thr Cys Thr Val Ser Gly Tyr Ala Phe Thr Asn Cys
                 20                  25                  30

Trp Met Asn Trp Ile Arg Gln Pro Pro Gly Lys Gly Leu Glu Trp Ile
             35                  40                  45

Gly Arg Ile Phe Pro Gly Asn Gly His Thr Asn Tyr Ser Pro Ser Leu
         50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Asp Tyr Ser Asp Tyr Tyr Phe Asp Tyr Trp Gly Gln Gly Thr
            100                 105                 110
```

Leu Val Thr Val Ser Ser
        115

<210> SEQ ID NO 437
<211> LENGTH: 118
<212> TYPE: PRT
<213> ORGANISM: Artificial Sequence
<220> FEATURE:
<223> OTHER INFORMATION: Synthetic Construct

<400> SEQUENCE: 437

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Ala Phe Thr Asn Cys
            20                  25                  30

Trp Met Asn Trp Val Arg Gln Ala Pro Gly Lys Gly Leu Glu Trp Ile
        35                  40                  45

Gly Arg Ile Phe Pro Gly Asn Gly His Thr Asn Tyr Ser Ala Pro Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Arg Asp Tyr Ser Asp Tyr Tyr Phe Asp Tyr Trp Gly Gln Gly Thr
            100                 105                 110

Leu Val Thr Val Ser Ser
        115

<210> SEQ ID NO 438
<211> LENGTH: 118
<212> TYPE: PRT
<213> ORGANISM: Artificial Sequence
<220> FEATURE:
<223> OTHER INFORMATION: Synthetic Construct

<400> SEQUENCE: 438

Gln Leu Gln Leu Gln Glu Ser Gly Pro Gly Leu Val Lys Pro Ser Glu
1               5                   10                  15

Thr Leu Ser Leu Thr Cys Thr Val Ser Gly Tyr Ala Phe Thr Asn Cys
            20                  25                  30

Trp Met Asn Trp Ile Arg Gln Pro Pro Gly Lys Gly Leu Glu Trp Ile
        35                  40                  45

Gly Arg Ile Phe Pro Gly Asn Gly His Thr Asn Tyr Ser Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Tyr Ser Asp Tyr Tyr Phe Asp Tyr Trp Gly Gln Gly Thr
            100                 105                 110

Leu Val Thr Val Ser Ser
        115

<210> SEQ ID NO 439
<211> LENGTH: 121
<212> TYPE: PRT
<213> ORGANISM: Artificial Sequence
<220> FEATURE:
<223> OTHER INFORMATION: Synthetic Construct

<400> SEQUENCE: 439

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Phe Trp Val Arg Gln Ala Pro Gly Lys Gly Leu Glu Trp Val
        35                  40                  45

Ala Ser Ile Ser Ser Gly Gly Arg Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg His Ser Tyr Gly Ser Ser Tyr Trp Tyr Leu Asp Val Trp Gly
            100                 105                 110

Gln Gly Thr Leu Val Thr Val Ser Ser
        115                 120

<210> SEQ ID NO 440
<211> LENGTH: 121
<212> TYPE: PRT
<213> ORGANISM: Artificial Sequence
<220> FEATURE:
<223> OTHER INFORMATION: Synthetic Construct

<400> SEQUENCE: 440

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Phe Trp Val Arg Gln Ala Pro Gly Lys Gly Leu Glu Trp Val
        35                  40                  45

Ala Ser Ile Ser Ser Gly Gly Arg Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg His Ser Tyr Gly Ser Ser Tyr Trp Tyr Leu Asp Val Trp Gly
            100                 105                 110

Gln Gly Thr Leu Val Thr Val Ser Ser
        115                 120

<210> SEQ ID NO 441
<211> LENGTH: 121
<212> TYPE: PRT
<213> ORGANISM: Artificial Sequence
<220> FEATURE:
<223> OTHER INFORMATION: Synthetic Construct

<400> SEQUENCE: 441

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Phe Trp Val Arg Gln Ala Pro Gly Lys Gly Leu Glu Trp Val
        35                  40                  45

```
Ala Ser Ile Ser Ser Gly Gly Arg Tyr Thr Tyr Tyr Pro Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Arg His Ser Tyr Gly Ser Ser Tyr Trp Tyr Leu Asp Val Trp Gly
                100                 105                 110

Gln Gly Thr Leu Val Thr Val Ser Ser
            115                 120

<210> SEQ ID NO 442
<211> LENGTH: 121
<212> TYPE: PRT
<213> ORGANISM: Artificial Sequence
<220> FEATURE:
<223> OTHER INFORMATION: Synthetic Construct

<400> SEQUENCE: 442

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Thr Tyr
                 20                  25                  30

Ala Met Phe Trp Val Arg Gln Ala Pro Gly Lys Gly Leu Glu Trp Val
             35                  40                  45

Ala Ser Ile Ser Ser Gly Gly Arg Tyr Thr Tyr Tyr Pro Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Arg His Ser Tyr Gly Ser Ser Tyr Trp Tyr Leu Asp Val Trp Gly
                100                 105                 110

Gln Gly Thr Leu Val Thr Val Ser Ser
            115                 120

<210> SEQ ID NO 443
<211> LENGTH: 121
<212> TYPE: PRT
<213> ORGANISM: Artificial Sequence
<220> FEATURE:
<223> OTHER INFORMATION: Synthetic Construct

<400> SEQUENCE: 443

Gln Val Gln Leu Val Gln Ser Gly Ala Glu Val Lys Lys Pro Gly Ala
  1               5                  10                  15

Ser Val Lys Val Ser Cys Lys Ala Ser Gly Phe Thr Phe Ser Thr Tyr
                 20                  25                  30

Ala Met Phe Trp Val Arg Gln Ala Pro Gly Gln Gly Leu Glu Trp Val
             35                  40                  45

Ala Ser Ile Ser Ser Gly Gly Arg Tyr Thr Tyr Tyr Pro Gln Lys Phe
    50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95
```

Val Arg His Ser Tyr Gly Ser Ser Tyr Trp Tyr Leu Asp Val Trp Gly
            100                 105                 110

Gln Gly Thr Leu Val Thr Val Ser Ser
        115                 120

<210> SEQ ID NO 444
<211> LENGTH: 121
<212> TYPE: PRT
<213> ORGANISM: Artificial Sequence
<220> FEATURE:
<223> OTHER INFORMATION: Synthetic Construct

<400> SEQUENCE: 444

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Thr Tyr
            20                  25                  30

Ala Met Phe Trp Val Arg Gln Ala Pro Gly Gln Gly Leu Glu Trp Val
        35                  40                  45

Ala Ser Ile Ser Ser Gly Gly Arg Tyr Thr Tyr Tyr Pro Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Arg His Ser Tyr Gly Ser Ser Tyr Trp Tyr Leu Asp Val Trp Gly
            100                 105                 110

Gln Gly Thr Leu Val Thr Val Ser Ser
        115                 120

<210> SEQ ID NO 445
<211> LENGTH: 121
<212> TYPE: PRT
<213> ORGANISM: Artificial Sequence
<220> FEATURE:
<223> OTHER INFORMATION: Synthetic Construct

<400> SEQUENCE: 445

Glu Val Gln Leu Val Gln Ser Gly Ala Glu Val Lys Lys Pro Gly Glu
1               5                   10                  15

Ser Leu Lys Ile Ser Cys Lys Gly Ser Gly Phe Thr Phe Ser Thr Tyr
            20                  25                  30

Ala Met Phe Trp Val Arg Gln Met Pro Gly Lys Gly Leu Glu Trp Val
        35                  40                  45

Ala Ser Ile Ser Ser Gly Gly Arg Tyr Thr Tyr Tyr Pro Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Val Arg His Ser Tyr Gly Ser Ser Tyr Trp Tyr Leu Asp Val Trp Gly
            100                 105                 110

Gln Gly Thr Leu Val Thr Val Ser Ser
        115                 120

<210> SEQ ID NO 446
<211> LENGTH: 121
<212> TYPE: PRT

<213> ORGANISM: Artificial Sequence
<220> FEATURE:
<223> OTHER INFORMATION: Synthetic Construct

<400> SEQUENCE: 446

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Thr Phe Ser Thr Tyr
            20                  25                  30

Ala Met Phe Trp Ile Arg Gln Pro Pro Gly Lys Gly Leu Glu Trp Val
        35                  40                  45

Ala Ser Ile Ser Ser Gly Gly Arg Tyr Thr Tyr Tyr Pro Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg His Ser Tyr Gly Ser Ser Tyr Trp Tyr Leu Asp Val Trp Gly
            100                 105                 110

Gln Gly Thr Leu Val Thr Val Ser Ser
        115                 120

<210> SEQ ID NO 447
<211> LENGTH: 121
<212> TYPE: PRT
<213> ORGANISM: Artificial Sequence
<220> FEATURE:
<223> OTHER INFORMATION: Synthetic Construct

<400> SEQUENCE: 447

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Phe Trp Val Arg Gln Ala Pro Gly Lys Gly Leu Glu Trp Val
        35                  40                  45

Ala Ser Ile Ser Ser Gly Gly Arg Tyr Thr Tyr Tyr Pro Ala Pro Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Val Arg His Ser Tyr Gly Ser Ser Tyr Trp Tyr Leu Asp Val Trp Gly
            100                 105                 110

Gln Gly Thr Leu Val Thr Val Ser Ser
        115                 120

<210> SEQ ID NO 448
<211> LENGTH: 121
<212> TYPE: PRT
<213> ORGANISM: Artificial Sequence
<220> FEATURE:
<223> OTHER INFORMATION: Synthetic Construct

<400> SEQUENCE: 448

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Thr Phe Ser Thr Tyr
            20                  25                  30

```
Ala Met Phe Trp Ile Arg Gln Pro Pro Gly Lys Gly Leu Glu Trp Val
            35                  40                  45

Ala Ser Ile Ser Ser Gly Gly Arg Tyr Thr Tyr Tyr Pro Pro Ser Leu
        50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Val Arg His Ser Tyr Gly Ser Ser Tyr Trp Tyr Leu Asp Val Trp Gly
                    100                 105                 110

Gln Gly Thr Leu Val Thr Val Ser Ser
            115                 120

<210> SEQ ID NO 449
<211> LENGTH: 112
<212> TYPE: PRT
<213> ORGANISM: Artificial Sequence
<220> FEATURE:
<223> OTHER INFORMATION: Synthetic Construct

<400> SEQUENCE: 449

Asp Val Glx Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
                20                  25                  30

Thr Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Leu Gly Val Tyr Phe Cys Ser Gln Asn
                85                  90                  95

Thr His Val Pro Tyr Thr Phe Gly Gly Gly Thr Lys Leu Glu Ile Lys
                    100                 105                 110

<210> SEQ ID NO 450
<211> LENGTH: 107
<212> TYPE: PRT
<213> ORGANISM: Artificial Sequence
<220> FEATURE:
<223> OTHER INFORMATION: Synthetic Construct

<400> SEQUENCE: 450

Asp Ile Gln Met Thr Gln Phe Pro Ala Thr Leu Ser Val Thr Pro Gly
 1               5                  10                  15

Asp Arg Val Ser Leu Ser Cys Arg Ala Ser Gln Ser Ile Ser Asp Tyr
                20                  25                  30

Leu His Trp Tyr Gln His Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Trp Asp Phe Thr Leu Ser Ile Asn Ser Val Glu Pro
 65                  70                  75                  80

Glu Asp Val Gly Ile Tyr Tyr Cys Gln Lys Gly Leu Asn Phe Pro Leu
                85                  90                  95
```

Thr Phe Gly Gly Gly Thr Lys Leu Glu Met Lys
            100                 105

<210> SEQ ID NO 451
<211> LENGTH: 104
<212> TYPE: PRT
<213> ORGANISM: Artificial Sequence
<220> FEATURE:
<223> OTHER INFORMATION: Synthetic Construct

<400> SEQUENCE: 451

Val Leu Thr Gln Ser Pro Ala Ile Met Ser Ala Ser Pro Gly Glu Lys
1               5                   10                  15

Val Thr Met Thr Cys Ser Ala Asn Ser Ser Phe Ile Tyr Met Tyr Trp
            20                  25                  30

Tyr Gln Gln Lys Pro Gly Ser Ser Pro Arg Leu Leu Ile Phe Asp Thr
        35                  40                  45

Ser Asn Leu Ala Ser Gly Val Pro Ile Arg Phe Ser Gly Ser Gly Ser
    50                  55                  60

Gly Thr Ser Tyr Ser Leu Thr Ile Ser Arg Met Glu Ala Glu Asp Thr
65                  70                  75                  80

Ala Thr Tyr Tyr Cys Gln Gln Trp Ser Ser Pro Leu Thr Phe Gly
                85                  90                  95

Gly Gly Thr Lys Leu Glu Leu Lys
            100

<210> SEQ ID NO 452
<211> LENGTH: 107
<212> TYPE: PRT
<213> ORGANISM: Artificial Sequence
<220> FEATURE:
<223> OTHER INFORMATION: Synthetic Construct

<400> SEQUENCE: 452

Asp Ile Gln Met Thr Gln Ser Leu Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Phe Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys His Gln Tyr Trp Asn Thr Pro Tyr
                85                  90                  95

Thr Phe Gly Gly Gly Thr Arg Leu Glu Ile Lys
            100                 105

<210> SEQ ID NO 453
<211> LENGTH: 112
<212> TYPE: PRT
<213> ORGANISM: Artificial Sequence
<220> FEATURE:
<223> OTHER INFORMATION: Synthetic Construct

<400> SEQUENCE: 453

Asp Val Glx Met Thr Gln Thr Pro Leu Ser Leu Pro Val Ser Leu Gly
1               5                   10                  15

```
Asp Gln Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Cys Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Tyr Thr Phe Gly Gly Gly Thr Lys Leu Glu Ile Lys
            100                 105                 110
```

<210> SEQ ID NO 454
<211> LENGTH: 112
<212> TYPE: PRT
<213> ORGANISM: Artificial Sequence
<220> FEATURE:
<223> OTHER INFORMATION: Synthetic Construct

<400> SEQUENCE: 454

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Thr Gly Asn Ile Tyr Leu His Trp Tyr Leu Gln Lys Pro Gly Gln Ser
        35                  40                  45

Pro Lys Leu Leu Ile Tyr Lys Val Ser Asn Arg Phe Glx Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Tyr Thr Phe Gly Gly Gly Thr Lys Leu Glu Ile Lys
            100                 105                 110
```

<210> SEQ ID NO 455
<211> LENGTH: 106
<212> TYPE: PRT
<213> ORGANISM: Artificial Sequence
<220> FEATURE:
<223> OTHER INFORMATION: Synthetic Construct

<400> SEQUENCE: 455

```
Asn Glx Met Thr Gln Phe Gln Lys Phe Met Ser Thr Ser Val Gly Asp
1               5                   10                  15

Arg Val Ser Leu Thr Cys Lys Ala Ser Gln Lys Val Gly Thr Asn Val
            20                  25                  30

Ala Gly Phe Gln Gln Lys Pro Gly His Ser Pro Lys Ala Gly Ile Tyr
        35                  40                  45

Ser Ala Ser Thr Arg His Arg Gly Val Gln Asp Arg Phe Thr Ala Arg
    50                  55                  60

Gly Leu Gly Ser Asp Phe Ile Leu Pro Ile Thr Thr Glx Gln Leu Glu
65                  70                  75                  80

Asp Leu Ala Glu Tyr Glx Cys His Gln Gly Asn Ser Val Gln Tyr Thr
                85                  90                  95

Phe Gly Gly Gly Thr Lys Leu Glu Ile Lys
            100                 105
```

<210> SEQ ID NO 456
<211> LENGTH: 108
<212> TYPE: PRT
<213> ORGANISM: Artificial Sequence
<220> FEATURE:
<223> OTHER INFORMATION: Synthetic Construct

<400> SEQUENCE: 456

Gly Glx Gln Asn Val Leu Thr Gln Ser Pro Ala Ile Leu Ser Ala Ser
1               5                   10                  15

Pro Gly Glu Lys Val Thr Met Thr Cys Ser Ala Asn Ser Ser Phe Thr
            20                  25                  30

Tyr Met Tyr Trp Tyr Gln Gln Lys Pro Gly Ser Ser Pro Arg Leu Leu
        35                  40                  45

Ile Phe Asp Thr Ser Asn Leu Ala Ser Gly Val Pro Ile Arg Phe Ser
    50                  55                  60

Gly Ser Gly Ser Gly Thr Ser Tyr Ser Leu Thr Ile Ser Arg Met Glu
65                  70                  75                  80

Ala Glu Asp Thr Ala Thr Tyr Tyr Cys Gln Gln Trp Ser Ser Ser Pro
                85                  90                  95

Leu Thr Phe Gly Ala Gly Thr Lys Leu Glu Leu Lys
            100                 105

<210> SEQ ID NO 457
<211> LENGTH: 107
<212> TYPE: PRT
<213> ORGANISM: Artificial Sequence
<220> FEATURE:
<223> OTHER INFORMATION: Synthetic Construct

<400> SEQUENCE: 457

Asp Ile Gln Met Thr Gln Glx Pro Ala Thr Leu Ser Val Thr Pro Gly
1               5                   10                  15

Asp Arg Val Ser Leu Ser Cys Arg Ala Ser Gln Ser Ile Ser Glu Tyr
            20                  25                  30

Leu His Trp Tyr His Gln Lys Ser His Glu Ser Pro Arg Leu Leu Ile
        35                  40                  45

Lys Phe Ala Ser Gln Ser Ile Cys Gly Ile Pro Ser Arg Phe Ser Gly
    50                  55                  60

Ser Gly Ser Gly Ser Asp Phe Thr Leu Thr Ile Asn Ser Val Glu Pro
65                  70                  75                  80

Glu Asp Val Gly Val Tyr Tyr Cys Gln Asn Gly His Asn Phe Pro Tyr
                85                  90                  95

Thr Phe Gly Gly Gly Thr Lys Leu Glu Ile Lys
            100                 105

<210> SEQ ID NO 458
<211> LENGTH: 107
<212> TYPE: PRT
<213> ORGANISM: Artificial Sequence
<220> FEATURE:
<223> OTHER INFORMATION: Synthetic Construct

<400> SEQUENCE: 458

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

```
Leu Ala Trp Tyr Gln Gln Lys Pro Gly Lys Ser Pro Gln Leu Leu Ile
             35                  40                  45

Tyr Ala Ala Thr Ser Leu Ala Asp Gly Val Pro Ser Arg Phe Ser Gly
 50                      55                  60

Ser Gly Ser Gly Thr Lys Phe Ser Phe Lys Ile Ser Ser Leu Gln Ala
 65                  70                  75                  80

Glu Asp Phe Val Ser Tyr Tyr Cys Gln Gln Leu Tyr Ser Thr Pro Tyr
                 85                  90                  95

Thr Phe Gly Gly Gly Thr Lys Leu Glu Ile Lys
                100                 105
```

<210> SEQ ID NO 459
<211> LENGTH: 112
<212> TYPE: PRT
<213> ORGANISM: Artificial Sequence
<220> FEATURE:
<223> OTHER INFORMATION: Synthetic Construct

<400> SEQUENCE: 459

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
             20                  25                  30

Thr Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Leu Gly Val Tyr Phe Cys Ser Gln Asn
                 85                  90                  95

Thr His Val Pro Tyr Thr Phe Gly Gly Gly Thr Lys Leu Glu Ile Lys
                100                 105                 110
```

<210> SEQ ID NO 460
<211> LENGTH: 105
<212> TYPE: PRT
<213> ORGANISM: Artificial Sequence
<220> FEATURE:
<223> OTHER INFORMATION: Synthetic Construct

<400> SEQUENCE: 460

```
Glx Met Thr Gln Phe Thr Ser Ser Met Ser Gly Ser Glu Gly Asp Arg
 1               5                  10                  15

Val Thr Ile Ser His Arg Ala Ser Gln Asp Ile Ser Glx Tyr Leu Asn
             20                  25                  30

Trp Tyr Glu Gln Lys Ala Asp Gly Thr Ala Asn Leu Ile Ile Tyr Leu
         35                  40                  45

Ser Ser Arg Leu His Ser Gly Glx Pro Ser Arg Leu Ser Gly Glx Gly
 50                  55                  60

Trp Val Thr Asp Tyr Phe Leu Pro Ile His Thr Ser Glu Gln Glu Asp
 65                  70                  75                  80

Arg Gly Ser Tyr Phe Cys Gln Gln Gly His Thr Gly Ala Trp Thr Phe
                 85                  90                  95

Gly Gly Gly Thr Lys Leu Glu Ile Lys
                100                 105
```

<210> SEQ ID NO 461

```
<211> LENGTH: 107
<212> TYPE: PRT
<213> ORGANISM: Artificial Sequence
<220> FEATURE:
<223> OTHER INFORMATION: Synthetic Construct

<400> SEQUENCE: 461

Asp Ile Gln Met Thr Gln Phe Pro Ala Thr Leu Ser Gly Thr Pro Gly
1               5                   10                  15

Asp Arg Val Glx Leu Ser Arg Arg Ala Ser Gln Ser Ile Arg Glu Tyr
            20                  25                  30

Leu His Trp Tyr Gln Gln Lys Ser His Glu Ser Pro Arg Leu Glx Ile
        35                  40                  45

Lys Phe Ala Ser Gln Ser Ile Cys Gly Ile Pro Ser Arg Phe Ser Gly
    50                  55                  60

Ser Gly Ser Gly Ser Asp Phe Thr Leu Ser Ile Asn Thr Val Glu Pro
65                  70                  75                  80

Glu Asp Val Gly Val Tyr Tyr Cys Gln Lys Ala His Asn Phe Pro Tyr
                85                  90                  95

Thr Phe Gly Gly Gly Thr Lys Leu Glu Ile Lys
            100                 105

<210> SEQ ID NO 462
<211> LENGTH: 118
<212> TYPE: PRT
<213> ORGANISM: Artificial Sequence
<220> FEATURE:
<223> OTHER INFORMATION: Synthetic Construct

<400> SEQUENCE: 462

Gln Val Gln Leu Gln Gln Ser Gly Ser Glu Leu Arg Ser Pro Gly Ser
1               5                   10                  15

Ser Val Lys Leu Ser Cys Lys Asp Phe Asp Ser Glu Val Phe Pro Ile
            20                  25                  30

Thr Tyr Met Asn Trp Val Arg Gln Lys Pro Gly His Gly Phe Glu Trp
        35                  40                  45

Ile Gly Asp Ile Leu Pro Ser Ile Gly Arg Thr Met Tyr Gly Glu Lys
    50                  55                  60

Phe Glu Asp Lys Ala Thr Leu Asp Ala Asp Thr Val Ser Asn Thr Ala
65                  70                  75                  80

Tyr Leu Glu Leu Asn Ser Leu Thr Ser Glu Asp Ser Ala Ile Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ala
        115

<210> SEQ ID NO 463
<211> LENGTH: 120
<212> TYPE: PRT
<213> ORGANISM: Artificial Sequence
<220> FEATURE:
<223> OTHER INFORMATION: Synthetic Construct

<400> SEQUENCE: 463

Gln Val Gln Leu Gln Gln Ser Gly Ala Glu Leu Val Arg Pro Gly Ala
1               5                   10                  15

Ser Val Lys Leu Ser Cys Ser Ala Ser Gly Phe Asn Ile Lys Gly Ser
            20                  25                  30
```

```
Leu Leu His Trp Ile Lys Gln Arg Pro Leu Gln Gly Leu Glu Trp Ile
        35                  40                  45

Gly Trp Ile Asp Pro Glu Asp Gly Glu Thr Arg Phe Asp Pro Lys Phe
 50                  55                  60

Gln Asp Lys Ala Phe Leu Thr Ala Asp Thr Ser Ser Thr Thr Ala Tyr
 65                  70                  75                  80

Leu Gln Leu Ser Ser Leu Thr Ser Glu Asp Thr Ala Ile Tyr Tyr Cys
                 85                  90                  95

Ala Arg Thr Glu Tyr Ser Asn Pro Ala Trp Phe Ala Tyr Trp Gly Gln
             100                 105                 110

Gly Thr Leu Val Thr Val Ser Ala
         115                 120

<210> SEQ ID NO 464
<211> LENGTH: 121
<212> TYPE: PRT
<213> ORGANISM: Artificial Sequence
<220> FEATURE:
<223> OTHER INFORMATION: Synthetic Construct

<400> SEQUENCE: 464

Glu Val Lys Leu Val Glu Ser Gly Gly Thr Leu Val Lys Pro Gly Gly
 1               5                  10                  15

Ser Leu Lys Ile Ser Cys Ala Ala Ser Gly Phe Thr Phe Ser Asn Tyr
             20                  25                  30

Asp Met Ser Trp Val Arg Gln Asn Pro Glu Lys Arg Leu Glu Trp Val
         35                  40                  45

Ala Thr Ile Ser Ser Gly Gly Asp Tyr Thr Tyr Tyr Pro Asp Ile Phe
 50                  55                  60

Lys Gly Arg Phe Thr Ile Ser Arg Asp Asp Ala Lys Asn Ala Leu Tyr
 65                  70                  75                  80

Leu Gln Met Ser Ser Leu Arg Ser Glu Asp Thr Ala Leu Tyr Tyr Cys
                 85                  90                  95

Ala Arg His Gly Tyr Gly Asn Tyr Asp Trp Tyr Phe Asp Val Trp Gly
             100                 105                 110

Ala Gly Ala Thr Val Thr Val Ser Ser
         115                 120

<210> SEQ ID NO 465
<211> LENGTH: 118
<212> TYPE: PRT
<213> ORGANISM: Artificial Sequence
<220> FEATURE:
<223> OTHER INFORMATION: Synthetic Construct

<400> SEQUENCE: 465

Gln Val Gln Leu Gln Gln Ser Gly Ser Glu Leu Arg Ser Pro Gly Ser
 1               5                  10                  15

Ser Val Lys Leu Ser Cys Lys Asp Phe Asp Ser Glu Val Phe Pro Ile
             20                  25                  30

Thr Tyr Met Asn Trp Val Arg Gln Lys Pro Gly His Gly Phe Glu Trp
         35                  40                  45

Ile Gly Asp Ile Leu Pro Ser Ile Gly Arg Thr Met Tyr Gly Glu Lys
 50                  55                  60

Phe Glu Asp Lys Ala Thr Leu Asp Ala Asp Thr Val Ser Asn Thr Ala
 65                  70                  75                  80

Tyr Leu Glu Leu Asn Ser Leu Thr Ser Glu Asp Ser Ala Ile Tyr Tyr
                 85                  90                  95
```

Cys Ala Arg Ser Glu Gly Tyr Leu Leu Ala Tyr Trp Gly Gln Gly Thr
                100                 105                 110

Leu Val Thr Val Ser Ala
        115

<210> SEQ ID NO 466
<211> LENGTH: 116
<212> TYPE: PRT
<213> ORGANISM: Artificial Sequence
<220> FEATURE:
<223> OTHER INFORMATION: Synthetic Construct

<400> SEQUENCE: 466

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Ile Phe Thr Asp Tyr
                20                  25                  30

Gly Ile Thr Trp Val Lys Gln Arg Thr Gly Gln Gly Leu Glu Trp Ile
            35                  40                  45

Gly Glu Ile Ser Pro Arg Ser Gly Glu Thr Tyr Phe Asn Glu Asn Tyr
    50                  55                  60

Arg Val Lys Ala Thr Leu Thr Ala Asp Lys Ser Ser Thr Ala Tyr
65                  70                  75                  80

Met Gln Leu Phe Ser Leu Thr Ser Glu Asp Ser Ala Val Tyr Phe Cys
                85                  90                  95

Ala Arg Glu Gly Asn Pro Phe Thr Tyr Trp Gly His Gly Thr Leu Val
                100                 105                 110

Thr Val Ser Ala
        115

<210> SEQ ID NO 467
<211> LENGTH: 118
<212> TYPE: PRT
<213> ORGANISM: Artificial Sequence
<220> FEATURE:
<223> OTHER INFORMATION: Synthetic Construct

<400> SEQUENCE: 467

Gln Val Gln Leu Gln Gln Ser Gly Ser Glu Leu Arg Ser Pro Gly Ser
1               5                   10                  15

Ser Val Lys Leu Ser Cys Lys Asp Phe Asp Ser Glu Val Phe Pro Ile
                20                  25                  30

Thr Tyr Met Asn Trp Val Arg Gln Lys Pro Gly His Gly Phe Glu Trp
            35                  40                  45

Ile Gly Asp Ile Leu Pro Ser Ile Gly Arg Thr Met Tyr Gly Glu Lys
    50                  55                  60

Phe Glu Asp Lys Ala Thr Leu Asp Ala Asp Thr Val Ser Asn Thr Ala
65                  70                  75                  80

Tyr Leu Glu Leu Asn Ser Leu Thr Ser Glu Asp Ser Ala Ile Tyr Tyr
                85                  90                  95

Cys Ala Arg Ser Glu Gly Tyr Leu Leu Ala Tyr Trp Gly Gln Gly Thr
                100                 105                 110

Leu Val Thr Val Ser Ala
        115

<210> SEQ ID NO 468
<211> LENGTH: 117
<212> TYPE: PRT

<213> ORGANISM: Artificial Sequence
<220> FEATURE:
<223> OTHER INFORMATION: Synthetic Construct

<400> SEQUENCE: 468

Gln Val Gln Leu Gln Gln Ser Gly Ala Glu Leu Val Lys Pro Gly Ala
1               5                   10                  15

Ser Val Lys Leu Ser Cys Lys Thr Ser Gly Tyr Thr Phe Thr Asn Tyr
                20                  25                  30

Trp Ile Asn Trp Val Lys Gln Arg Pro Gly Gln Gly Leu Glu Trp Ile
            35                  40                  45

Gly Asn Ile Tyr Ser Gly Ser Ser Arg Thr Asn Tyr Asn Glu Lys Phe
    50                  55                  60

Lys Ser Lys Ala Thr Leu Thr Val Asp Thr Ser Ser Thr Ala Tyr
65                  70                  75                  80

Met Gln Leu Ser Ser Leu Thr Ser Asp Asp Ser Ala Val Tyr Tyr Cys
                85                  90                  95

Ala Arg Glu Gly Leu Arg Ala Met Asp Tyr Trp Gly Gln Gly Thr Ser
            100                 105                 110

Val Thr Val Ser Ser
        115

<210> SEQ ID NO 469
<211> LENGTH: 121
<212> TYPE: PRT
<213> ORGANISM: Artificial Sequence
<220> FEATURE:
<223> OTHER INFORMATION: Synthetic Construct

<400> SEQUENCE: 469

Glu Val Lys Leu Ala Asp Ser Gly Gly Ala Leu Val Asn Pro Gly Gly
1               5                   10                  15

Ser Leu Lys Ile Ser Cys Ala Val Ser Gly Phe Ile Phe Ser Asn Tyr
                20                  25                  30

Asp Met Ser Trp Val Arg Gln Asn Pro Glu Lys Arg Leu Glu Trp Val
            35                  40                  45

Ala Thr Ile Ser Ser Gly Gly Gly Tyr Thr Tyr Tyr Pro Asp Ser Val
    50                  55                  60

Lys Gly Arg Phe Thr Ile Ser Arg Asp Asn Ala Lys Asn Ala Leu Tyr
65                  70                  75                  80

Leu Gln Met Ser Ser Leu Arg Ser Glu Asp Thr Ala Leu Tyr Tyr Cys
                85                  90                  95

Thr Arg His Gly Tyr Gly Asn Tyr Asp Trp Tyr Phe Asp Val Trp Gly
            100                 105                 110

Ala Gly Ala Thr Val Thr Val Ser Ser
        115                 120

<210> SEQ ID NO 470
<211> LENGTH: 118
<212> TYPE: PRT
<213> ORGANISM: Artificial Sequence
<220> FEATURE:
<223> OTHER INFORMATION: Synthetic Construct

<400> SEQUENCE: 470

Leu Val Glx Ser Gly Gly Ala Leu Val Lys Pro Gly Gly Ser Leu Lys
1               5                   10                  15

Leu Ser Cys Ala Ala Ser Gly Phe Thr Phe Ser Asn Tyr Ala Met Ser
                20                  25                  30

```
Trp Val Arg Gln Thr Pro Glu Lys Arg Leu Glu Trp Val Ala Ser Ile
            35                  40                  45

Ser Ser Gly Gly Ser Tyr Asn Tyr Tyr Pro Asp Ser Val Lys Gly Arg
    50                  55                  60

Phe Thr Ile Ser Arg Asp Asn Ala Arg Asn Thr Leu Tyr Leu Gln Met
65                  70                  75                  80

Ser Ser Leu Arg Ser Lys Asp Thr Ala Met Tyr Tyr Cys Ala Ser Gln
                85                  90                  95

Ser Tyr Gly Ser Ser Tyr Trp Tyr Phe Asp Val Trp Gly Ala Gly Thr
                100                 105                 110

Thr Val Thr Val Ser Ser
            115

<210> SEQ ID NO 471
<211> LENGTH: 116
<212> TYPE: PRT
<213> ORGANISM: Artificial Sequence
<220> FEATURE:
<223> OTHER INFORMATION: Synthetic Construct

<400> SEQUENCE: 471

Gln Val Gln Leu Lys Gln Ser Gly Pro Val Leu Val Ala Pro Ser Gln
1               5                   10                  15

Ser Leu Ser Ile Thr Cys Thr Val Ser Gly Phe Ser Leu Ser Asn Tyr
            20                  25                  30

Gly Val His Trp Val Arg Gln Phe Pro Gly Lys Gly Leu Glu Trp Leu
        35                  40                  45

Gly Val Ile Trp Ala Gly Gly Ile Thr Asn Tyr Asn Ser Val Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Lys Gln Gly Gly Thr Ser Phe Ser Tyr Trp Gly Gln Gly Thr Leu Val
                100                 105                 110

Thr Val Ser Ala
            115

<210> SEQ ID NO 472
<211> LENGTH: 118
<212> TYPE: PRT
<213> ORGANISM: Artificial Sequence
<220> FEATURE:
<223> OTHER INFORMATION: Synthetic Construct

<400> SEQUENCE: 472

Gln Val Gln Leu Gln Gln Ser Gly Ser Glu Leu Arg Ser Pro Gly Ser
1               5                   10                  15

Ser Val Lys Leu Ser Cys Lys Asp Phe Asp Ser Glu Val Phe Pro Ile
            20                  25                  30

Thr Tyr Met Asn Trp Val Arg Gln Lys Pro Gly His Gly Phe Glu Trp
        35                  40                  45

Ile Gly Asp Ile Leu Pro Ser Ile Gly Arg Thr Met Tyr Gly Glu Lys
    50                  55                  60

Phe Glu Asp Lys Ala Thr Leu Asp Ala Asp Thr Val Ser Asn Thr Ala
65                  70                  75                  80
```

```
Tyr Leu Glu Leu Asn Ser Leu Thr Ser Glu Asp Ser Ala Ile Tyr Tyr
                85                  90                  95

Cys Ala Arg Ser Glu Gly Tyr Leu Leu Ala Tyr Trp Gly Gln Gly Thr
            100                 105                 110

Leu Val Thr Val Ser Ala
        115

<210> SEQ ID NO 473
<211> LENGTH: 118
<212> TYPE: PRT
<213> ORGANISM: Artificial Sequence
<220> FEATURE:
<223> OTHER INFORMATION: Synthetic Construct

<400> SEQUENCE: 473

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Thr Asn Cys
            20                  25                  30

Trp Met Asn Trp Val Arg Gln Arg Pro Gly Lys Gly Leu Asp Trp Ile
        35                  40                  45

Gly Arg Ile Phe Pro Gly Asn Gly His Thr Asn Tyr Ser Gly Lys Phe
    50                  55                  60

Lys Asp Lys Ala Thr Leu Thr Glu Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Asp Tyr Ser Asp Tyr Tyr Phe Asp Tyr Trp Gly Gln Gly Thr
            100                 105                 110

Thr Leu Thr Val Ser Ser
        115

<210> SEQ ID NO 474
<211> LENGTH: 121
<212> TYPE: PRT
<213> ORGANISM: Artificial Sequence
<220> FEATURE:
<223> OTHER INFORMATION: Synthetic Construct

<400> SEQUENCE: 474

Glu Val Lys Leu Val Glu Phe Gly Gly Ala Leu Val Lys Pro Gly Gly
1               5                   10                  15

Ser Leu Lys Leu Ser Cys Ala Ala Leu Gly Phe Thr Phe Ser Thr Tyr
            20                  25                  30

Ala Met Phe Arg Val Arg Gln Thr Pro Glu Lys Arg Glu Glu Gly Val
        35                  40                  45

Ala Ser Ile Ser Ser Gly Gly Arg Tyr Thr Tyr Tyr Pro Asp Ser Ala
    50                  55                  60

Lys Asp Arg His Pro Ile Phe Arg Asp Asn Ala Arg Asn Thr Leu Tyr
65                  70                  75                  80

Leu Gln Met Ser Ser Leu Arg Ser Lys Asp Thr Ala Met Tyr Tyr Cys
                85                  90                  95

Val Arg His Ser Tyr Gly Ser Ser Tyr Trp Tyr Leu Asp Val Trp Gly
            100                 105                 110

Ala Gly Thr Thr Val Thr Val Ser Ser
        115                 120
```

```
<210> SEQ ID NO 475
<211> LENGTH: 110
<212> TYPE: PRT
<213> ORGANISM: Artificial Sequence
<220> FEATURE:
<223> OTHER INFORMATION: Synthetic Construct

<400> SEQUENCE: 475
```

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro
            100                 105                 110

```
<210> SEQ ID NO 476
<211> LENGTH: 11
<212> TYPE: PRT
<213> ORGANISM: Artificial Sequence
<220> FEATURE:
<223> OTHER INFORMATION: Synthetic Construct

<400> SEQUENCE: 476
```

Arg Ala Ser Gln Asp Ile Asn Thr Tyr Leu Asn
1               5                   10

```
<210> SEQ ID NO 477
<211> LENGTH: 7
<212> TYPE: PRT
<213> ORGANISM: Artificial Sequence
<220> FEATURE:
<223> OTHER INFORMATION: Synthetic Construct

<400> SEQUENCE: 477
```

Tyr Thr Ser Arg Leu His Ser
1               5

```
<210> SEQ ID NO 478
<211> LENGTH: 9
<212> TYPE: PRT
<213> ORGANISM: Artificial Sequence
<220> FEATURE:
<223> OTHER INFORMATION: Synthetic Construct

<400> SEQUENCE: 478
```

Gln Gln Gly Asn Thr Leu Pro Trp Thr
1               5

```
<210> SEQ ID NO 479
<211> LENGTH: 10
<212> TYPE: PRT
<213> ORGANISM: Artificial Sequence
<220> FEATURE:
<223> OTHER INFORMATION: Synthetic Construct
```

<400> SEQUENCE: 479

Gly Tyr Ala Phe Thr Asn Cys Trp Met Asn
1               5                   10

<210> SEQ ID NO 480
<211> LENGTH: 14
<212> TYPE: PRT
<213> ORGANISM: Artificial Sequence
<220> FEATURE:
<223> OTHER INFORMATION: Synthetic Construct

<400> SEQUENCE: 480

Val Ser Thr Ile Ser Ser Gly Gly Gly Tyr Thr Tyr Tyr Ala
1               5                   10

<210> SEQ ID NO 481
<211> LENGTH: 14
<212> TYPE: PRT
<213> ORGANISM: Artificial Sequence
<220> FEATURE:
<223> OTHER INFORMATION: Synthetic Construct

<400> SEQUENCE: 481

Val Ala Thr Ile Ser Ser Gly Gly Gly Tyr Thr Tyr Tyr Ala
1               5                   10

<210> SEQ ID NO 482
<211> LENGTH: 10
<212> TYPE: PRT
<213> ORGANISM: Artificial Sequence
<220> FEATURE:
<223> OTHER INFORMATION: Synthetic Construct

<400> SEQUENCE: 482

Arg Ile Phe Pro Gly Asn Gly His Thr Asn
1               5                   10

<210> SEQ ID NO 483
<211> LENGTH: 9
<212> TYPE: PRT
<213> ORGANISM: Artificial Sequence
<220> FEATURE:
<223> OTHER INFORMATION: Synthetic Construct

<400> SEQUENCE: 483

Asp Tyr Ser Asp Tyr Tyr Phe Asp Tyr
1               5

<210> SEQ ID NO 484
<211> LENGTH: 106
<212> TYPE: PRT
<213> ORGANISM: Artificial Sequence
<220> FEATURE:
<223> OTHER INFORMATION: Synthetic Construct

<400> SEQUENCE: 484

Glu Ile Val Leu Thr Gln Ser Pro Ala Thr Leu Ser Leu Ser Pro Gly
1               5                   10                  15

Glu Arg Ala Thr Leu Ser Cys Ser Ala Asn Ser Ser Phe Thr Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Pro Leu Thr
                85                  90                  95

Phe Gly Gln Gly Thr Lys Leu Glu Ile Lys
            100                 105

<210> SEQ ID NO 485
<211> LENGTH: 106
<212> TYPE: PRT
<213> ORGANISM: Artificial Sequence
<220> FEATURE:
<223> OTHER INFORMATION: Synthetic Construct

<400> SEQUENCE: 485

Glu Ile Val Leu Thr Gln Ser Pro Ala Thr Leu Ser Leu Ser Pro Gly
1               5                   10                  15

Glu Arg Val Thr Met Ser Cys Ser Ala Asn Ser Ser Phe Thr Tyr Met
                20                  25                  30

Tyr Trp Tyr Gln Gln Lys Pro Gly Gln Ala Pro Arg Leu Leu Ile Tyr
            35                  40                  45

Asp Thr Ser Asn Leu Ala Ser Gly Val Pro Ala Arg Phe Ser Gly Ser
        50                  55                  60

Gly Ser Gly Thr Asp Tyr Thr Leu Thr Ile Ser Ser Met Glu Pro Glu
65                  70                  75                  80

Asp Phe Ala Val Tyr Tyr Cys Gln Gln Trp Ser Ser Pro Leu Thr
                85                  90                  95

Phe Gly Gln Gly Thr Lys Leu Glu Ile Lys
            100                 105

<210> SEQ ID NO 486
<211> LENGTH: 106
<212> TYPE: PRT
<213> ORGANISM: Artificial Sequence
<220> FEATURE:
<223> OTHER INFORMATION: Synthetic Construct

<400> SEQUENCE: 486

Glu Ile Val Leu Thr Gln Ser Pro Ala Thr Leu Ser Leu Ser Pro Gly
1               5                   10                  15

Glu Arg Val Thr Met Ser Cys Ser Ala Asn Ser Ser Phe Thr Tyr Met
                20                  25                  30

Tyr Trp Tyr Gln Gln Lys Pro Gly Gln Ala Pro Arg Leu Leu Ile Phe
            35                  40                  45

Asp Thr Ser Asn Leu Ala Ser Gly Val Pro Ala Arg Phe Ser Gly Ser
        50                  55                  60

Gly Ser Gly Thr Asp Tyr Thr Leu Thr Ile Ser Ser Met Glu Pro Glu
65                  70                  75                  80

Asp Phe Ala Val Tyr Tyr Cys Gln Gln Trp Ser Ser Pro Leu Thr
                85                  90                  95

Phe Gly Gln Gly Thr Lys Leu Glu Leu Lys
            100                 105

<210> SEQ ID NO 487
<211> LENGTH: 107
<212> TYPE: PRT
<213> ORGANISM: Artificial Sequence
<220> FEATURE:
<223> OTHER INFORMATION: Synthetic Construct

<400> SEQUENCE: 487

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Thr Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Leu Glu Ile Lys
            100                 105

<210> SEQ ID NO 488
<211> LENGTH: 107
<212> TYPE: PRT
<213> ORGANISM: Artificial Sequence
<220> FEATURE:
<223> OTHER INFORMATION: Synthetic Construct

<400> SEQUENCE: 488

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Thr Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Leu Glu Ile Lys
            100                 105

<210> SEQ ID NO 489
<211> LENGTH: 107
<212> TYPE: PRT
<213> ORGANISM: Artificial Sequence
<220> FEATURE:
<223> OTHER INFORMATION: Synthetic Construct

<400> SEQUENCE: 489

Asp Val Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Thr Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

-continued

Glu Asp Phe Ala Thr Tyr Tyr Cys Gln Gln Gly Asn Thr Leu Pro Trp
                85                  90                  95

Thr Phe Gly Gln Gly Thr Lys Leu Glu Ile Lys
            100                 105

<210> SEQ ID NO 490
<211> LENGTH: 121
<212> TYPE: PRT
<213> ORGANISM: Artificial Sequence
<220> FEATURE:
<223> OTHER INFORMATION: Synthetic Construct

<400> SEQUENCE: 490

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asn Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Gly Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 491
<211> LENGTH: 121
<212> TYPE: PRT
<213> ORGANISM: Artificial Sequence
<220> FEATURE:
<223> OTHER INFORMATION: Synthetic Construct

<400> SEQUENCE: 491

Glu Val Gln Leu Val Glu Ser Gly Gly Gly Leu Val Lys Pro Gly Gly
1               5                   10                  15

Ser Leu Arg Leu Ser Cys Ala Val Ser Gly Phe Ile Phe Ser Asn Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Gly Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 492
<211> LENGTH: 121
<212> TYPE: PRT

<213> ORGANISM: Artificial Sequence
<220> FEATURE:
<223> OTHER INFORMATION: Synthetic Construct

<400> SEQUENCE: 492

Glu Val Gln Leu Val Glu Ser Gly Gly Gly Leu Val Lys Pro Gly Gly
1               5                   10                  15

Ser Leu Arg Ile Ser Cys Ala Val Ser Gly Phe Ile Phe Ser Asn Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Gly Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg His Gly Tyr Gly Asn Tyr Asp Trp Tyr Phe Asp Val Trp Gly
            100                 105                 110

Gln Gly Ala Leu Val Thr Val Ser Ser
        115                 120

<210> SEQ ID NO 493
<211> LENGTH: 118
<212> TYPE: PRT
<213> ORGANISM: Artificial Sequence
<220> FEATURE:
<223> OTHER INFORMATION: Synthetic Construct

<400> SEQUENCE: 493

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Cys
            20                  25                  30

Trp Met Asn Trp Val Arg Gln Ala Pro Gly Gln Gly Leu Glu Trp Met
        35                  40                  45

Gly Arg Ile Phe Pro Gly Asn Gly His Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
            100                 105                 110

Leu Val Thr Val Ser Ser
        115

<210> SEQ ID NO 494
<211> LENGTH: 118
<212> TYPE: PRT
<213> ORGANISM: Artificial Sequence
<220> FEATURE:
<223> OTHER INFORMATION: Synthetic Construct

<400> SEQUENCE: 494

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Cys
            20                  25                  30

Trp Met Asn Trp Val Arg Gln Ala Pro Gly Gln Gly Leu Glu Trp Ile
            35                  40                  45

Gly Arg Ile Phe Pro Gly Asn Gly His Thr Asn Tyr Ala Gln Lys Phe
        50                  55                  60

Gln Gly Arg Val Thr Met Thr Glu Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
            100                 105                 110

Leu Val Thr Val Ser Ser
        115

<210> SEQ ID NO 495
<211> LENGTH: 118
<212> TYPE: PRT
<213> ORGANISM: Artificial Sequence
<220> FEATURE:
<223> OTHER INFORMATION: Synthetic Construct

<400> SEQUENCE: 495

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ala Phe Thr Asn Cys
            20                  25                  30

Trp Met Asn Trp Val Arg Gln Ala Pro Gly Gln Gly Leu Glu Trp Ile
            35                  40                  45

Gly Arg Ile Phe Pro Gly Asn Gly His Thr Asn Tyr Ala Gln Lys Phe
        50                  55                  60

Gln Gly Arg Ala Thr Leu Thr Glu Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
            100                 105                 110

Leu Leu Thr Val Ser Ser
        115

<210> SEQ ID NO 496
<211> LENGTH: 118
<212> TYPE: PRT
<213> ORGANISM: Artificial Sequence
<220> FEATURE:
<223> OTHER INFORMATION: Synthetic Construct

<400> SEQUENCE: 496

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ala Phe Thr Asn Cys
            20                  25                  30

Trp Met Asn Trp Val Arg Gln Ala Pro Gly Gln Gly Leu Glu Trp Ile
            35                  40                  45

Gly Arg Ile Phe Pro Gly Asn Gly His Thr Asn Tyr Ala Gln Lys Phe
        50                  55                  60

Gln Gly Arg Ala Thr Leu Thr Glu Asp Lys Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Asp Tyr Ser Asp Tyr Phe Asp Tyr Trp Gly Gln Gly Thr
            100                 105                 110

Leu Leu Thr Val Ser Ser
        115
```

<210> SEQ ID NO 497
<211> LENGTH: 95
<212> TYPE: PRT
<213> ORGANISM: Artificial Sequence
<220> FEATURE:
<223> OTHER INFORMATION: Synthetic Construct

<400> SEQUENCE: 497

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95
```

<210> SEQ ID NO 498
<211> LENGTH: 12
<212> TYPE: PRT
<213> ORGANISM: Artificial Sequence
<220> FEATURE:
<223> OTHER INFORMATION: Synthetic Construct

<400> SEQUENCE: 498

```
Tyr Thr Phe Gly Gln Gly Thr Lys Leu Glu Ile Lys
1               5                   10
```

<210> SEQ ID NO 499
<211> LENGTH: 106
<212> TYPE: PRT
<213> ORGANISM: Artificial Sequence
<220> FEATURE:
<223> OTHER INFORMATION: Synthetic Construct

<400> SEQUENCE: 499

```
Gln Ile Val Leu Thr Gln Ser Pro Ala Ile Leu Ser Ala Ser Pro Gly
1               5                   10                  15

Glu Lys Val Thr Met Thr Cys Ser Ala Asn Ser Ser Phe Thr Tyr Met
            20                  25                  30

Tyr Trp Tyr Gln Gln Lys Pro Gly Ser Ser Pro Arg Leu Leu Ile Phe
        35                  40                  45

Asp Thr Ser Asn Leu Ala Ser Gly Val Pro Ile Arg Phe Ser Gly Ser
    50                  55                  60

Gly Ser Gly Thr Ser Tyr Ser Leu Thr Ile Ser Arg Met Glu Ala Glu
65                  70                  75                  80

Asp Thr Ala Thr Tyr Tyr Cys Gln Gln Trp Ser Ser Ser Pro Leu Thr
                85                  90                  95
```

```
Phe Gly Ala Gly Thr Lys Leu Glu Leu Lys
            100                 105

<210> SEQ ID NO 500
<211> LENGTH: 106
<212> TYPE: PRT
<213> ORGANISM: Artificial Sequence
<220> FEATURE:
<223> OTHER INFORMATION: Synthetic Construct

<400> SEQUENCE: 500

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Gly Gln Gly Thr Lys Leu Glu Ile Lys
            100                 105

<210> SEQ ID NO 501
<211> LENGTH: 106
<212> TYPE: PRT
<213> ORGANISM: Artificial Sequence
<220> FEATURE:
<223> OTHER INFORMATION: Synthetic Construct

<400> SEQUENCE: 501

Glu Ile Val Leu Thr Gln Ser Pro Ala Thr Leu Ser Leu Ser Pro Gly
1               5                   10                  15

Glu Arg Ala Thr Leu Ser Cys Ser Ala Asn Ser Ser Phe Thr Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Pro Leu Thr
                85                  90                  95

Phe Gly Gln Gly Thr Lys Leu Glu Ile Lys
            100                 105

<210> SEQ ID NO 502
<211> LENGTH: 106
<212> TYPE: PRT
<213> ORGANISM: Artificial Sequence
<220> FEATURE:
<223> OTHER INFORMATION: Synthetic Construct

<400> SEQUENCE: 502

Glu Ile Val Leu Thr Gln Ser Pro Ala Thr Leu Ser Leu Ser Pro Gly
1               5                   10                  15
```

Glu Arg Val Thr Met Ser Cys Ser Ala Asn Ser Ser Phe Thr Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Met Glu Pro Glu
65                  70                  75                  80

Asp Phe Ala Val Tyr Tyr Cys Gln Gln Trp Ser Ser Ser Pro Leu Thr
                85                  90                  95

Phe Gly Gln Gly Thr Lys Leu Glu Ile Lys
            100                 105

<210> SEQ ID NO 503
<211> LENGTH: 106
<212> TYPE: PRT
<213> ORGANISM: Artificial Sequence
<220> FEATURE:
<223> OTHER INFORMATION: Synthetic Construct

<400> SEQUENCE: 503

Glu Ile Val Leu Thr Gln Ser Pro Ala Thr Leu Ser Leu Ser Pro Gly
1               5                   10                  15

Glu Arg Val Thr Met Ser Cys Ser Ala Asn Ser Ser Phe Thr Tyr Met
            20                  25                  30

Tyr Trp Tyr Gln Gln Lys Pro Gly Gln Ala Pro Arg Leu Leu Ile Phe
        35                  40                  45

Asp Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Met Glu Pro Glu
65                  70                  75                  80

Asp Phe Ala Val Tyr Tyr Cys Gln Gln Trp Ser Ser Ser Pro Leu Thr
                85                  90                  95

Phe Gly Gln Gly Thr Lys Leu Glu Leu Lys
            100                 105

<210> SEQ ID NO 504
<211> LENGTH: 95
<212> TYPE: PRT
<213> ORGANISM: Artificial Sequence
<220> FEATURE:
<223> OTHER INFORMATION: Synthetic Construct

<400> SEQUENCE: 504

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr
                85                  90                  95

<210> SEQ ID NO 505
<211> LENGTH: 15
<212> TYPE: PRT
<213> ORGANISM: Artificial Sequence
<220> FEATURE:
<223> OTHER INFORMATION: Synthetic Construct

<400> SEQUENCE: 505

```
Tyr Phe Asp Tyr Trp Gly Gln Gly Thr Leu Val Thr Val Ser Ser
1               5                   10                  15
```

<210> SEQ ID NO 506
<211> LENGTH: 121
<212> TYPE: PRT
<213> ORGANISM: Artificial Sequence
<220> FEATURE:
<223> OTHER INFORMATION: Synthetic Construct

<400> SEQUENCE: 506

```
Glu Val Gln Leu Val Glu Ser Gly Gly Ala Leu Val Lys Pro Gly
1               5                   10                  15

Ser Leu Lys Ile Ser Cys Ala Val Ser Gly Phe Ile Phe Ser Asn Tyr
                20                  25                  30

Asp Met Ser Trp Val Arg Gln Asn Pro Glu Lys Arg Leu Glu Trp Val
            35                  40                  45

Ala Thr Ile Ser Ser Gly Gly Gly Tyr Thr Tyr Tyr Pro Asp Ser Val
        50                  55                  60

Lys Gly Arg Phe Thr Ile Ser Arg Asp Asn Ala Lys Asn Ala Leu Tyr
65                  70                  75                  80

Leu Gln Met Ser Ser Leu Arg Ser Glu Asp Thr Ala Leu Tyr Tyr Cys
                85                  90                  95

Thr Arg His Gly Tyr Gly Asn Tyr Asp Trp Tyr Phe Asp Val Trp Gly
            100                 105                 110

Ala Gly Ala Thr Val Thr Val Ser Ser
        115                 120
```

<210> SEQ ID NO 507
<211> LENGTH: 109
<212> TYPE: PRT
<213> ORGANISM: Artificial Sequence
<220> FEATURE:
<223> OTHER INFORMATION: Synthetic Construct

<400> SEQUENCE: 507

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Ser Tyr Ile Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser
            100                 105
```

<210> SEQ ID NO 508

```
<211> LENGTH: 121
<212> TYPE: PRT
<213> ORGANISM: Artificial Sequence
<220> FEATURE:
<223> OTHER INFORMATION: Synthetic Construct

<400> SEQUENCE: 508

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asn Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Gly Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 509
<211> LENGTH: 121
<212> TYPE: PRT
<213> ORGANISM: Artificial Sequence
<220> FEATURE:
<223> OTHER INFORMATION: Synthetic Construct

<400> SEQUENCE: 509

Glu Val Gln Leu Val Glu Ser Gly Gly Gly Leu Val Lys Pro Gly Gly
1               5                   10                  15

Ser Leu Arg Leu Ser Cys Ala Val Ser Gly Phe Ile Phe Ser Asn Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Gly Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg His Gly Tyr Gly Asn Tyr Asp Trp Tyr Phe Asp Val Trp Gly
            100                 105                 110

Gln Gly Thr Leu Val Thr Val Ser Ser
        115                 120

<210> SEQ ID NO 510
<211> LENGTH: 121
<212> TYPE: PRT
<213> ORGANISM: Artificial Sequence
<220> FEATURE:
<223> OTHER INFORMATION: Synthetic Construct

<400> SEQUENCE: 510

Glu Val Gln Leu Val Glu Ser Gly Gly Gly Leu Val Lys Pro Gly Gly
1               5                   10                  15
```

-continued

Ser Leu Arg Ile Ser Cys Ala Val Ser Gly Phe Ile Phe Ser Asn Tyr
            20                  25                  30

Asp Met Ser Trp Val Arg Gln Ala Pro Gly Lys Gly Leu Glu Trp Val
            35                  40                  45

Ala Thr Ile Ser Ser Gly Gly Gly Tyr Thr Tyr Tyr Ala Asp Ser Val
50                      55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg His Gly Tyr Gly Asn Tyr Asp Trp Tyr Phe Asp Val Trp Gly
            100                 105                 110

Gln Gly Ala Leu Val Thr Val Ser Ser
        115                 120

<210> SEQ ID NO 511
<211> LENGTH: 94
<212> TYPE: PRT
<213> ORGANISM: Artificial Sequence
<220> FEATURE:
<223> OTHER INFORMATION: Synthetic Construct

<400> SEQUENCE: 511

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr
                85                  90

<210> SEQ ID NO 512
<211> LENGTH: 12
<212> TYPE: PRT
<213> ORGANISM: Artificial Sequence
<220> FEATURE:
<223> OTHER INFORMATION: Synthetic Construct

<400> SEQUENCE: 512

Tyr Thr Phe Gly Gln Gly Thr Lys Leu Glu Ile Lys
1               5                   10

<210> SEQ ID NO 513
<211> LENGTH: 107
<212> TYPE: PRT
<213> ORGANISM: Artificial Sequence
<220> FEATURE:
<223> OTHER INFORMATION: Synthetic Construct

<400> SEQUENCE: 513

Asp Val Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Thr Tyr
            20                  25                  30

```
Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 514
<211> LENGTH: 106
<212> TYPE: PRT
<213> ORGANISM: Artificial Sequence
<220> FEATURE:
<223> OTHER INFORMATION: Synthetic Construct

<400> SEQUENCE: 514

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Phe Gly Gln Gly Thr Lys Leu Glu Ile Lys
            100                 105

<210> SEQ ID NO 515
<211> LENGTH: 107
<212> TYPE: PRT
<213> ORGANISM: Artificial Sequence
<220> FEATURE:
<223> OTHER INFORMATION: Synthetic Construct

<400> SEQUENCE: 515

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Thr Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Leu Glu Ile Lys
            100                 105
```

<210> SEQ ID NO 516
<211> LENGTH: 107
<212> TYPE: PRT
<213> ORGANISM: Artificial Sequence
<220> FEATURE:
<223> OTHER INFORMATION: Synthetic Construct

<400> SEQUENCE: 516

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Thr Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Leu Glu Ile Lys
            100                 105
```

<210> SEQ ID NO 517
<211> LENGTH: 107
<212> TYPE: PRT
<213> ORGANISM: Artificial Sequence
<220> FEATURE:
<223> OTHER INFORMATION: Synthetic Construct

<400> SEQUENCE: 517

```
Asp Val Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Thr Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Leu Glu Ile Lys
            100                 105
```

<210> SEQ ID NO 518
<211> LENGTH: 94
<212> TYPE: PRT
<213> ORGANISM: Artificial Sequence
<220> FEATURE:
<223> OTHER INFORMATION: Synthetic Construct

<400> SEQUENCE: 518

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45
```

```
Gly Ile Ile Asn Pro Ser Gly Gly Ser Thr Ser Tyr Ala Gln Lys Phe
            50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr
                85                  90
```

<210> SEQ ID NO 519
<211> LENGTH: 15
<212> TYPE: PRT
<213> ORGANISM: Artificial Sequence
<220> FEATURE:
<223> OTHER INFORMATION: Synthetic Construct

<400> SEQUENCE: 519

```
Tyr Phe Asp Tyr Trp Gly Gln Gly Thr Leu Val Thr Val Ser Ser
  1               5                  10                  15
```

<210> SEQ ID NO 520
<211> LENGTH: 118
<212> TYPE: PRT
<213> ORGANISM: Artificial Sequence
<220> FEATURE:
<223> OTHER INFORMATION: Synthetic Construct

<400> SEQUENCE: 520

```
Gln Val His Leu Gln Gln Ser Gly Pro Glu Leu Val Lys Pro Gly Ala
  1               5                  10                  15

Ser Val Lys Ile Ser Cys Lys Ala Ser Gly Tyr Ala Phe Thr Asn Cys
             20                  25                  30

Trp Met Asn Trp Val Arg Gln Arg Pro Gly Lys Gly Leu Asp Trp Ile
         35                  40                  45

Gly Arg Ile Phe Pro Gly Asn Gly His Thr Asn Tyr Ser Gly Lys Phe
     50                  55                  60

Lys Asp Lys Ala Thr Leu Thr Glu Asp Lys Ser Ser Thr Ala Tyr
 65                  70                  75                  80

Met Gln Leu Ser Ser Leu Thr Ser Glu Asp Ser Ala Val Tyr Phe Cys
                85                  90                  95

Ala Arg Asp Tyr Ser Asp Tyr Tyr Phe Asp Tyr Trp Gly Gln Gly Thr
            100                 105                 110

Thr Leu Thr Val Ser Ser
        115
```

<210> SEQ ID NO 521
<211> LENGTH: 109
<212> TYPE: PRT
<213> ORGANISM: Artificial Sequence
<220> FEATURE:
<223> OTHER INFORMATION: Synthetic Construct

<400> SEQUENCE: 521

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
         35                  40                  45

Gly Ile Ile Asn Pro Ser Gly Gly Ser Thr Ser Tyr Ala Gln Lys Phe
     50                  55                  60
```

-continued

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Gly Gln Gly Thr Leu Val Thr Val Ser Ser
            100                 105

<210> SEQ ID NO 522
<211> LENGTH: 118
<212> TYPE: PRT
<213> ORGANISM: Artificial Sequence
<220> FEATURE:
<223> OTHER INFORMATION: Synthetic Construct

<400> SEQUENCE: 522

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Cys
                20                  25                  30

Trp Met Asn Trp Val Arg Gln Ala Pro Gly Gln Gly Leu Glu Trp Met
            35                  40                  45

Gly Arg Ile Phe Pro Gly Asn Gly His Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
            100                 105                 110

Leu Val Thr Val Ser Ser
        115

<210> SEQ ID NO 523
<211> LENGTH: 118
<212> TYPE: PRT
<213> ORGANISM: Artificial Sequence
<220> FEATURE:
<223> OTHER INFORMATION: Synthetic Construct

<400> SEQUENCE: 523

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Cys
                20                  25                  30

Trp Met Asn Trp Val Arg Gln Ala Pro Gly Gln Gly Leu Glu Trp Ile
            35                  40                  45

Gly Arg Ile Phe Pro Gly Asn Gly His Thr Asn Tyr Ala Gln Lys Phe
    50                  55                  60

Gln Gly Arg Val Thr Met Thr Glu Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
            100                 105                 110

Leu Val Thr Val Ser Ser
        115

<210> SEQ ID NO 524

```
<211> LENGTH: 118
<212> TYPE: PRT
<213> ORGANISM: Artificial Sequence
<220> FEATURE:
<223> OTHER INFORMATION: Synthetic Construct

<400> SEQUENCE: 524

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ala Phe Thr Asn Cys
                20                  25                  30

Trp Met Asn Trp Val Arg Gln Ala Pro Gly Gln Gly Leu Glu Trp Ile
            35                  40                  45

Gly Arg Ile Phe Pro Gly Asn Gly His Thr Asn Tyr Ala Gln Lys Phe
    50                  55                  60

Gln Gly Arg Ala Thr Leu Thr Glu Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
                100                 105                 110

Leu Leu Thr Val Ser Ser
            115

<210> SEQ ID NO 525
<211> LENGTH: 118
<212> TYPE: PRT
<213> ORGANISM: Artificial Sequence
<220> FEATURE:
<223> OTHER INFORMATION: Synthetic Construct

<400> SEQUENCE: 525

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ala Phe Thr Asn Cys
                20                  25                  30

Trp Met Asn Trp Val Arg Gln Ala Pro Gly Gln Gly Leu Glu Trp Ile
            35                  40                  45

Gly Arg Ile Phe Pro Gly Asn Gly His Thr Asn Tyr Ala Gln Lys Phe
    50                  55                  60

Gln Gly Arg Ala Thr Leu Thr Glu Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
                100                 105                 110

Leu Leu Thr Val Ser Ser
            115

<210> SEQ ID NO 526
<211> LENGTH: 21
<212> TYPE: DNA
<213> ORGANISM: Artificial Sequence
<220> FEATURE:
<223> OTHER INFORMATION: Synthetic Construct

<400> SEQUENCE: 526
ctccactcac ggcaaattca a                                            21
```

```
<210> SEQ ID NO 527
<211> LENGTH: 22
<212> TYPE: DNA
<213> ORGANISM: Artificial Sequence
<220> FEATURE:
<223> OTHER INFORMATION: Synthetic Construct

<400> SEQUENCE: 527
gatgacaagc ttcccattct cg                                          22

<210> SEQ ID NO 528
<211> LENGTH: 21
<212> TYPE: DNA
<213> ORGANISM: Artificial Sequence
<220> FEATURE:
<223> OTHER INFORMATION: Synthetic Construct

<400> SEQUENCE: 528
ccgtcagccg atttgctatc t                                           21

<210> SEQ ID NO 529
<211> LENGTH: 22
<212> TYPE: DNA
<213> ORGANISM: Artificial Sequence
<220> FEATURE:
<223> OTHER INFORMATION: Synthetic Construct

<400> SEQUENCE: 529
acggcagaga ggaggttgac tt                                          22

<210> SEQ ID NO 530
<211> LENGTH: 22
<212> TYPE: DNA
<213> ORGANISM: Artificial Sequence
<220> FEATURE:
<223> OTHER INFORMATION: Synthetic Construct

<400> SEQUENCE: 530
acaacaaaaa agcctcgtgc tg                                          22

<210> SEQ ID NO 531
<211> LENGTH: 22
<212> TYPE: DNA
<213> ORGANISM: Artificial Sequence
<220> FEATURE:
<223> OTHER INFORMATION: Synthetic Construct

<400> SEQUENCE: 531
ccattgaggt ggagagcttt ca                                          22

<210> SEQ ID NO 532
<211> LENGTH: 22
<212> TYPE: DNA
<213> ORGANISM: Artificial Sequence
<220> FEATURE:
<223> OTHER INFORMATION: Synthetic Construct

<400> SEQUENCE: 532
ggcaaaccca aggtctacgt tc                                          22

<210> SEQ ID NO 533
<211> LENGTH: 21
<212> TYPE: DNA
<213> ORGANISM: Artificial Sequence
<220> FEATURE:
<223> OTHER INFORMATION: Synthetic Construct
```

```
<400> SEQUENCE: 533
tacctcattg gccagctgct t                                              21

<210> SEQ ID NO 534
<211> LENGTH: 20
<212> TYPE: DNA
<213> ORGANISM: Artificial Sequence
<220> FEATURE:
<223> OTHER INFORMATION: Synthetic Construct

<400> SEQUENCE: 534
aggacctggg ttggaagtgg                                                20

<210> SEQ ID NO 535
<211> LENGTH: 20
<212> TYPE: DNA
<213> ORGANISM: Artificial Sequence
<220> FEATURE:
<223> OTHER INFORMATION: Synthetic Construct

<400> SEQUENCE: 535
agttggcatg gtagcccttg                                                20

<210> SEQ ID NO 536
<211> LENGTH: 21
<212> TYPE: PRT
<213> ORGANISM: Artificial Sequence
<220> FEATURE:
<223> OTHER INFORMATION: Synthetic Construct

<400> SEQUENCE: 536

Met Glu Val Gly Trp Tyr Arg Ser Pro Phe Ser Arg Val Val His Leu
1               5                   10                  15

Tyr Arg Asn Gly Lys
            20

<210> SEQ ID NO 537
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 2, 3
<223> OTHER INFORMATION: Xaa = Any Amino Acid and up to 2 of them can be
      present or absent
<220> FEATURE:
<221> NAME/KEY: VARIANT
<222> LOCATION: 5, 6
<223> OTHER INFORMATION: Xaa = Any Amino Acid
<220> FEATURE:
<221> NAME/KEY: VARIANT
<222> LOCATION: 7
<223> OTHER INFORMATION: Xaa = Leu or Ile
<220> FEATURE:
<221> NAME/KEY: VARIANT
<222> LOCATION: 8, 9, 10, 11, 12, 13, 14, 15
<223> OTHER INFORMATION: Xaa = Any Amino Acid and up to 2 of them can be
      present or absent
<220> FEATURE:
<221> NAME/KEY: VARIANT
<222> LOCATION: 17, 18
<223> OTHER INFORMATION: Xaa = Any Amino Acid
<220> FEATURE:
<221> NAME/KEY: VARIANT
```

-continued

```
<222> LOCATION: 19
<223> OTHER INFORMATION: Xaa = Leu or Ile

<400> SEQUENCE: 537

Xaa Xaa Xaa Tyr Xaa Xaa Xaa Xaa Xaa Xaa Xaa Xaa Xaa Xaa Tyr
1               5                   10                  15

Xaa Xaa Xaa
```

ANTI-SIGLEC-7 ANTIBODIES AND METHODS OF USE THEREOF

CROSS-REFERENCE TO RELATED APPLICATIONS

This application is a divisional of U.S. application Ser. No. 15/756,043, filed Aug. 26, 2016, which is a U.S. national stage application of PCT/US2016/049032, filed internationally on Aug. 26, 2016, which claims the benefit of U.S. Provisional Application No. 62/211,656, filed Aug. 28, 2015, and U.S. Provisional Application No. 62/265,742, filed Dec. 10, 2015, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735022000810SEQLIST.TXT, date recorded: Jan. 27, 2020, size: 406 KB).

FIELD OF THE INVENTION

This present disclosure relates to anti-Siglec-7 antibodies and therapeutic uses of such antibodies.

BACKGROUND OF THE INVENTION

Sialic acid-binding Ig-like lectin-7 (Siglec-7), is a type 1, immunoglobulin-like, transmembrane protein expressed on immune and hematopoietic cells, including immature and mature myeloid cells, such as monocytes, macrophages, dendritic cells, neutrophils, mast cells, and microglial cells, as well as lymphoid cells, such as natural killer cells, and subsets of T cells (Crocker et al. (2007) Nat Rev Immunol. 7:255-266; Angata and Varki (2000) Glycobiology 10:4: 431-438. Nicoll et al (1999) JBC 274:48: 34089-34095; Falco et al. (1999) J. Exp. Med. 190: 793-802). Siglec-7 is a member of the Siglec family of lectins that bind sialic acid residues of glycoproteins and glycolipids. One potential binding target for Siglec proteins are gangliosides; that is, glycolipids that consist of a ceramide linked to a sialylated glycan. Most gangliosides share a common lacto-ceramide core and one or more sialic acid residues. Diversity in the Siglec ligands is generated by the addition of other neutral sugars and sialic acid in different linkages, and modification of sialic acid itself.

Fourteen Siglec proteins have been identified in humans and nine in mice that are comprised of 2-17 extracellular Ig domains including an amino-terminal V-set domain that contains the sialic acid-binding site. The sialic acid-binding region is located on the V-set Ig-like domain, which contains a two aromatic residues and one arginine motif highly conserved in all Siglecs (Crocker et al. (2007) Nat Rev Immunol. 7:255-266; McMillan and Crocker (2008) Carbohydr Res. 343:2050-2056; Von Gunten and Bochner (2008) Ann NY Acad Sci. 1143:61-82; May et al. (1998) Mol Cell. 1:719-728; Crocker et al. (1999) Biochem J. 341:355-361; and Crocker and Varki (2001) Trends Immunol. 2:337-342). The binding sites to sialylated ligands have been mapped by crystal structures with and without ligand bound (Alphey et al., (2003) J. Biol. Chem. 278:5: 3372-3377; Attrill et al., (2006) J. Biol. Chem. 281 32774-32783; and Varki et al., Glycobiology, 16 pp. 1R-27R). Since cell membranes are rich in sialic acids, ligand binding by Siglecs can occur in cis and in trans, both affecting their functional properties. Each Siglec has a distinct preference for binding the diverse types of sialylated glycans that are found on the surface of mammalian cells (Crocker et al. (2007) Nat Rev Immunol. 7:255-266; and Crocker et al. (2007) Nat Rev Immunol. 7:255-266). Most Siglec proteins, including Siglec-7, contain one or more immunoreceptor tyrosine-based inhibitory motif (ITIM) sequences in their cytoplasmic tails, which enable them as inhibitory receptors and negative regulators of immune functions through recruitment of the tyrosine phosphatases SHP1 and SHP2 (Crocker et al. (2007) Nat Rev Immunol. 7:255-266; McMillan and Crocker (2008) Carbohydr Res. 343:2050-2056; and Von Gunten and Bochner (2008) Ann NY Acad Sci. 1143:61-82). Certain Siglecs contain immunoreceptor tyrosine-based activating motif (ITAM) sequences in their cytoplasmic tails, which enable them to act as activating receptors and positive regulators of immune function through predicted recruitment of spleen tyrosine kinase (Syk) (Macauley S M. et al., (2014) Nature Reviews Immunology 14, 653-666). The Siglec protein family is associated with multiple human disease including, autoimmunity, susceptibility to infection, multiple types of cancer including lymphoma, leukemia and acute myeloid leukemia, systemic lupus erythematosus, rheumatoid arthritis, neurodegenerative disorders, asthma, allergy, sepsis, chronic obstructive pulmonary disease, graft-versus-host disease, eosinophilia, and osteoporosis (Macauley S M. et al., (2014) Nature Reviews Immunology 14, 653-666).

Siglec-7 was cloned in 1999 (Falco et al. (1999) J. Exp. Med. 190: 793-802; Nicoll et al (1999) JBC 274:48: 34089-34095; Angata and Varki (2000) Glycobiology 10:4: 431-438), and selective expression was detected on granulocytes, monocytes, resting and activated natural killer cells and a subset of resting $CD8^+$ T cells in human peripheral blood (Nicoll et al (1999) JBC 274:48: 34089-34095; Falco et al. (1999) J. Exp. Med. 190: 793-802).

Siglec-7 contains an extracellular N-terminal Ig-like (immunoglobulin-like) V-type domain, two Ig-like C2-set domains as well as one consensus ITIM motif and a nonconforming membrane-distal ITIM-like motif in its cytoplasmic domain. Siglec-7 was shown to bind red blood cells in a sialic acid dependent manner due to loss of binding upon sialidase treatment. The binding is thought to be mediated by α2-3 or α2-6 sialic acid linkages (Nicoll et al (1999) JBC 274:48: 34089-34095; Angata and Varki (2000) Glycobiology 10:4: 431-438). Further investigation revealed that Siglec-7 more potently binds α2-8 disialyl residues with 10 nM affinity and demonstrates higher affinity for branched α2-6 sialyl residues compared to terminal α2-3 or α2-6 sialic acids (Yamaji (2002) J. Biol. Chem. 277:8 6324-6332). In vivo Siglec-7 ligands are expressed on b-series gangliosides such as GD2, GD3, and GT1b, which can be found on cells of the central nervous system, melanoma cells, and subsets of T cells (Urmacher et al. (1989) Am. J. Dermatopathol. 11: 577-581, Kniep et al. (1993) Blood 82: 1776-1786). High resolution crystal structure of the N-terminal V-set Ig-like domain of Siglec-7 suggests that ligand binding specificity of Siglec family members resides in the variable C-C' loop (Alphey et al. (2003) J. Biol. Chem 278:5 3372-3377).

Siglec-7 undergoes phosphorylation of Tyr-437, and Tyr-460 by tyrosine kinases, likely c-Src or Lck (Avril et al., (2004) J. Imm. 173: 6841-6849). Following phosphorylation predominantly on the proximal Tyr-437, but also on distal Tyr-460 of its ITIM domains, Siglec-7 binds SHP-2/PTPN11 and SHP-1/PTPN6 (Avril et al., (2004) J. Imm.

173: 6841-6849). Phosphatase activity is associated with decreased intracellular calcium mobilization, and decreased tyrosine phosphorylation on multiple proteins (Ulyanova, T., et al., (1999) *Eur J Immunol* 29, 3440-3449; Paul, S. P., et al., (2000). *Blood* 96, 483-490) as well as with blockade of signal transduction and immune response, in part, through dephosphorylation of signaling molecules on adjacent activating receptors, including those that contain ITAM motifs, pattern recognition receptors, Toll-like receptors and damage-associated molecular pattern (DAMP) receptors.

Some, but not all, Siglec ligands induce receptor downregulation (Macauley S M. et al., (2014) *Nature Reviews Immunology* 14, 653-666). Ligand-induced receptor degradation has been reported for tyrosine kinase receptors (Monsonego-Oran et al., (2002) Febs letters 528, 83-89; and Fasen et al., (2008) Cell & Molecular Biology 9. 251-266), as well as steroid receptors (Callige et al., (2005) Mol. Cell. Biol. 25. 4349-4358; and Pollenz et al., (2006) Chemico-Biological Interactions. 164, 49-59). Suppressor of cytokine signaling 3 (SOCS3) has been shown to compete with SHP-1/2 and binds Siglec-7 upon ITIM phosphorylation in the presence of Siglec-7 crosslinking (Orr et al. (2007) J. Biol. Chem. 282: 3418-3422). SOCS3 binding results in ECS E3 ligase targeting of Siglec-7 for proteasomeal degradation (Willams and Palmer (2012) Biochem. Soc. Trans. 40: 215-218; Orr et al. (2007) J. Biol. Chem. 282: 3418-3422).

Activation of Siglec-7 signaling has also been shown to be associated with an increase in production of proinflammatory cytokines IL-6, IL-1alpha, MIP-1beta, IL-8 and TNFalpha, as well as upregulation of adhesion molecules ICAM-1 and CD49e selectively in human monocytes (Varchetta et al. (2012) PLOS One 7: 9: e45821). These activities of Siglec-7 appear to be mediated through the phosphorylation of ERK (Varchetta et al. (2012) PLOS One 7: 9: e45821). It has been proposed that the association between ITIM-containing Siglec receptors and activating receptors may be mediated by extracellular ligands that bind and bridge these receptors (Macauley S M. et al., (2014) *Nature Reviews Immunology* 14, 653-666).

Multiple studies indicate an inhibitory role for Siglec-7 in function of natural killer cells, regulation of T cell receptor signaling, and attenuation of signaling in DCs (Crocker et al., (2012) Ann. N Y Acad. Sci. 1253, 102-111; Pillai et al., (2012) Annu. Rev. Immunol. 30, 357-392; von Gunten and Bochner (2008) Ann. N Y Acad. Sci. 1143, 61-82; Ikehara et al. (2004) J. Biol. Chem. 279:41 43117-43125; Nicoll et al. (2003) Eur. J. Imm. 33:6:1642-1648; Hudak et al. (2013) Nat. Chem. Biol.; Bax et al. (2007) J. Imm 179: 12: 8216-8224; Lock et al. (2004) Immunobiology 209: 1-2: 199-207). Functional studies in natural killer cells have demonstrated that tumor cells expressing Siglec-7 binding sialic acid ligands inhibit NK cell activation and tumor cell killing. Many human tumors robustly upregulate sialic acid ligands, which enables immune evasion and cancer progression (Jandus et al. (2014) J. Clinic. Invest. 124:4: 1810-1820). Moreover, Hudak et al. performed glycocalyx engineering and showed that cells coated with synthetic sialoside glycopolymers were protected from NK cytotoxicity. It is proposed that sialic acid upregulation on tumors facilitates a state of "super self" that strongly inhibits natural killer cell immunosurveillance (Macauley and Paulson (2014) Nat. Chem. Biol. 10:1: 7-8).

There is no apparent mouse homolog of Siglec-7; however mouse Siglec-E is 53% similar, therefore the closest related Siglec. In mice, genetic inactivation of Siglec-E does not lead to obvious developmental, histological, or behavioral abnormalities; and Siglec-E-deficient mice breed normally, indicating that Siglec-E is not an essential gene and that its function may be limited to innate immunity (McMillan et al. (2013) Blood 121:11: 2084-2094). Upon challenge of Siglec-E deficient mice with aerosol LPS, increased neutrophil recruitment in the lung was demonstrated, which could be reversed by blockade of the β2-integrin CD11b. The Siglec-E deficient neutrophils were shown to have increased phosphorylation of Syk and p38 MAPK in a CD11b-dependent manner. This data suggests that Siglec-E functions to suppress neutrophil recruitment in a model of acute lung inflammation (McMillan et al. (2013) Blood 121:11: 2084-2094).

In oncology, Siglec-7 has been suggested as a therapeutic target for chronic and acute myeloid leukemic as crosslinking Siglec-7 inhibited cellular proliferation (Vitale et al. (1999) PNAS 96: 15091-15096; Vitale et al. (2001) PNAS 98:10: 5764-5769). Siglec-7 activity has also been shown to inhibit cytokine-induced cellular proliferation (Orr et al. (2007) J. Biol. Chem. 282: 3418-3422).

Antibodies to Siglec-7 have been described in, for example, WO2011038301, Jandus et al. (2014) J. Clinical Invest. 124:4: 1810-1820, Varchetta et al. (2012) PLOS One 7: 9: e45821 et al. (2012). Falco et al. (1999) J. Exp. Med. 190: 793-802, Nicoll et al (1999) JBC 274:48: 34089-34095, Nicoll et al. (2003) Eur. J. Imm. 33: 1642-1648. However, these antibodies do not display the functional characteristics required for a therapeutic antibody.

Accordingly, there is a need for therapeutic antibodies that specifically bind Siglec-7 and reduce Siglec-7 expression on the cell surface, reduce interactions between Siglec-7 and one or more Siglec-7 ligands, and/or reduce one or more Siglec-7 activities in order to treat one or more diseases, disorders, and conditions associated with undesired Siglec-7 activity.

All references cited herein, including patents, patent applications and publications, are hereby incorporated by reference in their entirety.

SUMMARY OF THE INVENTION

The present disclosure is generally directed to Siglec-7 agents, such as anti-Siglec-7 antibodies, and methods of using such Siglec-7 agents. The methods provided herein find use in preventing, reducing risk, or treating an individual having dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, conical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, solid and blood cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7 and/or Siglec-7 ligands, thyroid cancer, infections, CNS herpes, parasitic infections, Trypanosome infection, Cruzi infection, Pseudomonas aeruginosa infection, Leishmania donovani infection, group B Streptococcus infection, Campylobacter jejuni infection, Neisseria meningiditis infection, type I HIV, and Haemophilus influenza. The methods provided herein also find use in inducing or promoting the survival, maturation, functionality, migration, or proliferation of one or more immune cells in an individual in need thereof. The methods provided herein find further use in decreasing the activity, functionality, or survival of regulatory T cells, tumor-imbedded immunosuppressor dendritic cells, tumor-imbedded immunosuppressor macrophages, neutrophils, natural killer (NK) cells, myeloid-derived suppressor cells, tumor-associated macrophages, neutrophils, NK cells, acute myeloid leukemia (AML) cells, chronic lymphocytic leukemia (CLL) cell, or chronic myeloid leukemia (CML) cell in an individual in need thereof.

Certain aspects of the present disclosure are based, at least in part, on the identification of anti-Siglec-7 antibodies that are capable of decreasing cell surface levels of Siglec-7 on human primary immune cells and Siglec-7-expressing cell lines and/or that are capable of inhibiting the binding of Siglec-7 ligands to Siglec-7 (see, e.g., Examples 3-5).

Accordingly, certain aspects of the present disclosure relate to an isolated monoclonal anti-Siglec-7 antibody, wherein the anti-Siglec-7 antibody decreases cellular levels of Siglec-7. In some embodiments, the anti-Siglec-7 antibody decreases cellular levels of Siglec-7 without inhibiting interaction between Siglec-7 and one or more Siglec-7 ligands. In some embodiments, the antibody further inhibits interaction between Siglec-7 and one or more Siglec-7 ligands.

Other aspects of the present disclosure relate to an isolated monoclonal anti-Siglec-7 antibody, wherein the anti-Siglec-7 antibody decreases cellular levels of Siglec-7 and inhibits interaction between Siglec-7 and one or more Siglec-7 ligands.

In some embodiments that may be combined with any of the preceding embodiments, the anti-Siglec-7 antibody decreases cell surface levels of Siglec-7, decreases intracellular levels of Siglec-7, decreases total levels of Siglec-7, or any combination thereof. In some embodiments that may be combined with any of the preceding embodiments, the anti-Siglec-7 antibody induces Siglec-7 degradation, Siglec-7 cleavage, Siglec-7 internalization, Siglec-7 shedding, downregulation of Siglec-7 expression, or any combination thereof. In some embodiments that may be combined with any of the preceding embodiments, antibody decreases cellular levels of Siglec-7 in vivo. In some embodiments that may be combined with any of the preceding embodiments, the anti-Siglec-7 antibody inhibits cell surface clustering of Siglec-7. In some embodiments that may be combined with any of the preceding embodiments, the anti-Siglec-7 antibody inhibits one or more Siglec-7 activities. In some embodiments that may be combined with any of the preceding embodiments, the one or more Siglec-7 activities are selected from: (a) Siglec-7 binding to one or more Siglec-7 ligands, optionally wherein the one or more Siglec-7 ligands are selected from sialic acid-containing glycoproteins, sialic acid-containing glycolipids, and any combination thereof; (b) Siglec-7 binding to SHP1 or SHP2; (c) phosphorylation of Tyr-437, Tyr-460, or both, induced by one or more SRC family tyrosine kinases, optionally, wherein the one or more SRC family tyrosine kinases are selected from Syk, LCK, FYM, and ZAP-70; (d) modulated expression of one or more pro-inflammatory cytokines, optionally wherein the one or more pro-inflammatory cytokines are selected from a group consisting IFN-a4, IFN-beta, IL-1β, IL-1alpha, TNF-α, IL-6, IL-8, CRP, IL-20 family members, LIF, IFN-gamma, OSM, CNTF, GM-CSF, IL-11, IL-12, IL-17, IL-18, IL-33, MCP-1, and MIP-1-beta; (e) modulated expression of one or more pro-inflammatory cytokines in one or more cells selected from macrophages, neutrophils, NK cells, dendritic cells, bone marrow-derived dendritic cells, monocytes, osteoclasts, T cells, T helper cells, cytotoxic T cells, granulocytes, and microglial cells; (f) modulated expression of one or more anti-inflammatory cytokines, optionally wherein the one or more anti-inflammatory cytokines are selected from IL-4, IL-10, IL-13, IL-35, IL-16, TGF-beta, IL-1Ra, G-CSF, and soluble receptors for TNF, IFN-beta1a, IFN-beta1b, or IL-6; (g) modulated expression of one or more anti-inflammatory cytokines in one or more cells selected from macrophages, neutrophils, NK cells, dendritic cells, bone marrow-derived dendritic cells, monocytes, osteoclasts, T cells, T helper cells, cytotoxic T cells, granulocytes, and microglial cells; (h) modulate expression of one or more proteins selected from the group consisting of C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, and PYCARD; (i) inhibition of extracellular signal-regulated kinase (ERK) phosphorylation; (j) decreasing tyrosine phosphorylation on one or more cellular proteins, optionally, wherein the one or more cellular proteins comprise ZAP-70 and the tyrosine phosphorylation occurs on Tyr-319 of ZAP-70; (k) modulated expression of C-C chemokine receptor 7 (CCR7); (l) inhibition of microglial cell chemotaxis toward CCL19-expressing and CCL21-expressing cells; (m) decreasing T cell proliferation induced by one or more cells selected from dendritic cells, bone marrow-derived dendritic cells, monocytes, microglia, M1 microglia, activated M1 microglia, M2 microglia, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, and M2 NK cells; (n) inhibition of osteoclast production, decreased rate of osteoclastogenesis, or both; (o) decreasing survival of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (p) decreasing proliferation of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (q) inhibiting migration of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (r) inhibiting one or more functions of one or more cells selected from dendritic cells, bone marrow-derived dendritic cells, macrophages, neutrophils, NK cells, M1 macrophages, M1 neutrophils, M1 NK cells, activated M1 macrophages, activated M neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (s) inhibiting maturation of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (t) inhibition of one or more types of clearance selected from apoptotic neuron clearance, nerve tissue debris clearance, dysfunctional synapse clearance, non-nerve tissue debris clearance, bacteria clearance, other foreign body clearance, disease-causing protein clearance, disease-causing peptide clearance, and tumor cell clearance; optionally wherein the disease-causing protein is selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein A1, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides and the tumor cell is from a cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; (u) inhibition of phagocytosis of one or more of apoptotic neurons, nerve tissue debris, dysfunctional synapses, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein A1, serum amyloid A, medin, prolactin, transthyretin, lysozyme, beta 2 microglobulin, gelsolin, keratoepithelin, cystatin, immunoglobulin light chain AL, S-IBM protein. Repeat-associated non-ATG (RAN) translation products. DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells are from a cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer; (v) binding to Siglec-7 ligand on tumor cells; (w) binding to Siglec-7 ligand on cells selected from neutrophils, dendritic cells, bone marrow-derived dendritic cells, monocytes, microglia, macrophages, and NK cells; (x) inhibition of tumor cell killing by one or more of microglia, macrophages, neutrophils, NK cells, dendritic cells, bone marrow-derived dendritic cells, neutrophils, T cells, T helper cells, or cytotoxic T cells; (y) inhibiting anti-tumor cell proliferation activity of one or more of microglia, macrophages, neutrophils, NK cells, dendritic cells, bone marrow-derived dendritic cells, neutrophils, T cells, T helper cells, or cytotoxic T cells; (z) inhibition of anti-tumor cell metastasis activity of one or more of microglia, macrophages, neutrophils, NK cells, dendritic cells, bone marrow-derived dendritic cells, neutrophils, T cells. T helper cells, or cytotoxic T cells; (aa) inhibition of one or more ITAM motif containing receptors, optionally wherein the one or more ITAM motif containing receptors are selected from TREM1. TREM2, Sirp beta, FcgR, DAP10, and DAP12; (bb) inhibition of signaling by one or more pattern recognition receptors (PRRs), optionally wherein the one or more PRRs are selected from receptors that identify pathogen-associated molecular patterns (PAMPs), receptors that identify damage-associated molecular patterns (DAMPs), and any combination thereof; (cc) inhibition of one or more receptors comprising the motif D/Ex$_{0-2}$ YxxL/IX$_{6-8}$ YxxL/I (SEQ ID NO: 537); (dd) inhibition of signaling by one or more Toll-like receptors; (ee) inhibition of the JAK-STAT signaling pathway; (ff) inhibition of nuclear factor kappa-light-chain-enhancer of activated B cells (NFκB); (gg) de-phosphorylation of an ITAM motif containing receptor; (hh) modulated expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils, T cells, T helper cells, or cytotoxic T cells; (ii) increasing expression of one or more Siglec-7-dependent genes; (jj) normalization of disrupted Siglec-7-dependent gene expression; (kk) decreasing expression of one or more ITAM-dependent genes, optionally wherein the one more ITAM-dependent genes are activated by nuclear factor of activated T cells (NFAT) transcription factors; (11) promoting differentiation of one or more of immunosuppressor dendritic cells, immunosuppressor macrophages, immunosuppressor neutrophils, immunosuppressor NK cells, myeloid derived suppressor cells, tumor-associated macrophages, tumor-associated neutrophils, tumor-associated NK cells, and regulatory T cells; (mm) promoting or rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; (nn) increasing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells into tumors; (oo) increasing the number of tumor-promoting myeloid/granulocytic immune-suppressive cells in a tumor, in peripheral blood, or other lymphoid organ; (pp) enhancing tumor-promoting activity of myeloid-derived suppressor cells; (qq) increasing expression of tumor-promoting cytokines in a tumor or in peripheral blood, optionally wherein the tumor-promoting cytokines are TGF-beta or IL-10; (rr) increasing tumor infiltration of tumor-promoting FoxP3+ regulatory T lymphocytes; (ss) enhancing tumor-promoting activity of myeloid-derived suppressor cells (MDSC); (tt) decreasing activation of tumor-specific T lymphocytes with tumor killing potential; (uu) decreasing infiltration of tumor-specific NK cells with tumor killing potential; (vv) decreasing the tumor killing potential of NK cells; (ww) decreasing infiltration of tumor-specific B lymphocytes with potential to enhance immune response; (xx) decreasing infiltration of tumor-specific T lymphocytes with tumor killing potential; (yy) increasing tumor volume; (zz) increasing tumor growth rate; (aaa) increasing metastasis; (bbb) increasing rate of tumor recurrence; (ccc) decreasing efficacy of one or more immune-therapies that modulate anti-tumor T cell responses, optionally wherein the one or more immune-therapies are immune-therapies that target one or more target proteins selected from PD1/PDL1, CD40, OX40, ICOS, CD28, CD137/4-1BB, CD27, GITR, PD-L1, CTLA4, PD-L2, PD-1. B7-H3, B7-H4, HVEM, BTLA, KIR, GAL9, TIM3, A2AR, LAG, DR-5, TREM1, TREM2, CSF-1 receptor, and any combination thereof, or of one or more cancer vaccines; (ddd) inhibition of PLCγ/PKC/calcium mobilization; and (eee) inhibition of PI3K/Akt, Ras/MAPK signaling. In some embodiments that may be combined with any of the preceding embodiments, the one or more Siglec-7 activities are selected from: (a) Siglec-7 binding to one or more Siglec-7 ligands, optionally wherein the one or more Siglec-7 ligands are selected from the group consisting of sialic acid-containing glycoproteins, sialic acid-containing glycolipids, and any combination thereof; (b) decreasing proliferation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (c) inhibiting migration of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (d) inhibiting one or more functions of one or more cells selected from the group consisting of dendritic cells, bone marrow-derived dendritic cells, macrophages, neutrophils, NK cells, M1 macrophages, M1 neutrophils, M1 NK cells, activated M macrophages, activated M1 neutrophils, activated M1 NK cells, M2 macrophages, M2 neutrophils, M2 NK cells, monocytes, osteoclasts. T cells, T helper cells, cytotoxic T cells, granulocytes, neutrophils, microglia, M1 microglia, activated M1 microglia, and M2 microglia; (c) inhibition of one or more types of clearance selected from the group consisting of apoptotic neuron clearance, nerve tissue debris clearance, dysfunctional synapse clearance, non-nerve tissue debris clearance, bacteria clearance, other foreign body clearance, disease-causing protein clearance, disease-causing peptide clearance, and tumor cell clearance; optionally wherein the disease-causing protein is selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL. S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides and the tumor cell is from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; (f) inhibition of tumor cell killing by one or more of microglia, macrophages, neutrophils, NK cells, dendritic cells, bone marrow-derived dendritic cells, neutrophils, T cells, T helper cells, or cytotoxic T cells; (g) inhibiting anti-tumor cell proliferation activity of one or more of microglia, macrophages, neutrophils, NK cells, dendritic cells, bone marrow-derived dendritic cells, neutrophils, T cells, T helper cells, or cytotoxic T cells; (h) modulated expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils, T cells, T helper cells, or cytotoxic T cells; (i) promoting or rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; (j) increasing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells into tumors; (k) increasing the number of tumor-promoting myeloid/granulocytic immune-suppressive cells in a tumor, in peripheral blood, or other lymphoid organ; (l) enhancing tumor-promoting activity of myeloid-derived suppressor cells (MDSC); (m) decreasing activation of tumor-specific T lymphocytes with tumor killing potential; (n) decreasing infiltration of tumor-specific T lymphocytes with tumor killing potential; (o) increasing tumor volume; (p) increasing tumor growth rate; and (q) decreasing efficacy of one or more immune-therapies that modulate anti-tumor T cell responses, optionally wherein the one or more immune-therapies are immune-therapies that target one or more target proteins selected from the group consisting of PD1/PDL1, CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG. DR-5, TREM1, TREM2, CSF-1 receptor, and any combination thereof, or of one or more cancer vaccines. In some embodiments that may be combined with any of the preceding embodiments, the anti-Siglec-7 antibody exhibits one or more activities selected from the group consisting of: (a) increasing the number of tumor infiltrating $CD3^+$ T cells; (b) inhibiting Siglec-7 binding to one or more Siglec-7 ligands; (c) decreasing cellular levels of Siglec-7 in peripheral immune cells; (d) reducing the number of non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in blood; (e) reducing the number of non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in the tumor; (f) reducing PD-L1 levels in one or more cells, optionally wherein the one or more cells are non-tumorigenic myeloid-derived suppressor cells (MDSC); (g) reducing PD-L2 levels in one or more cells, optionally wherein the one or more cells are non-tumorigenic myeloid-derived suppressor cells (MDSC); (h) reducing CD11b levels in one or more cells, optionally wherein the one or more cells are non-tumorigenic myeloid-derived suppressor cells (MDSC); (i) reducing B7-H3 levels in one or more cells, optionally wherein the one or more cells are non-tumorigenic myeloid-derived suppressor cells (MDSC); (j) reducing CD200R levels in one or more cells, optionally wherein the one or more cells are non-tumorigenic myeloid-derived suppressor cells (MDSC); (k) reducing CD163 levels in one or more cells, optionally wherein the one or more cells are non-tumorigenic myeloid-derived suppressor cells (MDSC); (l) reducing CD206 levels in one or more cells, optionally wherein the one or more cells are non-tumorigenic myeloid-derived suppressor cells (MDSC); (m) decreasing tumor growth rate of solid tumors; (n) reducing tumor volume; (o) increasing efficacy of one or more PD-1 inhibitors; (p) increasing efficacy of one or more checkpoint inhibitor therapies and/or immune-modulating therapies, optionally wherein the one or more checkpoint inhibitor therapies and/or immune-modulating therapies target one or more of CTL4, the adenosine pathway, PD-L1, PD-L2, OX40, TIM3, LAG3, or any combination thereof; (q) inhibiting differentiation, survival, and/or one or more functions of non-tumorigenic myeloid-derived suppressor cells (MDSC); (r) inducing cell death of one or more myeloid-derived suppressor cells (MDSC); and (s) increasing proliferation of T cells in the presence of non-tumorigenic myeloid-derived suppressor cells (MDSC). In some embodiments that may be combined with any of the preceding embodiments, the one or more Siglec-7 ligands are selected from Siglec-7 ligands expressed on red blood cells, Siglec-7 ligands expressed on bacterial cells, Siglec-7 ligands expressed on apoptotic cells, Siglec-7 ligands expressed on nerve cells, Siglec-7 ligands expressed on glial cells, Siglec-7 ligands expressed on microglia, Siglec-7 ligands expressed on astrocytes, Siglec-7 ligands expressed on tumor cells, Siglec-7 ligands expressed on viruses, Siglec-7 ligands expressed on dendritic cells, Siglec-7 ligands bound to beta amyloid plaques, Siglec-7 ligands bound to Tau tangles, Siglec-7 ligands on disease-causing proteins, Siglec-7 ligands on disease-causing peptides, Siglec-7 ligands expressed on macrophages, Siglec-7 ligands expressed on neutrophils, Siglec-7 ligands expressed on monocytes, Siglec-7 ligands expressed on natural killer cells, Siglec-7 ligands expressed on T cells, Siglec-7 ligands expressed on T helper cells, Siglec-7 ligands expressed on cytotoxic T cells, Siglec-7 ligands expressed on B cells, Siglec-7 ligands expressed on tumor-imbedded immunosuppressor dendritic cells, Siglec-7 ligands expressed on tumor-imbedded immunosuppressor macrophages, Siglec-7 ligands expressed on tumor-imbedded immunosuppressor neutrophils, Siglec-7 ligands expressed on tumor-imbedded immunosuppressor NK cells, Siglec-7 ligands expressed on myeloid-derived suppressor cells, Siglec-7 ligands expressed on regulatory T cells, secreted mucins, sialic acid, sialic acid-containing glycolipids, sialic acid-containing glycoproteins, alpha-2,8-disialyl containing glycolipids, branched alpha-2,6-linked sialic acid-containing glycoproteins, terminal alpha-2,6-linked sialic acid-containing glycolipids, terminal alpha-2,3-linked sialic acid-containing glycoproteins, and disialogangliosides. In some embodiments that may be combined with any of the preceding embodiments, the cellular levels of Siglec-7 are measured on primary cells selected from dendritic cells, bone marrow-derived dendritic cells, monocytes, microglia, macrophages, neutrophils, and NK cells, or on cell lines, and wherein the cellular levels of Siglec-7 are measured utilizing an in vitro cell assay. In some embodiments that may be combined with any of the preceding embodiments, the anti-Siglec-7 antibody does not reduce TREM2 expression. In some embodiments that may be combined with any of the preceding embodiments, the anti-Siglec-7 antibody does not reduce cell surface levels of TREM2, does not reduce intracellular levels of TREM2, does not reduce total levels of TREM2, or any combination thereof. In some embodiments that may be combined with any of the preceding embodiments, the anti-Siglec-7 antibody does not reduce cellular levels of TREM2 in vivo. In some embodiments that may be combined with any of the preceding embodiments, the cellular levels of TREM2 are measured on primary cells selected from dendritic cells, bone marrow-derived dendritic cells, monocytes, microglia, macrophages, neutrophils, and NK cells, or on cell lines, and wherein the cellular levels of TREM2 are measured utilizing an in vitro cell assay.

In some embodiments that may be combined with any of the preceding embodiments, the anti-Siglec-7 antibody binds a discontinuous Siglec-7 epitope. In some embodiments that may be combined with any of the preceding embodiments, the discontinuous Siglec-7 epitope comprises two or more peptides, three or more peptides, four or more peptides, five or more peptides, six or more peptides, seven or more peptide, eight or more peptides, nine or more peptides, or 10 or more peptides. In some embodiments that may be combined with any of the preceding embodiments, each of the peptides comprise five or more, six or more, seven or more, eight or more, nine or more, 10 or more, 11 or more, 12 or more, 13 or more 14 or more, 15 or more, 16 or more, 17 or more, 18 or more, 19 or more, or 20 or more amino acid residues of the amino acid sequence of SEQ ID NO: 1; or five or more, six or more, seven or more, eight or more, nine or more, 10 or more, 11 or more, 12 or more, 13 or more 14 or more, 15 or more, 16 or more, 17 or more, 18 or more, 19 or more, or 20 or more amino acid residues on a mammalian Siglec-7 protein corresponding to the amino acid sequence of SEQ ID NO: 1. In some embodiments that may be combined with any of the preceding embodiments, the anti-Siglec-7 antibody binds to a conformational epitope of Siglec-7. In some embodiments that may be combined with any of the preceding embodiments, the anti-Siglec-7 antibody binds to one or more amino acids within amino acid residues 39-353, 39-149, 93-104, 95-105, 39-122, 123-149, 150-233, 240-336, 264-273, 295-306, 327-341, or 337-353 of SEQ ID NO: 1; or within amino acid residues on a mammalian Siglec-7 protein corresponding to amino acid residues 39-353, 39-149, 93-104, 95-105, 39-122, 123-149, 150-233, 240-336, 264-273, 295-306, 327-341, or 337-353 of SEQ ID NO: 1. In some embodiments that may be combined with any of the preceding embodiments, the anti-Siglec-7 antibody binds to one or more amino acids within amino acid residues selected from the group consisting of: i. amino acid residues 60-69 of SEQ ID NO: 1, or amino acid residues on a mammalian Siglec-7 protein corresponding to amino acid residues 60-69 of SEQ ID NO: 1; ii. amino acid residues 60-69 and 84-95 of SEQ ID NO: 1, or amino acid residues on a mammalian Siglec-7 protein corresponding to amino acid residues 60-69 and 84-95 of SEQ ID NO: 1; iii. amino acid residues 60-69 and 117-127 of SEQ ID NO: 1, or amino acid residues on a mammalian Siglec-7 protein corresponding to amino acid residues 60-69 and 117-127 of SEQ ID NO: 1; iv. amino acid residues 68-78 of SEQ ID NO: 1, or amino acid residues on a mammalian Siglec-7 protein corresponding to amino acid residues 68-78 of SEQ ID NO: 1; v, amino acid residues 84-95 of SEQ ID NO: 1, or amino acid residues on a mammalian Siglec-7 protein corresponding to amino acid residues 84-95 of SEQ ID NO: 1; vi. amino acid residues 111-122 of SEQ ID NO: 1, or amino acid residues on a mammalian Siglec-7 protein corresponding to amino acid residues 111-122 of SEQ ID NO: 1; vii. amino acid residues 111-122 and 282-291 of SEQ ID NO: 1, or amino acid residues on a mammalian Siglec-7 protein corresponding to amino acid residues 111-122 and 282-291 of SEQ ID NO: 1; viii. amino acid residues 113-123 of SEQ ID NO: 1, or amino acid residues on a mammalian Siglec-7 protein corresponding to amino acid residues 113-123 of SEQ ID NO: 1; ix, amino acid residues 113-125 of SEQ ID NO: 1, or amino acid residues on a mammalian Siglec-7 protein corresponding to amino acid residues 113-125 of SEQ ID NO: 1; x, amino acid residues 117-127 of SEQ ID NO: 1, or amino acid residues on a mammalian Siglec-7 protein corresponding to amino acid residues 117-127 of SEQ ID NO: 1; and xi. amino acid residues 282-291 of SEQ ID NO: 1, or amino acid residues on a mammalian Siglec-7 protein corresponding to amino acid residues 282-291 of SEQ ID NO: 1. In some embodiments that may be combined with any of the preceding embodiments, the anti-Siglec-7 antibody binds to one or more amino acids within amino acid residues 60-69 of human Siglec-7 (SEQ ID NO: 1), or within amino acid residues on a Siglec-7 homolog or ortholog corresponding to amino acid residues 60-69 of SEQ ID NO: 1. In some embodiments that may be combined with any of the preceding embodiments, the anti-Siglec-7 antibody binds to one or more amino acids within amino acid residues 60-69 and 84-95 of human Siglec-7 (SEQ ID NO: 1), or within amino acid residues on a Siglec-7 homolog or ortholog corresponding to amino acid residues 60-69 and 84-95 of SEQ ID NO: 1. In some embodiments that may be combined with any of the preceding embodiments, the anti-Siglec-7 antibody binds to one or more amino acids within amino acid residues 60-69 and 117-127 of human Siglec-7 (SEQ ID NO: 1), or within amino acid residues on a Siglec-7 homolog or ortholog corresponding to amino acid residues 60-69 and 117-127 of SEQ ID NO: 1. In some embodiments that may be combined with any of the preceding embodiments, the anti-Siglec-7 antibody binds to one or more amino acids within amino acid residues 68-78 of human Siglec-7 (SEQ ID NO: 1), or within amino acid residues on a Siglec-7 homolog or ortholog corresponding to amino acid residues 68-78 of SEQ ID NO: 1. In some embodiments that may be combined with any of the preceding embodiments, the anti-Siglec-7 antibody binds to one or more amino acids within amino acid residues 84-95 of human Siglec-7 (SEQ ID NO: 1), or within amino acid residues on a Siglec-7 homolog or ortholog corresponding to amino acid residues 84-95 of SEQ ID NO: 1. In some embodiments that may be combined with any of the preceding embodiments, the anti-Siglec-7 antibody binds to one or more amino acids within amino acid residues 111-122 of human Siglec-7 (SEQ ID NO: 1), or within amino acid residues on a Siglec-7 homolog or ortholog corresponding to amino acid residues 111-122 of SEQ ID NO: 1. In some embodiments that may be combined with any of the preceding embodiments, the anti-Siglec-7 antibody binds to one or more amino acid residues 111-122 and 282-291 of human Siglec-7 (SEQ ID NO: 1), or within amino acid residues on a Siglec-7 homolog or ortholog corresponding to amino acid residues 111-122 and 282-291 of SEQ ID NO: 1. In some embodiments that may be combined with any of the preceding embodiments, the anti-Siglec-7 antibody binds to one or more amino acids within amino acid residues 113-123 of human Siglec-7 (SEQ ID NO: 1), or within amino acid residues on a Siglec-7 homolog or ortholog corresponding to amino acid residues 113-123 of SEQ ID NO: 1. In some embodiments that may be combined with any of the preceding embodiments, the anti-Siglec-7 antibody binds to one or more amino acids within amino acid residues 113-125 of human Siglec-7 (SEQ ID NO: 1), or within amino acid residues on a Siglec-7 homolog or ortholog corresponding to amino acid residues 113-125 of SEQ ID NO: 1. In some embodiments that may be combined with any of the preceding embodiments, the anti-Siglec-7 antibody binds to one or more amino acids within amino acid residues 117-127 of human Siglec-7 (SEQ ID NO: 1), or within amino acid residues on a Siglec-7 homolog or ortholog corresponding to amino acid residues 117-127 of SEQ ID NO: 1. In some embodiments that may be combined with any of the preceding embodiments, the anti-Siglec-7 antibody binds to one or more amino acids within amino acid residues 282-291 of human Siglec-7 (SEQ ID NO: 1), or within amino acid residues on a Siglec-7 homolog or ortholog corresponding to amino acid residues 282-29 of SEQ ID NO: 1. In some embodiments that may be combined with any of the preceding embodiments, the anti-Siglec-7 antibody binds to one or more amino acid residues selected from the group consisting of M30, Q31, V44, R45, S47, F48, Y50, I72, W74, N81, T103, K104, T107, and R124 of SEQ ID NO: 1, or one or more amino acid residues on a mammalian Siglec-7 protein corresponding to an amino acid residue selected from the group consisting of M30, Q31, V44, R45, S47, F48, Y50, I72, W74, N81, T103, K104, T107, and R124 of SEQ ID NO: 1. In some embodiments that may be combined with any of the preceding embodiments, the anti-Siglec-7 antibody competes with one or more antibodies selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, 10G8, and any combination thereof for binding to Siglec-7. In some embodiments that may be combined with any of the preceding embodiments, the anti-Siglec-7 antibody comprises a light chain variable domain and a heavy chain variable domain, wherein the light chain variable domain, the heavy chain variable domain, or both comprise at least one, two, three, four, five, or six HVRs selected from HVR-L1, HVR-L2, HVR-L3, HVR-H1, HVR-H2, and HVR-H3 of a monoclonal antibody selected from: 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8. In some embodiments that may be combined with any of the preceding embodiments: (a) the HVR-L1 comprises an amino acid sequence selected from SEQ ID NOs: 7-19 and 476; (b) the HVR-L2 comprises an amino acid sequence selected from SEQ ID NOs: 20-32 and 477; (c) the HVR-L3 comprises an amino acid sequence selected from SEQ ID NOs: 33-45 and 478; (d) the HVR-H1 comprises an amino acid sequence selected from SEQ ID NOs: 46-58 and 479; (e) the HVR-H2 comprises an amino acid sequence selected from SEQ ID NOs: 59-71 and 480-482; or (f) the HVR-H3 comprises an amino acid sequence selected from SEQ ID NOs: 72-84 and 483. In some embodiments that may be combined with any of the preceding embodiments: (a) the HVR-L1 comprises the amino acid sequence of SEQ ID NO: 7, the HVR-L2 comprises the amino acid sequence of SEQ ID NO: 20, the HVR-L3 comprises the amino acid sequence of SEQ ID NO: 33, the HVR-H1 comprises the amino acid sequence of SEQ ID NO: 46, the HVR-H2 comprises the amino acid sequence of SEQ ID NO: 59, and the HVR-H3 comprises the amino acid sequence of SEQ ID NO: 72; (b) the HVR-L1 comprises the amino acid sequence of SEQ ID NO: 8, the HVR-L2 comprises the amino acid sequence of SEQ ID NO: 21, the HVR-L3 comprises the amino acid sequence of SEQ ID NO: 34, the HVR-H1 comprises the amino acid sequence of SEQ ID NO: 47, the HVR-H2 comprises the amino acid sequence of SEQ ID NO: 60, and the HVR-H3 comprises the amino acid sequence of SEQ ID NO: 73; (c) the HVR-L1 comprises the amino acid sequence of SEQ ID NO: 10, the HVR-L2 comprises the amino acid sequence of SEQ ID NO: 23, the HVR-L3 comprises the amino acid sequence of SEQ ID NO: 36, the HVR-H1 comprises the amino acid sequence of SEQ ID NO: 49, the HVR-H2 comprises the amino acid sequence of SEQ ID NO: 62, and the HVR-H3 comprises the amino acid sequence of SEQ ID NO: 75; (d) the HVR-L1 comprises the amino acid sequence of SEQ ID NO: 11, the HVR-L2 comprises the amino acid sequence of SEQ ID NO: 24, the HVR-L3 comprises the amino acid sequence of SEQ ID NO: 37, the HVR-H1 comprises the amino acid sequence of SEQ ID NO: 50, the HVR-H2 comprises the amino acid sequence of SEQ ID NO: 63, and the HVR-H3 comprises the amino acid sequence of SEQ ID NO: 76; (e) the HVR-L1 comprises the amino acid sequence of SEQ ID NO: 12, the HVR-L2 comprises the amino acid sequence of SEQ ID NO: 25, the HVR-L3 comprises the amino acid sequence of SEQ ID NO: 38, the HVR-H1 comprises the amino acid sequence of SEQ ID NO: 51, the HVR-H2 comprises the amino acid sequence of SEQ ID NO: 64, and the HVR-H3 comprises the amino acid sequence of SEQ ID NO: 77; (f) the HVR-L1 comprises the amino acid sequence of SEQ ID NO: 13, the HVR-L2 comprises the amino acid sequence of SEQ ID NO: 26, the HVR-L3 comprises the amino acid sequence of SEQ ID NO: 39, the HVR-H1 comprises the amino acid sequence of SEQ ID NO: 52, the HVR-H2 comprises the amino acid sequence of SEQ ID NO: 65, and the HVR-H3 comprises the amino acid sequence of SEQ ID NO: 78; (g) the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 66, and the HVR-H3 comprises the amino acid sequence of SEQ ID NO: 79; (h) the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 480, and the HVR-H3 comprises the amino acid sequence of SEQ ID NO: 74; (i) the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 481 and the HVR-H3 comprises the amino acid sequence of SEQ ID NO: 79; (j) the HVR-L1 comprises the amino acid sequence of SEQ ID NO: 15, the HVR-L2 comprises the amino acid sequence of SEQ ID NO: 28, the HVR-L3 comprises the amino acid sequence of SEQ ID NO: 41, the HVR-H1 comprises the amino acid sequence of SEQ ID NO: 54, the HVR-H2 comprises the amino acid sequence of SEQ ID NO: 67, and the HVR-H3 comprises the amino acid sequence of SEQ ID NO: 80; (k) the HVR-L1 comprises the amino acid sequence of SEQ ID NO: 16, the HVR-L2 comprises the amino acid sequence of SEQ ID NO: 29, the HVR-L3 comprises the amino acid sequence of SEQ ID NO: 42, the HVR-H1 comprises the amino acid sequence of SEQ ID NO: 55, the HVR-H2 comprises the amino acid sequence of SEQ ID NO: 68, and the HVR-H3 comprises the amino acid sequence of SEQ ID NO: 81; (l) the HVR-L1 comprises the amino acid sequence of SEQ ID NO: 17, the HVR-L2 comprises the amino acid sequence of SEQ ID NO: 30, the HVR-L3 comprises the amino acid sequence of SEQ ID NO: 43, the HVR-H1 comprises the amino acid sequence of SEQ ID NO: 56, the HVR-H2 comprises the amino acid sequence of SEQ ID NO: 69, and the HVR-H3 comprises the amino acid sequence of SEQ ID NO: 82; (m) the HVR-L1 comprises the amino acid sequence of SEQ ID NO: 18, the HVR-L2 comprises the amino acid sequence of SEQ ID NO: 31, the HVR-L3 comprises the amino acid sequence of SEQ ID NO: 44, the HVR-H1 comprises the amino acid sequence of SEQ ID NO: 57, the HVR-H2 comprises the amino acid sequence of SEQ ID NO: 70, and the HVR-H3 comprises the amino acid sequence of SEQ ID NO: 83; (n) the HVR-L1 comprises the amino acid sequence of SEQ ID NO: 476, the HVR-L2 comprises the amino acid sequence of SEQ ID NO: 477, the HVR-L3 comprises the amino acid sequence of SEQ ID NO: 478, the HVR-H1 comprises the amino acid sequence of SEQ ID NO: 57, the HVR-H2 comprises the amino acid sequence of SEQ ID NO: 70, and the HVR-H3 comprises the amino acid sequence of SEQ ID NO: 83; (o) the HVR-L1 comprises the amino acid sequence of SEQ ID NO: 18, the HVR-L2 comprises the amino acid sequence of SEQ ID NO: 31, the HVR-L3 comprises the amino acid sequence of SEQ ID NO: 44, the HVR-H1 comprises the amino acid sequence of SEQ ID NO: 479, the HVR-H2 comprises the amino acid sequence of SEQ ID NO: 482, and the HVR-H3 comprises the amino acid sequence of SEQ ID NO: 483; or (p) the HVR-L1 comprises the amino acid sequence of SEQ ID NO: 19, the HVR-L2 comprises the amino acid sequence of SEQ ID NO: 32, the HVR-L3 comprises the amino acid sequence of SEQ ID NO: 45, the HVR-H1 comprises the amino acid sequence of SEQ ID NO: 58, the HVR-H2 comprises the amino acid sequence of SEQ ID NO: 71, and the HVR-H3 comprises the amino acid sequence of SEQ ID NO: 84. In some embodiments that may be combined with any of the preceding embodiments, the HVR-L1 comprises the amino acid sequence of SEQ ID NO: 7, the HVR-L2 comprises the amino acid sequence of SEQ ID NO: 20, the HVR-L3 comprises the amino acid sequence of SEQ ID NO: 33, the HVR-H1 comprises the amino acid sequence of SEQ ID NO: 46, the HVR-H2 comprises the amino acid sequence of SEQ ID NO: 59, and the HVR-H3 comprises the amino acid sequence of SEQ ID NO: 72. In some embodiments that may be combined with any of the preceding embodiments, the HVR-L1 comprises the amino acid sequence of SEQ ID NO: 8, the HVR-L2 comprises the amino acid sequence of SEQ ID NO: 21, the HVR-L3 comprises the amino acid sequence of SEQ ID NO: 34, the HVR-H1 comprises the amino acid sequence of SEQ ID NO: 47, the HVR-H2 comprises the amino acid sequence of SEQ ID NO: 60, and the HVR-H3 comprises the amino acid sequence of SEQ ID NO: 73. In some embodiments that may be combined with any of the preceding embodiments, the HVR-L1 comprises the amino acid sequence of SEQ ID NO: 10, the HVR-L2 comprises the amino acid sequence of SEQ ID NO: 23, the HVR-L3 comprises the amino acid sequence of SEQ ID NO: 36, the HVR-H1 comprises the amino acid sequence of SEQ ID NO: 49, the HVR-H2 comprises the amino acid sequence of SEQ ID NO: 62, and the HVR-H3 comprises the amino acid sequence of SEQ ID NO: 75. In some embodiments that may be combined with any of the preceding embodiments, the HVR-L1 comprises the amino acid sequence of SEQ ID NO: 11, the HVR-L2 comprises the amino acid sequence of SEQ ID NO: 24, the HVR-L3 comprises the amino acid sequence of SEQ ID NO: 37, the HVR-H1 comprises the amino acid sequence of SEQ ID NO: 50, the HVR-H2 comprises the amino acid sequence of SEQ ID NO: 63, and the HVR-H3 comprises the amino acid sequence of SEQ ID NO: 76. In some embodiments that may be combined with any of the preceding embodiments, the HVR-L1 comprises the amino acid sequence of SEQ ID NO: 12, the HVR-L2 comprises the amino acid sequence of SEQ ID NO: 25, the HVR-L3 comprises the amino acid sequence of SEQ ID NO: 38, the HVR-H1 comprises the amino acid sequence of SEQ ID NO: 51, the HVR-H2 comprises the amino acid sequence of SEQ ID NO: 64, and the HVR-H3 comprises the amino acid sequence of SEQ ID NO: 77. In some embodiments that may be combined with any of the preceding embodiments, the HVR-L1 comprises the amino acid sequence of SEQ ID NO: 13, the HVR-L2 comprises the amino acid sequence of SEQ ID NO: 26, the HVR-L3 comprises the amino acid sequence of SEQ ID NO: 39, the HVR-H1 comprises the amino acid sequence of SEQ ID NO: 52, the HVR-H2 comprises the amino acid sequence of SEQ ID NO: 65, and the HVR-H3 comprises the amino acid sequence of SEQ ID NO: 78. In some embodiments that may be combined with any of the preceding embodiments, the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 66, and the HVR-H3 comprises the amino acid sequence of SEQ ID NO: 79. In some embodiments that may be combined with any of the preceding embodiments, the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 480, and the HVR-H3 comprises the amino acid sequence of SEQ ID NO: 74. In some embodiments that may be combined with any of the preceding embodiments, the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 481, and the HVR-H3 comprises the amino acid sequence of SEQ ID NO: 79. In some embodiments that may be combined with any of the preceding embodiments, the HVR-L1 comprises the amino acid sequence of SEQ ID NO: 15, the HVR-L2 comprises the amino acid sequence of SEQ ID NO: 28, the HVR-L3 comprises the amino acid sequence of SEQ ID NO: 41, the HVR-H1 comprises the amino acid sequence of SEQ ID NO: 54, the HVR-H2 comprises the amino acid sequence of SEQ ID NO: 67, and the HVR-H3 comprises the amino acid sequence of SEQ ID NO: 80. In some embodiments that may be combined with any of the preceding embodiments, the HVR-L1 comprises the amino acid sequence of SEQ ID NO: 16, the HVR-L2 comprises the amino acid sequence of SEQ ID NO: 29, the HVR-L3 comprises the amino acid sequence of SEQ ID NO: 42, the HVR-H1 comprises the amino acid sequence of SEQ ID NO: 55, the HVR-H2 comprises the amino acid sequence of SEQ ID NO: 68, and the HVR-H3 comprises the amino acid sequence of SEQ ID NO: 81. In some embodiments that may be combined with any of the preceding embodiments, the HVR-L1 comprises the amino acid sequence of SEQ ID NO: 17, the HVR-L2 comprises the amino acid sequence of SEQ ID NO: 30, the HVR-L3 comprises the amino acid sequence of SEQ ID NO: 43, the HVR-H1 comprises the amino acid sequence of SEQ ID NO: 56, the HVR-H2 comprises the amino acid sequence of SEQ ID NO: 69, and the HVR-H3 comprises the amino acid sequence of SEQ ID NO: 82. In some embodiments that may be combined with any of the preceding embodiments, the HVR-L1 comprises the amino acid sequence of SEQ ID NO: 18, the HVR-L2 comprises the amino acid sequence of SEQ ID NO: 31, the HVR-L3 comprises the amino acid sequence of SEQ ID NO: 44, the HVR-H1 comprises the amino acid sequence of SEQ ID NO: 57, the HVR-H2 comprises the amino acid sequence of SEQ ID NO: 70, and the HVR-H3 comprises the amino acid sequence of SEQ ID NO: 83. In some embodiments that may be combined with any of the preceding embodiments, the HVR-L1 comprises the amino acid sequence of SEQ ID NO: 476, the HVR-L2 comprises the amino acid sequence of SEQ ID NO: 477, the HVR-L3 comprises the amino acid sequence of SEQ ID NO: 478, the HVR-H1 comprises the amino acid sequence of SEQ ID NO: 57, the HVR-H2 comprises the amino acid sequence of SEQ ID NO: 70, and the HVR-H3 comprises the amino acid sequence of SEQ ID NO: 83. In some embodiments that may be combined with any of the preceding embodiments, the HVR-L1 comprises the amino acid sequence of SEQ ID NO: 18, the HVR-L2 comprises the amino acid sequence of SEQ ID NO: 31, the HVR-L3 comprises the amino acid sequence of SEQ ID NO: 44, the HVR-H1 comprises the amino acid sequence of SEQ ID NO: 479, the HVR-H2 comprises the amino acid sequence of SEQ ID NO: 482, and the HVR-H3 comprises the amino acid sequence of SEQ ID NO: 483. In some embodiments that may be combined with any of the preceding embodiments, the HVR-L1 comprises the amino acid sequence of SEQ ID NO: 19, the HVR-L2 comprises the amino acid sequence of SEQ ID NO: 32, the HVR-L3 comprises the amino acid sequence of SEQ ID NO: 45, the HVR-H1 comprises the amino acid sequence of SEQ ID NO: 58, the HVR-H2 comprises the amino acid sequence of SEQ ID NO: 71, and the HVR-H3 comprises the amino acid sequence of SEQ ID NO: 84. In some embodiments that may be combined with any of the preceding embodiments, the anti-Siglec-7 antibody comprises a light chain variable domain and a heavy chain variable domain, wherein the light chain variable domain comprises: (a) an HVR-L1 comprising an amino acid sequence selected from SEQ ID NOs: 7-19 and 476, or an amino acid sequence with at least about 90% homology to an amino acid sequence selected from SEQ ID NOs: 7-19 and 476; (b) an HVR-L2 comprising an amino acid sequence selected from SEQ ID NOs: 20-32 and 477, or an amino acid sequence with at least about 90% homology to an amino acid sequence selected from SEQ ID NOs: 20-32 and 477; and (c) an HVR-L3 comprising an amino acid sequence selected from SEQ ID NOs: 33-45 and 478, or an amino acid sequence with at least about 90% homology to an amino acid sequence selected from SEQ ID NOs: 33-45 and 478; and wherein the heavy chain variable domain comprises: (a) an HVR-H1 comprising an amino acid sequence selected from SEQ ID NOs: 46-58 and 479, or an amino acid sequence with at least about 90% homology to an amino acid sequence selected from SEQ ID NOs: 46-58 and 479; (b) an HVR-H2 comprising an amino acid sequence selected from SEQ ID NOs: 59-71 and 480-482, or an amino acid sequence with at least about 90% homology to an amino acid sequence selected from SEQ ID NOs: 59-71 and 480-482; and (c) an HVR-H3 comprising an amino acid sequence selected from SEQ ID NOs: 72-84 and 483, or an amino acid sequence with at least about 90% homology to an amino acid sequence selected from SEQ ID NOs: 72-84 and 483. In some embodiments that may be combined with any of the preceding embodiments, the anti-Siglec-7 antibody comprises a light chain variable domain comprising an amino acid sequence selected from SEQ ID NOs: 189-318, 449-461, and 484-489; and/or a heavy chain variable domain comprising an amino acid sequence selected from SEQ ID NOs: 319-448, 462-474, and 490-496. In some embodiments that may be combined with any of the preceding embodiments, the anti-Siglec-7 antibody comprises a light chain variable domain of a monoclonal antibody selected from: 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8; and/or a heavy chain variable domain of a monoclonal antibody selected from: 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8.

Other aspects of the present disclosure relate to an isolated monoclonal anti-Siglec-7 antibody, wherein the anti-Siglec-7 antibody binds to one or more amino acids within amino acid residues 39-353, 39-149, 93-104, 95-105, 39-122, 123-149, 150-233, 240-336, 264-273, 295-306, 327-341, or 337-353 of SEQ ID NO: 1; or within amino acid residues on a mammalian Siglec-7 protein corresponding to amino acid residues 39-353, 39-149, 93-104, 95-105, 39-122, 123-149, 150-233, 240-336, 264-273, 295-306, 327-341, or 337-353 of SEQ ID NO: 1. In some embodiments that may be combined with any of the preceding embodiments, the anti-Siglec-7 antibody binds to one or more amino acids within amino acid residues selected from the group consisting of: i. amino acid residues 60-69 of SEQ ID NO: 1, or amino acid residues on a mammalian Siglec-7 protein corresponding to amino acid residues 60-69 of SEQ ID NO: 1; ii. amino acid residues 60-69 and 84-95 of SEQ ID NO: 1, or amino acid residues on a mammalian Siglec-7 protein corresponding to amino acid residues 60-69 and 84-95 of SEQ ID NO: 1; iii. amino acid residues 60-69 and 117-127 of SEQ ID NO: 1, or amino acid residues on a mammalian Siglec-7 protein corresponding to amino acid residues 60-69 and 117-127 of SEQ ID NO: 1; iv. amino acid residues 68-78 of SEQ ID NO: 1, or amino acid residues on a mammalian Siglec-7 protein corresponding to amino acid residues 68-78 of SEQ ID NO: 1; v. amino acid residues 84-95 of SEQ ID NO: 1, or amino acid residues on a mammalian Siglec-7 protein corresponding to amino acid residues 84-95 of SEQ ID NO: 1; vi. amino acid residues 111-122 of SEQ ID NO: 1, or amino acid residues on a mammalian Siglec-7 protein corresponding to amino acid residues 111-122 of SEQ ID NO: 1; vii. amino acid residues 111-122 and 282-291 of SEQ ID NO: 1, or amino acid residues on a mammalian Siglec-7 protein corresponding to amino acid residues 111-122 and 282-291 of SEQ ID NO: 1; viii. amino acid residues 113-123 of SEQ ID NO: 1, or amino acid residues on a mammalian Siglec-7 protein corresponding to amino acid residues 113-123 of SEQ ID NO: 1; ix. amino acid residues 113-125 of SEQ ID NO: 1, or amino acid residues on a mammalian Siglec-7 protein corresponding to amino acid residues 113-125 of SEQ ID NO: 1; x. amino acid residues 117-127 of SEQ ID NO: 1, or amino acid residues on a mammalian Siglec-7 protein corresponding to amino acid residues 117-127 of SEQ ID NO: 1; and xi. amino acid residues 282-291 of SEQ ID NO: 1, or amino acid residues on a mammalian Siglec-7 protein corresponding to amino acid residues 282-291 of SEQ ID NO: 1. In some embodiments that may be combined with any of the preceding embodiments, the anti-Siglec-7 antibody binds to one or more amino acids within amino acid residues 60-69 of human Siglec-7 (SEQ ID NO: 1), or within amino acid residues on a Siglec-7 homolog or ortholog corresponding to amino acid residues 60-69 of SEQ ID NO: 1. In some embodiments that may be combined with any of the preceding embodiments, the anti-Siglec-7 antibody binds to one or more amino acids within amino acid residues 60-69 and 84-95 of human Siglec-7 (SEQ ID NO: 1), or within amino acid residues on a Siglec-7 homolog or ortholog corresponding to amino acid residues 60-69 and 84-95 of SEQ ID NO: 1. In some embodiments that may be combined with any of the preceding embodiments, the anti-Siglec-7 antibody binds to one or more amino acids within amino acid residues 60-69 and 117-127 of human Siglec-7 (SEQ ID NO: 1), or within amino acid residues on a Siglec-7 homolog or ortholog corresponding to amino acid residues 60-69 and 117-127 of SEQ ID NO: 1. In some embodiments that may be combined with any of the preceding embodiments, the anti-Siglec-7 antibody binds to one or more amino acids within amino acid residues 68-78 of human Siglec-7 (SEQ ID NO: 1), or within amino acid residues on a Siglec-7 homolog or ortholog corresponding to amino acid residues 68-78 of SEQ ID NO: 1. In some embodiments that may be combined with any of the preceding embodiments, the anti-Siglec-7 antibody binds to one or more amino acids within amino acid residues 84-95 of human Siglec-7 (SEQ ID NO: 1), or within amino acid residues on a Siglec-7 homolog or ortholog corresponding to amino acid residues 84-95 of SEQ ID NO: 1. In some embodiments that may be combined with any of the preceding embodiments, the anti-Siglec-7 antibody binds to one or more amino acids within amino acid residues 111-122 of human Siglec-7 (SEQ ID NO: 1), or within amino acid residues on a Siglec-7 homolog or ortholog corresponding to amino acid residues 111-122 of SEQ ID NO: 1. In some embodiments that may be combined with any of the preceding embodiments, the anti-Siglec-7 antibody binds to one or more amino acids within amino acid residues 111-122 and 282-291 of human Siglec-7 (SEQ ID NO: 1), or within amino acid residues on a Siglec-7 homolog or ortholog corresponding to amino acid residues 111-122 and 282-291 of SEQ ID NO: 1. In some embodiments that may be combined with any of the preceding embodiments, the anti-Siglec-7 antibody binds to one or more amino acids within amino acid residues 113-123 of human Siglec-7 (SEQ ID NO: 1), or within amino acid residues on a Siglec-7 homolog or ortholog corresponding to amino acid residues 113-123 of SEQ ID NO: 1. In some embodiments that may be combined with any of the preceding embodiments, the anti-Siglec-7 antibody binds to one or more amino acids within amino acid residues 113-125 of human Siglec-7 (SEQ ID NO: 1), or within amino acid residues on a Siglec-7 homolog or ortholog corresponding to amino acid residues 113-125 of SEQ ID NO: 1. In some embodiments that may be combined with any of the preceding embodiments, the anti-Siglec-7 antibody binds to one or more amino acids within amino acid residues 117-127 of human Siglec-7 (SEQ ID NO: 1), or within amino acid residues on a Siglec-7 homolog or ortholog corresponding to amino acid residues 117-127 of SEQ ID NO: 1. In some embodiments that may be combined with any of the preceding embodiments, the anti-Siglec-7 antibody binds to one or more amino acids within amino acid residues 282-291 of human Siglec-7 (SEQ ID NO: 1), or within amino acid residues on a Siglec-7 homolog or ortholog corresponding to amino acid residues 282-29 of SEQ ID NO: 1. Other aspects of the present disclosure relate to an isolated monoclonal anti-Siglec-7 antibody, wherein the anti-Siglec-7 antibody binds to one or more amino acid residues selected from the group consisting of M30, Q31, V44, R45, S47, F48, Y50, I72, W74, N81, T103, K104, T107, and R124 of SEQ ID NO: 1, or one or more amino acid residues on a mammalian Siglec-7 protein corresponding to an amino acid residue selected from the group consisting of M30, Q31, V44, R45, S47, F48, Y50, I72, W74, N81, T103, K104, T107, and R124 of SEQ ID NO: 1.

Other aspects of the present disclosure relate to an isolated monoclonal anti-Siglec-7 antibody, wherein the anti-Siglec-7 antibody comprises a light chain variable domain and a heavy chain variable domain, wherein the light chain variable domain, the heavy chain variable domain, or both comprise at least one, two, three, four, five, or six HVRs selected from HVR-L1, HVR-L2, HVR-L3, HVR-H1, HVR-H2, and HVR-H3 of a monoclonal antibody selected from: 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8.

In some embodiments that may be combined with any of the preceding embodiments: (a) the HVR-L1 comprises an amino acid sequence selected from SEQ ID NOs: 7-19 and 476; (b) the HVR-L2 comprises an amino acid sequence selected from SEQ ID NOs: 20-32 and 477; (c) the HVR-L3 comprises an amino acid sequence selected from SEQ ID NOs: 33-45 and 478; (d) the HVR-H1 comprises an amino acid sequence selected from SEQ ID NOs: 46-58 and 479, (e) the HVR-H2 comprises an amino acid sequence selected from SEQ ID NOs: 59-71 and 480-482; or (f) the HVR-H3 comprises an amino acid sequence selected from SEQ ID NOs: 72-84 and 483. In some embodiments that may be combined with any of the preceding embodiments: (a) the HVR-L1 comprises the amino acid sequence of SEQ ID NO: 7, the HVR-L2 comprises the amino acid sequence of SEQ ID NO: 20, the HVR-L3 comprises the amino acid sequence of SEQ ID NO: 33, the HVR-H1 comprises the amino acid sequence of SEQ ID NO: 46, the HVR-H2 comprises the amino acid sequence of SEQ ID NO: 59, and the HVR-H3 comprises the amino acid sequence of SEQ ID NO: 72; (b) the HVR-L1 comprises the amino acid sequence of SEQ ID NO: 8, the HVR-L2 comprises the amino acid sequence of SEQ ID NO: 21, the HVR-L3 comprises the amino acid sequence of SEQ ID NO: 34, the HVR-H1 comprises the amino acid sequence of SEQ ID NO: 47, the HVR-H2 comprises the amino acid sequence of SEQ ID NO: 60, and the HVR-H3 comprises the amino acid sequence of SEQ ID NO: 73; (c) the HVR-L1 comprises the amino acid sequence of SEQ ID NO: 9, the HVR-L2 comprises the amino acid sequence of SEQ ID NO: 22, the HVR-L3 comprises the amino acid sequence of SEQ ID NO: 35, the HVR-H1 comprises the amino acid sequence of SEQ ID NO: 48, the HVR-H2 comprises the amino acid sequence of SEQ ID NO: 61, and the HVR-H3 comprises the amino acid sequence of SEQ ID NO: 74; (d) the HVR-L1 comprises the amino acid sequence of SEQ ID NO: 10, the HVR-L2 comprises the amino acid sequence of SEQ ID NO: 23, the HVR-L3 comprises the amino acid sequence of SEQ ID NO: 36, the HVR-H1 comprises the amino acid sequence of SEQ ID NO: 49, the HVR-H2 comprises the amino acid sequence of SEQ ID NO: 62, and the HVR-H3 comprises the amino acid sequence of SEQ ID NO: 75; (e) the HVR-L1 comprises the amino acid sequence of SEQ ID NO: 11, the HVR-L2 comprises the amino acid sequence of SEQ ID NO: 24, the HVR-L3 comprises the amino acid sequence of SEQ ID NO: 37, the HVR-H1 comprises the amino acid sequence of SEQ ID NO: 50, the HVR-H2 comprises the amino acid sequence of SEQ ID NO: 63, and the HVR-H3 comprises the amino acid sequence of SEQ ID NO: 76; (f) the HVR-L1 comprises the amino acid sequence of SEQ ID NO: 12, the HVR-L2 comprises the amino acid sequence of SEQ ID NO: 25, the HVR-L3 comprises the amino acid sequence of SEQ ID NO: 38, the HVR-H1 comprises the amino acid sequence of SEQ ID NO: 51, the HVR-H2 comprises the amino acid sequence of SEQ ID NO: 64, and the HVR-H3 comprises the amino acid sequence of SEQ ID NO: 77; (g) the HVR-L1 comprises the amino acid sequence of SEQ ID NO: 13, the HVR-L2 comprises the amino acid sequence of SEQ ID NO: 26, the HVR-L3 comprises the amino acid sequence of SEQ ID NO: 39, the HVR-H1 comprises the amino acid sequence of SEQ ID NO: 52, the HVR-H2 comprises the amino acid sequence of SEQ ID NO: 65, and the HVR-H3 comprises the amino acid sequence of SEQ ID NO: 78; (h) the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 66, and the HVR-H3 comprises the amino acid sequence of SEQ ID NO: 79; (i) the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 480, and the HVR-H3 comprises the amino acid sequence of SEQ ID NO: 74; (j) the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 481 and the HVR-H3 comprises the amino acid sequence of SEQ ID NO: 79; (k) the HVR-L1 comprises the amino acid sequence of SEQ ID NO: 15, the HVR-L2 comprises the amino acid sequence of SEQ ID NO: 28, the HVR-L3 comprises the amino acid sequence of SEQ ID NO: 41, the HVR-H1 comprises the amino acid sequence of SEQ ID NO: 54, the HVR-H2 comprises the amino acid sequence of SEQ ID NO: 67, and the HVR-H3 comprises the amino acid sequence of SEQ ID NO: 80; (l) the HVR-L1 comprises the amino acid sequence of SEQ ID NO: 16, the HVR-L2 comprises the amino acid sequence of SEQ ID NO: 29, the HVR-L3 comprises the amino acid sequence of SEQ ID NO: 42, the HVR-H1 comprises the amino acid sequence of SEQ ID NO: 55, the HVR-H2 comprises the amino acid sequence of SEQ ID NO: 68, and the HVR-H3 comprises the amino acid sequence of SEQ ID NO: 81; (m) the HVR-L1 comprises the amino acid sequence of SEQ ID NO: 17, the HVR-L2 comprises the amino acid sequence of SEQ ID NO: 30, the HVR-L3 comprises the amino acid sequence of SEQ ID NO: 43, the HVR-H1 comprises the amino acid sequence of SEQ ID NO: 56, the HVR-H2 comprises the amino acid sequence of SEQ ID NO: 69, and the HVR-H3 comprises the amino acid sequence of SEQ ID NO: 82; (n) the HVR-L1 comprises the amino acid sequence of SEQ ID NO: 18, the HVR-L2 comprises the amino acid sequence of SEQ ID NO: 31, the HVR-L3 comprises the amino acid sequence of SEQ ID NO: 44, the HVR-H1 comprises the amino acid sequence of SEQ ID NO: 57, the HVR-H2 comprises the amino acid sequence of SEQ ID NO: 70, and the HVR-H3 comprises the amino acid sequence of SEQ ID NO: 83; (o) the HVR-L1 comprises the amino acid sequence of SEQ ID NO: 476, the HVR-L2 comprises the amino acid sequence of SEQ ID NO: 477, the HVR-L3 comprises the amino acid sequence of SEQ ID NO: 478, the HVR-H1 comprises the amino acid sequence of SEQ ID NO: 57, the HVR-H2 comprises the amino acid sequence of SEQ ID NO: 70, and the HVR-H3 comprises the amino acid sequence of SEQ ID NO: 83; (p) the HVR-L1 comprises the amino acid sequence of SEQ ID NO: 18, the HVR-L2 comprises the amino acid sequence of SEQ ID NO: 31, the HVR-L3 comprises the amino acid sequence of SEQ ID NO: 44, the HVR-H1 comprises the amino acid sequence of SEQ ID NO: 479, the HVR-H2 comprises the amino acid sequence of SEQ ID NO: 482, and the HVR-H3 comprises the amino acid sequence of SEQ ID NO: 483; or (q) the HVR-L1 comprises the amino acid sequence of SEQ ID NO: 19, the HVR-L2 comprises the amino acid sequence of SEQ ID NO: 32, the HVR-L3 comprises the amino acid sequence of SEQ ID NO: 45, the HVR-H1 comprises the amino acid sequence of SEQ ID NO: 58, the HVR-H2 comprises the amino acid sequence of SEQ ID NO: 71, and the HVR-H3 comprises the amino acid sequence of SEQ ID NO: 84. In some embodiments that may be combined with any of the preceding embodiments, the HVR-L1 comprises the amino acid sequence of SEQ ID NO: 7, the HVR-L2 comprises the amino acid sequence of SEQ ID NO: 20, the HVR-L3 comprises the amino acid sequence of SEQ ID NO: 33, the HVR-H1 comprises the amino acid sequence of SEQ ID NO: 46, the HVR-H2 comprises the amino acid sequence of SEQ ID NO: 59, and the HVR-H3 comprises the amino acid sequence of SEQ ID NO: 72. In some embodiments that may be combined with any of the preceding embodiments, the HVR-L1 comprises the amino acid sequence of SEQ ID NO: 8, the HVR-L2 comprises the amino acid sequence of SEQ ID NO: 21, the HVR-L3 comprises the amino acid sequence of SEQ ID NO: 34, the HVR-H1 comprises the amino acid sequence of SEQ ID NO: 47, the HVR-H2 comprises the amino acid sequence of SEQ ID NO: 60, and the HVR-H3 comprises the amino acid sequence of SEQ ID NO: 73. In some embodiments that may be combined with any of the preceding embodiments, the HVR-L1 comprises the amino acid sequence of SEQ ID NO: 9, the HVR-L2 comprises the amino acid sequence of SEQ ID NO: 22, the HVR-L3 comprises the amino acid sequence of SEQ ID NO: 35, the HVR-H1 comprises the amino acid sequence of SEQ ID NO: 48, the HVR-H2 comprises the amino acid sequence of SEQ ID NO: 61, and the HVR-H3 comprises the amino acid sequence of SEQ ID NO: 74. In some embodiments that may be combined with any of the preceding embodiments, the HVR-L1 comprises the amino acid sequence of SEQ ID NO: 10, the HVR-L2 comprises the amino acid sequence of SEQ ID NO: 23, the HVR-L3 comprises the amino acid sequence of SEQ ID NO: 36, the HVR-H1 comprises the amino acid sequence of SEQ ID NO: 49, the HVR-H2 comprises the amino acid sequence of SEQ ID NO: 62, and the HVR-H3 comprises the amino acid sequence of SEQ ID NO: 75. In some embodiments that may be combined with any of the preceding embodiments, the HVR-L1 comprises the amino acid sequence of SEQ ID NO: 11, the HVR-L2 comprises the amino acid sequence of SEQ ID NO: 24, the HVR-L3 comprises the amino acid sequence of SEQ ID NO: 37, the HVR-H1 comprises the amino acid sequence of SEQ ID NO: 50, the HVR-H2 comprises the amino acid sequence of SEQ ID NO: 63, and the HVR-H3 comprises the amino acid sequence of SEQ ID NO: 76. In some embodiments that may be combined with any of the preceding embodiments, the HVR-L1 comprises the amino acid sequence of SEQ ID NO: 12, the HVR-L2 comprises the amino acid sequence of SEQ ID NO: 25, the HVR-L3 comprises the amino acid sequence of SEQ ID NO: 38, the HVR-H1 comprises the amino acid sequence of SEQ ID NO: 51, the HVR-H2 comprises the amino acid sequence of SEQ ID NO: 64, and the HVR-H3 comprises the amino acid sequence of SEQ ID NO: 77. In some embodiments that may be combined with any of the preceding embodiments, the HVR-L1 comprises the amino acid sequence of SEQ ID NO: 13, the HVR-L2 comprises the amino acid sequence of SEQ ID NO: 26, the HVR-L3 comprises the amino acid sequence of SEQ ID NO: 39, the HVR-H1 comprises the amino acid sequence of SEQ ID NO: 52, the HVR-H2 comprises the amino acid sequence of SEQ ID NO: 65, and the HVR-H3 comprises the amino acid sequence of SEQ ID NO: 78. In some embodiments that may be combined with any of the preceding embodiments, the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 66, and the HVR-H3 comprises the amino acid sequence of SEQ ID NO: 79. In some embodiments that may be combined with any of the preceding embodiments, the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 480, and the HVR-H3 comprises the amino acid sequence of SEQ ID NO: 74. In some embodiments that may be combined with any of the preceding embodiments, he HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 481 and the HVR-H3 comprises the amino acid sequence of SEQ ID NO: 79. In some embodiments that may be combined with any of the preceding embodiments, the HVR-L1 comprises the amino acid sequence of SEQ ID NO: 15, the HVR-L2 comprises the amino acid sequence of SEQ ID NO: 28, the HVR-L3 comprises the amino acid sequence of SEQ ID NO: 41, the HVR-H1 comprises the amino acid sequence of SEQ ID NO: 54, the HVR-H2 comprises the amino acid sequence of SEQ ID NO: 67, and the HVR-H3 comprises the amino acid sequence of SEQ ID NO: 80. In some embodiments that may be combined with any of the preceding embodiments, the HVR-L1 comprises the amino acid sequence of SEQ ID NO: 16, the HVR-L2 comprises the amino acid sequence of SEQ ID NO: 29, the HVR-L3 comprises the amino acid sequence of SEQ ID NO: 42, the HVR-H1 comprises the amino acid sequence of SEQ ID NO: 55, the HVR-H2 comprises the amino acid sequence of SEQ ID NO: 68, and the HVR-H3 comprises the amino acid sequence of SEQ ID NO: 81. In some embodiments that may be combined with any of the preceding embodiments, the HVR-L1 comprises the amino acid sequence of SEQ ID NO: 17, the HVR-L2 comprises the amino acid sequence of SEQ ID NO: 30, the HVR-L3 comprises the amino acid sequence of SEQ ID NO: 43, the HVR-H1 comprises the amino acid sequence of SEQ ID NO: 56, the HVR-H2 comprises the amino acid sequence of SEQ ID NO: 69, and the HVR-H3 comprises the amino acid sequence of SEQ ID NO: 82. In some embodiments that may be combined with any of the preceding embodiments, the HVR-L1 comprises the amino acid sequence of SEQ ID NO: 18, the HVR-L2 comprises the amino acid sequence of SEQ ID NO: 31, the HVR-L3 comprises the amino acid sequence of SEQ ID NO: 44, the HVR-H1 comprises the amino acid sequence of SEQ ID NO: 57, the HVR-H2 comprises the amino acid sequence of SEQ ID NO: 70, and the HVR-H3 comprises the amino acid sequence of SEQ ID NO: 83. In some embodiments that may be combined with any of the preceding embodiments, the HVR-L1 comprises the amino acid sequence of SEQ ID NO: 476, the HVR-L2 comprises the amino acid sequence of SEQ ID NO: 477, the HVR-L3 comprises the amino acid sequence of SEQ ID NO: 478, the HVR-H1 comprises the amino acid sequence of SEQ ID NO: 57, the HVR-H2 comprises the amino acid sequence of SEQ ID NO: 70, and the HVR-H3 comprises the amino acid sequence of SEQ ID NO: 83. In some embodiments that may be combined with any of the preceding embodiments, the HVR-L1 comprises the amino acid sequence of SEQ ID NO: 18, the HVR-L2 comprises the amino acid sequence of SEQ ID NO: 31, the HVR-L3 comprises the amino acid sequence of SEQ ID NO: 44, the HVR-H1 comprises the amino acid sequence of SEQ ID NO: 479, the HVR-H2 comprises the amino acid sequence of SEQ ID NO: 482, and the HVR-H3 comprises the amino acid sequence of SEQ ID NO: 483. In some embodiments that may be combined with any of the preceding embodiments, the HVR-L1 comprises the amino acid sequence of SEQ ID NO: 19, the HVR-L2 comprises the amino acid sequence of SEQ ID NO: 32, the HVR-L3 comprises the amino acid sequence of SEQ ID NO: 45, the HVR-H1 comprises the amino acid sequence of SEQ ID NO: 58, the HVR-H2 comprises the amino acid sequence of SEQ ID NO: 71, and the HVR-H3 comprises the amino acid sequence of SEQ ID NO: 84. In some embodiments, the light chain variable domain comprises: (a) an HVR-L1 comprising an amino acid sequence selected from SEQ ID NOs: 7-19 and 476, or an amino acid sequence with at least about 90% homology to an amino acid sequence selected from SEQ ID NOs: 7-19 and 476; (b) an HVR-L2 comprising an amino acid sequence selected from SEQ ID NOs: 20-32 and 477, or an amino acid sequence with at least about 90% homology to an amino acid sequence selected from SEQ ID NOs: 20-32 and 477; and (c) an HVR-L3 comprising an amino acid sequence selected from SEQ ID NOs: 33-45 and 478, or an amino acid sequence with at least about 90% homology to an amino acid sequence selected from SEQ ID NOs: 33-45 and 478; and wherein the heavy chain variable domain comprises: (a) an HVR-H1 comprising an amino acid sequence selected from SEQ ID NOs: 46-58 and 479, or an amino acid sequence with at least about 90% homology to an amino acid sequence selected from SEQ ID NOs: 46-58 and 479; (b) an HVR-H2 comprising an amino acid sequence selected from SEQ ID NOs: 59-71 and 480-482, or an amino acid sequence with at least about 90% homology to an amino acid sequence selected from SEQ ID NOs: 59-71 and 480-482; and (c) an HVR-H3 comprising an amino acid sequence selected from SEQ ID NOs: 72-84 and 483, or an amino acid sequence with at least about 90% homology to an amino acid sequence selected from SEQ ID NOs: 72-84 and 483.

Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 7, the HVR-L2 comprises the amino acid sequence of SEQ ID NO: 20, the HVR-L3 comprises the amino acid sequence of SEQ ID NO: 33, the HVR-H1 comprises the amino acid sequence of SEQ ID NO: 46, the HVR-H2 comprises the amino acid sequence of SEQ ID NO: 59, and the HVR-H3 comprises the amino acid sequence of SEQ ID NO: 72. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 8, the HVR-L2 comprises the amino acid sequence of SEQ ID NO: 21, the HVR-L3 comprises the amino acid sequence of SEQ ID NO: 34, the HVR-H1 comprises the amino acid sequence of SEQ ID NO: 47, the HVR-H2 comprises the amino acid sequence of SEQ ID NO: 60, and the HVR-H3 comprises the amino acid sequence of SEQ ID NO: 73. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the amino acid sequence of SEQ ID NO: 9, the HVR-L2 comprises the amino acid sequence of SEQ ID NO: 22, the HVR-L3 comprises the amino acid sequence of SEQ ID NO: 35, the HVR-H1 comprises the amino acid sequence of SEQ ID NO: 48, the HVR-H2 comprises the amino acid sequence of SEQ ID NO: 61, and the HVR-H3 comprises the amino acid sequence of SEQ ID NO: 74. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 10, the HVR-L2 comprises the amino acid sequence of SEQ ID NO: 23, the HVR-L3 comprises the amino acid sequence of SEQ ID NO: 36, the HVR-H1 comprises the amino acid sequence of SEQ ID NO: 49, the HVR-H2 comprises the amino acid sequence of SEQ ID NO: 62, and the HVR-H3 comprises the amino acid sequence of SEQ ID NO: 75. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 11, the HVR-L2 comprises the amino acid sequence of SEQ ID NO: 24, the HVR-L3 comprises the amino acid sequence of SEQ ID NO: 37, the HVR-H1 comprises the amino acid sequence of SEQ ID NO: 50, the HVR-H2 comprises the amino acid sequence of SEQ ID NO: 63, and the HVR-H3 comprises the amino acid sequence of SEQ ID NO: 76. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 12, the HVR-L2 comprises the amino acid sequence of SEQ ID NO: 25, the HVR-L3 comprises the amino acid sequence of SEQ ID NO: 38, the HVR-H1 comprises the amino acid sequence of SEQ ID NO: 51, the HVR-H2 comprises the amino acid sequence of SEQ ID NO: 64, and the HVR-H3 comprises the amino acid sequence of SEQ ID NO: 77. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 13, the HVR-L2 comprises the amino acid sequence of SEQ ID NO: 26, the HVR-L3 comprises the amino acid sequence of SEQ ID NO: 39, the HVR-H1 comprises the amino acid sequence of SEQ ID NO: 52, the HVR-H2 comprises the amino acid sequence of SEQ ID NO: 65, and the HVR-H3 comprises the amino acid sequence of SEQ ID NO: 78. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 66, and the HVR-H3 comprises the amino acid sequence of SEQ ID NO: 79. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 480, and the HVR-H3 comprises the amino acid sequence of SEQ ID NO: 74. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 481 and the HVR-H3 comprises the amino acid sequence of SEQ ID NO: 79. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 15, the HVR-L2 comprises the amino acid sequence of SEQ ID NO: 28, the HVR-L3 comprises the amino acid sequence of SEQ ID NO: 41, the HVR-H1 comprises the amino acid sequence of SEQ ID NO: 54, the HVR-H2 comprises the amino acid sequence of SEQ ID NO: 67, and the HVR-H3 comprises the amino acid sequence of SEQ ID NO: 80. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 16, the HVR-L2 comprises the amino acid sequence of SEQ ID NO: 29, the HVR-L3 comprises the amino acid sequence of SEQ ID NO: 42, the HVR-H1 comprises the amino acid sequence of SEQ ID NO: 55, the HVR-H2 comprises the amino acid sequence of SEQ ID NO: 68, and the HVR-H3 comprises the amino acid sequence of SEQ ID NO: 81. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 17, the HVR-L2 comprises the amino acid sequence of SEQ ID NO: 30, the HVR-L3 comprises the amino acid sequence of SEQ ID NO: 43, the HVR-H1 comprises the amino acid sequence of SEQ ID NO: 56, the HVR-H2 comprises the amino acid sequence of SEQ ID NO: 69, and the HVR-H3 comprises the amino acid sequence of SEQ ID NO: 82. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 18, the HVR-L2 comprises the amino acid sequence of SEQ ID NO: 31, the HVR-L3 comprises the amino acid sequence of SEQ ID NO: 44, the HVR-H1 comprises the amino acid sequence of SEQ ID NO: 57, the HVR-H2 comprises the amino acid sequence of SEQ ID NO: 70, and the HVR-H3 comprises the amino acid sequence of SEQ ID NO: 83. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 476, the HVR-L2 comprises the amino acid sequence of SEQ ID NO: 477, the HVR-L3 comprises the amino acid sequence of SEQ ID NO: 478, the HVR-H1 comprises the amino acid sequence of SEQ ID NO: 57, the HVR-H2 comprises the amino acid sequence of SEQ ID NO: 70, and the HVR-H3 comprises the amino acid sequence of SEQ ID NO: 83. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 18, the HVR-L2 comprises the amino acid sequence of SEQ ID NO: 31, the HVR-L3 comprises the amino acid sequence of SEQ ID NO: 44, the HVR-H1 comprises the amino acid sequence of SEQ ID NO: 479, the HVR-H2 comprises the amino acid sequence of SEQ ID NO: 482, and the HVR-H3 comprises the amino acid sequence of SEQ ID NO: 483. Other aspects of the present disclosure relate to an isolated monoclonal anti-Siglec-7 antibody, wherein the anti-Siglec-7 antibody comprises a light chain variable domain comprising an HVR-L1, an HVR-L2, and an HVR-L3, and a heavy chain variable domain comprising an HVR-H1, an HVR-H2, and an HVR-H3, wherein the HVR-L1 comprises the amino acid sequence of SEQ ID NO: 19, the HVR-L2 comprises the amino acid sequence of SEQ ID NO: 32, the HVR-L3 comprises the amino acid sequence of SEQ ID NO: 45, the HVR-H1 comprises the amino acid sequence of SEQ ID NO: 58, the HVR-H2 comprises the amino acid sequence of SEQ ID NO: 71, and the HVR-H3 comprises the amino acid sequence of SEQ ID NO: 84. Other aspects of the present disclosure relate to an isolated monoclonal anti-Siglec-7 antibody, wherein the anti-Siglec-7 antibody comprises a light chain variable domain comprising an amino acid sequence selected from SEQ ID NOs: 189-318, 449-461, and 484-489; and/or a heavy chain variable domain comprising an amino acid sequence selected from SEQ ID NOs: 319-448, 462-474, and 490-496. Other aspects of the present disclosure relate to an isolated monoclonal anti-Siglec-7 antibody, wherein the anti-Siglec-7 antibody comprises a light chain variable domain of a monoclonal antibody selected from: 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8; and/or a heavy chain variable domain of a monoclonal antibody selected from: 1A12, 1E8, 2G1, 2G4, 3E11, 4A1, 4D7, 4E3, 4E3H1, 4E3H2, 7A3, 7E11, 7F12, 10B5, 10B5L, 10B5H1, and 10G8. Other aspects of the present disclosure relate to an isolated monoclonal anti-Siglec-7 antibody, wherein the anti-Siglec-7 antibody competes with one or more antibodies selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, 10G8, and any combination thereof for binding to Siglec-7. Other aspects of the present disclosure relate to an isolated monoclonal anti-Siglec-7 antibody which binds essentially the same Siglec-7 epitope as a monoclonal antibody selected from: 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8. Other aspects of the present disclosure relate to an isolated monoclonal anti-Siglec-7 antibody, wherein the anti-Siglec-7 antibody comprises a light chain variable domain and a heavy chain variable domain, wherein the light chain variable domain comprises: (a) an HVR-L1 comprising an amino acid sequence selected from SEQ ID NOs: 7-19 and 476, or an amino acid sequence with at least about 90% homology to an amino acid sequence selected from SEQ ID NOs: 7-19 and 476; (b) an HVR-L2 comprising an amino acid sequence selected from SEQ ID NOs: 20-32 and 477, or an amino acid sequence with at least about 90% homology to an amino acid sequence selected from SEQ ID NOs: 20-32 and 477; and (c) an HVR-L3 comprising an amino acid sequence selected from SEQ ID NOs: 33-45 and 478, or an amino acid sequence with at least about 90% homology to an amino acid sequence selected from SEQ ID NOs: 33-45 and 478; and/or wherein the heavy chain variable domain comprises: (a) an HVR-H1 comprising an amino acid sequence selected from SEQ ID NOs: 46-58 and 479, or an amino acid sequence with at least about 90% homology to an amino acid sequence selected from SEQ ID NOs: 46-58 and 479; (b) an HVR-H2 comprising an amino acid sequence selected from SEQ ID NOs: 59-71 and 480-482, or an amino acid sequence with at least about 90% homology to an amino acid sequence selected from SEQ ID NOs: 59-71 and 480-482; and (c) an HVR-H3 comprising an amino acid sequence selected from SEQ ID NOs: 72-84 and 483, or an amino acid sequence with at least about 90% homology to an amino acid sequence selected from SEQ ID NOs: 72-84 and 483.

In some embodiments that may be combined with any of the preceding embodiments, the antibody is of the IgG class, the IgM class, or the IgA class. In some embodiments that may be combined with any of the preceding embodiments, the anti-Siglec-7 antibody has an IgG1, IgG2, IgG3, or IgG4 isotype. In some embodiments that may be combined with any of the preceding embodiments, the antibody binds an inhibitory Fc receptor. In some embodiments that may be combined with any of the preceding embodiments, the inhibitory Fc receptor is inhibitory Fc-gamma receptor IIB (FcγIIB). In some embodiments that may be combined with any of the preceding embodiments: (a) the anti-Siglec-7 antibody has a human or mouse IgG1 isotype and comprises one or more amino acid substitutions in the Fc region at a residue position selected from: N297A, D265A, D270A, L234A, L235A, G237A, P238D, L328E, E233D, G237D, H268D, P271G, A330R, C226S, C229S, E233P, L234V, L234F, L235E, P331S, S267E, L328F, A330L, M252Y, S254T, T256E, N297Q, P238S, P238A, A327Q, A327G, P329A, K322A, T394D, and any combination thereof, wherein the numbering of the residues is according to EU or Kabat numbering, or comprises an amino acid deletion in the Fc region at a position corresponding to glycine 236; (b) the anti-Siglec-7 antibody has an IgG1 isotype and comprises an IgG2 isotype heavy chain constant domain 1(CH1) and hinge region, optionally wherein the IgG2 isotype CH1 and hinge region comprises the amino acid sequence of ASTKGPSVFP LAPCSRSTSE STAALGCLVK DYFPEPVTVS WNSGALTSGVHTFPAVLQSS GLYSLSSVVT VPSSNFGTQT YTCNVDHKPS NTKVDKTVERKCCVECPPCP (SEQ ID NO: 475), and optionally wherein the antibody Fc region comprises a S267E amino acid substitution, a L328F amino acid substitution, or both, and/or a N297A or N297Q amino acid substitution, wherein the numbering of the residues is according to EU numbering; (c) the anti-Siglec-7 antibody has an IgG2 isotype and comprises one or more amino acid substitutions in the Fc region at a residue position selected from: P238S, V234A, G237A, H268A, H268Q, V309L, A330S, P331S, C214S, C232S, C233S, S267E, L328F, M252Y, S254T, T256E, H268E, N297A, N297Q, A330L, and any combination thereof, wherein the numbering of the residues is according to EU or Kabat numbering; (d) the anti-Siglec-7 antibody has a human or mouse IgG4 isotype and comprises one or more amino acid substitutions in the Fc region at a residue position selected from: L235A, G237A, S228P, L236E, S267E, E318A, L328F, M252Y, S254T, T256E, E233P, F234V, L234A/F234A, S228P, S241P, L248E, T394D, N297A, N297Q, L235E, and any combination thereof, wherein the numbering of the residues is according to EU or Kabat numbering; or (e) the anti-Siglec-7 antibody has a hybrid IgG2/4 isotype, and optionally wherein the antibody comprises an amino acid sequence comprising amino acids 118 to 260 of human IgG2 and amino acids 261 to 447 of human IgG4, wherein the numbering of the residues is according to EU or, Kabat numbering. In some embodiments that may be combined with any of the preceding embodiments: (a) the anti-Siglec-7 antibody has a human or mouse IgG1 isotype and comprises one or more amino acid substitutions in the Fc region at a residue position selected from: N297A, N297Q, D270A, D265A, L234A, L235A, C226S, C229S, P238S, E233P, L234V, P238A, A327Q, A327G, P329A, K322A, L234F, L235E, P331S, T394D, A330L, M252Y, S254T, T256E, and any combination thereof, wherein the numbering of the residues is according to EU or Kabat numbering; (b) the anti-Siglec-7 antibody has an IgG2 isotype and comprises one or more amino acid substitutions in the Fc region at a residue position selected from: P238S, V234A, G237A, H268A, H268Q, H268E, V309L, N297A. N297Q, A330S, P331S, C232S, C233S, M252Y, S254T, T256E, and any combination thereof, wherein the numbering of the residues is according to EU or Kabat numbering; or (c) the anti-Siglec-7 antibody has an IgG4 isotype and comprises one or more amino acid substitutions in the Fc region at a residue position selected from: E233P, F234V, L234A/F234A, L235A, G237A, E318A, S228P. L236E, S241P, L248E, T394D, M252Y, S254T, T256E, N297A, N297Q, and any combination thereof, wherein the numbering of the residues is according to EU or Kabat numbering. In some embodiments that may be combined with any of the preceding embodiments: (a) the Fc region further comprises one or more additional amino acid substitutions at a position selected from A330L, L234F; L235E, P331S, and any combination thereof, wherein the numbering of the residues is according to EU or Kabat numbering; (b) the Fc region further comprises one or more additional amino acid substitutions at a position selected from M252Y, S254T, T256E, and any combination thereof, wherein the numbering of the residues is according to EU or Kabat numbering; or (c) the Fc region further comprises a S228P amino acid substitution according to EU or Kabat numbering. In some embodiments that may be combined with any of the preceding embodiments, the antibody has an IgG4 isotype. In some embodiments, the anti-Siglec-7 antibody comprises an S228P amino acid substitution at residue position 228, an F234A amino acid substitution at residue position 234, and an L235A amino acid substitution at residue position 235, wherein the numbering of the residue position is according to EU numbering. In some embodiments that may be combined with any of the preceding embodiments, the antibody has an IgG4 isotype and comprises an S228P amino acid substitution at residue position 228, an F234A amino acid substitution at residue position 234, and an L235A amino acid substitution at residue position 235, wherein the numbering of the residue position is according to EU numbering. In some embodiments that may be combined with any of the preceding embodiments, the Siglec-7 protein is a mammalian protein or a human protein. In some embodiments that may be combined with any of the preceding embodiments, the Siglec-7 protein is a wild-type protein. In some embodiments that may be combined with any of the preceding embodiments, the Siglec-7 protein is a naturally occurring variant. In some embodiments that may be combined with any of the preceding embodiments, the Siglec-7 protein is expressed on one or more cells selected from human dendritic cells, human macrophages, human neutrophils, human NK cells, human monocytes, human osteoclasts, human T cells, human T helper cell, human cytotoxic T cells, human granulocytes, and human microglia. In some embodiments that may be combined with any of the preceding embodiments, the anti-Siglec-7 antibody binds specifically to a mammalian Siglec-7 protein, human Siglec-7 protein, or both. In some embodiments that may be combined with any of the preceding embodiments, the anti-Siglec-7 antibody binds Siglec-7 in a pH dependent manner. In some embodiments that may be combined with any of the preceding embodiments, the anti-Siglec-7 antibody binds Siglec-7 at a pH that ranges from 5.5 to 8.0. In some embodiments that may be combined with any of the preceding embodiments, the anti-Siglec-7 antibody dissociates from Siglec-7 at a pH of less than 5.0. In some embodiments that may be combined with any of the preceding embodiments, the anti-Siglec-7 antibody is an antibody fragment that binds to an epitope comprising amino acid residues on human Siglec-7 or a mammalian Siglec-7 protein. In some embodiments that may be combined with any of the preceding embodiments, the anti-Siglec-7 antibody is an antibody fragment that binds to one or more human proteins selected from human Siglec-7, a naturally occurring variant of human Siglec-7, and a disease variant of human Siglec-7. In some embodiments that may be combined with any of the preceding embodiments, the antibody fragment is cross-linked to a second antibody fragment that binds to one or more human proteins selected from human Siglec-7, a naturally occurring variant of human Siglec-7, and a disease variant of human Siglec-7. In some embodiments that may be combined with any of the preceding embodiments, the fragment is an Fab, Fab', Fab'-SH, F(ab')2, Fv, or scFv fragment. In some embodiments that may be combined with any of the preceding embodiments, the anti-Siglec-7 antibody is a murine antibody. In some embodiments that may be combined with any of the preceding embodiments, the anti-Siglec-7 antibody is a humanized antibody, a bispecific antibody, a monoclonal antibody, a multivalent antibody, a conjugated antibody, or a chimeric antibody. In some embodiments that may be combined with any of the preceding embodiments, the anti-Siglec-7 antibody is a bispecific antibody recognizing a first antigen and a second antigen. In some embodiments that may be combined with any of the preceding embodiments, the first antigen is Siglec-7 and the second antigen is: (a) an antigen facilitating transport across the blood-brain-barrier; (b) an antigen facilitating transport across the blood-brain-barrier selected from transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM30(A), a protein transduction domain, TAT, Syn-B, penetratin, a poly-arginine peptide, an angiopep peptide, and ANG1005; (c) a disease-causing agent selected from disease-causing peptides or proteins or, disease-causing nucleic acids, wherein the disease-causing nucleic acids are antisense GGCCCC (G2C4) repeat-expansion RNA, the disease-causing proteins are selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products. DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; (d) ligands and/or proteins expressed on immune cells, wherein the ligands and/or proteins selected from PD1/PDL1, CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, and phosphatidylserine; and (e) a protein, lipid, polysaccharide, or glycolipid expressed on one or more tumor cells. In some embodiments that may be combined with any of the preceding embodiments, the anti-Siglec-7 antibody is a conjugated antibody. In some embodiments that may be combined with any of the preceding embodiments, the anti-Siglec-7 antibody is conjugated to a detectable marker, a toxin, or a therapeutic agent. In some embodiments that may be combined with any of the preceding embodiments, the anti-Siglec-7 antibody is conjugated to a toxin selected from ricin, ricin A-chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, and a cisplatin. In some embodiments that may be combined with any of the preceding embodiments, the anti-Siglec-7 antibody is used in combination with one or more antibodies that specifically bind a disease-causing agent selected from disease-causing peptides, disease-causing proteins, amyloid beta, oligomeric amyloid beta, amyloid beta plaques, amyloid precursor protein or fragments thereof, Tau. IAPP, alpha-synuclein, TDP-43, FUS protein, C9orf72 (chromosome 9 open reading frame 72), prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein. Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and any combination thereof; or with one or more antibodies that bind an immunomodulatory protein selected from: PD1/PDL1, CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, TREM1, TREM2, CD33, Siglec-5, Siglec-9, Siglec-11, phosphatidylserine, disease-causing nucleic acids, antisense GGCCCC (G2C4) repeat-expansion RNA, and any combination thereof. In some embodiments that may be combined with any of the preceding embodiments, the anti-Siglec-7 antibody has a dissociation constant ($K_D$) for human Siglec-7 and mammalian Siglec-7 that ranges from about 10 nM to about 10 pM, or less than 10 pM. In some embodiments, the dissociation constant ($K_D$) is determined at a temperature of approximately 25° C. In some embodiments that may be combined with any of the preceding embodiments, the anti-Siglec-7 antibody has a dissociation constant ($K_D$) for human Siglec-7 that ranges from about 9.5 nM to about 17 pM, or less than 17 pM. In some embodiments, the dissociation constant ($K_D$) is determined at a temperature of approximately 25° C. In some embodiments that may be combined with any of the preceding embodiments, the anti-Siglec-7 antibody binds to human dendritic cells with an $EC_{50}$ that ranges from 2 nM to 100 pM. In some embodiments that may be combined with any of the preceding embodiments, the anti-Siglec-7 antibody binds to human dendritic cells with an $EC_{50}$ that ranges from 1.4 nM to 300 pM. In some embodiments, the $EC_{50}$ for binding to human dendritic cells is determined at a temperature of approximately 4° C. In some embodiments that may be combined with any of the preceding embodiments, the anti-Siglec-7 antibody decreases cellular levels of Siglec-7 with an $EC_{50}$ that ranges from 500 pM to 18 pM. In some embodiments that may be combined with any of the preceding embodiments, the anti-Siglec-7 antibody decreases cellular levels of Siglec-7 with an $EC_5$ that ranges from 350 pM to 33 pM. In some embodiments, the $EC_{50}$ is determined at a temperature of approximately 37° C.

Other aspects of the present disclosure relate to an isolated nucleic acid comprising a nucleic acid sequence encoding the anti-Siglec-7 antibody of any of the preceding embodiments. Other aspects of the present disclosure relate to a vector comprising the nucleic acid of any of the preceding embodiments. Other aspects of the present disclosure relate to an isolated host cell comprising the vector of any of the preceding embodiments. Other aspects of the present disclosure relate to a method of producing an anti-Siglec-7 antibody, comprising culturing the host cell of any of the preceding embodiments so that the anti-Siglec-7 antibody is produced. In some embodiments, the method further comprises recovering the anti-Siglec-7 antibody produced by the host cell. Other aspects of the present disclosure relate to an isolated anti-Siglec-7 antibody produced by the method of any of the preceding embodiments. Other aspects of the present disclosure relate to a pharmaceutical composition comprising the anti-Siglec-7 antibody of any of the preceding embodiments, and a pharmaceutically acceptable carrier.

Other aspects of the present disclosure relate to a method of preventing, reducing risk, or treating a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis. Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, tumors that express one or more Siglec-7 ligands, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza, comprising administering to an individual in need thereof a therapeutically effective amount of an agent that decreases cellular levels of Siglec-7, inhibits interaction between Siglec-7 and one or more Siglec-7 ligands, or both. In some embodiments, the cancer is selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), and multiple myeloma. Other aspects of the present disclosure relate to an agent that decreases cellular levels of Siglec-7, inhibits interaction between Siglec-7 and one or more Siglec-7 ligands, or both for use in preventing, reducing risk, or treating a disease, disorder, or injury selected from dementia, frontotemporal dementia, Alzheimer's disease, vascular dementia, mixed dementia Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy. Shy-Drager syndrome, progressive supranuclear palsy, conical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, tumors that express one or more Siglec-7 ligands, thyroid cancer, infections, CNS herpes, parasitic infections. Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza. Other aspects of the present disclosure relate to use of an agent that decreases cellular levels of Siglec-7, inhibits interaction between Siglec-7 and one or more Siglec-7 ligands, or both in the manufacture of a medicament for preventing, reducing risk, or treating a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus. Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, tumors that express one or more Siglec-7 ligands, thyroid cancer, infections, CNS herpes, parasitic infections. Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type 1 HIV, and *Haemophilus* influenza. In some embodiments, the agent is selected from an antibody, a soluble Siglec-7 receptor, a Siglec-7-Fc fusion protein, a Siglec-7 immunoadhesin, an antisense molecule, an siRNA, a small molecule inhibitor, a protein, and a peptide. In some embodiments, the agent is an isolated anti-Siglec-7 antibody. In some embodiments, the anti-Siglec-7 antibody is the anti-Siglec-7 antibody of any of the preceding embodiments. In some embodiments, the one or more immune cells are selected from dendritic cells, macrophages, neutrophils, NK cells, microglia, T cells, T helper cells, cytotoxic T cells, and any combination thereof. Other aspects of the present disclosure relate to a method of preventing, reducing risk, or treating a disease, disorder, or injury selected from dementia, frontotemporal dementia, Alzheimer's disease, vascular dementia, mixed dementia, taupathy disease, infections, and cancer, comprising administering to an individual in need thereof a therapeutically effective amount of an agent that decreases cellular levels of Siglec-7, inhibits interaction between Siglec-7 and one or more Siglec-7 ligands, or both. Other aspects of the present disclosure relate to an agent that decreases cellular levels of Siglec-7, inhibits interaction between Siglec-7 and one or more Siglec-7 ligands, or both for use in preventing, reducing risk, or treating a disease, disorder, or injury selected from dementia, frontotemporal dementia, Alzheimer's disease, vascular dementia, mixed dementia, taupathy disease, infections, and cancer. Other aspects of the present disclosure relate to use of an agent that decreases cellular levels of Siglec-7, inhibits interaction between Siglec-7 and one or more Siglec-7 ligands, or both in the manufacture of a medicament for preventing, reducing risk, or treating a disease, disorder, or injury selected from dementia, frontotemporal dementia, Alzheimer's disease, vascular dementia, mixed dementia, taupathy disease, infections, and cancer.

In some embodiments that may be combined with any of the preceding embodiments, the disease, disorder, or injury is cancer, and wherein the agent inhibits one or more Siglec-7 activities selected from: (a) promoting proliferation, maturation, migration, differentiation, and/or functionality of one or more of immunosuppressor dendritic cells, immunosuppressor macrophages, immunosuppressor neutrophils, immunosuppressor NK cells, myeloid derived suppressor cells, tumor-associated macrophages, tumor-associated suppressor neutrophils, tumor-associated suppressor NK cells, and regulatory T cells; (b) enhancing infiltration of one or more of immunosuppressor dendritic cells, immunosuppressor macrophages, immunosuppressor neutrophils, immunosuppressor NK cells, myeloid derived suppressor cells, tumor-associated macrophages, tumor-associated suppressor neutrophils, tumor-associated suppressor NK cells, and regulatory T cells into tumors; (c) increasing number of tumor-promoting myeloid/granulocytic immune-suppressive cells in a tumor, in peripheral blood, or other lymphoid organ; (d) enhancing tumor-promoting activity of myeloid-derived suppressor cells (MDSC); (e) increasing expression of tumor-promoting cytokines in a tumor or in peripheral blood, optionally wherein the tumor-promoting cytokines are TGF-beta or IL-10; (f) increasing tumor infiltration of tumor-promoting FoxP3+ regulatory T lymphocytes; (g) decreasing activation of tumor-specific T lymphocytes with tumor killing potential; (h) decreasing infiltration of tumor-specific T lymphocytes with tumor killing potential; (i) decreasing infiltration of tumor-specific NK cells with tumor killing potential; (j) decreasing the tumor killing potential of NK cells; (k) decreasing infiltration of tumor-specific B lymphocytes with potential to enhance immune response; (l) increasing tumor volume; (m) increasing tumor growth rate; (n) increasing metastasis; (o) increasing rate of tumor recurrence; (p) decreasing efficacy of one or more immune-therapies that modulate anti-tumor T cell responses, optionally wherein the one or more immune-therapies are immune-therapies that target one or more target proteins selected from PD1/PDL1, CTLA4, CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG. DR-5, and any combination thereof, or one or more cancer vaccines; (q) inhibition of PLCγ/PKC/calcium mobilization; and (r) inhibition of PI3K/Akt, Ras/MAPK signaling. In some embodiments that may be combined with any of the preceding embodiments, the cancer expresses Siglec-7 or one or more Siglec-7 ligands. In some embodiments that may be combined with any of the preceding embodiments, the cancer is selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), and multiple myeloma. In some embodiments that may be combined with any of the preceding embodiments, the agent exhibits one or more activities selected from the group consisting of: (a) increasing the number of tumor infiltrating $CD3^+$ T cells; (b) inhibiting Siglec-7 binding to one or more Siglec-7 ligands; (c) decreasing cellular levels of Siglec-7 in peripheral immune cells; (d) reducing the number of non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in blood; (e) reducing the number of non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in the tumor, (f) reducing PD-L1 levels in one or more cells, optionally wherein the one or more cells are non-tumorigenic myeloid-derived suppressor cells (MDSC); (g) reducing PD-L2 levels in one or more cells, optionally wherein the one or more cells are non-tumorigenic myeloid-derived suppressor cells (MDSC); (h) reducing CD11b levels in one or more cells, optionally wherein the one or more cells are non-tumorigenic myeloid-derived suppressor cells (MDSC); (i) reducing B7-H3 levels in one or more cells, optionally wherein the one or more cells are non-tumorigenic myeloid-derived suppressor cells (MDSC); (j) reducing CD200R levels in one or more cells, optionally wherein the one or more cells are non-tumorigenic myeloid-derived suppressor cells (MDSC); (k) reducing CD163 levels in one or more cells, optionally wherein the one or more cells are non-tumorigenic myeloid-derived suppressor cells (MDSC); (l) reducing CD206 levels in one or more cells, optionally wherein the one or more cells are non-tumorigenic myeloid-derived suppressor cells (MDSC); (m) decreasing tumor growth rate of solid tumors; (n) reducing tumor volume; (o) increasing efficacy of one or more PD-1 inhibitors; (p) increasing efficacy of one or more checkpoint inhibitor therapies and/or immune-modulating therapies, optionally wherein the one or more checkpoint inhibitor therapies and/or immune-modulating therapies target one or more of CTL4, the adenosine pathway, PD-L1, PD-L2, OX40, TIM3, LAG3, or any combination thereof; (q) inhibiting differentiation, survival, and/or one or more functions of non-tumorigenic myeloid-derived suppressor cells (MDSC); (r) inducing cell death of one or more myeloid-derived suppressor cells (MDSC); and (s) increasing proliferation of T cells in the presence of non-tumorigenic myeloid-derived suppressor cells (MDSC).

Other aspects of the present disclosure relate to a method of inducing or promoting the survival, maturation, functionality, migration, or proliferation of one or more immune cells in an individual in need thereof, comprising administering to the individual a therapeutically effective amount of an agent that that decreases cellular levels of Siglec-7, inhibits interaction between Siglec-7 and one or more Siglec-7 ligands, or both. Other aspects of the present disclosure relate to an agent that decreases cellular levels of Siglec-7, inhibits interaction between Siglec-7 and one or more Siglec-7 ligands, or both for use in inducing or promoting the survival, maturation, functionality, migration, or proliferation of one or more immune cells in an individual in need thereof. Other aspects of the present disclosure relate to use of an agent that decreases cellular levels of Siglec-7, inhibits interaction between Siglec-7 and one or more Siglec-7 ligands, or both in the manufacture of a medicament for inducing or promoting the survival, maturation, functionality, migration, or proliferation of one or more immune cells in an individual in need thereof. In some embodiments, the agent is selected from an antibody, a soluble Siglec-7 receptor, a Siglec-7-Fc fusion protein, a Siglec-7 immunoadhesin, an antisense molecule, an siRNA, a small molecule inhibitor, a protein, and a peptide. In some embodiments, the agent is an isolated anti-Siglec-7 antibody. In some embodiments, the anti-Siglec-7 antibody is the anti-Siglec-7 antibody of any of the preceding embodiments. In some embodiments, the one or more immune cells are selected from dendritic cells, macrophages, neutrophils, NK cells, microglia, T cells, T helper cells, cytotoxic T cells, and any combination thereof.

Other aspects of the present disclosure relate to a method of decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, or chronic myeloid leukemia (CML) cells in an individual in need thereof, comprising administering to the individual a therapeutically effective amount of an agent that binds or interacts with Siglec-7. Other aspects of the present disclosure relate to use of an agent that binds or interacts with Siglec-7 for use in decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, or chronic myeloid leukemia (CML) cells in an individual in need thereof. Other aspects of the present disclosure relate to use of an agent that binds or interacts with Siglec-7 in the manufacture of a medicament for decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, or chronic myeloid leukemia (CML) cells in an individual in need thereof. In some embodiments, the e agent is an isolated anti-Siglec-7 antibody or anti-Siglec-7 antibody conjugate. In some embodiments, the anti-Siglec-7 antibody is the anti-Siglec-7 antibody of any of the preceding embodiments.

Other aspects of the present disclosure relate to a method of decreasing cellular levels of Siglec-7 on one or more cells in an individual in need thereof, comprising administering to the individual a therapeutically effective amount of an isolated anti-Siglec-7 antibody. Other aspects of the present disclosure relate to use of an isolated anti-Siglec-7 antibody for use in decreasing cellular levels of Siglec-7 on one or more cells in an individual in need thereof. Other aspects of the present disclosure relate to use of an isolated anti-Siglec-7 antibody in the manufacture of a medicament for decreasing cellular levels of Siglec-7 on one or more cells in an individual in need thereof. In some embodiments, the anti-Siglec-7 antibody decreases cellular levels of Siglec-7 in vivo. In some embodiments, the anti-Siglec-7 antibody decreases cellular levels of Siglec-7 with an $EC_{50}$ that ranges from 500 pM to 18 pM. In some embodiments, the anti-Siglec-7 antibody decreases cellular levels of Siglec-7 with an $EC_{50}$ that ranges from 350 pM to 33 pM. In some embodiments, the $EC_{50}$ is determined at a temperature of approximately 37° C. In some embodiments, the anti-Siglec-7 antibody has a dissociation constant ($K_D$) for human Siglec-7 that ranges from about 10 nM to 10 pM, or less than 10 pM. In some embodiments that may be combined with any of the preceding embodiments, the anti-Siglec-7 antibody has a dissociation constant ($K_D$) for human Siglec-7 that ranges from about 9.5 nM to about 17 pM, or less than 17 pM. In some embodiments, the dissociation constant ($K_D$) is determined at a temperature of approximately 25° C. In some embodiments, the anti-Siglec-7 antibody binds to human dendritic cells with an $EC_{50}$ that ranges from 2 nM to 100 pM. In some embodiments that may be combined with any of the preceding embodiments, the anti-Siglec-7 antibody binds to human dendritic cells with an $EC_{50}$ that ranges from 1.4 nM to 300 pM. In some embodiments, the an $EC_{50}$ for binding to human dendritic cells is determined at a temperature of approximately 4° C. In some embodiments, the anti-Siglec-7 antibody is the anti-Siglec-7 antibody of any of the preceding embodiments.

In some embodiments that may be combined with any of the preceding embodiments, the method further comprising administering to the individual at least one antibody that specifically binds to an inhibitory checkpoint molecule, and/or one or more standard or investigational anti-cancer therapies. In some embodiments that may be combined with any of the preceding embodiments, the at least one antibody that specifically binds to an inhibitory checkpoint molecule is administered in combination with the anti-Siglec-7 antibody. In some embodiments that may be combined with any of the preceding embodiments, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, an anti-TNFa antibody,
an anti-CD33 antibody, an anti-Siglec-5 antibody, an anti-Siglec-9 antibody, an anti-Siglec-11 antibody, an antagonistic anti-TREM1 antibody, an antagonistic anti-TREM2 antibody, and any combination thereof. In some embodiments that may be combined with any of the preceding embodiments, the one or more standard or investigational anti-cancer therapies are selected from radiotherapy, cytotoxic chemotherapy, targeted therapy, imatinib therapy, trastuzumab therapy, etanercept therapy, adoptive cell transfer (ACT) therapy, chimeric antigen receptor T cell transfer (CAR-T) therapy, vaccine therapy, and cytokine therapy. In some embodiments that may be combined with any of the preceding embodiments, the method further comprising administering to the individual at least one antibody that specifically binds to an inhibitory cytokine. In some embodiments that may be combined with any of the preceding embodiments, the at least one antibody that specifically binds to an inhibitory cytokine is administered in combination with the anti-Siglec-7 antibody. In some embodiments that may be combined with any of the preceding embodiments, the at least one antibody that specifically binds to an inhibitory cytokine is selected from an anti-CCL2 antibody, an anti-CSF-1 antibody, an anti-IL-2 antibody, and any combination thereof. In some embodiments that may be combined with any of the preceding embodiments, the method further comprising administering to the individual at least one agonistic antibody that specifically binds to a stimulatory checkpoint protein. In some embodiments that may be combined with any of the preceding embodiments, the at least one agonistic antibody that specifically binds to a stimulatory checkpoint protein is administered in combination with the anti-Siglec-7 antibody. In some embodiments that may be combined with any of the preceding embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonistic anti-TREM1 antibody, an agonistic anti-TREM2 antibody, an agonist anti-CD137/4-1BB antibody, an agonist anti-CD27 antibody, an agonist anti-glucocorticoid-induced TNFR-related protein GITR antibody, and any combination thereof. In some embodiments that may be combined with any of the preceding embodiments, the method further comprising administering to the individual at least one stimulatory cytokine. In some embodiments that may be combined with any of the preceding embodiments, the at least one stimulatory cytokine is administered in combination with the anti-Siglec-7 antibody. In some embodiments that may be combined with any of the preceding embodiments, the at least one stimulatory cytokine is selected from IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, MCP-1, MIP-1-beta, and any combination thereof.

Other aspects of the present disclosure relate to a method of assessing responsiveness of an individual to an agent that binds or interacts with Siglec-7, the method comprising: a) measuring the expression levels of $CD45^+$ and $CD14^+$ on non-tumorigenic myeloid cells in a blood sample obtained from the individual prior to administering to the individual an agent that binds or interacts with Siglec-7; b) administering to the individual a therapeutically effective amount of the agent; and c) measuring the expression levels of $CD45^+$ and $CD14^+$ on non-tumorigenic myeloid cells in a blood sample obtained from the individual after administration of the agent. In some embodiments, a reduction in the levels of $CD45^+$ and $CD14^+$ on non-tumorigenic myeloid cells after administration of the agent that binds or interacts with Siglec-7 indicates the individual is responsive to the agent. In some embodiments, the method further comprises administering one or more additional therapeutically effective amounts of the agent. In some embodiments, the agent is selected from the group consisting of an antibody, a soluble Siglec-7 receptor, a Siglec-7-Fc fusion protein, a Siglec-7 immunoadhesin, an antisense molecule, an siRNA, a small molecule inhibitor, a protein, and peptide. In some embodiments, the agent is an isolated anti-Siglec-7 antibody or anti-Siglec-7 antibody-conjugate. In some embodiments, the anti-Siglec-7 antibody is any of the anti-Siglec-7 antibodies disclosed herein.

BRIEF DESCRIPTION OF THE DRAWINGS

FIG. 1A depicts an amino acid sequence alignment between human Siglec-7 (SEQ ID NO: 1), chimpanzee Siglec-7 (SEQ ID NO: 2), pygmy chimpanzee Siglec-7 (SEQ ID NO: 3), orangutan Siglec-7 (SEQ ID NO: 4), gorilla Siglec-7(SEQ ID NO: 5), and gibbon Siglec-7 (SEQ ID NO: 6). An asterisk ("*") indicates positions which have a single, fully conserved residue; A colon (":") indicates conservation between groups of strongly similar properties—scoring >0.5 in the Gonnet PAM 250 matrix; and a period (".") indicates conservation between groups of weakly similar properties—scoring=<0.5 in the Gonnet PAM 250 matrix.

FIG. 1F depicts binding reactivity in percentage to wild-type Siglec-7 (% WT) of antibodies of the present disclosure to the indicated Siglec-7 mutants.

FIG. 6B shows a schematic for combining antibody light chain variable region (VL) sequences of humanized versions of anti-Siglec-7 antibody 4E3 (mAb S7-4E3). Additionally variations are listed below each sequence. The figure includes sequences for versions of humanized antibody 4E3. IGKV3-11*01 (SEQ ID NO: 497); Joining region (SEQ ID NO: 498); S7-4E3 (SEQ ID NO: 499); 3-11*01 (SEQ ID NO: 500); h4E3-L1 (SEQ ID NO: 501); h4E3-L2 (SEQ ID NO: 502); h4E3-L3 (SEQ ID NO: 503). FIG. 6C shows a schematic for combining antibody heavy chain variable region (VH) sequences of humanized versions of anti-Siglec-7 antibody 4E3 (mAb S7-4E3). Additional variations are listed below each sequence. The figure includes sequences for versions of humanized antibody 4E3. IGHV3-21*01 (SEQ ID NO: 504); Joining region (SEQ ID NO: 505); S7-4E3 (SEQ ID NO: 506); 3-21'01 (SEQ ID NO: 507); h4E3-H1 (SEQ ID NO: 508); h4E3-H2 (SEQ ID NO: 509); h4E3-H3 (SEQ ID NO: 510). FIG. 6D shows a schematic for combining antibody light chain variable region (VL) sequences of humanized versions of anti-Siglec-7 antibody 10B5 (mAb S7-10B5). Additional variations are listed below each sequence. The figure includes sequences for versions of humanized antibody 10B5. IGKV1-39*01 (SEQ ID NO: 511); Joining region (SEQ ID NO: 512); S7-10B5.1 (SEQ ID NO: 513); 1-39*01 (SEQ ID NO: 514); h10B5-L1 (SEQ ID NO: 515); h10B5-L2 (SEQ ID NO: 516); h10B5-L3 (SEQ ID NO: 517). FIG. 6E shows a schematic for combining antibody heavy chain variable region (VH) sequences of humanized versions of anti-Siglec-7 antibody 10B5 (mAb S7-10B5). Additional variations are listed below each sequence. The figure includes sequences for versions of humanized antibody 10B5, IGHV1-46*01 (SEQ ID NO: 518); Joining region (SEQ ID NO: 519); S7-10B5.1 (SEQ ID NO: 520); 1-46*01 (SEQ ID NO: 521); h10B5-H1 (SEQ ID NO: 522); h10B5-H2 (SEQ ID NO: 523); h10B5-H3 (SEQ ID NO: 524); h10B5-H4 (SEQ ID NO: 525). For FIG. 6B-6E, CDR sequences are depicted in bold; residue numbering shown as sequential (seq) or according to Chothia; "b" refers to buried sidechain; "p" refers to partially buried; "i" refers to sidechain at interface between VH and VL domains; sequence differences between human and murine germlines are noted by an asterisk (*); potential additional mutations in frameworks are noted below the sequence; potential changes in CDR sequences are noted below each CDR sequence (such changes may prevent asparagine (N) deamidation, tryptophan (W) oxidation, or iso aspartate (DG) formation).

FIG. 7A depicts U937 histiocytic lymphoma. FIG. 7N depicts a 12-point titration curve showing the half-maximal effective concentration ($EC_{50}$) of Siglec-7 antibodies 4E3 and 10B5 for reducing cell surface expression of CD11c.

FIGS. 11A and 11B depict results showing Siglec-7 receptor and increased Siglec-7 ligand expression on human primary dendritic cells after treatment with tumor supernatant. FIGS. 11C and 11D depict results showing increased Siglec-7 ligand expression on human primary dendritic cells after treatment with tumor supernatant. FIGS. 11E and 11F depict results showing Siglec-7 receptor expression on human dendritic cells during LPS-induced inflammation. FIGS. 11G and 11H depict results showing an increase in sialic acid expression on human myeloid cells during LPS-induced inflammation. These finding indicate that tumors can evade immune surveillance by upregulating the level of inhibitory ligands to Siglec-7 on the tumor cells and on immune cells.

FIG. 13A depicts immunohistochemistry staining of Siglec-7-Fc in AD and non-AD brain samples from two donors (Donor 1 and Donor 2). FIG. 13B depicts results of one-way ANOVA statistical analysis of Siglec-7-Fc staining from 5 AD and 5 non-AD brain samples, indicating that inhibitory Siglec-7 ligand is upregulated and contributes to AD pathology.

DETAILED DESCRIPTION OF THE INVENTION

General Techniques

Figure 1B:
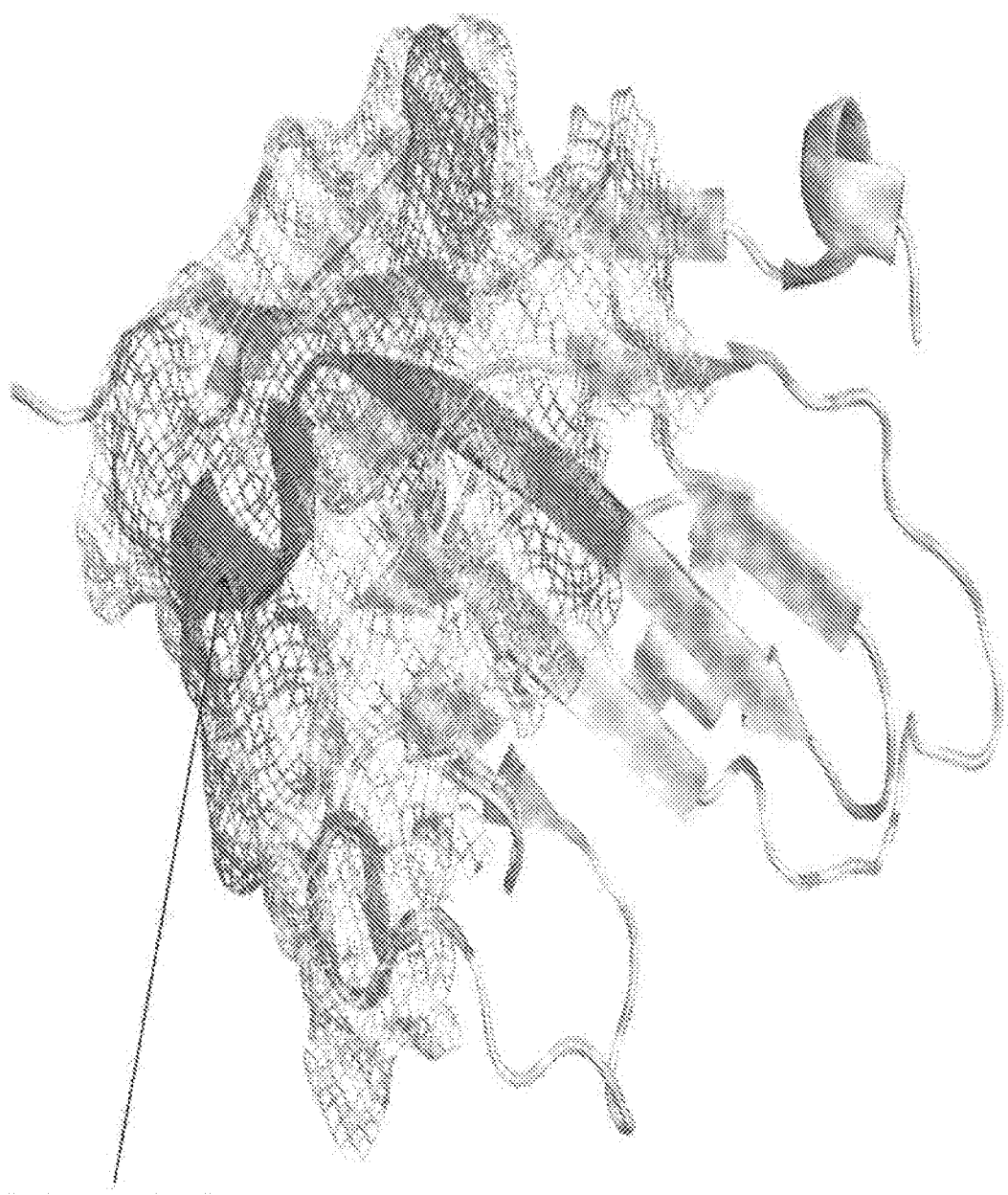
FIG. 1B depicts the 3D structure of Siglec-7. Amino acid residues 19-150 of the Siglec-7 amino acid sequence of SEQ ID NO: 1 are depicted in a cartoon representation. Also depicted is a cartoon rendering of an epitope for antibody 4A1. The binding region $^{113}$ARMS-DAGRYFFRM$^{125}$ (SEQ ID NO: 1) is listed in the figure. The protein surface of Siglec-7 is shown as mesh.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor. N.Y.; *Current Protocols in Molecular Biology* (F. M. Ausubel, et al. eds., (2003)); the series *Methods in Enzymology* (Academic Press. Inc.): PCR 2: A Practical Approach (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols Immunology* (J. E. Coligan et al., eds., 1991); *Short Protocols in Molecular Biology* (Wiley and Sons, 1999); *Immunobiology* (C. A. Janeway and P. Travers, 1997), Antibodies (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

Definitions

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved A "therapeutically effective amount" is at least the minimum concentration required to effect a measurable improvement of a particular disease, disorder, or condition. A therapeutically effective amount herein may vary according to factors such as the disease state, age, sex, and weight of the patient, and the ability of the Siglec-7 protein antagonist to elicit a desired response in the individual. A therapeutically effective amount is also one in which any toxic or detrimental effects of the Siglec-7 protein antagonist are outweighed by the therapeutically beneficial effects.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Preferably, the individual is human.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., *Basic and Clinical Immunology*. 8th Ed., Daniel P. Stites, Abba I. Terr and Tristram G. Parslow (eds.). Appleton & Lange, Norwalk, Conn., 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA. IgD. IgE, IgG, and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., *Cellular and Molecular Immunology*, $4^{th}$ ed. (W.B. Saunders Co., 2000).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated" antibody, such as an anti-Siglec-7 antibody of the present disclosure, is one that has been identified, separated and/or recovered from a component of its production environment (e.g., naturally or recombinantly). Preferably, the isolated polypeptide is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified; (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T cells since at least one component of the antibody's natural environment will not be present. Ordinarily, however, an isolated polypeptide or antibody will be prepared by at least one purification step.

The "variable region" or "variable domain" of an antibody, such as an anti-Siglec-7 antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-Siglec-7 antibodies of the present disclosure. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as an anti-Siglec-7 antibody of the present disclosure, obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against one or more antigenic sites. In some embodiments, a monoclonal antibody of the present disclosure can be a bispecific antibody. In contrast to polyclonal antibody preparations which typically include different antibodies directed against different determinants (epitopes), each monoclonal antibody is directed against a single determinant on the one or more antigenic sites. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, phage-display technologies (see, e.g., Clackson et al., *Nature*, 352:624-628 (1991); Marks et al., *J. Mol. Biol.* 222:581-597 (1992); Sidhu et al., *J. Mol. Biol.* 338(2); 299-310 (2004); Lee et al., *J. Mol. Biol.* 340(5):1073-1093 (2004); Fellouse. *Proc. Nat'l Acad. Sci. USA* 101(34):12467-472 (2004); and Lee et al., *J. Immunol. Methods* 284(1-2):119-132 (2004), the hybridoma method (e.g., Kohler and Milstein., *Nature*, 256:495-97 (1975); Hongo et al., *Hybridoma*, 14 (3):253-260 (1995), Harlow et al., *Antibodies: A Laboratory Manual*, (Cold Spring Harbor Laboratory Press, 2d ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Nat'l Acad Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,807; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

The terms "full-length antibody," "intact antibody" or "whole antibody" are used interchangeably to refer to an antibody, such as an anti-Siglec-7 antibody of the present disclosure, in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-Siglec-7 antibodies of the present disclosure, produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of antibodies, such as anti-Siglec-7 antibodies of the present disclosure, comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Nat'l Acad. Sci. USA* 90:6444-48 (1993).

As used herein, a "chimeric antibody" refers to an antibody (immunoglobulin), such as an anti-Siglec-7 antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l Acad Sci. USA.* 81:6851-55 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as anti-Siglec-7 antibodies of the present disclosure, are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, and the like. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example. Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one that possesses an amino-acid sequence corresponding to that of an antibody, such as an anti-Siglec-7 antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al., *J. Mol. Biol.,* 222:581 (1991). Also available for the preparation of human monoclonal antibodies are methods described in Cole et al., *Monoclonal Antibodies and Cancer Therapy.* Alan R. Liss, p. 77 (1985); Boerner et al., *J. Immunol.,* 147(1):86-95 (1991). See also van Dijk and van de Winkel, *Curr. Opin. Pharmacol.* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Nat'l Acad. Sci. USA.* 103:3557-3562 (2006) regarding human antibodies generated via a human B-cell hybridoma technology.

The term "hypervariable region," "HVR," or "HV," when used herein refers to the regions of an antibody-variable domain, such as that of an anti-Siglec-7 antibody of the present disclosure, that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu in *Methods in Molecular Biology* 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. The HVRs that are EU or Kabat complementarity-determining regions (CDRs) are based on sequence variability and are the most commonly used (Kabat et al., supra). Chothia refers instead to the location of the structural loops (Chothia and Lesk. *J. Mol. Biol.* 196:901-917 (1987)). The AbM HVRs represent a compromise between the EU or Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to EU or Kabat et al., supra, for each of these extended-HVR definitions.

"Framework" or "FR" residues are those variable-domain residues other than the HVR residues as herein defined.

The phrase "variable-domain residue-numbering as in EU or Kabat" or "amino-acid-position numbering as in EU or Kabat," and variations thereof, refers to the numbering system used for heavy-chain variable domains or light-chain variable domains of the compilation of antibodies in EU or Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The EU or Kabat numbering of residues may be determined for a given antibody by alignment at regions of homology of the sequence of the antibody with a "standard" Kabat numbered sequence.

The EU or Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU or Kabat numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU or Kabat numbering system (e.g., see United States Patent Publication No. 2010-280227).

An "acceptor human framework" as used herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the VL human immunoglobulin framework sequence or human consensus framework sequence.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* 5th Ed. Public Health Service, National Institutes of Health. Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra.

An "amino-acid modification" at a specified position, e.g., of an anti-Siglec-7 antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody, such as an anti-Siglec-7 antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and $V_L$-domain shuffling. Random mutagenesis of HVR and/or framework residues is described by, for example: Barbas et al. *Proc Nat. Acad. Sci. USA* 91:3809-3813 (1994), Schier et al. *Gene* 169:147-155 (1995); Yelton et al. *J. Immunol.* 155:1994-2004 (1995); Jackson et al., *J. Immunol.* 154(7):3310-9 (1995); and Hawkins et al. *J. Mol. Biol.* 226:889-896 (1992).

As use herein, the term "specifically recognizes" or "specifically binds" refers to measurable and reproducible interactions such as attraction or binding between a target and an antibody, such as an anti-Siglec-7 antibody of the present disclosure, that is determinative of the presence of the target in the presence of a heterogeneous population of molecules including biological molecules. For example, an antibody, such as an anti-Siglec-7 antibody of the present disclosure, that specifically or preferentially binds to a target or an epitope is an antibody that binds this target or epitope with greater affinity, avidity, more readily, and/or with greater duration than it binds to other targets or other epitopes of the target. It is also understood by reading this definition that, for example, an antibody (or a moiety) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ $M^{-1}$ or $10^4$ $M^{-1}$, sometimes about $10^5$ $M^{-1}$ or $10^6 M^{-1}$, in other instances about $10^6$ $M^{-1}$ or $10^7$ $M^{-1}$, about $10^8$ $M^{-1}$ to $10^9$ $M^{-1}$, or about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, an "interaction" between a Siglec-7 protein and a second protein encompasses, without limitation, protein-protein interaction, a physical interaction, a chemical interaction, binding, covalent binding, and ionic binding. As used herein, an antibody "inhibits interaction" between two proteins when the antibody disrupts, reduces, or completely eliminates an interaction between the two proteins. An antibody of the present disclosure, or fragment thereof, "inhibits interaction" between two proteins when the antibody or fragment thereof binds to one of the two proteins.

An "agonist" antibody or an "activating" antibody is an antibody, such as an agonist anti-Siglec-7 antibody of the present disclosure, that induces (e.g., increases) one or more activities or functions of the antigen after the antibody binds the antigen.

A "blocking" antibody, an "antagonist" antibody, or an "inhibitory" antibody is an antibody, such as an anti-Siglec-7 antibody of the present disclosure, that inhibits or reduces (e.g., decreases) antigen binding to one or more ligand after the antibody binds the antigen, and/or that inhibits or reduces (e.g., decreases) one or more activities or functions of the antigen after the antibody binds the antigen. In some embodiments, blocking antibodies, antagonist antibodies, or inhibitory antibodies substantially or completely inhibit antigen binding to one or more ligand and/or one or more activities or functions of the antigen.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU or Kabat numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. (see, e.g., M. Daëron, *Annu. Rev. Immunol.* 15:203-234 (1997)). FcRs are reviewed in Ravetch and Kinet. *Annu. Rev. Immunol.* 9:457-92 ($1^991$); Capel et al., *Immunomethods* 4:25-34 (1994); and de Haas et al., *J. Lab. Clin. Med.* 126: 330-41 (1995). Other FcRs, including those to be identified in the future, are encompassed by the term "FcR" herein. FcRs can also increase the serum half-life of antibodies.

Binding to FcRn in viva and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants with improved or diminished binding to FcRs. See also, e.g., Shields et al., *J. Biol. Chem.* 9(2):6591-6604 (2001).

As used herein. "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full length of the sequences being compared.

An "isolated" cell is a molecule or a cell that is identified and separated from at least one contaminant cell with which it is ordinarily associated in the environment in which it was produced. In some embodiments, the isolated cell is free of association with all components associated with the production environment. The isolated cell is in a form other than in the form or setting in which it is found in nature. Isolated cells are distinguished from cells existing naturally in tissues, organs, or individuals. In some embodiments, the isolated cell is a host cell of the present disclosure.

An "isolated" nucleic acid molecule encoding an antibody, such as an anti-Siglec-7 antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide." or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O- methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of the present disclosure.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

As used herein, the term "apoptosis" refers to gene-directed process of intracellular cell destruction. Apoptosis is distinct from necrosis; it includes cytoskeletal disruption, cytoplasmic shrinkage and condensation, expression of phosphatidylserine on the outer surface of the cell membrane and blebbing, resulting in the formation of cell membrane bound vesicles or apoptotic bodies. The process is also referred to as "programmed cell death." During apoptosis, characteristic phenomena such as curved cell surfaces, condensation of nuclear chromatin, fragmentation of chromosomal DNA, and loss of mitochondrial function are observed. Various known technologies may be used to detect apoptosis, such as staining cells with Annexin V, propidium iodide, DNA fragmentation assay and YO-PRO-1 (Invitrogen). In some embodiments, staining with Annexin V and propidium iodide may be used, and the combined percentages of the Annexin V+/PI+, Annexin V+/PI− and Annexin V−/PI+ populations are considered as dead cells.

As used herein, the term "agent that decreases cellular levels of Siglec-7, inhibits interaction between Siglec-7 and one or more Siglec-7 ligands, or both" refers to a molecule that reduces (including significantly), decreases, blocks, inhibits, or interferes with a Siglec-7 (mammalian, such as a human Siglec-7) biological activity in vitro, in situ, and/or in vivo. The term "agent" implies no specific mechanism of biological action whatsoever, and expressly includes and encompasses all possible pharmacological, physiological, and biochemical interactions with a Siglec-7 whether direct or indirect, and whether interacting with a Siglec-7, one or more of its ligands, or through another mechanism, and its consequences which can be achieved by a variety of different, and chemically divergent, compositions. Exemplary agents include, without limitation, an anti-Siglec-7 antibody that specifically binds to a Siglec-7, a soluble Siglec-7 receptor protein, a soluble Siglec-7-Fc fusion protein (e.g., Siglec-7 immunoadhesin), a soluble Siglec receptor that binds to a Siglec-7 ligand, a Siglec-Fc fusion protein (e.g., Siglec immunoadhesin) that binds to a Siglec-7 ligand, an anti-sense molecule directed to a nucleic acid encoding a Siglec-7, a short interfering RNA ("siRNA") molecule directed to a nucleic acid encoding a Siglec-7, a Siglec-7 inhibitory compound, an RNA or DNA aptamer that binds to a Siglec-7, and a Siglec-7 structural analog. In some embodiments, a Siglec-7 inhibitor (e.g., an antibody) binds (physically interacts with) an agent that decreases cellular levels of Siglec-7, inhibits interaction between Siglec-7 and one or more Siglec-7 ligands, or both, binds to a Siglec-7 ligand, and/or inhibits (reduces) Siglec-7 synthesis or production. In other embodiments, an agent of the present disclosure inhibitor binds a Siglec-7 and prevents its binding to one or more of its ligands. In still other embodiments, an agent of the present disclosure reduces or eliminates expression (i.e., transcription or translation) of a Siglec-7. Examples of types of agent that decreases cellular levels of Siglec-7, inhibits interaction between Siglec-7 and one or more Siglec-7 ligands, or both are provided herein.

As used herein, the term "agent that binds or interacts with Siglec-7" refers to a molecule that either directly or indirectly interacts with a Siglec-7 protein. The term "agent" implies no specific mechanism of biological action whatsoever, and expressly includes and encompasses all possible pharmacological, physiological, and biochemical interactions with a Siglec-7 whether direct or indirect and whether interacting with a Siglec-7 or through another mechanism, and its consequences which can be achieved by a variety of different, and chemically divergent, compositions. Exemplary agents include, without limitation, an anti-Siglec-7 antibody that specifically binds to a Siglec-7.

As used herein, the term "RNA interference" or "RNAi" refers generally to a process in which a double-stranded RNA molecule or a short hairpin RNA molecule reducing or inhibiting the expression of a nucleic acid sequence with which the double-stranded or short hairpin RNA molecule shares substantial or total homology. The term "short interfering RNA" or "siRNA" or "RNAi agent" refers to an RNA sequence that elicits RNA interference. See Kreutzer et al., WO 00/44895; Zernicka-Goetz et al., WO 01/36646; Fire, WO 99/32619; Mello and Fire, WO 01/29058. As used herein, siRNA molecules include RNA molecules encompassing chemically modified nucleotides and non-nucleotides. The term "ddRNAi agent" refers to a DNA-directed RNAi agent that is transcribed from an exogenous vector. The terms "short hairpin RNA" or "shRNA" refer to an RNA structure having a duplex region and a loop region. In certain embodiments, ddRNAi agents are expressed initially as shRNAs.

As used herein, the term "aptamer" refers to a heterologous oligonucleotide capable of binding tightly and specifically to a desired molecular target, such as, for example, common metabolic cofactors (e.g., Coenzyme A. S-adenosyl methionine, and the like), proteins (e.g., complement protein C5, antibodies, and the like), or conserved structural elements in nucleic acid molecules (e.g., structures important for binding of transcription factors and the like). Aptamers typically comprise DNA or RNA nucleotide sequences ranging from about 10 to about 100 nucleotides in length, from about 10 to about 75 nucleotides in length, from about 10 to about 50 nucleotides in length, from about 10 to about 35 nucleotides in length, and from about 10 to about 25 nucleotides in length. Synthetic DNA or RNA oligonucleotides can be made using standard solid phase phosphoramidite methods and equipment, such as by using a 3900 High Throughput DNA Synthesizer™, available from Applied Biosystems (Foster City, Calif.). Aptamers frequently incorporate derivatives or analogs of the commonly occurring nucleotides found in DNA and RNA (e.g., A, G, C, and T/U), including backbone or linkage modifications (e.g., peptide nucleic acid (PNA) or phosphothioate linkages) to increase resistance to nucleases, binding avidity, or to otherwise alter their pharmacokinetic properties. Exemplary modifications are set forth in U.S. Pat. Nos. 6,455,308; 4,469,863; 5,536,821; 5,541,306; 5,637,683; 5,637,684; 5,700,922; 5,717,083; 5,719,262; 5,739,308; 5,773,601; 5,886,165; 5,929,226; 5,977,296; 6,140,482; and in WIPO publications WO 00/56746 and WO 01/14398. Methods for synthesizing oligonucleotides comprising such analogs or derivatives are disclosed, for example, in the patent publications cited above, and in U.S. Pat. Nos. 6,455,308; 5,614,622; 5,739,314; 5,955,599; 5,962,674; 6,117,992; and in WO 00/75372.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

Overview

The present disclosure relates to agents (e.g., anti-Siglec-7 antibodies) that decrease cellular levels of Siglec-7 and/or inhibit interaction between Siglec-7 and one or more Siglec-7 ligands, methods of making and using such agents (e.g., anti-Siglec-7 antibodies); pharmaceutical compositions containing such agents (e.g., anti-Siglec-7 antibodies); nucleic acids encoding such agents (e.g., anti-Siglec-7 antibodies); and host cells containing nucleic acids encoding such agents (e.g., anti-Siglec-7 antibodies).

In some embodiments, anti-Siglec-7 antibodies of the present disclosure have one or more antagonistic activities that are due, at least in part, to the ability of the antibodies inhibit the interaction between Siglec-7 and one or more natural glycan ligands. In some embodiments, the anti-Siglec-7 antibodies of the present disclosure may have one or more antagonistic activities that are due, at least in part, to the ability of the antibodies to reduce cellular expression (e.g., cell surface expression) of Siglec-7 by inducing degradation, down regulation, cleavage, receptor desensitization, and/or lysosomal targeting of Siglec-7.

In some embodiments, antibody-induced Siglec-7 activity can be determined or tested in vitro by any of the techniques disclosed herein (see, e.g., Examples 1-5), including, without limitation, testing plate-binding of full-length anti-Siglec-7 antibodies to increase the density of antibodies exposed to Siglec-7, cross-linking anti-Siglec-7 antibodies with a secondary antibody, cross-linking anti-Siglec-7 antibodies with cells that express one or more Fcg receptors (e.g., FcgRIIB), using Siglec-7 antibodies in solution, and using Fab fragments of Siglec-7 antibodies.

In some embodiments, the anti-Siglec-7 antibodies of the present disclosure have one or more antagonistic activities that are due, at least in part, to the ability of the antibodies inhibit the interaction between Siglec-7 and one or more natural glycan ligands. In some embodiments, the anti-Siglec-7 antibodies of the present disclosure may have one or more antagonistic activities that are due, at least in part, to the ability of the antibodies to reduce cellular expression (e.g., cell surface expression) of Siglec-7 by inducing degradation, down regulation, cleavage, receptor desensitization, and/or lysosomal targeting of Siglec-7. In some embodiments, the anti-Siglec-7 antibodies exhibit one or more of the following properties: a. decrease cellular levels of Siglec-7 with a half-maximal effective concentration ($EC_{50}$) that is lower than that of the anti-Siglec-7 antibody Mab1138 (R&D Systems; Cat. No. MAB 1138); b. decrease red blood cell binding to Siglec-7-Fc up to 10 fold more effectively than the anti-Siglec-7 antibody Mab1138 (R&D Systems; Cat. No. MAB 1138); c. have a dissociation constant ($K_D$) for human Siglec-7 that may range from 10 nM to 10 pM, for example when the $K_D$ is determined at a temperature of approximately 25° C.; d. have a dissociation constant ($K_D$) for human cells, such as human dendritic cells, that may range from 2 nM to 100 pM, for example when the $K_D$ is determined at a temperature of approximately 4° C.; e. bind to human cells, such as human dendritic cells with a half-maximal effective concentration ($EC_{50}$) that may range from 2 nM to 100 pM, for example when the $EC_w$ is determined at a temperature of approximately 4° C.; or f. decrease cellular levels of Siglec-7 with a half-maximal effective concentration ($EC_{50}$) that may range from 350 pM to 33 pM. As disclosed herein half-maximal effective concentration ($EC_{50}$) refers to the concentration at which an anti-Siglec-7 antibody of the present disclosure reduces cellular levels of Siglec-7 on a cell or in a cell, or the concentration at which the antibody achieves half-maximal binding to Siglec-7 on a cell.

Advantageously, anti-Siglec-7 antibodies of the present disclosure have an improved $EC_{50}$ for binding Siglec-7 as compared to commercial anti-Siglec-7 antibodies, such as Mab1138 (R&D Systems; Cat. No. MAB 1138), reduce cell surface expression more potently (e.g., lower $EC_{50}$) than commercial anti-Siglec-7 antibodies, such as Mab1138 (R&D Systems; Cat. No. MAB 1138), and decreases red blood cell binding to Siglec-7-Fc more effectively (up to 10 fold) as compared to commercial anti-Siglec-7 antibodies, such as Mab1138 (R&D Systems; Cat. No. MAB 1138) (see, e.g., Examples 3 and 4).

Certain aspects of the present disclosure are based, at least in part, on the identification of agents, such as anti-Siglec-7 antibodies, that exhibit the ability to compete with one or more Siglec-7 ligands for binding to Siglec-7 and/or the ability to decrease cell surface levels of Siglec-7 on cells, resulting in the reduction, neutralization, prevention, or curbing of one or more Siglec-7 activities. Exemplary Siglec-7 activities include, without limitation, phosphorylation of Tyr-437 and Tyr-460 by a Src family tyrosine kinase, such as Syk, LCK, FYM, and/or ZAP70; recruitment of and binding to the tyrosine-specific protein phosphatases SHP1 and SHP2; recruitment of and binding to PLC-gamma1, which acts as a guanine nucleotide exchange factor for Dynamini-1; recruitment of and binding to SH2-domain containing protein (e.g., Crkl); recruitment of and binding to the spleen tyrosine kinase Syk; recruitment of and binding to SH3-SH2-SH3 growth factor receptor-bound protein 2 (Grb2); recruitment of and binding to multiple SH2-containing proteins; modulated expression of one or more pro-inflammatory cytokines, such as IF IFN-a4, IFN-beta, IL-1β, IL-1alpha, TNF-α, IL-6, IL-8, CRP, IL-20 family members, LIF, IFN-gamma, OSM, CNTF, GM-CSF, IL-11, IL-12, IL-17, IL-18, IL-33, MCP-1, and MIP-1-beta; modulated expression of one or more pro-inflammatory cytokines in one or more cells selected from macrophages, neutrophils, NK cells, dendritic cells, bone marrow-derived dendritic cells, monocytes, osteoclasts, T cells, T helper cells, cytotoxic T cells, granulocytes, and microglial cells; increased expression of one or more anti-inflammatory cytokines, such as IL-4, IL-10, IL-13, IL-35, IL-16, TGF-beta, IL-1Ra, G-CSF, and soluble receptors for TNF, IFN-beta1a, IFN-beta1b, or IL-6; modulated expression of one or more anti-inflammatory cytokines in one or more cells selected from macrophages, neutrophils, NK cells, dendritic cells, bone marrow-derived dendritic cells, monocytes, osteoclasts, T cells, T helper cells, cytotoxic T cells, granulocytes, and microglial cells; modulate expression of one or more proteins selected from C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, and PYCARD; inhibition of extracellular signal-regulated kinase (ERK) phosphorylation; decreasing tyrosine phosphorylation on one or more cellular proteins, optionally, wherein the one or more cellular proteins comprise ZAP-70 and the tyrosine phosphorylation occurs on Tyr-319 of ZAP-70; modulated expression of C-C chemokine receptor 7 (CCR7); inhibition of microglial cell chemotaxis toward CCL19-expressing and CCL21-expressing cells; decreasing T cell proliferation induced by one or more cells selected from dendritic cells, bone marrow-derived dendritic cells, monocytes, microglia, M1 microglia, activated M1 microglia, M2 microglia, macrophages, neutrophils, NK cells. M1 macrophages, M1 neutrophils, M1 NK cells, activated M1 macrophages, activated M1 neutrophils, activated M1 NK cells, M2 macrophages, M2 neutrophils, and M2 NK cells; inhibition of osteoclast production, decreased rate of osteoclastogenesis, or both; decreasing survival of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; decreasing proliferation of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting migration of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting one or more functions of one or more cells selected from—dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting maturation of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibition of one or more types of clearance selected from apoptotic neuron clearance, nerve tissue debris clearance, dysfunctional synapse clearance, non-nerve tissue debris clearance, bacteria clearance, other foreign body clearance, disease-causing protein clearance, disease-causing peptide clearance, disease-causing nucleic acid clearance, and tumor cell clearance; optionally wherein the disease-causing protein is selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, the disease-causing nucleic acid is an antisense GGCCCC (G2C4) repeat-expansion RNA, and the tumor cell is from a cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; inhibition of phagocytosis of one or more of apoptotic neurons, nerve tissue debris, dysfunctional synapses, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein A1, serum amyloid A, medin, prolactin, transthyretin, lysozyme, beta 2 microglobulin, gelsolin, keratoepithelin, cystatin, immunoglobulin light chain AL. S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells are from a cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer, binding to Siglec-7 ligand on tumor cells; binding to Siglec-7 ligand on cells selected from neutrophils, dendritic cells, bone marrow-derived dendritic cells, monocytes, microglia, macrophages, and NK cells; inhibition of tumor cell killing by one or more of microglia, macrophages, neutrophils, NK cells, dendritic cells, bone marrow-derived dendritic cells, neutrophils, T cells, T helper cells, or cytotoxic T cells; inhibiting anti-tumor cell proliferation activity of one or more of microglia, macrophages, neutrophils, NK cells, dendritic cells, bone marrow-derived dendritic cells, neutrophils, T cells, T helper cells, or cytotoxic T cells; inhibition of anti-tumor cell metastasis activity of one or more of microglia, macrophages, neutrophils, NK cells, dendritic cells, bone marrow-derived dendritic cells, neutrophils, T cells. T helper cells, or cytotoxic T cells; inhibition of one or more ITAM motif containing receptors, optionally wherein the one or more ITAM motif containing receptors are selected from TREM1, TREM2, Sirp beta, FcgR, DAP10, and DAP12; inhibition of signaling by one or more pattern recognition receptors (PRRs), optionally wherein the one or more PRRs are selected from receptors that identify pathogen-associated molecular patterns (PAMPs), receptors that identify damage-associated molecular patterns (DAMPs), and any combination thereof; inhibition of one or more receptors comprising the motif D/Ex$_{0-2}$YxxL/IX$_{6-8}$YxxL/I (SEQ ID NO: 537); inhibition of signaling by one or more Toll-like receptors; inhibition of the JAK-STAT signaling pathway; inhibition of nuclear factor kappa-light-chain-enhancer of activated B cells (NFêB); de-phosphorylation of an ITAM motif containing receptor, modulated expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils, T cells, T helper cells, or cytotoxic T cells; increasing expression of one or more Siglec-7-dependent genes; normalization of disrupted Siglec-7-dependent gene expression; decreasing expression of one or more ITAM-dependent genes, optionally wherein the one more ITAM-dependent genes are activated by nuclear factor of activated T cells (NFAT) transcription factors; promoting or rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; increasing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells into tumors; increasing the number of tumor-promoting myeloid/granulocytic immune-suppressive cells in a tumor, in peripheral blood, or other lymphoid organ; enhancing tumor-promoting activity of myeloid-derived suppressor cells; increasing expression of tumor-promoting cytokines in a tumor or in peripheral blood, optionally wherein the tumor-promoting cytokines are TGF-beta or IL-10; increasing tumor infiltration of tumor-promoting FoxP3+ regulatory T lymphocytes; enhancing tumor-promoting activity of myeloid-derived suppressor cells (MDSC); decreasing activation of tumor-specific T lymphocytes with tumor killing potential; decreasing infiltration of tumor-specific NK cells with tumor killing potential; decreasing the tumor killing potential of NK cells; decreasing infiltration of tumor-specific B lymphocytes with potential to enhance immune response; decreasing infiltration of tumor-specific T lymphocytes with tumor killing potential; increasing tumor volume: increasing tumor growth rate; increasing metastasis; increasing rate of tumor recurrence; decreasing efficacy of one or more immune-therapies that modulate anti-tumor T cell responses, optionally wherein the one or more immune-therapies are immune-therapies that target one or more target proteins selected from PD1/PDL1, CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, TREM1, TREM2, CSF-1 receptor, and any combination thereof, or of one or more cancer vaccines; inhibition of PLCã/PKC/calcium mobilization; and inhibition of PI3K/Akt, Ras/MAPK signaling.

In some embodiments, treatment of cancer with agents, such as Siglec-7 blocking antibodies: (i) directly or indirectly decrease the survival, proliferation, maturation, differentiation, and/or functionality of tumor-promoting myeloid/granulocytic immune-suppressive cells that accumulate in the tumor, in peripheral blood, and in lymphoid organs of cancer patients; (ii) decrease the number of tumor-promoting myeloid/granulocytic immune-suppressive cells in the tumor, in the peripheral blood, and in other lymphoid organs of a cancer patient; (iii) block tumor-promoting activity of myeloid-derived suppressor cells (MDSC); (iv) decrease expression of tumor-promoting cytokines, such as TGF-beta and IL-10, in the tumor and in the peripheral blood of a cancer patient; (v) decrease tumor-promoting FoxP3+ regulatory T lymphocyte infiltration in the tumor; (vi) increase infiltration and activation of T lymphocytes with tumor killing potential; (vii) increase infiltration of tumor-specific NK cells with tumor killing potential; (viii) increase the tumor killing potential of NK cells; (ix) increase infiltration of tumor-specific B lymphocytes with potential to enhance immune response; (x) decrease tumor volume; (xi) reduce tumor growth rate; (xii) reduce and/or inhibit metastasis; (xiii) reduce rate of tumor recurrence; (xiv) increase efficacy of immune-therapy that modulates anti-tumor T cell responses, such as PD1/PDL1, CTLA4, CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, and cancer vaccines, (xv) induce, activate, or otherwise increase PLCã/PKC/calcium mobilization; and (xvi) induce, activate, or otherwise increase PI3K/Akt, Ras/MAPK signaling.

Immunosuppressor cells are sometimes also referred to as myeloid-derived suppressor cells (MDSC). In humans, MDSCs can be defined by one of the following combination of markers: (1) $CD14^+$ HLA-$DR^{low/-}$, (2) $CD14^+$ $IL4R\alpha^+$, (3) $CD14^+$ HLA-$DR^-$ $IL4R\alpha^+$, (4) $CD34^+$ $CD14^+$ $CD11b^+$ Siglec-$7^+$, (5) $CD11b^+$ $CD14^+$ Siglec-$7^+$, (6) Siglec-$7^+$ HLA- DR⁻, (7) Lin⁻ HLA-DR⁻, (8) Lin⁻ HLA-DR⁻ Siglec-7⁻, (9) Lin⁻ HLA-DR⁻ Siglec-7⁺ CD11b⁺, (10) Lin⁻ Siglec-7⁺ CD11b⁺ CD15⁺, (11) Lin⁻ HLA-DR⁻ Siglec-7⁺ CD11b⁺ CD14⁻ CD15⁺, (12) CD11b⁺ CD14⁻ Siglec-7⁺, (13) CD11b⁺ CD14⁻ HLA-DR⁻ Siglec-7⁺ CD15⁺, (14) Siglec-7⁺ HLA-DR⁻ CD15⁺, (15) CD15⁺ IL4Rα⁺, (16) CD11b⁺ CD15⁺ CD66b⁺, (17) CD15⁺ FSC$^{low}$ SSC$^{high}$, (18) CD15$^{high}$ Siglec-7⁺, (19) CD11b⁺ CD14⁻ CD15⁺, (20) CD66b⁺ SSC$^{high}$, and (21) CD11b⁺ CD15⁺ (see also Solito S et al. Annals of the NY Academy of Sciences, 2014). In mice. MDSCs can be defined by the expression of the surface markers CD45⁺, CD11b⁺, Gr1⁺, and/or Il4Ra⁺. Additional exemplary immunosuppressive monocytic lineages are CD45⁺, CD11b⁺, Gr1$^{low}$; and CD45⁺, CD11c⁺.

The present disclosure further relates to agents that bind or interact with Siglec-7, such as anti-Siglec-7 antibodies. In certain embodiments, the anti-Siglec-7 antibodies do not significantly decrease cell surface levels of Siglec-7, and/or do not inhibit interaction between Siglec-7 and one or more Siglec-7 ligands.

Siglec-7 Proteins

In one aspect, the present disclosure provides agents, such as isolated (e.g., monoclonal) antibodies, that interact with or otherwise bind to regions, such as epitopes, within a Siglec-7 protein of the present disclosure. In some embodiments, agents of the present disclosure, such as anti-Siglec-7 antibodies of the present disclosure, bind to a Siglec-7 protein and modulate one or more Siglec-7 activities after binding to the Siglec-7 protein, for example, an activity associated with Siglec-7 expression in a cell. Siglec-7 proteins of the present disclosure include, without limitation, a mammalian Siglec-7 protein, human Siglec-7 protein, mouse Siglec-7 protein, and rat Siglec-7 protein.

Siglec-7 is variously referred to as a Siglec-7 molecule. Sialic acid-binding Ig-like lectin 7, AIRM1, CD328, CDw328, D-Siglec, QA79, SIGLEC$_{19}$P, SIGLECP2, p75, and p75/AIRM1.

Siglec-7 is an immunoglobulin-like receptor primarily expressed on immune and hematopoietic cells, including without limitation monocytes, macrophages, dendritic cells, neutrophils, mast cells, microglial cells, lymphoid cells, natural killer cells, and subsets of T cells.

Various Siglec-7 homologs are known, including without limitation, human Siglec-7, chimpanzee Siglec-7, pygmy chimpanzee Siglec-7, orangutan Siglec-7, gorilla Siglec-7, and gibbon Siglec-7. The amino acid sequence of human Siglec-7 is set forth below as SEQ ID NO: 1:

```
         10         20         30         40
MLLLLLLPLL WGRERVEGQK SNRKDYSLTM QSSVTVQEGM 50         60         70         80
CVHVRCSFSY PVDSQTDSDP VHGYWFRAGN DISWKAPVAT 90        100        110        120
NNPAWAVQEE TRDRFHLLGD PQTKNCTLSI RDARMSDAGR 130        140        150        160
YFFRMEKGNI KWNYKYDQLS VNVTALTHRP NILIPGTLES 170        180        190        200
GCFQNLTCSV PWACEQGTPP MISWMGTSVS PLHPSTTRSS 210        220        230        240
VLTLIPQPQH HGTSLTCQVT LPGAGVTTNR TIQLNVSYPP 250        260        270        280
QNLTVTVFQG EGTASTALGN SSSLSVLEGQ SLRLVCAVDS 290        300        310        320
NPPARLSWTW RSLTLYPSQP SNPLVLELQV HLGDEGEFTC 330        340        350        360
RAQNSLGSQH VSLNLSLQQE YTGKMRPVSG VLLGAVGGAG 370        380        390        400
ATALVFLSFC VIFIVVRSCR KKSARPAADV GDIGMKDANT 410        420        430        440
IRGSASQGNL TESWADDNPR HHGLAAHSSG EEREIQYAPL 450        460
SFHKGEPQDL SGQEATNNEY SEIKIPK
```

In some embodiments, the Siglec-7 is a preprotein that includes a signal sequence. In some embodiments, the Siglec-7 is a mature protein. In some embodiments, the mature Siglec-7 protein does not include a signal sequence. In some embodiments, the mature Siglec-7 protein is expressed on a cell. In some embodiments, the mature Siglec-7 protein is expressed on a cell, such as the surface of a cell, including, without limitation, human dendritic cells, human macrophages, human monocytes, human osteoclasts, human neutrophils, human T cells, human helper T cell, human cytotoxic T cells, human granulocytes, and human microglia. Agents of the present disclosure, such as anti-Siglec-7 antibodies of the present disclosure, may bind any of the Siglec-7 proteins of the present disclosure expressed on any cell disclosed herein.

Siglec-7 proteins of the present disclosure, such as human Siglec-7, contain several domains, including without limitation, a signal sequence located at amino acid residues 1-18 of SEQ ID NO: 1, an extracellular immunoglobulin-like variable-type (IgV) domain located at amino acid residues 39-122 of SEQ ID NO: 1, two Ig-like C2-type domains located at amino acid residues 150-233 and 240-336 of SEQ ID NO: 1, a transmembrane domain located at amino acid residues 354-376 of SEQ ID NO: 1, an ITIM motif 1 located at amino acid residues 435-440 of SEQ ID NO: 1, and an ITIM motif 2 located at amino acid residues 459-463 of SEQ ID NO: 1. As one of skill in the art will appreciate, the beginning and ending residues of the domains of the present disclosure may vary depending upon the computer modeling program used or the method used for determining the domain.

Certain aspects of the present disclosure provide anti-Siglec-7 antibodies that bind to a human Siglec-7, or a homolog thereof, including without limitation a mammalian Siglec-7 protein and Siglec-7 orthologs from other species. Exemplary Siglec-7 homologs and orthologs are listed in Table A.

TABLE A

Siglec-7 homologs and orthologs

| Organism | Siglec-7 Accession Number |
| --- | --- |
| Chimpanzee (*Pan troglodytes*) | NCBI Accession No. XP_009434417.1 |
| Pygmy chimpanzee (*Pan paniscus*) | NCBI Accession No. XP_008964443.1 |
| Orangutan (*Pongo abelii*) | NCBI Accession No. XP_009231247 |
| Gorilla (*Gorilla gorilla gorilla*) | NCBI Accession No. XP_004061321.1 |
| Gibbon (*Nomascus leucogenys*) | NCBI Accession No. XP_003269883.1 |

Accordingly, as used herein a "Siglec-7" protein of the present disclosure includes, without limitation, a mammalian Siglec-7 protein, human Siglec-7 protein, and primate Siglec-7 protein. Additionally, anti-Siglec-7 antibodies of the present disclosure may bind an epitope within one or more of a mammalian Siglec-7 protein, human Siglec-7 protein, and primate Siglec-7. In some embodiments, anti-Siglec-7 antibodies of the present disclosure may bind specifically to a mammalian Siglec-7 protein, human Siglec-7 protein, or both. In certain embodiments, anti-Siglec-7 antibodies of the present disclosure may bind specifically to human Siglec-7, primate Siglec-7, or both.

In some embodiments, agents of the present disclosure that decrease cellular levels of Siglec-7 and/or inhibit interaction between Siglec-7 and one or more Siglec-7 ligands, or that bind or interact with Siglec-7, such as anti-Siglec-7 antibodies of the present disclosure, may bind Siglec-7 in a pH dependent manner. In some embodiments, agents of the present disclosure, such as anti-Siglec-7 antibodies, can bind to Siglec-7 at a neutral pH and be internalized without dissociating from the Siglec-7 protein. Alternatively, at an acidic pH agents of the present disclosure, such as anti-Siglec-7 antibodies, may dissociate from Siglec-7 once they are internalized and are then degraded by endosome/lysosome pathway. In certain embodiments, an anti-Siglec-7 antibody binds Siglec-7 at a pH that ranges from 5.5 to 8.0, from 5.5 to 7.5, from 5.5 to 7.0, from 5.5 to 6.5, from 5.5 to 6.0, from 6.0 to 8.0, from 6.5 to 8.0, from 7.0 to 8.0, from 7.5 to 8.0, from 6.0 to 7.5, from 6.0 to 7.0, from 6.5 to 7.5. In certain embodiments, an anti-Siglec-7 antibody dissociates from Siglec-7 at a pH of less than 6.0, less than 5.5, less than 5.0, less than 4.5, less than 4.0, less than 3.5, less than 3.0, less than 2.5, or less than 2.0.

In some embodiments, agents of the present disclosure that decrease cellular levels of Siglec-7 and/or inhibit interaction between Siglec-7 and one or more Siglec-7 ligands, or that bind or interact with Siglec-7, such as anti-Siglec-7 antibodies of the present disclosure, bind to a wild-type Siglec-7 protein of the present disclosure, naturally occurring variants thereof, and/or disease variants thereof.

In some embodiments, agents of the present disclosure that decrease cellular levels of Siglec-7 and/or inhibit interaction between Siglec-7 and one or more Siglec-7 ligands, or that bind or interact with Siglec-7, such as anti-Siglec-7 antibodies of the present disclosure, bind a variant of human Siglec-7.

In some embodiments, agents of the present disclosure that decrease cellular levels of Siglec-7 and/or inhibit interaction between Siglec-7 and one or more Siglec-7 ligands, or that bind or interact with Siglec-7, such as anti-Siglec-7 antibodies of the present disclosure, bind to a Siglec-7 protein expressed on the surface of a cell including, without limitation, human dendritic cells, human macrophages, human NK cells, human monocytes, human osteoclasts, human neutrophils, human T cells, human T helper cell, human cytotoxic T cells, human granulocytes, and human microglia. In some embodiments, agents of the present disclosure that decrease cellular levels of Siglec-7 and/or inhibit interaction between Siglec-7 and one or more Siglec-7 ligands, or that bind or interact with Siglec-7, such as anti-Siglec-7 antibodies of the present disclosure, bind to a Siglec-7 protein expressed on the surface of a cell and modulate (e.g., induce or inhibit) at least one Siglec-7 activity of the present disclosure after binding to the surface expressed Siglec-7 protein. In some embodiments of the present disclosure, the anti-Siglec-7 antibody binds specifically to a Siglec-7 protein. In some embodiments of the present disclosure, the anti-Siglec-7 antibody further binds to at least one additional Siglec protein. In some embodiments, the anti-Siglec-7 antibody modulates one or more activities of the at least one additional Siglec protein or of a cell expressing the at least one additional Siglec protein.

Siglec-7 Ligands

Siglec-7 proteins of the present disclosure can interact with (e.g., bind to) one or more Siglec-7 ligands.

Exemplary Siglec-7 ligands include, without limitation, sialic acid, sialic acid-containing glycolipids, sialic acid-containing glycoproteins, alpha-2,8-disialyl containing glycolipids, branched alpha-2,6-linked sialic acid-containing glycoproteins, terminal alpha-2,6-linked sialic acid-containing glycolipids, terminal alpha-2,3-linked sialic acid-containing glycoproteins, disialogangliosides (e.g., gangliosides or glycolipids containing a ceramide linked to a sialylated glycan), secreted mucins, Siglec-7 ligands expressed on red blood cells, Siglec-7 ligands expressed on bacterial cells, Siglec-7 ligands expressed on apoptotic cells, Siglec-7 ligands expressed on nerve cells, Siglec-7 ligands expressed on glial cells, Siglec-7 ligands expressed on microglia, Siglec-7 ligands expressed on astrocytes, Siglec-7 ligands expressed on tumor cells, Siglec-7 ligands expressed on viruses, Siglec-7 ligands expressed on dendritic cells, Siglec-7 ligands bound to beta amyloid plaques, Siglec-7 ligands bound to Tau tangles, Siglec-7 ligands on disease-causing proteins, Siglec-7 ligands on disease-causing peptides, Siglec-7 ligands expressed on macrophages, Siglec-7 ligands expressed on neutrophils, Siglec-7 ligands expressed on monocytes, Siglec-7 ligands expressed on natural killer cells, Siglec-7 ligands expressed on T cells, Siglec-7 ligands expressed on T helper cells, Siglec-7 ligands expressed on cytotoxic T cells, Siglec-7 ligands expressed on B cells, Siglec-7 ligands expressed on tumor-imbedded immunosuppressor dendritic cells, Siglec-7 ligands expressed on tumor-imbedded immunosuppressor macrophages, Siglec-7 ligands expressed on tumor-imbedded immunosuppressor neutrophils, Siglec-7 ligands expressed on tumor-imbedded immunosuppressor NK cells, Siglec-7 ligands expressed on myeloid-derived suppressor cells, and Siglec-7 ligands expressed on regulatory T cells. In some embodiments, Siglec-7 ligands of the present disclosure are ganglioside (e.g., disialogangliosides). Disialogangliosides generally share a common lacto-ceramide core and one or more sialic acid residues.

Figure 2:
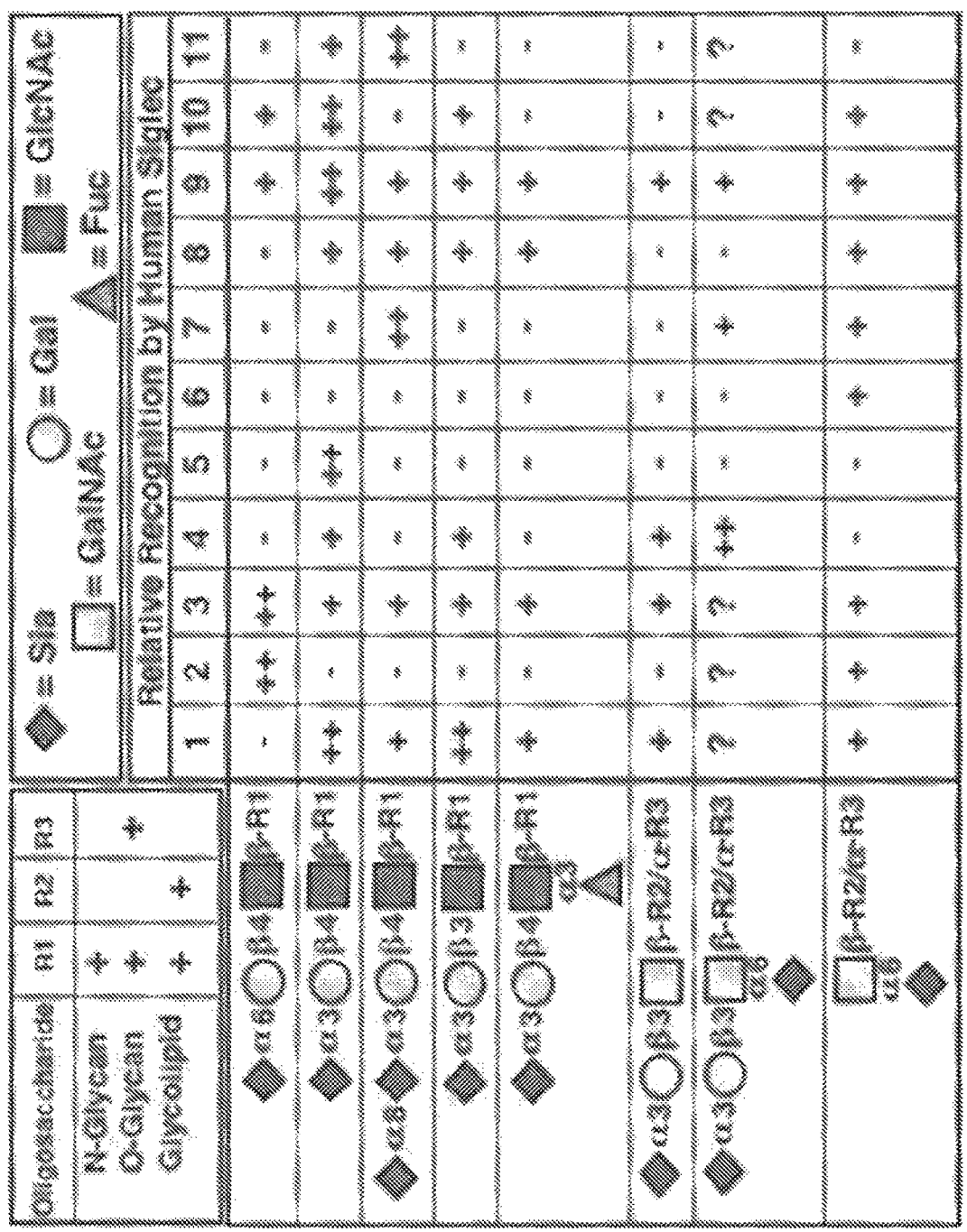
FIG. 2 shows glycan-binding specificities of human Siglec proteins, such as Siglec-7. This figure shows a summary of the most commonly reported specificities for the most commonly studied sialylated glycans. Relative binding within studies of each Siglec is indicated as ++, strong binding; +, detectable binding; and −, very weak or undetectable binding. Not shown is the recently reported strong-binding preference of hSiglec-8 and mSiglec-F for 6'-sulfated-sialyl-Lewis x (sLex) and of hSiglec-9 for 6-sulfated-sLex. With a few exceptions (CD22 and MAG), results of binding specificity studies of human Siglecs by different investigators using different assays have varied significantly. In addition to assay formats and glycan linker issues, the density and arrangement of the ligands studied could be responsible for this variation (Varki et al., (2006) Glycobiol. 16:1R-27R).

Further examples of suitable Siglec-7 ligands are depicted in FIG. 2.

Figure 3:
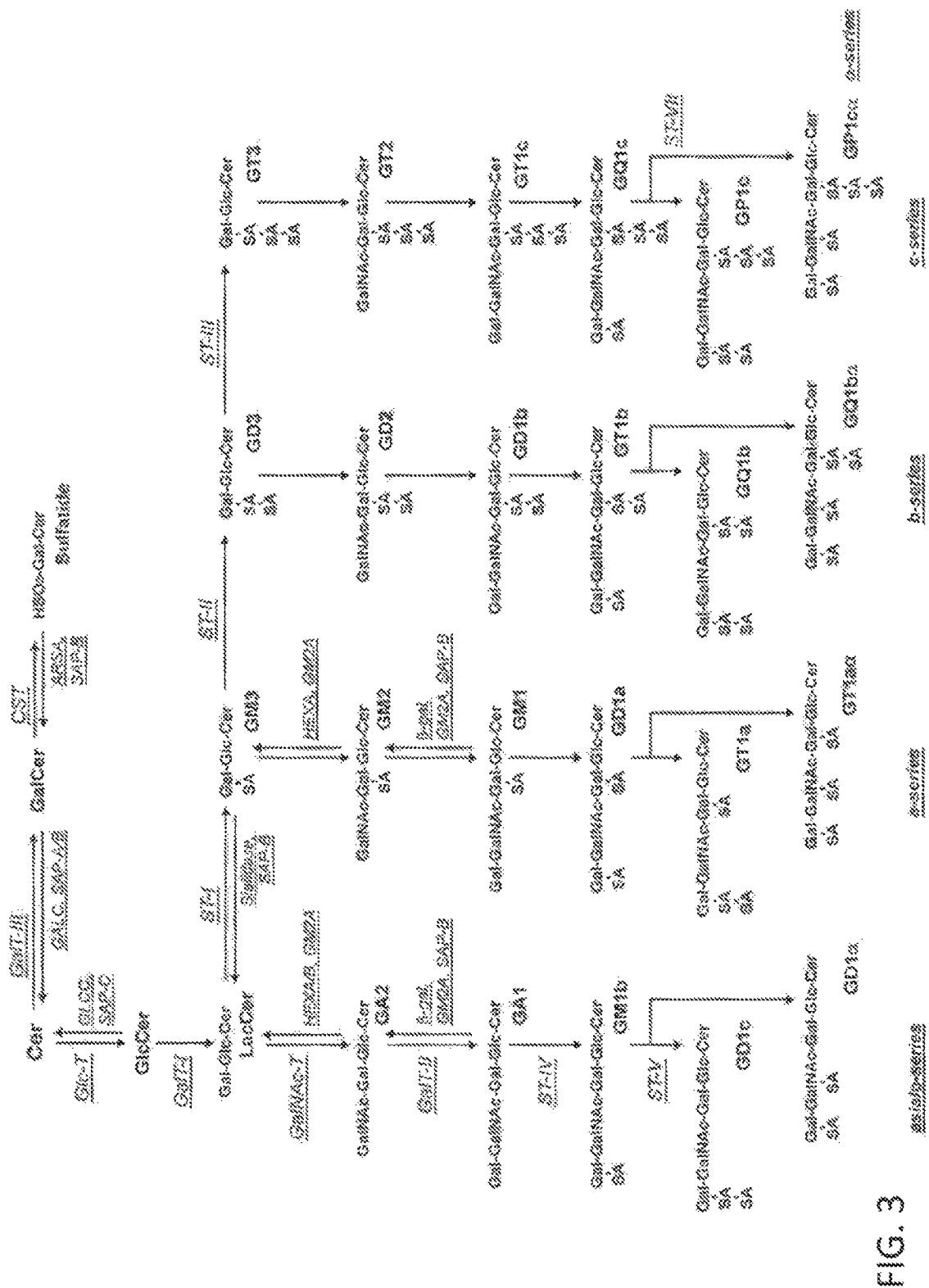
FIG. 3 shows the structure and metabolism of disialogangliosides in mammalian brain. The nomenclature of disialogangliosides in the figure follows the system of Svennerholm (1964) J. Lipid Res. 5:145-155 (Ariga T et al. (2008) J. Lipid Res. 49:1157-1175).

Further examples of suitable ganglioside (e.g., disialogangliosides) ligands are depicted in FIG. 3 and listed in Table B. Generally, a ganglioside (e.g., disialogangliosides) is a molecule composed of a glycosphingolipid with one or more sialic acids (e.g., n-acetyl-neuraminic acid, NANA) linked on the sugar chain.

TABLE B

Structures of exemplary ganglioside Siglec-7 ligands

GM2-1 = aNeu5Ac(2-3)bDGalp(1-?)bDGalNAc(1-?)bDGalNAc(1-?)bDGlcp(1-1)Cer
GM3 = aNeu5Ac(2-3)bDGalp(1-4)bDGlcp(1-1)Cer TABLE B-continued Structures of exemplary ganglioside Siglec-7 ligands GM2, GM2a(?) = bDGalpNAc(1-4)[aNeu5Ac(2-3)]bDGalp(1-4)bDGlcp(1-1)Cer
GM2b(?) = aNeu5Ac(2-8)aNeu5Ac(2-3)bDGalp(1-4)bDGlcp(1-1)Cer
GM1, GM1a = bDGalp(1-3)bDGalNAc[aNeu5Ac(2-3)]bDGalp(1-4)bDGlcp(1-1)Cer
asialo-GM1, GA1 = bDGalp(1-3)bDGalpNAc(1-4)bDGalp(1-4)bDGlcp(1-1)Cer
asialo-GM2, GA2 = bDGalpNAc(1-4)bDGalp(1-4)bDGlcp(1-1)Cer
GM1b = aNeu5Ac(2-3)bDGalp(1-3)bDGalNAc(1-4)bDGalp(1-4)bDGlcp(1-1)Cer
GD3 = aNeu5Ac(2-8)aNeu5Ac(2-3)bDGalp(1-4)bDGlcp(1-1)Cer
GD2 = bDGalpNAc(1-4)[aNeu5Ac(2-8)aNeu5Ac(2-3)]bDGalp(1-4)bDGlcp(1-1)Cer
GD1a = aNeu5Ac(2-3)bDGalp(1-3)bDGalNAc(1-4)]aNeu5Ac(2-3)]bDGalp(1-4)bDGlcp(1-1)Cer
GD1alpha = aNeu5Ac(2-3)bDGalp(1-3)bDGalNAc(1-4)[aNeu5Ac(2-6)]bDGalp(1-4)bDGlcp(1-1)Cer
GD1b = bDGalp(1-3)bDGalNAc(1-4)[aNeu5Ac(2-8)aNeu5Ac(2-3)]bDGalp(1-4)bDGlcp(1-1)Cer
GT1a = aNeu5Ac(2-8)aNen5Ac(2-3)bDGalp(1-3)bDGalNAc(1-4)[aNeu5Ac(2-3)]bDGalp(1-4)bDGlcp(1-1)Cer
GT1, GT1b = aNeu5Ac(2-3)bDGalp(1-3)bDGalNAc(1-4)]aNeu5Ac(2-8)aNeu5Ac(2-3)]bDGalp(1-4)bDGlcp(1-1)Cer
OAc-GT1b = aNeu5Ac(2-3)bDGalp(1-3)bDGalNAc(1-4)aXNeu5Ac9Ac(2-8)aNeu5Ac(2-3)lbDGalp(1-4)bDGlcp(1-1)Cer
GT1c = bDGalp(1-3)bDGalNAc(1-4)[aNeu5Ac(2-8)aNeu5Ac(2-8)aNeu5Ac(2-3)]bDGalp(1-4)bDGlp(1-1)Cer
GT3 = aNeu5Ac(2-8)aNeu5Ac(2-8)aNeu5Ac(2-3)bDGal(1-4)bDGlc(1-1)CerGQ1b = aNeu5Ac(2-8)aNeu5Ac(2-3)bDGalp(1-3)bDGalNAc(1-4)[aNeu5Ac(2-8)aNeu5Ac(2-3)]bDGalp(1-4)bDGlcp(1-1)Cer
GGa1 = aNeu5Ac(2-3)bDGalp(1-1)Cer
where:
aNeu5Ac = 5-acetyl-alpha-neuraminic acid
aNeu5Ac9Ac = 5,9-diacetyl-alpha-neuraminic acid
bDGalp = beta-D-galactopyranose
bDGalpNAc = N-acetyl-beta-D-galactopyranose
bDGlcp = beta-D-glucopyranose
Cer = ceramide (general N-acylated sphingoid)

Siglec-7 Agents

Certain aspects of the present disclosure relate to agents (e.g., Siglec-7 agents) that decrease cellular levels of Siglec-7 and/or inhibit interaction between Siglec-7 and one or more Siglec-7 ligands. Other aspects of the present disclosure relate to agents (e.g., Siglec-7 agents) that bind or interact with Siglec-7. In some embodiments, agents of the present disclosure block, inhibit, reduce, or interfere with one or more activities of a Siglec-7 protein in vitro, in situ, and/or in vivo. In some embodiments, agents of the present disclosure do not block, inhibit, reduce, or interfere with one or more activities of a Siglec-7 protein in vitro, in situ, and/or in vivo. In some embodiments, agents of the present disclosure, increase, activate or induce one or more activities of a Siglec-7 protein in vitro, m situ, and/or in vivo.

In certain embodiments, agents of the present disclosure are agents (e.g., Siglec-7 agents) that decrease cellular levels of Siglec-7 and/or inhibit interaction between Siglec-7 and one or more Siglec-7 ligand. An agent of the present disclosure that decreases cellular levels of Siglec-7 and/or inhibits interaction between Siglec-7 and one or more Siglec-7 ligands is a molecule having one or more of the following characteristics: (1) inhibits or reduces one or more Siglec-7activities; (2) the ability to inhibit or reduce binding of a Siglec-7 to one or more of its ligands; (3) the ability to reduce Siglec-7 expression (such as at the mRNA level and/or at protein level) in Siglec-7-expressing cells; (4) the ability to interact, bind, or recognize a Siglec-7 protein; (5) the ability to specifically interact with or bind to a Siglec-7 protein; and (6) the ability to treat, ameliorate, or prevent any aspect of a disease or disorder described or contemplated herein.

Exemplary agents that inhibit the production of Siglec-7 include, without limitation, compounds that specifically inhibit Siglec-7 synthesis and/or release, antisense molecules directed to a Siglec-7, or a short interfering RNA (siRNA) molecule directed to a nucleic acid encoding a Siglec-7. Additional exemplary agents that inhibit one or more Siglec-7 activities include, without limitation, anti-Siglec-7 antibodies that specifically bind to a Siglec-7 protein, compounds that specifically inhibit one or more Siglec-7 activities such as small molecule inhibitors and/or peptide inhibitors, compounds that specifically inhibit Siglec-7 binding to one or more ligands, a Siglec-7 structural analog, or an RNA or DNA aptamer that binds a Siglec-7. In some embodiments, an agent that decreases cellular levels of Siglec-7 and/or inhibits interaction between Siglec-7 and one or more Siglec-7 ligands is an allosteric inhibitor. In some embodiments, an agent that decreases cellular levels of Siglec-7 and/or inhibits interaction between Siglec-7 and one or more Siglec-7 ligands is an orthosteric inhibitor.

In certain embodiments, an agent that decreases cellular levels of Siglec-7 and/or inhibits interaction between Siglec-7 and one or more Siglec-7 ligands is a small molecule inhibitor, including, without limitation, small peptides or peptide-like molecules, soluble peptides, and synthetic non-peptidyl organic or inorganic compounds. A small molecule inhibitor may have a molecular weight of any of about 100 to about 20,000 daltons (Da), about 500 to about 15,000 Da, about 1000 to about 10,000 Da. Methods for making and testing the inhibitory effect a small molecule has on one or more Siglec-7 activities are well known in the art and such methods can be used to assess the effect of the small molecule inhibitor on Siglec-7 activity. For example, any of the methods and assays disclosed herein may be used to screen for small molecule inhibitors that decrease cellular levels of Siglec-7 and/or inhibit interaction between Siglec-7 and one or more Siglec-7 ligand.

In certain embodiments, an agent that decreases cellular levels of Siglec-7 and/or inhibits interaction between Siglec-7 and one or more Siglec-7 ligands is an anti-Siglec-7 antibody that binds or physically interacts with a Siglec-7. The antibody may have nanomolar or even picomolar affinities for the target antigen (e.g., Siglec-7). In certain embodiments, the Kd of the antibody is about 0.002 to about 100 nM. In certain embodiments, the Kd of the antibody is about 0.05 to about 100 nM. In certain embodiments, the Kd of the antibody is about 0.05 to about 50 nM. In certain embodiments, the Kd of the antibody is about 0.05 to about 10 nM. In certain embodiments, the Kd of the antibody is about 0.05 to about 2 nM. In certain embodiments, the Kd of the antibody is about 0.1 to about 2 nM. For example, Kd of the antibody is any of about 100 nM, about 90 nM, about 80 nM, about 70 nM, about 60 nM, about 50 nM, about 45 nM, about 40 nM, about 35 nM, about 30 nM, about 25 nM, about 20 nM, about 15 nM, about 10 nM, about 9 nM, about 8 nM, about 7 nM, about 6 nM, about 5 nM, about 4 nM, about 3 nM, about 2 nM, about 1 nM, about 900 pM, about 800 pM, about 700 pM, about 600 pM, about 500 pM, about 400 pM, about 300 pM, about 200 pM, about 100 pM, about 75 pM, or about 50 pM to any of about 2 pM, about 5 pM, about 10 pM, about 15 pM, about 20 pM, about 25 pM about 50 pM, about 75 pM, about 100 pM, about 200 pM, about 300 pM, about 400 pM, about 500 pM, about 600 pM, about 700 pM, about 800 pM, about 900 pM, about 1 nM, or about 2 nM. In some embodiments, the dissociation constant ($K_D$) for Siglec-7 is determined at a temperature of approximately 25° C. In some embodiments, the $K_D$ is determined using a monovalent antibody (e.g., a Fab) or a full-length antibody in a monovalent form. Methods for the preparation and selection of antibodies that interact and/or bind with specificity to a Siglec-7 are described herein. (e.g., see Example 1).

In certain embodiments, an agent that decreases cellular levels of Siglec-7 and/or inhibits interaction between Siglec-7 and one or more Siglec-7 ligands comprises at least one antisense molecule capable of blocking or decreasing the expression of a functional Siglec-7 by targeting nucleic acids encoding a Siglec-7. Nucleic acid sequences of Siglec-7 are known in the art. For example, a human Siglec-7 can have a nucleic acid sequence as shown in NCBI Accession number NM_014385.3 and a chimpanzee Siglec-7 can have a nucleic acid sequence as shown in NCBI Accession number XM_009436142.1. Methods are known for the preparation of antisense oligonucleotide molecules and such methods can be used to prepare antisense oligonucleotides that will specifically bind one or more of a Siglec-7 mRNA without cross-reacting with other polynucleotides. Exemplary sites of targeting include, but are not limited to, the initiation codon, the 5' regulatory regions, the coding sequence, including any conserved consensus regions, and the 3' untranslated region. In certain embodiments, the antisense oligonucleotides are about 10 to about 100 nucleotides in length, about 15 to about 50 nucleotides in length, about 18 to about 25 nucleotides in length, or more. In certain embodiments, the oligonucleotides further comprise chemical modifications to increase nuclease resistance and the like, such as, for example, phosphorothioate linkages and 2'-O-sugar modifications known to those of ordinary skill in the art.

In certain embodiments, an agent that decreases cellular levels of Siglec-7 and/or inhibits interaction between Siglec-7 and one or more Siglec-7 ligands comprises at least one siRNA molecule capable of blocking or decreasing the expression of a functional Siglec-7 by targeting nucleic acids encoding a Siglec-7. Methods for preparation of siRNA molecules are well known in the art and such methods can be used to prepare siRNA molecules that will specifically target a Siglec-7 mRNA without cross-reacting with other polynucleotides, siRNA molecules may be generated by methods such as by typical solid phase oligonucleotide synthesis, and often will incorporate chemical modifications to increase half-life and/or efficacy of the siRNA agent, and/or to allow for a more robust delivery formulation. Alternatively, siRNA molecules are delivered using a vector encoding an expression cassette for intracellular transcription of siRNA.

In certain embodiments, an agent that decreases cellular levels of Siglec-7 and/or inhibits interaction between Siglec-7 and one or more Siglec-7 ligands is an RNA or DNA aptamer that binds or physically interacts with a Siglec-7, and blocks interactions between a Siglec-7 and one or more of its ligands. In certain embodiments, the aptamer comprises at least one RNA or DNA aptamer that binds to a mature form of Siglec-7.

In certain embodiments, an agent that decreases cellular levels of Siglec-7 and/or inhibits interaction between Siglec-7 and one or more Siglec-7 ligands comprises at least one Siglec-7 structural analog. The term Siglec-7 structural analog refers to compounds that have a similar three dimensional structure as part of that of a Siglec-7 and which bind to one or more CD3 ligands under physiological conditions in vitro or in vivo, wherein the binding at least partially inhibits a Siglec-7 biological activity. Suitable Siglec-7 structural analogs can be designed and synthesized through molecular modeling of Siglec-7 binding to a ligand, such as a Siglec-7 ligand of the present disclosure. The Siglec-7 structural analogs can be monomers, dimers, or higher order multimers in any desired combination of the same or different structures to obtain improved affinities and biological effects. In some embodiments, the agent binds to or interacts with an amino acid sequence of a Siglec-7.

In certain embodiments, an agent that decreases cellular levels of Siglec-7 and/or inhibits interaction between Siglec-7 and one or more Siglec-7 ligands comprises a soluble Siglec-7 receptor protein, a soluble Siglec-7-Fc fusion protein (e.g., Siglec-7 immunoadhesin), a soluble Siglec receptor that binds to a Siglec-7 ligand, a Siglec-Fc fusion protein (e.g., Siglec immunoadhesin) that binds to a Siglec-7 ligand. In certain embodiments, such agents bind one or more Siglec-7 ligands and thereby prevent the interaction between a given Siglec-7 ligand and a functional Siglec-7 receptor.

In certain embodiments, agents of the present disclosure are agents (e.g., Siglec-7 agents) that bind or interact with Siglec-7. Exemplary agents that bind or interact with Siglec-7 include, without limitation, inert anti-Siglec-7 antibodies, agonist anti-Siglec-7 antibodies, Siglec-7 ligands, Siglec-7 ligand agonist fragments, Siglec-7 immunoadhesins, Siglec-7 soluble receptors, Siglec-Fc fusion proteins (e.g., Siglec immunoadhesins), soluble Siglec receptors, Siglec-7 ligand mimetics, and small molecule compounds. A small molecule compound may have a molecular weight of any of about 100 to about 20,000 daltons (Da), about 500 to about 15,000 Da, about 1000 to about 10,000 Da. Methods for making and testing the effect an agent has on one or more Siglec-7 activities are well known in the art and such methods can be used to assess the effect of the small molecule inhibitor on Siglec-7 activity. For example, any of the methods and assays disclosed herein may be used to screen for small molecule inhibitors that bind or interact with Siglec-7.

Assays

Agents that decrease cellular levels of Siglec-7 and/or inhibit interaction between Siglec-7 and one or more Siglec-7 ligands may be identified and/or characterized using methods well known in the art, such as, for example, radiolabeled inhibitor assays, optical assays, protein binding assays, biochemical screening assays, immunoassays, mass shift measurement assays, fluorescence assays, and/or fluorogenic peptide cleavage assays.

Binding Assays and Other Assays

In certain embodiments, agents that decrease cellular levels of Siglec-7 and/or inhibit interaction between Siglec-7 and one or more Siglec-7 ligands can be identified by techniques well known in the art for detecting the presence of a Siglec-7 agent candidate's interaction and/or binding affinity to a Siglec-7.

In certain embodiments, agents that interact with a Siglec-7 can be identified using a radiolabeled inhibitor assay. For example, a known amount of a radiolabeled agent candidate may be incubated with a known amount of immobilized Siglec-7 and a buffer. Subsequently, the immobilized Siglec-7 may be washed with a buffer and the immobilized Siglec-7 may be measured for the remaining presence of the radiolabeled Siglec-7 agent candidate using techniques known in the art, such as, for example, a gamma counter. A measurement indicating the presence of a radiolabeled substance may indicate the radiolabeled agent candidate is capable of interacting with and/or binding to Siglec-7.

In certain embodiments, an agent that interacts with a Siglec-7 may be identified using an optical technique. An exemplary optical technique to detect a Siglec-7 agent may include, e.g., attaching Siglec-7 to a colorimetric resonant grafting surface, thereby shifting the wavelength of reflected light due to changes in the optical path the light must take, and subsequently measuring additional changes in the wavelength of reflected light when a candidate agent is allowed to interact with Siglec-7. For example, no change in the measured wavelength of reflected light when an agent is incubated with Siglec-7 may indicate that the agent candidate is unable to interact with Siglec-7. Changes in the measured wavelength of reflected light when an agent candidate is incubated with Siglec-7 may indicate that the agent candidate is capable of binding and/or interacting with Siglec-7.

In certain embodiments, an agent that interacts with a Siglec-7 may be identified using a protein-binding assay. An exemplary protein-binding assay to detect a Siglec-7 agent may include, e.g., co-immunoprecipitation of a Siglec-7 in the presence of the agent candidate. For example, a Siglec-7 may be incubated with the agent candidate in buffer, and subsequently an immobilized molecule specific to capture a Siglec-7, such as, for example, an anti-Siglec-7 antibody, may be used to capture Siglec-7 in the presence of the agent candidate and bind the Siglec-7, potentially with an interacting agent candidate, during wash procedures known in the art. Subsequently, Siglec-7, potentially with an interacting agent candidate, can be released and the presence of an agent candidate may be detected, based on the agent candidate characteristics, by techniques, such as, for example, mass spectrometry and/or Western blot.

In certain embodiments, an agent that interacts with a Siglec-7 may be identified using a biochemical and/or an immunoassay assay well known in the art. An exemplary technique may include, e.g., an assay to quantitatively measure changes in Siglec-7 concentration and/or protein half-life using techniques, such as, for example, Western blot, immunostaining, and co-immunoprecipitation. For example, an agent candidate may be incubated with a sample containing a Siglec-7, such as a cell expressing Siglec-7 and subsequently Siglec-7 protein quantity and/or cellular levels may be measured at points during a time course study. Changes in protein quantity, cellular levels, and/or protein half-life in comparison to a control treatment may indicate that the Siglec-7 agent candidate may be capable of altering Siglec-7 half-life and/or activity.

In certain embodiments, a mass shift measurement assay may be used to identify an agent that interacts with a Siglec-7. An exemplary mass shift measurement assay may include, e.g., detecting the presence of a strongly and/or covalently bound Siglec-7 agent by measuring a change in Siglec-7 mass when the agent candidate is interacting with Siglec-7 by using instruments, such as, but not limited to, a mass spectrometer. For example, a mass shift assay may be performed on a whole protein and/or a peptide-based analysis, depending on the nature of the agent candidate interaction. Detection of a mass shift correlating with the addition of said agent candidate to Siglec-7 may indicate that the agent candidate may be capable of interacting with or otherwise inhibiting a Siglec-7. Additionally, an exemplary mass shift measurement assay may include, e.g., detecting the addition of mass to Siglec-7 correlating with the respective agent candidate mass when the agent candidate is interacting with Siglec-7 using techniques, such as, for example, surface plasmon resonance. For example, the change in the refractive index of light may be measured and correlated with a change in mass of Siglec-7 attached to a sensor surface.

In certain embodiments, a chemical cross-linking assay may be used to identify a Siglec-7 agent that interacts with a Siglec-7. For example, an agent candidate may be incubated with a Siglec-7, in vivo or in vitro, with a molecule cross-linker capable of covalently linking an agent candidate interacting with Siglec-7 to said Siglec-7 molecule. Subsequently, techniques, such as, but not limited to, mass spectrometry and/or Western blot, may be used to identify an agent candidate that may be capable of interacting with or otherwise inhibiting Siglec-7. For example, detection of Siglec-7covalently cross-linked with the agent candidate may indicate that the agent candidate may be capable of interacting with or otherwise inhibiting Siglec-7.

In certain embodiments, agents that interact with a Siglec-7 may be identified using a fluorescence assay. For example, a known amount of a fluorescent agent candidate may be incubated with a known amount of immobilized Siglec-7 and a buffer. Subsequently, the immobilized Siglec-7 may be washed with a buffer and the immobilized Siglec-7 may be measured for the remaining presence of a fluorescent Siglec-7 agent candidate using techniques known in the art, such as, but not limited to, fluorescence detection. A measurement indicating the presence of a fluorescent substance may indicate the fluorescent agent candidate is capable of interacting with and/or binding to Siglec-7.

Activity Assays

Assays known in the art and described herein (e.g., Examples 1-10) can be used for identifying and testing biological activities of Siglec-7 agents of the present disclosure. In some embodiments, assays for testing the ability of Siglec-7 agents for modulating one or more Siglec-7 activities are provided.

Anti-Siglec-7 Antibodies

Certain aspects of the present disclosure relate to anti-Siglec-7 antibodies that decrease cellular levels of Siglec-7 and/or inhibit interaction (e.g., binding) between Siglec-7 and one or more Siglec-7 ligands. In some embodiments, the anti-Siglec-7 antibody decreases cellular levels of Siglec-7 without inhibiting the interaction (e.g., binding) between Siglec-7 and one or more Siglec-7 ligands. In some embodiments, the anti-Siglec-7 antibody inhibits the interaction (e.g., binding) between Siglec-7 and one or more Siglec-7 ligands. In some embodiments, the anti-Siglec-7 antibody decreases cellular levels of Siglec-7 and inhibits the interaction (e.g., binding) between Siglec-7 and one or more Siglec-7 ligands.

Cellular levels of Siglec-7 may refer to, without limitation, cell surface levels of Siglec-7, intracellular levels of Siglec-7, and total levels of Siglec-7. In some embodiments, a decrease in cellular levels of Siglec-7 comprises decrease in cell surface levels of Siglec-7. As used herein, an anti-Siglec-7 antibody decreases cell surface levels of Siglec-7 if it induces a decrease of 21% or more in cell surface levels of Siglec-7 as measured by any in vitro cell-based assays or suitable in vivo model described herein or known in the art, for example, utilizing flow cytometry, such as fluorescence-activated cell sorting (FACS), to measure cell surface levels of Siglec-7. In some embodiments, a decrease in cellular levels of Siglec-7 comprises a decrease in intracellular levels of Siglec-7. As used herein, an anti-Siglec-7 antibody decreases intracellular levels of Siglec-7 if it induces a decrease of 21% or more in intracellular levels of Siglec-7 as measured by any in vitro cell-based assays or suitable in vivo model described herein or known in the art, for example immunostaining, Western blot analysis, co-immunoprecipitation, and cell cytometry. In some embodiments, a decrease in cellular levels of Siglec-7 comprises a decrease in total levels of Siglec-7. As used herein, an anti-Siglec-7 antibody decreases total levels of Siglec-7 if it induces a decrease of 21% or more in total levels of Siglec-7 as measured by any in vitro cell-based assays or suitable in vivo model described herein or known in the art, for example immunostaining. Western blot analysis, co-immunoprecipitation, and cell cytometry. In some embodiments, the anti-Siglec-7 antibodies induce Siglec-7 degradation, Siglec-7 cleavage, Siglec-7 internalization, Siglec-7 shedding, and/or downregulation of Siglec-7 expression. In some embodiments, cellular levels of Siglec-7 are measured on primary cells (e.g., dendritic cells, bone marrow-derived dendritic cells, monocytes, microglia, and macrophages) or on cell lines utilizing an in vitro cell assay.

In some embodiments, anti-Siglec-7 antibodies of the present disclosure decrease cellular levels of Siglec-7 by at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 650%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more as compared to cellular levels of Siglec-7 in the absence of the anti-Siglec-7 antibody.

In some embodiments, anti-Siglec-7 antibodies of the present disclosure bind to human cells, such as primary dendritic cells, with a half-maximal effective concentration ($EC_{50}$) that may be less than 10 nM, less than 9.5 nM, less than 9 nM, less than 8.5 nM, less than 8 nM, less than 7.5 nM, less than 7 nM, less than 6.5 nM, less than 6 nM, less than 5.5 nM, less than 5 nM, less than 4.5 nM, less than 4 nM, less than 3.5 nM, less than 3 nM, less than 2.5 nM, less than 2 nM, less than 1.5 nM, less than 1.4 nM, less than 1.3 nM, less than 1.2 nM, less than 1.1 nM, less than 1 nM, less than 500 pM, less than 450 pM, less than 400 pM, less than 350 pM, less than 300 pM, less than 250 pM, less than 200 pM, less than 175 pM, less than 170 pM, less than 169 pM, less than 168 pM, less than 167 pM, less than 166 pM, less than 166.2 pM, less than 165 pM, less than 164 pM, less than 163 pM, less than 162 pM, less than 161 pM, less than 160 pM, less than 150 pM, less than 145 pM, less than 140 pM, less than 139 pM, less than 138 pM, less than 138.2 pM, less than 137 pM, less than 136 pM, less than 135 pM, less than 134 pM, less than 133 pM, less than 132 pM, less than 131 pM, less than 130 pM, less than 120 pM, less than 110 pM, less than 100 pM, less than 90 pM, less than 80 pM, less than 70 pM, less than 60 pM, less than 50 pM, less than 40 pM, less than 35 pM, less than 33 pM, less than 30 pM, less than 20 pM, less than 19 pM, less than 18 pM, less than 17 pM, less than 16 pM, less than 15 pM, less than 14 pM, less than 13 pM, less than 12 pM, less than 11 pM, or less than 10 pM. In some embodiments, anti-Siglec-7 antibodies of the present disclosure bind to human cells, such as primary dendritic cells, with a half-maximal effective concentration ($EC_{50}$) that ranges from about 10 nM to about 10 pM, or less than 10 pM. In some embodiments, anti-Siglec-7 antibodies of the present disclosure bind to human cells, such as primary dendritic cells, with a half-maximal effective concentration ($EC_{50}$) that ranges from about 10 nM to about 100 pM, or less than 100 pM. In some embodiments, anti-Siglec-7 antibodies of the present disclosure bind to human cells, such as primary dendritic cells, with a half-maximal effective concentration ($EC_{50}$) that ranges from about 10 nM to about 300 pM, or less than 300 pM. In some embodiments, anti-Siglec-7 antibodies of the present disclosure bind to human cells, such as primary dendritic cells, with a half-maximal effective concentration ($EC_{50}$) that ranges from about 2 nM to about 10 pM, or less than 10 pM. In some embodiments, anti-Siglec-7 antibodies of the present disclosure bind to human cells, such as primary dendritic cells, with a half-maximal effective concentration ($EC_{50}$) that ranges from about 2 nM to about 100 pM, or less than 100 pM. In some embodiments, anti-Siglec-7 antibodies of the present disclosure bind to human cells, such as primary dendritic cells, with a half-maximal effective concentration ($EC_{50}$) that ranges from about 2 nM to about 300 pM, or less than 300 pM. In some embodiments, anti-Siglec-7 antibodies of the present disclosure bind to human cells, such as primary dendritic cells, with a half-maximal effective concentration ($EC_{50}$) that ranges from about 1.4 nM to about 10 pM, or less than 10 pM. In some embodiments, anti-Siglec-7 antibodies of the present disclosure bind to human cells, such as primary dendritic cells, with a half-maximal effective concentration ($EC_{50}$) that ranges from about 1.4 nM to about 100 pM, or less than 100 pM. In some embodiments, anti-Siglec-7 antibodies of the present disclosure bind to human cells, such as primary dendritic cells, with a half-maximal effective concentration ($EC_{50}$) that ranges from about 1.4 nM to about 300 pM, or less than 300 pM. Any suitable methods described herein (e.g., see Examples 1-3) may be used to calculate the half-maximal effective concentration ($EC_{50}$) for anti-Siglec-7 antibodies of the present disclosure binding to human cells, such as primary dendritic cells. In some embodiments, the half-maximal effective concentration ($EC_{50}$) is determined at a temperature of approximately 4° C.

In some embodiments, anti-Siglec-7 antibodies of the present disclosure decrease cellular levels of Siglec-7 with a half-maximal effective concentration ($EC_{50}$) that may be less than 500 pM, less than 450 pM, less than 400 pM, less than 350 pM, less than 3(00) pM, less than 250 pM, less than 200 pM, less than 175 pM, less than 170 pM, less than 169 pM, less than 168 pM, less than 167 pM, less than 166 pM, less than 166.2 pM, less than 165 pM, less than 164 pM, less than 163 pM, less than 162 pM, less than 161 pM, less than 160 pM, less than 150 pM, less than 145 pM, less than 140 pM, less than 139 pM, less than 138 pM, less than 138.2 pM, less than 137 pM, less than 136 pM, less than 135 pM, less than 134 pM, less than 133 pM, less than 132 pM, less than 131 pM, less than 130 pM, less than 120 pM, less than 110 pM, less than 100 pM, less than 90 pM, less than 80 pM, less than 70 pM, less than 60 pM, less than 50 pM, less than 40 pM, less than 35 pM, less than 33 pM, less than 30 pM, less than 20 pM, less than 19 pM, less than 18 pM, less than 17 pM, less than 16 pM, less than 15 pM, less than 14 pM, less than 13 pM, less than 12 pM, less than 11 pM, or less than 10 pM. In some embodiments, anti-Siglec-7 antibodies of the present disclosure decrease cellular levels of Siglec-7 with a half-maximal effective concentration ($EC_{50}$) that ranges from about 500 pM to about 18 pM, or less than 18 pM. In some embodiments, anti-Siglec-7 antibodies of the present disclosure decrease cellular levels of Siglec-7 with a half-maximal effective concentration ($EC_{50}$) that ranges from about 500 pM to about 33 pM, or less than 33 pM. In some embodiments, anti-Siglec-7 antibodies of the present disclosure decrease cellular levels of Siglec-7 with a half-maximal effective concentration ($EC_{50}$) that ranges from about 350 pM to about 18 pM, or less than 18 pM. In some embodiments, anti-Siglec-7 antibodies of the present disclosure decrease cellular levels of Siglec-7 with a half-maximal effective concentration ($EC_{50}$) that ranges from about 350 pM to about 33 pM, or less than 33 pM. Any suitable method (e.g., see Examples 1-3) may be used to measure the half-maximal effective concentration ($EC_{50}$) of the anti-Siglec-7 antibodies of the present disclosure. In some embodiments, the $EC_{50}$ is determined at a temperature of approximately 37° C.

Any in vitro cell-based assays or suitable in vivo model described herein or known in the art may be used to measure inhibition of interaction (e.g., binding) between Siglec-7 and one or more Siglec-7 ligands. In some embodiments, anti-Siglec-7 antibodies of the present disclosure inhibit interaction (e.g., binding) between Siglec-7 and one or more Siglec-7 ligands by at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more at saturating antibody concentrations (e.g., 67 nM) utilizing any in vitro assay or cell-based culture assay described herein or known in the art.

In some embodiments, anti-Siglec-7 antibodies of the present disclosure inhibit cell surface clustering of Siglec-7. In some embodiments, anti-Siglec-7 antibodies of the present disclosure inhibit one or more activities of a Siglec-7 protein, including, without limitation, phosphorylation of Tyr-437 and Tyr-460 by a Src family tyrosine kinase, such as Syk, LCK, FYM, and/orZAP70; recruitment of and binding to the tyrosine-specific protein phosphatases SHP1 and SHP2; recruitment of and binding to PLC-gamma1, which acts as a guanine nucleotide exchange factor for Dynamini-1; recruitment of and binding to SH2-domain containing protein (e.g., Crkl); recruitment of and binding to the spleen tyrosine kinase Syk; recruitment of and binding to SH3-SH2-SH3 growth factor receptor-bound protein 2 (Grb2); recruitment of and binding to multiple SH2-containing proteins; modulated expression of one or more pro-inflammatory cytokines, optionally wherein the one or more anti-inflammatory cytokines are selected from a group consisting IFN-a4, IFN-beta, IL-1â, IL-1alpha, TNF-α, IL-6, IL-8, CRP, IL-20 family members, LIF, IFN-gamma, OSM, CNTF, GM-CSF, IL-11, IL-12, IL-17, IL-18, IL-33, MCP-1, and MIP-1-beta; modulated expression of one or more pro-inflammatory cytokines in one or more cells selected from macrophages, neutrophils, NK cells, dendritic cells, bone marrow-derived dendritic cells, monocytes, osteoclasts, T cells, T helper cells, cytotoxic T cells, granulocytes, and microglial cells; modulated expression of one or more anti-inflammatory cytokines, optionally wherein the one or more anti-inflammatory cytokines are selected from IL-4, IL-10, IL-13, IL-35, IL-16, TGF-beta, IL-1Ra, G-CSF, and soluble receptors for TNF, IFN-beta1a, IFN-beta1b, or IL-6; modulated expression of one or more anti-inflammatory cytokines in one or more cells selected from macrophages, neutrophils, NK cells, dendritic cells, bone marrow-derived dendritic cells, monocytes, osteoclasts, T cells, T helper cells, cytotoxic T cells, granulocytes, and microglial cells; modulate expression of one or more proteins selected from C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, and PYCARD; inhibition of extracellular signal-regulated kinase (ERK) phosphorylation; decreasing tyrosine phosphorylation on one or more cellular proteins, optionally, wherein the one or more cellular proteins comprise ZAP-70 and the tyrosine phosphorylation occurs on Tyr-319 of ZAP-70; modulated expression of C-C chemokine receptor 7 (CCR7); inhibition of microglial cell chemotaxis toward CCL19-expressing and CCL21-expressing cells; decreasing T cell proliferation induced by one or more cells selected from dendritic cells, bone marrow-derived dendritic cells, monocytes, microglia, M1 microglia, activated M1 microglia, M2 microglia, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, and M2 NK cells; inhibition of osteoclast production, decreased rate of osteoclastogenesis, or both; decreasing survival of one or more cells selected from dendritic cells, bone marrow-derived dendritic cells, macrophages, neutrophils, NK cells, M macrophages. M neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; decreasing proliferation of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting migration of one or more cells selected from dendritic cells, bone marrow-derived dendritic cells, macrophages, neutrophils, NK cells, M1 macrophages, M1 neutrophils. M NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting one or more functions of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting maturation of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibition of one or more types of clearance selected from apoptotic neuron clearance, nerve tissue debris clearance, dysfunctional synapse clearance, non-nerve tissue debris clearance, bacteria clearance, other foreign body clearance, disease-causing protein clearance, disease-causing peptide clearance, disease-causing nucleic acid clearance, and tumor cell clearance; optionally wherein the disease-causing protein is selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products. DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, the disease-causing nucleic acid is an antisense GGCCCC (G2C4) repeat-expansion RNA, and the tumor cell is from a cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; inhibition of phagocytosis of one or more of apoptotic neurons, nerve tissue debris, dysfunctional synapses, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products. DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells are from a cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer; binding to Siglec-7 ligand on tumor cells; binding to Siglec-7 ligand on cells selected from neutrophils, dendritic cells, bone marrow-derived dendritic cells, monocytes, microglia, macrophages, and NK cells; inhibition of tumor cell killing by one or more of microglia, macrophages, neutrophils, NK cells, dendritic cells, bone marrow-derived dendritic cells, neutrophils, T cells, T helper cells, or cytotoxic T cells; inhibiting anti-tumor cell proliferation activity of one or more of microglia, macrophages, neutrophils, NK cells, dendritic cells, bone marrow-derived dendritic cells, neutrophils, T cells, T helper cells, or cytotoxic T cells; inhibition of anti-tumor cell metastasis activity of one or more of microglia, macrophages, neutrophils, NK cells, dendritic cells, bone marrow-derived dendritic cells, neutrophils, T cells, T helper cells, or cytotoxic T cells; inhibition of one or more ITAM motif containing receptors, optionally wherein the one or more ITAM motif containing receptors are selected from TREM1, TREM2, Sirp beta, FcgR, DAP10, and DAP12 inhibition of signaling by one or more pattern recognition receptors (PRRs), optionally wherein the one or more PRRs are selected from receptors that identify pathogen-associated molecular patterns (PAMPs), receptors that identify damage-associated molecular patterns (DAMPs), and any combination thereof; inhibition of one or more receptors comprising the motif D/Ex$_{0-2}$YxxL/IX$_{6-8}$YxxL/I (SEQ ID NO: 537); inhibition of signaling by one or more Toll-like receptors; inhibition of the JAK-STAT signaling pathway; inhibition of nuclear factor kappa-light-chain-enhancer of activated B cells (NFêB); de-phosphorylation of an ITAM motif containing receptor, modulated expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils. T cells, T helper cells, or cytotoxic T cells; increasing expression of one or more Siglec-7-dependent genes; normalization of disrupted Siglec-7-dependent gene expression; decreasing expression of one or more ITAM-dependent genes, optionally wherein the one more ITAM-dependent genes are activated by nuclear factor of activated T cells (NFAT) transcription factors; promoting or rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; increasing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells into tumors; increasing the number of tumor-promoting myeloid/granulocytic immune-suppressive cells in a tumor, in peripheral blood, or other lymphoid organ; enhancing tumor-promoting activity of myeloid-derived suppressor cells; increasing expression of tumor-promoting cytokines, such as TGF-beta or IL-10, in a tumor or in peripheral blood; increasing tumor infiltration of tumor-promoting FoxP3+ regulatory T lymphocytes; enhancing tumor-promoting activity of myeloid-derived suppressor cells (MDSC); decreasing activation of tumor-specific T lymphocytes with tumor killing potential; decreasing infiltration of tumor-specific NK cells with tumor killing potential; decreasing the tumor killing potential of NK cells; decreasing infiltration of tumor-specific B lymphocytes with potential to enhance immune response; decreasing infiltration of tumor-specific T lymphocytes with tumor killing potential; increasing tumor volume; increasing tumor growth rate; increasing metastasis; increasing rate of tumor recurrence; decreasing efficacy of one or more immune-therapies that modulate anti-tumor T cell responses, such as immune-therapies are immune-therapies that target one or more target proteins selected from PD1/PDL1, CD40, OX40, ICOS, CD28, CD137/4-1BB, CD27, GITR, PD-L. CTLA4, PD-L2, PD-1, B7-H3, B7-H4, HVEM, BTLA, KIR, GAL9, TIM3, A2AR, LAG, DR-5, TREM1, TREM2, CSF-1 receptor, and any combination thereof, or of one or more cancer vaccines; inhibition of PLCã/PKC/calcium mobilization; and inhibition of PI3K/Akt, Ras/MAPK signaling.

In some embodiments, anti-Siglec-7 antibodies of the present disclosure exhibit one or more activities, including, without limitation, increasing the number of tumor infiltrating CD3+ T cells; inhibiting Siglec-7 binding to one or more Siglec-7 ligands; decreasing cellular levels of Siglec-7 in peripheral immune cells: reducing the number of non-tumorigenic CD14+ myeloid cells, optionally wherein the non-tumorigenic CD14+ myeloid cells are tumor infiltrating cells or optionally wherein the non-tumorigenic CD14+ myeloid cells are present in blood; reducing the number of non-tumorigenic CD14+ myeloid cells, optionally wherein the non-tumorigenic CD14+ myeloid cells are tumor infiltrating cells or optionally wherein the non-tumorigenic CD14+ myeloid cells are present in the tumor, reducing PD-L1 levels in one or more cells, optionally wherein the one or more cells are non-tumorigenic myeloid-derived suppressor cells (MDSC); reducing PD-L2 levels in one or more cells, optionally wherein the one or more cells are non-tumorigenic myeloid-derived suppressor cells (MDSC); reducing CD11b levels in one or more cells, optionally wherein the one or more cells are non-tumorigenic myeloid-derived suppressor cells (MDSC); reducing B7-H3 levels in one or more cells, optionally wherein the one or more cells are non-tumorigenic myeloid-derived suppressor cells (MDSC); reducing CD200R levels in one or more cells, optionally wherein the one or more cells are non-tumorigenic myeloid-derived suppressor cells (MDSC); reducing CD163 levels in one or more cells, optionally wherein the one or more cells are non-tumorigenic myeloid-derived suppressor cells (MDSC); reducing CD206 levels in one or more cells, optionally wherein the one or more cells are non-tumorigenic myeloid-derived suppressor cells (MDSC); decreasing tumor growth rate of solid tumors; reducing tumor volume; increasing efficacy of one or more PD-1 inhibitors; increasing efficacy of one or more checkpoint inhibitor therapies and/or immune-modulating therapies, optionally wherein the one or more checkpoint inhibitor therapies and/or immune-modulating therapies target one or more of CTL4, the adenosine pathway, PD-L1, PD-L2, OX40, TIM3, LAG3, or any combination thereof; inhibiting differentiation, survival, and/or one or more functions of non-tumorigenic myeloid-derived suppressor cells (MDSC); inducing cell death of one or more myeloid-derived suppressor cells (MDSC); and increasing proliferation of T cells in the presence of non-tumorigenic myeloid-derived suppressor cells (MDSC).

In some embodiments, the anti-Siglec-7 antibodies inhibit interaction (e.g., binding) between a Siglec-7 protein of the present disclosure and one or more Siglec-7 ligands including, without limitation, Siglec-7 ligands expressed on red blood cells, Siglec-7 ligands expressed on bacterial cells, Siglec-7 ligands expressed on apoptotic cells, Siglec-7 ligands expressed on nerve cells, Siglec-7 ligands expressed on glial cells, Siglec-7 ligands expressed on microglia, Siglec-7 ligands expressed on astrocytes, Siglec-7 ligands expressed on tumor cells, Siglec-7 ligands expressed on viruses, Siglec-7 ligands expressed on dendritic cells, Siglec-7 ligands bound to beta amyloid plaques, Siglec-7 ligands bound to Tau tangles, Siglec-7 ligands on disease-causing proteins, Siglec-7 ligands on disease-causing peptides, Siglec-7 ligands expressed on macrophages, Siglec-7 ligands expressed on neutrophils, Siglec-7 ligands expressed on monocytes, Siglec-7 ligands expressed on natural killer cells, Siglec-7 ligands expressed on T cells, Siglec-7 ligands expressed on T helper cells. Siglec-7 ligands expressed on cytotoxic T cells, Siglec-7 ligands expressed on B cells, Siglec-7 ligands expressed on tumor-imbedded immunosuppressor dendritic cells, Siglec-7 ligands expressed on tumor-imbedded immunosuppressor macrophages, Siglec-7 ligands expressed on tumor-imbedded immunosuppressor neutrophils, Siglec-7 ligands expressed on tumor-imbedded immunosuppressor NK cells, Siglec-7 ligands expressed on myeloid-derived suppressor cells, and Siglec-7 ligands expressed on regulatory T cells. In some embodiments, Siglec-7 ligands of the present disclosure are gangliosides (e.g., disialogangliosides).

In some embodiments, anti-Siglec-7 antibodies of the present disclosure bind to a Siglec-7 protein of the present disclosure expressed on the surface of cell and the naked antibodies inhibit interaction (e.g., binding) between the Siglec-7 protein and one or more Siglec-7 ligands. In some embodiments, anti-Siglec-7 antibodies of the present disclosure that bind to a Siglec-7 protein of the present disclosure inhibit interaction (e.g., binding) between the Siglec-7 protein and one or more Siglec-7 ligands by reducing the effective levels of Siglec-7 that is available to interact with these proteins either on the cell surface or inside the cell. In some embodiments, anti-Siglec-7 antibodies of the present disclosure that bind to a Siglec-7 protein of the present disclosure inhibit interaction (e.g., binding) between the Siglec-7 protein and one or more Siglec-7 ligands by inducing degradation of Siglec-7.

Other aspects of the present disclosure relate to anti-Siglec-7 antibodies that do not significantly decrease cell surface levels of Siglec-7 and/or do not inhibit interaction between Siglec-7 and one or more Siglec-7 ligands.

As used herein, an anti-Siglec-7 antibody does not significantly decrease cell surface levels of Siglec-7 if it decreases cell surface levels of Siglec-7 by less than 20% as compared to cellular levels of Siglec-7 in the absence of the anti-Siglec-7 antibody utilizing any in vitro cell-based assays or suitable in vivo model described herein or known in the art. In some embodiments, anti-Siglec-7 antibodies of the present disclosure decrease cell surface levels of Siglec-7 by less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% as compared to cellular levels of Siglec-7 in the absence of the anti-Siglec-7 antibody.

As used herein, an anti-Siglec-7 antibody does not inhibit the interaction (e.g., binding) between Siglec-7 and one or more Siglec-7 ligands if it decreases ligand binding to Siglec-7 by less than 20% at saturating antibody concentrations (e.g., 67 nM) utilizing any in vitro assay or cell-based culture assay described herein or known in the art. In some embodiments, anti-Siglec-7 antibodies of the present disclosure inhibit interaction (e.g., binding) between Siglec-7 and one or more Siglec-7 ligands by less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% at saturating antibody concentrations (e.g., 67 nM) utilizing any in vitro assay or cell-based culture assay described herein or known in the an.

As used herein, levels of Siglec-7 may refer to expression levels of the gene encoding Siglec-7; to expression levels of one or more transcripts encoding Siglec-7; to expression levels of Siglec-7 protein; and/or to the amount of Siglec-7 protein present within cells and/or on the cell surface. Any methods known in the an for measuring levels of gene expression, transcription, translation, and/or protein abundance or localization may be used to determine the levels of Siglec-7.

Additionally, anti-Siglec-7 antibodies of the present disclosure can be used to prevent, reduce risk of, or treat dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus. Behcet's disease, Parkinson's disease, dementia with Lewy bodies, multiple system atrophy. Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections. CNS herpes, parasitic infections. Trypanosome infection, Cruzi infection, Pseudomonas aeruginosa infection, Leishmania donovani infection, group B Streptococcus infection, Campylobacter jejuni infection, Neisseria meningiditis infection, type I HIV, and/or Haemophilus influenza. In some embodiments, anti-Siglec-7 antibodies of the present disclosure can be used for inducing or promoting the survival, maturation, functionality, migration, or proliferation of one or more immune cells in an individual in need thereof; or for decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, and/or chronic myeloid leukemia (CML) cell in an individual in need thereof. In some embodiments, anti-Siglec-7 antibodies of the present disclosure are monoclonal antibodies.

In some embodiments, an isolated anti-Siglec-7 antibody of the present disclosure decreases cellular levels of Siglec-7 (e.g., cell surface levels, intracellular levels, and/or total levels). In some embodiments, an isolated anti-Siglec-7 antibody of the present disclosure induces downregulation of Siglec-7. In some embodiments, an isolated anti-Siglec-7 antibody of the present disclosure induces cleavage of Siglec-7. In some embodiments, an isolated anti-Siglec-7 antibody of the present disclosure induces internalization of Siglec-7. In some embodiments, an isolated anti-Siglec-7 antibody of the present disclosure induces shedding of Siglec-7. In some embodiments, an isolated anti-Siglec-7 antibody of the present disclosure induces degradation of Siglec-7. In some embodiments, an isolated anti-Siglec-7 antibody of the present disclosure induces desensitization of Siglec-7. In some embodiments, an isolated anti-Siglec-7 antibody of the present disclosure acts as a ligand mimetic to transiently activate Siglec-7. In some embodiments, an isolated anti-Siglec-7 antibody of the present disclosure acts as a ligand mimetic and transiently activates Siglec-7 before inducing a decrease in cellular levels of Siglec-7 and/or inhibition of interaction (e.g., binding) between Siglec-7 and one or more Siglec-7 ligands. In some embodiments, an isolated anti-Siglec-7 antibody of the present disclosure acts as a ligand mimetic and transiently activates Siglec-7 before inducing degradation of Siglec-7. In some embodiments, an isolated anti-Siglec-7 antibody of the present disclosure acts as a ligand mimetic and transiently activates Siglec-7 before inducing cleavage of Siglec-7. In some embodiments, an isolated anti-Siglec-7 antibody of the present disclosure acts as a ligand mimetic and transiently activates Siglec-7 before inducing internalization of Siglec-7. In some embodiments, an isolated anti-Siglec-7 antibody of the present disclosure acts as a ligand mimetic and transiently activates Siglec-7 before inducing shedding of Siglec-7. In some embodiments, an isolated anti-Siglec-7 antibody of the present disclosure acts as a ligand mimetic and transiently activates Siglec-7 before inducing downregulation of Siglec-7 expression. In some embodiments, an isolated anti-Siglec-7 antibody of the present disclosure acts as a ligand mimetic and transiently activates Siglec-7 before inducing desensitization of Siglec-7.

In some embodiments, an isolated anti-Siglec-7 antibody of the present disclosure is a murine antibody. In some embodiments, an isolated anti-Siglec-7 antibody of the present disclosure is a human antibody, a humanized antibody, a bispecific antibody, a monoclonal antibody, a multivalent antibody, or a chimeric antibody. Exemplary descriptions of such antibodies are found throughout the present disclosure.

In some embodiments, anti-Siglec-7 antibodies of the present disclosure bind to a human Siglec-7, or a homolog thereof, including without limitation, a mammalian Siglec-7 protein, chimpanzee Siglec-7 protein (NCBI Accession No. XP_009434417.1), pygmy chimpanzee Siglec-7 protein (XP_008964443.1), orangutan Siglec-7 protein (NCBI Accession No. XP_009231247), gorilla Siglec-7 protein (NCBI Accession No. XP_004061321.1), or gibbon Siglec-7 protein (NCBI Accession No. XP_003269883.1). In some embodiments, anti-Siglec-7 antibodies of the present disclosure specifically bind to human Siglec-7. In some embodiments, anti-Siglec-7 antibodies of the present disclosure specifically bind to primate Siglec-7. In some embodiments, anti-Siglec-7 antibodies of the present disclosure specifically bind to both human Siglec-7 and primate Siglec-7.

In some embodiments, anti-Siglec-7 antibodies of the present disclosure are agonist antibodies or antagonist antibodies that bind to a Siglec-7 protein of the present disclosure expressed on the surface of a cell and modulate (e.g., induce or inhibit) one or more Siglec-7 activities of the present disclosure after binding to the surface-expressed Siglec-7 protein. In some embodiments, anti-Siglec-7 antibodies of the present disclosure are inert antibodies.

In some embodiments, anti-Siglec-7 antibodies of the present disclosure do not significantly reduce TREM2 expression, including, without limitation, cell surface levels of TREM2, intracellular levels of TREM2, and/or total levels of TREM2. In some embodiments, an anti-Siglec-7 antibody does not reduce cellular levels of TREM2 in vivo. In some embodiments, the cellular levels of TREM2 are measured on primary cells selected from dendritic cells, bone marrow-derived dendritic cells, monocytes, microglia, macrophages, neutrophils, and NK cells, or on cell lines, and wherein the cellular levels of TREM2 are measured utilizing an in vitro cell assay. As used herein, an anti-Siglec-7 antibody does not significantly reduce cTREM2 expression if it reduced TREM2 by less than 20% as compared to TREM2 expression in the absence of the anti-Siglec-7 antibody utilizing any in vitro cell-based assays or suitable in vivo model described herein or known in the art. In some embodiments, anti-Siglec-7 antibodies of the present disclosure decrease TREM2 expression by less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% as compared to TREM2 expression in the absence of the anti-Siglec-7 antibody.

Anti-Siglec-7 Antibody-Binding Regions

Certain aspects of the preset disclosure provide anti-Siglec-7 antibodies that bind to one or more amino acids within amino acid residues 9-353, 39-149, 93-104, 95-105, 39-122, 123-149, 150-233, 240-336, 264-273, 295-306, 327-341, or 337-353 of human Siglec-7 (SEQ ID NO: 1), or within amino acid residues on a Siglec-7 homolog or ortholog corresponding to amino acid residues 9-353, 39-149, 93-104, 95-105, 39-122, 123-149, 150-233, 240-336, 264-273, 295-306, 327-341, or 337-353 of SEQ ID NO: 1. In some embodiments, the anti-Siglec-7 antibody binds to one or more amino acids within amino acid residues 60-69 of human Siglec-7 (SEQ ID NO: 1), or within amino acid residues on a Siglec-7 homolog or ortholog corresponding to amino acid residues 60-69 of SEQ ID NO: 1. In some embodiments, the anti-Siglec-7 antibody binds to one or more amino acids within amino acid residues 60-69 and 84-95 of human Siglec-7 (SEQ ID NO: 1), or within amino acid residues on a Siglec-7 homolog or ortholog corresponding to amino acid residues 60-69 and 84-95 of SEQ ID NO: 1. In some embodiments, the anti-Siglec-7 antibody binds to one or more amino acids within amino acid residues 60-69 and 117-127 of human Siglec-7 (SEQ ID NO: 1), or within amino acid residues on a Siglec-7 homolog or ortholog corresponding to amino acid residues 60-69 and 117-127 of SEQ ID NO: 1. In some embodiments, the anti-Siglec-7 antibody binds to one or more amino acids within amino acid residues 68-78 of human Siglec-7 (SEQ ID NO: 1), or within amino acid residues on a Siglec-7 homolog or ortholog corresponding to amino acid residues 68-78 of SEQ ID NO: 1. In some embodiments, the anti-Siglec-7 antibody binds to one or more amino acids within amino acid residues 84-95 of human Siglec-7 (SEQ ID NO: 1), or within amino acid residues on a Siglec-7 homolog or ortholog corresponding to amino acid residues 84-95 of SEQ ID NO: 1. In some embodiments, the anti-Siglec-7 antibody binds to one or more amino acids within amino acid residues 111-122 of human Siglec-7 (SEQ ID NO: 1), or within amino acid residues on a Siglec-7 homolog or ortholog corresponding to amino acid residues 111-122 of SEQ ID NO: 1. In some embodiments, the anti-Siglec-7 antibody binds to one or more amino acids within amino acid residues 111-122 and 282-291 of human Siglec-7 (SEQ ID NO: 1), or within amino acid residues on a Siglec-7 homolog or ortholog corresponding to amino acid residues 111-122 and 282-291 of SEQ ID NO: 1. In some embodiments, the anti-Siglec-7 antibody binds to one or more amino acids within amino acid residues 113-123 of human Siglec-7 (SEQ ID NO: 1), or within amino acid residues on a Siglec-7 homolog or ortholog corresponding to amino acid residues 113-123 of SEQ ID NO: 1. In some embodiments, the anti-Siglec-7 antibody binds to one or more amino acids within amino acid residues 113-125 of human Siglec-7 (SEQ ID NO: 1), or within amino acid residues on a Siglec-7 homolog or ortholog corresponding to amino acid residues 113-125 of SEQ ID NO: 1. In some embodiments, the anti-Siglec-7 antibody binds to one or more amino acids within amino acid residues 117-127 of human Siglec-7 (SEQ ID NO: 1), or within amino acid residues on a Siglec-7 homolog or ortholog corresponding to amino acid residues 117-127 of SEQ ID NO: 1. In some embodiments, the anti-Siglec-7 antibody binds to one or more amino acids within amino acid residues 282-291 of human Siglec-7 (SEQ ID NO: 1), or within amino acid residues on a Siglec-7 homolog or ortholog corresponding to amino acid residues 282-29 of SEQ ID NO: 1.

In some embodiments, an anti-Siglec-7 antibody of the present disclosure binds to one or more amino acid residues selected from M30, Q31, V44, R45, S47, F48, Y50, I72, W74, N81, T103, K104, T107, and R124 of SEQ ID NO: 1, or one or more amino acid residues on a mammalian Siglec-7 protein corresponding to an amino acid residue selected from M30, Q31, V44, R45, S47, F48, Y50, I72, W74, N81, T103, K104, T107, and R124 of SEQ ID NO: 1. In some embodiments, an anti-Siglec-7 antibody of the present disclosure binds to one or more, two or more, three or more, or all four amino acid residues selected from I72, W74, N81, and R124 of SEQ ID NO: 1, or one or more, two or more, three or more, or all four amino acid residues on a mammalian Siglec-7 protein corresponding to an amino acid residue selected from I72, W74, N81, and R124 of SEQ ID NO: 1. In some embodiments, an anti-Siglec-7 antibody of the present disclosure binds to one or more, two or more, three or more, four or more, or all five amino acid residues selected from R45, S47, T103, K104, and T107 of SEQ ID NO: 1, or one or more, two or more, three or more, four or more, or all five amino acid residues on a mammalian Siglec-7 protein corresponding to an amino acid residue selected from R45, S47, T103, K104, and T107 of SEQ ID NO: 1. In some embodiments, an anti-Siglec-7 antibody of the present disclosure binds to one or more, two or more, three or more, four or more, five or more, six or more, seven or more, eight or more, nine or more, or all ten amino acid residues selected from M30, Q31, V44, R45, S47, F48, Y50, T103, K104, and T107 of SEQ ID NO: 1, or one or more, two or more, three or more, four or more, five or more, six or more, seven or more, eight or more, nine or more, or all ten amino acid residues on a mammalian Siglec-7 protein corresponding to an amino acid residue selected from M30, Q31, V44, R45, S47, F48, Y50, T103, K104, and T107 of SEQ ID NO: 1.

As indicated in Table 7B, the critical Siglec-7 residues involved in binding by antibody 4E3 corresponded to amino acid residues $I_{72}$, $W_{74}$, $N_{81}$, and $R_{124}$ of SEQ ID NO: 1. The critical Siglec-7 residues involved in binding by antibody 10B5 corresponded to amino acid residues $R_{45}$, $S_{47}$, $T_{103}$, $K_{104}$, and $T_{107}$ of SEQ ID NO: 1; and the secondary residues involved in binding by antibody 10B5 corresponded to amino acid residues $M_{30}$, $Q_{31}$, $V_{44}$, $F_{48}$, and $Y_{50}$ of SEQ ID NO: 1.

Other aspects of the preset disclosure provide anti-Siglec-7 antibodies that decrease cellular levels of Siglec-7 and/or inhibit interaction (e.g., binding) between Siglec-7 and one or more Siglec-7 ligands, and that bind to one or more amino acids within amino acid residues 60-69 of human Siglec-7 (SEQ ID NO: 1), or within amino acid residues on a Siglec-7 homolog or ortholog corresponding to amino acid residues 60-69 of SEQ ID NO: 1. Other aspects of the preset disclosure provide anti-Siglec-7 antibodies that decrease cellular levels of Siglec-7 and/or inhibit interaction (e.g., binding) between Siglec-7 and one or more Siglec-7 ligands, and that bind to one or more amino acids within amino acid residues 60-69 and 84-95 of human Siglec-7 (SEQ ID NO: 1), or within amino acid residues on a Siglec-7 homolog or ortholog corresponding to amino acid residues 60-69 and 84-95 of SEQ ID NO: 1. Other aspects of the preset disclosure provide anti-Siglec-7 antibodies that decrease cellular levels of Siglec-7 and/or inhibit interaction (e.g., binding) between Siglec-7 and one or more Siglec-7 ligands, and that bind to one or more amino acids within amino acid residues 60-69 and 117-127 of human Siglec-7 (SEQ ID NO: 1), or within amino acid residues on a Siglec-7 homolog or ortholog corresponding to amino acid residues 60-69 and 117-127 of SEQ ID NO: 1. Other aspects of the preset disclosure provide anti-Siglec-7 antibodies that decrease cellular levels of Siglec-7 and/or inhibit interaction (e.g., binding) between Siglec-7 and one or more Siglec-7 ligands, and that bind to one or more amino acids within amino acid residues 68-78 of human Siglec-7 (SEQ ID NO: 1), or within amino acid residues on a Siglec-7 homolog or ortholog corresponding to amino acid residues 68-78 of SEQ ID NO: 1. Other aspects of the preset disclosure provide anti-Siglec-7 antibodies that decrease cellular levels of Siglec-7 and/or inhibit interaction (e.g., binding) between Siglec-7 and one or more Siglec-7 ligands, and that bind to one or more amino acids within amino acid residues 84-95 of human Siglec-7 (SEQ ID NO: 1), or within amino acid residues on a Siglec-7 homolog or ortholog corresponding to amino acid residues 84-95 of SEQ ID NO: 1. Other aspects of the preset disclosure provide anti-Siglec-7 antibodies that decrease cellular levels of Siglec-7 and/or inhibit interaction (e.g., binding) between Siglec-7 and one or more Siglec-7 ligands, and that bind to one or more amino acids within amino acid residues 111-122 of human Siglec-7 (SEQ ID NO: 1), or within amino acid residues on a Siglec-7 homolog or ortholog corresponding to amino acid residues 111-122 of SEQ ID NO: 1. Other aspects of the preset disclosure provide anti-Siglec-7 antibodies that decrease cellular levels of Siglec-7 and/or inhibit interaction (e.g., binding) between Siglec-7 and one or more Siglec-7 ligands, and that bind to one or more amino acids within amino acid residues 111-122 and 282-291 of human Siglec-7 (SEQ ID NO: 1), or within amino acid residues on a Siglec-7 homolog or ortholog corresponding to amino acid residues 111-122 and 282-291 of SEQ ID NO: 1. Other aspects of the preset disclosure provide anti-Siglec-7 antibodies that decrease cellular levels of Siglec-7 and/or inhibit interaction (e.g., binding) between Siglec-7 and one or more Siglec-7 ligands, and that bind to one or more amino acids within amino acid residues 113-123 of human Siglec-7 (SEQ ID NO: 1), or within amino acid residues on a Siglec-7 homolog or ortholog corresponding to amino acid residues 113-123 of SEQ ID NO: 1. Other aspects of the preset disclosure provide anti-Siglec-7 antibodies that decrease cellular levels of Siglec-7 and/or inhibit interaction (e.g., binding) between Siglec-7 and one or more Siglec-7 ligands, and that bind to one or more amino acids within amino acid residues 113-125 of human Siglec-7 (SEQ ID NO: 1), or within amino acid residues on a Siglec-7 homolog or ortholog corresponding to amino acid residues 113-125 of SEQ ID NO: 1. Other aspects of the preset disclosure provide anti-Siglec-7 antibodies that decrease cellular levels of Siglec-7 and/or inhibit interaction (e.g., binding) between Siglec-7 and one or more Siglec-7 ligands, and that bind to one or more amino acids within amino acid residues 117-127 of human Siglec-7 (SEQ ID NO: 1), or within amino acid residues on a Siglec-7 homolog or ortholog corresponding to amino acid residues 117-127 of SEQ ID NO: 1. Other aspects of the preset disclosure provide anti-Siglec-7 antibodies that decrease cellular levels of Siglec-7 and/or inhibit interaction (e.g., binding) between Siglec-7 and one or more Siglec-7 ligands, and that bind to one or more amino acids within amino acid residues 282-291 of human Siglec-7 (SEQ ID NO: 1), or within amino acid residues on a Siglec-7 homolog or ortholog corresponding to amino acid residues 282-29 of SEQ ID NO: 1.

Other aspects of the preset disclosure provide anti-Siglec-7 antibodies that do not significantly decrease cell surface levels of Siglec-7 and/or do not inhibit interaction (e.g., binding) between Siglec-7 and one or more Siglec-7 ligands, and that bind to one or more amino acids within amino acid residues 60-69 of human Siglec-7 (SEQ ID NO: 1), or within amino acid residues on a Siglec-7 homolog or ortholog corresponding to amino acid residues 60-69 of SEQ ID NO: 1. Other aspects of the preset disclosure provide anti-Siglec-7 antibodies that do not significantly decrease cell surface levels of Siglec-7 and/or do not inhibit interaction (e.g., binding) between Siglec-7 and one or more Siglec-7 ligands, and that bind to one or more amino acids within amino acid residues 60-69 and 84-95 of human Siglec-7 (SEQ ID NO: 1), or within amino acid residues on a Siglec-7 homolog or ortholog corresponding to amino acid residues 60-69 and 84-95 of SEQ ID NO: 1. Other aspects of the preset disclosure provide anti-Siglec-7 antibodies that do not significantly decrease cell surface levels of Siglec-7 and/or do not inhibit interaction (e.g., binding) between Siglec-7 and one or more Siglec-7 ligands, and that bind to one or more amino acids within amino acid residues 60-69 and 117-127 of human Siglec-7 (SEQ ID NO: 1), or within amino acid residues on a Siglec-7 homolog or ortholog corresponding to amino acid residues 60-69 and 117-127 of SEQ ID NO: 1. Other aspects of the preset disclosure provide anti-Siglec-7 antibodies that do not significantly decrease cell surface levels of Siglec-7 and/or do not inhibit interaction (e.g., binding) between Siglec-7 and one or more Siglec-7 ligands, and that bind to one or more amino acids within amino acid residues 68-78 of human Siglec-7 (SEQ ID NO: 1), or within amino acid residues on a Siglec-7 homolog or ortholog corresponding to amino acid residues 68-78 of SEQ ID NO: 1. Other aspects of the preset disclosure provide anti-Siglec-7 antibodies that do not significantly decrease cell surface levels of Siglec-7 and/or do not inhibit interaction (e.g., binding) between Siglec-7 and one or more Siglec-7 ligands, and that bind to one or more amino acids within amino acid residues 84-95 of human Siglec-7 (SEQ ID NO: 1), or within amino acid residues on a Siglec-7 homolog or ortholog corresponding to amino acid residues 84-95 of SEQ ID NO: 1. Other aspects of the preset disclosure provide anti-Siglec-7 antibodies that do not significantly decrease cell surface levels of Siglec-7 and/or do not inhibit interaction (e.g., binding) between Siglec-7 and one or more Siglec-7 ligands, and that bind to one or more amino acids within amino acid residues 111-122 of human Siglec-7 (SEQ ID NO: 1), or within amino acid residues on a Siglec-7 homolog or ortholog corresponding to amino acid residues 111-122 of SEQ ID NO: 1. Other aspects of the preset disclosure provide anti-Siglec-7 antibodies that do not significantly decrease cell surface levels of Siglec-7 and/or do not inhibit interaction (e.g., binding) between Siglec-7 and one or more Siglec-7 ligands, and that bind to one or more amino acids within amino acid residues 111-122 and 282-291 of human Siglec-7 (SEQ ID NO: 1), or within amino acid residues on a Siglec-7 homolog or ortholog corresponding to amino acid residues 111-122 and 282-291 of SEQ ID NO: 1. Other aspects of the preset disclosure provide anti-Siglec-7 antibodies that do not significantly decrease cell surface levels of Siglec-7 and/or do not inhibit interaction (e.g., binding) between Siglec-7 and one or more Siglec-7 ligands, and that bind to one or more amino acids within amino acid residues 113-123 of human Siglec-7 (SEQ ID NO: 1), or within amino acid residues on a Siglec-7 homolog or ortholog corresponding to amino acid residues 113-123 of SEQ ID NO: 1. Other aspects of the preset disclosure provide anti-Siglec-7 antibodies that do not significantly decrease cell surface levels of Siglec-7 and/or do not inhibit interaction (e.g., binding) between Siglec-7 and one or more Siglec-7 ligands, and that bind to one or more amino acids within amino acid residues 113-125 of human Siglec-7 (SEQ ID NO: 1), or within amino acid residues on a Siglec-7 homolog or ortholog corresponding to amino acid residues 113-125 of SEQ ID NO: 1. Other aspects of the preset disclosure provide anti-Siglec-7 antibodies that do not significantly decrease cell surface levels of Siglec-7 and/or do not inhibit interaction (e.g., binding) between Siglec-7 and one or more Siglec-7 ligands, and that bind to one or more amino acids within amino acid residues 117-127 of human Siglec-7 (SEQ ID NO: 1), or within amino acid residues on a Siglec-7 homolog or ortholog corresponding to amino acid residues 117-127 of SEQ ID NO: 1. Other aspects of the preset disclosure provide anti-Siglec-7 antibodies that do not significantly decrease cell surface levels of Siglec-7 and/or do not inhibit interaction (e.g., binding) between Siglec-7 and one or more Siglec-7 ligands, and that bind to one or more amino acids within amino acid residues 282-291 of human Siglec-7 (SEQ ID NO: 1), or within amino acid residues on a Siglec-7 homolog or ortholog corresponding to amino acid residues 282-29 of SEQ ID NO: 1.

In some embodiments, anti-Siglec-7 antibodies of the present disclosure may bind a conformational epitope. In some embodiments, anti-Siglec-7 antibodies of the present disclosure may bind a discontinuous Siglec-7 epitope. In some embodiments, the discontinuous Siglec-7 epitope may have two or more peptides, three or more peptides, four or more peptides, five or more peptides, six or more peptides, seven or more peptide, eight or more peptides, nine or more peptides, or 10 or more peptides. As disclosed herein, Siglec-7 epitopes may comprise one or more peptides comprising five or more, six or more, seven or more, eight or more, nine or more, 10 or more, 11 or more, 12 or more, 13 or more 14 or more, 15 or more, 16 or more, 17 or more, 18 or more, 19 or more, or 20 or more amino acid residues of the amino acid sequence of SEQ ID NO: 1, or five or more, six or more, seven or more, eight or more, nine or more, 10 or more, 11 or more, 12 or more, 13 or more 14 or more, 15 or more, 16 or more, 17 or more, 18 or more, 19 or more, or 20 or more amino acid residues on a mammalian Siglec-7 protein corresponding to the amino acid sequence of SEQ ID NO: 1.

In some embodiments, anti-Siglec-7 antibodies of the present disclosure competitively inhibit binding of at least one antibody selected from any of the antibodies listed in Tables 2A, 2B, 3A, 3B, 6A, and 6B. In some embodiments, anti-Siglec-7 antibodies of the present disclosure competitively inhibit binding of at least one antibody selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8.

In some embodiments, anti-Siglec-7 antibodies of the present disclosure bind to an epitope of human Siglec-7 that is the same as or overlaps with the Siglec-7 epitope bound by at least one antibody selected from any of the antibodies listed in Tables 2A, 2B, 3A, 3B, 6A, and 6B. In some embodiments, anti-Siglec-7 antibodies of the present disclosure bind to an epitope of human Siglec-7 that is the same as or overlaps with the Siglec-7 epitope bound by at least one antibody selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8.

In some embodiments, anti-Siglec-7 antibodies of the present disclosure bind essentially the same Siglec-7 epitope bound by at least one antibody selected from any of the antibodies listed in Tables 2A, 2B, 3A, 3B, 6A, and 6B. In some embodiments, anti-Siglec-7 antibodies of the present disclosure bind essentially the same Siglec-7 epitope bound by at least one antibody selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8. Detailed exemplary methods for mapping an epitope to which an antibody binds are provided in Morris (1996) "Epitope Mapping Protocols," in *Methods in Molecular Biology* vol. 66 (Humana Press. Totowa, N.J.).

In some embodiments, anti-Siglec-7 antibodies of the present disclosure compete with one or more antibodies selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, 10G8, and any combination thereof for binding to Siglec-7.

In some embodiments, an anti-Siglec-7 antibody of the present disclosure competes with one or more antibodies selected from 1A12, 1E8, 2G11, 2G4, 3E11, 4A1, 4D7, 4E3, 4E3H1, 4E3H2, 7A3, 7E11, 7F12, 10B5, 10B5L1, 10B5H1, 10G8, and any combination thereof, for binding to Siglec-7 when the anti-Siglec-7 antibody reduces the binding of one or more antibodies selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, 10G8, and any combination thereof to Siglec-7 by an amount the ranges from about 50% to 100%, as compared to binding to Siglec-7 in the absence of the anti-Siglec-7 antibody. In some embodiments, an anti-Siglec-7 antibody of the present disclosure competes with one or more antibodies selected from 1A12, 1E8, 2G11, 2G4, 3E11, 4A1, 47, 4E3, 4E3H1, 4E3H2, 7A3, 7E11, 7F12, 10B5, 10B5L1, 10B5H1, 10G8, and any combination thereof for binding to Siglec-7 when the anti-Siglec-7 antibody reduces the binding of one or more antibodies selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, 10G8, and any combination thereof to Siglec-7 by at least 50%, at least 55%, by at least 60%, at least 65%, at least 70%, at least 75%, at least 80%, at least 85%, at least 90%, at least 95%, or 100%, as compared to binding to Siglec-7 in the absence of the anti-Siglec-7 antibody. In some embodiments, an anti-Siglec-7 antibody of the present disclosure that reduces the binding of one or more antibodies selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, 10G8, and any combination thereof to Siglec-7 by 100% indicates that the anti-Siglec-7 antibody essential completely blocks the binding of one or more antibodies selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, 10G8, and any combination thereof to Siglec-7. In some embodiments, the anti-Siglec-7 antibody and the one or more antibodies selected from 1A12, 1E8, 2G11, 2G4, 3E11, 4A1, 4D7, 4E3, 4E3H1, 4E3H2, 7A3, 7E11, 7F12, 10B5, 10B5L1, 10B5H1, 10G8, and any combination thereof are present in an amount that corresponds to a 10:1 ratio, 9:1 ratio, 8:1 ratio, 7:1 ratio, 6:1 ratio, 5:1 ratio, 4:1 ratio, 3:1 ratio, 2:1 ratio, 1:1 ratio, 0.75:1 ratio, 0.5:1 ratio, 0.25:1 ratio, 0.1:1 ratio, 0.075:1 ratio, 0.050:1 ratio, 0.025:1 ratio, 0.01:1 ratio, 0.0075: ratio, 0.0050:1 ratio, 0.0025:1 ratio, 0.001: ratio, 0.00075:1 ratio, 0.00050:1 ratio, 0.00025:1 ratio, 0.0001: ratio, 1:10 ratio, 1:9 ratio, 1:8 ratio, 1:7 ratio, 1:6 ratio, 1:5 ratio, 1:4 ratio, 1:3 ratio, 1:2 ratio, 1:0.75 ratio, 1:0.5 ratio, 1:0.25 ratio, 1:0.1 ratio, 1:0.075 ratio, 1:0.050 ratio, 1:0.025 ratio, 1:0.01 ratio, 1:0.0075 ratio, 1:0.0050 ratio, 1:0.0025 ratio, 1:0.001 ratio, 1:0.00075 ratio, 1:0.00050 ratio, 1:0.00025 ratio, or 1:0.0001 ratio of anti-Siglec-7 antibody to one or more antibodies selected from 1A12, 1E8, 2G11, 2G4, 3E11, 4A1, 4D7, 4E3, 4E3H1, 4E3H2, 7A3, 7E11, 7F12, 10B5, 10B5L1, 10B5H1, 10G8, and any combination thereof. In some embodiments, the anti-Siglec-7 antibody is present in excess by an amount that ranges from about 1.5-fold to 100-fold, or greater than 100-fold compared to the amount of the one or more antibodies selected from 1A12, 1E8, 2G11, 2G4, 3E11, 4A1, 4D7, 4E3, 4E3H1, 4E3H2, 7A3, 7E11, 7F12, 10B5, 10B5L1, 10B5H1, 10G8, and any combination thereof. In some embodiments, the anti-Siglec-7 antibody is present in an amount that is about a 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold excess compared to the amount of the one or more antibodies selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, 10G8, and any combination thereof.

Any suitable competition assay or Siglec-7 binding assay known in the art, such as BIAcore analysis, ELISA assays, or flow cytometry, may be utilized to determine whether an anti-Siglec-7 antibody competes with one or more antibodies selected from 1A12, 1E8, 2G11, 2G4, 3E11, 4A1, 4D7, 4E3, 4E3H1, 4E3H2, 7A3, 7E11, 7F12, 10B5, 10B5L1, 10B5H1, 10G8, and any combination thereof for binding to Siglec-7. In an exemplary competition assay, immobilized Siglec-7 or cells expressing Siglec-7 on the cell surface are incubated in a solution comprising a first labeled antibody that binds to Siglec-7 (e.g., human or non-human primate) and a second unlabeled antibody that is being tested for its ability to compete with the first antibody for binding to Siglec-7. The second antibody may be present in a hybridoma supernatant. As a control, immobilized Siglec-7 or cells expressing Siglec-7 is incubated in a solution comprising the first labeled antibody but not the second unlabeled antibody. After incubation under conditions permissive for binding of the first antibody to Siglec-7, excess unbound antibody is removed, and the amount of label associated with immobilized Siglec-7 or cells expressing Siglec-7 is measured. If the amount of label associated with immobilized Siglec-7 or cells expressing Siglec-7 is substantially reduced in the test sample relative to the control sample, then that indicates that the second antibody is competing with the first antibody for binding to Siglec-7. See, Harlow and Lane (1988) *Antibodies: A Laboratory Manual* ch. 14 (Cold Spring Harbor Laboratory. Cold Spring Harbor, N.Y.).

Anti-Siglec-7 Antibody Light Chain and Heavy Chain Variable Regions

In some embodiments, anti-Siglec-7 antibodies of the present disclosure comprise (a) a light chain variable region comprising at least one, two, or three HVRs selected from HVR-L1, HVR-L2, and HVR-L3 of any one of the antibodies listed in Tables 2A, 2B, 3A, 3B, 6A, and 6B, or selected from 1A12, 1E8, 2G11, 2G4, 3E11, 4A1, 4D7, 4E3, 4E3H1, 4E3H2, 7A3, 7E11, 7F12, 10B5, 10B5L1, 10B5H1, 10G8, and any combination thereof; and/or (b) a heavy chain variable region comprising at least one, two, or three HVRs selected from HVR-H1, HVR-H2, and HVR-H3 of any one of the antibodies listed in Tables 2A, 2B, 3A, 3B, 6A, and 6B, or selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, 10G8, and any combination thereof. In some embodiments, the HVR-L1, HVR-L2, HVR-L3, HVR-H1, HVR-H2, and HVR-H3 comprise EU or Kabat CDR, Chothia CDR, or Contact CDR sequences as shown in Tables 2A, 2B, 3A, 3B, 6A, and 6B, or from an antibody selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, 10G8, and any combination thereof.

In some embodiments, anti-Siglec-7 antibodies of the present disclosure comprise at least one, two, three, four, five, or six HVRs selected from (i) HVR-L1 comprising the amino acid sequence of any of the HVR-L1 sequences listed in Tables 2A, 2B, 3A, 3B, 6A, and 6B, or from an antibody selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8; (ii) HVR-L2 comprising the amino acid sequence of any of the HVR-L2 sequences listed in Tables 2A, 2B, 3A, 3B, 6A, and 6B, or from an antibody selected from 1A12, 1E8, 2G11, 2G4, 3E11, 4A1, 4D7, 4E3, 4E3H1, 4E3H2, 7A3, 7E11, 7F12, 10B5, 10B5L1, 10B5H1, and 10G8; (iii) HVR-L3 comprising the amino acid sequence of any of the HVR-L3 sequences listed in Tables 2A, 2B, 3A, 3B, 6A, and 6B, or from an antibody selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8; (iv) HVR-H1 comprising the amino acid sequence of any of the HVR-H1 sequences listed in Tables 2A, 2B, 3A, 3B, 6A, and 6B, or from an antibody selected from 1A12, 1E8, 2G11, 2G4, 3E11, 4A1, 4D7, 4E3, 4E3H1, 4E3H2, 7A3, 7E11, 7F12, 10B5, 10B5L1, 10B5H1, and 10G8; (v) HVR-H2 comprising the amino acid sequence of any of the HVR-H2 sequences listed in Tables 2A, 2B, 3A, 3B, 6A, and 6B, or from an antibody selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8; and (vi) HVR-H3 comprising the amino acid sequence of any of the HVR-H3 sequences listed in Tables 2A, 2B, 3A, 3B, 6A, and 6B, or from an antibody selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8. In some embodiments, anti-Siglec-7 antibodies of the present disclosure comprise a light chain variable domain and a heavy chain variable domain, wherein (a) the HVR-L1 comprises the amino acid sequence of SEQ ID NO: 7, the HVR-L2 comprises the amino acid sequence of SEQ ID NO: 20, the HVR-L3 comprises the amino acid sequence of SEQ ID NO: 33, the HVR-H1 comprises the amino acid sequence of SEQ ID NO: 46, the HVR-H2 comprises the amino acid sequence of SEQ ID NO: 59, and the HVR-H3 comprises the amino acid sequence of SEQ ID NO: 72; (b) the HVR-L1 comprises the amino acid sequence of SEQ ID NO: 8, the HVR-L2 comprises the amino acid sequence of SEQ ID NO: 21, the HVR-L3 comprises the amino acid sequence of SEQ ID NO: 34, the HVR-H1 comprises the amino acid sequence of SEQ ID NO: 47, the HVR-H2 comprises the amino acid sequence of SEQ ID NO: 60, and the HVR-H3 comprises the amino acid sequence of SEQ ID NO: 73; (c) the HVR-L1 comprises the amino acid sequence of SEQ ID NO: 9, the HVR-L2 comprises the amino acid sequence of SEQ ID NO: 22, the HVR-L3 comprises the amino acid sequence of SEQ ID NO: 35, the HVR-H1 comprises the amino acid sequence of SEQ ID NO: 48, the HVR-H2 comprises the amino acid sequence of SEQ ID NO: 61, and the HVR-H3 comprises the amino acid sequence of SEQ ID NO: 74; (d) the HVR-L1 comprises the amino acid sequence of SEQ ID NO: 10, the HVR-L2 comprises the amino acid sequence of SEQ ID NO: 23, the HVR-L3 comprises the amino acid sequence of SEQ ID NO: 36, the HVR-H1 comprises the amino acid sequence of SEQ ID NO: 49, the HVR-H2 comprises the amino acid sequence of SEQ ID NO: 62, and the HVR-H3 comprises the amino acid sequence of SEQ ID NO: 75; (e) the HVR-L1 comprises the amino acid sequence of SEQ ID NO: 11, the HVR-L2 comprises the amino acid sequence of SEQ ID NO: 24, the HVR-L3 comprises the amino acid sequence of SEQ ID NO: 37, the HVR-H1 comprises the amino acid sequence of SEQ ID NO: 50, the HVR-H2 comprises the amino acid sequence of SEQ ID NO: 63, and the HVR-H3 comprises the amino acid sequence of SEQ ID NO: 76; (f) the HVR-L1 comprises the amino acid sequence of SEQ ID NO: 12, the HVR-L2 comprises the amino acid sequence of SEQ ID NO: 25, the HVR-L3 comprises the amino acid sequence of SEQ ID NO: 38, the HVR-H1 comprises the amino acid sequence of SEQ ID NO: 51, the HVR-H2 comprises the amino acid sequence of SEQ ID NO: 64, and the HVR-H3 comprises the amino acid sequence of SEQ ID NO: 77; (g) the HVR-L1 comprises the amino acid sequence of SEQ ID NO: 13, the HVR-L2 comprises the amino acid sequence of SEQ ID NO: 26, the HVR-L3 comprises the amino acid sequence of SEQ ID NO: 39, the HVR-H1 comprises the amino acid sequence of SEQ ID NO: 52, the HVR-H2 comprises the amino acid sequence of SEQ ID NO: 65, and the HVR-H3 comprises the amino acid sequence of SEQ ID NO: 78; (h) the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 66, and the HVR-H3 comprises the amino acid sequence of SEQ ID NO: 79; (i) the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 480, and the HVR-H3 comprises the amino acid sequence of SEQ ID NO: 74; (j) the HVR-L1 comprises the amino acid sequence of SEQ ID NO: 14, the HVR-L2 comprises the amino acid sequence of SEQ ID NO: 27, the HVR-L3 comprises the amino acid sequence of SEQ ID NO: 40, the HVR-H1 comprises the amino acid sequence of SEQ ID NO: 53, the HVR-H2 comprises the amino acid sequence of SEQ ID NO: 481 and the HVR-H3 comprises the amino acid sequence of SEQ ID NO: 79; (k) the HVR-L1 comprises the amino acid sequence of SEQ ID NO: 15, the HVR-L2 comprises the amino acid sequence of SEQ ID NO: 28, the HVR-L3 comprises the amino acid sequence of SEQ ID NO: 41, the HVR-H1 comprises the amino acid sequence of SEQ ID NO: 54, the HVR-H2 comprises the amino acid sequence of SEQ ID NO: 67, and the HVR-H3 comprises the amino acid sequence of SEQ ID NO: 80; (l) the HVR-L1 comprises the amino acid sequence of SEQ ID NO: 16, the HVR-L2 comprises the amino acid sequence of SEQ ID NO: 29, the HVR-L3 comprises the amino acid sequence of SEQ ID NO: 42, the HVR-H1 comprises the amino acid sequence of SEQ ID NO: 55, the HVR-H2 comprises the amino acid sequence of SEQ ID NO: 68, and the HVR-H3 comprises the amino acid sequence of SEQ ID NO: 81; (m) the HVR-L1 comprises the amino acid sequence of SEQ ID NO: 17, the HVR-L2 comprises the amino acid sequence of SEQ ID NO: 30, the HVR-L3 comprises the amino acid sequence of SEQ ID NO: 43, the HVR-H1 comprises the amino acid sequence of SEQ ID NO: 56, the HVR-H2 comprises the amino acid sequence of SEQ ID NO: 69, and the HVR-H3 comprises the amino acid sequence of SEQ ID NO: 82; (n) the HVR-L1 comprises the amino acid sequence of SEQ ID NO: 18, the HVR-L2 comprises the amino acid sequence of SEQ ID NO: 31, the HVR-L3 comprises the amino acid sequence of SEQ ID NO: 44, the HVR-H1 comprises the amino acid sequence of SEQ ID NO: 57, the HVR-H2 comprises the amino acid sequence of SEQ ID NO: 70, and the HVR-H3 comprises the amino acid sequence of SEQ ID NO: 83; (n) the HVR-L1 comprises the amino acid sequence of SEQ ID NO: 476, the HVR-L2 comprises the amino acid sequence of SEQ ID NO: 477, the HVR-L3 comprises the amino acid sequence of SEQ ID NO: 478, the HVR-H1 comprises the amino acid sequence of SEQ ID NO: 57, the HVR-H2 comprises the amino acid sequence of SEQ ID NO: 70, and the HVR-H3 comprises the amino acid sequence of SEQ ID NO: 83; (o) the HVR-L1 comprises the amino acid sequence of SEQ ID NO: 18, the HVR-L2 comprises the amino acid sequence of SEQ ID NO: 31, the HVR-L3 comprises the amino acid sequence of SEQ ID NO: 44, the HVR-H1 comprises the amino acid sequence of SEQ ID NO: 479, the HVR-H2 comprises the amino acid sequence of SEQ ID NO: 482, and the HVR-H3 comprises the amino acid sequence of SEQ ID NO: 483; or (p) the HVR-L1 comprises the amino acid sequence of SEQ ID NO: 19, the HVR-L2 comprises the amino acid sequence of SEQ ID NO: 32, the HVR-L3 comprises the amino acid sequence of SEQ ID NO: 45, the HVR-H1 comprises the amino acid sequence of SEQ ID NO: 58, the HVR-H2 comprises the amino acid sequence of SEQ ID NO: 71, and the HVR-H3 comprises the amino acid sequence of SEQ ID NO: 84.

In some embodiments, anti-Siglec-7 antibodies of the present disclosure comprise a light chain variable domain and a heavy chain variable domain, wherein the light chain variable domain comprises one or more of: (a) an HVR-L1 comprising an amino acid sequence selected from SEQ ID NOs: 7-19 and 476, or an amino acid sequence with at least about 90% homology to an amino acid sequence selected from SEQ ID NOs: 7-19 and 476; (b) an HVR-L2 comprising an amino acid sequence selected from SEQ ID NOs: 20-32 and 477, or an amino acid sequence with at least about 90% homology to an amino acid sequence selected from SEQ ID NOs: 20-32 and 477; and (c) an HVR-L3 comprising an amino acid sequence selected from SEQ ID NOs: 33-45 and 478, or an amino acid sequence with at least about 90% homology to an amino acid sequence selected from SEQ ID NOs: 33-45 and 478; and/or wherein the heavy chain variable domain comprises one or more of: (a) a an HVR-H1 comprising an amino acid sequence selected from SEQ ID NOs: 46-58 and 479, or an amino acid sequence with at least about 90% homology to an amino acid sequence selected from SEQ ID NOs: 46-58 and 479; (b) an HVR-H2 comprising an amino acid sequence selected from SEQ ID NOs: 59-71 and 480-482, or an amino acid sequence with at least about 90% homology to an amino acid sequence selected from SEQ ID NOs: 59-71 and 480-482; and (c) an HVR-H3 comprising an amino acid sequence selected from SEQ ID NOs: 72-84 and 483, or an amino acid sequence with at least about 90%/0 homology to an amino acid sequence selected from SEQ ID NOs: 72-84 and 483.

In some embodiments, anti-Siglec-7 antibodies of the present disclosure comprise a light chain variable region of any one of the antibodies listed in Tables 2A, 2B, 3A, 3B, 6A, and 6B, or selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8; and/or a heavy chain variable region of any one of the antibodies listed in Tables 2A, 2B, 3A, 3B, 6A, and 6B, or selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8. In some embodiments, anti-Siglec-7 antibodies of the present disclosure comprise a light chain variable region comprising an amino acid sequence selected from any of SEQ ID NOs: 189-318, 449-461, and 484-489; and/or a heavy chain variable domain comprising an amino acid sequence selected from any of SEQ ID NOs: 319-448, 462-474, and 490-496.

In some embodiments, the anti-Siglec-7 antibody is anti-Siglec-7 monoclonal antibody 1A12. In some embodiments, the anti-Siglec-7 antibody is an isolated antibody which binds essentially the same TREM2 epitope as 1A12. In some embodiments, the anti-Siglec-7 antibody is an isolated antibody comprising the HVR-H1, HVR-H2, and HVR-H3 of the heavy chain variable domain of monoclonal antibody 1A12. In some embodiments, the anti-Siglec-7 antibody is an isolated antibody comprising the HVR-L1, HVR-L2, and HVR-L3 of the light chain variable domain of monoclonal antibody 1A 12. In some embodiments, the anti-Siglec-7 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody 1A12.

In some embodiments, the anti-Siglec-7 antibody is anti-Siglec-7 monoclonal antibody 1E8. In some embodiments, the anti-Siglec-7 antibody is an isolated antibody which binds essentially the same TREM2 epitope as 1E8. In some embodiments, the anti-Siglec-7 antibody is an isolated antibody comprising the HVR-H1, HVR-H2, and HVR-H3 of the heavy chain variable domain of monoclonal antibody 1E8. In some embodiments, the anti-Siglec-7 antibody is an isolated antibody comprising the HVR-L1, HVR-L2, and HVR-L3 of the light chain variable domain of monoclonal antibody 1E8. In some embodiments, the anti-Siglec-7 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody 1E8.

In some embodiments, the anti-Siglec-7 antibody is anti-Siglec-7 monoclonal antibody 2G1. In some embodiments, the anti-Siglec-7 antibody is an isolated antibody which binds essentially the same TREM2 epitope as 2G1. In some embodiments, the anti-Siglec-7 antibody is an isolated antibody comprising the HVR-H1, HVR-H2, and HVR-H3 of the heavy chain variable domain of monoclonal antibody 2G1. In some embodiments, the anti-Siglec-7 antibody is an isolated antibody comprising the HVR-L1, HVR-L2, and HVR-L3 of the light chain variable domain of monoclonal antibody 2G1. In some embodiments, the anti-Siglec-7 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody 2G1.

In some embodiments, the anti-Siglec-7 antibody is anti-Siglec-7 monoclonal antibody 2G4. In some embodiments, the anti-Siglec-7 antibody is an isolated antibody which binds essentially the same TREM2 epitope as 2G4. In some embodiments, the anti-Siglec-7 antibody is an isolated antibody comprising the HVR-H1, HVR-H2, and HVR-H3 of the heavy chain variable domain of monoclonal antibody 2G4. In some embodiments, the anti-Siglec-7 antibody is an isolated antibody comprising the HVR-L1, HVR-L2, and HVR-L3 of the light chain variable domain of monoclonal antibody 2G4. In some embodiments, the anti-Siglec-7 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody 2G4.

In some embodiments, the anti-Siglec-7 antibody is anti-Siglec-7 monoclonal antibody 3E11. In some embodiments, the anti-Siglec-7 antibody is an isolated antibody which binds essentially the same TREM2 epitope as 3E11. In some embodiments, the anti-Siglec-7 antibody is an isolated antibody comprising the HVR-H1, HVR-H2, and HVR-H3 of the heavy chain variable domain of monoclonal antibody 3E11. In some embodiments, the anti-Siglec-7 antibody is an isolated antibody comprising the HVR-L1, HVR-L2, and HVR-L3 of the light chain variable domain of monoclonal antibody 3E11. In some embodiments, the anti-Siglec-7 antibody is an isolated antibody comprising the HVR-H1 HVR-H2, and HVR-H3 of the heavy chain variable domain and the HVR-L1, HVR-L2, and HVR-L3 of the light chain variable domain of monoclonal antibody 3E111.

In some embodiments, the anti-Siglec-7 antibody is anti-Siglec-7 monoclonal antibody 4A. In some embodiments, the anti-Siglec-7 antibody is an isolated antibody which binds essentially the same TREM2 epitope as 4A1. In some embodiments, the anti-Siglec-7 antibody is an isolated antibody comprising the HVR-H1, HVR-H2, and HVR-H3 of the heavy chain variable domain of monoclonal antibody 4A1. In some embodiments, the anti-Siglec-7 antibody is an isolated antibody comprising the HVR-L1, HVR-L2, and HVR-L3 of the light chain variable domain of monoclonal antibody 4A1. In some embodiments, the anti-Siglec-7 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody 4A 1.

In some embodiments, the anti-Siglec-7 antibody is anti-Siglec-7 monoclonal antibody 4D7. In some embodiments, the anti-Siglec-7 antibody is an isolated antibody which binds essentially the same TREM2 epitope as 4D7. In some embodiments, the anti-Siglec-7 antibody is an isolated antibody comprising the HVR-H1, HVR-H2, and HVR-H3 of the heavy chain variable domain of monoclonal antibody 4D7. In some embodiments, the anti-Siglec-7 antibody is an isolated antibody comprising the HVR-L1, HVR-L2, and HVR-L3 of the light chain variable domain of monoclonal antibody 4D7. In some embodiments, the anti-Siglec-7 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody 4D7.

In some embodiments, the anti-Siglec-7 antibody is anti-Siglec-7 monoclonal antibody 4E3. In some embodiments, the anti-Siglec-7 antibody is an isolated antibody which binds essentially the same TREM2 epitope as 4E3. In some embodiments, the anti-Siglec-7 antibody is an isolated antibody comprising the HVR-H1, HVR-H2, and HVR-H3 of the heavy chain variable domain of monoclonal antibody 4E3. In some embodiments, the anti-Siglec-7 antibody is an isolated antibody comprising the HVR-H1, HVR-H2, and HVR-H3 of the heavy chain variable domain of monoclonal antibody 4E3H1. In some embodiments, the anti-Siglec-7 antibody is an isolated antibody comprising the HVR-H1, HVR-H2, and HVR-H3 of the heavy chain variable domain of monoclonal antibody 4E3H2. In some embodiments, the anti-Siglec-7 antibody is an isolated antibody comprising the HVR-H1, HVR-H2, and HVR-H3 of the heavy chain variable domain of monoclonal antibody 4E3H3. In some embodiments, the anti-Siglec-7 antibody is an isolated antibody comprising the HVR-L1, HVR-L2, and HVR-L3 of the light chain variable domain of monoclonal antibody 4E3. In some embodiments, the anti-Siglec-7 antibody is an isolated antibody comprising the HVR-L1, HVR-L2, and HVR-L3 of the light chain variable domain of monoclonal antibody 4E3L1. In some embodiments, the anti-Siglec-7 antibody is an isolated antibody comprising the HVR-L1, HVR-L2, and HVR-L3 of the light chain variable domain of monoclonal antibody 4E3L2. In some embodiments, the anti-Siglec-7 antibody is an isolated antibody comprising the HVR-L1, HVR-L2, and HVR-L3 of the light chain variable domain of monoclonal antibody 4E3L3. In some embodiments, the anti-Siglec-7 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody 4E3. In some embodiments, the anti-Siglec-7 antibody is an isolated antibody comprising the HVR-H1, HVR-H2, and HVR-H3 of the heavy chain variable domain of monoclonal antibody 4E3H1 and the HVR-L1, HVR-L2, and HVR-L3 of the light chain variable domain of monoclonal antibody 4E3. In some embodiments, the anti-Siglec-7 antibody is an isolated antibody comprising the HVR-H1, HVR-H2, and HVR-H3 of the heavy chain variable domain of monoclonal antibody 4E3H2 and the HVR-L1, HVR-L2, and HVR-L3 of the light chain variable domain of monoclonal antibody 4E3. In some embodiments, the anti-Siglec-7 antibody is an isolated antibody comprising the HVR-H1, HVR-H2, and HVR-H3 of the heavy chain variable domain of monoclonal antibody 4E3H1 and the HVR-L1, HVR-L2, and HVR-L3 of the light chain variable domain of monoclonal antibody 4E3L1. In some embodiments, the anti-Siglec-7 antibody is an isolated antibody comprising the HVR-H1, HVR-H2, and HVR-H3 of the heavy chain variable domain of monoclonal antibody 4E3H2 and the HVR-L1, HVR-L2, and HVR-L3 of the light chain variable domain of monoclonal antibody 4E3L2. In some embodiments, the anti-Siglec-7 antibody is an isolated antibody comprising the HVR-H1, HVR-H2, and HVR-H3 of the heavy chain variable domain of monoclonal antibody 4E3H2 and the HVR-L1, HVR-L2, and HVR-L3 of the light chain variable domain of monoclonal antibody 4E3L3. In some embodiments, the anti-Siglec-7 antibody is an isolated antibody comprising the HVR-H1, HVR-H2, and HVR-H3 of the heavy chain variable domain of monoclonal antibody 4E3H3 and the HVR-L1, HVR-L2, and HVR-L3 of the light chain variable domain of monoclonal antibody 4E3L2. In some embodiments, the anti-Siglec-7 antibody is an isolated antibody comprising the HVR-H1, HVR-H2, and HVR-H3 of the heavy chain variable domain of monoclonal antibody 4E3H3 and the HVR-L1, HVR-L2, and HVR-L3 of the light chain variable domain of monoclonal antibody 4E3L3.

In some embodiments, the anti-Siglec-7 antibody is anti-Siglec-7 monoclonal antibody 7A3. In some embodiments, the anti-Siglec-7 antibody is an isolated antibody which binds essentially the same TREM2 epitope as 7A3. In some embodiments, the anti-Siglec-7 antibody is an isolated antibody comprising the HVR-H1, HVR-H2, and HVR-H3 of the heavy chain variable domain of monoclonal antibody 7A3. In some embodiments, the anti-Siglec-7 antibody is an isolated antibody comprising the HVR-L1, HVR-L2, and HVR-L3 of the light chain variable domain of monoclonal antibody 7A3. In some embodiments, the anti-Siglec-7 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody 7A3.

In some embodiments, the anti-Siglec-7 antibody is anti-Siglec-7 monoclonal antibody 7E11. In some embodiments, the anti-Siglec-7 antibody is an isolated antibody which binds essentially the same TREM2 epitope as 7E11. In some embodiments, the anti-Siglec-7 antibody is an isolated antibody comprising the HVR-H1, HVR-H2, and HVR-H3 of the heavy chain variable domain of monoclonal antibody 7E11. In some embodiments, the anti-Siglec-7 antibody is an isolated antibody comprising the HVR-L1, HVR-L2, and HVR-L3 of the light chain variable domain of monoclonal antibody 7E1. In some embodiments, the anti-Siglec-7 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody 7E11.

In some embodiments, the anti-Siglec-7 antibody is anti-Siglec-7 monoclonal antibody 7F12. In some embodiments, the anti-Siglec-7 antibody is an isolated antibody which binds essentially the same TREM2 epitope as 7F12. In some embodiments, the anti-Siglec-7 antibody is an isolated antibody comprising the HVR-H1, HVR-H2, and HVR-H3 of the heavy chain variable domain of monoclonal antibody 7F12. In some embodiments, the anti-Siglec-7 antibody is an isolated antibody comprising the HVR-L1, HVR-L2, and HVR-L3 of the light chain variable domain of monoclonal antibody 7F12. In some embodiments, the anti-Siglec-7 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody 7F12.

In some embodiments, the anti-Siglec-7 antibody is anti-Siglec-7 monoclonal antibody 10B5. In some embodiments, the anti-Siglec-7 antibody is an isolated antibody which binds essentially the same TREM2 epitope as 10B5. In some embodiments, the anti-Siglec-7 antibody is an isolated antibody comprising the HVR-H1, HVR-H2, and HVR-H3 of the heavy chain variable domain of monoclonal antibody 10B5. In some embodiments, the anti-Siglec-7 antibody is an isolated antibody comprising the HVR-H1, HVR-H2, and HVR-H3 of the heavy chain variable domain of monoclonal antibody 10B5H1. In some embodiments, the anti-Siglec-7 antibody is an isolated antibody comprising the HVR-H1, HVR-H2, and HVR-H3 of the heavy chain variable domain of monoclonal antibody 10B5H2. In some embodiments, the anti-Siglec-7 antibody is an isolated antibody comprising the HVR-H1, HVR-H2, and HVR-H3 of the heavy chain variable domain of monoclonal antibody 10B5H3. In some embodiments, the anti-Siglec-7 antibody is an isolated antibody comprising the HVR-H1, HVR-H2, and HVR-H3 of the heavy chain variable domain of monoclonal antibody 10B5H4. In some embodiments, the anti-Siglec-7 antibody is an isolated antibody comprising the HVR-L1, HVR-L2, and HVR-L3 of the light chain variable domain of monoclonal antibody 10B5. In some embodiments, the anti-Siglec-7 antibody is an isolated antibody comprising the HVR-L1, HVR-L2, and HVR-L3 of the light chain variable domain of monoclonal antibody 10B5L1. In some embodiments, the anti-Siglec-7 antibody is an isolated antibody comprising the HVR-L1, HVR-L2, and HVR-L3 of the light chain variable domain of monoclonal antibody 10B5L2. In some embodiments, the anti-Siglec-7 antibody is an isolated antibody comprising the HVR-L1, HVR-L2, and HVR-L3 of the light chain variable domain of monoclonal antibody 10B5L3. In some embodiments, the anti-Siglec-7 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody 10B5. In some embodiments, the anti-Siglec-7 antibody is an isolated antibody comprising the HVR-H1, HVR-H2, and HVR-H3 of the heavy chain variable domain of monoclonal antibody 10B5H1 and the HVR-LL, HVR-L2, and HVR-L3 of the light chain variable domain of monoclonal antibody 10B5. In some embodiments, the anti-Siglec-7 antibody is an isolated antibody comprising the HVR-H1, HVR-H2, and HVR-H3 of the heavy chain variable domain of monoclonal antibody 10B5H2 and the HVR-L1 HVR-L2, and HVR-L3 of the light chain variable domain of monoclonal antibody 10B5. In some embodiments, the anti-Siglec-7 antibody is an isolated antibody comprising the HVR-H1, HVR-H2, and HVR-H3 of the heavy chain variable domain of monoclonal antibody 10B5 and the HVR-L L HVR-L2, and HVR-L3 of the light chain variable domain of monoclonal antibody 10B5L1. In some embodiments, the anti-Siglec-7 antibody is an isolated antibody comprising the HVR-H1, HVR-H2, and HVR-H3 of the heavy chain variable domain of monoclonal antibody 10B5H1 and the HVR-L1 HVR-L2, and HVR-L3 of the light chain variable domain of monoclonal antibody 10B5L1. In some embodiments, the anti-Siglec-7 antibody is an isolated antibody comprising the HVR-H1. HVR-H2, and HVR-H3 of the heavy chain variable domain of monoclonal antibody 10B5H2 and the HVR-L1 HVR-L2, and HVR-L3 of the light chain variable domain of monoclonal antibody 10B5L2. In some embodiments, the anti-Siglec-7 antibody is an isolated antibody comprising the HVR-H1. HVR-H2, and HVR-H3 of the heavy chain variable domain of monoclonal antibody 10B5H3 and the HVR-L1 HVR-L2, and HVR-L3 of the light chain variable domain of monoclonal antibody 10B5L2. In some embodiments, the anti-Siglec-7 antibody is an isolated antibody comprising the HVR-H1. HVR-H2, and HVR-H3 of the heavy chain variable domain of monoclonal antibody 10B5H2 and the HVR-L1 HVR-L2, and HVR-L3 of the light chain variable domain of monoclonal antibody 10B5L3. In some embodiments, the anti-Siglec-7 antibody is an isolated antibody comprising the HVR-H1, HVR-H2, and HVR-H3 of the heavy chain variable domain of monoclonal antibody 10B5H4 and the HVR-L1, HVR-L2, and HVR-L3 of the light chain variable domain of monoclonal antibody 10B5L3.

In some embodiments, the anti-Siglec-7 antibody is anti-Siglec-7 monoclonal antibody 10G8. In some embodiments, the anti-Siglec-7 antibody is an isolated antibody which binds essentially the same TREM2 epitope as 10G8. In some embodiments, the anti-Siglec-7 antibody is an isolated antibody comprising the HVR-H1, HVR-H2, and HVR-H3 of the heavy chain variable domain of monoclonal antibody 10G8. In some embodiments, the anti-Siglec-7 antibody is an isolated antibody comprising the HVR-L1, HVR-L2, and HVR-L3 of the light chain variable domain of monoclonal antibody 10G8. In some embodiments, the anti-Siglec-7 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody 10G8.

Any of the antibodies of the present disclosure may be produced by a cell line. In some embodiments, the cell line may be a mammalian cell line. In certain embodiments, the cell line may be a hybridoma cell line. In other embodiments, the cell line may be a yeast cell line. Any cell line known in the art suitable for antibody production may be used to produce an antibody of the present disclosure. Exemplary cell lines for antibody production are described throughout the present disclosure.

In some embodiments, the anti-Siglec-7 antibody is an anti-Siglec-7 monoclonal antibody selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8. In certain embodiments, the anti-Siglec-7 antibody is an antagonist antibody. In certain embodiments, the anti-Siglec-7 antibody is an agonist antibody or an inert antibody.

Anti-Siglec-7 Antibody Binding Affinity

The dissociation constants ($K_D$) of anti-Siglec-7 antibodies for human Siglec-7, mammalian Siglec-7, or both, may be less than 100 nM, less than 90 nM, less than 80 nM, less than 70 nM, less than 60 nM, less than 50 nM, less than 40 nM, less than 30 nM, less than 20 nM, less than 10 nM, less than 9.5 nM, less than 9 nM, less than 8.5 nM, less than 8 nM, less than 7.5 nM, less than 7 nM, less than 6.5 nM, less than 6 nM, less than 5.5 nM, less than 5 nM, less than 4.5 nM, less than 4 nM, less than 3.5 nM, less than 3 nM, less than 2.5 nM, less than 2 nM, less than 1.5 nM, less than 1 nM, less than 0.5 nM, less than 0.4 nM, less than 0.3 nM, less than 0.2 nM, less than 0.1 nM, less than 0.05 nM (i.e., 50 pM), less than 40 pM, less than 30 pM, less than 20 pM, less than 19 pM, less than 18 pM, less than 17 pM, less than 16 pM, less than 15 pM, less than 14 pM, less than 13 pM, less than 12 pM, less than 11 pM, less than 10 pM, or less than 5 pM. In some embodiments, the antibody has a dissociation constant ($K_D$) for human Siglec-7, mammalian Siglec-7, or both, that ranges from about 10 nM to about 10 pM (i.e., 0.01 nM), or less than 10 pM. In some embodiments, the antibody has a dissociation constant ($K_D$) for human Siglec-7 that ranges from about 9.5 nM to about 17 pM, or less than 17 pM. In some embodiments, the antibody has a dissociation constant (K) for human Siglec-7 that ranges from about 2 nM to about 100 pM. Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. In some embodiments, the dissociation constant (K) for Siglec-7 is determined at a temperature of approximately 25° C. In some embodiments, the $K_D$ is determined using a monovalent antibody (e.g., a Fab) or a full-length antibody. In some embodiments, the $K_D$ is determined using a full-length antibody in a monovalent form. In some embodiments, the $K_D$ is determined utilizing, for example, a surface plasmon resonance assay as described herein (see, e.g., Example 1).

Additional anti-Siglec-7 antibodies, e.g., antibodies that specifically bind to a Siglec-7 protein of the present disclosure, may be identified, screened, and/or characterized for their physical/chemical properties and/or biological activities by various assays known in the art.

Anti-Siglec-7 Antibodies Capable of Binding Fc Gamma Receptors

In some embodiments, anti-Siglec-7 antibodies of the present disclosure retain the ability to bind Fc gamma receptors. In some embodiments, such antibodies when they have the correct epitope specificity that is compatible with receptor activation may have features that enable them to cluster and transiently stimulate, for example, the Siglec-7 receptor. In some embodiments, such antibodies may subsequently act as longer-term inhibitors of Siglec-7 expression and/or one or more activities of a Siglec-7 protein by inducing Siglec-7 degradation, Siglec-7 desensitization, Siglec-7 cleavage, Siglec-7 internalization, Siglec-7 shedding, downregulation of Siglec-7 expression, and/or lysosomal degradation of Siglec-7.

In vivo, anti-Siglec-7 antibodies of the present disclosure may cluster receptors and transiently activate Siglec-7 by any one or more of multiple potential mechanisms. Some isotypes of human antibodies such as IgG2 have, due to their unique structure, an intrinsic ability to cluster receptors, or retain receptors in a clustered configuration, thereby transiently activating receptors such as Siglec-7 without binding to an Fc receptor (e.g., White et al., (2015) Cancer Cell 27, 138-148).

In some embodiments, other antibodies may cluster receptors (e.g., Siglec-7) by binding to Fcg receptors on adjacent cells. In some embodiments, binding of the constant IgG Fc region of the antibody to Fcg receptors may lead to aggregation of the antibodies, and the antibodies in turn may aggregate the receptors to which they bind through their variable region (Chu et al (2008) Mol Immunol, 45:3926-3933; and Wilson et al., (2011) Cancer Cell 19, 101-113). In some embodiments, binding to the inhibitory Fcg receptor FcgR (FcgRIIB) that does not elicit cytokine secretion, oxidative burst, increased phagocytosis, and enhanced antibody-dependent, cell-mediated cytotoxicity (ADCC) is a preferred way to cluster antibodies in vivo, since binding to FcgRIIB is not associated with adverse immune response effects.

There are other mechanisms by which anti-Siglec-7 antibodies of the present disclosure can cluster receptors. For example, antibody fragments (e.g., Fab fragments) that are cross-linked together may be used to cluster receptors (e.g., Siglec-7) in a manner similar to antibodies with Fc regions that bind Fcg receptors, as described above. In some embodiments, cross-linked antibody fragments (e.g., Fab fragments) may transiently function as agonist antibodies if they induce receptor clustering on the cell surface and bind an appropriate epitope on the target (e.g., Siglec-7).

Therefore, in some embodiments, antibodies of the present disclosure that bind a Siglec-7 protein may include agonist antibodies that due to their epitope specificity bind Siglec-7 and transiently activate one or more Siglec-7 activities before they, for example, decrease cellular levels of Siglec-7, inhibit one or more Siglec-7 activities, and/or inhibit interaction (e.g., binding) between Siglec-7 and one or more Siglec-7 ligands. In some embodiments, such antibodies may bind to the ligand-binding site on Siglec-7 and transiently mimic the action of a natural ligand, or stimulate the target antigen to transduce signal by binding to one or more domains that are not the ligand-binding sites. In some embodiments, such antibodies would not interfere with ligand binding. In some embodiments, regardless of whether antibodies bind or do not bind to the ligand-binding site on Siglec-7, the antibodies may subsequently act as longer term inhibitors of Siglec-7 expression and/or one or more activities of a Siglec-7 protein by inducing Siglec-7 degradation, Siglec-7 desensitization, Siglec-7 cleavage, Siglec-7 internalization, Siglec-7 shedding, downregulation of Siglec-7 expression, and/or lysosomal degradation of Siglec-7.

In some embodiments, an anti-Siglec-7 antibody of the present disclosure is a transient agonist antibody that transiently induces one or more activities of a Siglec-7 protein. In some embodiments, the antibody transiently induces the one or more activities after binding to a Siglec-7 protein that is expressed in a cell. In some embodiments, the Siglec-7 protein is expressed on a cell surface. In some embodiments, the one or more activities of a Siglec-7 protein that are transiently induced by transient agonist anti-Siglec-7 antibodies of the present disclosure may include, without limitation, phosphorylation of Tyr-437 and Tyr-460 by a Src family tyrosine kinase, such as Syk, LCK, FYM, and/or ZAP70; recruitment of and binding to the tyrosine-specific protein phosphatases SHP1 and SHP2; recruitment of and binding to PLC-gamma1, which acts as a guanine nucleotide exchange factor for Dynamini-1; recruitment of and binding to SH2-domain containing protein (e.g., Crkl); recruitment of and binding to the spleen tyrosine kinase Syk; recruitment of and binding to SH3-SH2-SH3 growth factor receptor-bound protein 2 (Grb2); recruitment of and binding to multiple SH2-containing proteins; modulated expression of one or more pro-inflammatory cytokines, such as IFN-a4, IFN-beta, IL-1â, IL-1alpha, TNF-á, IL-6, IL-8, CRP, IL-20 family members, LIF, IFN-gamma, OSM, CNTF, GM-CSF, IL-11, IL-12, IL-17, IL-18, CRP, MCP-1, and MIP-1-beta; modulated expression of one or more pro-inflammatory cytokines in one or more cells selected from macrophages, neutrophils, NK cells, dendritic cells, bone marrow-derived dendritic cells, monocytes, osteoclasts, T cells, T helper cells, cytotoxic T cells, granulocytes, and microglial cells; increased expression of one or more anti-inflammatory cytokines, such as IL-4, IL-10, IL-13, IL-35, IL-16, TGF-beta, IL-1Ra, G-CSF, and soluble receptors for TNF, IFN-beta1a, IFN-beta1b, or IL-6; modulated expression of one or more anti-inflammatory cytokines in one or more cells selected from macrophages, neutrophils, NK cells, dendritic cells, bone marrow-derived dendritic cells, monocytes, osteoclasts, T cells, T helper cells, cytotoxic T cells, granulocytes, and microglial cells; modulate expression of one or more proteins selected from C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, and PYCARD; inhibition of extracellular signal-regulated kinase (ERK) phosphorylation; decreasing tyrosine phosphorylation on one or more cellular proteins, optionally, wherein the one or more cellular proteins comprise ZAP-70 and the tyrosine phosphorylation occurs on Tyr-319 of ZAP-70; modulated expression of C-C chemokine receptor 7 (CCR7); inhibition of microglial cell chemotaxis toward CCL19-expressing and CCL21-expressing cells; decreasing T cell proliferation induced by one or more cells selected from dendritic cells, bone marrow-derived dendritic cells, monocytes, microglia, M1 microglia, activated M1 microglia, M2 microglia, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, and M2 NK cells; inhibition of osteoclast production, decreased rate of osteoclastogenesis, or both; decreasing survival of one or more cells selected from dendritic cells, bone marrow-derived dendritic cells, macrophages, neutrophils, NK cells, M1 macrophages, M1 neutrophils. M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; decreasing proliferation of one or more cells selected from dendritic cells, bone marrow-derived dendritic cells, macrophages, neutrophils, NK cells, M1 macrophages, M1 neutrophils, M1 NK cells, activated M1 macrophages, activated M neutrophils, activated M1 NK cells, M2 macrophages. M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting migration of one or more cells selected from dendritic cells, bone marrow-derived dendritic cells, macrophages, neutrophils, NK cells, M1 macrophages, M1 neutrophils, M1 NK cells, activated M macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M microglia, activated M microglia, and M2 microglia; inhibiting one or more functions of one or more cells selected from dendritic cells, bone marrow-derived dendritic cells, macrophages, neutrophils, NK cells, M1 macrophages, M1 neutrophils, M1 NK cells, activated M macrophages, activated M neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting maturation of one or more cells selected from dendritic cells, bone marrow-derived dendritic cells, macrophages, neutrophils, NK cells, M1 macrophages, M1 neutrophils, M1 NK cells, activated M macrophages, activated M neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M microglia, and M2 microglia; inhibition of one or more types of clearance selected from apoptotic neuron clearance, nerve tissue debris clearance, dysfunctional synapse clearance, non-nerve tissue debris clearance, bacteria clearance, other foreign body clearance, disease-causing protein clearance, disease-causing peptide clearance, and tumor cell clearance; optionally wherein the disease-causing protein is selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein. Repeat-associated non-ATG (RAN) translation products. DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides and the tumor cell is from a cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; inhibition of phagocytosis of one or more of apoptotic neurons, nerve tissue debris, dysfunctional synapses, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells are from a cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer, binding to Siglec-7 ligand on tumor cells; binding to Siglec-7 ligand on cells selected from neutrophils, dendritic cells, bone marrow-derived dendritic cells, monocytes, microglia, macrophages, and NK cells; inhibition of tumor cell killing by one or more of microglia, macrophages, neutrophils, NK cells, dendritic cells, bone marrow-derived dendritic cells, neutrophils, T cells, T helper cells, or cytotoxic T cells; inhibiting anti-tumor cell proliferation activity of one or more of microglia, macrophages, neutrophils, NK cells, dendritic cells, bone marrow-derived dendritic cells, neutrophils, T cells, T helper cells, or cytotoxic T cells; inhibition of anti-tumor cell metastasis activity of one or more of microglia, macrophages, neutrophils, NK cells, dendritic cells, bone marrow-derived dendritic cells, neutrophils, T cells, T helper cells, or cytotoxic T cells; inhibition of one or more ITAM motif containing receptors, optionally wherein the one or more ITAM motif containing receptors are selected from TREM1, TREM2. Sirp beta. FcgR, DAP10, and DAP12; inhibition of signaling by one or more pattern recognition receptors (PRRs), optionally wherein the one or more PRRs are selected from receptors that identify pathogen-associated molecular patterns (PAMPs), receptors that identify damage-associated molecular patterns (DAMPs), and any combination thereof; inhibition of one or more receptors comprising the motif D/Ex$_{0-2}$YxxL/IX$_{6-8}$YxxL/I (SEQ ID NO: 537); inhibition of signaling by one or more Toll-like receptors; inhibition of the JAK-STAT signaling pathway; inhibition of nuclear factor kappa-light-chain-enhancer of activated B cells (NFêB); de-phosphorylation of an ITAM motif containing receptor; modulated expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils, T cells, T helper cells, or cytotoxic T cells; increasing expression of one or more Siglec-7-dependent genes; normalization of disrupted Siglec-7-dependent gene expression; decreasing expression of one or more ITAM-dependent genes, optionally wherein the one more ITAM-dependent genes are activated by nuclear factor of activated T cells (NFAT) transcription factors; promoting or rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; increasing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells into tumors; increasing the number of tumor-promoting myeloid/granulocytic immune-suppressive cells in a tumor, in peripheral blood, or other lymphoid organ; enhancing tumor-promoting activity of myeloid-derived suppressor cells; increasing expression of tumor-promoting cytokines in a tumor or in peripheral blood, optionally wherein the tumor-promoting cytokines are TGF-beta or IL-10; increasing tumor infiltration of tumor-promoting FoxP3+ regulatory T lymphocytes; enhancing tumor-promoting activity of myeloid-derived suppressor cells (MDSC); decreasing activation of tumor-specific T lymphocytes with tumor killing potential; decreasing infiltration of tumor-specific NK cells with tumor killing potential; decreasing the tumor killing potential of NK cells; decreasing infiltration of tumor-specific B lymphocytes with potential to enhance immune response; decreasing infiltration of tumor-specific T lymphocytes with tumor killing potential; increasing tumor volume; increasing tumor growth rate; increasing metastasis; increasing rate of tumor recurrence; decreasing efficacy of one or more immune-therapies that modulate anti-tumor T cell responses, optionally wherein the one or more immune-therapies are immune-therapies that target one or more target proteins selected from PD1/PDL1, CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG. DR-5, TREM1, TREM2, CSF-1 receptor, and any combination thereof, or of one or more cancer vaccines; inhibition of PLCã/PKC/calcium mobilization; and inhibition of PI3K/Akt, Ras/MAPK signaling. Anti-Siglec-7 antibodies of the present disclosure may be tested for their ability to transiently induce one or more activities of a Siglec-7 protein utilizing any suitable technique or assay known in the art and disclosed herein. Regardless of the activities that such antibodies transiently induce, such antibodies may subsequently act as longer-term inhibitors of Siglec-7 expression and/or one or more activities of a Siglec-7 protein by inducing Siglec-7 degradation, Siglec-7 desensitization, Siglec-7 cleavage, Siglec-7 internalization, Siglec-7 shedding, downregulation of Siglec-7 expression, and/or lysosomal degradation of Siglec-7. In some embodiments, the Siglec-7 antibody transiently induces one or more activities of a Siglec-7 protein independently of binding to an Fc receptor.

Exemplary antibody Fc isotypes and modifications are provided in Table C below. In some embodiments, an anti-Siglec-7 antibody of the present disclosure that is capable of binding an Fc gamma receptor has an Fc isotype listed in Table C below.

TABLE C

Exemplary anti-Siglec-7 antibody Fc isotypes that are capable of binding Fc gamma receptor

| Fc Isotype | Mutation (EU numbering scheme) |
| --- | --- |
| IgG1 | N297A |
| IgG1 | D265A and N297A |
| IgG1 | D270A |
| IgG1 | L234A and L235A<br>L234A and G237A<br>L234A and L235A and G237A |
| IgG1 | D270A, and/or P238D, and/or L328E, and/or S267E/L328F, and or E233, and or/ G237D, and/or H268D, and/or P271G, and/or A330R |
| IgG1 | P238D and L328E and E233D and G237D and H268D and P271G and A330R |
| IgG1 | P238D and L328E and G237D and H268D and P271G and A330R |
| IgG1 | P238D and S267E and L328F and E233D and G237D and H268D and P271G and A330R |

TABLE C-continued

Exemplary anti-Siglec-7 antibody Fc isotypes that are capable of binding Fc gamma receptor

| Fc Isotype | Mutation (EU numbering scheme) |
|---|---|
| IgG1 | P238D and S267E and L328F and G237D and H268D and P271G and A330R |
| I2G2 | V234A and G237A |
| IgG4 | L235A and G237A and E318A |
| IgG4 | S228P and L236E |
| IgG2/4 hybrid | IgG2 aa 118 to 260 and IgG4 aa 261 to 447 H268Q and V309L; and A330S and P331S |
| IgG1 | C226S and C229S and E233P and L234V and L235A |
| IgG1 | L234F and L235E and P331S |
| IgG2 | C232S or C233S |
| IgG2 | A330S and P331S |
| IgG1 | S267E, and L328F<br>S267E alone |
| IgG2 | S267E and L328F |
| IgG4 | S267E and L328F |
| IgG2 | WT HC with Kappa (light chain) LC<br>HC C127S with Kappa LC<br>Kappa LC C214S<br>Kappa LC C214S and HC C233S<br>Kappa LC C214S and HC C232S<br>Any of the above listed mutations together with P330S and P331S mutations<br>F(ab')2 fragment of WT IgG1 and any of the above listed mutations |
| IgG1 | Substitute the Constant Heavy 1 (CH1) and hinge region of IgG1 With CH1 and hinge region of IGg2<br>ASTKGPSVFP LAPCSRSTSE STAALGCLVK<br>DYFPEPVTVS WNSGALTSGV HTFPAVLQSS<br>GLYSLSSVVT VPSSNGGTQT YTCNVDHKPS<br>NTKVDKTVER KCCVECPPCP (SEQ ID NO: 475)<br>With a Kappa LC |
| IgG1 | Any of the above listed mutations together with A330L and/or L234F and/or L235E and/or P331S |
| IgG1, IgG2, or IgG4 | Any of the above listed mutations together with M252Y and/or S254T and/or T256E |
| Mouse IgG1 | For mouse disease models |
| IgG4 | WT |

In addition to the isotypes described in Table C, and without wishing to be bound to theory, it is thought that antibodies with human IgG1 or IgG3 isotypes and mutants thereof (e.g. Strohl (2009) Current Opinion in Biotechnology 2009, 20:685-691) that bind the Fcg Receptors I, IIA, IIC, IIIA, IIIB in human and/or Fcg Receptors I, III and IV in mouse, may also act as transient agonist antibodies.

In some embodiments, the Fc gamma receptor-binding antibody is of the IgG class, the IgM class, or the IgA class. In some embodiments, the Fc gamma receptor-binding antibody has an IgG1, IgG2. IgG3, or IgG4 isotype.

In certain embodiments, the Fc gamma receptor-binding antibody has an IgG2 isotype. In some embodiments, the Fc gamma receptor-binding antibody contains a human IgG2 constant region. In some embodiments, the human IgG2 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from V234A (Alegre et al., (1994) *Transplantation* 57:1537-1543, 31; Xu et al., (2000) *Cell Immunol,* 200:16-26), G237A (Cole et al. (1999) *Transplantation,* 68:563-571), H268Q, V309L, A330S, P331S (US 2007/0148167; Armour et al. (1999) *Eur J Immunol* 29: 2613-2624; Armour et al. (2000) *The Haematology Journal*

1(Suppl.1):27; Armour et al. (2000) *The Haematology Journal* 1(Suppl.1):27), C232S, and/or C233S (White et al. (2015) *Cancer Cell* 27, 138-148), S267E, L328F (Chu et al., (2008) *Mol Immunol,* 45:3926-3933), M252Y, S254T, and/or T256E, where the amino acid position is according to the EU or Kabat numbering convention.

In some embodiments, the Fc gamma receptor-binding antibody has an IgG2 isotype with a heavy chain constant domain that contains a C127S amino acid substitution, where the amino acid position is according to the EU or Kabat numbering convention (White et al., (2015) *Cancer Cell* 27, 138-148; Lightle et al., (2010) *PROTEIN SCIENCE* 19:753-762; and WO2008079246).

In some embodiments, the Fc gamma receptor-binding antibody has an IgG2 isotype with a Kappa light chain constant domain that contains a C214S amino acid substitution, where the amino acid position is according to the EU or Kabat numbering convention (White et al., (2015) Cancer Cell 27, 138-148; Lightle et al., (2010) PROTEIN SCIENCE 19:753-762; and WO2008079246).

In certain embodiments, the Fc gamma receptor-binding antibody has an IgG1 isotype. In some embodiments, the Fc gamma receptor-binding antibody contains a mouse IgG1 constant region. In some embodiments, the Fc gamma receptor-binding antibody contains a human IgG1 constant region. In some embodiments, the human IgG1 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A (Bolt S et al. (1993) *Eur J Immunol* 23:403-411), D265A (Shields et al. (2001) *R. J. Biol. Chem.* 276, 6591-6604), D270A, L234A, L235A (Hutchins et al. (1995) *Proc Natl Acad Sci* USA, 92:11980-11984; Alegre et al., (1994) *Transplantation* 57:1537-1543, 31; Xu et al., (2000) *Cell Immunol,* 200:16-26). G237A (Alegre et al. (1994) *Transplantation* 57:1537-1543, 31; Xu et al. (2000) *Cell Immunol,* 200:16-26), P238D, L328E, E233D, G237D, H268D, P271G, A330R, C226S, C229S, P233P, L234V, L234F, L235E (McEarchern et al., (2007) *Blood,* 109:1185-1192), P331S (Sazinsky et al., (2008) *Proc Natl Acad Sci USA* 2008, 105:20167-20172), S267E, L328F, A330L, M252Y, S254T, T256E, N297Q, P238S, P238A, A327Q, A327G, P329A, K322A, and/or T394D where the amino acid position is according to the EU or Kabat numbering convention.

In some embodiments, the antibody includes an IgG2 isotype heavy chain constant domain 1(CH1) and hinge region (White et al., (2015) Cancer Cell 27, 138-148). In certain embodiments, the IgG2 isotype CH1 and hinge region contain the amino acid sequence of ASTKGPSVF-PLAPCSRSTSESTAALGCLVKDYF-PEPVTVSWNSGALTSGVHTFPAVLQSSGLY SLSSVVTVPSSNFGTQTYTCNVDHKPSNTKVDKTV-ERKCCVECPPCP (SEQ ID NO: 475). In some embodiments, the antibody Fc region contains a S267E amino acid substitution, a L328F amino acid substitution, or both, and/or a N297A or N297Q amino acid substitution, where the amino acid position is according to the EU or Kabat numbering convention.

In certain embodiments, the Fc gamma receptor-binding antibody has an IgG4 isotype. In some embodiments, the Fc gamma receptor-binding antibody contains a human IgG4 constant region. In some embodiments, the human IgG4 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from L235A, G237A, S228P, L236E (Reddy et al., (2000) *J Immunol,* 164:1925-1933), S267E, E318A, L328F, M252Y, S254T, and/or T256E, where the amino acid position is according to the EU or Kabat numbering convention.

In certain embodiments, the Fc gamma receptor-binding antibody has a hybrid IgG2/4 isotype. In some embodiments, the Fc gamma receptor-binding antibody includes an amino acid sequence containing amino acids 118 to 260 according to EU or. Kabat numbering of human IgG2 and amino acids 261-447 according to EU or. Kabat numbering of human IgG4 (WO 1997/11971; WO 2007/106585).

In certain embodiments, the antibody contains a mouse IgG4 constant region (Bartholomaeus, et al. (2014). J. Immunol. 192, 2091-2098).

In some embodiments, the Fc region further contains one or more additional amino acid substitutions selected from A330L, L234F; L235E, or P331S according to EU or, Kabat numbering; and any combination thereof.

Inert Antibodies

Another class of anti-Siglec-7 antibodies of the present disclosure includes inert antibodies. As used herein, "inert" antibodies refer to antibodies that specifically bind their target antigen (e.g., Siglec-7) but do not modulate (e.g., decrease/inhibit or activate/induce) antigen function. For example, in the case of Siglec-7, inert antibodies do not modulate cellular levels of Siglec-7, do not modulate interaction (e.g., binding) between Siglec-7 and one or more Siglec-7 ligands, or do not modulate one or more activities of a Siglec-7 protein. In some embodiments, antibodies that do not have the ability to cluster Siglec-7 on the cell surface may be inert antibodies even if they have an epitope specificity that is compatible with receptor activation.

In some embodiments, antibodies that bind a Siglec-7 protein may include antibodies that bind Siglec-7 but, due to their epitope specificity, or characteristics, do not decrease cellular levels of Siglec-7 and/or inhibit interaction (e.g., binding) between Siglec-7 and one or more Siglec-7 ligands. In some embodiments, such antibodies can be used as cargo to, for example, transport toxins (e.g., chemotherapeutics) into tumor cells. Such antibodies may be superior to current commercially available anti-Siglec-7 antibodies, such as antibody Mab1138 (R&D Systems; Cat. No. MAB 1138). In some embodiments, inert anti-Siglec-7 antibodies of the present disclosure may be superior to commercial antibodies, such as antibody Mab1138, because antibodies that do not decrease cellular levels of Siglec-7 will leave Siglec-7 intact on the surface of tumor cells for targeting by additional toxin-conjugated antibodies. In contrast, antibodies that decrease cellular levels of Siglec-7 will remove Siglec-7 from the cell surface and will lead to protection of the tumor cells from further targeting by toxin-conjugated antibodies. Therefore, in some embodiments, antibodies of the present disclosure are inert antibodies that bind Siglec-7 but are incapable of decreasing cellular levels of Siglec-7, inhibiting interaction (e.g., binding) between Siglec-7 and one or more Siglec-7 ligands, or inducing one or more activities of a Siglec-7 protein.

Antibodies that either decrease or do not decrease cellular levels of Siglec-7 on cells can be combined with an inert Fc region that displays reduced binding to one or more Fcg Receptor. Examples of such Fc regions and modifications are provided in Table D below. In some embodiments, the antibody with an inert Fc region has an Fc isotype listed in Table D below.

Antagonist Anti-Siglec-7 Antibodies

A third class of anti-Siglec-7 antibodies of the present disclosure includes antagonist antibodies. In some embodiments, antibodies that bind a Siglec-7 protein may include antagonist antibodies that reduce cellular levels of Siglec-7, inhibit interaction (e.g., binding) between Siglec-7 and/or one or more Siglec-7 ligands, and inhibit one or more activities of a Siglec-7 protein. Such antibodies inhibit one or more activities of a Siglec-7 protein either by preventing interaction (e.g., binding) between Siglec-7 and one or more Siglec-7 ligands or by preventing signal transduction from the extracellular domain of Siglec-7 into the cell cytoplasm in the presence of one or more Siglec-7 ligands. Antagonist antibodies also can inhibit one or more activities of a Siglec-7 protein by decreasing cell surface levels of Siglec-7 by inducing Siglec-7 degradation, Siglec-7 desensitization, Siglec-7 cleavage, Siglec-7 internalization, Siglec-7 shedding, downregulation of Siglec-7 expression, and/or lysosomal degradation of Siglec-7. In some embodiments, such antagonist anti-Siglec-7 antibodies may not transiently activate Siglec-7.

In some embodiments, antagonist anti-Siglec-7 antibodies of the present disclosure may have the epitope specificity of a transient agonist anti-Siglec-7 antibody of the present disclosure, but have an Fc domain that is not capable of binding Fcg receptors and thus is unable to, for example, transiently clustering and activating Siglec-7.

In some embodiments, antagonist anti-Siglec-7 antibodies of the present disclosure have, without limitation, one or more of the following activities: the ability to decrease binding of a Siglec-7 protein to one or more Siglec-7 ligands, such as sialic acid-containing glycolipids or sialic acid-containing glycoproteins, the ability to decrease the binding of a suppressor of cytokine signaling (SOCS) protein (e.g., SOCS3 protein) to a Siglec-7 protein, the ability to increase the proteasomal degradation of a Siglec-7 protein, the ability to reduce functional expression of Siglec-7 on the surface of circulating dendritic cells, macrophages, monocytes, T cells, and/or microglia, the ability to decrease or inhibit phosphorylation of Tyr-437 and Tyr-460 by a Src family tyrosine kinase, such as Syk, LCK. FYM, and/orZAP70; the ability to inhibit recruitment of and binding to the tyrosine-specific protein phosphatases SHP 1 and SHP2; the ability to inhibit recruitment of and binding to PLC-gamma1, which acts as a guanine nucleotide exchange factor for Dynamini-1; the ability to inhibit recruitment of and binding to SH2-domain containing protein (e.g., Crkl); the ability to inhibit recruitment of and binding to the spleen tyrosine kinase Syk; the ability to inhibit recruitment of and binding to SH3-SH2-SH3 growth factor receptor-bound protein 2 (Grb2); the ability to inhibit recruitment of and binding to multiple SH2-containing proteins; the ability to modulate expression of one or more pro-inflammatory cytokines, optionally wherein the one or more anti-inflammatory cytokines are selected from IFN-a4, IFN-beta, IL-1β, IL-1alpha, TNF-α, IL-6, IL-8, CRP, IL-20 family members, LIF, IFN-gamma, OSM, CNTF, GM-CSF, IL-11, IL-12, IL-17, IL-18, IL-33, MCP-1, and MIP-1-beta; the ability to modulate expression of one or more pro-inflammatory cytokines in one or more cells selected from macrophages, neutrophils, NK cells, dendritic cells, bone marrow-derived dendritic cells, monocytes, osteoclasts, T cells, T helper cells, cytotoxic T cells, granulocytes, and microglial cells; the ability to modulate expression of one or more anti-inflammatory cytokines, optionally wherein the one or more anti-inflammatory cytokines are selected from IL-4, IL-10, IL-13, IL-35, IL-16, TGF-beta, IL-Ra, G-CSF, and soluble receptors for TNF, IFN-beta1a, IFN-beta1b, or IL-6; the ability to modulate expression of one or more anti-inflammatory cytokines in one or more cells selected from macrophages, neutrophils, NK cells, dendritic cells, bone marrow-derived dendritic cells, monocytes, osteoclasts, T cells, T helper cells, cytotoxic T cells, granulocytes, and microglial cells; the ability to modulate expression of one or more proteins selected from C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, and PYCARD; the ability to counteract inhibition of extracellular signal-regulated kinase (ERK) phosphorylation; the ability to prevent decreased tyrosine phosphorylation on one or more cellular proteins, optionally, wherein the one or more cellular proteins comprise ZAP-70 and the tyrosine phosphorylation occurs on Tyr-319 of ZAP-70; the ability to modulate expression of C-C chemokine receptor 7 (CCR7); the ability to prevent inhibition of microglial cell chemotaxis toward CCL19-expressing and CCL21-expressing cells; the ability to prevent decreasing T cell proliferation induced by one or more cells selected from dendritic cells, bone marrow-derived dendritic cells, monocytes, microglia, M1 microglia, activated M1 microglia, M2 microglia, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, and M2 NK cells; the ability to prevent inhibition of osteoclast production, the ability to prevent decreased rate of osteoclastogenesis, or both; the ability to prevent decreased survival of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia. M microglia, activated M microglia, and M2 microglia; the ability to prevent decreased proliferation of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; the ability to enhance migration of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; the ability to prevent a decrease in one or more functions of one or more cells selected from dendritic cells, bone marrow-derived dendritic cells, macrophages, neutrophils, NK cells, M1 macrophages. M neutrophils, M1 NK cells, activated M1 macrophages, activated M1 neutrophils, activated M1 NK cells, M2 macrophages, M2 neutrophils, M2 NK cells, monocytes, osteoclasts. T cells, T helper cells, cytotoxic T cells, granulocytes, neutrophils, microglia, M1 microglia, activated M1 microglia, and M2 microglia; the ability to enhance maturation of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; the ability to enhance one or more types of clearance selected from apoptotic neuron clearance, nerve tissue debris clearance, dysfunctional synapse clearance, non-nerve tissue debris clearance, bacteria clearance, other foreign body clearance, disease-causing protein clearance, disease-causing peptide clearance, and tumor cell clearance; optionally wherein the disease-causing protein is selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10. Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein. Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides and the tumor cell is from a cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; inhibition of phagocytosis of one or more of apoptotic neurons, nerve tissue debris, dysfunctional synapses, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10. Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein. Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells are from a cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer; binding to Siglec-7 ligand on tumor cells; binding to Siglec-7 ligand on cells selected from neutrophils, dendritic cells, bone marrow-derived dendritic cells, monocytes, microglia, macrophages, and NK cells; inhibition of tumor cell killing by one or more of microglia, macrophages, neutrophils, NK cells, dendritic cells, bone marrow-derived dendritic cells, neutrophils, T cells, T helper cells, or cytotoxic T cells; activating anti-tumor cell proliferation activity of one or more of microglia, macrophages, neutrophils, NK cells, dendritic cells, bone marrow-derived dendritic cells, neutrophils. T cells, T helper cells, or cytotoxic T cells; the ability to enhance anti-tumor cell metastasis activity of one or more of microglia, macrophages, neutrophils, NK cells, dendritic cells, bone marrow-derived dendritic cells, neutrophils, T cells, T helper cells, or cytotoxic T cells; the ability to enhance the activity of one or more ITAM motif containing receptors, optionally wherein the one or more ITAM motif containing receptors are selected from TREM1, TREM2, SIRP beta. FcgR, DAP10, and DAP12; the ability to enhance signaling by one or more pattern recognition receptors (PRRs), optionally wherein the one or more PRRs are selected from receptors that identify pathogen-associated molecular patterns (PAMPs), receptors that identify damage-associated molecular patterns (DAMPs), and any combination thereof; the ability to enhance activity of one or more receptors comprising the motif $D/Ex_{0-2}YxxL/IX_{6-8}YxxL/I$ (SEQ ID NO: 537); the ability to enhance signaling by one or more Toll-like receptors; the ability to enhance the JAK-STAT signaling pathway; the ability to enhance the activity of nuclear factor kappa-light-chain-enhancer of activated B cells (NFêB); the ability to increase phosphorylation of an ITAM motif containing receptor; the ability to increase expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils, T cells, T helper cells, or cytotoxic T cells; the ability to decrease expression of one or more Siglec-7-dependent genes; the ability to enhance expression of one or more ITAM-dependent genes, optionally wherein the one more ITAM-dependent genes are activated by nuclear factor of activated T cells (NFAT) transcription factors; the ability to decrease or otherwise inhibit differentiation of one or more of immunosuppressor dendritic cells, immunosuppressor macrophages, immunosuppressor neutrophils, immunosuppressor NK cells, myeloid derived suppressor cells, tumor-associated macrophages, tumor-associated neutrophils, tumor-associated NK cells, and regulatory T cells; the ability to decrease or otherwise inhibit functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; the ability to decrease or otherwise inhibit infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells into tumors; the ability to decrease or otherwise inhibit the number of tumor-promoting myeloid/granulocytic immune-suppressive cells in a tumor, in peripheral blood, or other lymphoid organ; the ability to decrease or otherwise inhibit tumor-promoting activity of myeloid-derived suppressor cells; the ability to decrease or otherwise inhibit expression of tumor-promoting cytokines, such as TGF-beta or IL-10, in a tumor or in peripheral blood; the ability to decrease or otherwise inhibit tumor infiltration of tumor-promoting FoxP3+ regulatory T lymphocytes; the ability to decrease or otherwise inhibit tumor-promoting activity of myeloid-derived suppressor cells (MDSC); the ability to increase or otherwise enhance tumor-specific T lymphocytes with tumor killing potential; the ability to increase or otherwise enhance infiltration of tumor-specific NK cells with tumor killing potential; the ability to increase or otherwise enhance the tumor killing potential of NK cells; the ability to increase or otherwise enhance infiltration of tumor-specific B lymphocytes with potential to enhance immune response; the ability to increase or otherwise enhance infiltration of tumor-specific T lymphocytes with tumor killing potential; the ability to decrease tumor volume; the ability to decrease tumor growth rate; the ability to decrease or otherwise inhibit metastasis; the ability to decrease rate of tumor recurrence; the ability to increase or otherwise enhance efficacy of one or more immune-therapies that modulate anti-tumor T cell responses, optionally wherein the one or more immune-therapies are immune-therapies that target one or more target proteins selected from PD1/PDL1, CD40, OX40, ICOS, CD28, CD137/4-1BB, CD27. GITR, PD-L1, CTLA4, PD-L2, PD-1, B7-H3, B7-H4, HVEM, BTLA, KIR, GAL9, TIM3, A2AR, LAG, DR-5, TREM1, TREM2, CSF-1 receptor, and any combination thereof, or of one or more cancer vaccines; the ability to increase or otherwise enhance PLCã/PKC/calcium mobilization; and the ability to increase or otherwise enhance PI3K/Akt, Ras/MAPK signaling.

In some embodiments, antagonist anti-Siglec-7 antibodies of the present disclosure have an Fc region that displays reduced binding to one or more Fcg Receptor. Examples of such Fc regions and modifications are provided in Table D below. In some embodiments, the antibody has an Fc isotype listed in Table D below.

Antibody Fc Isotypes with Reduced Binding to Fc Gamma Receptors

In some embodiments, anti-Siglec-7 antibodies with reduced binding to Fc gamma receptors have an Fc isotype listed in Table D below.

TABLE D

Exemplary anti-Siglec-7 antibody Fc isotypes with reduced binding to Fc gamma receptor

| Fc Isotype | Mutation (EU numbering scheme) |
|---|---|
| IgG1 | N297A or N297Q |
| IgG1 | D265A, D270A, and N297A |
| IgG1 | L234A and L235A |
| IgG2 | V234A and G237A |
| IgG4 | F235A and G237A and E318A |
| | E233P and/or F234V |
| | N297A or N297Q |
| IgG4 | S228P and L236E |
| | S241P |
| | S241P and L248E |
| | S228P and F234A and L235A |
| IgG2 | H268Q and V309L and A330S and P331S |
| IgG1 | C220S and C226S and C229S and P238S |

TABLE D-continued

Exemplary anti-Siglec-7 antibody Fc isotypes with reduced binding to Fc gamma receptor

| Fc Isotype | Mutation (EU numbering scheme) |
|---|---|
| IgG1 | C226S and C229S and E233P and L234V, and L235A |
| IgG1 | E233P and L234V and L235A and G236-deleted |
| | P238A |
| | D265A |
| | N297A |
| | A327Q or A327G |
| | P329A |
| IgG1 | K322A and L234A and L235A |
| IgG1 | L234Fand L235E and P331S |
| IgG1 or IgG4 | T394D |
| IgG2 | C232S or C233S |
| | N297Aor N297Q |
| IgG2 | V234A and G237A and P238S and H268A and V309L and A330S and P331S |
| IgG1, IgG2, or IgG4 | delta a, b , c, ab, ac, g modifications |
| IgG1 | Any of the above listed mutations together with A330L or L234F and/or L235E and/or P331S |
| IgG1, IgG2, or IgG4 | Any of the above listed mutations together with M252Y and/or S254T and/or T256E |

In certain embodiments, the anti-Siglec-7antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the Fc region contains one or more modifications. For example, in some embodiments, the Fc region contains one or more amino acid substitutions (e.g., relative to a wild-type Fc region of the same isotype).

In some embodiments, the one or more amino acid substitutions are selected from N297A, N297Q (Bolt S et al. (1993) Eur J Immunol 23:403-411), D270A, D265A, L234A, L235A (McEarchern et al., (2007) Blood, 109:1185-1192). C226S, C229S (McEarchern et al., (2007) Blood, 109:1185-1192), P238S (Davis et al., (2007) J Rheumatol. 34:2204-2210), E233P, L234V (McEarchern et al., (2007) Blood, 109:1185-1192), P238A, A327Q, A327G, P329A (Shields R L. et al., (2001) J Biol Chem. 276(9):6591-604), K322A, L234F, L235E (Hezareh, et al., (2001) J Virol 75, 12161-12168; Oganesyan et al., (2008). Acta Crystallographica 64, 700-704), P331S (Oganesyan et al., (2008) Acta Crystallographica 64, 700-704), T394D (Wilkinson et al. (2013) MAbs 5(3): 406-417), A330L, M252Y, S254T, and/or T256E, where the amino acid position is according to the EU or Kabat numbering convention. In certain embodiments, the Fc region further includes an amino acid deletion at a position corresponding to glycine 236 according to the EU or Kabat numbering convention.

In some embodiments, the anti-Siglec-7 antibody has an IgG1 isotype with a heavy chain constant region that contains a C220S amino acid substitution according to the EU or Kabat numbering convention. In some embodiments, the Fc region further contains one or more additional amino acid substitutions selected from t A330L, L234F; L235E, and/or P331 S according to EU or Kabat numbering convention. In certain embodiments, the anti-Siglec-7 antibody has an IgG2 isotype. In some embodiments, the anti-Siglec-7 antibody contains a human IgG2 constant region. In some embodiments, the human IgG2 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from P238S. V234A, G237A, H268A, H268Q, H268E, V309L, N297A, N297Q, V309L, A330S, P331S, C232S, C233S, M252Y, S254T, and/or T256E, where the amino acid position is according to the EU or Kabat numbering convention (Vafa O, et al., (2014) Methods 65:114-126).

In certain embodiments, the anti-Siglec-7 antibody has an IgG4 isotype. In some embodiments, the anti-Siglec-7 antibody contains a human IgG4 constant region. In some embodiments, the human IgG4 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from E233P, F234V, L235A, G237A, E318A (Hutchins et al. (1995) *Proc Natl Acad Sci USA*, 92:11980-11984), S228P, L234A/F234A, L236E, S241P, L248E (Reddy et al., (2000) *J Immunol.* 164:1925-1933; Angal et al., (1993) *Mol Immunol.* 30(1):105-8; U.S. Pat. No. 8,614,299 B2; Vafa O. et al., (2014) Methods 65:114-126), T394D, M252Y, S254T, T256E, N297A, and/or N297Q, where the amino acid position is according to the EU or Kabat numbering convention.

In some embodiments, the Fc region further contains one or more additional amino acid substitutions selected from a M252Y, S254T, and/or T256E, where the amino acid position is according to the EU or Kabat numbering convention.

Further IgG Mutations

In some embodiments, one or more of the IgG1 variants described herein may be combined with an A330L mutation (Lazar et al., (2006) Proc Natl Acad Sci USA, 103:4005-4010), or one or more of L234F, L235E, and/or P331S mutations (Sazinsky et al., (2008) Proc Natl Acad Sci USA. 105:20167-20172), where the amino acid position is according to the EU or Kabat numbering convention, to eliminate complement activation. In some embodiments, the IgG variants described herein may be combined with one or more mutations to enhance the anti-Siglec-7 antibody half-life in human serum (e.g. M252Y, S254T, T256E mutations according to the EU or Kabat numbering convention) (Dall'Acqua et al., (2006) J Biol Chem. 281:23514-23524; and Strohl e al., (2009) Current Opinion in Biotechnology, 20:685-691).

In some embodiments, an IgG4 variant of the present disclosure may be combined with an S228P mutation according to the EU or Kabat numbering convention (Angal et al., (1993) Mol Immunol. 30:105-108), an F234A mutation, an L235A mutation, and/or with one or more mutations described in Peters et al., (2012) J Biol Chem. 13; 287(29): 24525-33) to enhance antibody stabilization.

In some embodiments, anti-Siglec-7 antibodies of the present disclosure have an IgG4 isotype. In some embodiments, the antibody Fc region contains an S228P amino acid substitution at residue position 228, an F234A amino acid substitution at residue position 234, and an L235A amino acid substitution at residue position 235, according to EU numbering.

Bispecific Antibodies

Certain aspects of the present disclosure relate to bispecific antibodies that bind to one or more domains on a Siglec-7 protein of the present disclosure and a second antigen. Methods of generating bispecific antibodies are well known in the art and described herein. In some embodiments, bispecific antibodies of the present disclosure bind to one or more amino acid residues of a Siglec-7 protein of the present disclosure, such as one or more amino acid residues of human Siglec-7 (SEQ ID NO: 1), or amino acid residues on a Siglec-7 protein corresponding to amino acid residues of SEQ ID NO: 1. In some embodiments, bispecific antibodies of the present disclosure recognize a first antigen and a second antigen. In some embodiments, the first antigen is a Siglec-7 protein or a naturally occurring variant thereof. In some embodiments, the second antigen is also a Siglec-7 protein, or a naturally occurring variant thereof. In some embodiments, the second antigen is an antigen facilitating transport across the blood-brain-barrier (see, e.g., Gabathuler R., *Neurobiol. Dis.* 37 (2010) 48-57). Such second antigens include, without limitation, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM30(A), a protein transduction domain, TAT, Syn-B, penetratin, a poly-arginine peptide. Angiopep peptides such as ANG1005 (see, e.g., Gabathuler, 2010), and other cell surface proteins that are enriched on blood-brain barrier endothelial cells (see, e.g., Daneman et al., PLoS One. 2010 Oct. 29; 5(10): e13741). In some embodiments, the second antigen is a disease-causing protein including, without limitation, amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products. DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides. In some embodiments, the second antigen is one or more ligands and/or proteins expressed on immune cells, including without limitation, CD40, OX40, ICOS, CD28, CD137/4-1BB, CD27, GITR, PD-LL. CTLA4, PD-L2, PD-1, B7-H3, B7-H4, HVEM, BTLA, KIR, GAL9, TIM3, A2AR, LAG. DR-5, CD3, and phosphatidylserine. In some embodiments, the second antigen is a protein, lipid, polysaccharide, or glycolipid expressed on one or more tumor cells.

Antibody Fragments

Certain aspects of the present disclosure relate to antibody fragments that bind to one or more of a Siglec-7 protein of the present disclosure, a naturally occurring variant of a Siglec-7 protein, and a disease variant of a Siglec-7 protein. In some embodiments, the antibody fragment is an Fab, Fab', Fab'-SH, F(ab')2. Fv or scFv fragment.

In some embodiments, the antibody fragment is used in combination with a second Siglec-7 antibody and/or with one or more antibodies that specifically bind a disease-causing protein selected from: amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein. Repeat-associated non-ATG (RAN) translation products. DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and any combination thereof, or with one or more antibodies that bind an immunomodulatory protein selected from: CD40, OX40, ICOS, CD28. CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, TREM1, TREM2, CSF-1 receptor, CD33, Siglec-5, Siglec-9, Siglec-11, phosphatidylserine, and any combination thereof.

In some embodiments, antibody fragments of the present disclosure may be functional fragments that bind the same epitope as any of the anti-Siglec-7 antibodies of the present disclosure. In some embodiments, the antibody fragments are miniaturized versions of the anti-Siglec-7 antibodies or antibody fragments of the present disclosure that have the same epitope of the corresponding full-length antibody, but have much smaller molecule weight. Such miniaturized anti-Siglec-7 antibody fragments may have better brain penetration ability and a shorter half-life, which is advantageous for imaging and diagnostic utilities (see e.g., Lütje S et al., *Bioconjug Chem.* 2014 Feb. 19; 25(2):335-41; Tavaré R et al., *Proc Natl Acad Sci USA.* 2014 Jan. 21; 11 (3):1108-13; and Wiehr S et al., *Prostate.* 2014 May; 74(7): 743-55). Accordingly, in some embodiments, anti-Siglec-7 antibody fragments of the present disclosure have better brain penetration as compared to their corresponding full-length antibodies and/or have a shorter half-life as compared to their corresponding full-length antibodies.

Antibody Frameworks

Any of the antibodies described herein further include a framework. In some embodiments, the framework is a human immunoglobulin framework. For example, in some embodiments, an antibody (e.g., an anti-Siglec-7 antibody) comprises HVRs as in any of the above embodiments and further comprises an acceptor human framework, e.g., a human immunoglobulin framework or a human consensus framework. Human immunoglobulin frameworks may be part of the human antibody, or a non-human antibody may be humanized by replacing one or more endogenous frameworks with human framework region(s). Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad Sci. USA.* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In some embodiments, an antibody comprises a light chain variable region comprising an HVR-L1, an HVR-L2, and an HVR-L3 of the present disclosure and one, two, three or four of the light chain framework regions as shown in Table 3A. In some embodiments, an antibody comprises a heavy chain variable region comprising an HVR-H1, an HVR-H2, and an HVR-H3 of the present disclosure and one, two, three or four of the heavy chain framework regions as shown in Table 3B. In some embodiments, an antibody comprises a light chain variable region comprising an HVR-L1, an HVR-L2, and an HVR-L3 of the present disclosure and one, two, three or four of the light chain framework regions as shown in Table 3A, and further comprises a heavy chain variable region comprising an HVR-H1, an HVR-H2, and an HVR-H3 of the present disclosure and one, two, three or four of the heavy chain framework regions as shown in Table 3B.

Antibody Preparation

Anti-Siglec-7 antibodies of the present disclosure can encompass polyclonal antibodies, monoclonal antibodies, humanized and chimeric antibodies, human antibodies, antibody fragments (e.g., Fab, Fab'-SH, Fv, scFv, and F(ab')$_2$), bispecific and polyspecific antibodies, multivalent antibodies, heteroconjugate antibodies, conjugated antibodies, library derived antibodies, antibodies having modified effector functions, fusion proteins containing an antibody portion, and any other modified configuration of the immunoglobulin molecule that includes an antigen recognition site, such as an epitope having amino acid residues of a Siglec-7 protein of the present disclosure, including glycosylation variants of antibodies, amino acid sequence variants of antibodies, and covalently modified antibodies. The anti-Siglec-7 antibodies may be human, murine, rat, or of any other origin (including chimeric or humanized antibodies).

(1) Polyclonal Antibodies

Polyclonal antibodies, such as polyclonal anti-Siglec-7 antibodies, are generally raised in animals by multiple subcutaneous (sc) or intraperitoneal (ip) injections of the relevant antigen and an adjuvant. It may be useful to conjugate the relevant antigen (e.g., a purified or recombinant Siglec-7 protein of the present disclosure) to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues). N-hydroxysuccinimide (through lysine residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the desired antigen, immunogenic conjugates, or derivatives by combining, e.g., 100 μg (for rabbits) or 5 μg (for mice) of the protein or conjugate with 3 volumes of Freund's complete adjuvant and injecting the solution intradermally at multiple sites. One month later, the animals are boosted with ⅕ to 1/10 the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response.

(2) Monoclonal Antibodies

Monoclonal antibodies, such as monoclonal anti-Siglec-7 antibodies, are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal anti-Siglec-7 antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization (e.g., a purified or recombinant Siglec-7 protein of the present disclosure). Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986)).

The immunizing agent will typically include the antigenic protein (e.g., a purified or recombinant Siglec-7 protein of the present disclosure) or a fusion variant thereof. Generally peripheral blood lymphocytes ("PBLs") are used if cells of human origin are desired, while spleen or lymph node cells are used if non-human mammalian sources are desired. The lymphoctyes are then fused with an immortalized cell line using a suitable fusing agent, such as polyethylene glycol, to form a hybridoma cell. Goding. *Monoclonal Antibodies: Principles and Practice,* Academic Press (1986), pp. 59-103.

Immortalized cell lines are usually transformed mammalian cells, particularly myeloma cells of rodent, bovine or human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors (available from the Salk Institute Cell Distribution Center, San Diego, Calif. USA), as well as SP-2 cells and derivatives thereof (e.g., X63-Ag8-653) (available from the American Type Culture Collection, Manassas, Va. USA). Human myeloma and mouse-human heteromyeloma cell lines have also been described for the production of human monoclonal antibodies (Kozbor, *J. Immunol.,* 133:3001 (1984); Brodeur et al., *Monoclonal Antibody Production Techniques and Applications,* pp. 51-63 (Marcel Dekker. Inc., New York, 1987)).

Culture medium in which hybridoma cells are growing is assayed for production of monoclonal antibodies directed against the antigen (e.g., a Siglec-7 protein of the present disclosure). Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen (e.g., a Siglec-7 protein of the present disclosure). Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.,* 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose chromatography, hydroxylapatite chromatography, gel electrophoresis, dialysis, affinity chromatography, and other methods as described above.

Anti-Siglec-7 monoclonal antibodies may also be made by recombinant DNA methods, such as those disclosed in U.S. Pat. No. 4,816,567, and as described above. DNA encoding the monoclonal antibodies is readily isolated and sequenced using conventional procedures (e.g., by using oligonucleotide probes that specifically bind to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opin. Immmnol.,* 5:256-262 (1993) and Plückthun, *Immunol. Rev.* 130:151-188 (1992).

In certain embodiments, anti-Siglec-7 antibodies can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) described the isolation of murine and human antibodies, respectively, from phage libraries. Subsequent publications describe the production of high affinity (nanomolar ("nM") range) human antibodies by chain shuffling (Marks et al., *Bio Technology.* 10:779-783 (1992)), as well as combinatorial infection and in vivo recombination as a strategy for constructing very large phage libraries (Waterhouse et al., *Nucl. Acids Res.,* 21:2265-2266 (1993)). Thus, these techniques are viable alternatives to traditional monoclonal antibody hybridoma techniques for isolation of monoclonal antibodies of desired specificity (e.g., those that bind a Siglec-7 protein of the present disclosure).

The DNA encoding antibodies or fragments thereof may also be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein (e.g., anti-Siglec-7 antibodies of the present disclosure or fragments thereof) may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid anti-Siglec-7 antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(3) Humanized Antibodies

Anti-Siglec-7 antibodies of the present disclosure or antibody fragments thereof may further include humanized or human antibodies. Humanized forms of non-human (e.g., murine) antibodies are chimeric immunoglobulins, immunoglobulin chains or fragments thereof (such as Fab, Fab'-SH, Fv, scFv, F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances. Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally will also comprise at least a portion of an immunoglobulin constant region (Fc), typically that of a human immunoglobulin. Jones et al., *Nature* 321: 522-525 (1986); Riechmann et al., *Nature* 332: 323-329 (1988) and Presta, *Curr. Opin. Struct. Biol.* 2: 593-596 (1992).

Methods for humanizing non-human anti-Siglec-7 antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., *Nature* 321:522-525 (1986); Riechmann et al., *Nature* 332: 323-327 (1988); Verhoeyen et al., *Science* 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., *J. Immunol.,* 151:2296 (1993); Chothia et al., *J. Mol. Biol.,* 196:901 (1987). Another method uses a particular framework derived from the consensus sequence of all human antibodies of a particular subgroup of light or heavy chains. The same framework may be used for several different humanized antibodies. Carter et al., *Proc. Nat'l Acad. Sci. USA* 89:4285 (1992); Presta et al., *J. Immunol.* 151:2623 (1993).

Furthermore, it is important that antibodies be humanized with retention of high affinity for the antigen and other favorable biological properties. To achieve this goal, according to a preferred method, humanized antibodies are prepared by a process of analyzing the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen or antigens (e.g., Siglec-7 proteins of the present disclosure), is achieved. In general, the CDR residues are directly and most substantially involved in influencing antigen binding.

Various forms of the humanized anti-Siglec-7 antibody are contemplated. For example, the humanized anti-Siglec-7 antibody may be an antibody fragment, such as an Fab, which is optionally conjugated with one or more cytotoxic agent(s) in order to generate an immunoconjugate. Alternatively, the humanized anti-Siglec-7 antibody may be an intact antibody, such as an intact IgG1 antibody.

(4) Human Antibodies

Alternatively, human anti-Siglec-7 antibodies can be generated. For example, it is now possible to produce transgenic animals (e.g., mice) that are capable, upon immunization, of producing a full repertoire of human antibodies in the absence of endogenous immunoglobulin production. The homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Nat'l Acad Sci. USA,* 90:2551 (1993); Jakobovits et al., *Nature,* 362:255-258 (1993); Bruggermann et al., *Year in Immunol.,* 7:33 (1993); U.S. Pat. No. 5,591,669 and WO 97/17852.

Alternatively, phage display technology can be used to produce human anti-Siglec-7 antibodies and antibody fragments in vitro, from immunoglobulin variable (V) domain gene repertoires from unimmunized donors. McCafferty et al., *Nature* 348:552-553 (1990); Hoogenboom and Winter, *J. Mol. Biol.* 227: 381 (1991). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., *Curr. Opin Struct. Biol.* 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See also U.S. Pat. Nos. 5,565,332 and 5,573,905. Additionally, yeast display technology can be used to produce human anti-Siglec-7 antibodies and antibody fragments in vitro (e.g., WO 2009/036379; WO 2010/105256; WO 2012/009568; US 2009/0181855; US 2010/0056386; and Feldhaus and Siegel (2004) *J. Immunological Methods* 290:69-80). In other embodiments, ribosome display technology can be used to produce human anti-Siglec-7 antibodies and antibody fragments in vitro (e.g., Roberts and Szostak (1997) Proc Natl Acad Sci 94:12297-12302; Schaffitzel et al. (1999) J. Immunolical Methods 231:119-135; Lipovsek and Plückthun (2004) J. Immunological Methods 290:51-67).

The techniques of Cole et al., and Boerner et al., are also available for the preparation of human anti-Siglec-7 monoclonal antibodies (Cole et al., Monoclonal Antibodies and Cancer Therapy, Alan R. Liss, p. 77 (1985) and Boerner et al., *J. Immunol.* 147(1): 86-95 (1991). Similarly, human anti-Siglec-7 antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., *Bio/Technology* 10: 779-783 (1992); Lonberg et al., *Nature* 368: 856-859 (1994); Morrison, *Nature* 368: 812-13 (1994); Fishwild et al., *Nature Biotechnology* 14: 845-51 (1996); Neuberger, *Nature Biotechnology* 14: 826 (1996) and Lonberg and Huszar, *Intern. Rev. Immunol.* 13: 65-93 (1995).

Finally, human anti-Siglec-7 antibodies may also be generated in vitro by activated B-cells (see U.S. Pat. Nos. 5,567,610 and 5,229,275).

(5) Antibody Fragments

In certain embodiments there are advantages to using anti-Siglec-7 antibody fragments, rather than whole anti-Siglec-7 antibodies. Smaller fragment sizes allow for rapid clearance and better brain penetration.

Various techniques have been developed for the production of antibody fragments. Traditionally, these fragments were derived via proteolytic digestion of intact antibodies (see, e.g., Morimoto et al., *J. Biochem. Biophys. Method.* 24:107-117 (1992); and Brennan et al., *Science* 229:81 (1985)). However, these fragments can now be produced directly by recombinant host cells, for example, using nucleic acids encoding anti-Siglec-7 antibodies of the present disclosure. Fab. Fv and scFv antibody fragments can all be expressed in and secreted from *E. coli,* thus allowing the straightforward production of large amounts of these fragments. A anti-Siglec-7 antibody fragments can also be isolated from the antibody phage libraries as discussed above. Alternatively. Fab'-SH fragments can be directly recovered from *E. coli* and chemically coupled to form F(ab')2 fragments (Carter et al., *BioTechnology* 10:163-167 (1992)). According to another approach, F(ab')$_2$ fragments can be isolated directly from recombinant host cell culture. Production of Fab and F(ab')$_2$ antibody fragments with increased in vivo half-lives are described in U.S. Pat. No. 5,869,046. In other embodiments, the antibody of choice is a single chain Fv fragment (scFv). See WO 93/16185; U.S. Pat. Nos. 5,571,894 and 5,587,458. The anti-Siglec-7 antibody fragment may also be a "linear antibody." e.g., as described in U.S. Pat. No. 5,641,870. Such linear antibody fragments may be monospecific or bispecific.

(6) Bispecific and Polyspecific Antibodies

Bispecific antibodies (BsAbs) are antibodies that have binding specificities for at least two different epitopes, including those on the same or another protein (e.g., one or more Siglec-7 proteins of the present disclosure). Alternatively, one part of a BsAb can be armed to bind to the target Siglec-7 antigen, and another can be combined with an arm that binds to a second protein. Such antibodies can be derived from full length antibodies or antibody fragments (e.g., F(ab')$_2$ bispecific antibodies).

Methods for making bispecific antibodies are known in the an. Traditional production of full length bispecific antibodies is based on the coexpression of two immunoglobulin heavy-chain/light chain pairs, where the two chains have different specificities. Millstein et al., *Nature,* 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only half of the bispecific molecules provides for an easy way of separation. This approach is disclosed in WO 94/04690. For further details of generating bispecific antibodies, see, for example. Suresh et al., *Methods in Enzymology* 121: 210 (1986).

According to another approach described in WO 96/27011 or U.S. Pat. No. 5,731,168, the interface between a pair of antibody molecules can be engineered to maximize the percentage of heterodimers which are recovered from recombinant cell culture. The preferred interface comprises at least a part of the $C_H3$ region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')₂ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describes the production of fully humanized bispecific antibody F(ab')₂ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bivalent antibody fragments directly from recombinant cell culture have also been described. For example, bivalent heterodimers have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Nat'l Acad Sci. USA*, 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.*, 152:5368 (1994).

Antibodies with more than two valencies are also contemplated. For example, trispecific antibodies can be prepared. Tutt et al., *J. Immunol.* 147:60 (1991).

Exemplary bispecific antibodies may bind to two different epitopes on a given molecule (e.g., a Siglec-7 protein of the present disclosure). Alternatively, an arm targeting a Siglec-7 signaling component may be combined with an arm which binds to a triggering molecule on a leukocyte such as a T cell receptor molecule (e.g., CD2, CD3, CD28 or B7), or Fc receptors for IgG (FcγR), such as FcγRI (CD64), FcγRII (CD32) and FcγRIII (CD16) so as to focus cellular defense mechanisms to the cell expressing the particular protein. Bispecific antibodies may also be used to localize cytotoxic agents to cells which express a particular protein. Such antibodies possess a protein-binding arm and an arm which binds a cytotoxic agent or a radionuclide chelator, such as EOTUBE, DPTA, DOTA or TETA. Another bispecific antibody of interest binds the protein of interest and further binds tissue factor (TF).

(7) Multivalent Antibodies

A multivalent antibody may be internalized (and/or catabolized) faster than a bivalent antibody by a cell expressing an antigen to which the antibodies bind. The anti-Siglec-7 antibodies of the present disclosure or antibody fragments thereof can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises an Fc region or a hinge region. In this scenario, the antibody will comprise an Fc region and three or more antigen binding sites amino-terminal to the Fc region. The preferred multivalent antibody herein contains three to about eight, but preferably four, antigen binding sites. The multivalent antibody contains at least one polypeptide chain (and preferably two polypeptide chains), wherein the polypeptide chain or chains comprise two or more variable domains. For instance, the polypeptide chain or chains may comprise VD1-(X1)n-VD2-(X2)n-Fc, wherein VD1 is a first variable domain. VD2 is a second variable domain, Fc is one polypeptide chain of an Fc region. X1 and X2 represent an amino acid or polypeptide, and n is 0 or 1. Similarly, the polypeptide chain or chains may comprise $V_H$-$C_H$1-flexible linker-$V_H$-CH1-Fc region chain; or $V_H$—$C_H$I—$V_H$-$C_H$I-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain. The multivalent antibodies may recognize the Siglec-7 antigen as well as, without limitation, additional antigens A beta peptide, antigen or an alpha synuclain protein antigen or, Tau protein antigen or, TDP-43 protein antigen or, prion protein antigen or, huntingtin protein antigen, or RAN, translation Products antigen, including the DiPeptide Repeats, (DPRs peptides) composed of glycine-alanine (GA), glycine-proline (GP), glycine-arginine (GR), proline-alanine (PA), or proline-arginine (PR), insulin receptor, insulin like growth factor receptor, transferrin receptor, or any other antigen that facilitates antibody transfer across the blood brain barrier.

(8) Heteroconjugate Antibodies

Heteroconjugate antibodies are also within the scope of the present disclosure. Heteroconjugate antibodies are composed of two covalently joined antibodies (e.g., anti-Siglec-7 antibodies of the present disclosure or antibody fragments thereof). For example, one of the antibodies in the heteroconjugate can be coupled to avidin, the other to biotin. Such antibodies have, for example, been proposed to target immune system cells to unwanted cells, U.S. Pat. No. 4,676,980, and have been used to treat HIV infection. International Publication Nos. WO 91/00360, WO 92:200373 and EP 0308936. It is contemplated that the antibodies may be prepared in vitro using known methods in synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may be made using any convenient cross-linking methods. Suitable cross-linking agents are well known in the art, and are disclosed in U.S. Pat. No. 4,676,980, along with a number of cross-linking techniques.

(9) Effector Function Engineering

It may also be desirable to modify an anti-Siglec-7 antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII. In some embodiments, the effector function is impaired by removing N-glycosylation of the Fc region (e.g., in the CH2 domain of IgG) of the antibody. In some embodiments, the effector function is impaired by modifying regions such as 233-236, 297, and/or 327-331 of human IgG as described in PCT WO 99/58572 and Armour et al., *Molecular Immunology* 40: 585-593 (2003); Reddy et al., *J. immunology* 164:1925-1933 (2000).

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

(10) Other Amino Acid Sequence Modifications

Amino acid sequence modifications of anti-Siglec-7 antibodies of the present disclosure, or antibody fragments thereof, are also contemplated. For example, it may be desirable to improve the binding affinity and/or other biological properties of the antibodies or antibody fragments. Amino acid sequence variants of the antibodies or antibody fragments are prepared by introducing appropriate nucleotide changes into the nucleic acid encoding the antibodies or antibody fragments, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics (i.e., the ability to bind or physically interact with a Siglec-7 protein of the present disclosure). The amino acid changes also may alter post-translational processes of the antibody, such as changing the number or position of glycosylation sites.

A useful method for identification of certain residues or regions of the anti-Siglec-7 antibody that are preferred locations for mutagenesis is called "alanine scanning mutagenesis" as described by Cunningham and Wells in *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the target antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino-("N") and/or carboxy-("C") terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table E below under the heading of "preferred substitutions". If such substitutions result in a change in biological activity, then more substantial changes, denominated "exemplary substitutions" in Table E, or as further described below in reference to amino acid classes, may be introduced and the products screened.

TABLE E

Amino acid substitutions

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | Ser | ser |
| Trp (W) | tyr; phe | tyr |
| Tyr (Y) | tsp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

A particularly preferred type of substitutional variant involves substituting one or more hypervariable region residues of a parent antibody (e.g. a humanized or human anti-Siglec-7 antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen (e.g., a Siglec-7 protein of the present disclosure). Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IgE antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibodies (e.g., anti-Siglec-7 antibodies of the present disclosure) or antibody fragments.

(11) Antibody Conjugates

Anti-Siglec-7 antibodies of the present disclosure, or antibody fragments thereof, can be conjugated to a detectable marker, a toxin, or a therapeutic agent. Any suitable method known in the art for conjugating molecules, such as a detectable marker, a toxin, or a therapeutic agent to antibodies may be used.

For example, drug conjugation involves coupling of a biological active cytotoxic (anticancer) payload or drug to an antibody that specifically targets a certain tumor marker (e.g. a protein that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue, OncLive Jul. 5, 2012; ADC Review on antibody-drug conjugates; and Ducry et al., (2010). *Bioconjugate Chemistry* 21 (1): 5-13).

In some embodiments, an anti-Siglec-7 antibody of the present disclosure may be conjugated to a toxin selected from ricin, ricin A-chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, and a cisplatin.

(12) Other Antibody Modifications

Anti-Siglec-7 antibodies of the present disclosure, or antibody fragments thereof, can be further modified to contain additional non-proteinaceous moieties that are known in the art and readily available. Preferably, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in *Remington: The Science and Practice of Pharmacy*, 20th Ed., Alfonso Gennaro, Ed., Philadelphia College of Pharmacy and Science (2000).

Binding Assays and Other Assays

Anti-Siglec-7 antibodies of the present disclosure may be tested for antigen binding activity, e.g., by known methods such as ELISA, surface plasmon resonance (SPR). Western blot, etc.

In some embodiments, competition assays may be used to identify an antibody that competes with any of the antibodies listed in Tables 2A, 2B, 3A, 3B, 6A, and 6B, or selected from 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8. In certain embodiments, such a competing antibody binds to the same epitope (e.g., a linear or a conformational epitope) that is bound by any of the antibodies listed in Tables 2A, 2B, 3A, 3B, 6A, and 6B, or selected from 1A12, 1E8, 2G11, 2G4, 3E11, 4A1, 4D7, 4E3, 4E3H1, 4E3H2, 7A3, 7E11, 7F12, 10B5, 10B5L1, 10B5H1, and 10G8. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized Siglec-7 or cells expressing Siglec-7 on a cell surface are incubated in a solution comprising a first labeled antibody that binds to Siglec-7 (e.g., human or non-human primate) and a second unlabeled antibody that is being tested for its ability to compete with the first antibody for binding to Siglec-7. The second antibody may be present in a hybridoma supernatant. As a control, immobilized Siglec-7 or cells expressing Siglec-7 is incubated in a solution comprising the first labeled antibody but not the second unlabeled antibody. After incubation under conditions permissive for binding of the first antibody to Siglec-7, excess unbound antibody is removed, and the amount of label associated with immobilized Siglec-7 or cells expressing Siglec-7 is measured. If the amount of label associated with immobilized Siglec-7 or cells expressing Siglec-7 is substantially reduced in the test sample relative to the control sample, then that indicates that the second antibody is competing with the first antibody for binding to Siglec-7. See, Harlow and Lane (1988) *Antibodies: A Laboratory Manual* ch. 14 (Cold Spring Harbor Laboratory. Cold Spring Harbor, N.Y.).

Nucleic Acids, Vectors, and Host Cells

Anti-Siglec-7 antibodies of the present disclosure may be produced using recombinant methods and compositions, e.g., as described in U.S. Pat. No. 4,816,567. In some embodiments, isolated nucleic acids having a nucleotide sequence encoding any of the anti-Siglec-7 antibodies of the present disclosure are provided. Such nucleic acids may encode an amino acid sequence containing the VL and/or an amino acid sequence containing the VH of the anti-Siglec-7 antibody (e.g., the light and/or heavy chains of the antibody). In some embodiments, one or more vectors (e.g., expression vectors) containing such nucleic acids are provided. In some embodiments, a host cell containing such nucleic acid is also provided. In some embodiments, the host cell contains (e.g., has been transduced with); (1) a vector containing a nucleic acid that encodes an amino acid sequence containing the VL of the antibody and an amino acid sequence containing the VH of the antibody, or (2) a first vector containing a nucleic acid that encodes an amino acid sequence containing the VL of the antibody and a second vector containing a nucleic acid that encodes an amino acid sequence containing the VH of the antibody. In some embodiments, the host cell is eukaryotic, e.g., a Chinese Hamster Ovary (CHO) cell or lymphoid cell (e.g., Y0, NS0, Sp20 cell).

Methods of making an anti-Siglec-7 antibody of the present disclosure are provided. In some embodiments, the method includes culturing a host cell of the present disclosure containing a nucleic acid encoding the anti-Siglec-7 antibody, under conditions suitable for expression of the antibody. In some embodiments, the antibody is subsequently recovered from the host cell (or host cell culture medium).

For recombinant production of an anti-Siglec-7 antibody of the present disclosure, a nucleic acid encoding the anti-Siglec-7 antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors containing a nucleic acid sequence encoding any of the anti-Siglec-7 antibodies of the present disclosure, or fragments thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mpl8, mpl9, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the nucleic acids of interest can be introduced into the host cell by any of a number of appropriate means, including electroporation, transfection employing calcium chloride, rubidium chloride, calcium phosphate. DEAE-dextran, or other substances; microprojectile bombardment; lipofection; and infection (e.g., where the vector is an infectious agent such as vaccinia virus). The choice of introducing vectors or polynucleotides will often depend on features of the host cell. In some embodiments, the vector contains a nucleic acid containing one or more amino acid sequences encoding an anti-Siglec-7 antibody of the present disclosure.

Suitable host cells for cloning or expression of antibody-encoding vectors include prokaryotic or eukaryotic cells. For example, anti-Siglec-7 antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523; and Charlton, *Methods in Molecular Biology*, Vol. 248 (B. K. C. Lo, ed., Humana Press. Totowa, N.J. 2003), pp. 245-254, describing expression of antibody fragments in *E. coli*). After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross, *Nat. Biotech.* 22:1409-1414 (2004); and Li et al., *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N. Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press. Totowa, N.J.), pp. 255-268 (2003).

Siglec-7 Activities

PI3K Activation

In some embodiments, Siglec-7 agents of the present disclosure, such as anti-Siglec-7 antibodies of the present disclosure, may induce PI3K activation after binding to a Siglec-7 protein expressed in a cell.

PI3Ks are a family of related intracellular signal transducer kinases capable of phosphorylating the 3-position hydroxyl group of the inositol ring of phosphatidylinositol (PtdIns). The PI3K family is divided into three different classes (Class I, Class II, and Class III) based on primary structure, regulation, and in vitro lipid substrate specificity.

Activated PI3K produces various 3-phosphorylated phosphoinositides, including without limitation, PtdIns3P, PtdIns (3,4)P2, PtdIns(3,5)P2, and PtdIns(3,4,5)P3. These 3-phosphorylated phosphoinositides function in a mechanism by which signaling proteins are recruited to various cellular membranes. These signaling proteins contain phosphoinositide-binding domains, including without limitation, PX domains, pleckstrin homology domains (PH domains), and FYVE domains. Any method known in the art for determining PI3K activation may be used.

In some embodiments, Siglec-7 agents of the present disclosure, such as anti-Siglec-7 antibodies of the present disclosure, are beneficial for preventing, lowering the risk of, or treating conditions and/or diseases associated with decreased levels of PI3K activity, including, without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections. CNS herpes, parasitic infections. Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Modulated Expression of Cytokines

In some embodiments, Siglec-7 agents of the present disclosure, such as anti-Siglec-7 antibodies of the present disclosure, may modulate (e.g., increase or decrease) proinflammatory mediators in the brain after binding to a Siglec-7 protein expressed on a cell surface. In certain embodiments, Siglec-7 agents of the present disclosure, such as anti-Siglec-7 antibodies of the present disclosure, modulate the expression of cytokines (e.g., proinflammatory mediators) and/or reduce the expression of anti-inflammatory mediators after binding to a Siglec-7 protein expressed in a cell.

Inflammation is part of a complex biological response of vascular tissues to harmful stimuli, such as pathogens, damaged cells, and irritants. The classical signs of acute inflammation are pain, heat, redness, and swelling. Inflammation is an immune response that protects an organism by limiting the site of injury or clearing an infection by recruiting and activating cells of the immune system. The inflammatory response is tightly regulated and restricted in its duration and severity to avoid causing damage to the organism. Inflammation can be classified as either acute or chronic. Acute inflammation is driven by the innate immune response, which initially recognizes harmful stimuli and recruits leukocytes from the blood into the injured tissues. A cascade of biochemical events, including cytokine and chemokine release, propagates the inflammatory response, involving the local vascular system, the immune system, and various cells within the injured tissue. Chronic inflammation is prolonged and persistent which leads to a progressive shift in the type of immune cells participating in the inflammatory response. Chronic inflammation is characterized by progressive destruction and fibrosis of the tissue as a result of the inflammatory process.

As used herein, anti-inflammatory mediators are proteins involved either directly or indirectly (e.g., by way of an anti-inflammatory signaling pathway) in a mechanism that reduces, inhibits, or inactivates an inflammatory response. Any method known in the art for identifying and characterizing anti-inflammatory mediators may be used. Examples of anti-inflammatory mediators include, without limitation, cytokines, such as IL-4, IL-10, IL-13, IL-35, IL-16, IFN-alpha, TGF-beta, IL-1R$\alpha$, G-CSF, and soluble receptors for TNF, IFN-beta1a, IFN-beta1b, or IL-6. Examples of pro-inflammatory mediators include, without limitation, cytokines, such as IFN-a4, IFN-beta, IL-1$\beta$, IL-1alpha, TNF-$\alpha$, IL-6, IL-8, CRP, IL-20 family members, LIF, IFN-gamma, OSM, CNTF, GM-CSF, IL-11, IL-12, IL-17, IL-18, IL-23, CXCL10, IL-33, MCP-1, and MIP-1-beta.

In some embodiments, the Siglec-7 agents of the present disclosure, such as anti-Siglec-7 antibodies of the present disclosure, may modulate (e.g., increase or decrease) expression of cytokines, such as IL-1b, IL-8, and TNF-a. In certain embodiments, modulated expression of the cytokines occurs in macrophages, neutrophils, natural killer (NK) cells, dendritic cells, monocytes, osteoclasts, Langerhans cells of skin, Kupffer cells, T cells, and/or microglial cells. Modulated expression may include, without limitation, an increase in gene expression, an increase in transcriptional expression, or an increase in protein expression. Any method known in the art for determining gene, transcript (e.g., mRNA), and/or protein expression may be used. For example, Northern blot analysis may be used to determine cytokine gene expression levels, RT-PCR may be used to determine the level of cytokine transcription, and Western blot analysis may be used to determine cytokine protein levels.

As used herein, a cytokine may have modulated expression if its expression in one or more cells of a subject treated with an Siglec-7 agents of the present disclosure, such as anti-Siglec-7 antibodies of the present disclosure, is modulated as compared to the expression of the same cytokine expressed in one or more cells of a corresponding subject that is not treated with the Siglec-7 agent. In some embodiments, Siglec-7 agents of the present disclosure, such as anti-Siglec-7 antibodies of the present disclosure, may modulate cytokine expression in one or more cells of a subject by at least 10%, at least 15%, at least 20%, at least 25%, at least 30%, at least 35%, at least 40%, at least 45%, at least 50%, at least 55%, at least 60%, at least 650%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to cytokine expression in one or more cells of a corresponding subject that is not treated with the Siglec-7 agent. In other embodiments, Siglec-7 agents of the present disclosure, such as anti-Siglec-7 antibodies of the present disclosure, modulate cytokine expression in one or more cells of a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to cytokine expression in one or more cells of a corresponding subject that is not treated with the Siglec-7 agent.

In some embodiments, Siglec-7 agents of the present disclosure, such as anti-Siglec-7 antibodies of the present disclosure, are useful for preventing, lowering the risk of, or treating conditions and/or diseases associated with abnormal levels of one or more pro-inflammatory mediators, including without limitation, dementia, frontotemporal dementia, Alzheimer's disease, vascular dementia, mixed dementia, Creutzfeldt-Jakob disease, normal pressure hydrocephalus, amyotrophic lateral sclerosis. Huntington's disease, taupathy disease, Nasu-Hakola disease, stroke, acute trauma, chronic trauma, lupus, acute and chronic colitis, rheumatoid arthritis, wound healing. Crohn's disease, inflammatory bowel disease, ulcerative colitis, obesity, malaria, essential tremor, central nervous system lupus, Behcet's disease, Parkinson's disease, dementia with Lewy bodies, multiple system atrophy. Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Modulated Expression of Pro-Inflammatory Mediators

In some embodiments, Siglec-7 agents of the present disclosure, such as anti-Siglec-7 antibodies of the present disclosure, may modulate (e.g., increase or decrease) the expression of pro-inflammatory mediators after binding to a Siglec-7 protein expressed in a cell.

As used herein, pro-inflammatory mediators are proteins involved either directly or indirectly (e.g., by way of pro-inflammatory signaling pathways) in a mechanism that induces, activates, promotes, or otherwise increases an inflammatory response. Any method known in the art for identifying and characterizing pro-inflammatory mediators may be used.

Examples of pro-inflammatory mediators include, without limitation, cytokines, such as type I and II interferons, IFN-a4, IFN-beta, IL-1β, IL-1alpha, TNF-α, IL-6, IL-8, CRP, IL-20 family members, IL-33, LIF, IFN-gamma, OSM, CNTF, GM-CSF, IL-11, IL-12, IL-17, IL-18, CRP, MCP-1, and MIP-1-beta.

In some embodiments, the anti-Siglec-7 antibodies of the present disclosure may modulate functional expression and/or secretion of pro-inflammatory mediators, such as type I and II interferons, IFN-a, IFN-b, IL-1β, TNF-α, IL-6, IL-8, CRP, IL-20 family members, IL-33, LIF, IFN-gamma, OSM, CNTF, GM-CSF, IL-11, IL-12, IL-17, IL-18, IL-23, CXCL10, CRP, MCP-1, and MIP-1-beta. In certain embodiments, modulated expression of the pro-inflammatory mediators occurs in macrophages, neutrophils, NK cells, dendritic cells, monocytes, osteoclasts, Langerhans cells of skin, Kupffer cells, T cells, and/or microglial cells. Modulated expression may include, without limitation, a modulated gene expression, modulated transcriptional expression, or modulated protein expression. Any method known in the art for determining gene, transcript (e.g., mRNA), and/or protein expression may be used. For example. Northern blot analysis may be used to determine pro-inflammatory mediator gene expression levels, RT-PCR may be used to determine the level of pro-inflammatory mediator transcription, and Western blot analysis may be used to determine pro-inflammatory mediator protein levels.

In certain embodiments, pro-inflammatory mediators include inflammatory cytokines. Accordingly, in certain embodiments, the Siglec-7 agents of the present disclosure, such as anti-Siglec-7 antibodies of the present disclosure, may modulate secretion of one or more inflammatory cytokines. Examples of inflammatory cytokines whose secretion may be modulated by the anti-Siglec-7 antibodies of the present disclosure include, without limitation, such as type I and II interferons, IFN-a4, IFN-b, IL-1β, TNF-α, IL-6, IL-8, CRP, IL-20 family members, IL-33, LIF, IFN-gamma, OSM, CNTF, GM-CSF, IL-11, IL-12, IL-17, IL-18, IL-23, CXCL10, MCP-1, and MIP-1-beta.

In certain embodiments, pro-inflammatory mediators include inflammatory receptors. Accordingly, in certain embodiments, the Siglec-7 agents of the present disclosure, such as anti-Siglec-7 antibodies of the present disclosure, may modulate expression of one or more inflammatory receptors. Examples of inflammatory receptors whose expression may be modulated by the Siglec-7 agents of the present disclosure, such as anti-Siglec-7 antibodies of the present disclosure, include, without limitation, CD86, CD80, CD83.

As used herein, a pro-inflammatory mediator may have modulated expression if its expression in one or more cells of a subject treated with a Siglec-7 agent, such as an agonist anti-Siglec-7 antibody of the present disclosure is modulated (e.g., increased or decreased) as compared to the expression of the same pro-inflammatory mediator expressed in one or more cells of a corresponding subject that is not treated with the agonist anti-Siglec-7 antibody. In some embodiments, the anti-Siglec-7 antibody of the present disclosure may modulate pro-inflammatory mediator expression in one or more cells of a subject by at least 10%, at least 15%, at least 20%, at least 25%, at least 30%, at least 35%, at least 40%, at least 45%, at least 50%, at least 55%, at least 600%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to pro-inflammatory mediator expression in one or more cells of a corresponding subject that is not treated with the anti-Siglec-7 antibody. In other embodiments, the anti-Siglec-7 antibody may modulate pro-inflammatory mediator expression in one or more cells of a subject by at least at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to pro-inflammatory mediator expression in one or more cells of a corresponding subject that is not treated with the anti-Siglec-7 antibody.

In some embodiments, some Siglec-7 agents of the present disclosure, such as anti-Siglec-7 antibodies of the present disclosure, may be useful for preventing, lowering the risk of, or treating conditions and/or diseases associated with abnormal levels of one or more pro-inflammatory mediators, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection. *Campylobacter jejuni* infection, *Neisseria meningiditis* infection, type I HIV, and *Haemophilus* influenza.

ERK Phosphorylation

In some embodiments, Siglec-7 agents of the present disclosure, such as anti-Siglec-7 antibodies of the present disclosure, may induce extracellular signal-regulated kinase (ERK) phosphorylation after binding to a Siglec-7 protein expressed in a cell.

Extracellular-signal-regulated kinases (ERKs) are widely expressed protein kinase intracellular signaling kinases that are involved in, for example, the regulation of meiosis, mitosis, and postmitotic functions in differentiated cells. Various stimuli, such as growth factors, cytokines, virus infection, ligands for heterotrimeric G protein-coupled receptors, transforming agents, and carcinogens, activate ERK pathways. Phosphorylation of ERKs leads to the activation of their kinase activity.

In some embodiments, Siglec-7 agents of the present disclosure, such as anti-Siglec-7 antibodies of the present disclosure, are beneficial for preventing, lowering the risk of, or treating conditions and/or diseases associated with decreased levels of ERK phosphorylation, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus. Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Syk Phosphorylation

In some embodiments, Siglec-7 agents of the present disclosure, such as anti-Siglec-7 antibodies of the present disclosure, may induce spleen tyrosine kinase (Syk) phosphorylation after binding to a Siglec-7 protein expressed in a cell.

Spleen tyrosine kinase (Syk) is an intracellular signaling molecule that functions downstream of Siglec-7 by phosphorylating several substrates, thereby facilitating the formation of a signaling complex leading to cellular activation and inflammatory processes.

In some embodiments, Siglec-7 agents of the present disclosure, such as anti-Siglec-7 antibodies of the present disclosure, are beneficial for preventing, lowering the risk of, or treating conditions and/or diseases associated with decreased levels of Syk phosphorylation, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections. CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Siglec-7 Phosphorylation

In some embodiments, Siglec-7 agents of the present disclosure, such as anti-Siglec-7 antibodies of the present disclosure, may transiently induce Siglec-7 phosphorylation of Tyr-437 and Tyr-460 by a by Src family tyrosine kinase such as Src. Syk, Fyn, Fgr, Lck, Hck, Blk, Lyn, and Frk after binding to a Siglec-7 protein expressed in a cell.

In some embodiments, Siglec-7 agents of the present disclosure, such as anti-Siglec-7 antibodies of the present disclosure, are beneficial for preventing, lowering the risk of, or treating conditions and/or diseases associated with decreased levels of Siglec-7 phosphorylation, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy. Shy-Drager syndrome, progressive supranuclear palsy, conical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection. *Campylobacter jejuni* infection, *Neisseria meningiditis* infection, type I HIV, and *Haemophilus* influenza.

Phosphorylation of ITAM Motif Containing Receptors

In some embodiments, Siglec-7 agents of the present disclosure, such as anti-Siglec-7 antibodies of the present disclosure, may induce phosphorylate ITAM motif-containing receptors, such as TREM1, TREM2, Sirp beta, FcgR, DAP10, and DAP12, after binding to a Siglec-7 protein expressed in a cell.

In some embodiments, Siglec-7 agents of the present disclosure, such as anti-Siglec-7 antibodies of the present disclosure, are beneficial for preventing, lowering the risk of, or treating conditions and/or diseases associated with decreased levels of phosphorylation of ITAM motif-containing receptors, including without limitation, dementia, frontotemporal dementia, Alzheimer's disease, vascular dementia, mixed dementia, Creutzfeldt-Jakob disease, normal pressure hydrocephalus, amyotrophic lateral sclerosis. Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy. Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections. Trypanosome infection, *Cruzi* infection. *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Modulated Expression of C-C Chemokine Receptor 7

In some embodiments, Siglec-7 agents of the present disclosure, such as anti-Siglec-7 antibodies of the present disclosure, may modulate expression of C-C chemokine receptor 7 (CCR7) after binding to a Siglec-7 protein expressed in a cell. Modulated (e.g., increased or decreased) expression may include, without limitation, modulation in gene expression, modulation in transcriptional expression, or modulation in protein expression. Any method known in the art for determining gene, transcript (e.g., mRNA), and/or protein expression may be used. For example, Northern blot analysis may be used to determine anti-inflammatory mediator gene expression levels. RT-PCR may be used to determine the level of anti-inflammatory mediator transcription, and Western blot analysis may be used to determine anti-inflammatory mediator protein levels.

C-C chemokine receptor 7 (CCR7) is a member of the G protein-coupled receptor family. CCR7 is expressed in various lymphoid tissues and can activate B cells and T cells. In some embodiments, CCR7 may modulate the migration of memory T cells to secondary lymphoid organs, such as lymph nodes. In other embodiments, CCR7 may stimulate dendritic cell maturation. CCR7 is a receptor protein that can bind the chemokine (C-C motif) ligands CCL19/ELC and CCL21.

As used herein. CCR7 may have modulated expression if its expression in one or more cells of a subject treated with an Siglec-7 agents of the present disclosure, such as anti-Siglec-7 antibodies of the present disclosure, is modulated (e.g., increased or decreased) as compared to the expression of CCR7 expressed in one or more cells of a corresponding subject that is not treated with the Siglec-7 agent. In some embodiments, an Siglec-7 agent of the present disclosure, such as an anti-Siglec-7 antibody of the present disclosure, may modulate CCR7 expression in one or more cells of a subject by at least 10%, at least 15%, at least 20%, at least 25%, at least 30%, at least 35%, at least 40%, at least 45%, at least 50%, at least 55%, at least 60%, at least 65% at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to CCR7 expression in one or more cells of a corresponding subject that is not treated with the Siglec-7 agent. In other embodiments, an Siglec-7 agent of the present disclosure, such as an anti-Siglec-7 antibody of the present disclosure, modulates CCR7 expression in one or more cells of a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to CCR7 expression in one or more cells of a corresponding subject that is not treated with the Siglec-7 agent.

In some embodiments, increased expression of CCR7 occurs in macrophages, neutrophils, NK cells, dendritic cells, and/or microglial cells. Increased expression of CCR7 may induce microglial cell chemotaxis toward cells expressing the chemokines CCL19 and CCL21. Accordingly, in certain embodiments, anti-Siglec-7 antibodies of the present disclosure may induce microglial cell chemotaxis toward CCL19 and CCL21 expressing cells.

In some embodiments, Siglec-7 agents of the present disclosure, such as anti-Siglec-7 antibodies of the present disclosure, are useful for preventing, lowering the risk of, or treating conditions and/or diseases associated with abnormal levels of CCR7, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease. Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections. CNS herpes, parasitic infections. Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Modulated Expression of Immune-Related Proteins

In some embodiments, Siglec-7 agents of the present disclosure, such as anti-Siglec-7 antibodies of the present disclosure, may modulate expression of PD-L1, PD-L2, B7-H3, CD11b, CD200R, CD163 and/or CD206 after binding to a Siglec-7 protein expressed in a cell. Modulated (e.g., increased or decreased) expression may include, without limitation, modulation in gene expression, modulation in transcriptional expression, or modulation in protein expression. Any method known in the art for determining gene, transcript (e.g., mRNA), and/or protein expression may be used. For example, Northern blot analysis may be used to determine anti-inflammatory mediator gene expression levels. RT-PCR may be used to determine the level of anti-inflammatory mediator transcription, and Western blot analysis may be used to determine anti-inflammatory mediator protein levels.

As used herein, PD-L1, PD-L2, B7-H3, CD11b, CD200R, CD163 and/or CD206 may have modulated expression if its expression in one or more cells of a subject treated with a Siglec-7 agent of the present disclosure, such as anti-Siglec-7 antibodies of the present disclosure, is modulated (e.g., increased or decreased) as compared to the expression of PD-L1, PD-L2, B7-H3. CD11b. CD200R, CD163 and/or CD206 expressed in one or more cells of a corresponding subject that is not treated with the Siglec-7 agent. In some embodiments, a Siglec-7 agent of the present disclosure, such as an anti-Siglec-7 antibody of the present disclosure, may modulate PD-L. PD-L2, B7-H3, CD11b. CD200R, CD163 and/or CD206 expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to PD-L1, PD-L2, B7-H3, CD11b, CD200R, CD163 and/or CD206 expression in one or more cells of a corresponding subject that is not treated with the Siglec-7 agent. In other embodiments, a Siglec-7 agent of the present disclosure, such as an anti-Siglec-7 antibody of the present disclosure, modulates PD-L1, PD-L2, B7-H3, CD11b, CD200R, CD163 and/or CD206 expression in one or more cells of a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to PD-L1, PD-L2, B7-H3, CD11b, CD200R, CD163 and/or CD206 expression in one or more cells of a corresponding subject that is not treated with the Siglec-7 agent.

In some embodiments, Siglec-7 agents of the present disclosure, such as anti-Siglec-7 antibodies of the present disclosure, are useful for preventing, lowering the risk of, or treating conditions and/or diseases associated with abnormal levels of PD-L1, PD-L2, B7-H2, B7-H3, CD11b, CD200R, CD163 and/or CD206, including without limitation, dementia, frontotemporal dementia. Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus. Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections. CNS herpes, parasitic infections, Trypanosome infection, *Cruzi* infection, *Pseudomonas aeruginosa* infection, *Leishmania donovani* infection, group B *Streptococcus* infection. *Campylobacter jejuni* infection, *Neisseria meningiditis* infection, type I HIV, and *Haemophilus* influenza.

Enhancement or Normalization of the Ability of Bone Marrow-Derived Dendritic Cells to Induce Antigen-Specific T Cell Proliferation In some embodiments, Siglec-7 agents of the present disclosure, such as anti-Siglec-7 antibodies of the present disclosure, may enhance and/or normalize the ability of bone marrow-derived dendritic cells to induce antigen-specific T cell proliferation after binding to a Siglec-7 protein expressed in a cell.

In some embodiments, Siglec-7 agents of the present disclosure, such as antagonist anti-Siglec-7 antibodies of the present disclosure, may enhance and/or normalize the ability of bone marrow-derived dendritic cells to induce antigen-specific T cell proliferation in one or more bone marrow-derived dendritic cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 1500%, at least 160%, at least 170%, at least 180%, at least 190%, or at least 200% for example, as compared to the ability of bone marrow-derived dendritic cells to induce antigen-specific T cell proliferation in one or more bone marrow-derived dendritic cells of a corresponding subject that is not treated with the agent. In other embodiments, the Siglec-7 agent, such as an antagonist anti-Siglec-7 antibody, may enhance and/or normalize the ability of bone marrow-derived dendritic cells to induce antigen-specific T cell proliferation in one or more bone marrow-derived dendritic cells of a subject by at least at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the ability of bone marrow-derived dendritic cells to induce antigen-specific T cell proliferation in one or more bone marrow-derived dendritic cells of a corresponding subject that is not treated with the Siglec-7 agent.

In some embodiments, Siglec-7 agents of the present disclosure, such as anti-Siglec-7 antibodies of the present disclosure, are beneficial for preventing, lowering the risk of, or treating conditions and/or diseases associated with decreased or dysregulated ability of bone marrow-derived dendritic cells to induce antigen-specific T cell proliferation, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type 1 H1V, and *Haemophilus* influenza.

Osteoclast Production

In some embodiments, Siglec-7 agents of the present disclosure, such as anti-Siglec-7 antibodies of the present disclosure, may induce osteoclast production and/or increase the rate of osteoclastogenesis after binding to a Siglec-7 protein expressed in a cell.

As used herein, an osteoclast is a type of bone cell that can remove bone tissue by removing its mineralized matrix and breaking up the organic bone (e.g., bone resorption). Osteoclasts can be formed by the fusion of cells of the myeloid lineage. In some embodiments, osteoclasts may be characterized by high expression of tartrate resistant acid phosphatase (TRAP) and cathepsin K.

As used herein, the rate of osteoclastogenesis may be increased if the rate of osteoclastogenesis in a subject treated with a Siglec-7 agent of the present disclosure, such as antagonist anti-Siglec-7 antibody, is greater than the rate of osteoclastogenesis in a corresponding subject that is not treated with the Siglec-7 agent. In some embodiments, a Siglec-7 agent, such as an antagonist anti-Siglec-7 antibody of the present disclosure, may increase the rate of osteoclastogenesis in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 1100%, at least 115%, at least 120%, at least 125%, at least 130%, at least 135%, at least 140%, at least 145%, at least 150%, at least 160%, at least 170%, at least 180%, at least 190%, or at least 200% for example, as compared to rate of osteoclastogenesis in a corresponding subject that is not treated with the Siglec-7 agent. In other embodiments, a Siglec-7 agent, such as an antagonist anti-Siglec-7 antibody of the present disclosure, may increase the rate of osteoclastogenesis in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to rate of osteoclastogenesis in a corresponding subject that is not treated with the Siglec-7 agent.

As used herein, the rate of osteoclastogenesis may be decreased if the rate of osteoclastogenesis in a subject treated with a Siglec-7 agent, such as an agonist anti-Siglec-7 antibody of the present disclosure, is smaller than the rate of osteoclastogenesis in a corresponding subject that is not treated with the Siglec-7 agent. In some embodiments, a Siglec-7 agent, such as an agonist anti-Siglec-7 antibody of the present disclosure, may decrease the rate of osteoclastogenesis in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to rate of osteoclastogenesis in a corresponding subject that is not treated with the Siglec-7 agent. In other embodiments, a Siglec-7 agent, such as an agonist anti-Siglec-7 antibody of the present disclosure, may decrease the rate of osteoclastogenesis in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to rate of osteoclastogenesis in a corresponding subject that is not treated with the Siglec-7 agent.

In some embodiments, Siglec-7 agents of the present disclosure, such as anti-Siglec-7 antibodies of the present disclosure, are beneficial for preventing, lowering the risk of, or treating conditions and/or diseases associated with abnormal bone formation and maintenance including osteoporosis, which is associated with pathological decrease in bone density and osteoporotic diseases which are associated with pathological increase in bone density.

Proliferation and Survival of Siglec-7-Expressing Cells

In some embodiments, Siglec-7 agents of the present disclosure, such as anti-Siglec-7 antibodies of the present disclosure, may increase the proliferation, survival, and/or function of dendritic cells, macrophages, neutrophils, NK cells, monocytes, neutrophils, osteoclasts, Langerhans cells of skin. Kupffer cells, T cells, and microglial cells after binding to Siglec-7 protein expressed on a cell.

As used herein, macrophages of the present disclosure include, without limitation, M1 macrophages, activated M1 macrophages, and M2 macrophages. As used herein, neutrophils of the present disclosure include, without limitation, M1 neutrophils, activated M1 neutrophils, and M2 neutrophils. As used herein, natural killer (NK) cells of the present disclosure include, without limitation, M1 NK cells, activated M1 NK cells, and M2 NK cells. As used herein, microglial cells of the present disclosure include, without limitation, M1 microglial cells, activated M1 microglial cells, and M2 microglial cells.

Microglial cells are a type of glial cell that are the resident macrophages of the brain and spinal cord, and thus act as the first and main form of active immune defense in the central nervous system (CNS). Microglial cells constitute 20% of the total glial cell population within the brain. Microglial cells are constantly scavenging the CNS for plaques, damaged neurons and infectious agents. The brain and spinal cord are considered "immune privileged" organs in that they are separated from the rest of the body by a series of endothelial cells known as the blood-brain barrier, which prevents most pathogens from reaching the vulnerable nervous tissue. In the case where infectious agents are directly introduced to the brain or cross the blood-brain barrier, microglial cells must react quickly to limit inflammation and destroy the infectious agents before they damage the sensitive neural tissue. Due to the unavailability of antibodies from the rest of the body (few antibodies are small enough to cross the blood brain barrier), microglia must be able to recognize foreign bodies, swallow them, and act as antigen-presenting cells activating T cells. Since this process must be done quickly to prevent potentially fatal damage, microglial cells are extremely sensitive to even small pathological changes in the CNS. They achieve this sensitivity in part by having unique potassium channels that respond to even small changes in extracellular potassium.

In some embodiments, anti-Siglec-7 antibodies of the present disclosure may increase the expression of CD80, CD83 and/or CD86 on dendritic cells, monocytes, macrophages, neutrophils, NK cells, and/or microglia.

As used herein, the rate of proliferation, survival, and/or function of macrophages, neutrophils, NK cells, dendritic cells, monocytes, T cells, and/or microglia may include increased expression if the rate of proliferation, survival, and/or function of dendritic cells, macrophages, neutrophils, NK cells, monocytes, osteoclasts, Langerhans cells of skin. Kupffer cells, and/or microglia in a subject treated with a Siglec-7 agent, such as an anti-Siglec-7 antibody of the present disclosure, is greater than the rate of proliferation, survival, and/or function of dendritic cells, macrophages, neutrophils, NK cells, monocytes, osteoclasts. Langerhans cells of skin. Kupffer cells. T cells, and/or microglia in a corresponding subject that is not treated with the Siglec-7 agent. In some embodiments, a Siglec-7 agent, such as an anti-Siglec-7 antibody of the present disclosure, may increase the rate of proliferation, survival, and/or function of dendritic cells, macrophages, neutrophils, NK cells, monocytes, osteoclasts. Langerhans cells of skin, Kupffer cells, T cells, and/or microglia in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the rate of proliferation, survival, and/or function of dendritic cells, macrophages, neutrophils, NK cells, monocytes, osteoclasts, Langerhans cells of skin. Kupffer cells, T cells, and/or microglia in a corresponding subject that is not treated with the Siglec-7 agent. In other embodiments, a Siglec-7 agent, such as an anti-Siglec-7 antibody of the present disclosure, may increase the rate of proliferation, survival, and/or function of dendritic cells, macrophages, neutrophils, NK cells, monocytes, osteoclasts, Langerhans cells of skin, Kupffer cells, T cells, and/or microglia in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the rate of proliferation, survival, and/or function of dendritic cells, macrophages, neutrophils, NK cells, monocytes, osteoclasts, Langerhans cells of skin. Kupffer cells, T cells, and/or microglia in a corresponding subject that is not treated with the Siglec-7 agent.

In some embodiments, Siglec-7 agents of the present disclosure, such as anti-Siglec-7 antibodies of the present disclosure, are beneficial for preventing, lowering the risk of, or treating conditions and/or diseases associated with a reduction in proliferation, survival, increased apoptosis and/or function of dendritic cells, neutrophils, macrophages, neutrophils, NK cells, monocytes, osteoclasts, Langerhans cells of skin, Kupffer cells, T cells, and/or microglia including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Clearance and Phagocytosis

In some embodiments, Siglec-7 agents of the present disclosure, such as anti-Siglec-7 antibodies of the present disclosure, may induce clearance and/or phagocytosis after binding to a Siglec-7 protein expressed in a cell of one or more of apoptotic neurons, nerve tissue debris of the nervous system, dysfunctional synapses, non-nerve tissue debris of the nervous system, bacteria, other foreign bodies, disease-causing proteins, disease-causing peptides, disease-causing nucleic acid, or tumor cells. In certain embodiments, disease-causing proteins include, without limitation, amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides. In certain embodiments, disease-causing nucleic acids include, without limitation, antisense GGCCCC (G2C4) repeat-expansion RNA.

In some embodiments, the Siglec-7 agents of the present disclosure, such as anti-Siglec-7 antibodies of the present disclosure, may induce of one or more types of clearance, including without limitation, apoptotic neuron clearance, nerve tissue debris clearance, dysfunctional synapse clearance, non-nerve tissue debris clearance, bacteria or other foreign body clearance, disease-causing protein clearance, disease-causing peptide clearance, disease-causing nucleic acid clearance, and tumor cell clearance.

In some embodiments, the Siglec-7 agents of the present disclosure, such as anti-Siglec-7 antibodies of the present disclosure, may induce phagocytosis of one or more of apoptotic neurons, nerve tissue debris, dysfunctional synapses, non-nerve tissue debris, bacteria, other foreign bodies, disease-causing proteins, disease-causing peptides, disease-causing nucleic acid, and/or tumor cells.

In some embodiments, the Siglec-7 agents of the present disclosure, such as anti-Siglec-7 antibodies of the present disclosure, may increase phagocytosis by neutrophils, macrophages, neutrophils, NK cells, dendritic cells, monocytes, and/or microglia under conditions of reduced levels of macrophage colony-stimulating factor (M-CSF).

In some embodiments, Siglec-7 agents of the present disclosure, such as anti-Siglec-7 antibodies of the present disclosure, are beneficial for preventing, lowering the risk of, or treating conditions and/or diseases associated with apoptotic neurons, nerve tissue debris of the nervous system, non-nerve tissue debris of the nervous system, bacteria, other foreign bodies, disease-causing proteins, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection. *Campylobacter jejuni* infection, *Neisseria meningiditis* infection, type I HIV, and *Haemophilus* influenza.

Siglec-7-Dependent Gene Expression

In some embodiments, Siglec-7 agents of the present disclosure, such as antagonist anti-Siglec-7 antibodies of the present disclosure, may decrease the activity and/or expression of Siglec-7-dependent genes, and by that increase gene expression associated with signaling cascade that activate the immune system such as gene expression associated with ITAM containing receptors, pattern recognition receptors, of Toll-like receptors, of damage-associated molecular pattern (DAMP) receptors such as one or more transcription factors of the nuclear factor of activated T cells (NFAT) family of transcription factors.

In some embodiments, Siglec-7 agents of the present disclosure, such as antagonist anti-Siglec-7 antibodies of the present disclosure, are beneficial for preventing, lowering the risk of, or treating conditions and/or diseases associated with high levels of Siglec-7-dependent genes, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Siglec-7-Dependent Activation of T Cells

In some embodiments, Siglec-7 agents of the present disclosure, such as antagonist anti-Siglec-7 antibodies of the present disclosure, may increase the activity of cytotoxic T cells helper T cells or both. In some embodiments, Siglec-7 agents of the present disclosure, such as antagonist anti-Siglec-7 antibodies of the present disclosure, are beneficial for preventing, lowering the risk of, or treating conditions and/or diseases associated with decreased activity of cytotoxic T cells helper T cells or both, including without limitation, tumors, including solid tumors such as bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

In some embodiments, Siglec-7 agents of the present disclosure, such as antagonist anti-Siglec-7 antibodies of the present disclosure, may induce an increase in proliferation, survival, activity, and/or number of T cells, cytotoxic T cells, CD3$^+$ T cells (e.g., tumor infiltrating CD3$^+$ T cells, etc.), helper T cells, dendritic cells, macrophages, monocytes, neutrophils, osteoclasts, Langerhans cells of skin, Kupffer cells, and/or microglial cells. In some embodiments, Siglec-7 agents of the present disclosure, such as antagonist anti-Siglec-7 antibodies of the present disclosure, induce an increase in proliferation, survival, activity, and/or number of T cells, cytotoxic T cells, CD3$^+$ T cells, helper T cells, dendritic cells, macrophages, monocytes, neutrophils, osteoclasts. Langerhans cells of skin, Kupffer cells, and/or microglial cells in the presence of myeloid-derived suppressor cells (MDSC).

As used herein, the rate of proliferation, survival, activity, and/or number of T cells, cytotoxic T cells, CD3$^+$ T cells (e.g., tumor infiltrating CD3$^+$ T cells, etc.), helper T cells, dendritic cells, macrophages, monocytes, neutrophils, osteoclasts, Langerhans cells of skin. Kupffer cells, and/or microglial cells may include an increased rate if the rate of proliferation, survival, activity, and/or number of T cells, cytotoxic T cells, CD3$^+$ T cells, helper T cells, dendritic cells, macrophages, monocytes, neutrophils, osteoclasts. Langerhans cells of skin, Kupffer cells, and/or microglial cells in a subject treated with a Siglec-7 agent, such as an anti-Siglec-7 antibody of the present disclosure, is greater than the rate of proliferation, survival, activity, and/or number of T cells, cytotoxic T cells, CD3$^+$ T cells, helper T cells, dendritic cells, macrophages, monocytes, neutrophils, osteoclasts. Langerhans cells of skin, Kupffer cells, and/or microglial cells in a corresponding subject that is not treated with the Siglec-7 agent. In some embodiments, a Siglec-7 agent, such as an anti-Siglec-7 antibody of the present disclosure, may increase proliferation, survival, activity, and/or number of T cells, cytotoxic T cells, CD3$^+$ T cells, helper T cells, dendritic cells, macrophages, monocytes, neutrophils, osteoclasts. Langerhans cells of skin, Kupffer cells, and/or microglial cells in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a corresponding subject that is not treated with the Siglec-7 agent. In other embodiments, a Siglec-7 agent, such as an anti-Siglec-7 antibody of the present disclosure, may increase proliferation, survival, activity, and/or number of T cells, cytotoxic T cells. CD3$^+$ T cells, helper T cells, dendritic cells, macrophages, monocytes, neutrophils, osteoclasts, Langerhans cells of skin, Kupffer cells, and/or microglial cells in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of proliferation, survival, activity, and/or number of T cells, cytotoxic T cells, CD3$^+$ T cells, helper T cells, dendritic cells, macrophages, monocytes, neutrophils, osteoclasts. Langerhans cells of skin, Kupffer cells, and/or microglial cells in a corresponding subject that is not treated with the Siglec-7 agent.

In some embodiments, a Siglec-7 agent, such as an anti-Siglec-7 antibody of the present disclosure, may increase proliferation, survival, activity, and/or number of T cells, cytotoxic T cells, CD3$^+$ T cells, helper T cells, dendritic cells, macrophages, monocytes, neutrophils, osteoclasts, Langerhans cells of skin. Kupffer cells, and/or microglial cells in the presence of myeloid-derived suppressor cells (MDSC) by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in the presence of myeloid-derived suppressor cells (MDSC) that are not treated with the Siglec-7 agent. In other embodiments, a Siglec-7 agent, such as an anti-Siglec-7 antibody of the present disclosure, may increase proliferation, survival, activity, and/or number of T cells, cytotoxic T cells, CD3$^+$ T cells, helper T cells, dendritic cells, macrophages, monocytes, neutrophils, osteoclasts, Langerhans cells of skin. Kupffer cells, and/or microglial cells in the presence of myeloid-derived suppressor cells (MDSC) by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of proliferation, survival, activity, and/or number of T cells, cytotoxic T cells, CD3$^+$ T cells, helper T cells, dendritic cells, macrophages, monocytes, neutrophils, osteoclasts, Langerhans cells of skin. Kupffer cells, and/or microglial cells in the presence of myeloid-derived suppressor cells (MDSC) that are not treated with the Siglec-7 agent.

Siglec-7-Dependent Inhibition of Neutrophils

In some embodiments, Siglec-7 agents of the present disclosure, such as agonist anti-Siglec-7 antibodies of the present disclosure, may decrease the activity of neutrophils. In some embodiments, Siglec-7 agents of the present disclosure, such as agonist anti-Siglec-7 antibodies of the present disclosure, are beneficial for preventing, lowering the risk of, or treating conditions and/or diseases associated with decreased activity of the activity of natural killer cells, neutrophils or both, including without limitation, tumors, including solid tumors such as bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

Siglec-7-Dependent Enhanced Cell Killing by Natural Killer (NK) Cells

In some embodiments, Siglec-7 agents of the present disclosure, such as antagonist anti-Siglec-7 antibodies of the present disclosure, may increase the killing activity of NK cells. In some embodiments, Siglec-7 agents of the present disclosure, such as antagonistic anti-Siglec-7 antibodies of the present disclosure, are beneficial for preventing, lowering the risk of, or treating conditions and/or diseases associated with decreased activity of natural killer cells, neutrophils or both, including without limitation, tumors, including solid tumors such as bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

Siglec-7-Dependent Inhibition of Tumor-Associated Immune Cells

In some embodiments, Siglec-7 agents of the present disclosure, such as agonist anti-Siglec-7 antibodies of the present disclosure, may decrease the activity, decrease the proliferation, decrease the survival, decrease the functionality, decrease infiltration to tumors or lymphoid organs (e.g., the spleen and lymph nodes), and/or promote apoptosis of T-regulatory cells or inhibitory tumor-imbedded immunosuppressor dendritic cells or, tumor-associated macrophages, tumor-associated neutrophils, tumor-associated NK cells, or, myeloid-derived suppressor cells. In some embodiments, Siglec-7 agents of the present disclosure, such as agonist anti-Siglec-7 antibodies of the present disclosure, are beneficial for preventing, lowering the risk of, or treating conditions and/or diseases associated with the activity of one or more type of immune suppressor cells, including without limitation, tumors, including solid tumors that do not express Siglec-7 such as bladder cancer, brain cancer, breast cancer, colon cancer, rectal cancer, endometrial cancer, kidney cancer, renal cell cancer, renal pelvis cancer, lung cancer, melanoma, non-Hodgkin's lymphoma, pancreatic cancer, prostate cancer, ovarian cancer, fibrosarcoma, thyroid cancer, and blood tumors that express Siglec-7, such as leukemia cells.

In some embodiments, Siglec-7 agents of the present disclosure, such as antagonist anti-Siglec-7 antibodies of the present disclosure, may decrease the number of $CD14^+$ myeloid cells (e.g., the number of tumor-infiltrating $CD14^+$ myeloid cells, the number of peripheral blood $CD14^+$ myeloid cells, etc.), decrease tumor growth rate, reduce tumor volume, or reduce or inhibit differentiation, survival, and/or one or more functions of myeloid-derived suppressor cells (MDSC).

In some embodiments, a Siglec-7 agent, such as an anti-Siglec-7 antibody of the present disclosure, may decrease the number of $CD14^+$ myeloid cells (e.g., the number of tumor-infiltrating $CD14^+$ myeloid cells, the number of peripheral blood $CD14^+$ myeloid cells, etc.), decrease tumor growth rate, reduce tumor volume, or reduce or inhibit differentiation, survival, and/or one or more functions of myeloid-derived suppressor cells (MDSC) in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the number of $CD14^+$ myeloid cells, tumor growth rate, tumor volume, or level of differentiation, survival, and/or one or more functions of myeloid-derived suppressor cells (MDSC) in a corresponding subject that is not treated with the Siglec-7 agent. In other embodiments, a Siglec-7 agent, such as an anti-Siglec-7 antibody of the present disclosure, may decrease the number of $CD14^+$ myeloid cells (e.g., the number of tumor-infiltrating $CD14^+$ myeloid cells, the number of peripheral blood $CD14^+$ myeloid cells, etc.), decrease tumor growth rate, reduce tumor volume, or reduce or inhibit differentiation, survival, and/or one or more functions of myeloid-derived suppressor cells (MDSC) in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold at least 4.0 fold at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold at least 9.5 fold, or at least 10 fold, for example, as compared to the number of $CD14^+$ myeloid cells, tumor growth rate, tumor volume, or level of differentiation, survival, and/or one or more functions of myeloid-derived suppressor cells (MDSC) in a corresponding subject that is not treated with the Siglec-7 agent.

Increased Efficacy of Checkpoint Inhibitor Therapies

In some embodiments, Siglec-7 agents of the present disclosure, such as antagonist anti-Siglec-7 antibodies of the present disclosure, may increase the efficacy of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3.

In some embodiments, a Siglec-7 agent, such as an anti-Siglec-7 antibody of the present disclosure, may increase the efficacy of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3 in a subject receiving such one or more therapies by at least 100%, at least 15%, at least 20%, at least 25%, at least 30%, at least 35%, at least 40%, at least 45%, at least 50% at least 55%, at least 60%, at least 65%, at least 70%, at least 75%, at least 8%, at least 85%, at least 9%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of effectiveness of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3 in a corresponding subject receiving such one or more therapies that is not treated with the Siglec-7 agent. In other embodiments, a Siglec-7 agent, such as an anti-Siglec-7 antibody of the present disclosure, may increase the efficacy of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3 in a subject receiving such one or more therapies by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of effectiveness of one or more checkpoint inhibitor therapies and/or immune-modulating therapies, such as PD-1 inhibitors or therapies that target one or more of CTL4A, the adenosine pathway, PD-L1, PD-L2, OX40, TIM3, and/or LAG3 in a corresponding subject receiving such one or more therapies that is not treated with the Siglec-7 agent.

Increased Efficacy of Chemotherapeutic Agents

In some embodiments, Siglec-7 agents of the present disclosure, such as antagonist anti-Siglec-7 antibodies of the present disclosure, may increase the efficacy of one or more chemotherapy agents, such as gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), and/or carboplatin (Paraplatin®).

In some embodiments, a Siglec-7 agent, such as an anti-Siglec-7 antibody of the present disclosure, may increase the efficacy of one or more chemotherapy agents in a subject receiving such one or more therapies by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of effectiveness of one or more chemotherapy agents in a corresponding subject receiving such one or more therapies that is not treated with the Siglec-7 agent. In other embodiments, a Siglec-7 agent, such as an anti-Siglec-7 antibody of the present disclosure, may increase the efficacy of one or more chemotherapy agents in a subject receiving such one or more therapies by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of effectiveness of one or more chemotherapy agents in a corresponding subject receiving such one or more therapies that is not treated with the Siglec-7 agent.

Pharmaceutical Compositions

Siglec-7 agents of the present disclosure, such as anti-Siglec-7 antibodies of the present disclosure, can be incorporated into a variety of formulations for therapeutic administration by combining the agents, such as anti-Siglec-7 antibodies, with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS. Ringer's solution, dextrose solution, and Hank's solution. A pharmaceutical composition or formulation of the present disclosure can further include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

A pharmaceutical composition of the present disclosure can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, and enhance solubility or uptake). Examples of such modifications or complexing agents include, without limitation, sulfate, gluconate, citrate and phosphate. The polypeptides of a composition can also be complexed with molecules that enhance their in vivo attributes. Such molecules include, without limitation, carbohydrates, polyamines, amino acids, other peptides, ions (e.g., sodium, potassium, calcium, magnesium, manganese), and lipids.

Further examples of formulations that are suitable for various types of administration can be found in Remington's *Pharmaceutical Sciences*, Mace Publishing Company, Philadelphia, Pa., 17th ed. (1985). For a brief review of methods for drug delivery, see, Langer, *Science* 249:1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of an agent of the present disclosure, such as an anti-Siglec-7 antibody of the present disclosure, in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the poly saccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the present disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing a Siglec-7 agent of the present disclosure, such as an anti-Siglec-7 antibody of the present disclosure, may be administered to an individual in need of treatment with the Siglec-7 agent, preferably a human, in accord with known methods, such as intravenous administration as a bolus or by continuous infusion over a period of time, by intramuscular, intraperitoneal, intracerobrospinal, intracranial, intraspinal, subcutaneous, intra-articular, intrasynovial, intrathecal, oral, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

For in vive administration of any of the Siglec-7 agents of the present disclosure, such as any of the anti-Siglec-7 antibodies of the present disclosure, normal dosage amounts may vary from about 10 ng/kg up to about 100 mg/kg of an individual's body weight or more per day, preferably about 1 mg/kg/day to 10 mg/kg/day, depending upon the route of administration. For repeated administrations over several days or longer, depending on the severity of the disease, disorder, or condition to be treated, the treatment is sustained until a desired suppression of symptoms is achieved.

An exemplary dosing regimen may include administering an initial dose of a Siglec-7 agent of the present disclosure, such as an anti-Siglec-7 antibody, of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 gi/kg, about 30 µg/kg, about 100 µg/kg, about 300 µg/kg, about 1 mg/kg, and about 2/mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the Siglec-7 agent, such as the anti-Siglec-7 antibody administered, can vary over time independently of the dose used.

Dosages for a particular Siglec-7 agent, such as a particular anti-Siglec-7 antibody, may be determined empirically in individuals who have been given one or more administrations of the Siglec-7agent, such as the anti-Siglec-7 antibody. Individuals are given incremental doses of a Siglec-7 agent, such as an anti-Siglec-7 antibody. To assess efficacy of a Siglec-7 agent, such as an anti-Siglec-7 antibody, a clinical symptom of any of the diseases, disorders, or conditions of the present disclosure (e.g., frontotemporal dementia, Alzheimer's disease, vascular dementia, seizures, retinal dystrophy, a traumatic brain injury, a spinal cord injury, long-term depression, atherosclerotic vascular diseases, and undesirable symptoms of normal aging) can be monitored.

Administration of a Siglec-7 agent, such as an anti-Siglec-7 antibody of the present disclosure, can be continuous or intermittent, depending, for example, on the recipient's physiological condition, whether the purpose of the administration is therapeutic or prophylactic, and other factors known to skilled practitioners. The administration of a Siglec-7 agent, such as an anti-Siglec-7 antibody, may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the present disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Therapeutic Uses

Further aspects of the present disclosure provide methods of modulating (e.g., activating or inhibiting) one or more Siglec-7 activities, including with limitation, modulating (e.g., activating or inhibiting) a Siglec-7 protein of the present disclosure, counteracting one or more phosphorylation of Tyr-437 and Tyr-460 by a Src family tyrosine kinase, such as Syk, LCK, FYM, and/or ZAP70; recruitment of and binding to the tyrosine-specific protein phosphatases SHP1 and SHP2; recruitment of and binding to PLC-gamma1, which acts as a guanine nucleotide exchange factor for Dynamini-1; recruitment of and binding to SH2-domain containing protein (e.g., Crkl); recruitment of and binding to the spleen tyrosine kinase Syk; recruitment of and binding to SH3-SH2-SH3 growth factor receptor-bound protein 2 (Grb2); recruitment of and binding to multiple SH2-containing proteins; modulating (e.g., activating or inhibiting) expression of one or more pro-inflammatory cytokines, optionally wherein the one or more anti-inflammatory cytokines are selected from IFN-a4, IFN-beta. IL-1β, IL-1alpha, TNF-α, IL-6, IL-8, CRP, IL-20 family members, LIF, IFN-gamma, OSM, CNTF, GM-CSF, IL-11, IL-12, IL-17, IL-18, IL-33, MCP-1, and MIP-1-beta; modulating (e.g., activating or inhibiting) expression of one or more pro-inflammatory cytokines in one or more cells selected from macrophages, neutrophils, NK cells, dendritic cells, bone marrow-derived dendritic cells, monocytes, osteoclasts, T cells, T helper cells, cytotoxic T cells, granulocytes, and microglial cells; modulating (e.g., activating or inhibiting) expression of one or more anti-inflammatory cytokines, optionally wherein the one or more anti-inflammatory cytokines are selected from IL-4, IL-10, IL-13, IL-35, IL-16. TGF-beta, IL-1Ra, G-CSF, and soluble receptors for TNF, IFN-beta1a, IFN-beta1b, or IL-6; modulating (e.g., activating or inhibiting) expression of one or more anti-inflammatory cytokines in one or more cells selected from macrophages, neutrophils, NK cells, dendritic cells, bone marrow-derived dendritic cells, monocytes, osteoclasts, T cells, T helper cells, cytotoxic T cells, granulocytes, and microglial cells; modulating (e.g., activating or inhibiting) expression of one or more proteins selected from C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, and PYCARD; activation of extracellular signal-regulated kinase (ERK) phosphorylation; modulating (e.g., activating or inhibiting) tyrosine phosphorylation on one or more cellular proteins, optionally, wherein the one or more cellular proteins comprise ZAP-70 and the tyrosine phosphorylation occurs on Tyr-319 of ZAP-70; modulating (e.g., activating or inhibiting) expression of C-C chemokine receptor 7 (CCR7); activation of microglial cell chemotaxis toward CCL19-expressing and CCL21-expressing cells; modulating (e.g., activating or inhibiting) T cell proliferation induced by one or more cells selected from dendritic cells, bone marrow-derived dendritic cells, monocytes, microglia. M1 microglia, activated M1 microglia, M2 microglia, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, and M2 NK cells; modulating (e.g., activating or inhibiting) osteoclast production, modulating (e.g., activating or inhibiting) rate of osteoclastogenesis, or both; modulating (e.g., activating or inhibiting) survival of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; modulating (e.g., activating or inhibiting) proliferation of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; modulating (e.g., activating or inhibiting) migration of one or more cells selected from dendritic cells, bone marrow-derived dendritic cells, macrophages, neutrophils, NK cells, M1 macrophages, M1 neutrophils. M NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; modulating (e.g., activating or inhibiting) one or more functions of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; modulating (e.g., activating or inhibiting) maturation of one or more cells selected from dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils. M2 NK cells, monocytes, osteoclasts, T cells, T helper cells, cytotoxic T cells, granulocytes, neutrophils, microglia, M1 microglia, activated M1 microglia, and M2 microglia; activation of one or more types of clearance selected from apoptotic neuron clearance, nerve tissue debris clearance, dysfunctional synapse clearance, non-nerve tissue debris clearance, bacteria clearance, other foreign body clearance, disease-causing protein clearance, disease-causing peptide clearance, and tumor cell clearance; optionally wherein the disease-causing protein is selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides and the tumor cell is from a cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; activation of phagocytosis of one or more of apoptotic neurons, nerve tissue debris, dysfunctional synapses, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL. S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells are from a cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer; inhibiting binding to Siglec-7 ligand on tumor cells; modulating (e.g., activating or inhibiting) binding to Siglec-7 ligand on cells selected from neutrophils, dendritic cells, bone marrow-derived dendritic cells, monocytes, microglia, macrophages, and NK cells; activation of tumor cell killing by one or more of microglia, macrophages, neutrophils. NK cells, dendritic cells, bone marrow-derived dendritic cells, neutrophils, T cells, T helper cells, or cytotoxic T cells; activating anti-tumor cell proliferation activity of one or more of microglia, macrophages, neutrophils, NK cells, dendritic cells, bone marrow-derived dendritic cells, neutrophils, T cells, T helper cells, or cytotoxic T cells; activation of anti-tumor cell metastasis activity of one or more of microglia, macrophages, neutrophils, NK cells, dendritic cells, bone marrow-derived dendritic cells, neutrophils, T cells, T helper cells, or cytotoxic T cells; modulating (e.g., activating or inhibiting) of one or more ITAM motif containing receptors, optionally wherein the one or more ITAM motif containing receptors are selected from TREM1, TREM2, Sirp beta, FcgR, DAP10, and DAP12; modulating (e.g., activating or inhibiting) of signaling by one or more pattern recognition receptors (PRRs), optionally wherein the one or more PRRs are selected from receptors that identify pathogen-associated molecular patterns (PAMPs), receptors that identify damage-associated molecular patterns (DAMPs), and any combination thereof; modulating (e.g., activating or inhibiting) of one or more receptors comprising the motif $D/Ex_{0-2}YxxL/IX_{6-8} YxxL/I$ (SEQ ID NO: 537); modulating (e.g., activating or inhibiting) of signaling by one or more Toll-like receptors; modulating (e.g., activating or inhibiting) of the JAK-STAT signaling pathway; modulating (e.g., activating or inhibiting) of nuclear factor kappa-light-chain-enhancer of activated B cells (NFκB); phosphorylation of an ITAM motif containing receptor; modulating (e.g., activating or inhibiting) expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils, T cells, T helper cells, or cytotoxic T cells; modulating (e.g., activating or inhibiting) expression of one or more Siglec-7-dependent genes; normalization of disrupted Siglec-7-dependent gene expression; modulating (e.g., activating or inhibiting) expression of one or more ITAM-dependent genes, optionally wherein the one more ITAM-dependent genes are activated by nuclear factor of activated T cells (NFAT) transcription factors; rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; and/or reducing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells into tumors; increasing the number of tumor-promoting myeloid/granulocytic immune-suppressive cells in a tumor, in peripheral blood, or other lymphoid organ; enhancing tumor-promoting activity of myeloid-derived suppressor cells; increasing expression of tumor-promoting cytokines in a tumor or in peripheral blood, optionally wherein the tumor-promoting cytokines are TGF-beta or IL-10; increasing tumor infiltration of tumor-promoting FoxP3+ regulatory T lymphocytes; enhancing tumor-promoting activity of myeloid-derived suppressor cells (MDSC); decreasing activation of tumor-specific T lymphocytes with tumor killing potential; decreasing infiltration of tumor-specific NK cells with tumor killing potential; decreasing the tumor killing potential of NK cells; decreasing infiltration of tumor-specific B lymphocytes with potential to enhance immune response; decreasing infiltration of tumor-specific T lymphocytes with tumor killing potential; increasing tumor volume; increasing tumor growth rate; increasing metastasis; increasing rate of tumor recurrence; decreasing efficacy of one or more immune-therapies that modulate anti-tumor T cell responses, optionally wherein the one or more immune-therapies are immune-therapies that target one or more target proteins selected from PD1/PDL1, CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-S, TREM1, TREM2, CSF-1 receptor, and any combination thereof, or of one or more cancer vaccines; inhibition of PLCã/PKC/calcium mobilization; and/or inhibition of PI3K/Akt, Ras/MAPK signaling in an individual in need thereof, by administering to the individual a therapeutically effective amount of a Siglec-7 agent of the present disclosure, such as an anti-Siglec-7 antibody of the present disclosure, to modulate (e.g., activate or inhibit) one or more of the Siglec-7 activities in the individual.

As disclosed herein, Siglec-7 agents of the present disclosure that decrease cellular levels of Siglec-7 and/or inhibit interaction between Siglec-7 and one or more Siglec-7 ligands, such as anti-Siglec-7 antibodies of the present disclosure, may be used for preventing, reducing risk, or treating dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera essential thrombocytosis, primary or idiopathic myelofibrosis, primary or idiopathic myelosclerosis, myeloid-derived tumors, tumors that express Siglec-7, thyroid cancer, infections. CNS herpes, parasitic infections. Trypanosome infection, *Cruzi* infection, *Pseudomonas aeruginosa* infection, *Leishmania donovani* infection, group B *Streptococcus* infection. *Campylobacter jejuni* infection, *Neisseria meningiditis* infection, type I HIV, and/or *Haemophilus* influenza. In some embodiments, the agents are selected from antibodies, soluble Siglec-7 receptors, Siglec-7-Fc fusion proteins, Siglec-7 immunoadhesins, soluble Siglec receptors that binds one or more Siglec-7 ligands, Siglec-Fc fusion proteins, Siglec immunoadhesins, antisense molecules, siRNAs, small molecule inhibitors, proteins, and peptides. In some embodiments, the Siglec-7 agents are agonist antibodies. In some embodiments, the Siglec-7 agents are inert antibodies. In some embodiments, the Siglec-7 agents are antagonist antibodies.

In some embodiments, the present disclosure provides methods of preventing, reducing risk, or treating dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and/or *Haemophilus* influenza, by administering to an individual in need thereof a therapeutically effective amount of an agent of the present disclosure that decreases cellular levels of Siglec-7, inhibits interaction between Siglec-7 and one or more Siglec-7 ligands, or both. In some embodiments, the agent is selected from an antibody, a soluble Siglec-7 receptor, a Siglec-7-Fc fusion protein, a Siglec-7 immunoadhesin, a soluble Siglec receptor that binds one or more Siglec-7 ligands, a Siglec-Fc fusion protein, a Siglec immunoadhesin, an antisense molecule, an siRNA, a small molecule inhibitor, a protein, and a peptide. In some embodiments, the agent is an anti-Siglec-7 antibody of the present disclosure.

In some embodiments, the present disclosure provides methods of preventing, reducing risk, or treating cancer, by administering to an individual in need thereof, a therapeutically effective amount of an agent of the present disclosure that decreases cellular levels of Siglec-7, inhibits interaction between Siglec-7 and one or more Siglec-7 ligands, or both. In some embodiments, the agent is selected from an antibody, a soluble Siglec-7 receptor, a Siglec-7-Fc fusion protein, a Siglec-7 immunoadhesin, a soluble Siglec receptor that binds one or more Siglec-7 ligands, a Siglec-Fc fusion protein, a Siglec immunoadhesin, an antisense molecule, an siRNA, a small molecule inhibitor, a protein, and a peptide. In certain embodiments, the agent is an anti-Siglec-7 antibody of the present disclosure. In some embodiments, the cancer expresses Siglec-7 or one or more Siglec-7 ligands. In some embodiments, the cancer is bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), and/or multiple myeloma. In some embodiments, the anti-Siglec-7 antibody inhibits one or more Siglec-7 activities selected from: (a) promoting proliferation, maturation, migration, differentiation, and/or functionality of one or more of immunosuppressor dendritic cells, immunosuppressor macrophages, immunosuppressor neutrophils, immunosuppressor NK cells, myeloid derived suppressor cells, tumor-associated macrophages, tumor-associated suppressor neutrophils, tumor-associated suppressor NK cells, and regulatory T cells; (b) enhancing infiltration of one or more of immunosuppressor dendritic cells, immunosuppressor macrophages, immunosuppressor neutrophils, immunosuppressor NK cells, myeloid derived suppressor cells, tumor-associated macrophages, tumor-associated suppressor neutrophils, tumor-associated suppressor NK cells, and regulatory T cells into tumors; (c) increasing number of tumor-promoting myeloid/granulocytic immune-suppressive cells in a tumor, in peripheral blood, or other lymphoid organ; (d) enhancing tumor-promoting activity of myeloid-derived suppressor cells (MDSC); (e) increasing expression of tumor-promoting cytokines in a tumor or in peripheral blood, optionally wherein the tumor-promoting cytokines are TGF-beta or IL-10; (f) increasing tumor infiltration of tumor-promoting FoxP3+ regulatory T lymphocytes; (g) decreasing activation of tumor-specific T lymphocytes with tumor killing potential; (h) decreasing infiltration of tumor-specific T lymphocytes with tumor killing potential; (i) decreasing infiltration of tumor-specific NK cells with tumor killing potential; (j) decreasing the tumor killing potential of NK cells; (k) decreasing infiltration of tumor-specific B lymphocytes with potential to enhance immune response; (l) increasing tumor volume; (m) increasing tumor growth rate; (n) increasing metastasis; (o) increasing rate of tumor recurrence; (p) decreasing efficacy of one or more immune-therapies that modulate anti-tumor T cell responses, such as one or more immune-therapies are immune-therapies that target one or more target proteins selected from PD1/PDL1, CTLA4, CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, and any combination thereof, or cancer vaccines; (q) inhibition of PLCγ/PKC/calcium mobilization; and (r) inhibition of PI3K/Akt, Ras/MAPK signaling. In some embodiments, the agent exhibits one or more activities selected from: (a) increasing the number of tumor infiltrating $CD3^+$ T cells; (b) inhibiting Siglec-7 binding to one or more Siglec-7 ligands; (c) decreasing cellular levels of Siglec-7 in peripheral immune cells; (d) reducing the number of non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in blood; (e) reducing the number of non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in the tumor; (f) reducing PD-L1 levels in one or more cells, optionally wherein the one or more cells are non-tumorigenic myeloid-derived suppressor cells (MDSC); (g) reducing PD-L2 levels in one or more cells, optionally wherein the one or more cells are non-tumorigenic myeloid-derived suppressor cells (MDSC); (h) reducing CD11b levels in one or more cells, optionally wherein the one or more cells are non-tumorigenic myeloid-derived suppressor cells (MDSC); (i) reducing B7-H3 levels in one or more cells, optionally wherein the one or more cells are non-tumorigenic myeloid-derived suppressor cells (MDSC); (j) reducing CD200R levels in one or more cells, optionally wherein the one or more cells are non-tumorigenic myeloid-derived suppressor cells (MDSC); (k) reducing CD163 levels in one or more cells, optionally wherein the one or more cells are non-tumorigenic myeloid-derived suppressor cells (MDSC); (l) reducing CD206 levels in one or more cells, optionally wherein the one or more cells are non-tumorigenic myeloid-derived suppressor cells (MDSC); (m) decreasing tumor growth rate of solid tumors; (n) reducing tumor volume; (o) increasing efficacy of one or more PD-1 inhibitors; (p) increasing efficacy of one or more checkpoint inhibitor therapies and/or immune-modulating therapies, optionally wherein the one or more checkpoint inhibitor therapies and/or immune-modulating therapies target one or more of CTL4, the adenosine pathway, PD-L1, PD-L2, OX40, TIM3, LAG3, or any combination thereof; (q) inhibiting differentiation, survival, and/or one or more functions of non-tumorigenic myeloid-derived suppressor cells (MDSC); (r) inducing cell death of one or more myeloid-derived suppressor cells (MDSC); and (s) increasing proliferation of T cells in the presence of non-tumorigenic myeloid-derived suppressor cells (MDSC).

As disclosed herein, agents of the present disclosure, such as anti-Siglec-7 antibodies of the present disclosure, may also be used for inducing and/or promoting the survival maturation, functionality, migration, or proliferation of one or more immune cells (e.g., innate immune cells or adaptive immune cells). In some embodiments, the present disclosure provides methods of inducing or promoting the survival, maturation, functionality, migration, or proliferation of one or more immune cells in an individual in need thereof, by administering to the individual a therapeutically effective amount of an agent of the present disclosure that decreases cellular levels of Siglec-7, inhibits interaction between Siglec-7 and one or more Siglec-7 ligands, or both. In some embodiments, the agent is selected from an antibody, a soluble Siglec-7 receptor, a Siglec-7-Fc fusion protein, a Siglec-7 immunoadhesin, a soluble Siglec receptor that binds one or more Siglec-7 ligands, a Siglec-Fc fusion protein, a Siglec immunoadhesin, an antisense molecule, an siRNA, a small molecule inhibitor, a protein, and a peptide. In some embodiments, the agent is an isolated anti-Siglec-7 antibody of the present disclosure. In some embodiments, the one or more immune cells are selected from dendritic cells, macrophages, neutrophils, NK cells, microglia, T cells, T helper cells, cytotoxic T cells, and any combination thereof.

In some embodiments, the agent is an agonist anti-Siglec-7 antibody. In some embodiments, the agent is a transient agonist anti-Siglec-7 antibody of the present disclosure that initially acts as an agonist and then acts as a long-term antagonist antibody. In some embodiments, the agent is an inert anti-Siglec-7 antibody. In some embodiments, the agent is an antagonist anti-Siglec-7 antibody. In some embodiments, the anti-Siglec-7 antibody reduces cellular (e.g., cell surface, intracellular, or total) levels of Siglec-7. In some embodiments, the anti-Siglec-7 antibody induces degradation of Siglec-7. In some embodiments, the anti-Siglec-7 antibody induces cleavage of Siglec-7. In some embodiments, the anti-Siglec-7 antibody induces internalization of Siglec-7. In some embodiments, the anti-Siglec-7 antibody induces shedding of Siglec-7. In some embodiments, the anti-Siglec-7 antibody induces downregulation of Siglec-7 expression. In some embodiments, the anti-Siglec-7 antibody inhibits interaction (e.g., binding) between Siglec-7 and one or more Siglec-7 ligands. In some embodiments, the anti-Siglec-7 antibody transiently activates and then induces degradation of Siglec-7. In some embodiments, the anti-Siglec-7 antibody transiently activates and then induces cleavage of Siglec-7. In some embodiments, the anti-Siglec-7 antibody transiently activates and then induces internalization of Siglec-7. In some embodiments, the anti-Siglec-7 antibody transiently activates and then induces shedding of Siglec-7. In some embodiments, the anti-Siglec-7 antibody transiently activates and then induces downregulation of Siglec-7 expression. In some embodiments, the anti-Siglec-7 antibody transiently activates and then induces decreased expression of Siglec-7. In certain embodiments, the individual has a Siglec-7 variant allele.

As disclosed herein, agents of the present disclosure that bind or interact with Siglec-7, such as anti-Siglec-7 antibodies of the present disclosure, may further be used for decreasing the activity, functionality, or survival of regulatory T cells, tumor-imbedded immunosuppressor dendritic cells, tumor-imbedded immunosuppressor macrophages, tumor-imbedded immunosuppressor neutrophils, tumor-imbedded immunosuppressor NK cells, myeloid derived suppressor cells, tumor-associated macrophages, tumor-associated neutrophils, tumor-associated NK cells, acute myeloid leukemia (AML) cells, chronic lymphocytic leukemia (CLL) cell, and/or chronic myeloid leukemia (CML) cells. In some embodiments, the present disclosure provides methods of decreasing the activity, functionality, or survival of regulatory T cells, tumor-imbedded immunosuppressor dendritic cells, tumor-imbedded immunosuppressor macrophages, tumor-imbedded immunosuppressor neutrophils, tumor-imbedded immunosuppressor NK cells, myeloid-derived suppressor cells, tumor-associated macrophages, tumor-associated neutrophils, tumor-associated NK cells, acute myeloid leukemia (AML) cells, chronic lymphocytic leukemia (CLL) cell, or chronic myeloid leukemia (CML) cells in an individual in need thereof, by administering to the individual a therapeutically effective amount of an agent that binds or interacts with Siglec-7. In some embodiments, the agent is selected from an antibody, an antagonist antibody, an inert antibody, an agonist antibody, a Siglec-7 ligand, a Siglec-7 ligand agonist fragment, a Siglec-7 immunoadhesin, a Siglec-7 ligand mimetic, a soluble Siglec-7 receptor, a Siglec-7-Fc fusion protein, a soluble Siglec receptor that binds one or more Siglec-7 ligands, a Siglec-Fc fusion protein that binds one or more Siglec-7 ligands, and a small molecule compound. In some embodiments, the agent is an isolated anti-Siglec-7 antibody or anti-Siglec-7 antibody conjugate of the present disclosure. In some embodiments, the anti-Siglec-7 antibody conjugate comprises an anti-Siglec-7 antibody conjugated to a detectable marker, a toxin, or a therapeutic agent.

As disclosed herein, agents of the present disclosure that bind or interact with Siglec-7, such as anti-Siglec-7 antibodies of the present disclosure, may be used for decreasing cellular levels of Siglec-7 on one or more cells in vitro or in vivo, including without limitation, red blood cells, bacterial cells, apoptotic cells, nerve cells, glia cells, microglia, astrocytes, tumor cells, viruses, dendritic cells, Siglec-7 ligands bound to beta amyloid plaques, Siglec-7 ligands bound to Tau tangles, Siglec-7 ligands on disease-causing proteins, Siglec-7 ligands on disease-causing peptides, macrophages, neutrophils, natural killer cells, monocytes, T cells, T helper cells, cytotoxic T cells, B cells, tumor-imbedded immunosuppressor dendritic cells, tumor-imbedded immunosuppressor macrophages, myeloid-derived suppressor cells, and/or regulatory T cells. In some embodiments, the present disclosure provides methods of decreasing cellular levels of Siglec-7 on one or more cells in an individual in need thereof, by administering to the individual a therapeutically effective amount of an agent that binds or interacts with Siglec-7. In some embodiments, the agent is selected from an antibody, an antagonist antibody, an inert antibody, an agonist antibody, a Siglec-7 ligand, a Siglec-7 ligand agonist fragment, a Siglec-7 immunoadhesin, a Siglec-7 ligand mimetic, a soluble Siglec-7 receptor, a Siglec-7-Fc fusion protein, a soluble Siglec receptor that binds one or more Siglec-7 ligands, a Siglec-Fc fusion protein that binds one or more Siglec-7 ligands, and a small molecule compound. In some embodiments, the agent is an isolated anti-Siglec-7 antibody or anti-Siglec-7 antibody conjugate of the present disclosure. In some embodiments, the anti-Siglec-7 antibody conjugate comprises an anti-Siglec-7 antibody conjugated to a detectable marker, a toxin, or a therapeutic agent. In some embodiments, the one or more cells are selected from red blood cells, bacterial cells, apoptotic cells, nerve cells, glia cells, microglia, astrocytes, tumor cells, viruses, dendritic cells, Siglec-7 ligands bound to beta amyloid plaques, Siglec-7 ligands bound to Tau tangles, Siglec-7 ligands on disease-causing proteins, Siglec-7 ligands on disease-causing peptides, macrophages, neutrophils, natural killer cells, monocytes, T cells, T helper cells, cytotoxic T cells, B cells, tumor-imbedded immunosuppressor dendritic cells, tumor-imbedded immunosuppressor macrophages, myeloid-derived suppressor cells, regulatory T cells, and any combination thereof.

Cellular levels of Siglec-7 may refer to, without limitation, cell surface levels of Siglec-7, intracellular levels of Siglec-7, and total levels of Siglec-7. In some embodiments, a decrease in cellular levels of Siglec-7 comprises decrease in cell surface levels of Siglec-7. As used herein, an anti-Siglec-7 antibody decreases cell surface levels of Siglec-7 if it induces a decrease of 21% or more in cell surface levels of Siglec-7 as measured by any in vitro cell-based assays or suitable in vivo model described herein or known in the art. In some embodiments, a decrease in cellular levels of Siglec-7 comprises a decrease in intracellular levels of Siglec-7. As used herein, an anti-Siglec-7 antibody decreases intracellular levels of Siglec-7 if it induces a decrease of 21% or more in intracellular levels of Siglec-7 as measured by any in vitro cell-based assays or suitable in vivo model described herein or known in the art. In some embodiments, a decrease in cellular levels of Siglec-7 comprises a decrease in total levels of Siglec-7. As used herein, an anti-Siglec-7 antibody decreases total levels of Siglec-7 if it induces a decrease of 21% or more in total levels of Siglec-7 as measured by any in vitro cell-based assays or suitable in vivo model described herein or known in the art. In some embodiments, the anti-Siglec-7 antibodies induce Siglec-7 degradation, Siglec-7 cleavage, Siglec-7 internalization, Siglec-7 shedding, and/or downregulation of Siglec-7 expression. In some embodiments, cellular levels of Siglec-7 are measured on primary cells (e.g., dendritic cells, bone marrow-derived dendritic cells, monocytes, microglia, and macrophages) or on cell lines utilizing an in vitro cell assay. In some embodiments, the anti-Siglec-7 antibody decreases cellular levels of Siglec-7 with an $EC_{50}$ that ranges from 500 pM to 18 pM. In some embodiments, the anti-Siglec-7 antibody decreases cellular levels of Siglec-7 with an $EC_{50}$ that ranges from 350 pM to 33 pM. In some embodiments, the $EC_{50}$ is determined at a temperature of approximately 37° C. In some embodiments, the anti-Siglec-7 antibody has a dissociation constant ($K_D$) for human Siglec-7 that ranges from about 10 nM to 10 pM, or less than 10 pM. In some embodiments that may be combined with any of the preceding embodiments, the anti-Siglec-7 antibody has a dissociation constant ($K_D$) for human Siglec-7 that ranges from about 9.5 nM to about 17 pM, or less than 17 pM. In some embodiments, the dissociation constant ($K_D$) is determined at a temperature of approximately 25° C. In some embodiments, the anti-Siglec-7 antibody binds to human dendritic cells with an $EC_{50}$ that ranges from 2 nM to 100 pM. In some embodiments, the anti-Siglec-7 antibody binds to human dendritic cells with an $EC_{50}$ that ranges from 1.4 nM to 300 pM. In some embodiments, the $EC_{50}$ for binding to human dendritic cells is determined at a temperature of approximately 4° C.

In some embodiments the individual has a heterozygous variant of Siglec-7.

In some embodiments, the methods of the present disclosure may further involve the coadministration of Siglec-7 agents, such as anti-Siglec-7 antibodies or bispecific anti-Siglec-7 antibodies, with antibodies that bind to pattern recognition receptors, antibodies that bind to Toll-like receptors, antibodies that bind to damage-associated molecular pattern (DAMP) receptors, and/or antibodies that bind to cytokine or antibodies to interleukins).

In some embodiments, the methods of the present disclosure may further include administering to the individual at least one antibody that specifically binds to an inhibitory checkpoint molecule, and/or one or more standard or investigational anti-cancer therapies. In some embodiments, the at least one antibody that specifically binds to an inhibitory checkpoint molecule is administered in combination with the anti-Siglec-7 antibody. In some embodiments, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, an anti-TNFa antibody, an anti-CD33 antibody, an anti-Siglec-5 antibody, an anti-Siglec-9 antibody, an anti-Siglec-11 antibody, an antagonistic anti-TREM1 antibody, an antagonistic anti-TREM2 antibody, and any combination thereof. In some embodiments, the one or more standard or investigational anti-cancer therapies are selected from radiotherapy, cytotoxic chemotherapy, targeted therapy, imatinib therapy, trastuzumab therapy, etanercept therapy, adoptive cell transfer (ACT) therapy, chimeric antigen receptor T cell transfer (CAR-T) therapy, vaccine therapy, and cytokine therapy.

In some embodiments, the methods of the present disclosure may further include administering to the individual at least one antibody that specifically binds to an inhibitory cytokine. In some embodiments, the at least one antibody that specifically binds to an inhibitory cytokine is administered in combination with the Siglec-7 agent, such as an anti-Siglec-7 antibody. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the methods of the present disclosure may further include administering to the individual at least one agonistic antibody that specifically binds to a stimulatory checkpoint protein. In some embodiments, the at least one agonistic antibody that specifically binds to a stimulatory checkpoint protein is administered in combination with the Siglec-7 agent, such as an anti-Siglec-7 antibody. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonistic anti-TREM1 antibody, an agonistic anti-TREM2 antibody, an agonist anti-CD137/4-1BB antibody, an agonist anti-CD27 antibody, an agonist anti-glucocorticoid-induced TNFR-related protein GITR antibody, and any combination thereof.

In some embodiments, the methods of the present disclosure may further include administering to the individual at least one stimulatory cytokine. In some embodiments, the at least one stimulatory cytokine is administered in combination with the Siglec-7 agent, such as an anti-Siglec-7 antibody. In some embodiments, the at least one stimulatory cytokine is selected from IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, MCP-1, MIP-1-beta, and any combination thereof.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

In some embodiments, administering a Siglec-7 agent of the present disclosure, such as an anti-Siglec-7 antibody of the present disclosure, can prevent, reduce the risk, and/or treat dementia. In some embodiments, administering a Siglec-7 agent, such as an anti-Siglec-7 antibody, may modulate one or more Siglec-7 activities in an individual having dementia.

Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence. FTD accounts for 20% of pre-senile dementia cases. The clinical features of FTD include memory deficits, behavioral abnormalities, personality changes, and language impairments (Cruts, M. & Van Broeckhoven, C., Trends Genet. 24:186-194 (2008); Neary, D., et al., Neurology 51:1546-1554 (1998); Ratnavalli, E., Brayne, C., Dawson, K. & Hodges, J. R., Neurology 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., Nature 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., Arch. Neurol. 64:1388-1394 (2007)). A majority of those FTD cases with Ub inclusions (FTD-U) were shown to carry mutations in the Progranulin gene.

In some embodiments, administering a Siglec-7 agent of the present disclosure, such as an anti-Siglec-7 antibody of the present disclosure, can prevent, reduce the risk, and/or treat FTD. In some embodiments, administering a Siglec-7 agent, such as an anti-Siglec-7 antibody, may modulate one or more Siglec-7 activities in an individual having FTD.

Alzheimer's Disease

Alzheimer's disease (AD), is the most common form of dementia. There is no cure for the disease, which worsens as it progresses, and eventually leads to death. Most often, AD is diagnosed in people over 65 years of age. However, the less-prevalent early-onset Alzheimer's can occur much earlier.

Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

In some embodiments, administering a Siglec-7 agent of the present disclosure, such as an anti-Siglec-7 antibody of the present disclosure, can prevent, reduce the risk, and/or treat Alzheimer's disease. In some embodiments, administering a Siglec-7 agent, such as an anti-Siglec-7 antibody, may modulate one or more Siglec-7 activities in an individual having Alzheimer's disease.

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

In some embodiments, administering a Siglec-7 agent of the present disclosure, such as an anti-Siglec-7 antibody of the present disclosure, can prevent, reduce the risk, and/or treat Parkinson's disease. In some embodiments, administering a Siglec-7 agent, such as an anti-Siglec-7 antibody, may modulate one or more Siglec-7 activities in an individual having Parkinson's disease.

Amyotrophic Lateral Sclerosis (ALS)

As used herein, amyotrophic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

It has been shown that Progranulin plays a role in ALS (Schymick, J C et al., (2007) J Neurol Neurosurg Psychiatry; 78:754-6) and protects again the damage caused by ALS causing proteins such as TDP-43 (Laird, A S et al., (2010). PLoS ONE 5: e13368). It was also demonstrated that pro-NGF induces p75 mediated death of oligodendrocytes and corticospinal neurons following spinal cord injury (Beatty et al., Neuron (2002), 36, pp. 375-386; Giehl et al. Proc. Natl. Acad. Sci USA (2004), 101, pp 6226-30).

In some embodiments, administering a Siglec-7 agent of the present disclosure, such as an anti-Siglec-7 antibody of the present disclosure, can prevent, reduce the risk, and/or treat ALS. In some embodiments, administering a Siglec-7 agent, such as an anti-Siglec-7 antibody, may modulate one or more Siglec-7 activities in an individual having amyotrophic lateral sclerosis.

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

In some embodiments, administering a Siglec-7 agent of the present disclosure, such as an anti-Siglec-7 antibody of the present disclosure, can prevent, reduce the risk, and/or treat Huntington's disease (HD). In some embodiments, administering a Siglec-7 agent, such as an anti-Siglec-7 antibody, may modulate one or more Siglec-7 activities in an individual having Huntington's disease.

Taupathy Disease

Taupathy diseases, or Tauopathies, are a class of neurodegenerative disease caused by aggregation of the microtubule-associated protein tau within the brain. Alzheimer's disease (AD) is the most well-known taupathy disease, and involves an accumulation of tau protein within neurons in the form of insoluble neurofibrillary tangles (NFTs). Other taupathy diseases and disorders include progressive supranuclear palsy, dementia pugilistica (chromic traumatic encephalopathy), frontotemporal dementia and parkinsonism linked to chromosome 17, Lytico-Bodig disease (Parkinson-dementia complex of Guam). Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, and frontotemporal lobar degeneration.

In some embodiments, administering a Siglec-7 agent of the present disclosure, such as an anti-Siglec-7 antibody of the present disclosure, can prevent, reduce the risk, and/or treat taupathy disease. In some embodiments, administering a Siglec-7 agent, such as an anti-Siglec-7 antibody, may modulate one or more Siglec-7 activities in an individual having a taupathy disease.

Multiple Sclerosis

Multiple sclerosis (MS) can also be referred to as disseminated sclerosis or encephalomyelitis disseminata. MS is an inflammatory disease in which the fatty myelin sheaths around the axons of the brain and spinal cord are damaged, leading to demyelination and scarring as well as a broad spectrum of signs and symptoms. MS affects the ability of nerve cells in the brain and spinal cord to communicate with each other effectively. Nerve cells communicate by sending electrical signals called action potentials down long fibers called axons, which are contained within an insulating substance called myelin. In MS, the body's own immune system attacks and damages the myelin. When myelin is lost, the axons can no longer effectively conduct signals. MS onset usually occurs in young adults, and is more common in women.

Symptoms of MS include, without limitation, changes in sensation, such as loss of sensitivity or tingling; pricking or numbness, such as hypoesthesia and paresthesia; muscle weakness; clonus; muscle spasms; difficulty in moving; difficulties with coordination and balance, such as ataxia; problems in speech, such as dysarthria, or in swallowing, such as dysphagia; visual problems, such as nystagmus, optic neuritis including phosphenes, and diplopia; fatigue; acute or chronic pain; and bladder and bowel difficulties cognitive impairment of varying degrees; emotional symptoms of depression or unstable mood; Uhthoff's phenomenon, which is an exacerbation of extant symptoms due to an exposure to higher than usual ambient temperatures; and Lhermitte's sign, which is an electrical sensation that runs down the back when bending the neck.

In some embodiments, administering a Siglec-7 agent of the present disclosure, such as an anti-Siglec-7 antibody of the present disclosure, can prevent, reduce the risk, and/or treat multiple sclerosis. In some embodiments, administering a Siglec-7 agent, such as an anti-Siglec-7 antibody, may modulate one or more Siglec-7 activities in an individual having multiple sclerosis.

Cancer

Further aspects of the present disclosure provide methods for preventing, reducing risk, or treating cancer, by administering to an individual in need thereof a therapeutically effective amount of a Siglec-7 agent of the present disclosure, such as an isolated anti-Siglec-7 antibody of the present disclosure. Any of the isolated antibodies of the present disclosure may be used in these methods. In some embodiments, the isolated antibody is an agonist antibody of the present disclosure. In other embodiments, the isolated antibody is an antagonist antibody of the present disclosure. In other embodiments, the isolated antibody is an inert antibody of the present disclosure. In other embodiments, the isolated antibody is an antibody conjugate of the present disclosure.

As disclosed herein, the tumor microenvironment is known to contain a heterogeneous immune infiltrate, which includes T lymphocytes, macrophages, neutrophils, NK cells, and cells of myeloid/granulocytic lineage. The presence and activity of T-regulatory cells, tumor-imbedded immunosuppressor myeloid cells, and/or M2-macrophages, M2-neutrophils, and/or M2-NK cells in tumors is associated with poor prognosis. In contrast, the presence and activity of cytotoxic T cells is beneficial for cancer therapy. Therapies that directly or indirectly enhance the activity of cytotoxic T cells and reduce the number and activity of the various immunosuppressor cells, are expected to provide significant therapeutic benefit. A seminal preclinical study has shown synergies between drugs that target immunosuppressor cells (e.g., CSF1/CSF1R blocking antibodies) and immune checkpoint blocking antibodies that activate cytotoxic T cells, indicating that manipulating both cell types shows efficacy in tumor models where individual therapies are poorly effective (Zhu Y. Cancer Res. 2014 Sep. 15; 74(18): 5057-69). Therefore, in some embodiments, blocking Siglec-7, which is expressed on myeloid cells, subset of T cells, and tumor-associated immune cells, may stimulate beneficial anti-tumor immune response, resulting in a therapeutic anti-tumor immune response.

In some embodiments, the methods for preventing, reducing risk, or treating an individual having cancer further include administering to the individual at least one antibody that specifically binds to an inhibitory checkpoint molecule. Examples of antibodies that specifically bind to an inhibitory checkpoint molecule include, without limitation, an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-BTLA antibody, an anti-GAL9 antibody, an anti-TIM3 antibody, an anti-A2AR antibody, an anti-LAG-3 antibody, an anti-phosphatidylserine antibody, and any combination thereof. In some embodiments, the at least one antibody that specifically binds to an inhibitory checkpoint molecule is administered in combination with a Siglec-7 agent of the present disclosure, such as an antagonist anti-Siglec-7 antibody of the present disclosure.

In some embodiments, a cancer to be prevented or treated by the methods of the present disclosure includes, without limitation, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B cell lymphoma; chronic lymphocytic leukemia (CLL); acute lymphoblastic leukemia (ALL); hairy cell leukemia; chronic myeloblastic leukemia, and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In some embodiments, the cancer is colorectal cancer. In some embodiments, the cancer is selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), and multiple myeloma. In some embodiments, the cancer is selected from non-small cell lung cancer, glioblastoma, neuroblastoma, renal cell carcinoma, bladder cancer, ovarian cancer, melanoma, breast carcinoma, gastric cancer, and hepatocellular carcinoma. In some embodiments, the cancer is triple-negative breast carcinoma. In some embodiments, the cancer may be an early stage cancer or a late stage cancer. In some embodiments, the cancer may be a primary tumor. In some embodiments, the cancer may be a metastatic tumor at a second site derived from any of the above types of cancer.

In some embodiments, Siglec-7 agents of the present disclosure, such as anti-Siglec-7 antibodies of the present disclosure, may be used for preventing, reducing risk, or treating cancer, including, without limitation, bladder cancer, breast cancer, colon and rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

In some embodiments, the present disclosure provides methods of preventing, reducing risk, or treating an individual having cancer, by administering to the individual a therapeutically effective amount of a Siglec-7 agent of the present disclosure, such as an anti-Siglec-7 antibody of the present disclosure.

In some embodiments, the method further includes administering to the individual at least one antibody that specifically binds to an inhibitory immune checkpoint molecule, and/or another standard or investigational anti-cancer therapy. In some embodiments, the at least one antibody that specifically binds to an inhibitory checkpoint molecule is administered in combination with the Siglec-7 agent, such as an anti-Siglec-7 antibody of the present disclosure. In some embodiments, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, and any combination thereof. In some embodiments, the standard or investigational anti-cancer therapy is one or more therapies selected from radiotherapy, cytotoxic chemotherapy, targeted therapy, imatinib (Gleevec®), trastuzumab (Herceptin®), adoptive cell transfer (ACT), chimeric antigen receptor T cell transfer (CAR-T), vaccine therapy, and cytokine therapy.

In some embodiments, the method further includes administering to the individual at least one antibody that specifically binds to an inhibitory cytokine. In some embodiments, the at least one antibody that specifically binds to an inhibitory cytokine is administered in combination with the Siglec-7 agent, such as an anti-Siglec-7 antibody of the present disclosure. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the method further includes administering to the individual at least one agonistic antibody that specifically binds to a stimulatory immune checkpoint protein. In some embodiments, the at least one agonistic antibody that specifically binds to a stimulatory checkpoint protein is administered in combination with the Siglec-7 agent, such as an anti-Siglec-7 antibody of the present disclosure. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonist anti-CD137/4-1BB antibody, an agonist anti-CD27 antibody, an agonist anti-glucocorticoid-induced TNFR-related protein GITR antibody, and any combination thereof.

In some embodiments, the method further includes administering to the individual at least one stimulatory cytokine. In some embodiments, the at least one stimulatory cytokine is administered in combination with the Siglec-7 agent, such as an anti-Siglec-7 antibody of the present disclosure. In some embodiments, the at least one stimulatory cytokine is selected from IFN-a4, IFN-b, IL-1β, TNF-a, IL-6, IL-8, CRP, IL-20 family members, LIF, IFN-gamma, OSM, CNTF, GM-CSF, IL-1, IL-12, IL-17, IL-18, IL-23, CXCL10, IL-33, MCP-1, MIP-1-beta, and any combination thereof.

Methods of Assessment

The present disclosure also provides methods of assessing responsiveness of an individual to an agent that binds or interacts with Siglec-7. In some embodiments, the method comprises: measuring the expression levels of one or more markers on non-tumorigenic myeloid cells in a blood sample obtained from the individual prior to administering to the individual an agent that binds or interacts with Siglec-7; administering to the individual a therapeutically effective amount of the agent; and measuring the expression levels of the one or more markers on non-tumorigenic myeloid cells in a blood sample obtained from the individual after administration of the agent. In some embodiments, a reduction in the levels of the one or more markers on non-tumorigenic myeloid cells after administration of the agent that binds or interacts with Siglec-7 indicates the individual is responsive to the agent. In some embodiments, the one or more markers are one or more of CD45 and CD14. In some embodiments, the method further comprises administering one or more additional therapeutically effective amounts of the agent. In some embodiments, the agent is any Siglec-7 agent disclosed herein. In some embodiments, the agent is selected from the group consisting of an antibody, a soluble Siglec-7 receptor, a Siglec-7-Fc fusion protein, a Siglec-7 immunoadhesin, an antisense molecule, an siRNA, a small molecule inhibitor, a protein, and peptide. In some embodiments, the agent is an isolated anti-Siglec-7 antibody or anti-Siglec-7 antibody-conjugate. In some embodiments, the anti-Siglec-7 antibody is any of the anti-Siglec-7 antibodies disclosed herein.

The present disclosure also provides methods of assessing responsiveness of an individual to an agent that binds or interacts with Siglec-7. In some embodiments, the method comprises: measuring the expression levels of CD45 and $CD14^+$ on non-tumorigenic myeloid cells in a blood sample obtained from the individual prior to administering to the individual an agent that binds or interacts with Siglec-7; administering to the individual a therapeutically effective amount of the agent; and measuring the expression levels of CD45 and $CD14^+$ on non-tumorigenic myeloid cells in a blood sample obtained from the individual after administration of the agent. In some embodiments, a reduction in the levels of CD45 and $CD14^+$ on non-tumorigenic myeloid cells after administration of the agent that binds or interacts with Siglec-7 indicates the individual is responsive to the agent. In some embodiments, the method further comprises administering one or more additional therapeutically effective amounts of the agent. In some embodiments, the agent is any Siglec-7 agent disclosed herein. In some embodiments, the agent is selected from the group consisting of an antibody, a soluble Siglec-7 receptor, a Siglec-7-Fc fusion protein, a Siglec-7 immunoadhesin, an antisense molecule, an siRNA, a small molecule inhibitor, a protein, and peptide. In some embodiments, the agent is an isolated anti-Siglec-7 antibody or anti-Siglec-7 antibody-conjugate. In some embodiments, the anti-Siglec-7 antibody is any of the anti-Siglec-7 antibodies disclosed herein.

In some embodiments, a reduction of at least 5%, at least 100%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, 105%, at least 110%, at least 115%, at least 120%, at least 125%, at least 130%, at least 135%, at least 140%, at least 145%, at least 150%, at least 155%, at least 160%, at least 1650%, at least 170%, at least 175%, at least 180%, at least 185%, at least 190%, at least 195%, at least 200%, at least 250%, or at least 500% in the levels of CD45 and CD14 on non-tumorigenic myeloid cells after administration of the agent that binds or interacts with Siglec-7 indicates the individual is responsive to the agent. In some embodiments, a reduction of at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold in the levels of CD45 and CD14 on non-tumorigenic myeloid cells after administration of the agent that binds or interacts with Siglec-7 indicates the individual is responsive to the agent.

Kits/Articles of Manufacture

The present disclosure also provides kits and/or articles of manufacture containing a Siglec-7 agent of the present disclosure (e.g., an anti-Siglec-7 antibody described herein), or a functional fragment thereof. Kits and/or articles of manufacture of the present disclosure may include one or more containers comprising a purified antibody of the present disclosure. In some embodiments, the kits and/or articles of manufacture further include instructions for use in accordance with the methods of this disclosure. In some embodiments, these instructions comprise a description of administration of the Siglec-7 agent of the present disclosure (e.g., an anti-Siglec-7 antibody described herein) to prevent, reduce risk, or treat an individual having a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza, according to any methods of this disclosure.

In some embodiments, the instructions comprise a description of how to detect a Siglec-7 protein, for example in an individual, in a tissue sample, or in a cell. The kit and/or article of manufacture may further comprise a description of selecting an individual suitable for treatment based on identifying whether that individual has the disease and the stage of the disease.

In some embodiments, the kits and/or articles of manufacture may further include another antibody of the present disclosure (e.g., at least one antibody that specifically binds to an inhibitory checkpoint molecule, at least one antibody that specifically binds to an inhibitory cytokine, and/or at least one agonistic antibody that specifically binds to a stimulatory checkpoint protein) and/or at least one stimulatory cytokine. In some embodiments, the kits and/or articles of manufacture may further include instructions for using the antibody and/or stimulatory cytokine in combination with a Siglec-7 agent of the present disclosure (e.g., an anti-Siglec-7 antibody described herein), instructions for using a Siglec-7 agent of the present disclosure (e.g., an anti-Siglec-7 antibody described herein) in combination with an antibody and/or stimulatory cytokine, or instructions for using a Siglec-7 agent of the present disclosure (e.g., an anti-Siglec-7 antibody described herein) and an antibody and/or stimulatory cytokine, according to any methods of this disclosure.

The instructions generally include information as to dosage, dosing schedule, and route of administration for the intended treatment. The containers may be unit doses, bulk packages (e.g., multi-dose packages) or sub-unit doses. Instructions supplied in the kits and/or articles of manufacture of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a disease of the present disclosure. Instructions may be provided for practicing any of the methods described herein.

The kits and/or articles of manufacture of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit and/or article of manufacture may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is a Siglec-7 agent of the present disclosure (e.g., an anti-Siglec-7 antibody described herein). The container may further comprise a second pharmaceutically active agent.

Kits and/or articles of manufacture may optionally provide additional components such as buffers and interpretive information. Normally, the kit comprises a container and a label or package insert(s) on or associated with the container.

Diagnostic Uses

The Siglec-7 agents of the present disclosure, such as the isolated antibodies of the present disclosure (e.g., an anti-Siglec-7 antibody described herein) also have diagnostic utility. This disclosure therefore provides for methods of using the antibodies of this disclosure, or functional fragments thereof, for diagnostic purposes, such as the detection of a Siglec-7 protein in an individual or in tissue samples derived from an individual.

In some embodiments, the individual is a human. In some embodiments, the individual is a human patient suffering from, or at risk for developing a disease, disorder, or injury of the present disclosure. In some embodiments, the diagnostic methods involve detecting a Siglec-7 protein in a biological sample, such as a biopsy specimen, a tissue, or a cell. A Siglec-7 agent of the present disclosure (e.g., an anti-Siglec-7 antibody described herein) is contacted with the biological sample and antigen-bound antibody is detected. For example, a biopsy specimen may be stained with an anti-Siglec-7 antibody described herein in order to detect and/or quantify disease-associated cells. The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}$F and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

In other embodiments, an isolated antibody of the present disclosure (e.g., an anti-Siglec-7 antibody described herein) may be used to detect and/or quantify, for example, microglia in a brain specimen taken from a preclinical disease model (e.g., a non-human disease model). As such, an isolated antibody of the present disclosure (e.g., an anti-Siglec-7 antibody described herein) may be useful in evaluating therapeutic response after treatment in a model for a nervous system disease or injury such as frontotemporal dementia, Alzheimer's disease, vascular dementia, seizures, retinal dystrophy, atherosclerotic vascular diseases, Nasu-Hakola disease, or multiple sclerosis, as compared to a control.

The present disclosure will be more fully understood by reference to the following Examples. They should not, however, be construed as limiting the scope of the present disclosure. All citations throughout the disclosure are hereby expressly incorporated by reference.

EXAMPLES

Example 1: Production, Identification, and Characterization of Anti-Siglec-7 Antibodies Introduction The amino acid sequence of human Siglec-7 is set forth below in SEQ ID NO: 1. Human Siglec-7 contains a signal sequence located at amino acid residues 1-18 SEQ ID NO: 1, an extracellular immunoglobulin-like variable-type (IgV) domain located at amino acid residues 39-122 of SEQ ID NO: 1, two Ig-like C2-type domains located at amino acid residues 150-233 and 240-336 of SEQ ID NO: 1, a transmembrane domain located at amino acid residues 354-376 of SEQ ID NO: 1, an ITIM motif 1 located at amino acid residues 435-440 of SEQ ID NO: 1, and an ITIM motif 2 located at amino acid residues 459-463 of SEQ ID NO: 1. An alignment of human Siglec-7 with Siglec-7 homologs is shown in FIG. 1A, and a three-dimensional representation of human Siglec-7 is shown in FIG. 1B.

```
Siglec-7 amino acid sequence (SEQ ID NO: 1):
         10          20          30          40
MLLLLLLPLL  WGRERVEGQK  SNRKDYSLTM  QSSVTVQEGM 50          60          70          80
CVHVRCSFSY  PVDSQTDSDP  VHGYWFRAGN  DISWKAPVAT 90         100         110         120
NNPAWAVQEE  TRDRFHLLGD  PQTKNCTLSI  RDARMSDAGR 130         140         150         160
YFFRMEKGNI  KWNYKYDQLS  VNVTALTHRP  NILIPGTLES 170         180         190         200
GCFQNLTCSV  PWACEQGTPP  MISWMGTSVS  PLHPSTTRSS 210         220         230         240
VLTLIPQPQH  HGTSLTCQVT  LPGAGVTTNR  TIQLNVSYPP 250         260         270         280
QNLTVTVFQG  EGTASTALGN  SSSLSVLEGQ  SLRLVCAVDS 290         300         310         320
NPPARLSWTW  RSLTLYPSQP  SNPLVLELQV  HLGDEGEFTC
```

```
            330        340        350        360
        RAQNSLGSQH VSLNLSLQQE YTGKMRPVSG VLLGAVGGAG 370        380        390        400
        ATALVFLSFC VIFIVVRSCR KKSARPAADV GDIGMKDANT 410        420        430        440
        IRGSASQGNL TESWADDNPR HHGLAAHSSG EEREIQYAPL 450        460
        SFHKGEPQDL SGQEATNNEY SEIKIPK
```

The purpose of the following Example was to produce Siglec-7-binding antibodies (e.g., antagonistic antibodies, Siglec-7 specific antibodies) that enhance the beneficial effects of dendritic cells, monocytes, macrophages, neutrophils, NK cells, T cells, and/or microglia. Antibodies that bind the extracellular domain of Siglec-7, particularly the IgV domain (amino acid residues 39-122 of SEQ ID NO: 1) are generated using mouse hybridoma technology, phage display technology, and yeast display technology. Antibodies are identified and then screened for their ability to compete with Siglec-7 ligands on binding to Siglec-7, to induce Siglec-7 downregulation, to induce Siglec-7 desensitization, to induce Siglec-7 degradation, to induce Siglec-7 targeting to the lysosome, to induce Siglec-7 cleavage, to modulate Siglec-7 signaling and/or one or more functions in cells and in animals in vivo, as described in the following Examples. Exemplary ligands bound by Siglec-7 are depicted in FIG. 2 and FIG. 3.

For example, anti-Siglec-7 antibodies are selected that target the IgV domain (amino acid residues 39-122) of Siglec-7. The IgV domain binds to sialic acid targets, and this binding can be blocked with the antibody. Thus, amino acid residues 39-122 correspond to a Siglec-7 peptide target for antibodies that will block binding of Siglec-7 to one or more endogenous targets (e.g., ligands).

As described herein, 13 anti-Siglec-7 antibodies were identified and characterized.

Results
Anti-Siglec-7 Antibody Production
Immunization Procedure
Rapid Prime Method:

Four 50-day old female BALB/c mice were immunized using the following procedure. A series of subcutaneous aqueous injections containing human Siglec-7 antigen but no adjuvant were given over a period of 19 days. Mice were housed in a ventilated rack system from Lab Products. All four mice were euthanized on Day 19 and lymphocytes were harvested for hybridoma cell line generation.

Standard Method:

Four 50-day old female BALB/c or NZB/W mice were immunized using the following procedure. Mice were housed in a ventilated rack system from Lab Products. Mice were injected intraperitoneally every 3 weeks with a human Siglec-7 antigen mixed in CpG-ODN adjuvant at 25 µg protein antigen per mouse (total volume 125 µL per mouse). Test bleeds were done by saphenous vein lancing seven days after the second boost. The test bleed (immune sera) was tested by indirect ELISA assay to determine the best two responding mice for the fusion. The mice may require a 3rd and 4th boost and another test bleed 7 days after boost to assess titre before fusion. When the antibody titre is high enough the best two responding mice are given a final intravenous boost via lateral tail vein. Four days after the IV boost the mice were euthanized for fusion. The spleens were harvested and lymphocytes isolated from the spleen were used in the fusion process to produce hybridomas.

Hybridoma Development

Lymphocytes were isolated and fused with murine SP2/0 myeloma cells in the presence of poly-ethylene glycol (PEG 1500) as per standard Roche Protocol. Fused cells were cultured using a single-step cloning method (RAT selection). This method uses a semi-solid methylcellulose-based HAT selective medium to combine the hybridoma selection and cloning into one step. Single cell-derived hybridomas grow to form monoclonal colonies on the semi-solid media. Ten days after the fusion event, 948 of the resulting hybridoma clones were transferred to 96-well tissue culture plates and grown in HT containing medium until mid-log growth was reached (5 days).

Hybridoma Screening

Tissue culture supernatants from the 948 hybridomas were tested by indirect ELISA on screening antigen (Primary Screening) and probed for both IgG and IgM antibodies using a Goat anti-IgG/IgM(H&L)-HRP secondary and developed with TMB substrate. Clones >0.2 OD in this assay were taken to the next round of testing. Positive cultures were retested on screening antigen to confirm secretion and on an irrelevant antigen (Human Transferrin) to eliminate non-specific or "sticky" mAbs and rule out false positives. All clones of interest were isotyped by antibody trapping ELISA to determine if they are IgG or IgM isotype.

Hybridoma Cell Culture

The hybridoma cell lines of interest were maintained in culture in 24-well culture plates for 32 days post transfer to 96-well plates. This is referred to as the stability period and tests whether clones remain stable and secreting. During this stability period time temporary frozen cell line back up is made of all the clones of interest for −80° C. storage (viable 6 months). Hybridomas were periodically tested during this time period for secretion and specificity.

Subcloning

The top hybridoma cell lines (clones) were subcloned to ensure monoclonality. Subcloning was performed by plating parental clones out again using the single-step cloning system. Between 24 and 90 subclones were transferred to 96-well culture plates. Subclones were screened by indirect ELISA and antibody trapping ELISA. The top subclones for each parent were taken for expansion in culture. Any parental clones that were <50% clonal had a second round of subcloning performed.

The antibodies were then screened for Siglec-7 binding. Antibodies that were positive for binding to human Siglec-7 were tested for ability to block ligand binding and ability to reduce surface levels of Siglec-7 in multiple cell types. Thirteen Silgec-7 antibodies were identified. The isotype and bin category are listed in Table 1.

TABLE 1

| Anti-Siglec-7 antibodies | | |
|---|---|---|
| Ab ID | Ab Isotype | Bin |
| 1A12 | mIgG2a | 2 |
| 1E8 | mIgG1 | 2 |
| 2G1 | mIgG2b | 1 |
| 2G4 | mIgG1/2a* | 2 |
| 3E11 | mIgG1 | 1 |
| 4A1 | mIgG2a | 2 |
| 4D7 | mIgG1 | 5 |
| 4E3 | mIgG1 | 1 |
| 7A3 | mIgG1 | 4 |

TABLE 1-continued

Anti-Siglec-7 antibodies

| Ab ID | Ab Isotype | Bin |
|---|---|---|
| 7E11 | mIgG2a | 3 |
| 7F12 | mIgG2a | 2 |
| 10B5 | mIgG2a | 5 |
| 10G8 | mIgG1 | 4 |

Antibody Heavy Chain and Light Chain Variable Domain Sequences

Using standard techniques, the amino acid sequences encoding the light chain variable and the heavy chain variable domains of the generated antibodies were determined. The EU or Kabat light chain CDR sequences of the antibodies are set forth in Table 2A. The EU or Kabat heavy chain CDR sequences of the antibodies are set forth in Table 2B. The EU or Kabat light chain framework (FR) sequences of the antibodies are set forth in Table 3A. The EU or Kabat heavy chain framework (FR) sequences of the antibodies are set forth in Table 3B.

TABLE 2A

EU or Kabat light chain CDR sequences of anti-Siglec-7 antibodies

| Ab ID | CDR L1 | CDR L2 | CDR L3 |
|---|---|---|---|
| 1A12 | RSSQSLVHSTGNTYLH (SEQ ID NO: 7) | KVSNRFS (SEQ ID NO: 20) | SQNTHVPYT (SEQ ID NO: 33) |
| 1E8 | RASQSISDYLH (SEQ ID NO: 8) | YASQSIS (SEQ ID NO: 21) | QKGLNFPLT (SEQ ID NO: 34) |
| 2G1 | SANSSFIYMY (SEQ ID NO: 9) | DTSNLAS (SEQ ID NO: 22) | QQWSSSPLT (SEQ ID NO: 35) |
| 2G4 | KASDHINNWLA (SEQ ID NO: 10) | GATSLET (SEQ ID NO: 23) | HQYWNTPYT (SEQ ID NO: 36) |
| 3E11 | RSSQSLVHSTGNTYLH (SEQ ID NO: 11) | KVSNRFC (SEQ ID NO: 24) | SQNTHVPYT (SEQ ID NO: 37) |
| 4A1 | RSSQSLVHSTGNIYLH (SEQ ID NO: 12) | KVSNRFZ (SEQ ID NO: 25) | SQNTHVPYT (SEQ ID NO: 38) |
| 4D7 | KASQKVGTNVA (SEQ ID NO: 13) | SASTRHR (SEQ ID NO: 26) | HQGNSVQYT (SEQ ID NO: 39) |
| 4E3 | SANSSFTYMY (SEQ ID NO: 14) | DTSNLAS (SEQ ID NO: 27) | QQWSSSPLT (SEQ ID NO: 40) |
| 7A3 | RASQSISEYLH (SEQ ID NO: 15) | FASQSIC (SEQ ID NO: 28) | QNGHNFPYT (SEQ ID NO: 41) |
| 7E11 | LASQTIGTWLA (SEQ ID NO: 16) | AATSLAD (SEQ ID NO: 29) | QQLYSTPYT (SEQ ID NO: 42) |
| 7F12 | RSSQSLVHSTGNTYLH (SEQ ID NO: 17) | KVSNRFS (SEQ ID NO: 30) | SQNTHVPYT (SEQ ID NO: 43) |
| 10B5 | RASQDISZYLN (SEQ ID NO: 18) | LSSRLHS (SEQ ID NO: 31) | QQGHTGAWT (SEQ ID NO: 44) |
| 10B5L1 | RASQDINTYLN (SEQ ID NO: 476) | YTSRLHS (SEQ ID NO: 477) | QQGNTLPWT (SEQ ID NO: 478) |
| 10G8 | RASQSIREYLH (SEQ ID NO: 19) | FASQSIC (SEQ ID NO: 32) | QKAHNFPYT (SEQ ID NO: 45) |

TABLE 2B

EU or Kabat heavy chain CDR sequences of anti-Siglec-7 antibodies

| Ab ID | CDR H1 | CDR H2 | CDR H3 |
|---|---|---|---|
| 1A12 | SEVFPITYMN (SEQ ID NO: 46) | IGDILPSIGRTMYG (SEQ ID NO: 59) | ARSEGYLLAY (SEQ ID NO: 72) |
| 1E8 | FNIKGSLLH (SEQ ID NO: 47) | IGWIDPEDGETRFD (SEQ ID NO: 60) | ARTEYSNPAWFAY (SEQ ID NO: 73) |
| 2G1 | FTFSNYDMS (SEQ ID NO: 48) | VATISSGGDYTYYP (SEQ ID NO: 61) | ARHGYGNYDWYFDV (SEQ ID NO: 74) |

TABLE 2B-continued

EU or Kabat heavy chain CDR sequences of anti-Siglec-7 antibodies

| Ab ID | CDR H1 | CDR H2 | CDR H3 |
|---|---|---|---|
| 2G4 | SEVFPITYMN (SEQ ID NO: 49) | IGDILPSIGRTMYG SEQ ID NO: 62) | ARSEGYLLAY (SEQ ID NO: 75) |
| 3E11 | YIFTDYGIT (SEQ ID NO: 50) | IGEISPRSGETYFN (SEQ ID NO: 63) | AREGNPFTY (SEQ ID NO: 76) |
| 4A1 | SEVFPITYMN (SEQ ID NO: 51) | IGDILPSIGRTMYG (SEQ ID NO: 64) | ARSEGYLLAY (SEQ ID NO: 77) |
| 4D7 | YTFTNYWIN (SEQ ID NO: 52) | IGNIYSGSSRTNYN (SEQ ID NO: 65) | AREGLRAMDY (SEQ ID NO: 78) |
| 4E3 | FIFSNYDMS (SEQ ID NO: 53) | VATISSGGGYTYYP (SEQ ID NO: 66) | TRHGYGNYDWYFDV (SEQ ID NO: 79) |
| 4E3H1 | FIFSNYDMS (SEQ ID NO: 53) | VSTISSGGGYTYYA (SEQ ID NO: 480) | ARHGYGNYDWYFDV (SEQ ID NO: 74) |
| 4E3H2 | FIFSNYDMS (SEQ ID NO: 53) | VATISSGGGYTYYA (SEQ ID NO: 481) | TRHGYGNYDWYFDV (SEQ ID NO: 79) |
| 7A3 | FTFSNYAMS (SEQ ID NO: 54) | VASISSGGSYNYYP (SEQ ID NO: 67) | ASQSYGSSYWYFDV (SEQ ID NO: 80) |
| 7E11 | FSLSNYGVH (SEQ ID NO: 55) | LGVIWAGGITNYN (SEQ ID NO: 68) | AKQGGTSFSY (SEQ ID NO: 81) |
| 7F12 | SEVFPITYMN (SEQ ID NO: 56) | IGDILPSIGRTMYG (SEQ ID NO: 69) | ARSEGYLLAY (SEQ ID NO: 82) |
| 10B5 | YAFTNCWMN (SEQ ID NO: 57) | IGRIFPGNGHTNYS (SEQ ID NO: 70) | ARDYSDYYFDY (SEQ ID NO: 83) |
| 10B5H1 | GYAFTNCWMN (SEQ ID NO: 479) | RIFPGNGHTN (SEQ ID NO: 482) | DYSDYYFDY (SEQ ID NO: 483) |
| 10G8 | FTFSTYAMF (SEQ ID NO: 58) | VASISSGGRYTYYP (SEQ ID NO: 71) | VRHSYGSSYWYLDV (SEQ ID NO: 84) |

TABLE 3A

EU or Kabat light chain Framework sequences of anti-Siglec-7 antibodies

| Ab ID | VL FR1 | VL FR2 | VL FR3 | VL FR4 |
|---|---|---|---|---|
| 1A12 | DVZMTQTPLSLPVS LGDQASISC (SEQ ID NO: 85) | WYLQKPGQSPKLLI Y (SEQ ID NO: 98) | GVPDRFSGSGAGTDFTL KISRVEAEDLGVYFC (SEQ ID NO: 111) | FGGGTKLEIK (SEQ ID NO: 124) |
| 1E8 | DIQMTQFPATLSVT PGDRVSLSC (SEQ ID NO: 86) | WYQHKSHESPRLLI K (SEQ ID NO: 99) | GIPSRFSGSGSGWDFTLS INSVEPEDVGIYYC (SEQ ID NO: 112) | FGGGTKLEMK (SEQ ID NO: 125) |
| 2G1 | VLTQSPAIMSASPG EKVTMTC (SEQ ID NO: 87) | WYQQKPGSSPRLLI F (SEQ ID NO: 100) | GVPIRFSGSGSGTSYSLTI SRMEAEDTATYYC (SEQ ID NO: 113) | FGGGTKLELK (SEQ ID NO: 126) |
| 2G4 | DIQMTQSLSYLSVS LGGRVTITC (SEQ ID NO: 88) | WYQQKPGNAPRLL IS (SEQ ID NO: 101) | GFPSRFSGSGSGKDYTLS ITSLQTEDVATYYC (SEQ ID NO: 114) | FGGGTRLEIK (SEQ ID NO: 127) |
| 3E11 | DVZMTQTPLSLPVS LGDQASISC (SEQ ID NO: 89) | WYLQKPGQSPKLLI Y (SEQ ID NO: 102) | GVPDRFSGSGAGTDFTL KISRVEAEDLGVYFC (SEQ ID NO: 115) | FGGGTKLEIK (SEQ ID NO: 128) |
| 4A1 | DVVMTQTPLSLPVS LGDQASISC (SEQ ID NO: 90) | WYLQKPGQSPKLLI Y (SEQ ID NO: 103) | GVPDRFSGSGSGTDFTL KISRVEAEDLGVYFC (SEQ ID NO: 116) | FGGGTKLEIK (SEQ ID NO: 129) |
| 4D7 | NZMTQFQKFMSTS VGDRVSITC (SEQ ID NO: 91) | GFQQKPGHSPKAGI Y (SEQ ID NO: 104) | GVQDRFTARGLGSDFIL PITTZQLEDLAEYZC (SEQ ID NO: 117) | FGGGTKLEIK (SEQ ID NO: 130) |

TABLE 3A-continued

EU or Kabat light chain Framework sequences of anti-Siglec-7 antibodies

| Ab ID | VL FR1 | VL FR2 | VL FR3 | VL FR4 |
|---|---|---|---|---|
| 4E3 | GZQNVLTQSPAILS ASPGEKVTMTC (SEQ ID NO: 92) | WYQQKPGSSPRLLI F (SEQ ID NO: 105) | GVPIRFSGSGSGTSYSLTI SRMEAEDTATYYC (SEQ ID NO: 118) | FGAGTKLELK (SEQ ID NO: 131) |
| 7A3 | DIQMTQZPATLSVT PGDRVSLSC (SEQ ID NO: 93) | WYHQKSHESPRLLI K (SEQ ID NO: 106) | GIPSRFSGSGSGSDFTLTI NSVEPEDVGVYYC (SEQ ID NO: 119) | FGGGTKLEIK (SEQ ID NO: 132) |
| 7E11 | DIQMTQSPASQSAS LGESVTITC (SEQ ID NO: 94) | WYQQKPGKSPQLLI Y (SEQ ID NO: 107) | GVPSRFSGSGSGTKFSFK ISSLQAEDFVSYYC (SEQ ID NO: 120) | FGGGTKLEIK (SEQ ID NO: 133) |
| 7F12 | DVLMTQTPLSLPVS LGDQASISC (SEQ ID NO: 95) | WYLQKPGQSPKLLI Y (SEQ ID NO: 108) | GVPDRFSGSGAGTDFTL KISRVEAEDLGVYFC (SEQ ID NO: 121) | FGGGTKLEIK (SEQ ID NO: 134) |
| 10B5 | ZMTQFTSSMSGSEG DRVTISH (SEQ ID NO: 96) | WYEQKADGTANLII Y (SEQ ID NO: 109) | GZPSRLSGZGWVTDYFL PIHTSEQEDRGSYFC (SEQ ID NO: 122) | FGGGTKLEIK (SEQ ID NO: 135) |
| 10G8 | DIQMTQFPATLSGT PGDRVZLSR (SEQ ID NO: 97) | WYQQKSHESPRLZI K (SEQ ID NO: 110) | GIPSRFSGSGSGSDFTLSI NTVEPEDVGVYYC (SEQ ID NO: 123) | FGGGTKLEIK (SEQ ID NO: 136) |

TABLE 3B

EU or Kabat heavy chain Framework sequences of anti-Siglec-7 antibodies

| Ab ID | VH FR1 | VH FR2 | VH FR3 | VH FR4 |
|---|---|---|---|---|
| 1A12 | QVQLQQSGSELRSP GSSVKLSCKDFD (SEQ ID NO: 137) | WVRQKPGHGFE W (SEQ ID NO: 150) | EKFEDKATLDADTVSN TAYLELNSLTSEDSAIY YC (SEQ ID NO: 163) | WGQGTLVTVSA (SEQ ID NO: 176) |
| 1E8 | QVQLQQSGAELVR PGASVKLSCSASG (SEQ ID NO: 138) | WIKQRPLQGLEW (SEQ ID NO: 151) | PKFQDKAFLTADTSSTT AYLQLSSLTSEDTAIYY C (SEQ ID NO: 164) | WGQGTLVTVSA (SEQ ID NO: 177) |
| 2G1 | EVKLVESGGTLVKP GGSLKISCAASG (SEQ ID NO: 139) | WVRQNPEKRLE W (SEQ ID NO: 152) | DIFKGRFTISRDDAKNA LYLQMSSLRSEDTALY YC (SEQ ID NO: 165) | WGAGATVTVSS (SEQ ID NO: 178) |
| 2G4 | QVQLQQSGSELRSP GSSVKLSCKDFD (SEQ ID NO: 140) | WVRQKPGHGFE W (SEQ ID NO: 153) | EKFEDKATLDADTVSN TAYLELNSLTSEDSAIY YC (SEQ ID NO: 166) | WGQGTLVTVSA (SEQ ID NO: 179) |
| 3E11 | QVQLQQSGAELAR PGASVKLSCKASG (SEQ ID NO: 141) | WVKQRTGQGLE W (SEQ ID NO: 154) | ENYRVKATLTADKSSS TAYMQLFSLTSEDSAV YFC (SEQ ID NO: 167) | WGHGTLVTVSA (SEQ ID NO: 180) |
| 4A1 | QVQLQQSGSELRSP GSSVKLSCKDFD (SEQ ID NO: 142) | WVRQKPGHGFE W (SEQ ID NO: 155) | EKFEDKATLDADTVSN TAYLELNSLTSEDSAIY YC (SEQ ID NO: 168) | WGQGTLVTVSA (SEQ ID NO: 181) |
| 4D7 | QVQLQQSGAELVK PGASVKLSCKTSG (SEQ ID NO: 143) | WVKQRPGQGLE W (SEQ ID NO: 156) | EKFKSKATLTVDTSSST AYMQLSSLTSDDSAVY YC (SEQ ID NO: 169) | WGQGTSVTVSS (SEQ ID NO: 182) |
| 4E3 | EVKLADSGGALVN PGGSLKISCAVSG (SEQ ID NO: 144) | WVRQNPEKRLE W (SEQ ID NO: 157) | DSVKGRFTISRDNAKN ALYLQMSSLRSEDTAL YYC (SEQ ID NO: 170) | WGAGATVTVSS (SEQ ID NO: 183) |
| 7A3 | LVZSGGALVKPGG SLKLSCAASG (SEQ ID NO: 145) | WVRQTPEKRLE W (SEQ ID NO: 158) | DSVKGRFTISRDNARNT LYLQMSSLRSKDTAMY YC (SEQ ID NO: 171) | WGAGTTVTVSS (SEQ ID NO: 184) |
| 7E11 | QVQLKQSGPVLVA PSQSLSITCTVSG (SEQ ID NO: 146) | WVRQFPGKGLE W (SEQ ID NO: 159) | SVLMSRLSISKDNSKSQ VFLKMNSLQTDDTAM YYC (SEQ ID NO: 172) | WGQGTLVTVSA (SEQ ID NO: 185) |

TABLE 3B-continued

EU or Kabat heavy chain Framework sequences of anti-Siglec-7 antibodies

| Ab ID | VH FR1 | VH FR2 | VH FR3 | VH FR4 |
|---|---|---|---|---|
| 7F12 | QVQLQQSGSELRSP GSSVKLSCKDFD (SEQ ID NO: 147) | WVRQKPGHGFE W (SEQ ID NO: 160) | EKFEDKATLDADTVSN TAYLELNSLTSEDSAIY YC (SEQ ID NO: 173) | WGQGTLVTVSA (SEQ ID NO: 186) |
| 10B5 | QVQLQQSGPELVK PGASVKISCKASG (SEQ ID NO: 148) | WVRQRPGKGLD W (SEQ ID NO: 161) | GKFKDKATLTEDKSSS TAYMQLSSLTSEDSAV YFC (SEQ ID NO: 174) | WGQGTTLTVSS (SEQ ID NO: 187) |
| 10G8 | EVKLVEFGGALVK PGGSLKLSCAALG (SEQ ID NO: 149) | RVRQTPEKREEG (SEQ ID NO: 162) | DSAKDRHPIFRDNARN TLYLQMSSLRSKDTAM YYC (SEQ ID NO: 175) | WGAGTTVTVSS (SEQ ID NO: 188) |

Characterization of Siglec-7 Antibody Binding

Initial characterization of Siglec-7 antibodies involved determining their ability to bind Siglec-7 expressed on human primary monocytes, human primary macrophages, human primary dendritic cells, human primary neutrophils, and human primary natural killer (NK) cells. Cells were harvested, plated at $10^6$/ml in a 96 well plate, and incubated in 100 ul PBS containing 2% FBS, 2 mM EDTA and 10 μg/ml Mab and Fc blocking reagent for 1 hour in ice. Cells were washed twice and incubated in 100 ul PBS containing 2% FBS, 2 mM EDTA and 5 ug/ml PE-conjugated secondary antibody for 30 minutes on ice. Cells were washed twice in cold PBS and analyze by flow cytometry on a BD FACS Canto. Data analysis and calculation of MFI values was performed with FlowJo (TreeStar) software version 10.0.7.

Figure 4:
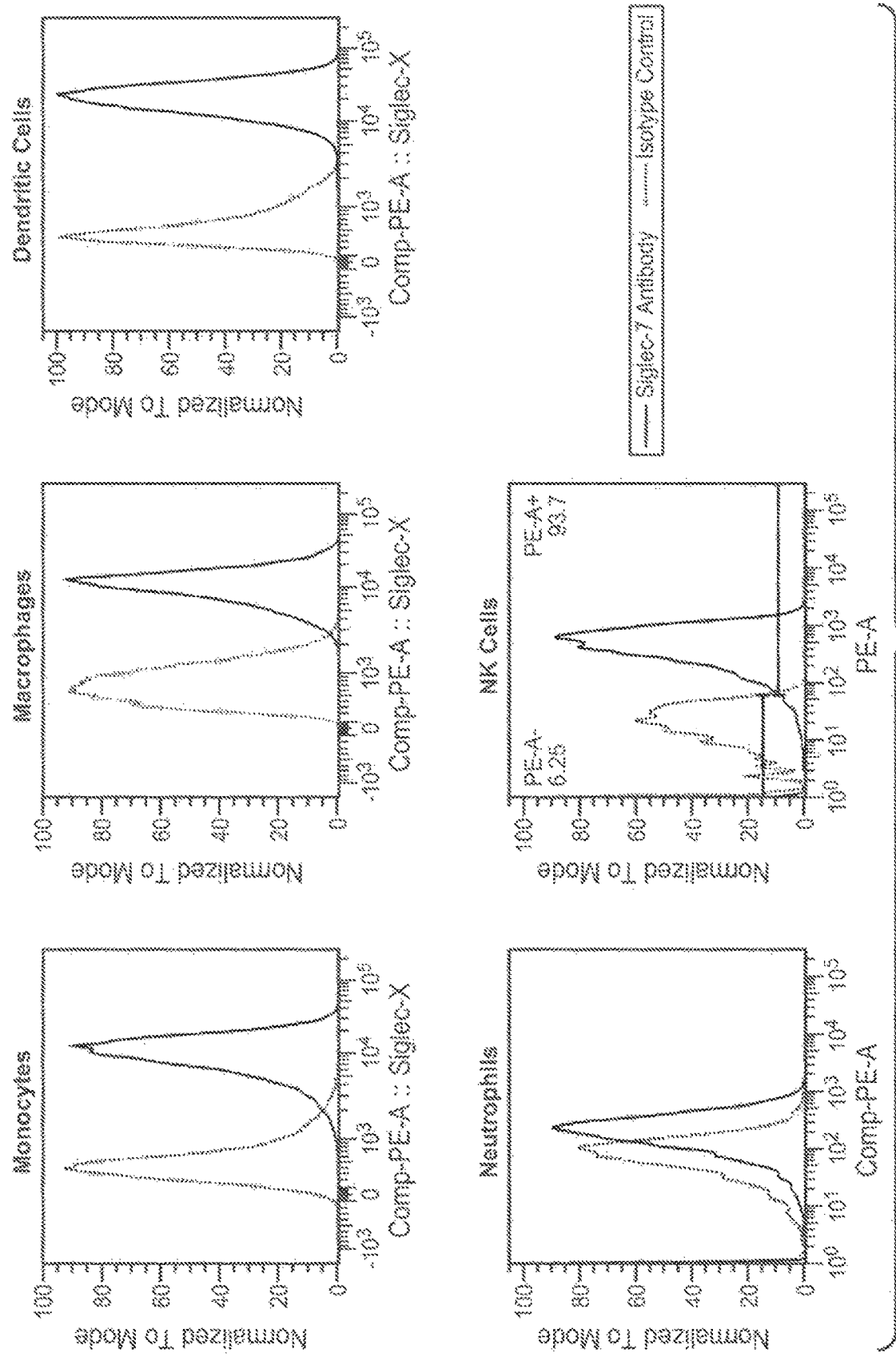
FIG. 4 depicts results of FACS analysis demonstrating Siglec-7 expression in human primary immune cells.

FACS staining analysis indicates that Siglec-7 is expressed on primary myeloid and lymphoid cells, including human primary monocytes, macrophages, dendritic cells, neutrophils, and NK cells (FIG. 4).

Figure 5A:
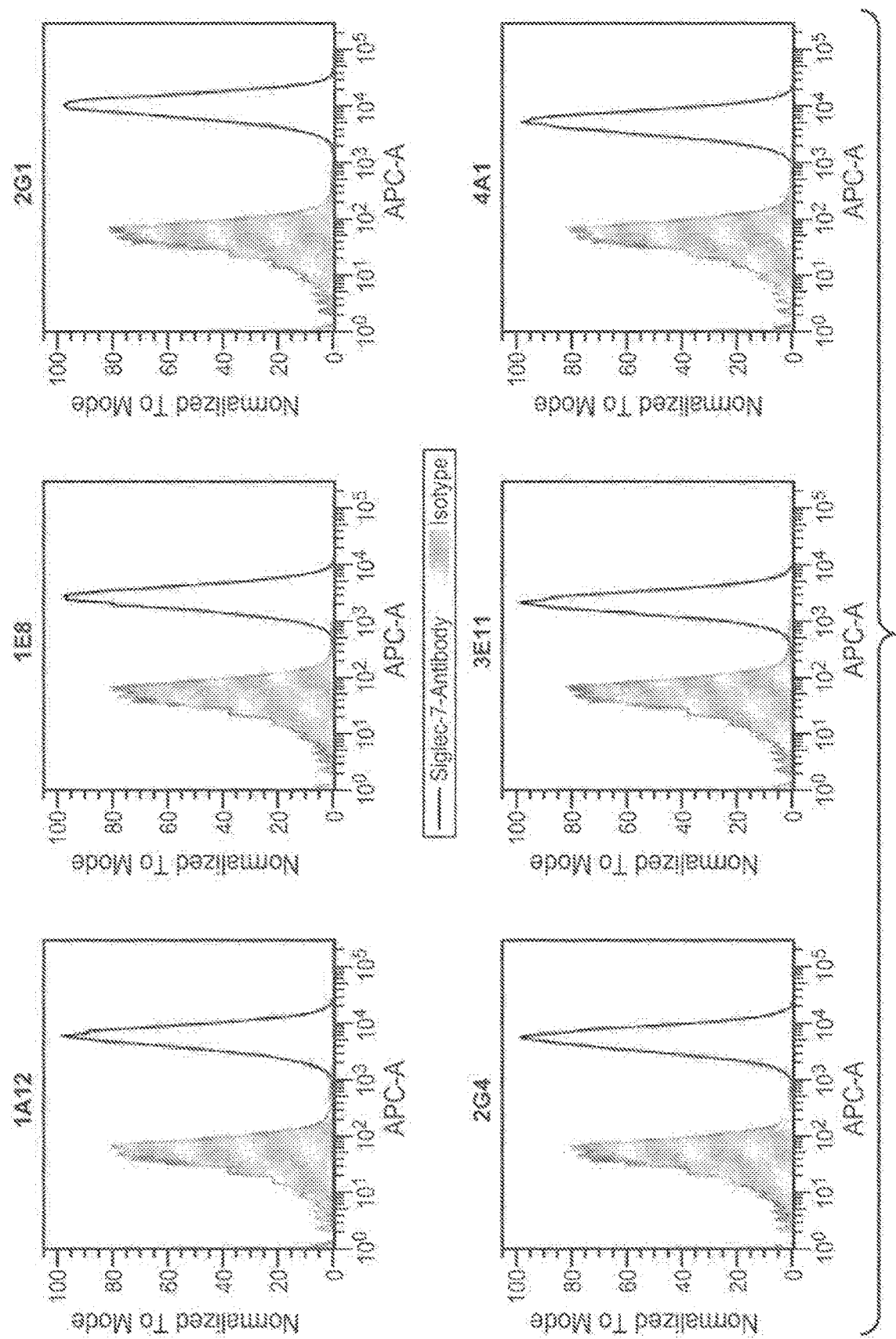
FIG. 5A depicts FACS analysis of Siglec-7 antibodies binding to human primary dendritic cells compared to isotype controls.
Figure 5A:
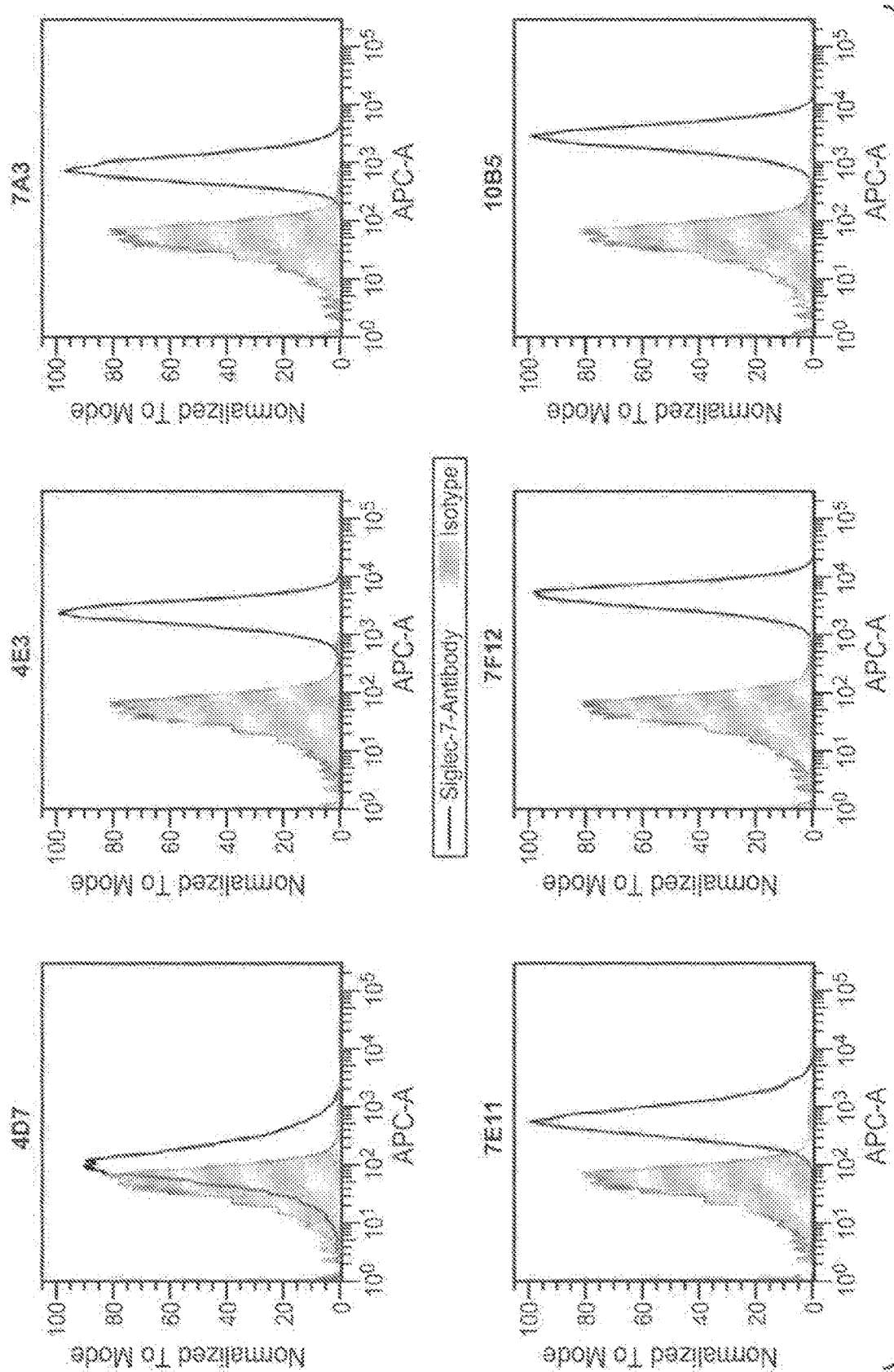
Figure 5A:
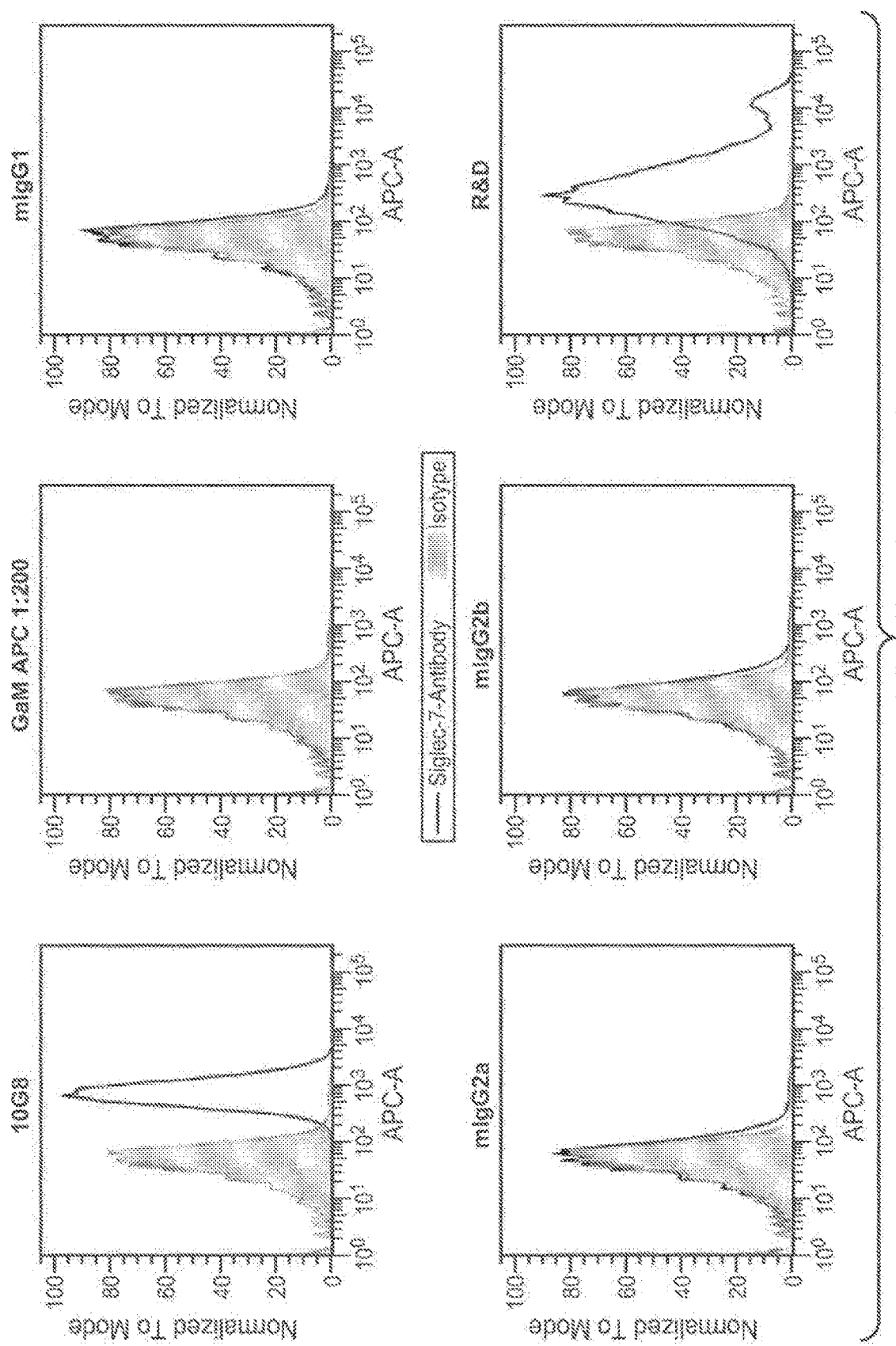

Table 4A demonstrates antibody binding to human primary cells expressing Siglec-7. Percent positive binding and mean fluorescent intensity (MFI) values for cell types bound by Siglec-7 antibodies are listed in Table 4A. Binding is compared to an isotype control. The antibodies bind to human primary monocytes, human primary dendritic cells, and human primary macrophages. In Table 4A, "Buffer" refers to cells that were treated only with the PBS buffer described supra; "Secondary Ab" refers to cells that were treated only with the PE-conjugated secondary antibody; "mIgG1," "mIgG2a," and "mIgG2b" refer to isotype control antibodies; and "RDS7" refers to commerically available anti-Siglec-7 antibody Mab1138 (R&D Systems; Cat. No. MAB 1138). FIG. 5A demonstrates antibody binding to human primary dendritic cells.

TABLE 4A

Siglec-7 antibody binding to human primary cells

| Anti-body | Monocytes | | Dendritic Cells | | Macrophages | |
|---|---|---|---|---|---|---|
| | % Positive | MFI | % Positive | MFI | % Positive | MFI |
| 1A12 | 99.3 | 505 | 99.7 | 6092 | 99.4 | 15788 |
| 1E8 | 99.3 | 428 | 99.7 | 2936 | 99.5 | 5446 |
| 2G1 | 99.4 | 577 | 99.7 | 10245 | 99.5 | 25666 |
| 2G4 | 99.3 | 512 | 99.7 | 5752 | 99.5 | 15472 |
| 3E11 | 98.7 | 380 | 99.6 | 2522 | 99.6 | 4043 |
| 4A1 | 99.4 | 486 | 99.7 | 5450 | 99.3 | 14578 |
| 4D7 | 90.5 | 262 | 26.1 | 250 | 99.4 | 4260 |
| 4E3 | 98.6 | 362 | 99.7 | 2648 | 99.6 | 4150 |
| 7A3 | 97.9 | 407 | 99.7 | 956 | 99.7 | 2841 |

TABLE 4A-continued

Siglec-7 antibody binding to human primary cells

| Anti-body | Monocytes | | Dendritic Cells | | Macrophages | |
|---|---|---|---|---|---|---|
| | % Positive | MFI | % Positive | MFI | % Positive | MFI |
| 7E11 | 93.3 | 278 | 98.4 | 845 | 99.8 | 2381 |
| 7F12 | 99.3 | 472 | 99.7 | 4995 | 99.3 | 12325 |
| 10B5 | 99.2 | 417 | 99.6 | 3226 | 99.7 | 6028 |
| 10G8 | 99.1 | 523 | 99.5 | 897 | 99.7 | 3277 |
| Controls | | | | | | |
| Buffer | 0.2 | 63 | 0.2 | 39 | 0.0 | 122 |
| Secondary Ab | 9.1 | 107 | 2.4 | 91 | 23.9 | 398 |
| mIgG1 | 10.6 | 115 | 2.8 | 83 | 21.7 | 368 |
| mIgG2a | 14.0 | 141 | 4.5 | 134 | 35.8 | 648 |
| mIgG2b | 13.9 | 128 | 5.0 | 130 | 79.5 | 2059 |
| RDS7 | 19.9 | 175 | 73.9 | 1452 | 98.6 | 4219 |

Figure 5B:
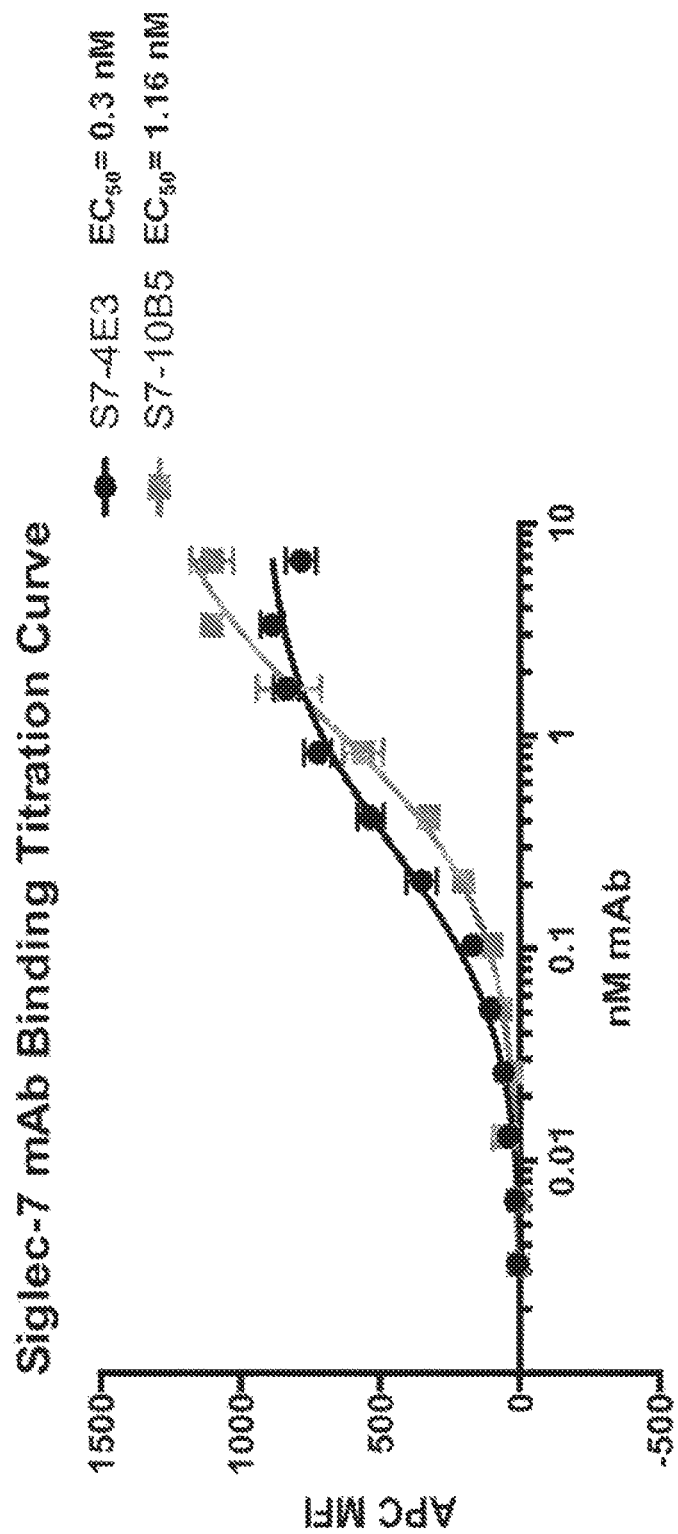
FIG. 5B depicts a 12-point titration curve to assess binding and calculate the half-maximal effective concentration values ($EC_{50}$) for binding of Siglec-7 antibodies 4E3 and 10B5 to the surface of primary human dendritic cells.

Two Siglec-7 antibodies, 4E3 and 10B5, were titrated 2-fold for a 12-point curve with a concentration range of 6.67-0.00325 nM to assess binding and calculate half-maximal concentration ($EC_{50}$) for binding to primary human dendritic cells (FIG. 5B). Antibodies were serially diluted and incubated with cells in PBS with 1% BSA, 1 mM EDTA for 1 hour on ice (4° C.). Cells were pelleted and resuspended with goat anti-mouse secondary antibody conjugated with APC (BD Biosciences) at a 1:200 dilution in buffer. Secondary detection antibody was incubated for 30 minutes on ice (4° C.), then cells were washed 3 times in buffer before analyzing on a BD FACS Canto for APC MR. Data were analyzed with FlowJo Software (TreeStar).

In vitro studies demonstrated that anti-Siglec-7 antibodies 4E3 and 10B5 bound to human dendritic cells from two different donors (Table 4B). Anti-Siglec-7 antibody 4E3 bound to human dendritic cells from donor number 359 with an $EC_{50}$ of 0.3 nM (with a 95% confidence interval range of 0.1701 to 0.4313 nM), while anti-Siglec-7 antibody 10B5 bound dendritic cells from this donor with an $EC_{50}$ of 1.158 nM (with a 95% confidence interval range of 0.7821 to 1.533 nM). Anti-Siglec-7 antibodies 4E3 and 10B5 bound to the dendritic cells from a second donor with an $EC_{50}$ of 0.3364 (95% confidence interval of 0.1052 to 0.5677) and 1.427 (with 95% confidence interval 0.9209 to 1.933), respectively.

TABLE 4B

EC$_{50}$ determination of two Siglec-7 antibodies
for binding to primary human dendritic cells

| | Antibody: 4E3 | | Antibody: 10B5 | |
|---|---|---|---|---|
| Donor # | EC$_{50}$ value (nN) | 95% CI (nM) | EC$_{50}$ value (nM) | 95% CI (nM) |
| 358 | 0.3364 | 0.1052 to 0.5677 | 1.427 | 0.9209 to 1.933 |
| 359 | 0.3007 | 0.1701 to 0.4313 | 1.158 | 0.7821 to 1.533 |

After determining the EC$_{50}$ for the two anti-Siglec-7 antibodies on human dendritic cells, the binding affinity of 13 anti-Siglec-7 antibodies for Siglec-7 was determined by measuring their K$_D$s by surface plasmon resonance (SPR) assays. SPR data was collected at a rate of 10 Hz at 25' C on a BiaCore T200 instrument. Data analysis was performed using BiaCore T200 Evaluation Software, version 2.0. HBS-EP+ (100 mM HEPES, 1.5 M NaCl, 30 mM EDTA, 0.5% v/v Surfactant P20, pH 7.4) was used as running buffer and for preparing reagents.

Mouse-derived antibodies (25 nM) against Siglec-7 were captured (60 s contact time, 30 µL/min flow rate, 0 s stabilization time) on a CM5 sensor chip (GE Healthcare) immobilized with anti-mouse IgG. Histidine-tagged human Siglec-7 (NovoProtein) was then flowed over the captured anti-Siglec-7 surface (120 s contact time, 30 µL/min flow rate, 300 s dissociation time). Concentration of antigen ranged from 5 nM to 100 nM, depending on information obtained from an initial screen. Duplicate single-concentration trials were performed and bracketed by a blank (0 nM antigen) sample. The chip surface was regenerated in between cycles using 10 mM glycine-HCl, pH1.7 (60 s contact time, 30 µL/min flow rate, 60 s stabilization time). The resulting SPR signal was obtained as the difference in response from measurements performed on a blank flow cell.

Single-concentration kinetic analysis (Canziani, et al. (2004) Analytical Biochemistry 325:301-307) was performed using a 1:1 interaction model to extract association and dissociation rate constants (k$_a$ and k$_d$, respectively) for each antibody. Affinity constants (K$_D$) were calculated from the ratio k$_d$/k$_a$. For one antibody (clone 1E8), we validated the single-concentration analysis with a multiple-concentration approach (five concentrations of antigen used, plus one blank).

Figure 6A:
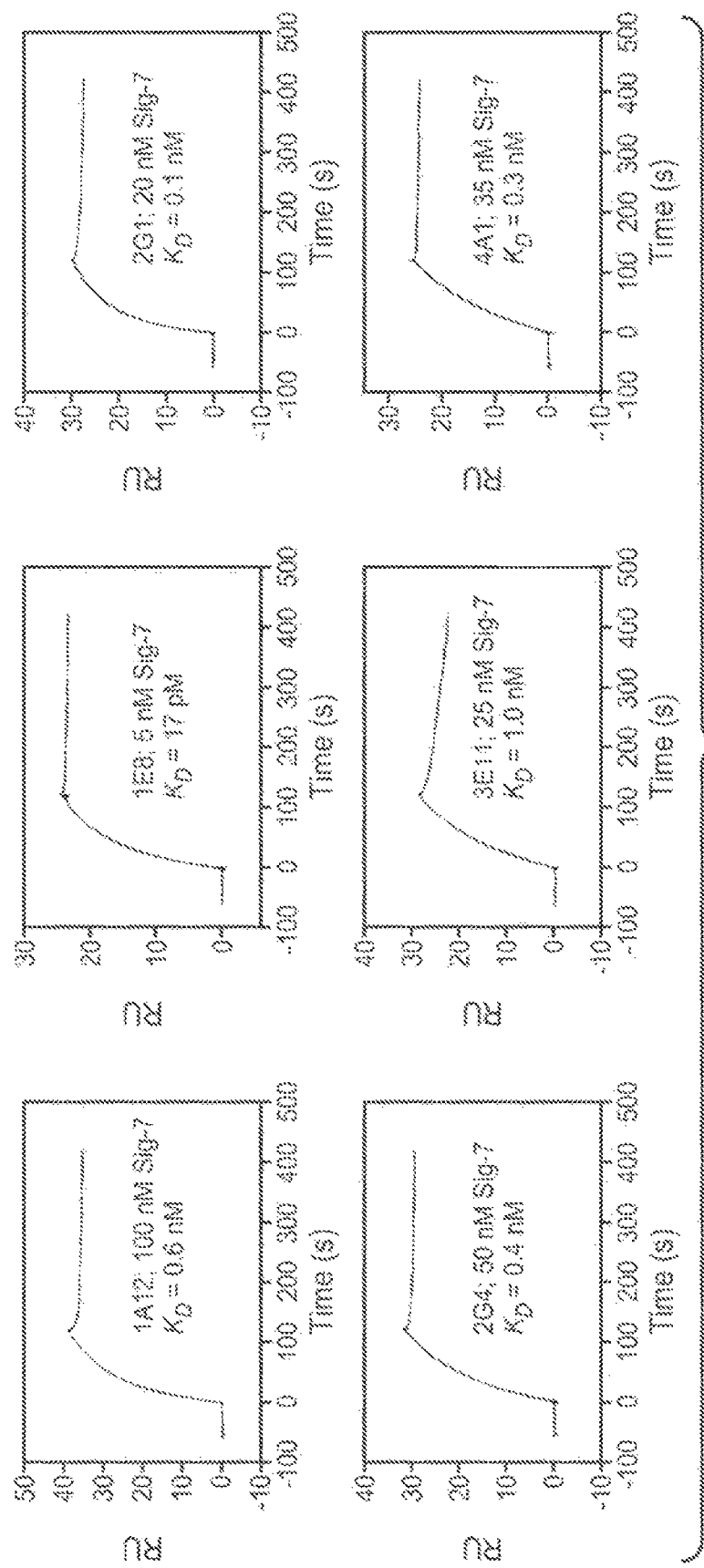
FIG. 6A depicts Biacore sensorgrams showing binding affinity of Siglec-7 antibodies of the present disclosure to purified Siglec-7-his tagged protein.
Figure 6A:
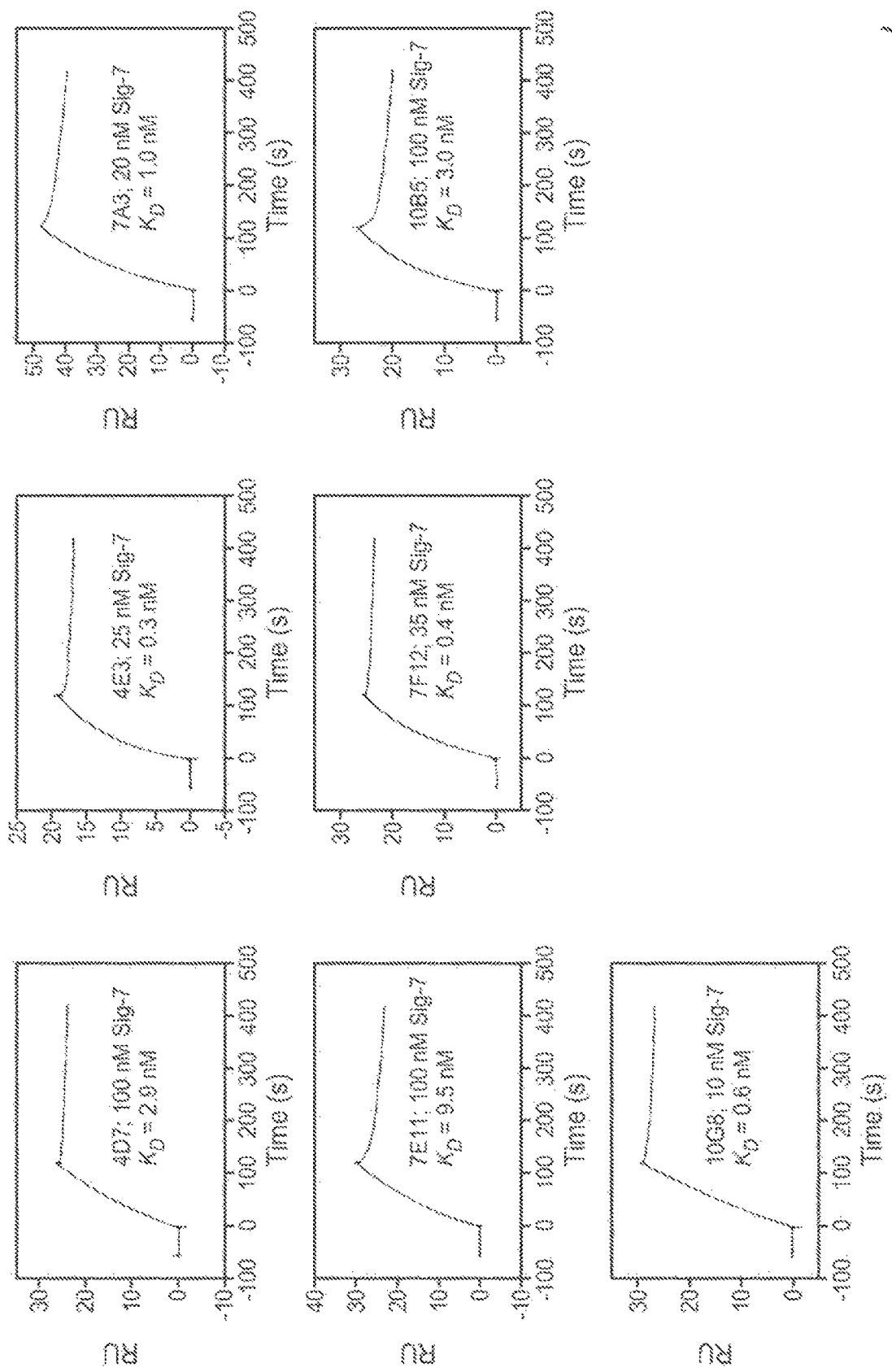

The results are listed in Table 5. FIG. 6A shows SPR sensograms depicting antibody affinity.

TABLE 5

Siglec-7 antibody affinities

| Antibody | in Ab nM | Siglec-7 nM | K$_D$ |
|---|---|---|---|
| 1A12 | 25 | 100 | 0.6 nM |
| 1E8 | 25 | 5 | 17 nM |
| 2G1 | 25 | 20 | 0.1 nM |
| 2G4 | 25 | 50 | 0.4 nM |
| 3E11 | 25 | 25 | 1.0 nM |
| 4A1 | 25 | 35 | 0.3 nM |
| 4D7 | 25 | 100 | 2.9 nM |
| 4E3 | 25 | 25 | 0.3 nM |
| 7A3 | 25 | 20 | 1.0 nM |
| 7E11 | 25 | 100 | 9.5 nM |
| 7F12 | 25 | 35 | 0.4 nM |
| 10B5 | 25 | 100 | 3.0 nM |
| 10G8 | 25 | 10 | 0.6 nM |

In Silico Antibody Humanization

Antibody humanization is used to transform antibodies generated in a different species to best resemble a human antibody through sequence and structural relationships in order to prevent immunogenicity in human administration. Antibodies from different species share characteristic sequence and structural features that allow the grafting of the specificity-determining regions (SDRs) of the non-human antibody onto a human antibody framework. This results in retention of the specificity of the non-human antibody. The humanization process involves identification of the non-human antibody sequence and features, including the framework regions and SDRs. The following criteria are used to humanize an antibody: 1) percent similarity in framework regions between non-human and known human antibodies, 2) length similarity in SDRs between non-human and known human antibodies, 3) genes used to generate the framework regions of the human antibody, and 4) previous use of human antibody frameworks in humanizations and as therapeutics. Similarity in framework regions and SDR lengths are important because differences can generate structural differences in the antibody that can alter the specificity of the antibody. Specific genes used to generate the framework of human antibodies are known to be beneficial or detrimental to the stability or specificity of the antibody and are selectively used or avoided, accordingly. Lastly, previously successful humanization frameworks, including those used in human therapeutics, which are well tolerated with good half-lives, are likely candidates for future successful humanizations.

As shown in Tables 6A and 6B, 10 humanized light chain and 10 humanized heavy variable region sequences were identified for each of the antibodies 1A12, 1E8, 2G1, 2G4, 3E11, 4A1, 4D7, 4E3, 4E3H1, 4E3H2, 7A3, 7E11, 7F12, 10B5, 10B5L1, 10B5H1, and 10G8. In Tables 6A and 6B, bolded letters indicate CDR sequences.

TABLE 6A

Humanized light chain variable regions

| Antibody variant | Humanized sequences |
|---|---|
| Antibody 1A12 | Antibody 1A12 |
| 1A12V2-30 | DVVMTQSPLSLPVTLGQPASLSCRSSQSLVHSTGNTYLHWFQQRPGQSPRRLIYKVSNRFSGVPDRFSGSGSGTDFTLKISRVEAEDVGVYYCSQNTHVPYTFGQGTKVEIK (SEQ ID NO: 189) |
| 1A12V2-28 | DIVMTQSPLSLPVTPGEPASISCRSSQSLVHSTGNTYLHWYLQKPGQSPQLLIYKVSNRFSGVPDRFSGSGSGTDFTLKISRVEAEDVGVYYCSQNTHVPYTFGQGTKVEIK (SEQ ID NO: 190) |

TABLE 6A-continued

Humanized light chain variable regions

| Antibody variant | Humanized sequences |
|---|---|
| 1A12V4-1 | DIVMTQSPDSLAVSLGERATINCRSSQSLVHSTGNTYLHWYQQKPGQPPKLLIYKVSNRFSGVPDRFSGSGSGTDFTLTISSLQAEDVAVYYCSQNTHVPYTFGQGTKVEIK (SEQ ID NO: 191) |
| 1A12V3-11 | EIVLTQSPATLSLSPGERATLSCRSSQSLVHSTGNTYLHWYQQKPGQAPRLLIYKVSNRFSGIPARFSGSGSGTDFTLTISSLEPEDFAVYYCSQNTHVPYTFGQGTKVEIK (SEQ ID NO: 192) |
| 1A12V1-33 | DIQMTQSPSSLSASVGDRVTITCRSSQSLVHSTGNTYLHWYQQKPGKAPKLLIYKVSNRFSGVPSRFSGSGSGTDFTFTISSLQPEDIATYYCSQNTHVPYTFGQGTKVEIK (SEQ ID NO: 193) |
| 1A12V3-15 | EIVMTQSPATLSVSTGERATLSCRSSQSLVHSTGNTYLHWYQQKPGQAPRLLIYKVSNRFSGIPARFSGSGSGTEFTLTISSLQSEDFAVYYCSQNTHVPYTFGQGTKVEIK (SEQ ID NO: 194) |
| 1A12V1-5 | DIQMTQSPSTLSASVGDRVTITCRSSQSLVHSTGNTYLHWYQQKPGKAPKLLIYKVSNRFSGVPSRFSGSGSGTEFTLTISSLQPDDFATYYCSQNTHVPYTFGQGTKVEIK (SEQ ID NO: 195) |
| 1A12V1-9 | DIQLTQSPSFLSASVGDRVTITCRSSQSLVHSTGNTYLHWYQQKPGKAPKLLIYKVSNRFSGVPSRFSGSGSGTEFTLTISSLQPEDFATYYCSQNTHVPYTFGQGTKVEIK (SEQ ID NO: 196) |
| 1A12V1-39 | DIQMTQSPSSLSASVGDRVTITCRSSQSLVHSTGNTYLHWYQQKPGKAPKLLIYKVSNRFSGVPSRFSGSGSGTDFTLTISSLQPEDFATYYCSQNTHVPYTFGQGTKVEIK (SEQ ID NO: 197) |
| 1A12V3-20 | EIVLTQSPGTLSLSPGERATLSCRSSQSLVHSTGNTYLHWYQQKPGQAPRLLIYKVSNRFSGIPDRFSGSGSGTDFTLTISRLEPEDFAVYYCSQNTHVPYTFGQGTKVEIK (SEQ ID NO: 198) |
| Antibody 1E8 | Antibody 1E8 |
| 1E8V1-39 | DIQMTQSPSSLSASVGDRVTITCRASQSISDYLHWYQQKPGKAPKLLIYYASQSISGVPSRFSGSGSGTDFTLTISSLQPEDFATYYCQKGLNFPLTFGQGTKVEIK (SEQ ID NO: 199) |
| 1E8V1-5 | DIQMTQSPSTLSASVGDRVTITCRASQSISDYLHWYQQKPGKAPKLLIYYASQSISGVPSRFSGSGSGTEFTLTISSLQPDDFATYYCQKGLNFPLTFGQGTKVEIK (SEQ ID NO: 200) |
| 1E8V1-9 | DIQLTQSPSFLSASVGDRVTITCRASQSISDYLHWYQQKPGKAPKLLIYYASQSISGVPSRFSGSGSGTEFTLTISSLQPEDFATYYCQKGLNFPLTFGQGTKVEIK (SEQ ID NO: 201) |
| 1E8V3-11 | EIVLTQSPATLSLSPGERATLSCRASQSISDYLHWYQQKPGQAPRLLIYYASQSISGIPARFSGSGSGTDFTLTISSLEPEDFAVYYCQKGLNFPLTFGQGTKVEIK (SEQ ID NO: 202) |
| 1E8V1-33 | DIQMTQSPSSLSASVGDRVTITCRASQSISDYLHWYQQKPGKAPKLLIYYASQSISGVPSRFSGSGSGTDFTFTISSLQPEDIATYYCQKGLNFPLTFGQGTKVEIK (SEQ ID NO: 203) |
| 1E8V3-15 | EIVMTQSPATLSVSPGERATLSCRASQSISDYLHWYQQKPGQAPRLLIYYASQSISGIPARFSGSGSGTEFTITISSLQSEDFAVYYCQKGLNFPLTFGQGTKVEIK (SEQ ID NO: 204) |
| 1E8V3-20 | EIVLTQSPGTLSLSPGERATISCRASQSISDYLHWYQQKPGQAPRLLIYYASQSISGIPDRFSGSGSGTDFTLTISRLEPEDFAVYYCQKGLNFPLTFGQGTKVEIK (SEQ ID NO: 205) |
| 1E8V2-28 | DIVMTQSPLSLPVTPGEPASISCRASQSISDYLHWYLQKPGQSPQLLIYYASQSISGVPDRFSGSGSGTDFTLKISRVEAEDVGVYYCQKGLNFPLTFGQGTKVEIK (SEQ ID NO: 206) |
| 1E8V2-30 | DVVMTQSPLSLPVTLGQPASISCRASQSISDYLHWFQQRPGQSPRRLIYYASQSISGVPDRFSGSGSGTDFTLKISRVEAEDVGVYYCQKGLNFPLTFGQGTKVEIK (SEQ ID NO: 207) |
| 1E8V4-1 | DIVMTQSPDSLAVSLGERATINCRASQSISDYLHWYQQKPGQPPKLLIYYASQSISGVPDRFSGSGSGTDFTLTISSLQAEDVAVYYCQKGLNFPLTFGQGTKVEIK (SEQ ID NO: 208) |

TABLE 6A-continued

Humanized light chain variable regions

| Antibody variant | Humanized sequences |
| --- | --- |
| Antibody 2G1 | Antibody 2G1 |
| 2G1V3-11 | EIVLTQSPATLSLSPGERATLSCSANSSFIYMYWYQQKPGQAPRLLIYDTSNLASGI PARFSGSGSGTDFTLTISSLEPEDFAVYYCQQWSSSPLTFGQGTKVEIK (SEQ ID NO: 209) |
| 2G1V1-39 | DIQMTQSPSSLSASVGDRVTITCSANSSFIYMYWYQQKPGKAPKLLIYDTSNLASG VPSRFSGSGSGTDFTLTISSLQPEDFATYYCQQWSSSPLTFGQGTKVEIK (SEQ ID NO: 210) |
| 2G1V1-5 | DIQMTQSPSTLSASVGDRVTITCSANSSFIYMYWYQQKPGKAPKLLIYDTSNLASG VPSRFSGSGSGTEFTLTISSLQPDDFATYYCQQWSSSPLTFGQGTKVEIK (SEQ ID NO: 211) |
| 2G1V1-33 | DIQMTQSPSSLSASVGDRVTITCSANSSFIYMYWYQQKPGKAPKLLIYDTSNLASG VPSRFSGSGSGTDFTFTISSLQPEDIATYYCQQWSSSPLTFGQGTKVEIK (SEQ ID NO: 212) |
| 2G1V1-9 | DIQLTQSPSFLSASVGDRVTITCSANSSFIYMYWYQQKPGKAPKLLIYDTSNLASG VPSRFSGSGSGTEFTLTISSLQPEDFATYYCQQWSSSPLTFGQGTKVEIK (SEQ ID NO: 213) |
| 2G1V3-15 | EIVMTQSPATLSVSPGERATLSCSANSSFIYMYWYQQKPGQAPRLLIYDTSNLASG IPARFSGSGSGTEFTLTISSLQSEDFAVYYCQQWSSSPLTFGQGTKVEIK (SEQ ID NO: 214) |
| 2G1V3-20 | EIVLTQSPGTLSLSPGERATLSCSANSSFIYMYWYQQKPGQAPRLLIYDTSNLASGI PDRFSGSGSGTDFTLTISRLEPEDFAVYYCQQWSSSPLTFGQGTKVEIK (SEQ ID NO: 215) |
| 2G1V2-28 | DIVMTQSPLSLPVTPGEPASISCSANSSFIYMYWYLQKPGQSPQLLIYDTSNLASGV PDRFSGSGSGTDFTLKISRVEAEDVGVYACQQWSSSPLTFGQGTKVEIK (SEQ ID NO: 216) |
| 2G1V2-30 | DVVMTQSPLSLPVTLGQPASISCSANSSFIYMYWFQQRPGQSPRRLIYDTSNLASG VPDRFSGSGSGTDFTLKISRVEAEDVGVYYCQQWSSSPLTFGQGTKVEIK (SEQ ID NO: 217) |
| 2G1V4-1 | DIVMTQSPDSLAVSLGERATINCSANSSFIYMYWYQQKPGQPPKLLIYDTSNLASG VPDRFSGSGSGTDFTLTISSLQAEDVAVYYCQQWSSSPLTFGQGTKVEIK (SEQ ID NO: 218) |
| Antibody 2G4 | Antibody 2G4 |
| 2G4V1-5 | DIQMTQSPSTLSASVGDRVTITCKASDHINNWLAWYQQKPGKAPKLLIYGATSLE TGVPSRFSGSGSGTEFTLTISSLQPDDFATYYCHQYWNTPYTFGQGTKVEIK (SEQ ID NO: 219) |
| 2G4V1-33 | DIQMTQSPSSLSASVGDRVTITCKASDHINNWLAWYQQKPGKAPKLLIYGATSLE TGVPSRFSGSGSGTDFTFTISSLQPEDIATYYCHQYWNTPVTFGQGTKVEIK (SEQ ID NO: 220) |
| 2G4V1-39 | DIQMTQSPSSLSASVGDRVTITCKASDHINNWLAWYQQKPGKAPKLLIYGATSLE TGVPSRFSGSGSGTDFTLTISSLQPEDFATYYCHQYWNTPYTFGQGTKVEIK (SEQ ID NO: 221) |
| 2G4V1-9 | DIQLTQSPSFLSASVGDRVTITCKASDHINNWLAWYQQKPGKAPKLLIYGATSLE TGVPSRFSGSGSGTEFTLTISSLQPEDFATYYCHQYWNTPYTFGQGTKVEIK (SEQ ID NO: 222) |
| 2G4V3-15 | EIVMTQSPATLSVSPGERATLSCKASDHINNWLAWYQQKPGQAPRLLIYGATSLE TGIPARFSGSGSGTEFTLTISSLQSEDFAVYYCHQYWNTPYTFGQGTKVEIK (SEQ ID NO: 223) |
| 2G4V3-11 | EIVLTQSPATLSLSPGERATISCKASDHINNWLAWYQQKPGQAPRLLIYGATSLE TGIPARFSGSGSGTDFTLTISSLEPEDFAVYYCHQYWNTPYTFGQGTKVEIK (SEQ ID NO: 224) |
| 2G4V3-20 | EIVLTQSPGTLSLSPGERATLSCKASDHINNWLAWYQQKPGQPRLLIYGATSLE TGIPDRFSGSGSGTDFTLTISRLEPEDFAVYYCHQYWNTPYTFGQGTKVEIK (SEQ ID NO: 225) |
| 2G4V4-1 | DIVMTQSPDSLAVSLGERATINCKASDHINNWLAWYQQKPGQPPKLLIYGATSLE TGVPDRFSGSGSGTDFTLTISSLQAEDVAVYYCHQYWNTPYTFGQGTKVEIK (SEQ ID NO: 226) |

TABLE 6A-continued

Humanized light chain variable regions

| Antibody variant | Humanized sequences |
|---|---|
| 2G4V2-30 | DVVMTQSPLSLPVTLGQPASISCKASDHINNWLAWFQQRPGQSPRRLIYGATSLE TGVPDRFSGSGSGTDFTLKISRVEAEDVGVYYCHQYWNTPYTFGQGTKVEIK (SEQ ID NO: 227) |
| 2G4V2-28 | DIVMTQSRLSLPVTPGEPASISCKASDHINNWLAWYLQKPGQSPQLLIYGATSLET GVPDRFSGSGSGTDFTLKISRVEAEDVGVYYCHQYWNTPYTFGQGTKVEIK (SEQ ID NO: 228) |
| Antibody 3E11 | Antibody 3E11 |
| 3E11V2-30 | DVVMTQSPLSLPVITLGQPASISCRSSQSLVHSTGNTYLHWFQQRPGQSPRRLIYK VSNRFCGVPDRFSGSGSGTDFTLKISRVEAEDVGVYYCSQNTHVPYTFGQGTKVE IK (SEQ ID NO: 229) |
| 3E11V2-28 | DIVMTQSPLSLPVTPGEPASISCRSSQSLVHSTGNTYLHWYLQKPGQSPQLLIYKV SNRFCGVPDRFSGSGSGTDFTLKISRVEAEDVGVYYCSQNTHVPYTFGQGTKVEI K (SEQ ID NO: 230) |
| 3E11V4-1 | DIMVTQSPDSLAVLSGERATINCRSSQSLVHSTGNTYLHWYQQKPGQPPKLLIYK VSNRFCGVPDRFSGSGSGTDFTLTISSLQAEDVAVYYCSQNTHVPYTFGQGTKVE IK (SEQ ID NO: 231) |
| 3E11V3-11 | EIVLTQSPATLSLSPGERATLSCRSSQSLVHSTGNTYLHWYQQKPGQAPRLLIYKV SNRFCGIPARFSGSGSGTDFTLTISSLEPEDFAVYYCSQNTHVPYTFGQGTKVEIK (SEQ ID NO: 232) |
| 3E11V1-33 | DIQMTQSPSSLSASVGDRVTITCRSSQSLVHSTGNTYLHWYQQKPGKAPKLLIYK VSNRFCGVPSRFSGSGSGTDFTFTISSLQPEDIATYYCSQNTHVPYTFGQGTKVEIK (SEQ ID NO: 233) |
| 3E11V3-15 | EIVMTQSPATLSVSPGERATLSCRSSQSLVHSTGNTYLHWYQQKPGQAPRLLIYK VSNRFCGIPARFSGSGSGTEFTLTISSLQSEDFAVYYCSQNTHVPYTFGQGTKVEIK (SEQ ID NO: 234) |
| 3E11V3-20 | EIVLTQSPGTLSLSPGERATLSCRSSQSLVHSTGNTYLHWYQQKPGQAPRLLIYKV SNRFCGIPDRFSGSGSGTDFTLTISRLEPEDFAVYYCSQNTHVPYTFGQGTKVEIK (SEQ ID NO: 235) |
| 3E11V1-9 | DIQLTQSPSFLSASVGDRVTITCRSSQSLVHSTGNTYLHWYQQKPGKAPKLLIYK VSNRFCGVPSRFSGSGSGTEFTLTISSLQPEDFATYYCSQNTHVPYTFGQGTKVEI K (SEQ ID NO: 236) |
| 3E11V1-39 | DIQMTQSPSSLSASVGDRVTITCRSSQSLVHSTGNTYLHWYQQKPGKAPKLLIYK VSNRFCGVPSRFSGSGSGTDFTLTISSLQPEDFATYYCSQNTHVPYTFGQGTKVEI K (SEQ ID NO: 237) |
| 3E11V1-5 | DIQMTQSPSTLSASVGDRVTITCRSSQSLVHSTGNTYLHWYQQKPGKAPKLLIYK VSNRFCGVPSRFSGSGSGTEFTLTISSLQPDDFATYYCSQNTHVPYTFGQGTKVEI K (SEQ ID NO: 238) |
| Antibody 4A1 | Antibody 4A1 |
| 4A1V2-30 | DVVMTQSPLSLPVTLGQPASISCRSSQSLVHSTGNIYLHWFQQRPGQSPRRLIYKV SNRFZGVPDRFSGSGSGTDFTLKISRVEAEDVGVYYCSQNTHVPYTFGQGTKVEI K (SEQ ID NO: 239) |
| 4A1V2-28 | DIVMTQSPLSLPVTPGEPASISCRSSQSLVHSTGNIYLHWYLQKPGQSPQLLIYKVS NRFZGVPDRFSGSGSGTDFTLKISRVEAEDVGVYYCSQNTHVPYTFGQGTKVEIK (SEQ ID NO: 240) |
| 4A1V4-1 | DIVMTQSPDSLAVSLGERATINCRSSQSLVHSTGNIYLHWYQQKPGQPPKLLIYK VSNRFZGVPDRFSGSGSGTDFTLTISSLQAEDVAVYYCSQNTHVPYTFGQGTKVEI K (SEQ ID NO: 241) |
| 4A1V3-11 | EIVLTQSPATLSLSPGERATLSCRSSQSLVHSTGNIYLHWYQQKPGQAPRLLIYKV SNRFZGIPARFSGSGSGTDFTLTISSLEPEDFAVYYCSQNTHVPYTFGQGTKVEIK (SEQ ID NO: 242) |
| 4A1V1-33 | DIQMTQSPSSLSASVGDRVTITCRSSQSLVHSTGNIYLHWYQQKPGKAPKLLIYK VSNRFZGVPSRFSGSGSGTDFTFTISSLQPEDIATYYCSQNTHVPYTFGQGTKVEIK (SEQ ID NO: 243) |
| 4A1V3-15 | EIVMTQSPATLSVSPGERATLSCRSSQSLVHSTGNIYLHWYQQKPGQAPRLLIYK VSNRFZGIPARFSGSGSGTEFTLTISSLQSEDFAVYYCSQNTHVPYTFGQGTKVEIK (SEQ ID NO: 244) |

TABLE 6A-continued

| Humanized light chain variable regions | |
|---|---|
| Antibody variant | Humanized sequences |
| 4A1V3-20 | EIVLTQSPGTLSLSPGERATLSCRSSQSLVHSTGNIYLHWYQQKPGQAPRLLIYKV SNRFZGIPDRFSGSGSGTDFTLTISRLEPEDFAVYYCSQNTHVPYTFGQGTKVEIK (SEQ ID NO: 245) |
| 4A1V1-5 | DIQMTQSPSTLSASVGDRVTITCRSSQSLVHSTGNIYLHWYQQKPGKAPKLLIYKVSNRFZGVPSRFSGSGSGTEFTLTISSLQPDDFATYYCSQNTHVPYTFGQGTKVEIK (SEQ ID NO: 246) |
| 4A1V1-9 | DIQLTQSPSFLSASVGDRVTITCRSSQSLVHSTGNIYLHWYQQKPGKAPKLLIYKV SNRFZGVPSRFSGSGSGTEFTLTISSLQPEDFATYYCSQNTHVPYTFGQGTKVEIK (SEQ ID NO: 247) |
| 4A1V1-39 | DIQMTQSPSSLSASVGDRVTITCRSSQSLVHSTGNIYLHWYQQKPGKAPKLLIYKVSNRFZGVPSRFSGSGSGTDFTLTISSLQPEDFATYYCSQNTHWVPYTFGQGTKVEIK (SEQ ID NO: 248) |
| Antibody 4D7 | Antibody 4D7 |
| 4D7V3-15 | EIVMTQSPATLSVSPGERATLSCKASQKVGTNVAWYQQKPGQAPRLLIYSASTRH RGIPARFSGSGSGTEFTLTISSLQSEDFAVYYCHQGNSVQYTFGQGTKVEIK (SEQ ID NO: 249) |
| 4D7V3-11 | EIVLTQSPATLSLSPGERATLSCKASQKVGTNVAWYQQKPCQAPRLLIYSASTRH RGIPARFSGSGSGTDFTLTISSLEPEDFAVYYCHQGNSVQYTFGQGTKVEIK (SEQ ID NO: 250) |
| 4D7V1-9 | DIQLTQSPSFLSASVGDRVTITCKASQKVGTNVAWYQQKPGKAPKLLIYSASTRH RGVPSRFSGSGSGTEFTLTISSLQPEDFATYYCHQGNSVQYTFGQGTKVEIK (SEQ ID NO: 251) |
| 4D7V1-5 | DIQMTQSPSTLSASVGDRVTITCKASQKVGTNVAWYQQKPGKAPKLLIYSASTRH RGVPSRFSGSGSGTEFTLTISSLQPDDFATYYCHQGNSVQYTFGQGTKVEIK (SEQ ID NO: 252) |
| 4D7V1-39 | DIQMTQSPSSLSASVGDRVTITCKASQKVGFNVAWYQQKPGKAPKLLIYSASTRH RGVPSRFSGSGSGTDFTLTISSLQPEDFATYYCHQGNSVQYTFGQGTKVEIK (SEQ ID NO: 253) |
| 4D7V1-33 | DIQMTQSPSSLSASVGDRVTITCKASQKVGTNVAWYQQKPGKAPKLLIYSASTRH RGVPSRFSGSGSGTDFTFTISSLQPEDIATYYCHQGNSVQYTFGQGTKVEIK (SEQ ID NO: 254) |
| 4D7V3-20 | EIVLTQSPGTLSLSPGERATLSCKASQKVGTNVAWYQQKPGQAPRLLIYSASTRH RGIPDRFSGSGSGTDFTLTISRLEPEDFAVYYCHQGNSVQYTFGQGTKVEIK (SEQ ID NO: 255) |
| 4D7V4-1 | DIVMTQSPDSLAVSLGERATINCKASQKVGTNVAWYQQKPGQPPKLLIYSASTRH RGVPDRFSGSGSGTDFTLTISSLQAEDVAVYYCHQGNSVQYTFGQGTKVEIK (SEQ ID NO: 256) |
| 4D7V2-28 | DIVMTQSPLSLPVTPGEPASISCKASQKVGTNVAWYLQKPGQSPQLLIYSASTRHRGVPDRFSGSGSGTDFTLKISRVEAEDVGVYYCHQGNSVQYTFGQGTKVEIK (SEQ ID NO: 257) |
| 4D7V2-30 | DVVMTQSPLSLPVTLGQPASISCKASQKVGTNVAWFQQRPGQSPRRLIYSASTRH RGVPDRFSGSGSGTDFTLKISRVEAEDVGVYYCHQGNSVQYTFGQGTKVEIK (SEQ ID NO: 258) |
| Antibody 4E3 | Antibody 4E3 |
| 4E3V3-11 | EIVLTQSPATLSLSPGERATLSCSANSSFTYMYWYQQKPGQAPRLLIYDTSNLASGIPARFSGSGSGTDFTLTISSLEPEDFAVYYCQQWSSSPLTFGQGTKVEIK (SEQ ID NO: 259) |
| 4E3V1-33 | DIQMTQSPSSLSASVGDRVTITCSANSSFTYMYWYQQKPGKAPKLLIYDTSNLASGVPSRFSGSGSGTDFTFTISSLQPEDIATYYCQQWSSSPLTFGQGTKVEIK (SEQ ID NO: 260) |
| 4E3V1-39 | DIQMTQSPSSLSASVGDRVTITCSANSSFTYMYWYQQKPGKAPKLLIYDTSNLASGVPSRFSGSGSGTDFTLTISSLQPEDFATYYCQQWSSSPLTFGQGTKVEIK (SEQ ID NO: 261) |
| 4E3V1-5 | DIQMTQSPSTLSASVGDRVTITCSANSSFTYMYWYQQKPGKAPKLLIYDTSNLASGVPSRFSGSGSGTEFTLTISSLQPDDFATYYCQQWSSSPLTFGQGTKVEIK (SEQ ID NO: 262) |

TABLE 6A-continued

Humanized light chain variable regions

| Antibody variant | Humanized sequences |
|---|---|
| 4E3V1-9 | DIQLTQSPSFLSASVGDRVTITCSANSSFTYMYWYQQKPCKAPKLLIYDTSNLASGVPSRFSGSGSGTEFTLTISSLQPEDFATYYCQQWSSSPLTFGQGTKVEIK (SEQ ID NO: 263) |
| 4E3V3-15 | EIVMTQSPATLSVSPGERATLSCSANSSFTYMYWYQQKPGQAPRLLIYDTSNLASGIPARFSGSGSGTEFTLTISSLQSEDFAVYYCQQWSSSPLTGGQGTKVEIK (SEQ ID NO: 264) |
| 4E3V3-20 | EIVLTQSPGTLSLSTGERATLSCSANSSFTYMYWYQQKPGQAPRLLIYDTSNLASGIPDRFSGSGSGTDFTLTISRLEPEDFAVYYCQQWSSSPLTFGQGTKVEIK (SEQ ID NO: 265) |
| 4E3V2-28 | DIVMTQSPLSLPVTPGEPASISCSANSSFTYMYWYLQKPGQSPQLLIYDTSNLASGVPDRFSGSGSGTDFTLKISRVEAEDVGVYYCQQWSSSPLTFGQGTKVEIK (SEQ ID NO: 266) |
| 4E3V2-30 | DVVMTQSPLSLPVTLGQPASISCSANSSFTYMYWFQQRPGQSPRRLIYDTSNLASGVPDRFSGSGSGTDFTLKISRVEAEDVGVYYCQQWSSSPLTFGQGTKVEIK (SEQ ID NO: 267) |
| 4E3V4-1 | DIVMTQSPDSLAVSLGERATINCSANSSFTYMYWYQQKPGQPPKLLIYDTSNLASGVPDRFSGSGSGTDFTLTISSLQAEDVAVYYCQQWSSSPLTFGQGTKVEIK (SEQ ID NO: 268) |
| 4E3L1 | EIVLTQSPATLSLSPGERATLSCSANSSFTYMYWYQQKPGQAPRLLIYDTSNLASGIPARFSGSGSGTDFTLTISSLEPEDFAVYYCQQWSSSPLTFGQGTKLEIK (SEQ ID NO: 484) |
| 4E3L2 | EIVLTQSPATLSLSPGERVTMSCSANSSFTYMYWYQQKPGQAPRLLIYDTSNLASGVPARFSGSGSGTDYTLTISSMEPEDFAVYYCQQWSSSPLTFGQGTKLEIK (SEQ ID NO: 485) |
| 4E3L3 | EIVLTQSPATLSLSPGERVTMSCSANSSFTYMYWYQQKPGQAPRLLIFDTSNLASGVPARFSGSGSGTDYTLTISSMEPEDEAVYYCQQWSSSPLTFGQGTKLELK (SEQ ID NO: 486) |
| Antibody 7A3 | Antibody 7A3 |
| 7A3V1-39 | DIQMTQSPSSLSASVGDRVTITCRASQSISEYLHWYQQKPGKAPKLLIYFASQSICGVPSRFSGSGSGTDFTLTISSLQPEDFATYYCQNGHNFPYTFGQGTKVEIK (SEQ ID NO: 269) |
| 7A3V1-9 | DIQLTQSPSFLSASVGDRVTITCRASQSISEYLHWYQQKPGKAPKLLIYFASQSICGVPSRFSGSGSGTEFTLTISSLQPEDEATYYCQNGHNFPYTFGQGTKVEIK (SEQ ID NO: 270) |
| 7A3V1-5 | DIQMTQSPSTLSASVGDRVTITCRASQSISEYLHWYQQKPGKAPKLLIYFASQSICGVPSRFSGSGSGTEFTLTISSLQPDDFATYYCQNGHNFPYTFGQGTKVEIK (SEQ ID NO: 271) |
| 7A3V3-11 | EIVLTQSPATLSLSPGERATLSCRASQSISEYLHWYQQKPGQAPRLLIYFASQSICGIPARFSGSGSGTDFTLTISSLEPEDFAVYYCQNGHNFPYTFGQGTKVEIK (SEQ ID NO: 272) |
| 7A3V1-33 | DIQMTQSPSSLSASVGDRVTITCRASQSISEYLHWYQQKPGKAPKLLIYFASQSICGVPSRFSGSGSGTDFTFTISSLQPEDIATYYCQNGHNFPYTFGQGTKVEIK (SEQ ID NO: 273) |
| 7A3V3-15 | EIVMTQSPATLSVSPGERATLSCRASQSISEYLHWYQQKPGQAPRLLIYFASQSICGIPARFSGSGSGTEFTLTISSLQSEDEAVYYCQNGHNFPYTFGQGTKVEIK (SEQ ID NO: 274) |
| 7A3V3-20 | EIVLTQSPGTLSLSPGERATLSCRASQSISEYLHWYQQKPGQAPRLLIYFASQSICGIPDRFSGSGSGTDFTLTISRLEPEDFAVYYCQNGHNFPYTFGQGTKVEIK (SEQ ID NO: 275) |
| 7A3V2-30 | DVVMTQSPLSLPVTLGQPASISCRASQSISEYLHWFQQRPGQSPRRLIYFASQSICGVPDRFSGSGSGTDFTLKISRVEAEDVGVYYCQNGHNFPYTFGQGTKVEIK (SEQ ID NO: 276) |
| 7A3V2-28 | DIVMTQSPLSLPVTPGEPASISCRASQSISEYLHWYLQKPGQSPQLLIYFASQSICGVPDRFSGSGSGTDFTLKISRVEAEDVGVYYCQNGHNFPYTFGQGTKVEIK (SEQ? ID NO: 277) |

TABLE 6A-continued

Humanized light chain variable regions

| Antibody variant | Humanized sequences |
|---|---|
| 7A3V4-1 | DIVMTQSPDSLAVSLGERATINCRASQSISEYLHWYQQKPGQPPKLLIYFASQSICGVPDRFSGSGSGTDFTLTISSLQAEDVAVYYCQNGHNFPYTFGQGTKVEIK (SEQ ID NO: 278) |
| Antibody 7E11 | Antibody 7E11 |
| 7E11V1-5 | DIQMTQSPSTLSASVGDRVTITCLASQTIGTWLAWYQQKPGKAPKLLIYAATSLADGVPSRFSGSGSGTEFTLTISSLQPDDFATYYCQQLYSTPYTFGQGTKVEIK (SEQ ID NO: 279) |
| 7E11V1-39 | DIQMTQSPSSLSASVGDRVTITCLASQTIGTWLAWYQQKPGKAPKLLIYAATSLADGVPSRFSGSGSGTDFTLTISSLQPEDFATYYCQQLYSTPYTFGQGTKVEIK (SEQ ID NO: 280) |
| 7E11V1-9 | DIQLTQSPSFLSASVGDRVTITCLASQTIGTWLAWYQQKPGKAPKLLIYAATSLADGVPSRFSGSGSGTEFTLTISSLQPEDFATYYCQQLYSTPYTFGQGTKVEIK (SEQ ID NO: 281) |
| 7E11V3-15 | EIVMTQSPATLSVSPGERATLSCLASQGTIGTWLAWYQQKPGQAPRLLIYAATSLADGIPARFSGSGSGTEFTLTISSLQSEDFAVYYCQQLYSTPYTFGQGTKVEIK (SEQ ID NO: 282) |
| 7E11V3-11 | EIVLTQSPATLSLSPGERATLSCLASQTIGTWLAWYQQKPGQAPRLLIYAATSLADGIPARFSGSGSGTDFTLTISSLEPEDFAVYYCQQLYSTPYTFGQGTKVEIK (SEQ ID NO: 283) |
| 7E11V1-33 | DIQMTQSPSSLSASVGDRVTITCLASQTIGTWLAWYQQKPGKAPKLLIYAATSLADGVPSRFSGSGSGTDFTFTISSLQPEDIATYYCQQLYSTPYTFGQGTKVEIK (SEQ ID NO: 284) |
| 7E11V3-20 | EIVLTQSPGTLSLSPGERATLSCLASQTIGTWLAWYQQKPGQAPRLLIYAATSLADGIPDRFSGSGSGTDFTLTISRLEPEDFAVYYCQQLYSTPYTFGQGTKVEIK (SEQ ID NO: 285) |
| 7E11V2-28 | DIVMTQSPLSLPVTPGEPASISCLASQTIGTWLAWYLQKPGQSPQLLIYAATSLADGVPDRFSGSGSGTDFTLKISRVEAEDVGVYYCQQLYSTPYTFGQGTKVEIK (SEQ ID NO: 286) |
| 7E11V4-1 | DIVMTQSPDSLAVSLGERATINCLASQTIGTWLAWYQQKPGQPPKLLIYAATSLADGVPDRFSGSGSGTDFTLTISSLQAEDVAVYYCQQLYSTPYTFGQGTKVEIK (SEQ ID NO: 287) |
| 7E11V2-30 | DVVMTQSPLSLPVTLGQPASISCLASQTIGTWLAWFQQRPGQSPRRLIYAATSLADGVPDRFSGSGSGTDFTLKISRVEAEDVGVYYCQQLYSTPYTFGQGTKVEIK (SEQ ID NO: 288) |
| Antibody 7F12 | Antibody 7F12 |
| 7F12V2-30 | DVVMTQSPLSLPVTLGQPASISCRSSQSLVHSTGNTYLHWFQQRPGQSPRRLIYKVSNRFSGVPDRFSGSGSGTDFTLKISRVEAEDVGVYYCSQNTHVPYTFGQGTKVEIK (SEQ ID NO: 289) |
| 7F12V2-28 | DIVMTQSPLSLPVTPGEPASISCRSSQSLVHSTGNTYLHWYLQKPGQSPQLLIYKVSNRFSGVPDRFSGSGSGTDFTLKISRVEAEDVGVYYCSQNTHVPYTFGQGTKVEIK (SEQ ID NO: 290) |
| 7F12V4-1 | DIVMTQSPDSLAVSLGERATINCRSSQSLVHSTGNTYLHWYQQKPGQPPKLLIYKVSNRFSGVPDRFSGSGSGTDFTLTISSLQAEDVAVYYCSQNTHVPYTFGQGTKVEIK (SEQ ID NO: 291) |
| 7F12V3-11 | EIVLTQSPATLSLSPGERATLSCRSSQSLVHSTGNTYLHWYQQKPGQAPRLLIYKVSNRFSGIPARFSGSGSGTDFTLTISSLEPEDFAVYYCSQNTHVPYTFGQGTKVEIK (SEQ ID NO: 292) |
| 7F12V1-33 | DIQMTQSPSSLSASVGDRVTITCRSSQSLVHSTGNTYLHWYQQKPGKAPKLLIYKVSNRFSGVPSRFSGSGSGTDFTFTISSLQPEDIATYYCSQNTHVPYTFGQGTKVEIK (SEQ ID NO: 293) |
| 7F12V3-15 | EIVMTQSPATLSVSPGERATLSCRSSQSLVHSTGNTYLHWYQQKPGQAPRLLIYKVSNRFSGIPARFSGSGSGTEFTLTISSLQSEDFAVYYCSQNTHVPYTFGQGTKVEIK (SEQ ID NO: 294) |
| 7F12V1-5 | DIQMTQSPSTLSASVGDRVTITCRSSQSLVHSTGNTYLHWYQQKPGKAPKLLIYKVSNRFSGVPSRFSGSGSGTEFTLTISSLQPDDFATYYCSQNTHVPYTFGQGTKVEIK (SEQ ID NO: 295) |

TABLE 6A-continued

Humanized light chain variable regions

| Antibody variant | Humanized sequences |
| --- | --- |
| 7F12V1-9 | DIQLTQSPSFLSASVGDRVTITCRSSQSLVHSTGNTVLHWYQQKPGKAPKLLIYKVSNRFSGVPSRFSGSGSGTEFTLTISSLQPEDFATYYCSQNTHVPYTFGQGTKVEIK (SEQ ID NO: 296) |
| 7F12V1-39 | DIQMTQSPSSLSASVGDRVTITCRSSQSLVHSTGNTYLHWYQQKPGKAPKLLIYKVSNRFSGVPSRFSGSGSGTDFTLTISSLQPEDFATYYCSQNTHVPYTFGQGTKVEIK (SEQ ID NO: 297) |
| 7F12V3-20 | EIVLTQSPGTLSLSPGERATLSCRSSQSLVHSTGNTYLHWYQQKPGQAPRLLIYKVSNRFSGIPDRFSGSGSGTDFTLTISRLEPEDFAVYYCSQNTHVPYTFGQGTKVEIK (SEQ ID NO: 298) |
| Antibody 10B5 | Antibody 10B5 |
| 10B5V1-39 | DIQMTQSPSSLSASVGDRVTITCRASQDISZYLNWYQQKPGKAPKLLIYLSSRLHSGVPSRFSGSGSGTDFTLTISSLQPEDFATYYCQQGHTGAWTFGQGTKVEIK (SEQ ID NO: 299) |
| 10B5V1-33 | DIQMTQSPSSLSASVGDRVTITCRASQDISZYLNWYQQKPGKAPKLLIYLSSRLHSGVPSRFSGSGSGTDFTFTISSLQPEDIATYYCQQGHTGAWTFGQGTKVEIK (SEQ ID NO: 300) |
| 10B5V1-9 | DIQLTQSPSFLSASVGDRVTITCRASQDISZYLNWYQQKPGKAPKLLIYLSSRLHSGVPSRFSGSGSGTEFTLTISSLQPEDFATYYCQQGHTGAWTFGQGTKVEK (SEQ ID NO: 301) |
| 10B5V1-5 | DIQMTQSPSTLSASVGDRVTITCRASQDISZYLNWYQQKPGKAPKLLIYLSSRLHSGVPSRFSGSGSGTEFTLTISSLQPDDFATYYCQQGHTGAWTFGQGFKVEK (SEQ ID NO: 302) |
| 10B5V3-11 | EIVLTQSPATLSLSPGERATLSCRASQDISZYLNWYQQKPGQAPRLLIYLSSRLHSGIPARFSGSGSGTDFTLTISSLEPEDFAVYYCQQGHTGAWTFGQGTKVEIK (SEQ ID NO: 303) |
| 10B5V3-15 | EIVMTQSPATLSVSPGERATLSCRASQDISZYLNWYQQKPGQAPRLLIYLSSRLHSGIPARFSGSGSGTEFTLTISSLQSEDFAVYYCQQGHTGAWTFGQGTKVEIK (SEQ ID NO: 304) |
| 10B5V3-20 | EIVLTQSPGTLSLSPGERATLSCRASQDISZYLNWYQQKPGQAPRLLIYLSSRLHSGIPDRFSGSGSGTDFTLTISRLEPEDFAVYYCQQGHTGAWTFGQGTKVEIK (SEQ ID NO: 305) |
| 10B5V2-28 | DIVMTQSPLSLPVTPGEPASISCRASQDISZYLNWYLQKPGQSPQLLIYLSSRLHSGVPDRESGSGSGTDFTLKISRVEAEDVGVYYCQQGHTGAWTFGQGTKVEIK (SEQ ID NO: 306) |
| 10B5V2-30 | DVVMTQSPLSLPVTLGQPASISCRASQDISZYLNWFQQRPGQSPRRLIYLSSRLHSGVPDRFSGSGSGTDFTLKISRVEAEDVGVYYCQQGHTGAWTFGQGTKVEIK (SEQ ID NO: 307) |
| 10B5V4-1 | DIVMTQSPDSLAVSLGERATINCRASQDISZYLNWYQQKPGQPPKLLIYLSSRLHSGVPDRFSGSGSGTDFTLTISSLQAEDVAVYYCQQGHTGAWTFGQGTKVEIK (SEQ ID NO: 308) |
| 10B5L1 | DIQMTQSPSSLSASVGDRVTITCRASQDINTYLNWYQQKPGKAPKLLIYYTSRLHSGVPSRFSGSGSTDFTLTISSLQPEDFATYYCQQGNTLPWTFGQGTKLEIK (SEQ ID NO: 487) |
| 10B5L2 | DIQMTQSPSSLSASVGDRVTITCRASQDINTYLNWYQQKPGKAPKLLIYYTSRLHSGVPSRFSGSGSGTDYTLTISSLQPEDFATYYCQQGNTLPWTFGQGTKLEIK (SEQ ID NO: 488) |
| 10B5L3 | DVQMTQSPSSLSASVGDRVTITCRASQDINTYLNWYQQKPGKAPKLLIYYTSRLHSGVPSRFSGSGSGTDYTLTISSLQPEDFATYYCQQGNTLPWTFGQGTKLEIK (SEQ ID NO: 489) |
| Antibody 10G8 | Antibody 10G8 |
| 10G8V1-39 | DIQMTQSPSSLSASVGDRVTITCRASQSIREYLHWYQQKPGKAPKLLIYFASQSICGVPSRFSGSGSGTDFTLTISSLQPEDFATYYCQKAHNFPYTFGQGTKVEIK (SEQ ID NO: 309) |
| 10G8V1-9 | DIQLTQSPSFLSASVGDRVTITCRASQSIREYLHWYQQKPGKAPKLLIYFASQSICGVPSRFSGSGSGTEFTLTISSLQPEDFATYYCQKAHNFPYTFGQGTKVEIK (SEQ ID NO: 310) |

TABLE 6A-continued

Humanized light chain variable regions

| Antibody variant | Humanized sequences |
|---|---|
| 10G8V3-11 | EIVLTQSPATLSLSPGERATLSCRASQSIREYLHWYQQKPGQAPRLLIYFASQSICG IPARFSGSGSGTDFTLTISSLEPEDFAVYYCQKAHNFPYTFGQGTKVEIK (SEQ ID NO: 311) |
| 10G8V1-5 | DIQMTQSPSTLSASVGDRVTITCRASQSIREYLHWYQQKPGKAPKLLIYFASQSIC GVPSRFSGSGSGTEFTLTISSLQPDDFATYYCQKAHNFPYTFGQGTKVEIK (SEQ ID NO: 312) |
| 10G8V3-15 | EIVMTQSPATLSVSPGERATLSCRASQSIREYLHWYQQKPGQAPRLLIYFASQSIC GIPARFSGSGSGTEFTLTISSLQSEDFAVYYCQKAHNFPYTFGQGTKVEIK (SEQ ID NO: 313) |
| 10G8V1-33 | DIQMTQSPSSLSASVGDRVTITCRASQSIREYLHWYQQKPGKAPKLLIYFASQSIC GVPSRFSGSGSGTDFTFTISSLQPEDIATYYCQKAHNFPYTFGQGTKVEIK (SEQ ID NO: 314) |
| 10G8V3-20 | EIVLTQSPGTLSLSPGERATLSCRASQSIREYLHWYQQKPGQAPRLLIYFASQSICG IPDRFSGSGSGTDFTLTISRLEPEDFAVYYCQKAHNFPYTFGQGTKVEIK (SEQ ID NO: 315) |
| 10G8V4-1 | DIVMTQSPDSLAVSLGERATINCRASQSIREYLHWYQQKPGQPPKLLIYFASQSIC GVPDRFSGSGSGTDFTLTISSLQAEDVAVYYCQKAHNFPYTFGQGTKVEIK (SEQ ID NO: 316) |
| 10G8V2-30 | DVVMTQSPLSLPVTLGQPASISCRASQSIREYLHWFQQRPGQSPRRLIYFASQSIC GVPDRFSGSGSGTDFTLKISRVEAEDVGVYYCQKAHNFPYTFGQGTKVEIK (SEQ ID NO: 317) |
| 10G8V2-28 | DIMVTQSPLSLPVTPGEPASISCRASQSIREYLHWYLQKPGQSPQLLIYFASQSICG VPDRFSGSGSGTDFTLKISRVEAEDVGVYYCQKAHNFPYTFGQGTKVEIK (SEQ ID NO: 318) |

TABLE 6B

Humanized heavy chain variable regions

| Antibody variant | Humanized sequences |
|---|---|
| Antibody 1A12 | Antibody 1A12 |
| 1A12V1-46 | QVQLVQSGAEVKKPGASVKVSCKASGSEVFPITYMNWVRQAPGQGLEWIGDILP SIGRTMYGQKFQGRVTMTRDTSTSTVYMELSSLRSEDTAVYYCARSEGYLLAYW GQGTLVTVSS (SEQ ID NO: 319) |
| 1A12V3-23 | EVQLLESGGGLVQPGGSLRLSCAASGSEVFPITYMNWVRQAPGKGLEWIGDILPSI GRTMYGDSVKGRFTISRDNSKNTLYLQMNSLRAEDTAVYYCARSEGYLLAYWG QGTLVTVSS (SEQ ID NO: 320) |
| 1A12V1-69 | QVQLVQSGAEVKKPGSSVKVSCKASGSEVFPITYMNWVRQAPGQGLEWIGDILPS IGRTMYGQKFQGRVTITADESTSTAYMELSSLRSEDTAVYYCARSEGYLLAYWG QGTLVTVSS (SEQ ID NO: 321) |
| 1A12V5-51 | EVQLVQSGAEVKKPGESLKISCKGSGSEVFPITYMNWVRQMPGKGLEWIGDILPSI GRTMYGPSFQGQVTISADKSISTAYLQWSSLKASDTAMYYCARSEGYLLAYWGQ GTLVTVSS (SEQ ID NO: 322) |
| 1A12V3-48 | EVQLVESGGGLVQPGGSLRLSCAASGSEVFPITYMNWVRQAPGKGLEWIGDILPSI GRTMYGDSVKGRFTISRDNAKNSLYLQMNSLRAEDTAVYYCARSEGYLLAYWG QGTLVTVSS (SEQ ID NO: 323) |
| 1A12V3-7 | EVQLVESGGGLVQPGGSLRLSCAASGSEVFPITYMNWVRQAPGKGLEWIGDILPSI GRTMYGDSVKGRFTISRDNAKNSLYLQMNSLRAEDTAVYYCARSEGYLLAYWG QGTLVTVSS (SEQ ID NO: 324) |
| 1A12V3-30 | QVQLVESGGGVVQPGRSLRLSCAASGSEVFPITYMNWVRQAPGKGLEWIGDILPS IGRTMYGDSVKGRFTISRDNSKNTLYLQMNSLRAEDTAVYYCARSEGYLLAYWG QGTLVTVSS (SEQ ID NO: 325) |
| 1A12V4-59 | QVQLQESGPGLVKPSETLSLTCTVSGSEVFPITYMNWIRQPPGKGLEWIGDILPSIG RTMYGPSLKSRVTISVDTSKNQFSLKLSSVTAADTAVYYCARSEGYLLAYWGQGT LVTVSS (SEQ ID NO: 326) |

TABLE 6B-continued

Humanized heavy chain variable regions

| Antibody variant | Humanized sequences |
|---|---|
| 1A12V4-39 | QLQLQESGPGLVKPSETLSLTCTVSGSEVFPITYMNWIRQPPGKGLEWIGDILPSIG RTMYGPSLKSRVTISVDTSKNQFSEKLSSVTAADTAVYYCARSEGYLLAYWGQGT LVTVSS (SEQ ID NO: 327) |
| 1A12V4-30 | QVQLQESGPGLVKPSQTLSLTCTVSGSEVFPITYMNWIRQPPGKGLEWIGDILPSIG RTMYGPSLKSRVTISVDTSKNQFSLKLSSVTAADTAVYYCARSEGYLLAYWGQGT LVTVSS (SEQ ID NO: 328) |
| Antibody 1E8 | Antibody 1E8 |
| 1E8V1-46 | QVQLVQSGAEVKKPGASVKVSCKASGFNIKGSLLHWVRQAPGQGLEWIGWIDPE DGETRFDQKFQGRVTMTRDTSTSTVYMELSSLRSEDTAVYYCARTEYSNPAWFA YWGQGTLVTVSS (SEQ ID NO: 329) |
| 1E8V5-51 | EVQLVQSGAEVKKPGESLKISCKGSGFNIKGSLLHWVRQMPGKGLEWIGWIDPED GETRFDPSFQGQVTISADKSISTAYLQWSSLKASDTAMYYCARTEYSNPAWFAY WGQGTLVTVSS (SEQ ID NO: 330) |
| 1E8V3-23 | EVQLLESGGGLVQPGGSLRLSCAASGFNIKGSLLHWVRQAPGKGLEWIGWIDPED GETRFDDSVKGRFTISRDNSKNTLYLQMNSLRAEDTAVYYCARTEYSNPAWFAY WGQGTLVTVSS (SEQ ID NO: 331) |
| 1E8V1-69 | QVQLVQSGAEVKKPGSSVKVSCKASGFNIKGSLLHWVRQAPGQGLEWIGWIDPE DGETRFDQKFQGRVTITADESTSTAYMELSSLRSEDTAVYYCARTEYSNPAWFAY WGQGTLVTVSS (SEQ ID NO: 332) |
| 1E8V3-30 | QVQLVESGGGVVQPGRSLRLSCAASGFNIKGSLLHWVRQAPGKGLEWIGWIDPE DGETRFDDSVKGRFTISRDNSKNTLYLQMNSLRAEDTAVYYCARTEYSNPAWFA YWGQGTLVTVSS (SEQ ID NO: 333) |
| 1E8V3-7 | EVQLVESGGGLVQPGGSLRLSCAASGFNIKGSLLHWVRQAPGKGLEWIGWIDPE DGETRFDDSVKGRFTISRDNAKNSLYLQMNSLRAEDTAVYYCARTEYSNPAWFA YWGQGTLVTVSS (SEQ ID NO: 334) |
| 1E8V3-48 | EVQLVESGGGLVQPGGSLRLSCAASGFNIKGSLLHWVRQAPGKGLEWIGWIDPE DGETRFDDSVKGRFTISRDNAKNSLYLQMNSLRAEDTAVYYCARTEYSNPAWFA YWGQGTLVTVSS (SEQ ID NO: 335) |
| 1E8V4-59 | QVQLQESGPGLVKPSETLSLTCTVSGFNIKGSLLHWIRQPPGKGLEWIGWIDPEDG ETRFDPSLKSRVTISVDTSKNQFSLIKLSSVTAADTAVYYCARTEYSNPAWFAYW GQGTLVTVSS (SEQ ID NO: 336) |
| 1E8V3-15 | EVQLVESGGGLVKPGGSLRLSCAASGFNIKGSLLHWVRQAPGKGLEWIGWIDPE DGETRFDAPVKGRFTISRDDSKNTLYLQMNSLKTEDTAVYYCARTEYSNPAWFA YWGQGTLVTVSS (SEQ ID NO: 337) |
| 1E8V4-30 | QVQLQESGPGLVKPSQTLSLTCTVSGFNIKGSLLHWIRQPPGKGLEWIGWIDPEDG ETRFDPSLKSRVTISVDTSKNQFSLKLSSVTAADTAVYYCARTEYSNPAWFAYW QGTLVTVSS (SEQ ID NO: 338) |
| Antibody 2G1 | Antibody 2G1 |
| 2G1V3-23 | EVQLLESGGGLVQPGGSLRLSCAASGFTSNYDMSWVRQAPGKGLEWVATISSGG DYTYYPDSVKGRFTISRDNSKNTLYLQMNSLRAEDTAVYYCARHGYGNYDWYF DVWGQGTLVTVSS (SEQ ID NO: 339) |
| 2G1V3-7 | EVQLVESGGGLVQPGGSLRLSCAASGFTSNYDMSWVRQAPGKGLEWVATISSG GDYTYYPDSVKGRFTISRDNAKNSLYLQMNSLRAEDTAVYYCARHGYGNYDWY FDVWGQGTLVTVSS (SEQ ID NO: 340) |
| 2G1V3-30 | QVQLVESGGGVVQPGRSLRLSCAASGFTSNYDMSWVRQAPGKGLEWVATISSG GDYTYYPDSVKGRFTISRDNSKNTLYLQMNSLRAEDTAVYYCARHGYGNYDWY FDVWGQGTLVTVSS (SEQ ID NO: 341) |
| 2G1V3-48 | EVQLVESGGGLVQPGGSLRLSCAASGFTSNYDMSWVRQAPGKGLEWVATISSG GDYTYYPDSVKGRFTISRDNAKNSLYLQMNSLRAEDTAVYYCARHGYGNYDWY FDVWGQGTLVTVSS (SEQ ID NO: 342) |
| 2G1V1-46 | QVQLVQSGAEVKKPGASVKVSCKASGFTSNYDMSWVRQAPGQGLEWVATISSG GDYTYYPQKFQGRVTMTRDTSTSTVYMELSSLRSEDTAVYYCARHGYGNYDWY FDVWGQGTLVTVSS (SEQ ID NO: 343) |
| 2G1V1-69 | QVQLVQSGAEVKKPGSSVKVSCKASGFTSNYDMSWVRQAPGQGLEWVATISSG GDYTYYPQKFQGRVTITADESTSTAYMELSSLRSEDTAVYYCARHGYGNYDWYF DVWGQGTLVTVSS (SEQ ID NO: 344) |

TABLE 6B-continued

Humanized heavy chain variable regions

| Antibody variant | Humanized sequences |
|---|---|
| 2G1V5-51 | EVQLVQSGAEVKKPGESLKISCKGSGFTFSNYDMSWVRQMPGKGLEWVATISSG GDYTYYPSFQGQVTISADKSISTAYLQWSSLKASDTAMYYCARHGYGNYDWYF DVWGQGTLVTVSS (SEQ ID NO: 345) |
| 2G1V4-59 | QVQLQESGPGLVKPSETLSLTCTVSGFTFSNYDMSWIRQPPGKGLEWVATISSGGD YTYYPPSLKSRVTISVDTSKNQFSLKLSSVTAADTAVYYCARHGYGNYDWYFDV WGQGTLVTVSS (SEQ ID NO: 346) |
| 2G1V3-15 | EVQLVESGGGLVKPGSLRLSCAASGFTFSNYDMSWVRQAPGKGLEWVATISSG GDYTYYPAPVKGRFTISRDDSKNTLYLQMNSLKTEDTAVYYCARHGYGNYDWY FDVWGQGTLVTVSS (SEQ ID NO: 347) |
| 2G1V4-39 | QLQLQESGPGLVKPSETLSLTCTVSGFTFSNYDMSWIRQPPGKGLEWVATISSGGD YTYYPPSLKSRVTISVDTSKNQFSLKLSSVTAADTAVYYCARHGYGNYDWYFDV WGQGTLVTVSS (SEQ ID NO: 348) |
| Antibody 2G4 | Antibody 2G4 |
| 2G4V1-46 | QVQLVQSGAEVKKPGASVKVSCKASGSEVFPITYMNWVRQAPGQGLEWIGDILP SIGRTMYGQKFQGRVTMTRDTSTSTVYMELSSLRSEDTAVYYCARSEGYLLAYW GGTTLTVSS (SEQ ID NO: 349) |
| 2G4V3-23 | EVQLLESGGGLVQPGGSLRLSCAASGSEVFPITYMNWVRQAPGKGLEWIGDILPSI GRTMYGDSVKGRFTISRDNSKNTLYLQMNSLRAEDTAVYYCARSEGYLLAYWG QGTLVTVSS (SEQ ID NO: 350) |
| 2G4V1-69 | QVQLVQSGAEVKKPGSSVKVSCKASGSEVFPITYMNWVRQAPGQGLEWIGDILPS IGRTMYGQKFQGRVTITADESTSTAYMELSSLRSEDTAVYYCARSEGYLLAYWG QGTLVTVSS (SEQ ID NO: 351) |
| 2G4V5-51 | EVQLVQSGAEVKKPGESLKISCKGSGSEVFPITYMNWVRQMPGKGLEWIGDILPSI GRTMYGPSFQGQVTISADKSISTAYLQWSSLKASDTAMYYCARSEGYLLAYWGQ GTLVTVSS (SEQ ID NO: 352) |
| 2G4V3-48 | EVQLVESGGGLVQPGGSLRLSCAASGSEVFPITYMNWVRQAPGKGLEWIGDILPSI GRTMYGDSVKGRFTISRDNAKNSLYLQMNSLRAEDTAVYYCARSEGYLLAYWG QGTLVTVSS (SEQ ID NO. 353) |
| 2G4V3-7 | EVQLVESGGGLVQPGGSLRLSCAASGSEVFPITYMNWVRQAPGKGLEWIGDILPSI GRTMYGDSVKGRFTISRDNAKNSLYLQMNSLRAEDTAVYYCARSEGYLLAYWG QGTLVTVSS (SEQ ID NO: 354) |
| 2G4V3-30 | QVQLVESGGGVVQPGRSLRLSCAASGSEVFPITYMNWVRQAPGKGLEWIGDILPS IGRTMYGDSVKGRFTISRDNSKNTLYLQMNSLRAEDTAVYYCARSEGYLLAYWG QGTLVTVSS (SEQ ID NO: 355) |
| 2G4V4-59 | QVQLQESGPGLVKPSETLSLTCTVSGSEVFPITYMNWIRQPPGKGLEWIGDILPSIG RTMYGPSLKSRVTISVDTSKNQFSLKLSSVTAADTAVYYCARSEGYLLAYWGQGT LVTVSS (SEQ ID NO: 356) |
| 2G4V4-39 | QLQLQESGPGLVKPSETLSLTCTVSGSEVFPITYMNWIRQPPGKGLEWIGDILPSIG RTMYGPSLKSRVTISVDTSKNQFSLKLSSVTAADTAVYYCARSEGYLLAYWGQGT LVTVSS (SEQ ID NO: 357) |
| 2G4V4-30 | QVQLQESGPGLVKPSQTLSLTCTVSGSEVFPITYMNWIRQPPGKGLEWIGDILPSIG RTMYGPSLKSRVTISVDTSKNQFSLKLSSVTAADTAVYYCARSEGYLLAYWGQGT LVTVSS (SEQ ID NO: 358) |
| Antibody 3E11 | Antibody 3E11 |
| 3E11V5-51 | EVQLVQSGAEVKKPGESLKISCKGSGYIFTDYGITWVRQMPGKGLEWIGEISPRSG ETYFNPSFQGQVTISADKSISTAYLQWSSLKASDTAMYYCAREGNPFTYWGQGTL VTVSS (SEQ ID NO: 359) |
| 3E11V1-46 | QVQLVQSGAEVKKPGASVKVSCKASGYIFTDYGITWVRQAPGQGLEWIGEISPRS GETYFNQKFQGRVTMTRDTSTSTVYMELSSLRSEDTAVYYCAREGNPFTYWGQG TLVTVSS (SEQ ID NO: 360) |
| 3E11V3-23 | EVQLLESGGGLVQPGGSLRLSCAASGYIFTDYGITWVRQAPGKGLEWIGEISPRSG ETYFNDSVKGRFTISRDNSKNTLYLQMNSLRAEDTAVYYCAREGNPFTYWGQGT LVTVSS (SEQ ID NO: 361) |
| 3E11V1-69 | QVQLVQSGAEVKKPGSSVKVSCKASGYIFTDYGITWVRQAPGQGLEWIGEISPRS GETYFNQKFQGRVTITADESTSTAYMELSSLRSEDTAVYYCAREGNPFTYWGQGT LVTVSS (SEQ ID NO: 362) |

TABLE 6B-continued

Humanized heavy chain variable regions

| Antibody variant | Humanized sequences |
|---|---|
| 3E11V3-48 | EVQLVESGGGLVQPGGSLRLSCAASGYIFTDYGITWVRQAPGKGLEWIGEISPRSG ETYFNDSVKGRFTISRDNAKNSLYLQMNSLRAEDTAVYYCAREGNPFTYWGQGT LVTVSS (SEQ ID NO: 363) |
| 3E11V3-7 | EVQLVESGGGLVQPGGSLRLSCAASGYIFTDYGITWVRQAPGKGLEWIGEISPRSG ETYFNDSVKGRFTISRDNAKNSLYLQMNSLRAEDTAVYYCAREGNPFTYWGQGT LVTVSS (SEQ ID NO: 364) |
| 3E11V3-30 | QVQLVESGGGVVQPGRSLRLSCAASGYIFTDYGITWVRQAPGKGLEWIGEISPRS GETYFNDSVKGRFTISRDNSKNTLYLQMNSLRAEDTAVYYCAREGNPFTYWGQG TLTVSS (SEQ ID NO: 365) |
| 3E11V4-59 | QVQLQESGPGLVKPSETLSLTCTVSGYIFTDYGITWIRQPPGKGLEWIGEISPRSGE TYFNPSLKSRVTISVDTSKNQFSLKLSSVTAADTAVYYCAREGNPFTYWGQGTLV TVSS (SEQ ID NO: 366) |
| 3E11V3-15 | EVQLVESGGGLVKPGGSLRLSCAASGYIFTDYGITWVRQAPGKGLEWIGEISPRSG ETYFNAPVKGRFTISRDDSKNTLYLQMNSLKTEDTAVYYCAREGNPFTYWGQGT LVTVSS (SEQ ID NO: 367) |
| 3E11V4-30 | QVQLQESGPGLVKPSQTLSLTCTVSGYIFTDYGITWIRQPPGKGLEWIGEISPRSGE TYFNPSLKSRVTISVDTSKNQFSLKLSSVTAADTAVYYCAREGNPFTYWGQGTLV TVSS (SEQ ID NO: 368) |
| Antibody 4A1 | Antibody 4A1 |
| 4A1V1-46 | QVQLVQSGAEVKKPGASVKVSCKASGSEVFPITYMNWVRQAPGQGLEWIGDILP SIGRTMYGQKFQGRVTMTRDTSTSTVYMELSSLRSEDTAVYYCARSEGYLLAYW GQGTLATTVSS (SEQ ID NO: 369) |
| 4A1V3-23 | EVQLLESGGGLVQPGGSLRLSCAASGSEVFPITYMNWVRQAPGKGLEWIGDILPSI GRTMYGDSVKGRFTISRDNSKNTLYLQMNSLRAEDTAVYYCARSEGYLLAYWG QGTLVTVSS (SEQ ID NO: 370) |
| 4A1V1-69 | QVQLVQSGAEVKKPGSSVKVSCKASGSEVFPITYMNWVRQAPGQGLEWIGDILPS IGRTMYGQKFQGRVTITADESTSTAYMELSSLRSEDTAVYYCARSEGYLLAYWG QGTLVTVSS (SEQ ID NO: 371) |
| 4A1V5-51 | EVQLVQSGAEVKKPGESLKISCKGSGSEVFPITYMNWVRQMPGKGLEWIGDILPSI GRTMYGPSFQGQVTISADKSISTAYLQWSSLKASDTAMYYCARSEGYLLAYWGQ GTLVTVSS (SEQ ID NO: 372) |
| 4A1V3-48 | EVQLVESGGGLVQPGGSLRLSCAASGSEVFPITYMNWVRQAPGKGLEWIGDILPSI GRTMYGDSVKGRFTISRDNAKNSLYLQMNSLRAEDTAVYYCARSEGYLLAYWG QGTLVTVSS (SEQ ID NO: 373) |
| 4A1V3-7 | EVQLVESGGGLVQPGGSLRLSCAASGSEVFPITYMNWVRQAPGKGLEWIGDILPSI GRTMYGDSVKGRFTISRDNAKNSLYLQMNSLRAEDTAVYYCARSEGYLLAYWG QGTLVTVSS (SEQ ID NO: 374) |
| 4A1V3-30 | QVQLVESGGGVVQPGRSLRLSCAASGSEVFPITYMNWVRQAPGKGLEWIGDILPS IGRTMYGDSVKGRFTISRDNSKNTLYLQMNSLRAEDTAVYYCARSEGYLLAYWG QGTLVTVSS (SEQ ID NO: 375) |
| 4A1V4-59 | QVQLQESGPGLVKPSETLSLCTVSGSEVFPITYMNWIRQPPGKGLEWIGDILPSIG RTMYGPSLKSRVTISVDTSKNQFSLKLSSVTAADTAVYYCARSEGYLLAYWGQGT LVTVSS (SEQ ID NO: 376) |
| 4A1V4-39 | QLQLQESGPGLVKPSETLSLTCTVSGSEVFPITYMNWIRQPPGKGLEWIGDILPSIG RTMYGPSLKSRVTISVDTSKNQFSLKLSSVTAADTAVYYCARSEGVLLAYWGQGT LVTVSS (SEQ ID NO: 377) |
| 4A1V4-30 | QVQLQESGPGLVKPSQTLSLTCTVSGSEVFPITYMNWIRQPPGKGLEWIGDILPSIG RTMYGPSLKSRVTISVDTSKNQFSLKLSSVTAADTAVYYCARSEGYLLAYWGQG LVTVSS (SEQ ID NO: 378) |
| Antibody 4D7 | Antibody 4D7 |
| 4D7V5-51 | EVQLVQSGAEVKKPGESLKISCKGSGYTFTNYWINWVRQMPGKGLEWIGNIYSGS SRTNYNPSFQGQVTISADKSISTAYLQWSSLKASDTAMYYCAREGLRAMDYWGQ GTLVTVSS (SEQ ID NO: 379) |
| 4D7V3-48 | EVQLVESGGGLVQPGGSLRLSCAASGYTFTNYWINWVRQAPGKGLEWIGNIYSGS SRTNYNDSVKGRFTISRDNAKNSLYLQMNSLRAEDTAVYYCAREGLRAMDYWG QGTLVTVSS (SEQ ID NO: 380) |

TABLE 6B-continued

Humanized heavy chain variable regions

| Antibody variant | Humanized sequences |
|---|---|
| 4D7V1-46 | QVQLVQSGAEVKKPGASVKVSCKASGYTFTNYWINWVRQAPGQGLEWIGNIYSG SSRTNYNQKFQGRVTMTRDTSTSTVYMELSSLRSEDTAVYYCAREGLRAMDYWG QGTLVTVSS (SEQ ID NO: 381) |
| 4D7V3-7 | EVQLVESGGGLVQPGGSLRLSCAASGYTFTNYWINWVRQAPGKGLEWIGNIYSGS SRTNYNDSVKGRFTISRDNAKNSLYLQMNSLRAEDTAVYYCAREGLRAMDYWG QGTLVTVSS (SEQ ID NO: 382) |
| 4D7V1-69 | QVQLVQSGAEVKKPGSSVKVSCKASGYTFTNYWINWVRQAPGQGLEWIGNIYSG SSRTNYNQKFQGRVTITADESTSTAYMELSSLRSEDTAVYYCAREGLRAMDYWG QGTLVTVSS (SEQ ID NO: 383) |
| 4D7V3-30 | QVQLVESGGGVVQPGRSLRLSCAASGYTFTNYWINWVRQAPGKGLEWIGNIYSG SSRTNYNDSVKGRFTISRDNSKNTLYLQMNSLRAEDTAVYYCAREGLRAMDYWG QGTLVTVSS (SEQ ID NO: 384) |
| 4D7V3-23 | EVQLLESGGGLVQPGGSLRLSCAASGYTFNYWINWVRQAPGKGLEWIGNIYSGS SRTNYNDSVKGRFTISRDNSKNTLYLQMNSLRAEDTAVYYCAREGLRAMDYWG QGTLVTVSS (SEQ ID NO: 385) |
| 4D7V4-59 | QVQLQESGPGLVKPSETLSLTCTVSGYTFTNYWINWIRQPPGKGLEWIGNIYSGSS RTNYNPSLKSRVTISVDTSKNQFSLKLSSVTAADTAVYYCAREGLRAMDYWGQG TLVTVSS (SEQ ID NO: 386) |
| 4D7V3-15 | EVQLVESGGGLVKPGGSLRLSCAASGYTFTNYWINWVRQAPGKGLEWIGNIYSGS SRTNYNAPVKGRFTISRDDSKNTLYLQMNSLKTEDTAVYYCAREGLRAMDYWG QGTLVTVSS (SEQ ID NO: 387) |
| 4D7V4-30 | QVQLQESGPGLVKPSQTLSLTCTVSGYTFTNYWINWIRQPPGKGLEWIGNIYSGSS RTNYNPSLKSRVTISVDTSKNQFSLKLSSVTAADTAVYYCAREGLRAMDYWGQG TLVTVSS (SEQ ID NO: 388) |
| Antibody 4E3 | Antibody 4E3 |
| 4E3V3-23 | EVQLLESGGGLVQPGGSLRLSCAASGFIFSNYDMSWVRQAPGKGLEWVATISSGG GYTYYPDSVKGRFTISRDNSKNTLYLQMNSLRAEDTAVYYCTRHGYGNYDWYF DVWGQGTLVTVSS (SEQ ID NO: 389) |
| 4E3V3-7 | EVQLVESGGGLVQPGGSLRLSCAASGFIFSNYDMSWVRQAPGKGLEWVATISSGG GYTYYPDSVKGRFTISRDNAKNSLYLQMNSLRAEDTAVYYCTRHGYGNYDWYF DVWGQGTLVTVSS (SEQ ID NO: 390) |
| 4E3V73-30 | QVQLVESGGGVVQPGRSLRLSCAASGFIFSNYDMSWVRQAPGKGLEWVATISSGG GYTYYPDSVKGRFTISRDNSKNTLYLQMNSLRAEDTAVYYCTRHGYGNYDWYF DVWGQGTLVTVSS (SEQ ID NO: 391) |
| 4E3V3-48 | EVQLVESGGGLVQPGGSLRLSCAASGFIFSNYDMSWVRQAPGKGLEWVATISSGG GYTYYPDSVKGRFTISRDNAKNSLYLQMNSLRAEDTAVYYCTRHGYGNYDWYF DVWGQGTLVTVSS (SEQ ID NO: 392) |
| 4E3V1-46 | QVQLVQSGAEVKKPGASVKVSCKASGFIFSNYDMSWVRQAPGQGLEWVATISSG GGYTYYPQKFQGRVTMTRDTSTSTVYMELSSLRSEDTAVYYCTRHGYGNYDWY FDVWGQGTLVTVSS (SEQ ID NO: 393) |
| 4E3V1-69 | QVQLVQSGAEVKKPGSSVKVSCKASGFIFSNYDMSWVRQAPGQGLEWVATISSG GGYTYYPQKFQGRVTITADESTSTAYMELSSLRSEDTAVYYCTRHGYGNYDWYF DVWGQGTLVTVSS (SEQ ID NO: 394) |
| 4E3V5-51 | EVQLVQSGAEVKKPGESLKISCKGSGFIFSNYDMSWVRQMPGKGLEWVATISSGG GYTYYPPSFQGQVTISADKSISTAYLQWSSLKASDTAMYYCTRHGYGNYDWYFD VWGQGTLVTVSS (SEQ ID NO: 395) |
| 4E3V4-59 | QVQLQESGPGLVKPSETLSLTCTVSGFIFSNYDMSWIRQPPGKGLEWVATISSGGG YTYYPPSLKSRVTISVDTSKNQFSLKLSSVTAADTAVYYCTRHGYGNYDWYFDV WGQGTLVTVSS (SEQ ID NO: 396) |
| 4E3V3-15 | EVQLVESGGGLVKPGGSLRLSCAASGFIFSNYDMSWVRQAPGKGLEWVATISSGG GYTYYPAPVKGRFTISRDDSKNTLYLQMNSLKTEDTAVYYCTRHGYGNYDWYF DVWGQGTLVTVSS (SEQ ID NO: 397) |
| 4E3V4-39 | QLQLQESGPGLVKPSETLSLTCTVSGFIFSNYDMSWIRQPPGKGLEWVATISSGGG YTYYPPSLKSRVTISVDTSKNQFSLKLSSVTAADTAVYYCTRHGYGNYDWYFDV WGQGTLVTVSS (SEQ ID NO: 398) |

TABLE 6B-continued

Humanized heavy chain variable regions

| Antibody variant | Humanized sequences |
|---|---|
| 4E3H1 | EVQLVESGGGLVKPGGSLRLSCAASGFIFSNYDMSWVRQAPGKGLEWVSTISSGG GYTYYADSVKGRFTISRDNAKNSLYLQMNSLRAEDTAVYYCARHGYGNYDWYF DVWGQGTLVTVSS (SEQ ID NO: 490) |
| 4E3H2 | EVQLVESGGGLVKTPGSLRLSCAASGFIFSNYDMSWVRQAPGKGLEWVATISSGG GYTYYADSVKGRFTISRDNAKNSLYLQMNSLRAEDTAVYYCARHGYGNYDWYF DVWGQGTLVTVSS (SEQ ID NO: 491) |
| 4E3H3 | EVQLVESGGGLVKPGGSLRISCAVSGFIFSNYDMSWVRQAPGKGLEWVATISSGG GYTYYADSVKGRFTISRDNAKNSLYLQMNSLRAEDTAVYYCTRHGYGNYDWYF DVWGQGALVTVSS  (SEQ ID NO: 492) |
| Antibody 7A3 | Antibody 7A3 |
| 7A3V3-7 | EVQLVESGGGLVQPGGSLRLSCAASGFTFSNYAMSWVRQAPGKGLEWVASISSGG SYNYYPDSVKGRFTISRDNAKNSLYLQMNSLRAEDTAVYYCASQSYGSSYWYFD VWGQGTLVTVSS (SEQ ID NO: 399) |
| 7A3V3-23 | EVQLLESGGGLVQPGGSLRLSCAASGFTFSNYAMSWVRQAPGKGLEWVASISSGG SYNYYPDSVKGRFTISRDNSKNTLYLQMNSLRAEDTAVYYCASQSYGSSYWYFDV WGQGTLVTVSS (SEQ ID NO: 400) |
| 7A3V3-30 | QVQLVESGGGVVQPGRSLRLSCAASGFTFSNYAMSWVRQAPGKGLEWVASISSG GSYNYYPDSVKGRFTISRDNSKNTLYLQMNSLRAEDTAVYYCASQSYGSSYWYF DVWGQGTLVTVSS (SEQ ID NO: 401) |
| 7A3V3-48 | EVQLVESGGGLVQPGGSTRLSCAASGFTFSNYAMSWVRQAPGKGLEWVASISSGG SYNYYPDSVKGRFTISRDNAKNSLYLQMNSLRAEDTAVYYCASQSYGSSYWYFD VWGQGTLVTVSS (SEQ ID NO: 402) |
| 7A3V1-69 | QVQLVQSGAEVKKPGSSVKVSCKASGFTFSNYAMSWVRQAPGQGLEWVASISSG GSYNYYPQKFQGRVTITADESTSTAYMELSSLRSEDTAVYYCASQSYGSSYWYFD VWGQGTLVTVSS (SEQ ID NO: 403) |
| 7A3V1-46 | QVQLVQSGAEVKKPGASVKVSCKASGFTFSNYAMSWVRQAPGQGLEWVASISSG GSYNYYPQKFQGRVTMTRDTSTSTVYMELSSLRSEDTAVYYCASQSYGSSYWYF DVWGQGILVTVSS (SEQ ID NO: 404) |
| 7A3V5-51 | EVQLVQSGAEVKKPGESLKISCKGSGFTFSNYAMSWVRQMPGKGLEWVASISSGG SYNYYPPSFQGQVTISADKSISTAYLQWSSLKASDTAMYYCASQSYGSSWYFDV WGQGTLVTVSS (SEQ ID NO: 405) |
| 7A3V4-59 | QVQLQESGPGLVKPSETLSETCTVSGFTFSNYAMSWIRQPPGKGLEWVASISSGGS YNYYPPSLKSKVTISVDTSKNQFSLKLSSVTAADTAVYYCASQSYGSSYWYFDVW GQGTLVTVSS (SEQ ID NO: 406) |
| 7A3V3-15 | EVQLVESGGGLVKPGGSLRLSCAASGFTFSNYAMSWVRQAPGKGLEWVASISSGG SYNYYPAPVKGRFTISRDDSKNTLYLQMNSLKTEDTAVYYCASQSYGSSYWYFDV WGQGTLVTVSS (SEQ ID NO: 407) |
| 7A3V4-30 | QVQLQESGPGLVKPSQTLSLTCTVSGFTFSNYAMSWIRQPPGKGLEWVASISSGGS YNYYPPSLKSRVTISVDTSKNQFSLKLSSVTAADTAVYYCASQSYGSSYWYFDVW GQGTLVTVSS (SEQ ID NO: 408) |
| Antibody 7E11 | Antibody 7E11 |
| 7E11V4-59 | QVQLQESGPGLVKPSETLSLTCTVSGFSLSNYGVHWIRQPPGKGLEWLGVIWAGG ITNYNPSLKSRVTISVDTSKNQFSLKLSSVTAADTAVYYCAKQGGTSFSYWGQGTL VTVSS (SEQ ID NO: 409) |
| 7E11V3-30 | QVQLVESGGGVVQPGRSLRLSCAASGFSLSNYGVHWVRQAPGKGLEWLGVIWA GGITNYNDSVKGRFTISRDNSKNTLYLQMNSLRAEDTAVYYCAKQGGTSFSYWG QGTLVTVSS (SEQ ID NO: 410) |
| 7E11V3-48 | EVQLVESGGGLVQPGGSLRLSCAASGFSLSNYGVHWVRQAPGKGLEWLGVIWAG GITNYNDSVKGRFTISRDNAKNSLYLQMNSLRAEDTAVYYCAKQGGTSFSYWGQ GTLVTVSS (SEQ ID NO: 411) |
| 7E11V3-7 | EVQLVESGGGLVQPGGSLRLSCAASGFSLSNYGVHWVRQAPGKGLEWLGVIWAG GITNYNDSVKGRFTISRDNAKNSLYLQMNSLRAEDTAVYYCAKQGGTSFSYWGQ GTLVTVSS (SEQ ID NO: 412) |
| 7E11V3-23 | EVQLLESGGGLVQPGGSLRLSCAASGFSLSNYGVHWVRQAPGKGLEWLGVIWAG GITNYNDSVKGRFTISRDNSKNTLYLQMNSLRAEDTAVYYCAKQGGTSFSYWGQ GTLVTVSS (SEQ ID NO: 413) |

TABLE 6B-continued

Humanized heavy chain variable regions

| Antibody variant | Humanized sequences |
|---|---|
| 7E11V5-51 | EVQLVQSGAEVKKPGESLKISCKGSGFSLSNYGVHWVRQMPGKGLEWLGVIWAG GITNYNPSFQGQVTISADKSISTAYLQWSSLKASDTAMYYCAKQGGTSFSYWGQG TLVTVSS (SEQ ID NO: 414) |
| 7E11V1-69 | QVQLVQSGAEVKKPGSSVKVSCKASGFSLSNYGVHWVRQAPGQGLEWLGVIWA GGITNVNQKFQGRVTITADESTSTAYMELSSLRSEDTAVYYCAKQGGTSFSYWGQ GTLVTVSS (SEQ ID NO: 415) |
| 7E11V1-46 | QVQLVQSGAEVKKPGASVKVSCKASGFSLSNYGVHWVRQAPGQGLEWLGVIWA GGITNYNQKFQGRVTMTRDTSTSTVYMELSSLRSEDTAVYYCAKQGGTSFSYWG QGTLVTVSS (SEQ ID NO: 416) |
| 7E11V4-30 | QVQLQESGPGLVKPSQTLSLTCTVSGFSLSNYGVHWIRQPPGKGLEWLGVIWAGG ITNYNPSLKSRVTISVDTSKNQFSLKLSSVTAADTAVYYCAKQGGTSFSYWGQGTL VTVSS (SEQ ID NO: 417) |
| 7E11V4-39 | QLQLQESGPGLVKPSETLSLTCTVSGFSLSNYGVHWIRQPPGKGLEWLGVIWAGG ITNYNPSLKSRVTISVDTSKNQFSLKSSVTAADTAVTTCAKQGGTSFSYWGQGTL VTVSS (SEQ ID NO: 418) |
| Antibody 7F12 | Antibody 7F12 |
| 7F12V1-46 | QVQLVQSGAEVKKPGASVKVSCKASGSEVFPITYMNWVRQAPGQGLEWIGDILP SIGRTMYGQKFQGRVTMTRDTSTSTVYMELSSLRSEDTAVYYCARSEGYLLAYW GQGTLVTVSS (SEQ ID NO: 419) |
| 7F12V3-23 | EVQLLESGGGLVQPGGSLRLSCAASGSEVFPITYMNWVRQAPGKGLEWIGDILPSI GRTMYGDSVKGRFTISRDNSKNTLYLQMNSLRAEDTAVYYCARSEGYLLAYWG QGTLVTVSS (SEQ ID NO: 420) |
| 7F12V1-69 | QVQLVQSGAEVKKPGSSVKVSCKASGSEVFPITYMNWVRQAPGQGLEWIGDILPS IGRTMYGQKFQGRVTITADESTSTAYMELSSERSEDTAVYYCARSEGYLLAYWG QGTLVTVSS (SEQ ID NO: 42]) |
| 7F12V5-51 | EVQLVQSGAEVKKPGESLKISCKGSGSEVFPITYMNWVRQMPGKGLEWIGDILPSI GRTMYGPSFQGQVTISADKSISTAYLQWSSLKASDTAMYYCARSEGYLLAYWGQ GTLVTVSS (SEQ ID NO: 422) |
| 7F12V3-48 | EVQLVESGGGLVQPGGSLRLSCAASGSEVFPITYMNWVRQAPGKGLEWIGDILPSI GRTMYGDSVKGRFTISRDNAKNSLYLQMNSLRAEDTAVYYCARSEGYLLAYWG QGTLVTVSS (SEQ ID NO: 423) |
| 7F12V3-7 | EVQLVESGGGLVQPGGSLRLSCAASGSEVFPITYMNWVRQAPGKGLEWIGDILPSI GRTMYGDSVKGRFTISRDNAKNSLYLQMNSLRAEDTAVYYCARSEGYLLAYWG QGTLVTVSS (SEQ ID NO: 424) |
| 7F12V3-30 | QVQLVESGGGVVQPGRSLRLSCAASGSEVFPITYMNWVRQAPGKGLEWIGDILPS IGRTMYGDSVKGRFTISRDNSKNTLYLQMNSLRAEDTAVYYCARSEGYLLAYWG QGTLVTVSS (SEQ ID NO: 425) |
| 7F12V4-59 | QVQLQESGPGLVKPSETLSLTCTVSGSEVFPITYMNWIRQPPGKGLEWIGDILPSIG RTMYGPSLKSRVTISVDTSKNQFSLKLSSVTAADTAVYYCARSEGYLLAYWGQGT LVTVSS (SEQ ID NO: 426) |
| 7F12V4-39 | QLQLQESGPGLVKPSETLSLTCTVSGSEVFPITYMNWIRQPPGKGLEWIGDILPSIG RTMYGPSLKSRVTISVDTSKNQFSLKLSSVTAADTAVYYCARSEGYLLAYWGQGT LVTVSS (SEQ ID NO: 427) |
| 7F12V4-30 | QVQLQESGPGLVKPSQTLSLTCTVSGSEVFPITYMNWIRQPPGKGLEWIGDILPSIG RTMYGPSLKSRVTISVDTSKNQFSLKLSSVTAADTAVYYCARSEGYLLAYWGQGT LVTVSS (SEQ ID NO: 428) |
| Antibody 10B5 | Antibody 10B5 |
| 10B5V5-51 | EVQLVQSGAEVKKPGESLKISCKGSGYAFTNCWMNWVRQMPGKGLEWIGRIFPG NGHTNYSPSFQGQVTISADKSISTAYLQWSSLKASDTAMYYCARDYSDYYFDYW GQGTLVTVSS (SEQ ID NO: 429) |
| 10B5V1-46 | QVQLVQSGAEVKKPGASVKVSCKASGYAFTNCWMNWVRQAPGQGLEWIGRIFP GNGHTNYSQKFQGRVTMTRDTSTSTVYMELSSLRSEDTAVYYCARDVSDYYFDY WGQGTLVTVSS (SEQ ID NO: 430) |
| 10B5V1-69 | QVQLVQSGAEVKKPGSSVKVSCKASGYAFTNCWMNWVRQAPGQGLEWIGRIFP GNGHTNYSQKFQGRVTITADESTSTAYMELSSERSEDTAVYYCARDYSDYYFDY WGQGTLVTVSS (SEQ ID NO: 431) |

TABLE 6B-continued

| Humanized heavy chain variable regions | |
|---|---|
| Antibody variant | Humanized sequences |
| 10B5V3-23 | EVQLLESGGGLVQPGGSLRLSCAASGYAFTNCWMNWVRQAPGKGLEWIGRIFPG NGHTNYSDSVKGRFTISRDNSKNTLYLQMNSLRAEDTAVYYCARDYSDYYFDYW GQGTLVTVSS (SEQ ID NO: 432) |
| 10B5V3-48 | EVQLVESGGGLVQPGGSLRLSCAASGYAFTNCWMNWVRQAPGKGLEWIGRIFPG NGHTNYSDSVKGRFTISRDNAKNSLYLQMNSLRAEDTAVYYCARDYSDYYFDYW GQGTLVTVSS (SEQ ID NO: 433) |
| 10B5V3-7 | EVQLVESGGGLVQPGGSLRLSCAASGYAFTNCWMNWVRQAPGKGLEWIGRIFPG NGHTNYSDSVKGRFTISRDNAKNSLYLQMNSLRAEDTAVYYCARDYSDYYFDYW GQGTLVTVSS (SEQ ID NO: 434) |
| 10B5V3-30 | QVQLVESGGGVVQPGRSLRLSCAASGYAFTNCWMNWVRQAPGKGLEWIGRIFP GNGHTNYSDSVKGRFTISRDNSKNTLYLQMNSLRAEDTAVYYCARDYSDYYFDY WGQGTLVTVSS (SEQ ID NO: 435) |
| 10B5V4-59 | QVQLQESGPGLVKPSETLSLTCTVSGYAFTNCWMNWIRQPPGKGLEWIGRIFPGN GHTNYSPSLKSRVTISVDTSKNQFSLKLSSVTAADTAVYYCARDYSDYYFDYWGQ GTLVTVSS (SEQ ID NO: 436) |
| 10B5V3-15 | EVQLVESGGGLVKPGGSLRLSCAASGYAFTNCWMNWVRQAPGKGLEWIGRIFPG NGHTNYSAPVKGRFTISRDDSKNTLYLQMNSLKTEDTAVYYCARDYSDYYFDYW GQGTLVTVSS (SEQ ID NO: 437) |
| 10B5V4-39 | QLQLQESGPGLVKPSETLSLTCTVSGYAFTNCWMNWIRQPPGKGLEWIGRIFPGN GHTNYSPSLKSRVTISVDTSKNQFSLKLSSVTAADTAVYYCARDYSDYYVDYWGQ GTLVTVSS (SEQ ID NO: 438) |
| 10B5H1 | QVQLVQSGAEVKKPGASVKVSCKASGYAFTNCWMNWVRQAPGQGLEWMGRIF PGNGHTNYAQKFQGRVTMTRDTSTSTVYMELSSLRSEDTAVYYCARDYSDYYFD YWGQGTLVTVSS (SEQ ID NO: 493) |
| 10B5H2 | QVQLVQSGAEVKKPGASVKVSCKASGYAFTNCWMNWVRQAPGQGLEWIGRIFP GNGHTNYAQKFQGRVTMTEDTSTSTVYMELSSLRSEDTAVYYCARDYSDYYFDY WGQGTLVTVSS (SEQ ID NO: 494) |
| 10B5H3 | QVQLVQSGAEVKKPGASVKISCKASGYAFTNCWMNWVRQAPGQGLEWIGRIFPG NGHTNYAQKFQGRATLTEDTSTSTAYMELSSLRSEDTAVYYCARDYSDYYFDYW GQGTLLTVSS (SEQ ID NO: 495) |
| 10B5H4 | QVQLVQSGAEVKKPGASVKISCKASGYAFTNCWMNWVRQAPGQGLEWIGRIFPG NGHTNYAQKFQGRATLTEDKSTSTAYMELSSLRSEDTAVYYCARDYSDYYFDYW GQGTLLTVSS (SEQ ID NO: 496) |
| Antibody 10G8 | Antibody 10G8 |
| 10G8V3-23 | EVQLLESGGGLVQPGGSLRLSCAASGFTFSTYAMFWVRQAPGKGLEWVASISSGG RYTYYPDSVKGRFTISRDNSKNTLYLQMNSLRAEDTAVYYCVRHSYGSSYWYLD VWGQGTLVTVSS (SEQ ID NO: 439) |
| 10G8V3-48 | EVQLVESGGGLVQPGGSLRLSCAASGFTFSTYAMFWVRQAPGKGLEWVASISSGG RYTYYPDSVKGRFTISRDNAKNSLYLQMNSLRAEDTAVYYCVRHSYGSSYWYLD VWGQGTLVTVSS (SEQ ID NO: 440) |
| 10G8V3-7 | EVQLVESGGGLVQPGGSLRLSCAASGFTFSTYAMFWVRQAPGKGLEWVASISSGG RYTYYPDSVKGRFTISRDNAKNSLYLQMNSLRAEDTAVYYCVRHSYGSSYWYLD VWGQGTLVTVSS (SEQ ID NO: 441) |
| 10G8V3-30 | QVQLVESGGGVVQPGRSLRLSCAASGFTFSTYAMFWVKQAPGKGLEWVASISSG GRYTYYPDSVKGRFTISRDNSKNTLYLQMNSLRAEDTAVYYCVRHSYGSSYWYL DVWGQGTLVTVSS (SEQ ID NO: 442) |
| 10G8V1-46 | QVQLVQSGAEVKKPGASVKVSCKASGFTFSTYAMFWVRQAPGQGLEWVASISSG GRYTYYPQKFQGRVTMTRDTSTSTVYMELSSLRSEDTAVYYCVRHSYGSSYWYL DVWGQGTLVTVSS (SEQ ID NO: 443) |
| 10G8V1-69 | QVQLVQSGAEVKKPGSSVKVSCKASGFTFSTYAMFWVRQAPGQGLEWVASISSG GRYTYYPQKFQGRVTITADESTSTAYMELSSLRSEDTAVYYCVRHSYGSSYWYLD VWGQGTLVTVSS (SEQ ID NO: 444) |
| 10G8V5-51 | EVQLVQSGAEVKKPGESLKISCKGSGFTFSTYAMFWVRQMPGKGLEWVASISSGG RYTYYPPSFQGQVTISADKSISTAYLQWSSLKASDTAMYYCVRHSYGSSYWYLDV WGQGTLVTVSS (SEQ ID NO: 445) |

TABLE 6B-continued

Humanized heavy chain variable regions

| Antibody variant | Humanized sequences |
|---|---|
| 10G8V4-59 | QVQLQESGPGLVKPSETLSLTCTVSGFTFSTYAMFWIRQPPGKGLEWVASISSGGR YTYYPPSLKSRVTISVDTSKNQFSLKLSSVTAADTAVYYCVRHSYGSSYWLDVW GQGTLVTVSS (SEQ ID NO: 446) |
| 10G8V3-15 | EVQLVESGGGLVKPGGSLRLSCAASGFTFSTYAMFWVRQAPGKGLEWVASISSGG RYTYYPAPVKGRFTISRDDSKNTLYLQMNSLKTEDTAVYYCVRHSYGSSYWYLD VWGQGTLVTVSS (SEQ ID NO: 447) |
| 10G8V4-39 | QLQLQESGPGLVKPSETLSLTCTVSGFTFSTYAMFWIRQPPGKGLEWVASISSGGR YTYYPPSLKSRVTISVDTSKNQFSLKLSSVTAADTAVYYCVRHSYGSSYWYLDVW GGGTLVTVSS (SEQ ID NO: 448) |

Humanization of Antibody 4E3

The heavy chain variable region (VH) and light chain variable region (VL) sequences of murine anti-Siglec-7 antibody 4E3 (S7-4E3) were used as input to the IgBLAST program on the NCBI website (Ye, J, et al. Nucleic Acids Research 41:W34-W40 (2013)). IgBLAST takes a murine VH or VL sequence and compares it to a library of known human germline sequences. The databases used were IMGT human VH genes (F+ORF, 273 germline sequences) and IMGT human VLkappa genes (F+ORF, 74 germline sequences). For the 4E3 antibody VL, human germline IGKV3-11 (allele 1) was chosen as the acceptor sequence and human light chain IGKJ2 (allele 1) joining region (J gene) was chosen from human joining region sequences compiled at IMGT® the international ImMunoGeneTics information System®, (FIG. 6B). For the 4E3 antibody VH, human germline IGHV3-21 (allele 1) was chosen as the acceptor sequence and the human heavy chain IGHJ4 (allele 1) joining region (J gene) was chosen from human joining region sequences compiled at IMGT® the international ImMmuoGeneTics information System® (FIG. 6C). Complementarity determining regions (CDRs) for the antibody VL and VH were defined according to the AbM definition (AbM antibody modeling software).

Alteration of human germline framework (i.e., non-CDR residues in the VH and $V_L$) positions to corresponding parental murine sequences may be required to optimize binding of the humanized antibody. Potential changes for each humanized sequence are noted in FIGS. 6B and 6C.

FIGS. 6B and 6C show sequences of humanized versions of anti-Siglec-7 antibody 4E3. In the VL domain of antibody 4E3, Asp26 within the CDR-L1 and Asn52 within the CDR-L2 have low potential for deamidation based on sequence and conformation and may show a low level of this post-translational modification (FIG. 6B). Trp90 within the CDR-L3 of antibody 4E3 appears to be solvent-exposed and may show a low level of oxidation, more so under stress conditions (FIG. 6B). Variant VL sequences based on the above are listed in Table 6A.

In the VH domain of antibody 4E3, Asn31 within the CDR-H1 and Asn103 within the CDR-H3 have a low potential for deamidation based on sequence and conformation but could show a low level of this post-translational modification (FIG. 6C). Trp106 within the CDR-H3 appears to be solvent-exposed and may show a low level of oxidation, more so under stress conditions (FIG. 6C). Variant VH sequences based on the above are listed in Table 6B.

Humanization of Antibody 10B5

The heavy chain variable region (VH) and light chain variable region (VL) sequences of murine anti-Siglec-7 antibody 10B5 (S7-10B5) were used as input to the IgBLAST program on the NCBI website (Ye, J, et al. Nucleic Acids Research 41:W34-W40 (2013)). IgBLAST takes a murine VH or VL sequence and compares it to a library of known human germline sequences. The databases used were IMGT human VH genes (F+ORF, 273 germline sequences) and IMGT human VLkappa genes (F+ORF, 74 germline sequences). For the 10B5 antibody VL, human germline IGKV1-39 (allele 1) was chosen as the acceptor sequence and human light chain IGKJ2 (allele 1) joining region (J gene) was chosen from human joining region sequences compiled at IMGT® the international ImMuno-GeneTics information System® (FIG. 6D). For the 10B5 antibody VH, human germline IGHV1-46 (allele 1) was chosen as the acceptor sequence and the human heavy chain IGHJ4 (allele 1) joining region (J gene) was chosen from human joining region sequences compiled at IMGT® the international ImMunoGeneTics information System® (FIG. 6E). Complementarity determining regions (CDRs) for the antibody $V_L$ and VH were defined according to the AbM definition (AbM antibody modeling software).

Alteration of human germline framework (i.e., non-CDR residues in the VH and VL) positions to corresponding parental murine sequences may be required to optimize binding of the humanized antibody. Potential changes for each humanized sequence are noted in FIGS. 6D and 6E.

FIGS. 6D and 6E show sequences of humanized versions of anti-Siglec-7 antibody 10B5. In the VL domain of antibody 10B5, Asp30 within the CDR-L1 and Asn92 within the CDR-L3 have low to medium potential for deamidation based on sequence and conformation and may show a low level of this post-translational modification (FIG. 6D). Trp33 within the CDR-L1 of antibody 10B5 appears to be solvent-exposed and may show a low level of oxidation, more so under stress conditions (FIG. 6D). There is also a free Cys within the CDR-LI that is likely to be solvent-exposed, and which may be altered to a Ser to evaluate its effect on binding. Variant VL sequences based on the above are listed in Table 6A.

In the VH domain of antibody 10B5, Asp54-Gly55 within the CDR-H2 has a medium potential for deamidation followed by isoaspartate formation (FIG. 6E). Post-translational modification at this site may affect binding of the antibody to target. The parental mouse antibody may be analyzed to determine the level of post-translational modification. Alternatively, antibody 10B5 can be humanized and then in a final step the NG may be modified to, for example QG, to determine if binding is maintained. Asn31 within the CDR-H and Asn58 within the CDR-H2 have a low potential for deamidation based on sequence and conformation but could show a low level of this post-translational modification (FIG. 6E). Modifications to the CDRs may be made after humanization, such as by analyzing the Asn54-Gly55 within the CDR-H2 and altering the Cys32Ser within the CDR-H1 (FIG. 6E). Variant VH sequences based on the above are listed in Table 6B.

Example 2: Epitope Mapping of Siglec-7 Antibodies

Siglec-7 antibodies were tested for their ability to bind 15 or 25-mer peptides spanning the entire human Siglec-7. The Siglec-7 antibodies were also compared to a reference Siglec-7 antibody by determining their Siglec-7 binding region.

Methodology

Linear 15-mer peptides were synthesized based on the sequence of human Siglec-7 (SEQ ID NO: 1), with a 14 residue overlap. In addition, linear 25-mer peptides were synthesized based on sequence of human Siglec-7 (SEQ ID NO: 1) with a single residue shift. The binding of Siglec-7 antibodies to each of the synthesized peptides was tested in an ELISA based method. In this assay, the peptide arrays were incubated with primary antibody solution (overnight at 4° C.). After washing, the peptide arrays were incubated with a 1/1000 dilution of an antibody peroxidase conjugate (SBA, cat. nr. 2010-05) for one hour at 25° C. After washing, the peroxidase substrate 2,2'-azino-di-3-ethylbenzthiazoline sulfonate (ABTS) and 2 µl/ml of 3% $H_2O_2$ were added. After one hour, the color development was measured. The color development was quantified with a charge coupled device (CCD) camera and an image processing system.

Epitope binning of the antibodies was performed on a Forte Bio Octet Red384 system (Pall Forte Bio Corporation, Menlo Park, Calif.) using a standard sandwich format binning assay (see Estep et al. (2013) *MAbs* 5(2):270-8). Control anti-target IgG was loaded onto AHQ sensors and unoccupied Fc-binding sites on the sensor were blocked with a non-relevant human IgG1 antibody. The sensors were then exposed to 100 nM target antigen followed by a second anti-target antibody. Data was processed using ForteBio's Data Analysis Software 7.0. Additional binding by the second antibody after antigen association indicates an unoccupied epitope (non-competitor), while no binding indicates epitope blocking (competitor).

Alternatively, to reconstruct epitopes of the target molecule, libraries of looped and combinatorial peptides were synthesized. An amino functionalized polypropylene support was obtained by grafting with a proprietary hydrophilic polymer formulation, followed by reaction with t-butyloxy-carbonyl-hexamethylenediamine (BocHMDA) using dicyclohexylcarbodiimide (DCC) with N-hydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer).

Synthesis of structural mimics was done using Pepscan's proprietary Chemically Linked Peptides on Scaffolds (CLIPS) technology. CLIPS technology allows to structure peptides into single loops and double-loops. CLIPS templates are coupled to cysteine residues. The side-chains of multiple cysteines in the peptides are coupled to one or two CLIPS templates. For example, a 0.5 mM solution of the mP2 CLIPS (2,6-bis(bromomethyl)pyridine) is dissolved in ammonium bicarbonate (20 mM, pH7.8)/acetonitrile (1:3(v/v)). This solution is added onto the peptide arrays. The CLIPS template will bind to side-chains of two cysteines as present in the solid-phase bound peptides of the peptide-arrays (455 wells plate with 3 µl wells). The peptide arrays are gently shaken in the solution for 30 to 60 minutes while completely covered in solution. Finally, the peptide arrays are washed extensively with excess of $H_2O$ and sonicated in disrupt-buffer containing 1% SDS/0.1% β-mercaptoethanol in PBS (pH7.2) at 70° C. for 30 minutes, followed by sonication in $H_2O$ for another 45 minutes. The T3 CLIPS (2,4,6-tris(bromomethyl)pyridine) carrying peptides were made in a similar way but now with three cysteines.

Looped peptides: constrained peptides of length 17. Positions 2-16 are 15-mers derived from the target sequence. Native Cys residues are protected by acetamidomethyl group (ACM). Positions 1 and 17 are Cys that are linked by mP2 CLIPS moieties. Combinatorial peptides (discontinuous mimics): constrained peptides of length 33. Positions 2-16 and 18-32 are 15-mer peptides derived from the target sequence with native Cys residues protected by ACM. Positions 1, 17 and 33 are Cys that are linked by T3 CLIPS moieties.

The binding of antibody to each of the synthesized peptides is tested in a PEPSCAN-based ELISA. The peptide arrays are incubated with test antibody solution composed of the experimentally optimized concentration of the test antibody and blocking solution (for example 4% horse serum, 5% ovalbumin (w/v) in PBS/1% Tween80). The peptide arrays are incubated with the test antibody solution overnight at 4° C. After extensive washing with washing buffer (1×PBS, 0.05% Tween80), the peptide arrays are incubated with a 1/1000 dilution of an appropriate antibody peroxidase conjugate for one hour at 25° C. After washing with the washing buffer, the peroxidase substrate 2,2'-azino-di-3-ethylbenzthiazoline sulfonate (ABTS) and 2 µl/ml of 3% $H_2O_2$ are added. After one hour, the color development is measured. The color development is quantified with a charge coupled device (CCD)—camera and an image processing system.

Alternatively a mass spectrometry method is used to identify conformational epitopes. In order to determine the key residues of conformational epitopes on the Siglec 7 protein that anti-Siglec 7 antibodies bind to, with high resolution, antibody/antigen complexes are incubated with deuterated cross-linkers and subjected to multi-enzymatic proteolytic cleavage. After enrichment of the cross-linked peptides, the samples are analyzed by high resolution mass spectrometry (nLC-Orbitrap MS) and the data generated is analyzed using XQuest software. Specifically, Siglec 7 ECD/antibody complexes are generated by mixing equimolar solutions of Siglec-7 antigen and antibody (4 µM in 5 µl each). One µl of the mixture obtained is mixed with 1 µl of a matrix composed of a re-crystallized sinapinic acid matrix (10 mg/ml) in acetonitrile/water (1:1, v/v), TFA 0.1% (K200 MALDI Kit). After mixing, 1 µl of each sample is spotted on a MALDI plate (SCOUT 384). After crystallization at room temperature, the plate is introduced in a MALDI mass spectrometer and analyzed immediately. The analysis is repeated in triplicate. Peaks representing monomeric antibody, the antigen, and antibody and antigen/antibody complexes are detected at the predicted molecular weights.

It is then determined whether the epitope in conformational binding competes with unstructured C1 q peptides generated by proteolysis. Specifically, to determine if Siglec-7 ECD/antibody complexes can compete with linear peptides, the Siglec-7 ECD antigen is digested with immobilized pepsin. 25 µl of the antigen with a concentration of 10 µM are mixed with immobilized pepsin 5 µM and incubate at room temperature for 30 minutes. After the incubation time, the samples are centrifuged and the supernatant is pipetted. The completion of the proteolysis is controlled by High-Mass MALDI mass spectrometry in linear mode. The pepsin proteolysis is optimized in order to obtain a large amount of peptide in the 1000-3500 Da range. Next, 5 µl of the antigen peptides generated by proteolysis are mixed with 5 µl of antibodies (8 µM) and incubated at 37° C. for 6 hours. After incubation of the antibodies with the Siglec-7 antigen peptides, 5 µl of the mixture is mixed with 5 µl of the intact Siglec-7 antigen (4 µM) so the final mix contains 2 µM/2 µM/2.5 µM of Siglec-7/antibody/Siglec-7antigen peptides. The MALDI ToF MS analysis is performed using CovalX's HM3 interaction module with a standard nitrogen laser and focusing on different mass ranges from 0 to 2000 kDa. For the analysis, the following parameters are applied for the mass spectrometer: Linear and Positive mode; Ion Source 1: 20 kV; Ion Source 2: 17 kV; Pulse Ion Extraction: 400 ns; for HM3: Gain Voltage: 3.14 kV: Gain Voltage: 3.14 kV: Acceleration Voltage: 20 kV. To calibrate the instrument, an external calibration with clusters of Insulin, BSA and IgG is being applied. For each sample, 3 spots are analyzed (300 laser shots per spots). Presented spectrum corresponds to the sum of 300 laser shots. The MS data are analyzed using the Complex Tracker analysis software version 2.0 (CovalX Inc). To identify the conformational epitopes for Siglec-7 binding to antibodies, using chemical cross-linking, High-Mass MALDI mass spectrometry and nLCOrbitrap mass spectrometry the interaction interface between the antigen and antibodies the following procedure is followed. 5 µl of the sample antigen (concentration 4 µM) is mixed with 5 µl of the sample antibody (Concentration 4 µM) in order to obtain an antibody/antigen mix with final concentration 2 µM/2 µM. The mixture is incubated at 37° C. for 180 minutes. In a first step, 1 mg of DiSuccinimidylSuberate H12 (DSS-H12) cross-linker is mixed with 1 mg of DiSuccinimidylSuberate D12 (DSS-D12) cross-linker. The 2 mg prepared were mixed with 1 ml of DMF in order to obtain a 2 mg/ml solution of DSS H12/D12. 10 µl of the antibody/antigen mix prepared previously were mixed with 1 µl of the solution of cross-linker d0/d12 prepared (2 mg/ml). The solution is incubated 180 minutes at room temperature in order to achieve the cross-linking reaction.

In order to facilitate the proteolysis, it is necessary to reduce the disulfide bonds present in the protein. The cross-linked samples are mixed with 20 µl of ammonium bicarbonate (25 mM, pH 8.3). After mixing 2.5 µl of DTT (500 mM) is added to the solution. The mixture is then incubated 1 hour at 55° C. After incubation, 2.5 µl of iodioacetamide (1 M) is added before 1 hour of incubation at room temperature in a dark room. After incubation, the solution is diluted 1/5 by adding 120 µl of the buffer used for the proteolysis. 145 µl of the reduced/alkyled cross-linked sample is mixed with 2 µl of trypsin (Sigma. T6567). The proteolytic mixture is incubated overnight at 37° C. For a-chymotrypsin proteolysis, the buffer of proteolysis is Tris-HCL 100 mM, CaCl2 10 mM, pH7.8. The 145 µl of the reduced/alkyled cross-linked complex is mixed with 2 µl of α-chymorypsin 200 µM and incubated overnight at 30° C. For this analysis, an nLC in combination with Orbitrap mass spectrometry is used. The cross-linker peptides are analyzed using Xquest version 2.0 and stavrox software. The peptides and cross-linked amino acids are then identified.

Results

The Siglec-7 binding region was determined for 4 anti-Siglec-7 antibodies. The binding region is listed in Table 7A.

FIG. 1B-1E show a schematic representation of human Siglec-7, indicating the regions bound by anti-Siglec-7 antibodies.

TABLE 7A

Siglec-7 antibody binding region

| Antibody | Siglec-7 binding region | Amino acid region of SEQ ID: 1 |
|---|---|---|
| 1A12 4D7 | $^{111}$RDARMSDAGRYF$^{122}$ and $^{282}$PPARLSWTWR$^{291}$ | 111-122 and 282-291 |
| 1A12 1E8 2G1 4D7 | $^{113}$ARMSDAGRYFF$^{123}$ | 113-123 |
| 4A1 | $^{113}$ARMSDAGRYFFRM$^{125}$ | 113-125 |
| 7E11 | $^{68}$AGNDISWKAPV$^{78}$ | 68-78 |
| 10G8 | $^{60}$PVHGYWFRAG$^{69}$ and $^{84}$AWAVQEETRDRF$^{95}$ | 60-69 and 84-95 |
| 2G4 3E11 10B5 2G1 7F12 | $^{60}$PVHGYWFRAG$^{69}$ and $^{117}$DAGRYFFRMEK$^{127}$ | 60-69 and 117-127 |

As indicated in Table 7A, antibodies 1A12 and 4D7 showed robust binding exclusively for peptides within two extracellular domains (including the IgV domain and the second Ig-like C2-type domain) of Siglec-7. As indicated in Table 7A, the peptides recognized by antibodies 1A12 and 4D7 correspond to amino acid residues 111-122 and 282-291 of SEQ ID NO: 1 and have the amino acid sequences of: RDARMSDAGRYF and PPARLSWTWR.

As further indicated in Table 7A, antibodies1A12, 1E8, 2G11, 4D7, 4A1, 7E11, 10G8, 2G4, 3E11, 10B5, 2G11, and 7F12 showed robust binding exclusively for a peptide within the extracellular domain (including the IgV domain) of Siglec-7. As indicated in Table 7A, the peptide recognized by antibodies 1A12, 1E8, 2G11, and 4D7 corresponds to amino acid residues 113-123 of SEQ ID NO: 1 and has the amino acid sequence of: ARMSDAGRYFF. The peptide recognized by antibody 4A1 corresponds to amino acid residues 113-125 of SEQ ID NO: 1 and has the amino acid sequence of: ARMSDAGRYFFRM. The peptide recognized by antibody 7E11 corresponds to amino acid residues 68-78 of SEQ ID NO: 1 and has the amino acid sequence of: AGNDISWKAPV. The peptides recognized by antibody 10G8 correspond to amino acid residues 60-69 and 84-95 of SEQ ID NO: 1 and have the amino acid sequences of: PVHGYWFRAG and AWAVQEETRDRF. The peptides recognized by antibodies 2G4, 3E11, 10B5, 2G1, and 7F12 correspond to amino acid residues 60-69 and 117-127 of SEQ ID NO: 1 and have the amino acid sequences of: PVHGYWFRAG and DAGRYFFRMEK.

Figure 1D:
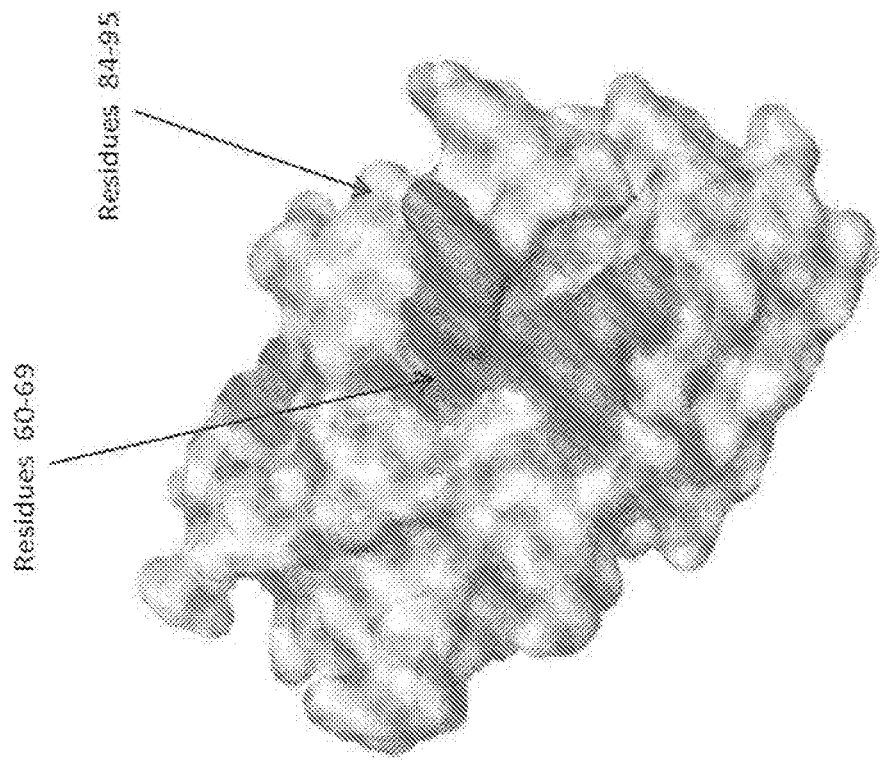
FIG. 1D depicts a cartoon rendering of binding sites of a discontinuous epitope for antibody 10G8 antibodies 2G4, 3E11, 10B5, 2G11, and 7F12. The discontinuous binding regions $^{60}$PVHGYWFRAG$^{69}$ (SEQ ID NO: 1) and $^{84}$AWAVQEETRDRF$^{95}$ (SEQ ID NO: 1) are listed in the figure.
Figure 1C:
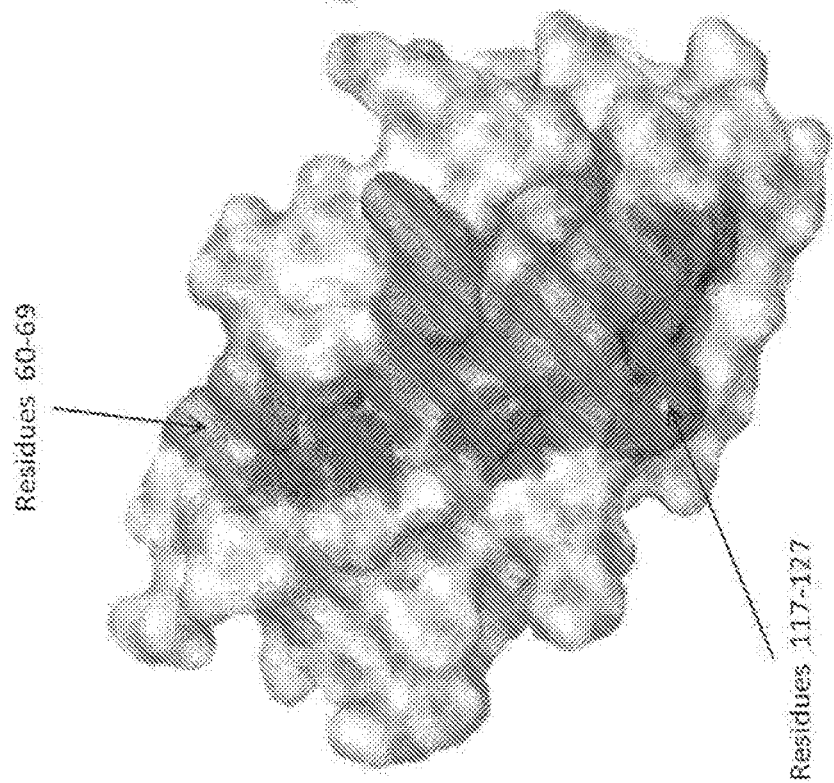
FIG. 1C depicts a cartoon rendering of binding sites of a discontinuous epitope for antibodies 2G4, 3E11, 10B5, 2G11, and 7F12. The discontinuous binding regions $^{60}$PVHGYWFRAG$^{69}$ (SEQ ID NO: 1) and $^{117}$DAGRYFFRMEK$^{127}$ (SEQ ID NO: 1) are listed in the figure.
Figure 1E:
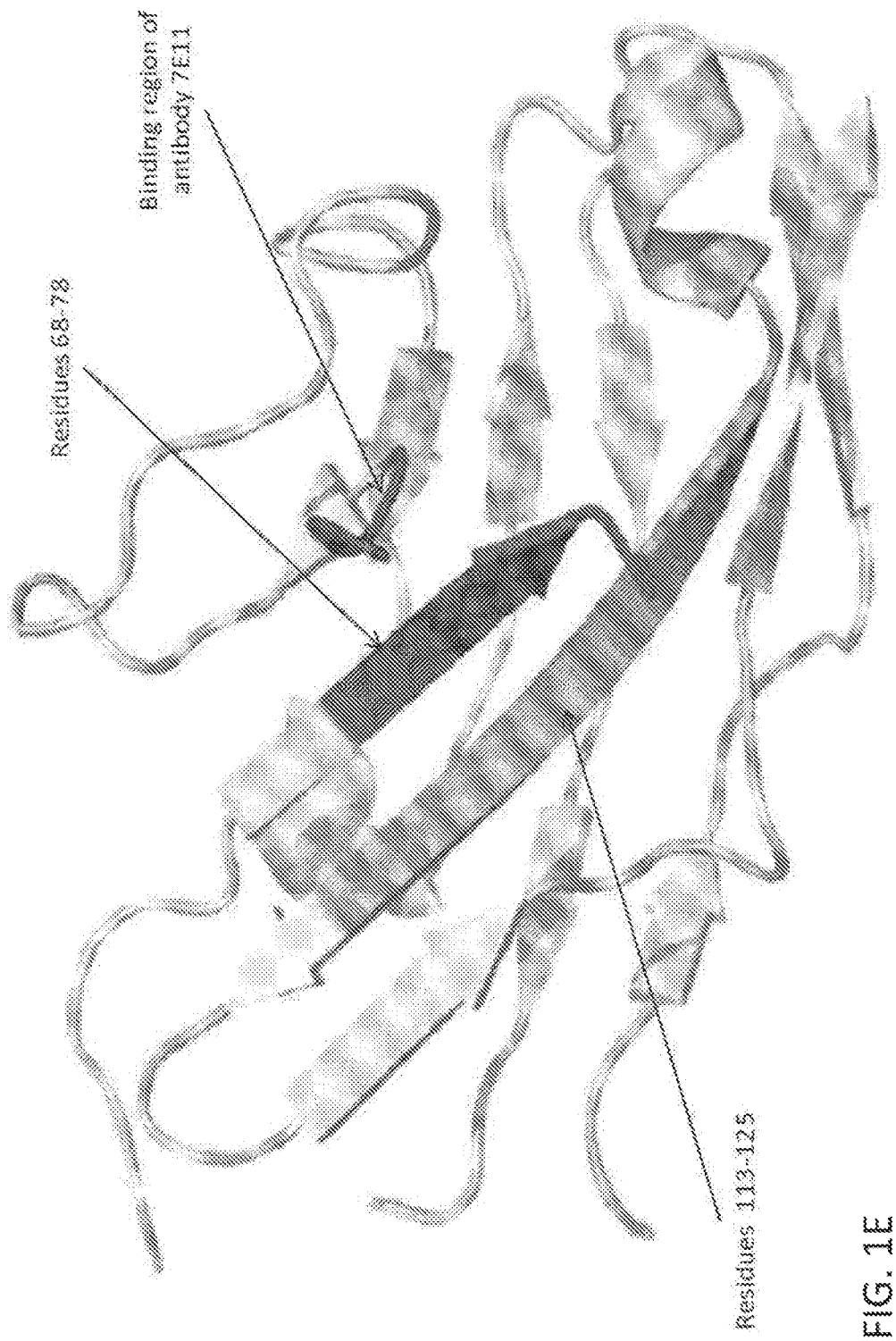
FIG. 1E depicts a cartoon rendering of an epitope for antibody 4A1. The binding region $^{113}$ARMS-DAGRYFFRM$^{125}$ (SEQ ID NO: 1) is listed in the figure. Binding sites of a conformational epitope for antibody 7E11 is also depicted. The binding regions $^{68}$AGNDISWKAPV$^{78}$ (SEQ ID NO: 1) is listed in the figure.
Figure 1G:
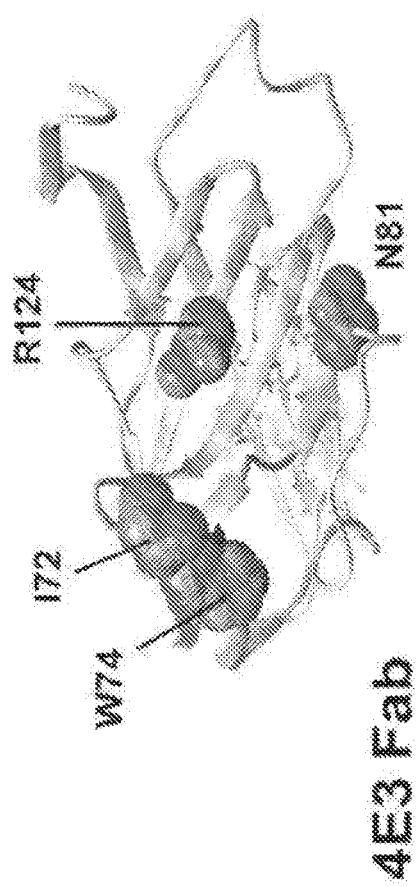
FIG. 1G depicts models of Siglec-7 indicating amino acid residues involved in antibody binding. Critical residues for binding are indicated with red spheres, secondary residues for binding are indicated with pink spheres.
Figure 1G:
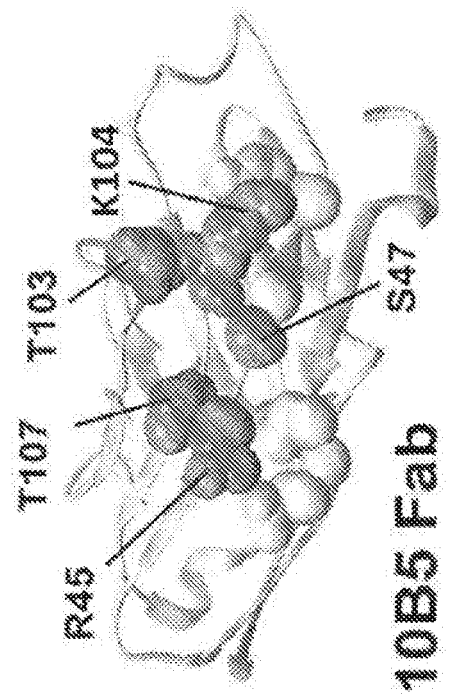
Figure 1G:
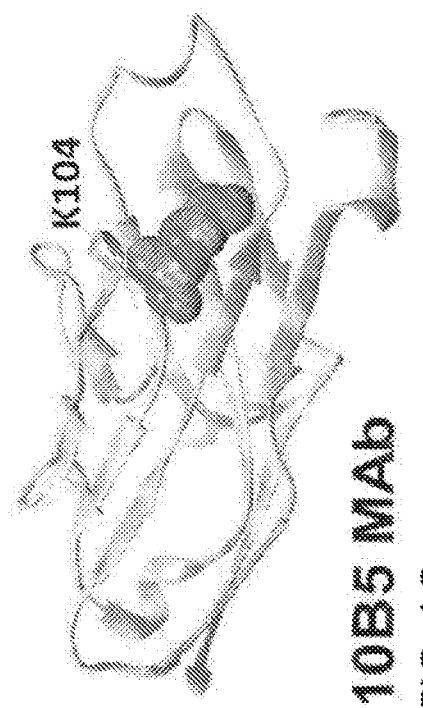

The Siglec-7 peptides bound by antibodies 4A1, 10G8, 2G4, 3E11, 10B5, 2G1, 7F12, and 7E11 are depicted in FIG. 1B-1E. The discontinuous peptides recognized by antibody 4A1 are shown in FIGS. 1B and 1E. The discontinuous peptides recognized by antibodies 2G4, 3E11, 10B5, 2G1, and 7F12 are depicted in FIG. 1C. The peptides recognized by antibody 10G8 is depicted in FIG. 1D. FIG. 1E depicts putative binding sites of a conformational epitope of Siglec-7 bound by antibody 7E11. The putative epitope includes a binding region that corresponds to amino acid residues 68-78 of SEQ ID NO: 1 and has the amino acid sequence of: AGNDISWKAPV.

Functional Mapping

Shotgun mutagenesis epitope mapping of anti-siglec-7 antibodies was performed using an alanine-scanning library for the siglec-7 protein. A siglec-7 expression construct (Uniprot id Q9Y286) encoding a C-terminal V5 epitope tag was subjected to high-throughput alanine scanning mutagenesis (outlined in Davidson and Doranz, 2014 Immunology 143, 13-20) to generate a comprehensive mutation library. Each of residues 19 to 353 was mutated, representing the siglec-7 extracellular domain, most to alanine, while alanine codons were mutated to serine. In total, 335 siglec-7 mutant expression constructs were generated, sequences confirmed, and arrayed into a 384-well plate, one mutant per well.

The siglec-7 mutation library clones, arrayed in a 384-well microplate, were transfected individually into HEK-293T cells and allowed to express for 22 hours. Cells were then incubated with MAbs diluted in 10% normal goat serum (NGS) (Sigma-Aldrich, St. Louis, Mo.). Prior to library screening, primary MAb concentrations were determined using an independent immunofluorescence titration curve against cells expressing wild-type siglec-7 to ensure that signals were within the linear range of detection. MAbs were detected using 3.75 µg/ml AlexaFluor488-conjugated secondary antibody (Jackson immunoResearch Laboratories, Westgrove, Pa.) in 10% NGS. Cells were washed twice with PBS-/- and resuspended in Cellstripper (Cellgro, Manassas, Va.) with 0.1% BSA (Sigma-Aldrich, St. Louis, Mo.). Mean cellular fluorescence was detected using the Intellicyt high throughput flow cytometer (HTFC, Intellicyt, Albuquerque, N. Mex.). MAb reactivities against each mutant clone were calculated relative to wild-type siglec-7 protein reactivity by subtracting the signal from mock-transfected controls, and normalizing to the signal from wild-type siglec-7-transfected controls.

Mutated residues within critical clones were identified as critical to the MAb epitope if they did not support reactivity of the test MAb but did support reactivity of commercially available reference MAbs 6-434 or S7.7 (Biolegend, Cat #:339202, 347702), or additional anti-siglec-7 MAbs. This counter-screen strategy facilitated the exclusion of siglec-7 mutants that were locally misfolded or that had an expression defect.

FIG. 1F depicts the mean binding reactivities and ranges for all critical residues identified in the screens. The range was the difference between the duplicate experimental binding values. Primary critical residues were identified as residues where mutations were negative for test antibody binding (<30% of binding to WT) but positive for the control antibody (>80% WT). FIG. 1G depicts a crystal structure model of the IgV domain of Siglec-7 (PDB ID 1O7V; Alphey et al., 2003) indicating the critical residues as red spheres and secondary residues as pink spheres for each antibody tested. The amino acid residues critical for antibody binding, as well as the secondary residues, are listed in Table 7B.

TABLE 7B

| Residues involved in anti-Siglec-7 antibody binding | | |
|---|---|---|
| Antibody | Critical Siglec-7 residues | Secondary Siglec-7 residues |
| 4E3 Fab | $I_{72}$; $W_{74}$; $N_{81}$; and $R_{124}$ | |
| 10B5 MAb | $K_{104}$ | |
| 10B5 Fab | $R_{45}$; $S_{47}$; $T_{103}$; $K_{104}$; and $T_{107}$ | $M_{30}$; $Q_{31}$; $V_{44}$; $F_{48}$; and $Y_{50}$ |

As indicated in Table 7B, the critical Siglec-7 residues involved in binding by antibody 4E3 corresponded to amino acid residues $I_{72}$, $W_{74}$, $N_{81}$, and $R_{124}$ of SEQ ID NO: 1. The critical Siglec-7 residues involved in binding by antibody 10B5 corresponded to amino acid residues $R_{45}$, $S_{47}$, $T_{103}$, $K_{104}$, and $T_{107}$ of SEQ ID NO: 1; and the secondary residues involved in binding by antibody 10B5 corresponded to amino acid residues $M_{30}$, $Q_{31}$, $V_{44}$, $F_{48}$, and $Y_{50}$ of SEQ ID NO: 1.

Example 3: Siglec-7 Antibody-Induced Decrease in Cell Surface Levels of Siglec-7 In Vitro and In Vivo In Vitro Expression of Siglec-7

The purpose of the following Example was to test whether anti-Siglec-7 and/or Siglec-7 bispecific antibodies reduce the cell surface level of Siglec-7 on monocytes, macrophages, neutrophils, NK cells, dendritic cells, T cells, and/or microglia.

The ability of anti-Siglec-7 antibodies to reduce cell surface levels of Siglec-7 on the histiocytic lymphoma cell line U937, as well as human primary monocytes, human primary dendritic cells (DC) derived from peripheral blood monocytes, human primary macrophages and NK cells derived from peripheral blood monocytes, and human primary microglia was evaluated. Cell samples were plated in 24-well plates at 200,000 cells per ml or in 6-well dishes at 500,000 cells in 2 ml of RPMI supplemented with 10% Hyclone FBS, 2 mM glutamine, penstrep, and non-essential amino acids, Siglec-7 antibodies or control isotypes were added at 1.0 μg/ml, and incubated for 24 hours at 37° C. with 5% $CO_2$.

To assess receptor dynamics, antibodies were allowed to bind cells for one hour, washed out and surface levels of Siglec-7 were determined 24 and 48 hours later.

Cell surface receptor expression was detected by FACS analysis. Cells were incubated with anti-Siglec-7-PE clone 6-434 (Biolegend), as well as a control surface marker (U937; Siglec-5, human monocytes: CD14, human dendritic cells: CD11c, human macrophages: CD11b, human NK cells: CD56) for 30 minutes on ice in the dark. Cells were washed 2× in FACS buffer (PBS+2% FBS, 2 mM EDTA) and flow cytometry was performed on a BD FACS Canto. Data was analyzed using TreeStar FlowJo software. Data was calculated as a percent of receptor expression in the absence of antibody using MFI values for the respective fluorophores.

Table 8A and 8B depict the results of Siglec-7 cell surface levels from human cells. In Table 8A and 8B, “No Ab” refers to cells that were that were not treated with an antibody; “mIgG1,” “mIgG2a,” and “mIgG2b” refer to isotype control antibodies; and “RDS7” refers commercially available anti-Siglec-7 antibody Mab1138 (R&D Systems; Cat. No. MAB 1138).

TABLE 8A

Siglec-7 antibodies reduce cell surface level of Siglec-7
in a human cell line and in human primary cells

| | Percent Siglec-7 Surface Expression | | | | | |
|---|---|---|---|---|---|---|
| | U937 cells | | Monocytes | | DCs | |
| Ab | % Siglec-7 | % control | % Siglec-7 | % control | % Siglec-7 | % control |
| 1A12 | 87.3 | 136.8 | 39.9 | 93.4 | 100.5 | 95.7 |
| 1E8 | 114.0 | 134.2 | 36.7 | 94.1 | 23.0 | 97.0 |
| 2G1 | 121.4 | 129.5 | 139.5 | 98.6 | 1104 | 102.2 |
| 2G4 | 84.6 | 136.2 | 29.3 | 95.1 | 98.1 | 96.2 |
| 3E11 | 82.4 | 128.1 | 23.9 | 89.0 | 19.9 | 97.6 |
| 4A1 | 89.5 | 131.9 | 39.8 | 90.4 | 99.6 | 95.1 |
| 4D7 | 84.7 | 119.0 | 33.9 | 83.5 | 73.3 | 106.5 |
| 4E3 | 30.8 | 94.0 | 15.1 | 87.8 | 11.2 | 96.9 |
| 7A3 | 76.3 | 136.3 | 23.7 | 69.7 | 11.0 | 119.3 |
| 7E11 | 75.2 | 127.1 | 8.1 | 77.4 | 19.3 | 103.9 |
| 7F12 | 86.3 | 124.4 | 39.0 | 88.4 | 96.9 | 91.5 |
| 10B5 | 36.5 | 122.6 | 6.7 | 75.3 | 16.8 | 112.1 |
| 10G8 | 83.8 | 133.4 | 30.9 | 70.1 | 10.5 | 121.4 |
| No Ab | 100 | 100 | 100 | 100 | 100 | 100 |
| mIgG1 | 101.8 | 100.4 | 96.2 | 93.9 | 100.8 | 97.7 |
| mIgG2a | 99.8 | 100.4 | 99.4 | 93.3 | 100.5 | 97.4 |
| mIgGb | 99.3 | 99.0 | 96.2 | 94.9 | 100.1 | 95.1 |
| RDS7 | 98.2 | 96.0 | 99.6 | 81.3 | 96.7 | 105.9 |

TABLE 8B

Siglec-7 antibodies reduce cell surface level of Siglec-7
in human primary cells

| | Percent Siglec-7 Surface Expression | | | | | |
|---|---|---|---|---|---|---|
| | Macrophages | | NK cells | | Microglia | |
| Ab | % Siglec-7 | % control | % Siglec-7 | % control | % Siglec-7 | % control |
| 1A12 | 13.4 | 103.6 | 136.5 | 99.6 | 28.6 | 88.6 |
| 1E8 | 9.1 | 88.8 | 143.6 | 98.5 | 41.3 | 71.1 |
| 2G1 | 95.7 | 92.3 | 113.9 | 98.8 | 106.2 | 82.6 |
| 2G-4, | 14.1 | 96.2 | 126.1 | 101.5 | 23.0 | 81.9 |
| 3E11 | 7.4 | 85.7 | 107.9 | 101.6 | 34.2 | 82.1 |
| 4A1 | 13.1 | 96.0 | 132.4 | 98.8 | 26.3 | 85.8 |
| 4D7 | 24.1 | 74.8 | 87.6 | 101.2 | 44.3 | 84.1 |
| 4E3 | 4.2 | 78.3 | 31.2 | 100.8 | 20.9 | 92.7 |
| 7A3 | 8.3 | 85.0 | 77.1 | 102.1 | ND | ND |
| 7E11 | 5.7 | 83.9 | 50.7 | 101.6 | 11.5 | 74.1 |
| 7F12 | 13.1 | 93.0 | 124.1 | 98.5 | 28.1 | 78.8 |
| 10B5 | 3.2 | 84.0 | 25.5 | 101.9 | 5.5 | 72.1 |
| 10G8 | 9.2 | 84.0 | 74.7 | 103.7 | ND | ND |
| No Ab | 100 | 100 | 100 | 100 | 100 | 100 |
| mIgG1 | 100.0 | 90.9 | 99.6 | 98.4 | 88.7 | 76.8 |
| mIgG2a | 100.0 | 96.0 | 100.9 | 99.2 | 84.2 | 85.2 |
| mIgG2b | 100.3 | 89.9 | 101.3 | 99.6 | 88.8 | 83.6 |
| RDS7 | 98.7 | 90.4 | 102.6 | 100.4 | 80.2 | 74.6 |

As shown in Table 8A and 8B, a majority of the antibodies were able to decrease cell surface levels of Siglec-7 on multiple types of human cells. However, using a threshold value of 80% or higher cell surface expression levels of Siglec-7, it was found that antibody 2G1 does not decrease cell surface levels of Siglec-7 on any of the tested human cells.

Figure 7A:
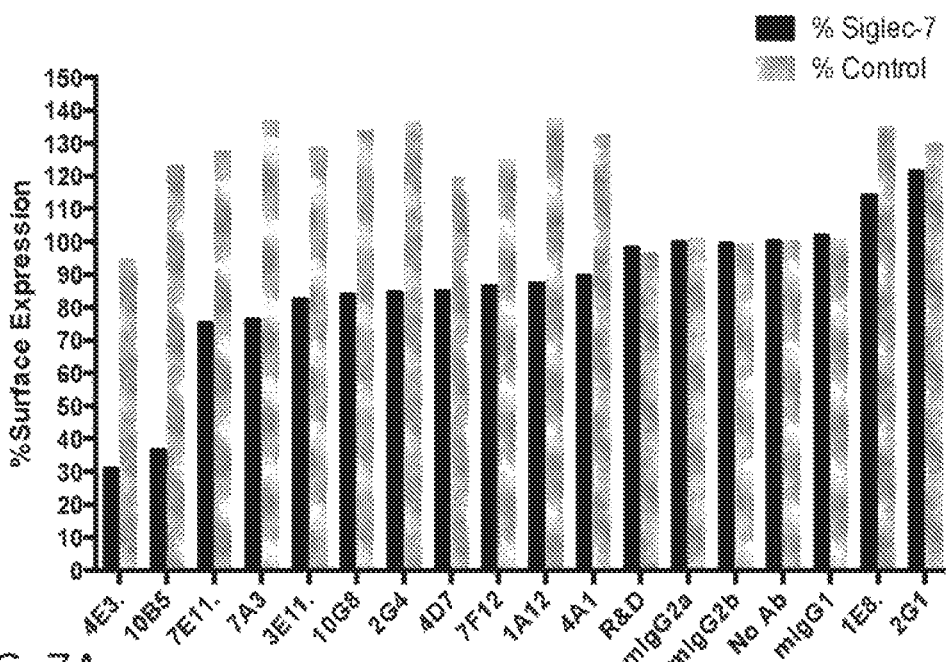
FIG. 7A-7N depict Siglec-7 antibody-dependent down-regulation of cell surface Siglec-7 receptor in vitro and in vivo.
Figure 7B:
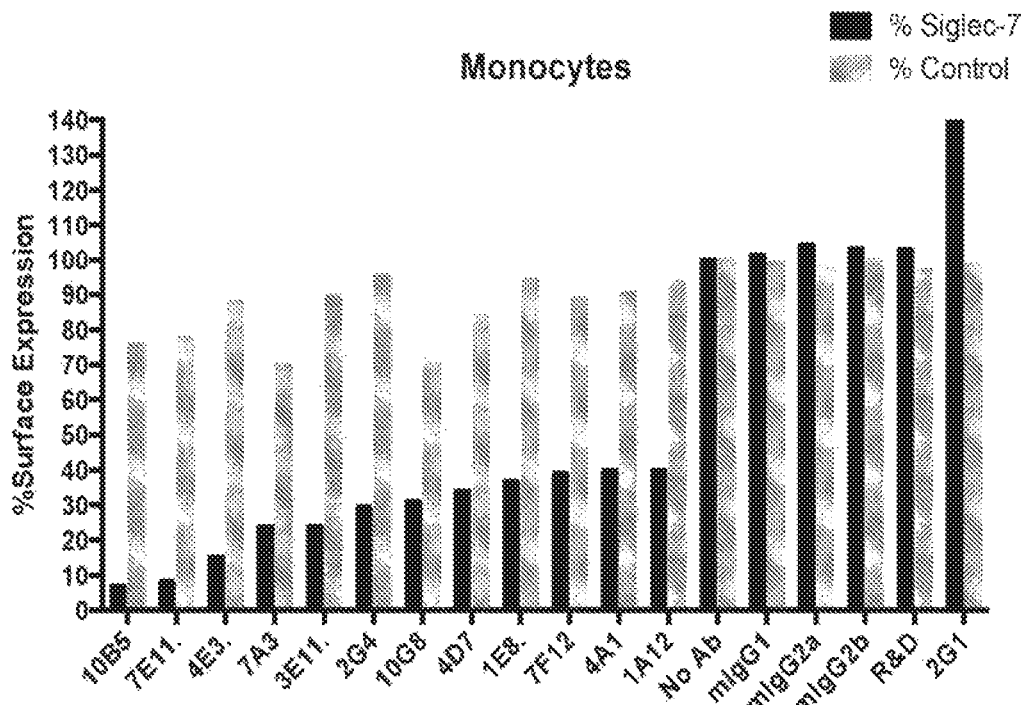
FIG. 7B depicts human primary monocytes.
Figure 7C:
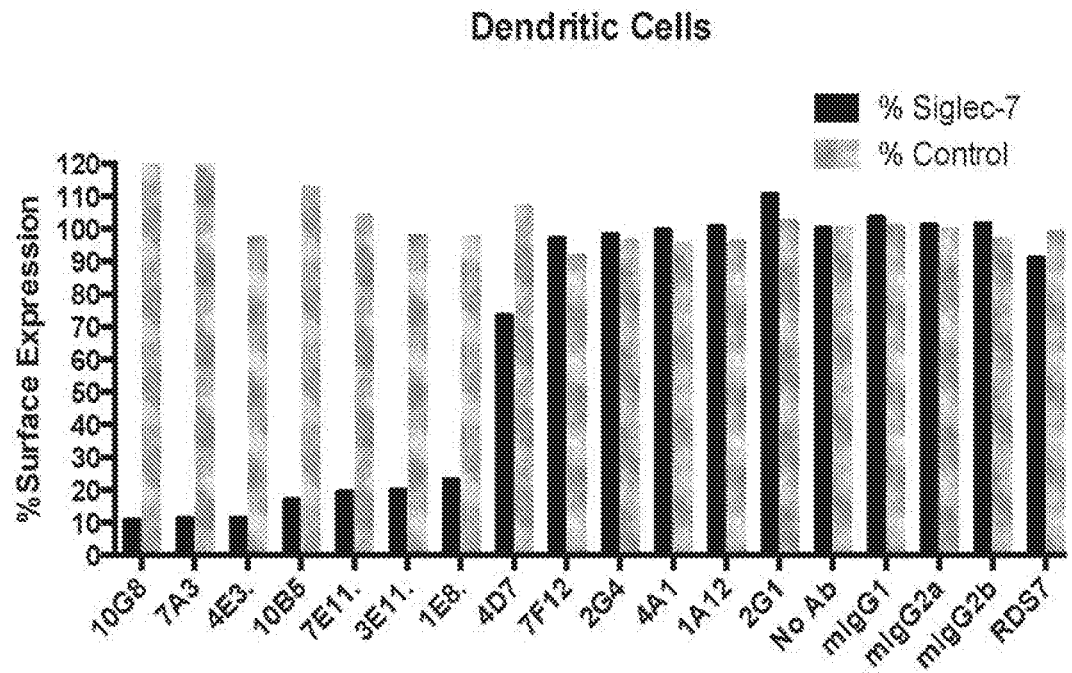
FIG. 7C depicts human primary dendritic cells.
Figure 7D:
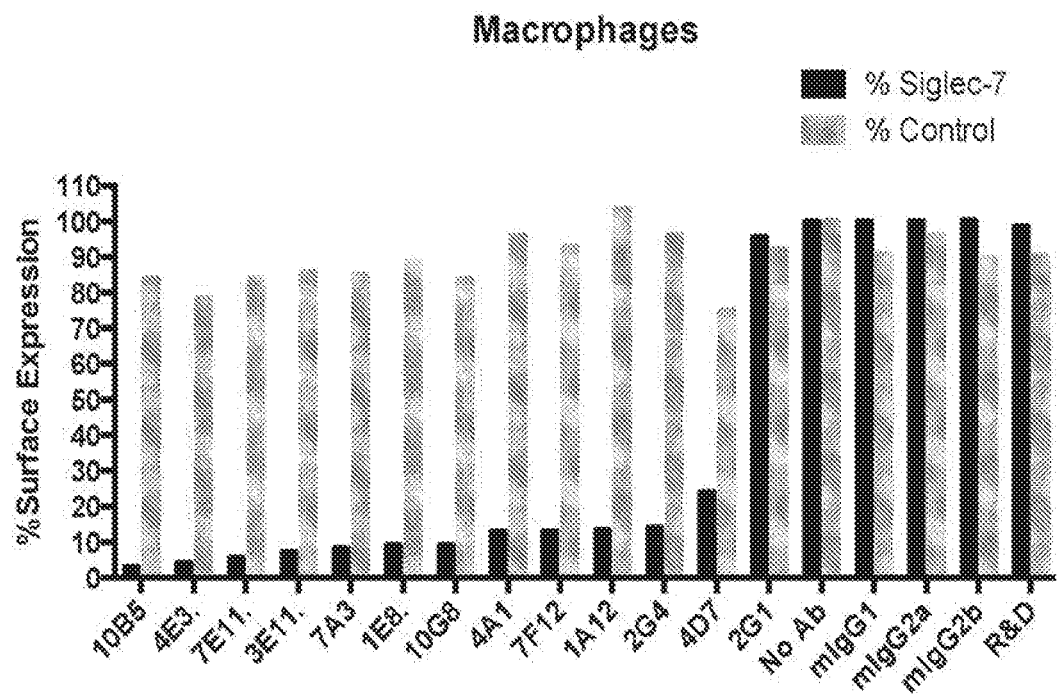
FIG. 7D depicts human primary macrophages.
Figure 7E:
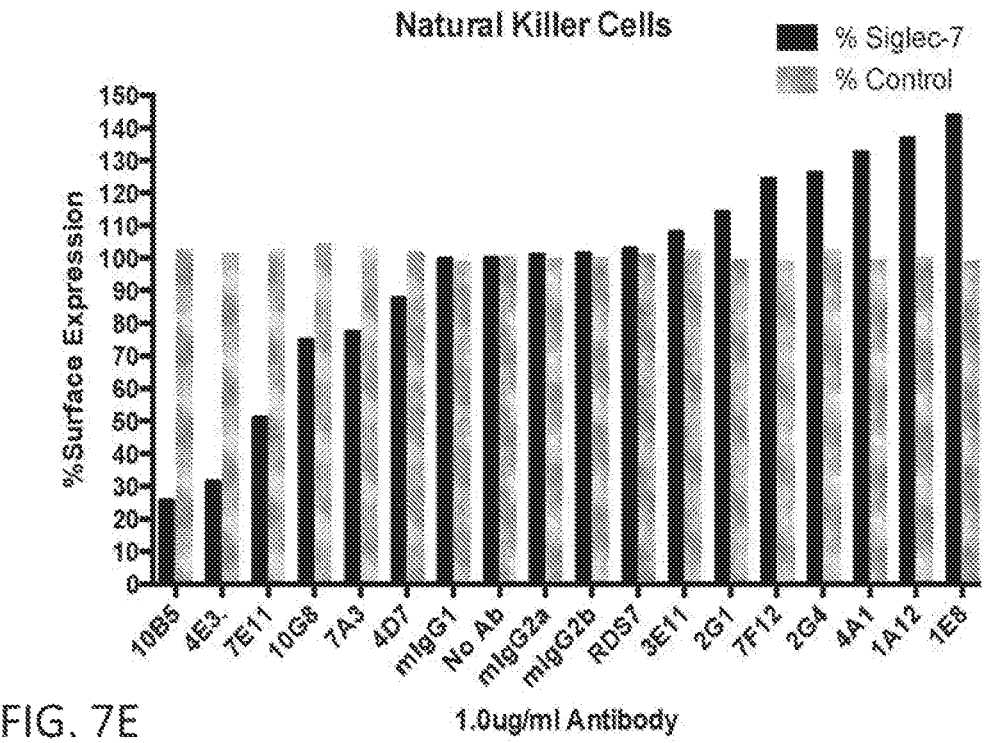
FIG. 7E depicts human primary natural killer (NK) cells.
Figure 7F:
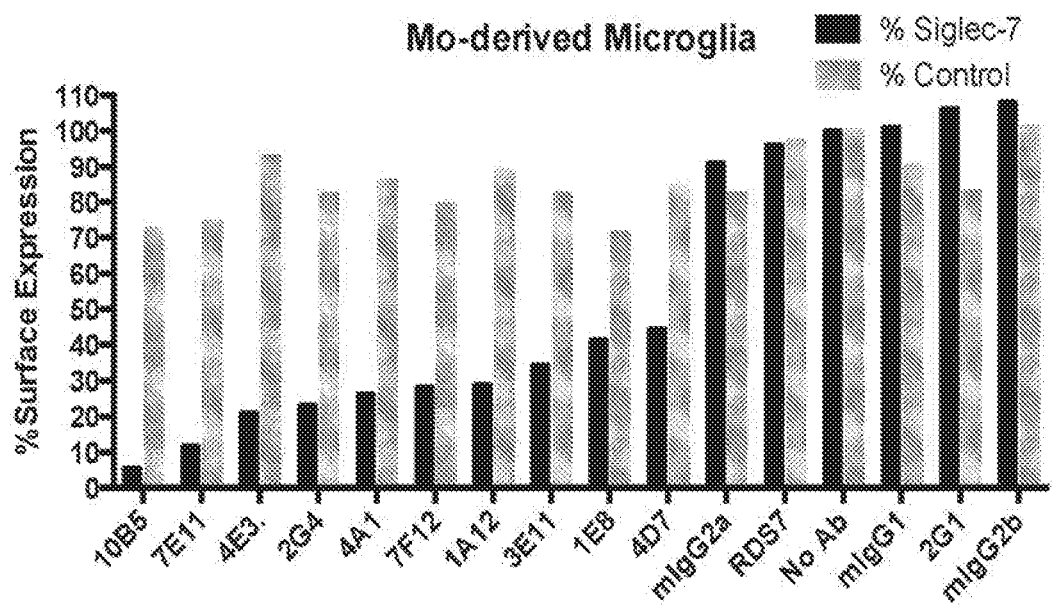
FIG. 7F depicts human primary monocyte-derived microglia.

FIG. 7A-7F further demonstrates that a majority of the antibodies were able to decrease cell surface levels of Siglec-7 on U937 cells (FIG. 7A), human primary monocytes (FIG. 7B), human primary dendritic cells (FIG. 7C), human primary macrophages (FIG. 7D), human primary NK cells (FIG. 7E), and human primary microglia (FIG. 7F).

Additionally, in vitro surface Siglec-7 downregulation studies were performed in which Siglec-7 antibodies 4E3 and 10B5 were titrated 2-fold for a 12-point curve. Primary human dendritic cells differentiated with GM-CSF and IL-4 from isolated human monocytes were harvested Day 5, and plated at 100,000 cells per well in a round bottom 96 well non-TC treated plate, Siglec-7 antibodies were titrated 2-fold for a 12-point curve with a concentration range of 6.67-0.00325 nM to assess binding and calculate half-maximal effective concentration ($EC_{50}$) values. Antibodies were serially diluted and incubated with cells at 37C overnight in RPMI media with 10% FBS (Hyclone) and normal supplements. The following day, cells were pelleted and resuspended with a non-competing FACS detection Siglec-7 APC-conjugated antibody clone 6-434 (Biolegend) and control receptor CD11c PE-Cy7 antibody (BD Biosciences) in PBS with 1% BSA and 1 mM EDTA. Cells were incubated with detection antibodies for 30 minutes on ice, then washed 3 times in buffer before analyzing on a BD FACS Canto. Data were analyzed with FlowJo Software (TreeStar).

Figure 7G:
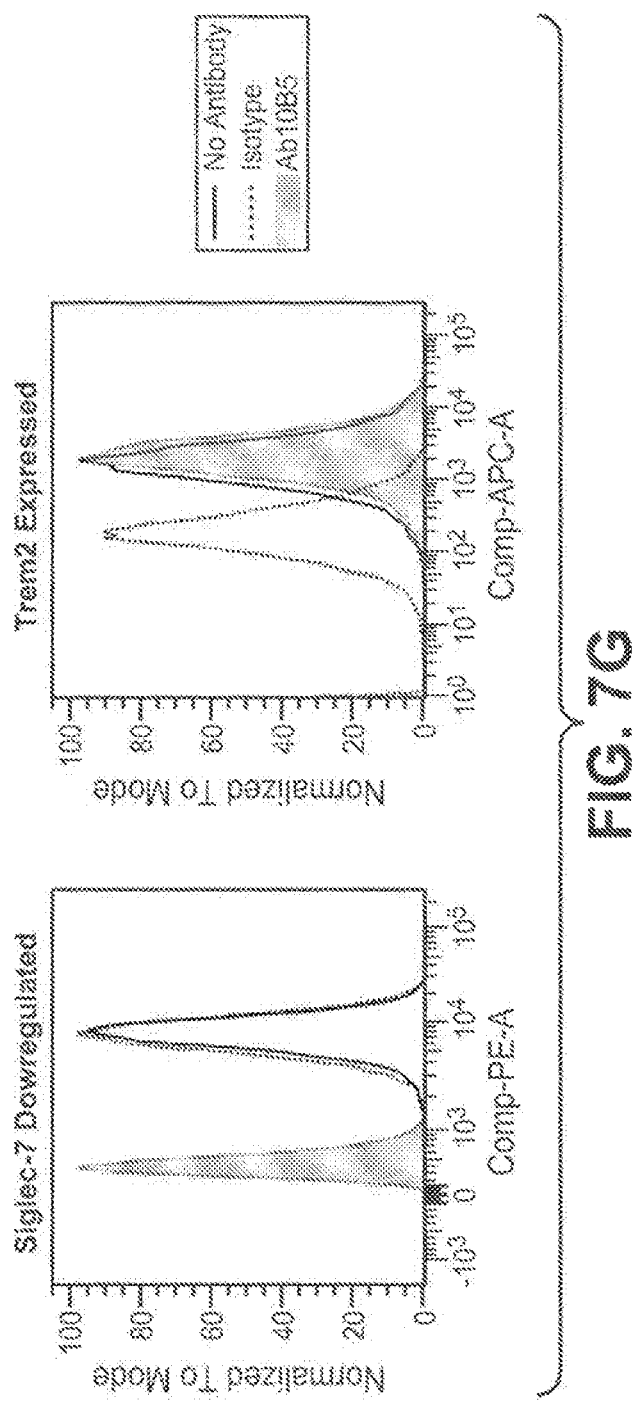
FIG. 7G depicts levels of Siglec-7 surface expression and TREM2 surface expression on human dendritic cells after treatment with an anti-Siglec-7 antibody 10B5 or an isotype control antibody, as compared to a no antibody control.
Figure 7H:
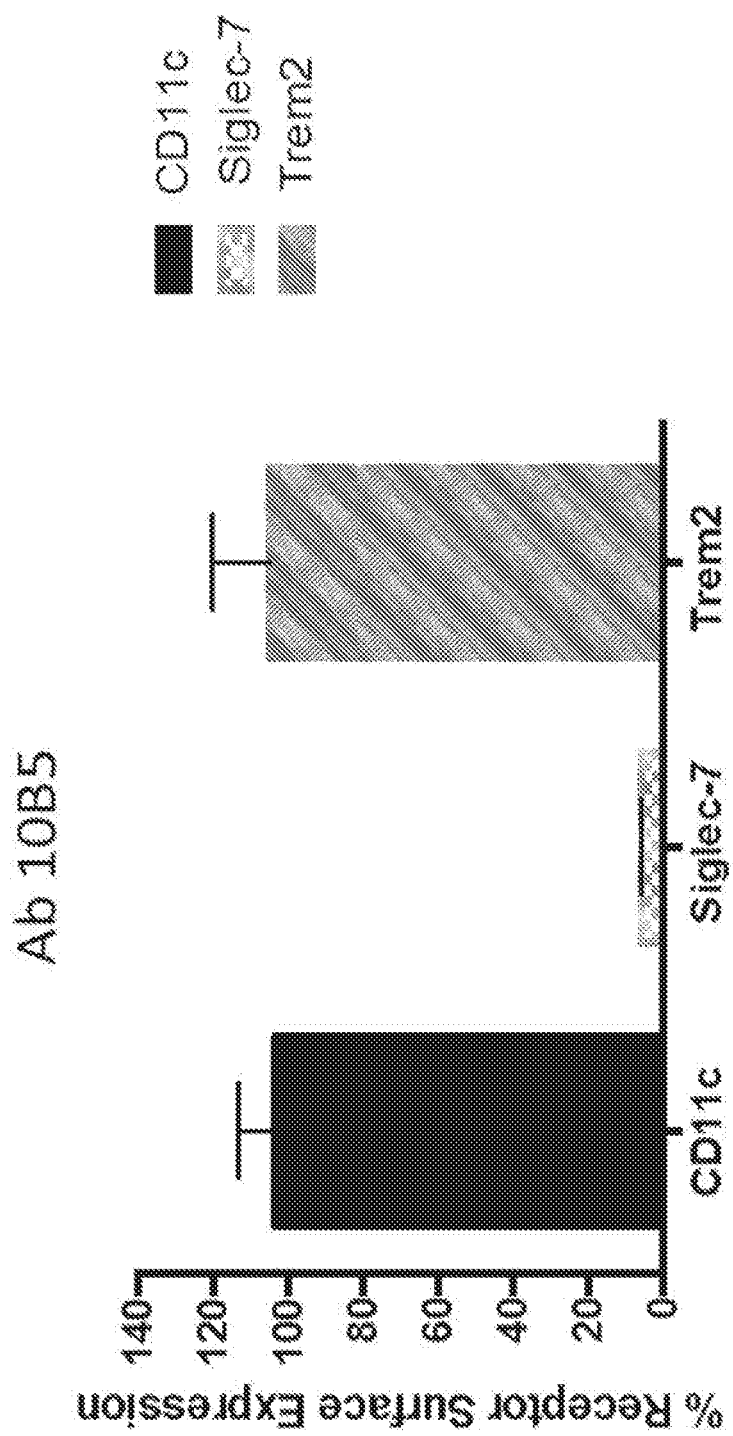
FIG. 7H depicts levels of CD11c surface expression, Siglec-7 surface expression, and TREM2 surface expression on human dendritic cells after treatment with an anti-Siglec-7 antibody 10B5.
Figure 7I:
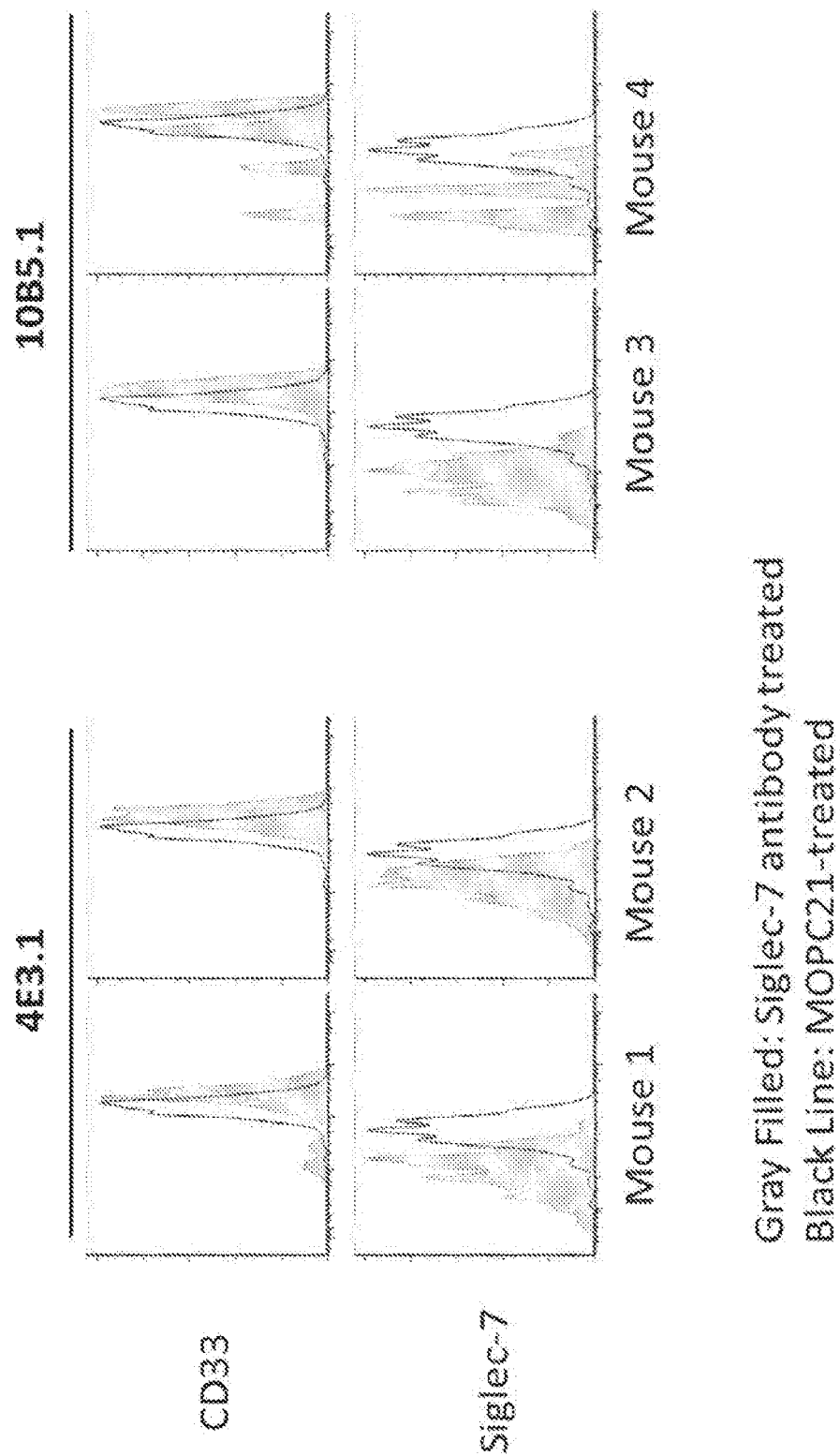
FIG. 7I depicts Siglec-7 and CD33 expression in peripheral blood samples from humanized NOG mice 14 days after treatment with anti-Siglec-7 antibodies of the present disclosure.
Figure 7J:
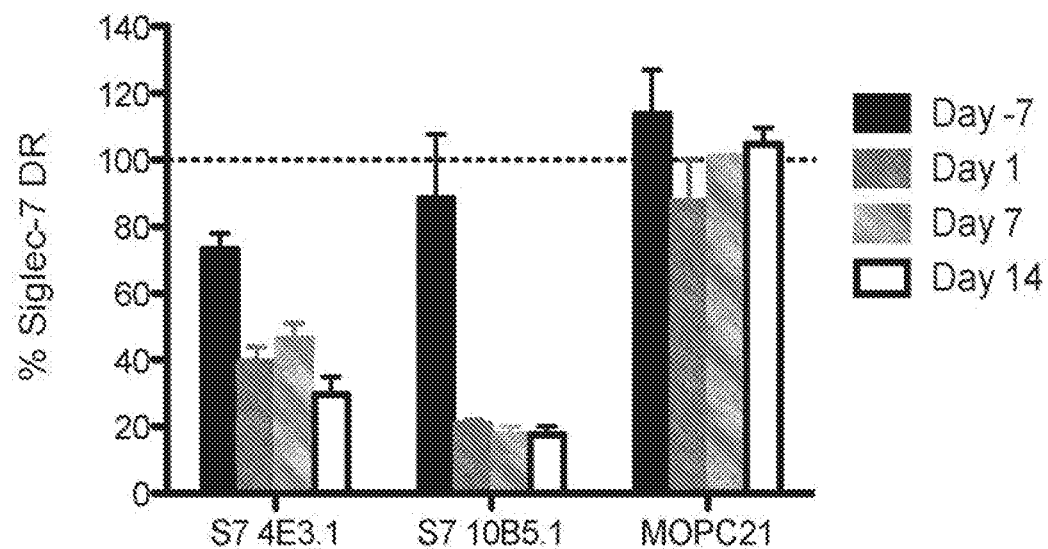
FIG. 7J shows in vivo reduction in cell surface levels of Siglec-7 following antibody treatment in vivo.
Figure 7K:
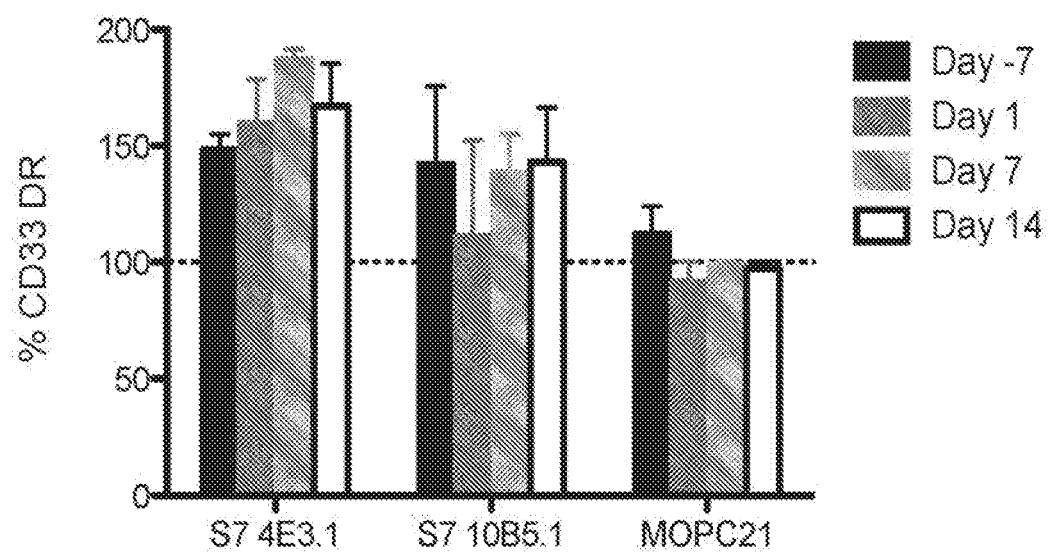
FIG. 7K shows expression of unrelated receptor CD33. CD33 was used as a control. Cell surface levels of CD33 were not significantly reduced following antibody treatment in vivo.
Figure 7L:
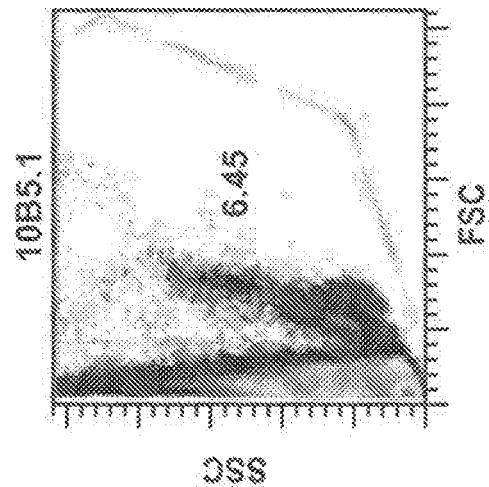
FIG. 7L shows FACS gating strategy for blood samples from humanized NOG mice 14 days after treatment with anti-Siglec-7 antibodies of the present disclosure.
Figure 7L:
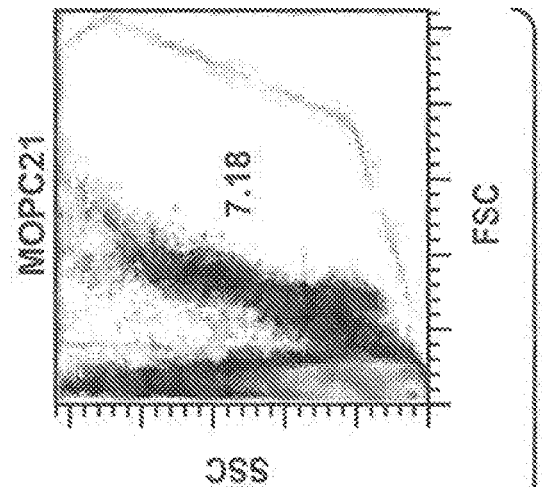
Figure 7L:
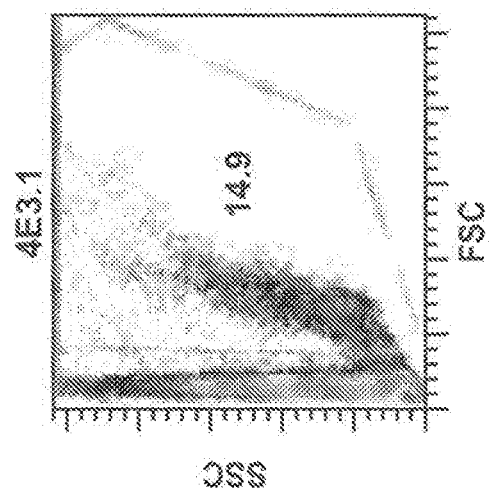
Figure 7L:
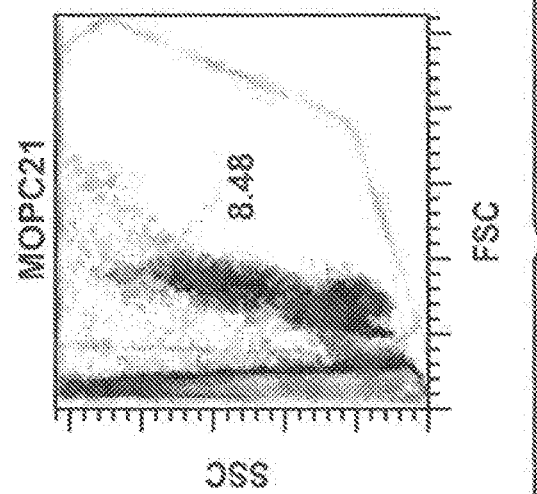
Figure 7L:
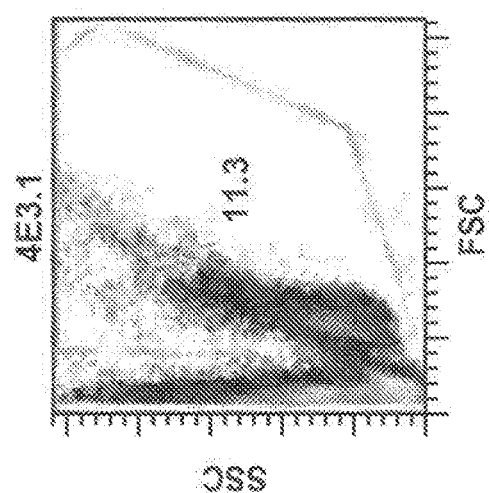
Figure 7L:
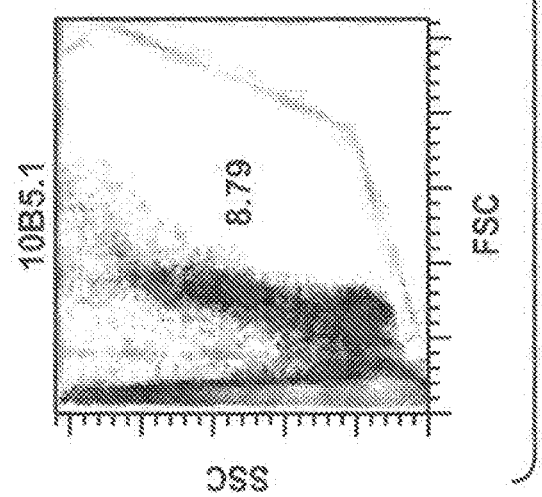
Figure 7L:
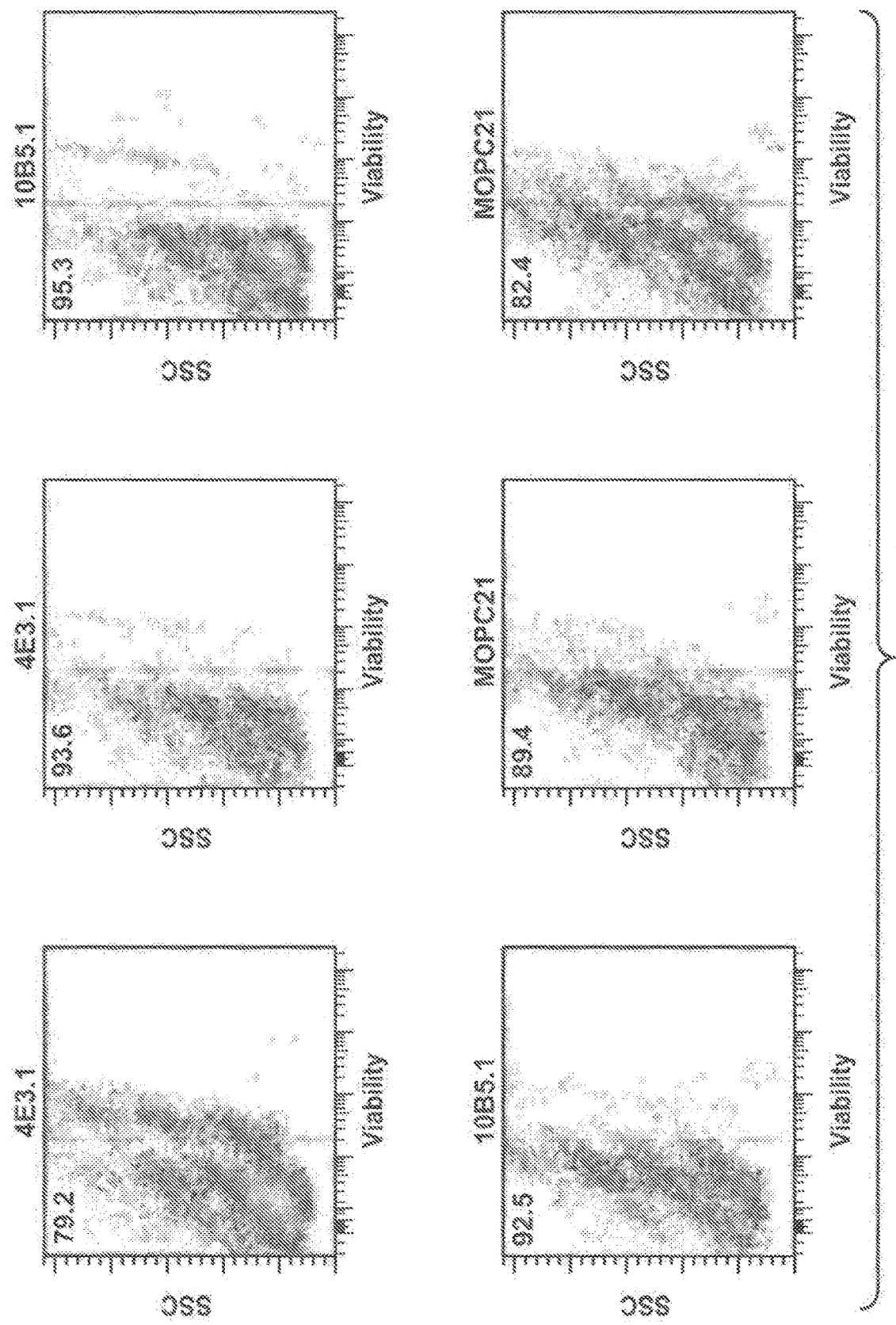
Figure 7L:
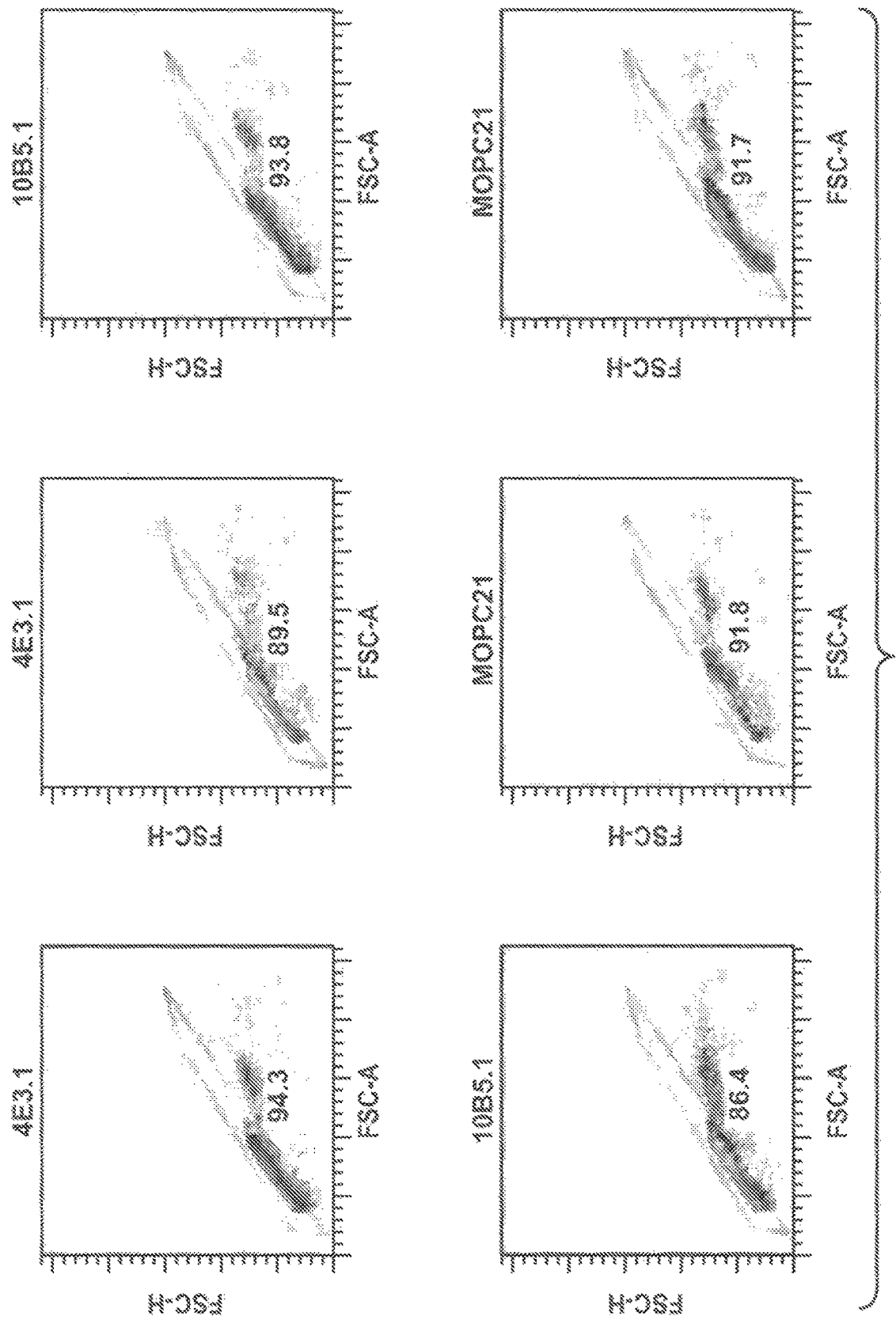
Figure 7L:
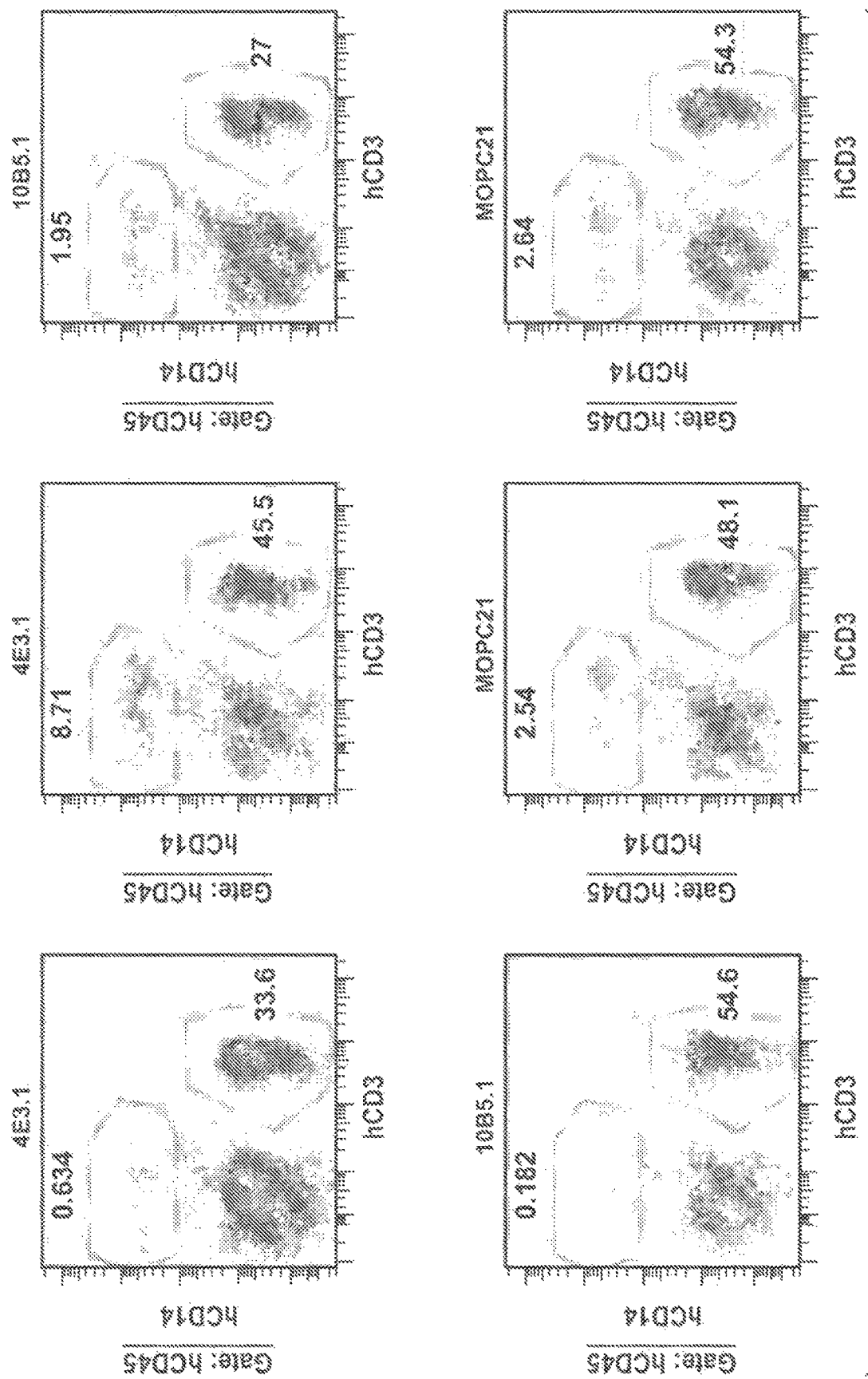
Figure 7M:
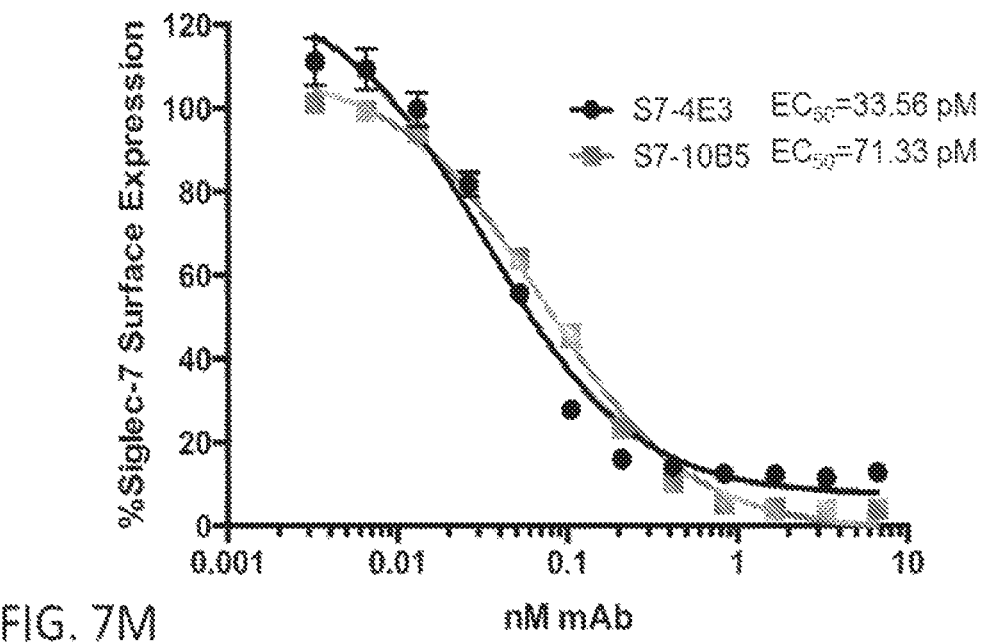
FIG. 7M depicts a 12-point titration curve showing the half-maximal effective concentration ($EC_{50}$) of Siglec-7 antibodies 4E3 and 10B5 for reducing cell surface expression of Siglec-7.
Figure 7N:
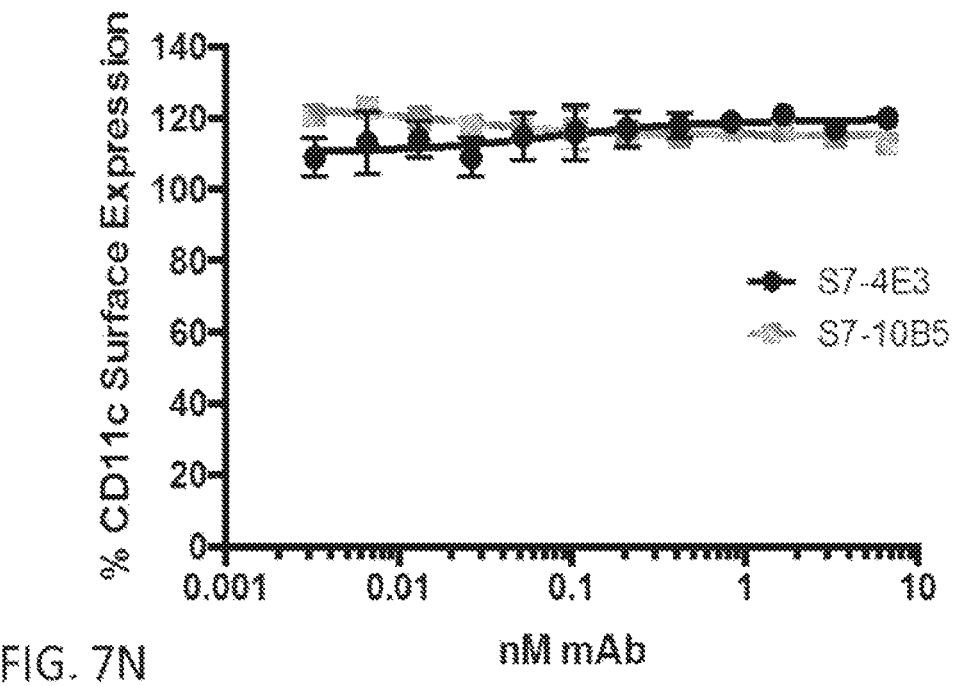

As shown in FIG. 7M, anti-Siglec-7 antibodies 4E3 and 10B5 were capable of downregulating cell surface expression of Siglec-7 on primary human dendritic cells. Cell surface expression of the CD11c control receptor was not affected by treatment with either Siglec-7 antibody (FIG. 7N). Table 8C summarizes the results of cell surface downregulation of Siglec-7 by the indicated antibodies on primary human dendritic cells isolated from four different donors.

TABLE 8C

Siglec-7 cell surface downregulation on primary
human dendritic cells by two Siglec-7 antibodies

| | Antibody: 4E3 | | Antibody: 10B5 | |
|---|---|---|---|---|
| Donor # | $EC_{50}$ value (pM) | 95% CI (pM) | $EC_{50}$ value (pM) | 95% CI (pM) |
| 365 | 33.56 | 18.58 to 48.53 | 71.33 | 54.41 to 88.24 |
| 364 | 49.94 | 23.09 to 76.80 | 102.5 | 67.33 to 137.6 |
| 362 | 114.1 | 78.37 to 149.8 | 143.7 | 113.2 to 174.3 |
| 363 | 94.96 | 27.75 to 162.2 | 350.4 | 220.2 to 480.5 |

The in vitro studies in which antibodies 4E3 and 10B5 were titrated 2-fold for a 12-point curve demonstrated robust Siglec-7 receptor downregulation with mouse Siglec-7 antibodies, while the CD11c control receptor was not affected upon antibody treatment. These data showed that mouse Siglec-7 antibody 4E3 downregulated 50% of the Siglec-7 receptor on human primary myeloid cells taken from donor 363 with an $EC_{50}$ of 94.96 pM (with a 95% confidence interval of 27.75 to 162.2 pM), and mouse Siglec-7 antibody 10B5 downregulated 50% of Siglec-7 receptor on human primary myeloid cells taken from the same donor with an $EC_{50}$ of 350.4 pM (with a 95% confidence interval of 220.2 to 480.5 pM).

Effect of Siglec-7 Antibody on Expression of TREM2

To test the ability of Siglec-7 antibodies that decrease cell surface levels of Siglec-7 to modulate TREM2 expression, human monocyte-derived dendritic cells differentiated with GM-CSF and IL-4 were harvested at day 6, and were plated at 500,000 cells per well in a 24 well dish overnight with 1.0 µg/ml anti-Silglec-7 antibody 10B5, isotype control antibody, or left untreated. Cell surface receptor expression for CD11c. TREM2, and Siglec-7 were detected the following day by FACS analysis. Cells were incubated with biotinylated anti-Siglec-7 clone 10A9 for 20 minutes on ice. After one wash, cells were incubated in FACS buffer with APC conjugated Strepavidin (BD Biosciences, 1:150 dilution), anti-Siglec-7-PE clone 6-434 (Biolegend), and anti- CD11c-PECy7 (BD Biosciences), for 30 minutes on ice in the dark. Cells were washed 3× in FACS buffer (PBS+2% FBS, 2 mM EDTA) and flow cytometry was performed on a BD FACS Canto. Data was analyzed using TreeStar FlowJo software. Data was calculated as a percent of receptor expression in the absence of antibody using MFI values for the respective fluorophores.

As shown in FIGS. 7G and 7H, anti-Siglec-7 antibody 10B5, which was able to able to decrease cell surface levels of Siglec-7, did not affect TREM2 expression.

Loss-of-function mutations in TREM2 have been associated with severe neurodegeneration, including Nasu-Hakola disease, frontotemporal dementia, and Alzheimer's disease. It is believed that modulation of ITIM-containing Siglec receptors may affect TREM2 expression. Therefore, anti-SIglec-7 antibodies that do not decrease TREM2 expression on human immune cells may be key to positive therapeutic outcomes. The results in FIGS. 7G and 7H demonstrate that anti-Siglec-7 antibody clone 10B5, which robustly decreases cell surface levels Siglec-7, does not reduce TREM2 expression on human dendritic cells.

In Vive Expression of Siglec-7

To test the ability of Siglec-7 antibodies to reduce cell surface level of Siglec-7 in vivo, humanized NOG mice (hu-NOG) were utilized. The genetic background of Hu-NOG mice is NOD.Cg-Prkdc$^{scid}$ Il2rg$^{tm1Sug}$/JicTac and engrafted with human CD34$^+$ hematopoietic stem cells. Female Hu-NOG mice were purchased from Taconic and utilized 15 weeks after engraftment with human cells. Mice received an intraperitoneal injection of 4) mg/kg anti-Siglec-7 antibodies 4E3 or 10B5, or an isotype control mouse IgG$_1$ antibody (clone MOPC-21) at day 0. At day 1, blood samples were drawn from mice into heparin and processed for FACS analysis. Briefly, blood samples were first incubated for 5 minutes in ice-cold ACK lysis buffer to lyse red blood cells and then washed extensively with cold PBS. This procedure was repeated twice. Cells were then incubated in FACS buffer (PBS+2% FBS, 2 mM EDTA) in the presence of anti-human-CD45-Pe-Cy 7, anti-mouse-CD45-APC-Cy7, anti-human-CD3-PerCP-Cy5.5, anti-human-CD14-FITC, anti-human-CD11 c-PB, anti-Siglec-7-APC, anti-CD33-PE, and a viability die (Life Technologies, Cat #L34957) for 30 min, on ice in the presence of Fc block solution, then washed twice with cold FACS buffer. 4% PFA-fixed samples were then acquired. Data were acquired on a BD FACS CANTO™ II cytometer (Becton Dickinson) and analyzed with FlowJo software by TreeStar. The level of expression of Siglec 7 and CD33 was determined in an hCD45+, hCD14+ cell population at day −7, 1, 7, and 14 post antibody treatment.

As shown in FIG. 7I-7L, treatment with the anti-Siglec-7 antibodies 4E3 and 10B5 was able to decrease cell surface levels of Siglec-7 in cells of peripheral blood of the treated hu-NOG mice, when compared to isotype control MOPC21 antibody treatment, Siglec-7 expression was decreased by ~60% as early as 1 day post antibody treatment with antibody 4E3, and ~80% as early as 1 day post antibody treatment with antibody 10B5 (FIG. 7J). As a comparison, cell surface expression of the unrelated surface receptor CD33 did not decrease significantly after anti-Siglec-7 antibody treatment, as compared to cell surface levels of CD33 after treatment with mIgG1 control antibody (FIG. 7K).

These results demonstrate that when utilizing humanized mice, Siglec-7 antibodies engage the Siglec-7 in vivo and functionally downregulate Siglec-7 on human immune cells. The results further demonstrate that Siglec-7 antibodies 4E3 and 10B5, when injected into humanized mice, engage Siglec-7 on peripheral monocytes circulating in the blood of the mice. Antibody engagement of Siglec-7 leads to receptor downregulation specifically for Siglec-7 and not a control receptor, CD33. After a single injection of 10B5 antibody, 80% of Siglec-7 expressed on human monocytes is downregulated 1 day after treatment. Receptor loss is sustained 7 and 14 days after treatment with a single treatment for both 4E3 and 10B5 antibodies.

Example 4: Siglec-7 Antibodies Compete with Siglec-7 Ligand for Binding to Human Siglec-7

The purpose of the following Example was to test whether anti-Siglec-7 antibodies recognize the ligand-binding site on Siglec-7 and compete with ligand binding on Siglec-7 receptors.

To determine which antibodies compete with ligand binding to Siglec-7, a red blood cell (RBC) solid adhesion assay was carried out in accordance with standard protocols (Kelm et al., *Current Biology*, 1994). Red blood cells are highly decorated with glycoproteins containing sialic acids; therefore, the ability of an antibody to block RBC binding to immobilized Siglec-7 can be used to determine ligand interference. Briefly, 5 µg/ml Siglec-7-Fc was coated overnight at RT in 96 well Immunolon plates, then washed with PBS, blocked for one hour with binding buffer (PBS containing %0.25 BSA 1 mM CaCl$_2$), Siglec-7 antibodies (0.5 µg/ml or 1.0 µg/ml) were bound for one hour at RT with gentle rocking. After removal of unbound antibody, red blood cells were added to each well at a concentration of 3.0×10$^6$ cells per ml and incubated at RT for one hour. Unbound RBCs were then carefully washed off 3× with PBS, and water was added to each well for hypotonic lysis of bound RBCs. The plate was transferred to −80° C. for 10 minutes, followed by 37° C. for 15 minutes. Bound RBCs were detected by peroxidase activity, followed by 2N sulfuric acid to stop the reaction. Signal was detected at 450 nM. Data was calculated as a percent of RBC binding to plate bound Siglec-7-Fc in the absence of antibody.

The results of the ligand competition assay are depicted in Table 9. In Table 9, "mIgG1," and "mIgG2b" refer to isotype control antibodies; "RDS7" refers commercially available anti-Siglec-7 antibody Mab1138 (R&D Systems; Cat. No. MAB 1138); and "RBC alone" refers to RBC that were not incubated with an antibody.

TABLE 9

Siglec-7 antibodies compete with ligand binding

| Antibody | Percent RBC Binding to Siglec-7 |
|---|---|
| 1A12 | 16.5 |
| 1E8 | 16.4 |
| 2G1 | 14.5 |
| 2G4 | 11.6 |
| 3E11 | 26.8 |
| 4A1 | 11.2 |
| 4D7 | 96.5 |
| 4E3. | 20.2 |
| 7A3 | 89.5 |
| 7E11 | 89.3 |
| 7F12 | 7.9 |
| 10B5 | 88.4 |
| 10G8 | 111.4 |
| mIgG1 | 106.9 |
| mIgG2b | 101.6 |
| RDS7 | 97.1 |
| RBC alone | 100.0 |

As shown in Table 9, antibodies 1A12, 1E8, 2G1, 2G4, 3E11, 4A1, 4E3, and 7F12 were able to block RBC binding to Siglec-7, thus indicating competitive binding of the antibodies to the ligand-binding site on Siglec-7, and their ability to inhibit the interaction between Siglec-7 and one or more Siglec-7 ligands (i.e., to block ligand binding to Siglec-7). However, using a threshold value of 80% or higher of RBC binding to Siglec-7, it was found that antibodies 4D7, 7A3, 7E11, 10B5, and 10G8 do not inhibit the interaction between Siglec-7 and one or more Siglec-7 ligands.

Figure 8:
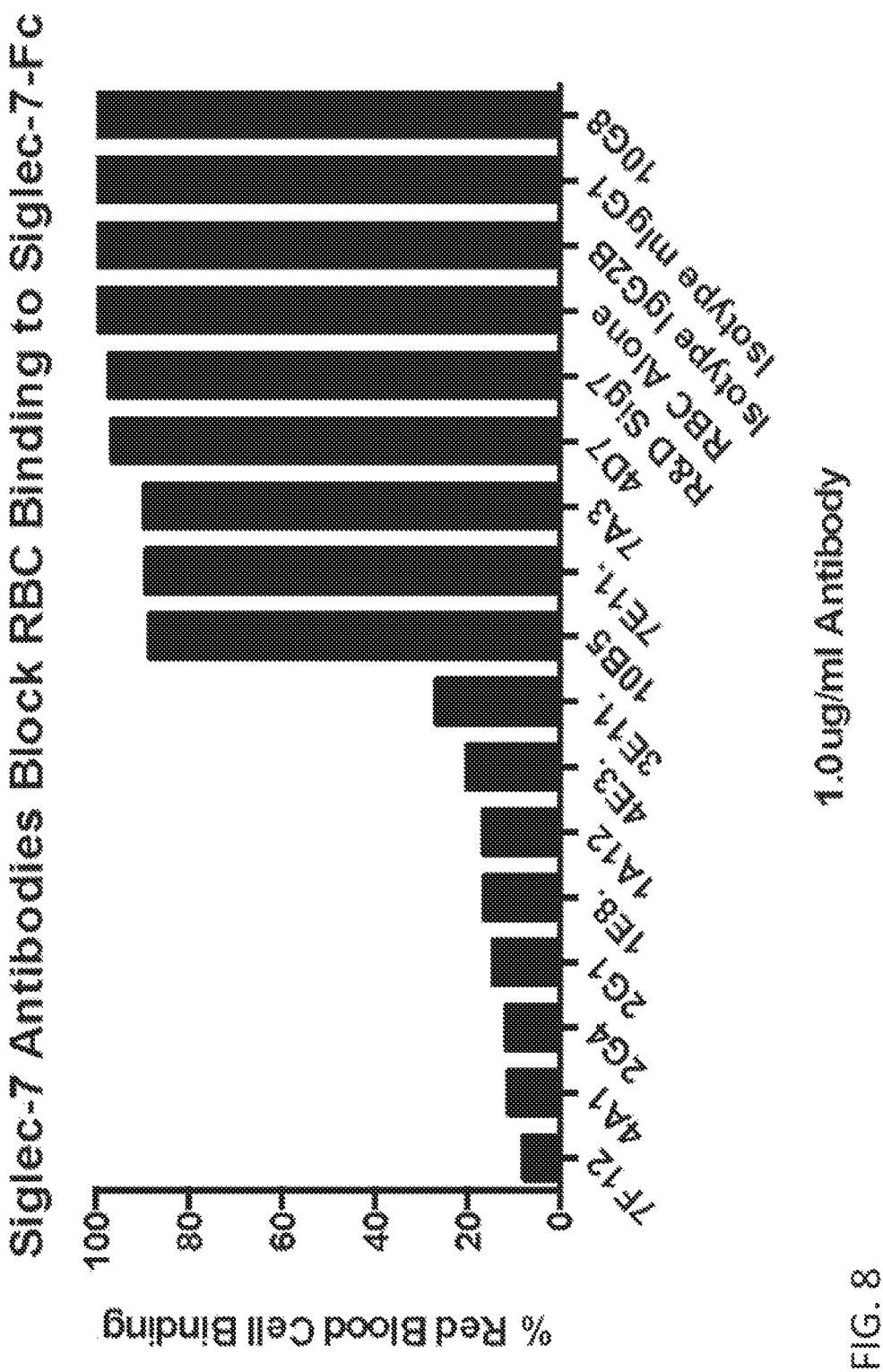
FIG. 8 depicts results demonstrating that Siglec-7 antibodies of the present disclosure can block binding of Siglec-7 ligand that is expressed on red blood cells to plate immobilized Siglec-7-Fc protein.

FIG. 8 further demonstrates that antibodies 1A12, 1E8, 2G1, 2G4, 3E11, 4A1, 4E3, and 7F12 are able to block RBC binding to Siglec-7, thus indicating competitive binding of the antibodies to the ligand-binding site on Siglec-7, and their ability to inhibit the interaction between Siglec-7 and one or more Siglec-7 ligands (i.e., to block ligand binding to Siglec-7).

Example 5: Summary of Siglec-7 Antibody Functional Studies

Table 10 summarizes results of the cell surface expression and ligand binding studies described in Examples 3 and 4 above. As indicated in Table 10, there were three general classes of Siglec-7 antibodies. One class of antibodies decreases cell surface level of Siglec-7 without inhibiting the interaction between Siglec-7 and one or more Siglec-7 ligands. A second class of antibodies both decreases cell surface level of Siglec-7 and inhibits the interaction between Siglec-7 and one or more Siglec-7 ligands. The third class of antibodies inhibits the interaction between Siglec-7 and one or more Siglec-7 ligands without decreasing cell surface level of Siglec-7.

Antibodies in the class of antibodies that decreases cell surface level of Siglec-7 without inhibiting the interaction between Siglec-7 and one or more Siglec-7 ligands include: 4D7, 7A3, 7E11, 10B5, and 10G8.

Antibodies in the class of antibodies that decreases cell surface level of Siglec-7 and inhibits the interaction between Siglec-7 and one or more Siglec-7 ligands include: 1A12, 1E8, 2G1, 2G4, 3E11, 4A1, 4E3, and 7F12.

Antibodies in the class of antibodies that inhibits the interaction between Siglec-7 and one or more Siglec-7 ligands without decreasing cell surface level of Siglec-7 include: 2G1.

TABLE 10

Siglec-7 antibody functional studies

| Antibody | Decreases cell surface Siglec-7 | Inhibits Siglec-7 ligand binding |
|---|---|---|
| 1A12 | X | X |
| 1E8 | X | X |
| 2G1 |  | X |
| 2G4 | X | X |
| 3E11 | X | X |
| 4A1 | X | X |
| 4D7 | X |  |
| 4E3 | X | X |
| 7A3 | X |  |
| 7E11 | X |  |
| 7F12 | X | X |
| 10B5 | X |  |
| 10G8 | X |  |

Example 6: Ligand Binding to Siglec-7 on Dendritic Cells Inhibits T Cell Proliferation and Phagocytosis Human dendritic cells (DCs) were differentiated from peripheral blood monocytes with GM-CSF and IL-4 and cultured for 5 days. Immature (suspension) DCs were harvested and plated at a density of 200,000 cells per ml in a 12 well dish. DCs were activated with a cytokine cocktail of TNFa (50 µg/ml), IL-1b (50 µg/ml), IL-6 (150 ng/ml), and Prostaglandin E2 (1 µg/ml) for 24 hours. Dendritic cell maturation was determined by flow cytometry with commercially available antibodies for LIN, CD11c. HLA-DR, CD86, and CD83 (BD Biosciences). Immediately prior to co-culture with allogenic isolated T cells, activated DCs were sialidase treated, or left untreated, for 2 hours at 37° C. with 100 mU/ml neuraminidase from *Vibrio cholera* in serum free media. Enzymatic activity was quenched by addition of serum-containing media, cells pelleted and resuspended in complete media. Sialidased activated, untreated activated, or unactivated DCs were co-cultured at a ratio of 1:10 with allogenic CFSE labeled T cells, CD3/CD28 Dynal beads were added to T cells alone as a positive control. Five days later T cell proliferation was measured by CFSE dilution on a BD FACS Canto.

Figure 9:
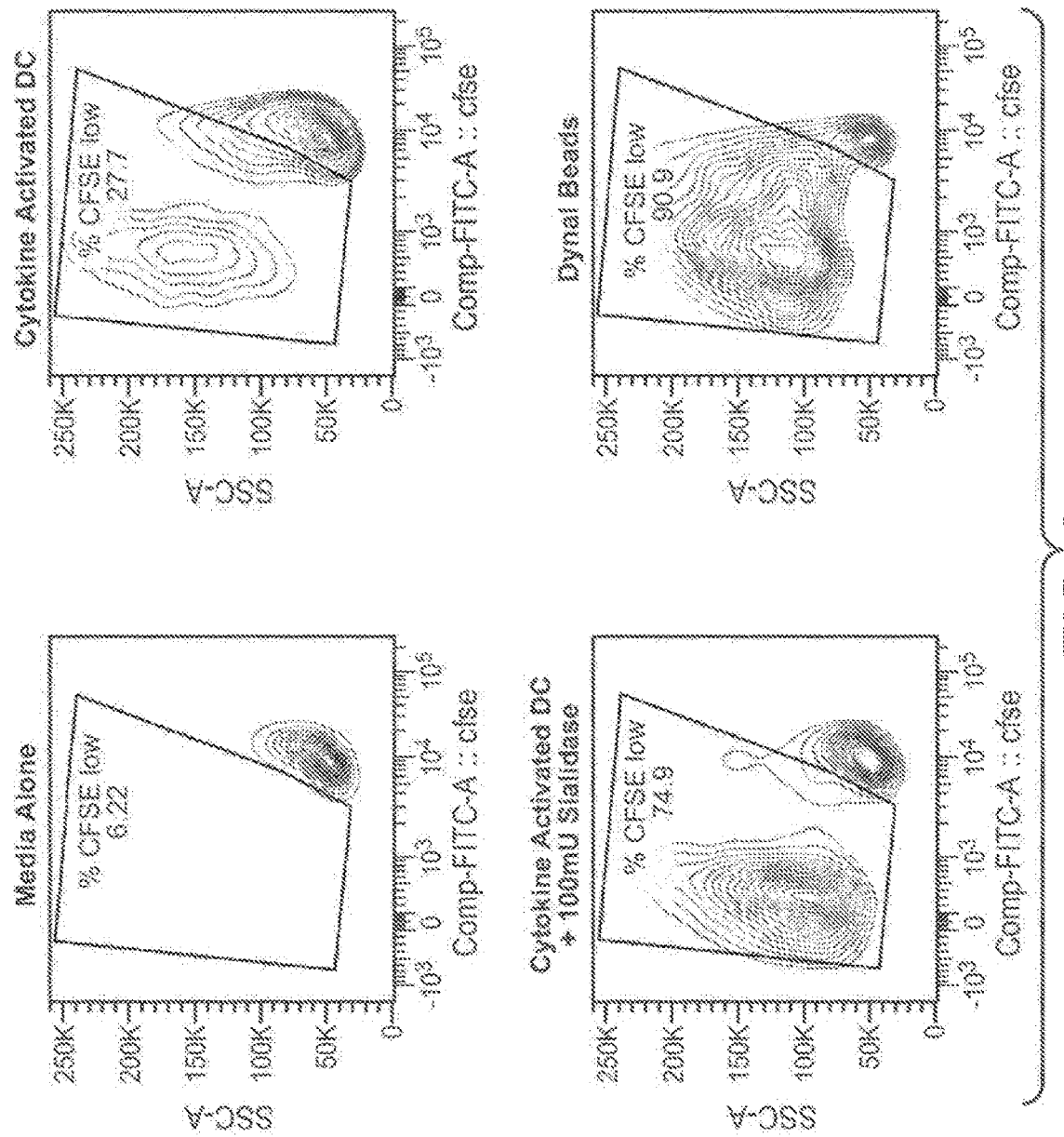
FIG. 9 depicts FACS analysis showing that sialic acid ligands on dendritic cells restrict T cell proliferation during mixed lymphocyte reaction with human primary cells.
Figure 10:
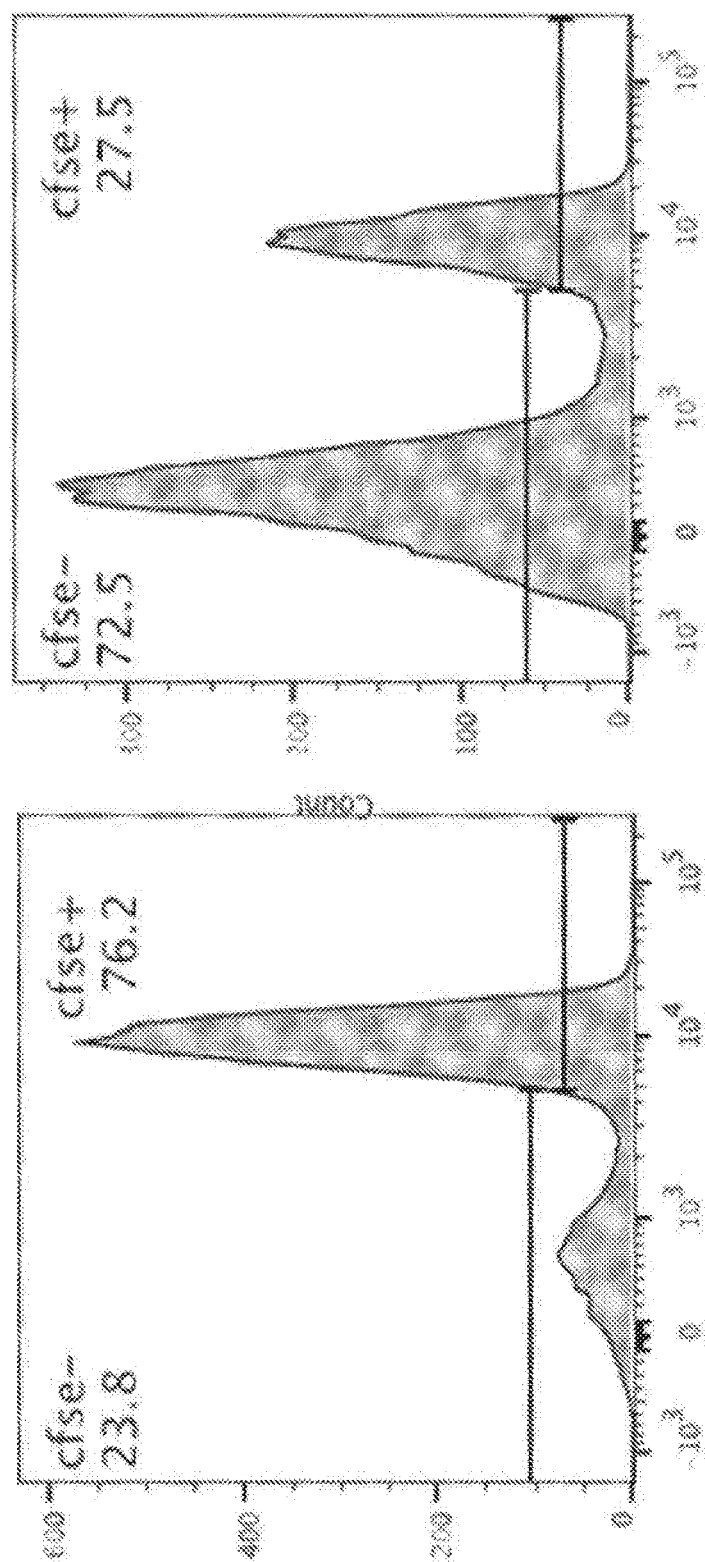
FIG. 10 depicts results showing that sialic acid Siglec-7 ligands on dendritic cells restrict T cell proliferation during mixed lymphocyte reaction.

FIGS. 9 and 10 show that sialic acids on dendritic cells restrict T cell proliferation during mixed lymphocyte reaction (MLR). FIG. 10 shows that DCs that normally express inhibitory ligands induce low levels of T cell proliferation (left panel), while the removal of the inhibitory ligands on DCs increases T cell proliferation (right panel).

As shown in FIGS. 9 and 10, enzymatic removal of sialic acids from activated DCs increased T cell proliferation when compared to untreated activated DCs. These results indicate that sialic acids present on DCs act on T cells in a suppressive manner to restrict T cell proliferation when co-cultured with allogenic DCs. These results indicate that antibodies that block Siglec-7 on T cells or dendritic cells enhance T cell and/or dendritic cell functionality, CD3/CD28 Dynal beads were used as a positive control. Furthermore, these results indicate that blocking sialic acid interactions with DCs or any other cellular or biological source may increase T cell function.

Example 7: Inflammatory Conditions Induce Siglec-7 Sialic Acid Ligand Expression in Myeloid Cells Human dendritic cells (DCs) were differentiated from peripheral blood monocytes with GM-CSF and IL-4 and cultured for 5 days. Immature human DCs were harvested on day 5 and co-cultured with sterile-filtered supernatant from B16, Lewis lung, MC38 tumor supernatant or 10 ng/ml LPS. 24 hours later Siglec-7 expression was determined by flow cytometry with a directly conjugated Siglec-7-PE antibody. Sialic acid ligand expression was assessed by incubation for 30 minutes on ice with 50 µg/ml soluble Siglec-7 fused to human IgG1-Fc, IgG1-Fc alone was used a negative control in the presence of human Fc block. Binding of the soluble receptor to sialic acids on cells was detected after a wash step and incubation for 30 minutes on ice with anti-human secondary conjugated to PE. Flow cytometry analysis was performed on a BD FACS Canto.

To elicit primary macrophages, human monocytes from peripheral human blood samples are isolated and either used directly or differentiated into macrophages with 50 µg/ml M-CSF for 5 days. In order to determine the role of Siglec-7 in inflammatory cytokine production, human macrophages are cultured with various inflammatory mediators, and cytokine levels are measured in the culture supernatants. To generate human macrophages, monocytes from peripheral human blood samples are isolated and either used directly or differentiated into macrophages with 50 µg/ml M-CSF or dendritic cells with 100 µg/ml GM-CSF and 100 µg/ml IL-4 for 5 days. Cells are cultured for 5 days, and adherent cells were detached with 1 mM EDTA in PBS. Cells are plated on 96-well plates at $10^5$ cells/well and allowed to adhere for 4 h at 37° C. Cells are then stimulated with TLR agonists LPS (*Salmonella abortus equi*) or zymosan (*Saccharomyces cerevisiae*) at concentrations ranging from 0.01-100 ng/ml (LPS) or 0.01-100 µg/ml (zymosan). Alternatively, macrophages are cultured in the presence of 10 ng/ml of the cytokine IL-4 or 50 ng/ml of IFN-g. Cell culture supernatant are collected 24 or 48 hours after stimulation and the levels of TNFa, IL-6, IL-10, and MCP-1 cytokines are measured by using Cytometric Bead Array Inflammation Kit (BD) according to manufacturer's protocol. Macrophages stimulated with the inflammatory mediators LPS or zymosan are expected to secrete more inflammatory cytokines TNFa, IL-6, IL-10, and MCP-1 when treated with Siglec-7 antagonistic antibodies or with enzymes that remove the inhibitory glycol ligands.

Figure 11A:
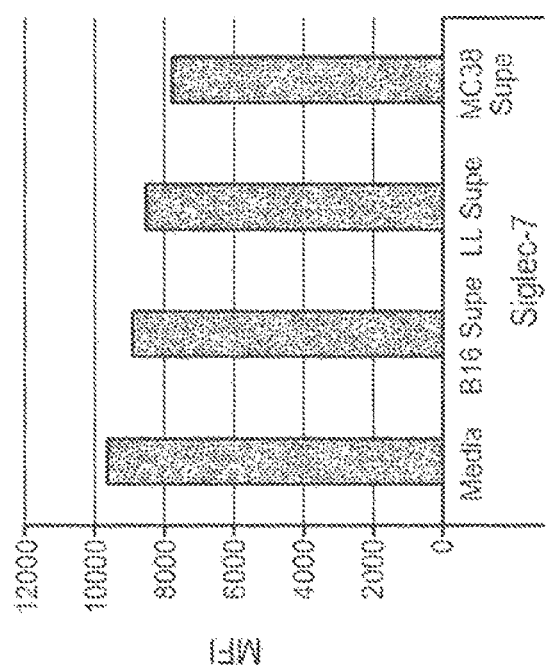
FIG. 11A-11H depict results showing Siglec-7 receptor and increased Siglec-7 ligand expression on human myeloid cells induced by various stimuli.
Figure 11B:
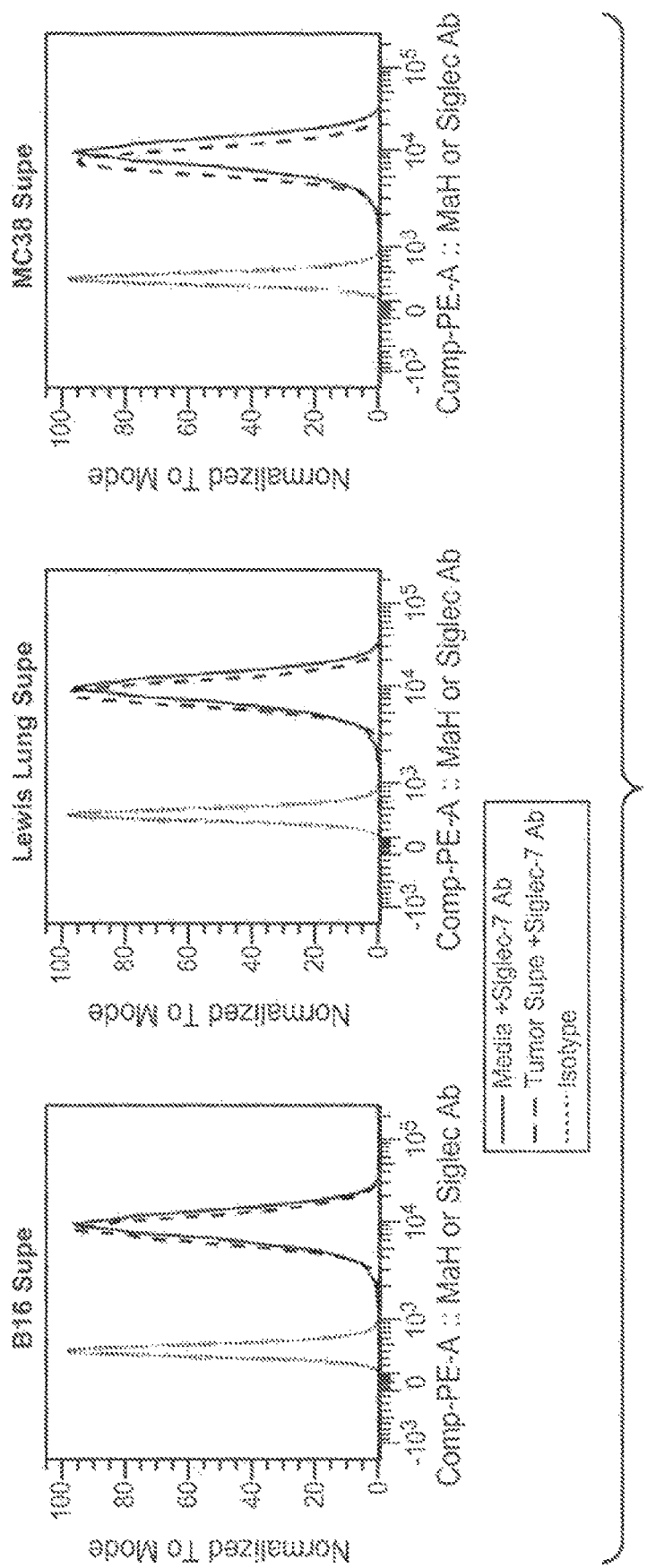
Figure 11C:
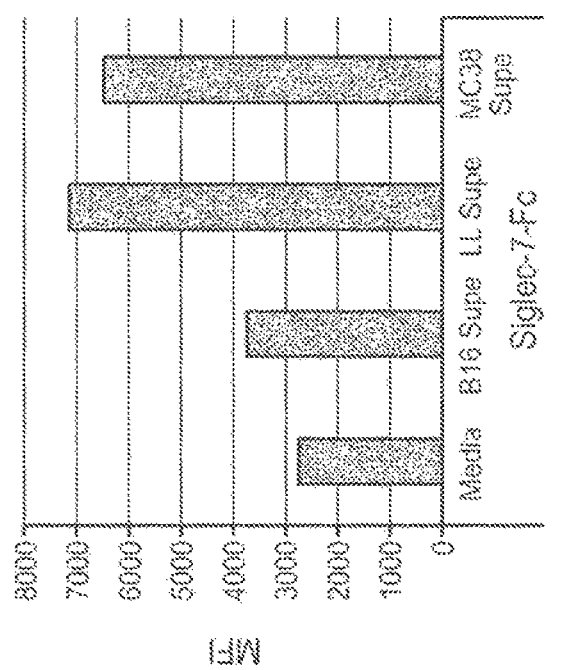
Figure 11D:
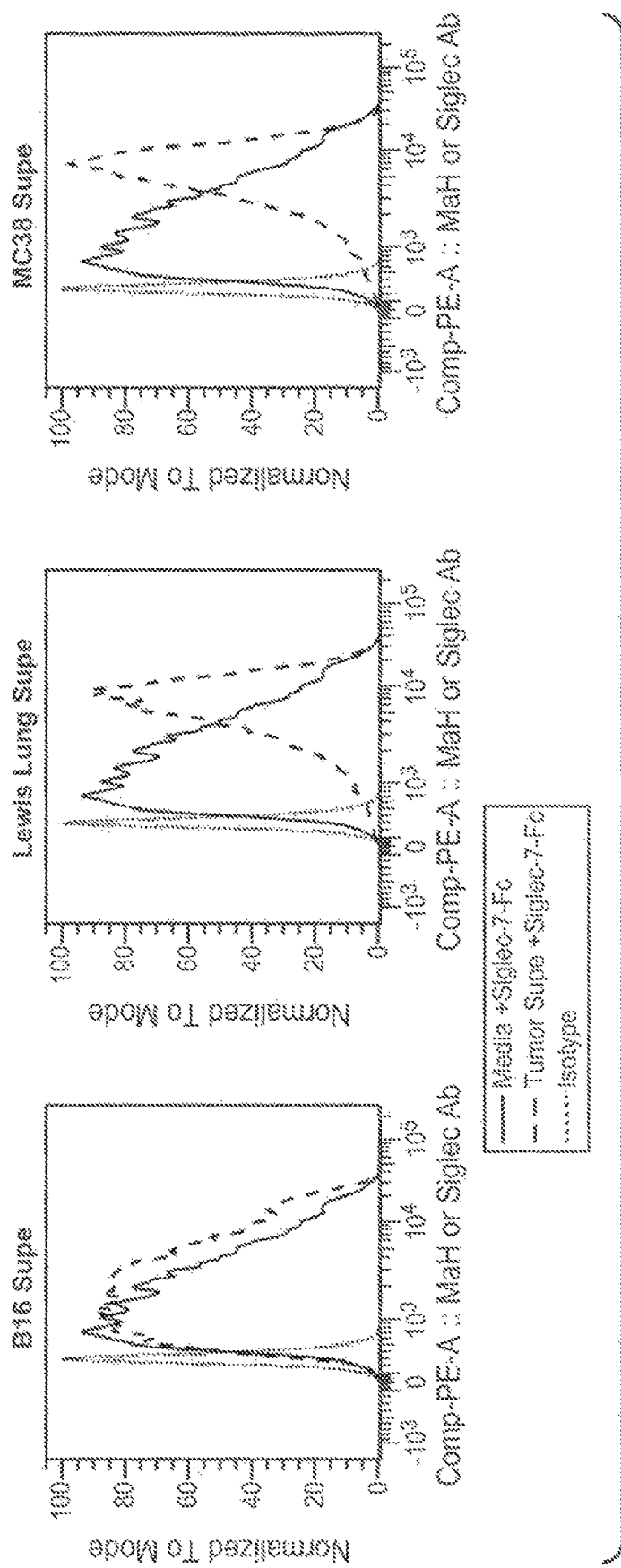
Figure 11F:
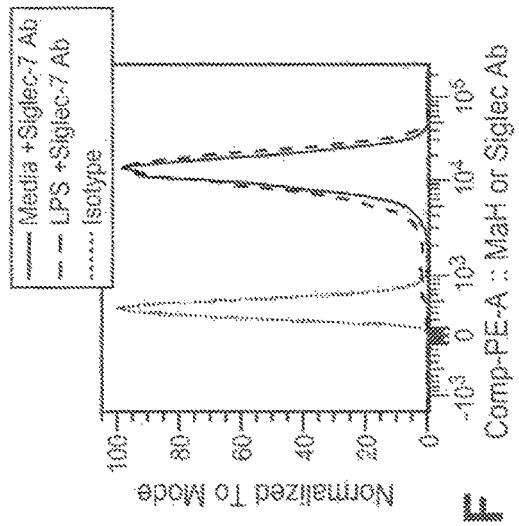
Figure 11H:
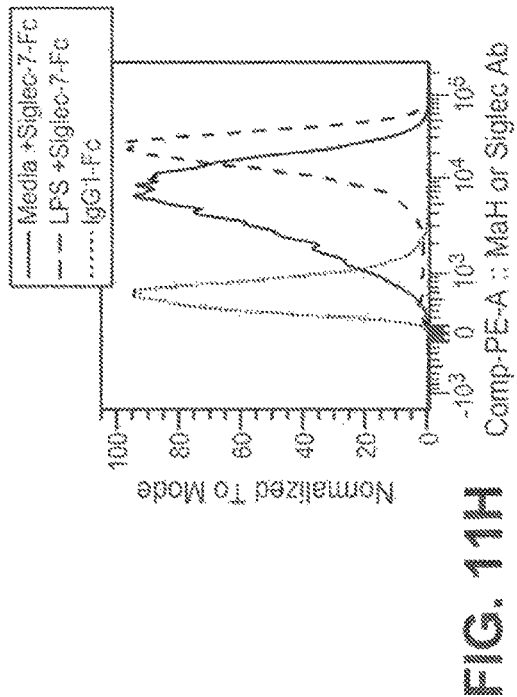
Figure 11E:
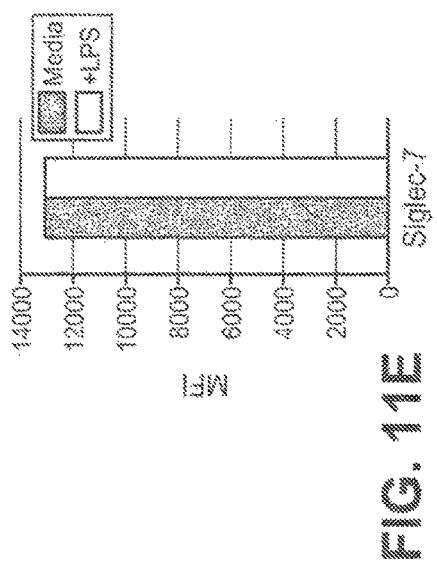
Figure 11G:
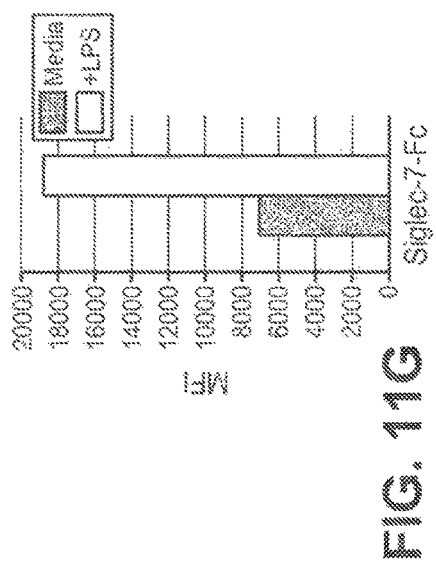

FIGS. 11A and 11B show that Siglec-7 expression is maintained on human dendritic cells after exposure to tumor supernatant. FIGS. 11C and 11D show that tumor supernatant increases expression of sialic acid (a Siglec-7 ligand). FIGS. 11E and 11F show that Siglec-7 expression is maintained on human dendritic cells during LPS-induced inflammation. FIGS. 11G and 11H show that LPS-induced inflammation increases expression of sialic acid (a Siglec-7 ligand).

These results indicate that inflammatory conditions and tumor environment lead to upregulation of both Siglec-7 and sialic acid ligands. The results also demonstrate that increased Siglec-7 function can immunosuppress human primary dendritic cells. These results indicate that inhibiting Siglec-7 with downregulating or blocking antibodies may relieve immunosuppressed myeloid-derived or tumor-associated myeloid cells and restore immune function. These results further indicate that antibodies that block Siglec-7 on myeloid cells enhance myeloid cell functionality.

Example 8: Increased *E. coli* Phagocytosis by Dendritic Cells with Sialidase Treatment The purpose of the following Example was to test whether antagonistic anti-Siglec-7 antibodies and/or Siglec-7 bispecific antibodies induce phagocytosis of apoptotic neurons, nerve tissue debris, non-nerve tissue debris, bacteria, other foreign bodies, and disease-causing proteins, such as A beta peptide, alpha synuclain protein, Tau protein. TDP-43 protein, prion protein, huntingtin protein, RAN, translation products antigene, including the DiPeptide Repeats, (DPRs peptides) composed of glycine-alanine (GA), glycine-proline (GP), glycine-arginine (GR), proline-alanine (PA), or proline-arginine (PR) in cells from the myeloid lineage, such as monocytes, dendritic cells macrophages and microglia. The bispecific antibodies may be antibodies that recognize the Siglec-7 antigen and a second antigen that includes, without limitation, CD3, A beta peptide, antigen or an alpha synuclain protein antigene or, Tau protein antigene or, TDP-43 protein antigene or, prion protein antigene or, huntingtin protein antigene, or RAN, translation Products antigene, including the DiPeptide Repeats, (DPRs peptides) composed of glycine-alanine (GA), glycine-proline (GP), glycine-arginine (GR), proline-alanine (PA), or proline-arginine (PR).

Monocytes from peripheral human blood samples were isolated using the RosetteSep™ monocyte isolation antibody cocktail (StemCell Technologies), and differentiated into dendritic cells with GM-CSF and IL-4 (PeproTech) and cultured for 5 days. Cells were plated on culture dishes in RPMI medium (Invitrogen) containing 10% fetal calf serum (Hyclone) and cultured at 37° C. in 5% $CO_2$. Non-adherent cells were collected and used for phagocytosis experiments.

To conduct bacterial phagocytosis assay, dendritic cells were harvested and plated in 96 well flat bottom plates without cytokine for 2 hours, pHrodo-labeled *E. coli* BioParticles were resuspended according to manufacturer's protocol and were treated with 0.2 U/ml or 0.4 U/ml sialidase from Vibro cholera, or PBS alone for 2.5 hours at 37° C. BioParticles were washed, resuspended in RPMI and added 20 µg/well. Dendritic cells and *E. coli* cells were mixed, pelleted, and incubated at 37 C for 30 minutes. Cytochalasin D was added at 10 µM to control wells. Immediately prior to FACS analysis, cells were transferred to ice and washed 2× in FACS buffer at 4° C. pHrodo-labeled *E. coli* phagocytosis was detected in the PE channel by flow cytometry on a BD FACS Canto.

Figure 12:
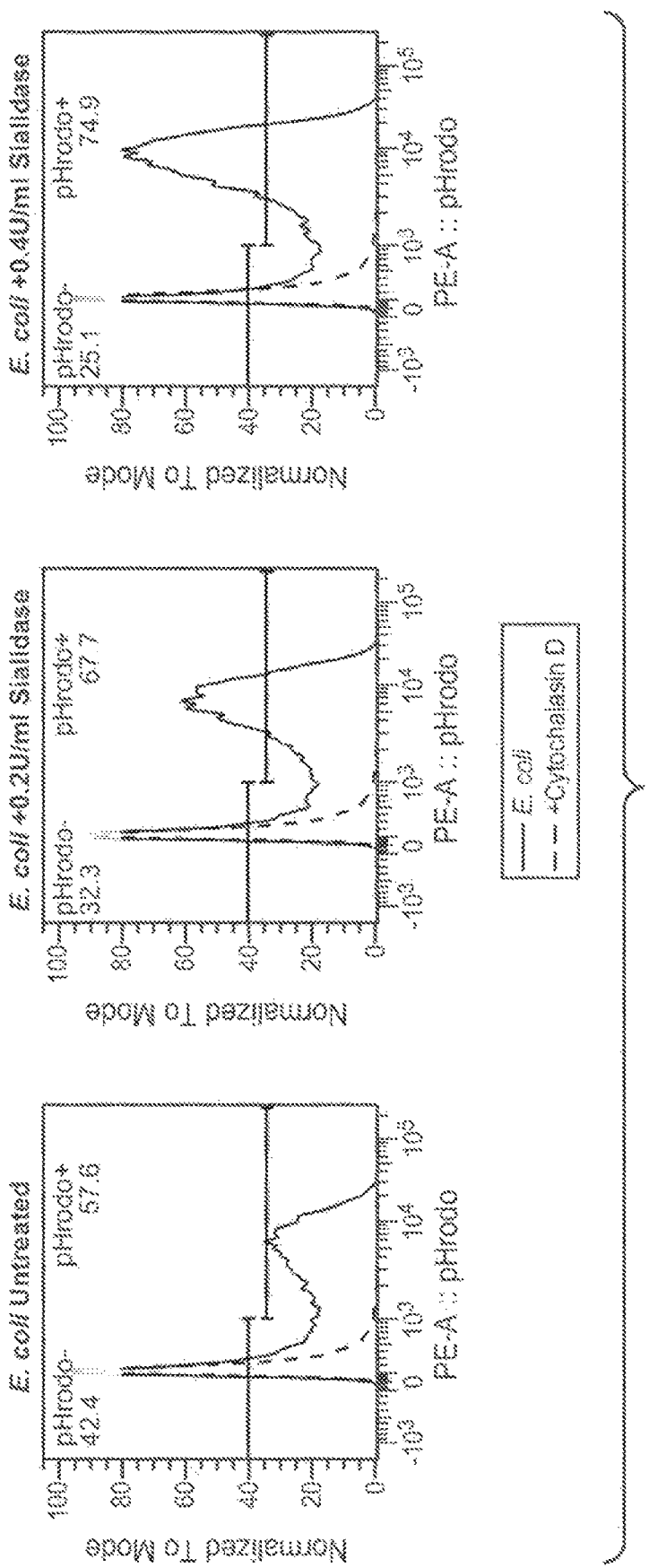
FIG. 12 depicts results showing that sialidase treatment to remove Siglec-7 ligands from E. coli increases phagocytosis by human primary dendritic cells.

FIG. 12 shows that sialidase treatment increased dendritic cell-mediated phagocytosis of *E. coli*. These results indicate that antagonistic anti-Siglec-7 antibodies and/or Siglec-7 bispecific antibodies that, for example, decrease cell surface expression of Siglec-7 and/or inhibit the binding of one or more Siglec-7 ligands to Siglec-7 can also be used to induce or otherwise increase phagocytosis.

Example 9: Increased Expression of Siglec-7 Ligand in Brain Sections of Alzheimer's Disease Patients Sialic acid ligand expression was detected in the brains of normal and Alzheimer's disease (AD) patients by immunohistochemistry with biotinylated Siglec-7-Fc (R&D). The Siglec-7-Fc protein was biotinylated with the EZ-Link Sulfo-NHS-Biotin (Thermo Scientific) according to manufacturer's instructions. The IHC procedure, with the exception of the overnight incubation, was performed on a shaker. Samples were incubated for 15 minutes in 10% MeOH, 3% $H_2O_2$ in PBS, followed by 3 washes in PBS with 4% serum. Next, samples were incubated for 30 minutes in 0.2% triton-X, 4% serum, 0.019% L-lysine in PBS, followed by an hour in primary antibody then overnight at 4 C in PBS with 4% serum. The next day samples were placed on a shaker for one hour followed by 3 washes, then samples were incubated for one hour in ABC buffer and washed 3 times. Samples were developed with a Vector DAB peroxidase kit, washed 3 times and dehydrated and imaged with a Nikon 90i microscope with color camera, magnification of 200×. The quantification was performed using Nikon Elements BR image analysis software.

Figure 13A:
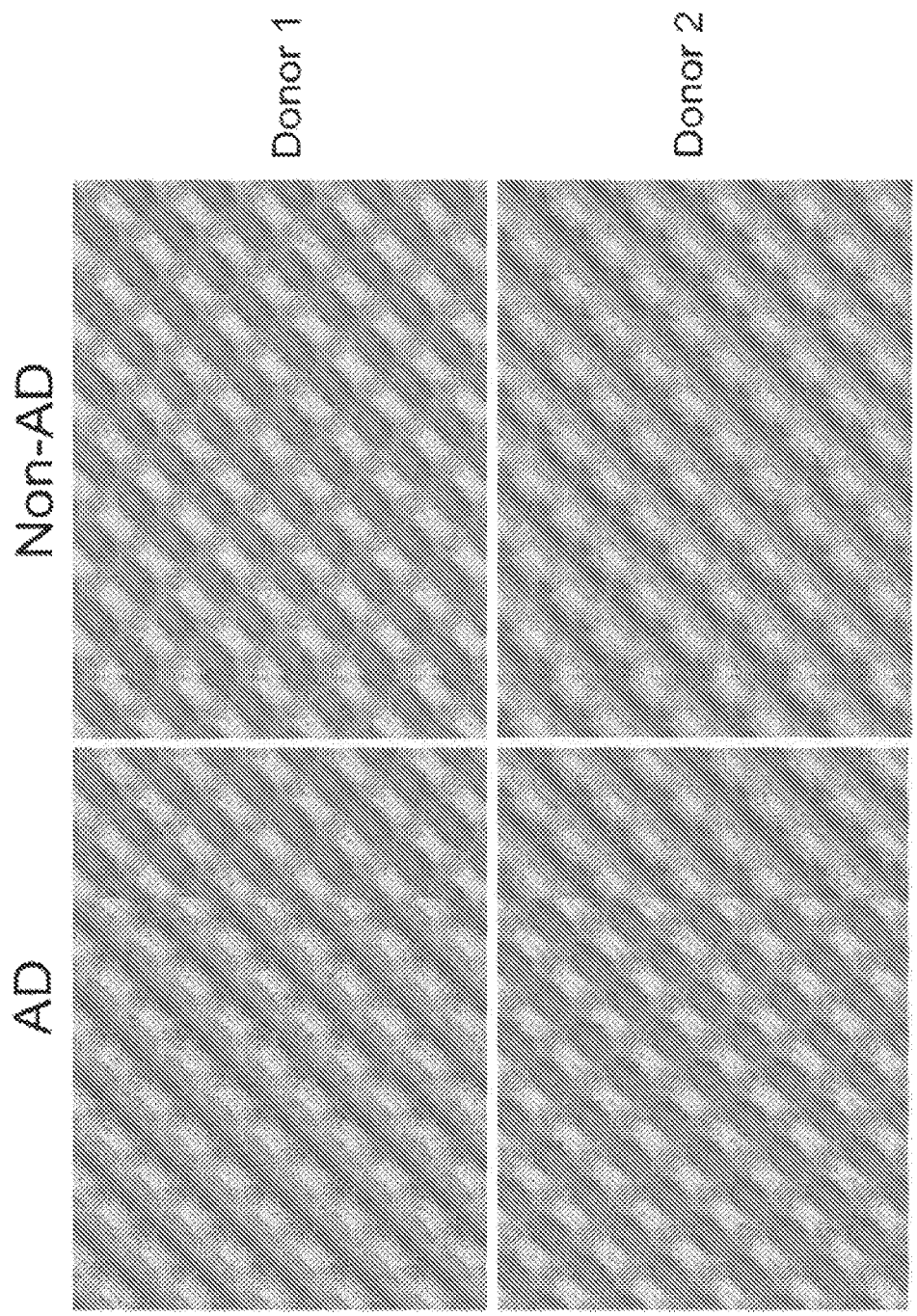
FIGS. 13A and 13B depict Siglec-7 ligand expression in brain sections from an Alzheimer's disease brain (AD) and a healthy brain (non-AD).
Figure 13B:
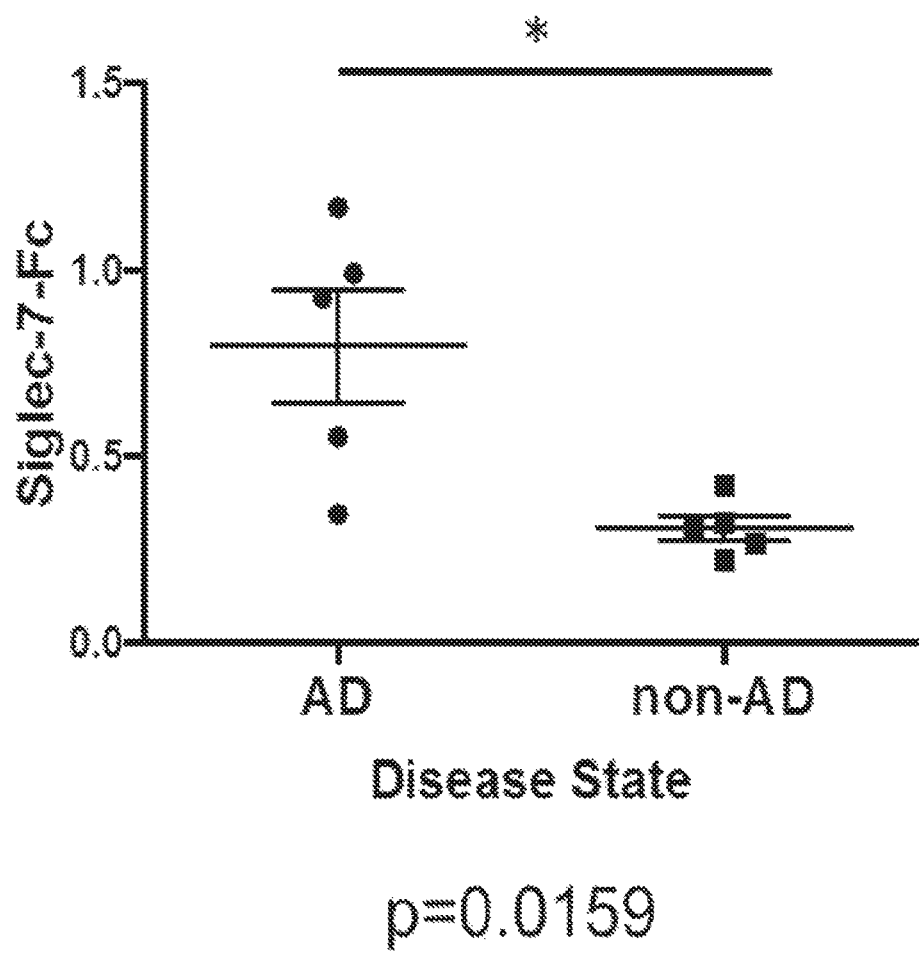

FIGS. 13A and 13B show that sialic acid Siglec-7 ligands are upregulated in brain sections from two AD patients (Donor 1 and Donor 2). Data from 5 AD and 5 non-AD human brains show a statistically significant increase in expression of Siglec-7 sialic acid ligands by one way ANOVA, p=0.0159 (FIG. 13B).

These results indicate that antibodies that remove Siglec-7 from the cell surface or block increased ligand interactions may relieve inhibitory Siglec-7-dependent signaling on microglia or other myeloid cells in the brain and restore normal functions to these cells, with beneficial effects for Alzheimer's disease.

Example 10: Increased Expression of Siglec-7 Ligand in Cancer Cells

In Vitro Studies

Mouse melanoma (B16), Lewis lung tumor cells, or colon carcinoma (MC38) were cultured and incubated with 50 ug/ml Siglec-7-Fc or an IgG1-Fc control on ice for 30 minutes to determine the level of Siglec-7 binding sialic acid ligand expression on these cell types. Binding interactions were performed in PBS with 0.25% BSA, 1 mM $CaCl_2$. To detect Siglec-7 receptor binding, a goat anti-human Fc-PE secondary antibody was incubated for 30 minutes on ice after washing off unbound Siglec-7-Fc. Cells were washed three times in Binding Buffer and analyzed by flow cytometry on a BD FACS Canto.

Figure 14:
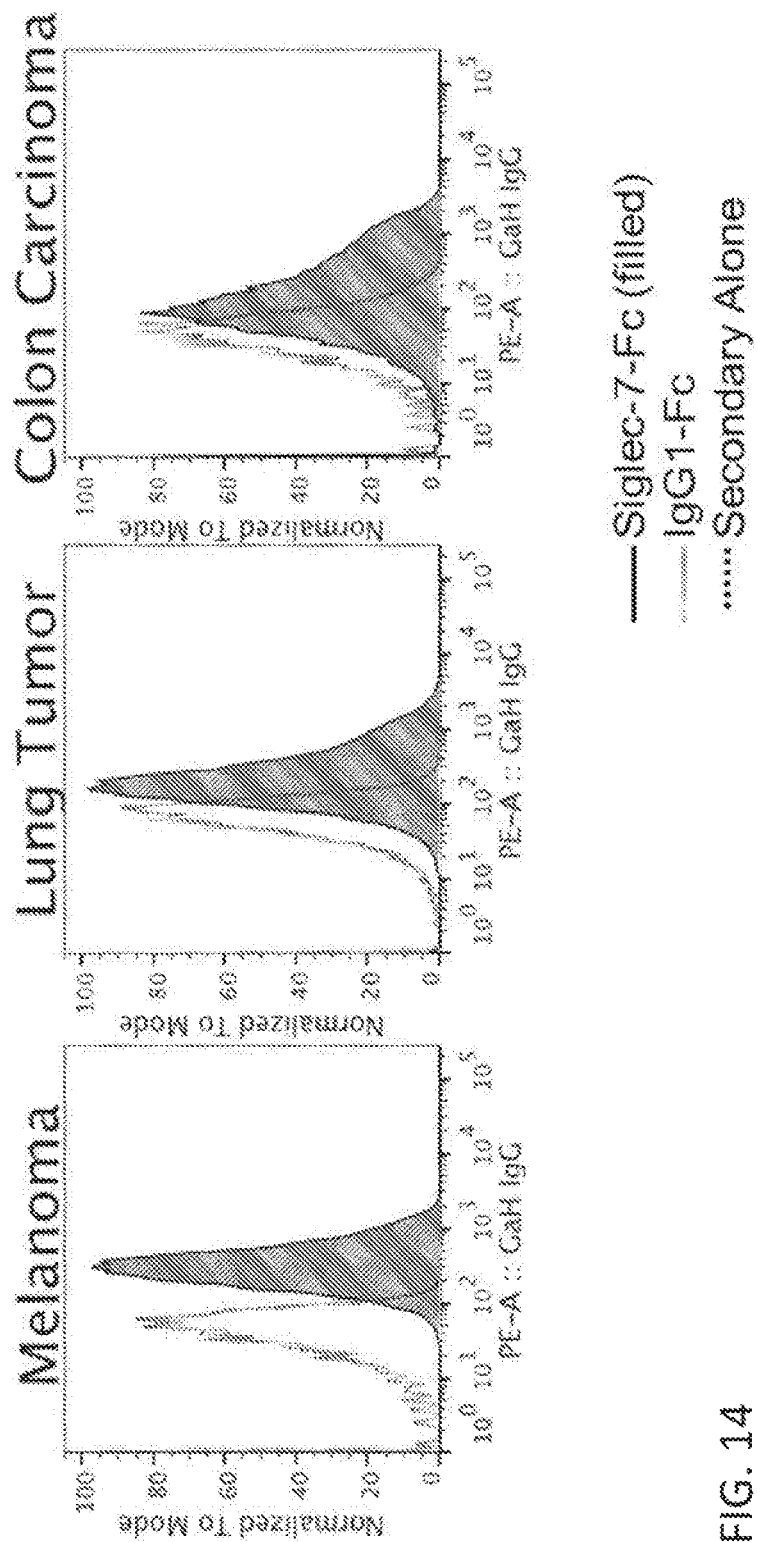
FIG. 14 depicts results showing that expression of inhibitory Siglec-7 ligands is increased in lung tumor cells, melanoma cells, and colon cancer cells. The results indicate that inhibitory Siglec-7 ligands contribute to cancer pathology in these tumor types.

FIG. 14 shows that the expression of an inhibitory Siglec-7 ligand is increased at least 20-fold over background in melanoma cells, lung tumor cells, and colon cancer cells. Without wishing to be bound by theory, identification of inhibitory sialic acid ligand expression on these tumor cells indicates a contributing mechanism by which cancer cells evade immune recognition and clearance. Sialic acid ligands on tumor cells can mediate immunosuppressive interactions via Siglec-7 expressed on myeloid and lymphoid immune cells. These results indicate that antibodies that remove Siglec-7 from the cell surface or block increased ligand interactions may relieve inhibitory effects of tumors on the immune system and enhance cancer therapy.

In Vivo Studies

Four week-old female Taconic NOG mice were myeloablated approximately 24 hours before engraftment with human fetal liver $CD34^+$ cells (100.000 cells/mouse) by intravenous injection. Reconstitution of immune cells was monitored by flow cytometry of peripheral blood. Twelve weeks after engraftment, the Champions tumorgraft melanoma model was implanted subcutaneously. Approximately 8-10 weeks later, when the tumor reached a size of 150-200 $mm^3$, blood, spleen and tumors were harvested and processed for analysis by flow cytometry on a BD FACS Canto. Flow cytometric analysis was performed to determine the expression of Siglec-7 in different compartments of the human ($hCD45^+$) immune system. Specifically, expression was analyzed in $CD3^+$ T cells, $CD14^+$ monocyte/macrophages and other CD3-CD14− human immune cells cells. Data were analyzed with FlowJo software version 10.0.6 by TreeStar.

Figure 15:
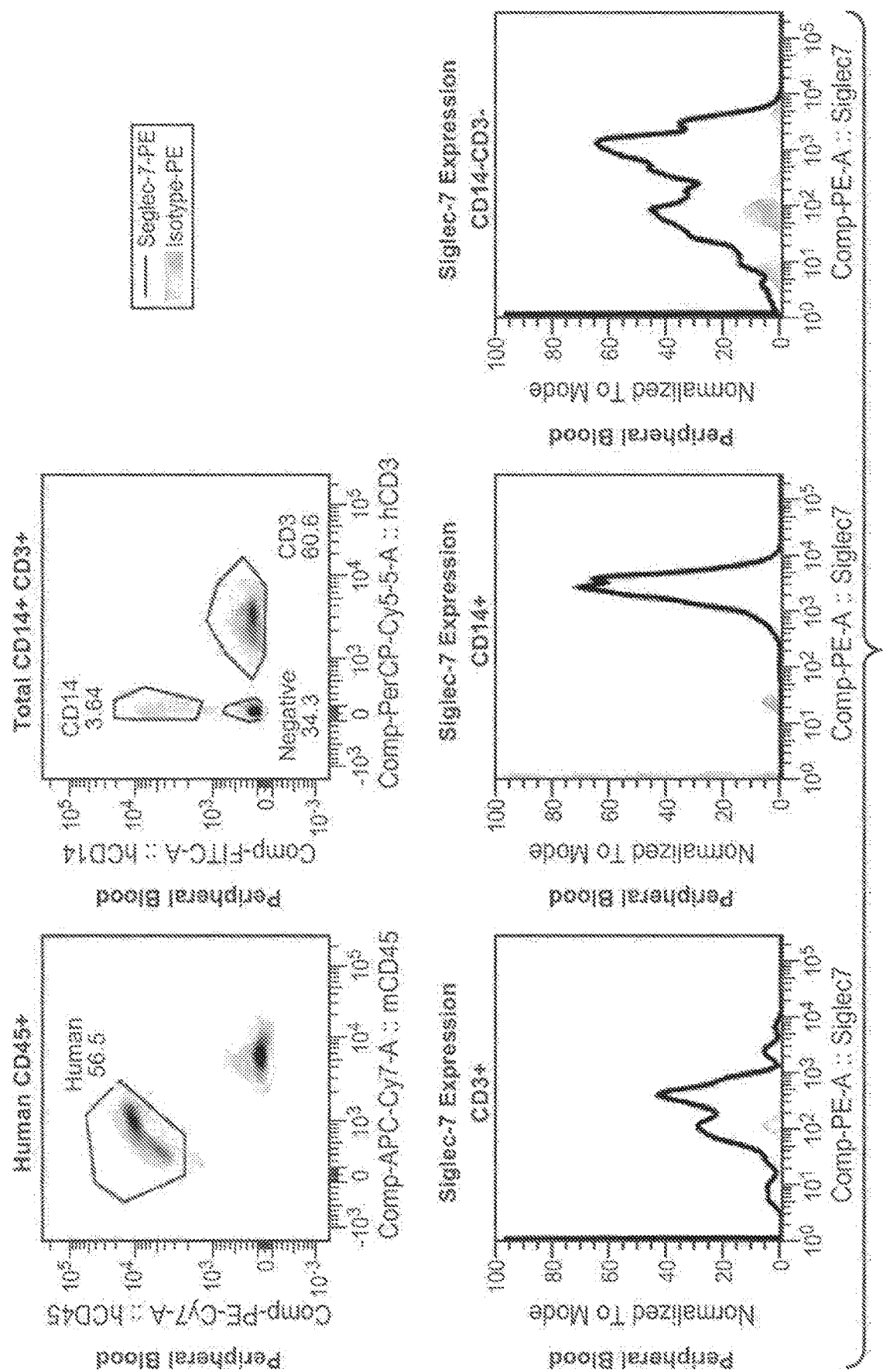
FIG. 15 depicts expression of Siglec-7 in cells of NOG mice injected with human peripheral blood cells. 12 weeks after engraftment with human fetal liver $CD34^+$ cells, humanized mice were transplanted with patient-derived melanoma. Peripheral blood, spleen, and tumor tissues were dissociated and analyzed for immune cell markers and Siglec-7 expression. For FACS analysis, human hematopoietic cells were identified by CD45 expression, then gated CD14+, CD3+ populations. The results indicate that inhibitory Siglec-7 ligands contribute to cancer pathology in this tumor type.
Figure 15:
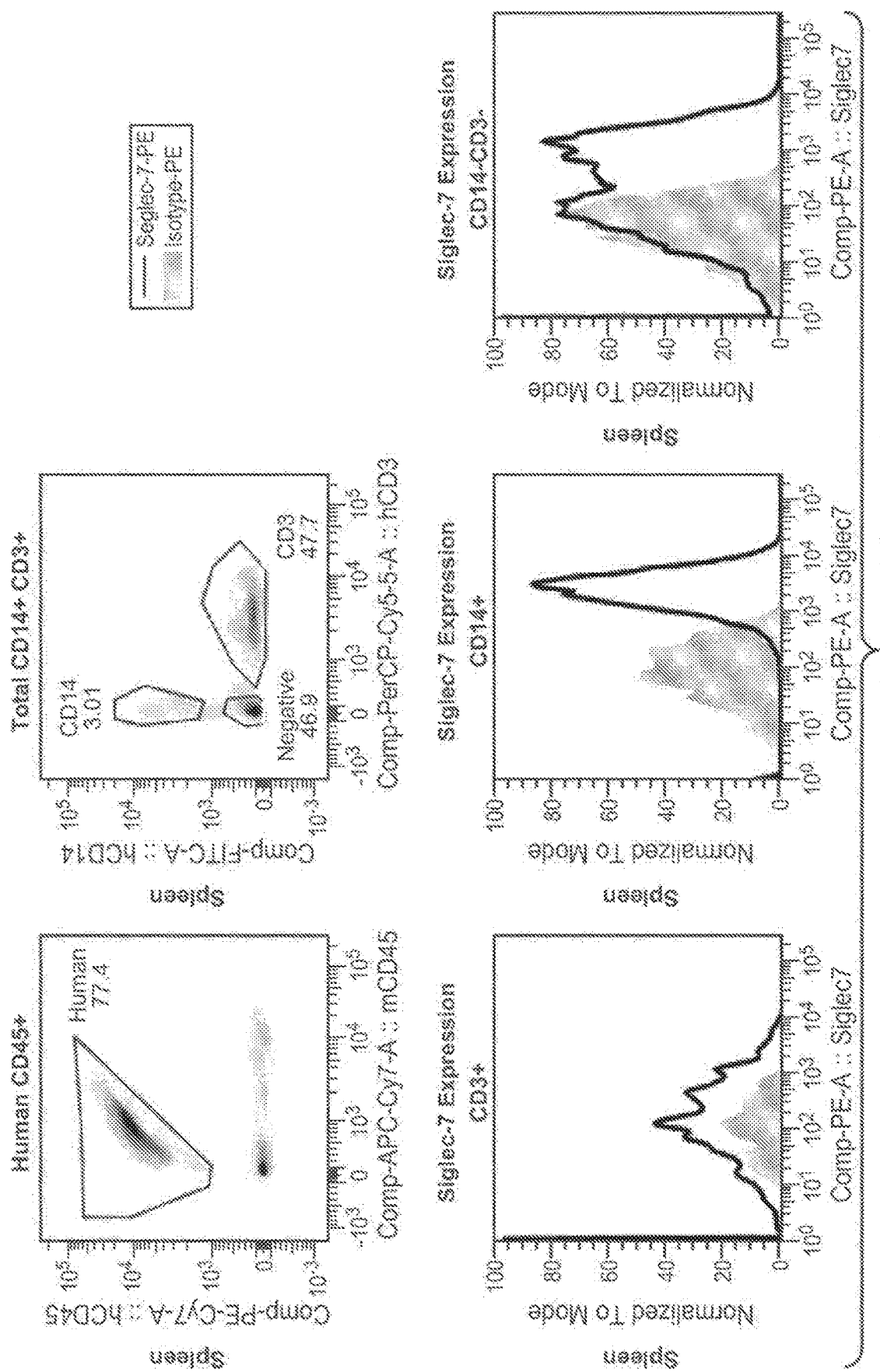
Figure 15:
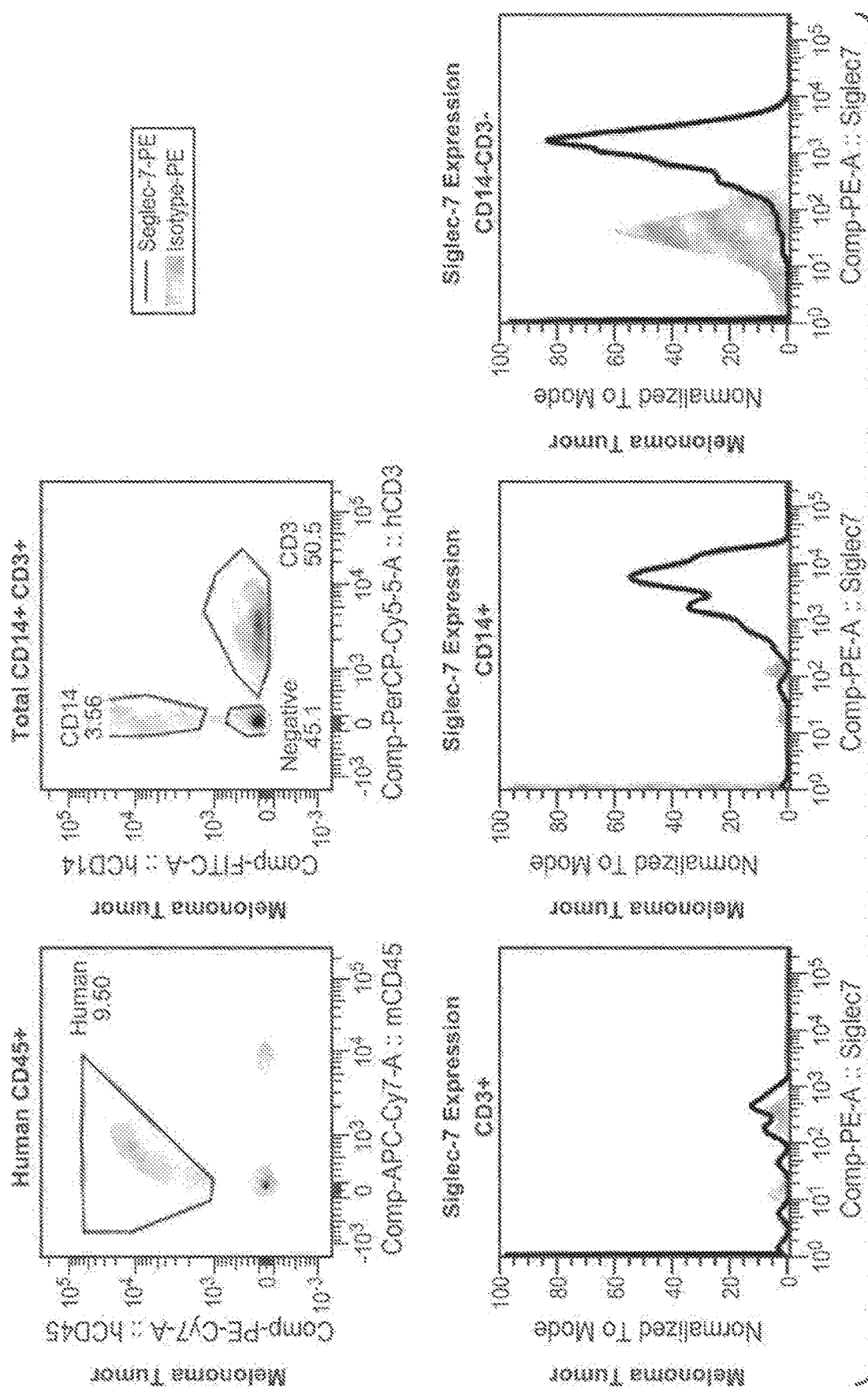

As depicted in FIG. 15, the results indicated that Siglec-7 is expressed in peripheral blood, spleen, and tumor infiltrating immune cells in transplanted melanoma tumors of humanized mice. Importantly, Siglec-7 is significantly upregulated in human immune cells infiltrating melanoma tumors. This demonstrates the relevance of this mouse model to assessing the therapeutic ability of S Siglec-7 antibodies.

Example 11: Reduction of the Anti-Inflammatory Cytokine IL-10 in Myeloid Cells by Antagonistic and/or Bispecific Siglec-7 Antibodies The purpose of this Example is to test whether bone marrow-derived myeloid cells show a decrease in the anti-inflammatory cytokine IL-10 and other anti-inflammatory mediators following treatment with antagonistic anti-Siglec-7 and/or Siglec-7 bispecific antibodies and stimulation with 100 ng/ml LPS (Sigma), by co-culturing with apoptotic cells, or by a similar stimulus.

Isolation of human myeloid precursor cells is performed as previously described. Medium is changed after 5 d and cells are cultured for an additional 10-11 d. Supernatant is collected after 24 h, and the level of IL-10 and other anti-inflammatory cytokines released from the cells is determined by IL-10 ELISA according to manufacturer's instructions (R&D Systems) (JEM (2005), 201; 647-657; and PLoS Medicine (2004), 4|Issue 4|e124).

Example 12: Induction of Phagocytosis in Cells from the Myeloid Lineage by Antagonistic and/or Bispecific Siglec-7 Antibodies The purpose of this Example is to test whether antagonistic anti-Siglec-7 antibodies and/or Siglec-7 bispecific antibodies induce phagocytosis of apoptotic neurons, nerve tissue debris, non-nerve tissue debris, bacteria, other foreign bodies, and disease-causing proteins, such as A beta peptide, alpha synuclain protein. Tau protein, TDP-43 protein, prion protein, huntingtin protein, RAN, translation products antigene, including the DiPeptide Repeats, (DPRs peptides) composed of glycine-alanine (GA), glycine-proline (GP), glycine-arginine (GR), proline-alanine (PA), or proline-arginine (PR) in cells from the myeloid lineage, such as monocytes, Dendritic cells macrophages and microglia. The bispecific antibodies may be antibodies that recognize the Siglec-7 antigen and a second antigen that includes, without limitation. A beta peptide, antigen or an alpha synuclain protein antigene or, Tau protein antigene or, TDP-43 protein antigene or, prion protein antigene or, huntingtin protein antigene, or RAN, translation Products antigene, including the DiPeptide Repeats, (DPRs peptides) composed of glycine-alanine (GA), glycine-proline (GP), glycine-arginine (GR), proline-alanine (PA), or proline-arginine (PR).

Monocytes from peripheral human blood samples are isolated using the RosetteSep monocyte isolation antibody cocktail (StemCell Technologies) and differentiated into macrophages, neutrophils, and NK cells with 50 µg/ml M-CSF (PeproTech) for 5 days. Cells are plated on culture dishes in RPMI medium (Invitrogen) containing 10% fetal calf serum (Hyclone) and cultured at 37° C. in 5% $CO_2$. Adherent cells are collected by gentle scraping and used for phagocytosis experiments.

Human microglial cells are prepared from peripheral blood monocytes by culture in serum-free RPMI with 1% Pen/Strep, 10 ng/ml GM-CSF, 10 ng/ml M-CSF, 10 ng/ml beta-NGF, 100 ng/ml CCL-2, 100 ng/ml IL-34 according to protocols described in Etemad et al., *JI* (2012), and Ohgidani et al., *Scientific Reports* (2014). Cells were harvested at day 7-10 when ramified morphology appeared.

To conduct phagocytosis assays microglia, macrophages, neutrophils, NK cells or dendritic cells are cultured with apoptotic neurons, nerve tissue debris, non-nerve tissue debris, bacteria, other foreign bodies, and disease-causing proteins. Neurons are cultured for 5-10 d, and okadaic acid is then added at the final concentration of 30 nM for 3 h to induce apoptosis. Neuronal cell membranes are labeled with CellTracker CM-DiI membrane dye (Molecular Probes). After incubation, apoptotic neurons or other targets of phagocytosis are washed two times and added to the transduced microglial culture at an effector/target ratio of 1:20. At 1 and 24 h after addition of apoptotic neurons, the number of microglia having phagocytosed neuronal cell membranes is counted under a confocal fluorescence microscope (Leica). Apoptotic cells are counted in three different areas at a magnification of 60. The amount of phagocytosis is confirmed by flow cytometry. Moreover, 24, 48, or 72 h after the addition of apoptotic neurons, cells are collected and used for RT-PCR of cytokines.

To conduct microsphere bead or bacterial phagocytosis assay, microglia, macrophages, neutrophils, NK cells, or dendritic cells are treated with anti-Siglec-7 agonistic antibodies. Cells are harvested and plated in 96 well flat bottom plates without cytokine for 2 hours, pHrodo-labeled E. coli BioParticles are resuspended according to manufacturer's protocol and are treated with 0.2 U/ml or 0.4 U/ml sialidase from Vibro cholera, or PBS alone for 2.5 hours at 37 C. BioParticles are washed, resuspended in RPMI and added 20 ug/well. Cells and E. coli were mixed, pelleted, and incubated at 37 C for 30 minutes. Cytochalasin D is added at 10 uM to control wells. Immediately prior to FACS analysis, cells are transferred to ice and washed 2× in FACS buffer at 4 C. The pHrodo-labeled E. coli phagocytosis is detected in the PE channel by flow cytometry on a BD FACS Canto.

After 24 h, 1.00 μm of red fluorescent microsphere beads (Fluoresbrite Polychromatic Red Mi-crospheres; Polysciences Inc.) are added for 1 h. Phagocytosis of microsphere beads by microglia is analyzed by fluorescence microscopy. Furthermore, microglia are collected from the culture plates and analyzed by flow cytometry. The percentage of microglia having phagocytosed beads is determined. Because phagocytosis varies from one experiment to the other, the relative change in phagocytosis is also determined. Data are shown as the relative change in phagocytosis between microglia cultured with agonistic antibodies and control antibody.

To conduct RT-PCR for analysis of inflammatory gene transcripts, microglia are transduced with a Siglec-7 vector or a GFP1 control vector. Cells are then cultured on dishes and treated with anti-Siglec-7 agonistic antibodies. After 24, 48, and 72 h. RNA is isolated from microglia using an RNeasy Mini Kit (QIAGEN). RNA is also collected from microglia that have been transduced with sh-Siglec-7 RNA, sh-control RNA, wSiglec-7, GFP2, mtDAP12-GFP, and GFP1 vector and co-cultured with apoptotic neurons for 48 h.

Reverse transcription of RNA is then performed. Quantitative RT-PCR by SYBR Green is performed on an ABI Prism 5700 Sequence Detection System (PerkinElmer). Amplification of GAPDH is used for sample normalization. The amplification protocol followed the GeneAmp 5700 Sequence Detection System Software (version 1.3). For detection of GAPDH, TNF-alpha, IL-1. NOS2, and TGF-beta transcripts, the following forward and reverse primers were used at final concentrations of 200 nM:

```
GAPDH forward primer:
                                  (SEQ ID NO: 526)
5'-CTCCACTCACGGCAAATTCAA-3',
and GAPDH reverse primer:
                                  (SEQ ID NO: 527)
5'-GATGACAAGGTTCCCATTCTCG-3';

TNF-α forward primer:
                                  (SEQ ID NO: 528)
5'-CCGTCAGCCGATTTGCTATCT-3',
and TNF-α reverse primer:
                                  (SEQ ID NO: 529)
5'-ACGGCAGAGAGGAGGTTGACTT-3';

IL-1α forward primer:
                                  (SEQ ID NO: 530)
5'-ACAA-CAAAAAAGCCTCGTGCTG-3',
and IL-1α reverse primer:
                                  (SEQ ID NO: 531)
5'-CCATTGAGGTGGAGAGCTTTCA-3';

NOS2 forward primer:
                                  (SEQ ID NO: 532)
5'-GGCAAACCCAAGGTCTACGTTC-3', NOS2 reverse primer:
                                  (SEQ ID NO: 533)
5'-TACCTCATTGGCCAGCTGCTT-3';
and TGF-β1 forward primer:
                                  (SEQ ID NO: 534)
5'-AGGACCTGGGTTGGAAGTGG-3',
and TGF-β1 reverse primer:
                                  (SEQ ID NO: 535)
5'-AGTTGGCATGGTAGCCCTTG-3',
```

To conduct amyloid phagocytosis assay, HiLyteFluor™ 647 (Anaspec)-Abeta-(1-40) is resuspended in Tris/EDTA (pH8.2) at 20 mM and then incubated in the dark for 3 d at 37° C. to promote aggregation. Microglia, macrophages, neutrophils, NK cells, or dendritic cells are pretreated in low serum (0.5% FBS supplemented with insulin), LPS (50 ng/ml), IFNc (100 units/ml), and anti-Siglec-7 antagonistic antibodies for 24 h prior to the addition of aggregated fluorescently labeled a beta peptide. Amyloid phagocytosis and surface expression of Siglec-7 are determined by flow cytometric analysis 5 h post-addition of 100 nM aggregated HiLyteFluor™ 647-Ab-(1-40) (ASN NEURO (2010) 2(3): 157-170). Phagocytosis of other disease-causing proteins is conducted in a similar manner.

Example 13: Induction of SYK and/or ERK Activation by Antagonistic Siglec-7 Antibodies and/or Bispecific Antibodies The purpose of this Example is to test whether agonistic anti-Siglec-7 antibodies and/or Siglec-7 bispecific antibodies induce Syk and ERK activation.

Microglia, macrophages, neutrophils, NK cells, or dendritic cells are exposed to agonistic anti-Siglec-7 and/or Siglec-7 bispecific antibodies for 1 h. After stimulation, cells are lysed in reducing sample buffer for Western blot analysis. Phosphorylation of ERK and total amount of Syk and/or ERK are determined by immuno-detection with anti-phospho-Syk or ERK and anti-Syk or ERK antibodies, respectively (both from Cell Signaling Technology) by Western blot analysis (JEM (2005), 201, 647-657).

Example 14: Siglec-7 Antibodies and/or Bispecific Antibodies Induce Syk Phosphor Lation Spleen tyrosine kinase (Syk) is an intracellular signaling molecule that functions downstream of Siglec-7 by phosphorylating several substrates, thereby facilitating the formation of a signaling complex leading to cellular activation and inflammatory processes. The ability of agonist Siglec-7 antibodies to induce Syk activation is determined by culturing human macrophages, human neutrophils, human NK cells, and human primary dendritic cells and measuring the phosphorylation state of Syk protein in cell extracts.

Human primary dendritic cells are starved for 4 hours in 1% serum RPMI and then removed from tissue culture dishes with PBS-EDTA, washed with PBS, and counted. The cells are coated with full-length agonist Siglec-7 antibodies, or control antibodies for 15 minutes on ice. After washing with cold PBS, cells are incubated at 37° C. for the indicated period of time in the presence of goat anti-human IgG. After stimulation, cells are lysed with lysis buffer (1% v/v NP-40%, 50 Mm Tris-HCl (pH8.0), 150 mM NaCl, 1 mM EDTA, 1.5 mM $MgCl_2$, 10% glycerol, plus protease and phosphatase inhibitors) followed by centrifugation at 16,000 g for 10 min at 4° C. to remove insoluble materials. Lysates are then immunoprecipitated with anti-Syk Ab (4D10 for human DCs, Santa Cruz Biotechnology). Precipitated proteins are fractionated by SDS-PAGE, transferred to PVDF membranes and probed with anti-phosphotyrosine Ab (4G10, Millipore). To confirm that all substrates are adequately immunoprecipitated, immunoblots are reprobed with anti-Syk (Novus Biological, for human DCs). Visualization is performed with the enhanced chemiluminescence (ECL) system (GE healthcare), as described (e.g., Peng et al., (2010) Sci Signal., 3(122): ra38).

Example 15: Induction of CCR7 and Migration Toward CCL19 and CCL21 in Microglia Macrophages, Neutrophils, NK Cells, and Dendritic Cells by Antagonistic Siglec-7 Antibodies and/or Bispecific Antibodies The purpose of this Example is to test whether anti-Siglec-7 antibodies and/or Siglec-7 bispecific antibodies induce CCR7 and migration toward CCL19 and CCL21 in microglial cells, macrophages, neutrophils, NK cells, and dendritic cells.

Microglial, macrophages or dendritic cells are either cultured with agonistic anti-Siglec-7 and/or Siglec-7/DAP12 bispecific antibodies, or with a control antibody. Cells are collected after 72 h, immuno-labeled with CCR7 specific anti-bodies, and analyzed by flow cytometry.

To determine any functional consequences of increased CCR7 expression, a chemotaxis assay is performed. Microglia, macrophages, neutrophils, NK cells, or dendritic cells are stimulated via Siglec-7 with the antagonistic anti-Siglec-7 and/or Siglec-7/DAP12 bispecific antibodies and placed in a two-chamber system. The number of microglial cells migrating toward the chemokine ligands CCL19 and CCL21 is quantified (JEM (2005), 201, 647-657).

For the chemotaxis assay, microglial, macrophages, neutrophils, NK cells, or dendritic cells are exposed to the antagonistic anti-Siglec-7 antibodies or Siglec-7 bispecific antibodies and treated with 1 µg/ml LPS. Microglia, macrophages, neutrophils, NK cells, or dendritic cells are transferred into the upper chamber of a transwell system (3 µm pore filter, Millipore) containing 450 µl medium with 100 ng/ml CCL19 or CCL21 (both from PeproTech) in the lower chamber. After a 1 h incubation period, the number of microglial macrophages, neutrophils, NK cells, or dendritic cells that have migrated to the lower chamber is counted in three independent areas by microscopy (JEM (2005), 201, 647-657).

Example 16: Induction of F-Actin in Microglia, Macrophages, Neutrophils, NK Cells, and Dendritic Cells by Antagonistic Siglec-7 Antibodies and/or Bispecific Antibodies The purpose of this Example is to test whether antagonistic anti-Siglec-7 antibodies, or Siglec-7 bispecific antibodies induce F-actin in microglial cells, macrophages, neutrophils, NK cells, and dendritic cells.

Microglia, macrophages, neutrophils, NK cells, or dendritic cells and other cells of interest that are transduced with Siglec-7 or that express Siglec-7 are added to culture plates and then exposed to antagonistic anti-Siglec-7 and/or Siglec-7 bispecific antibodies, or a control antibody. Cells are fixed, blocked, and then stained with Alexa Fluor 546-conjugated phalloidin (Molecular Probes) after 1 h and F-actin is labeled with a fluorescence dye. Images are collected by confocal laser scanning microscopy with a 40× objective lens (Leica). (JEM (2005), 201, 647-657).

Example 17: Induction of Osteoclast Production and Increased Rate of Osteoclastogenesis by Antagonistic Siglec-7 Antibodies and/or Bispecific Antibodies The purpose of this Example is to test whether antagonistic anti-Siglec-7 antibodies and/or Siglec-7 bispecific antibodies induce osteoclast production and increase the rate of osteoclastogenesis.

Human monocyte derived monocyte/macrophage are maintained in RPMI-1640 medium (Mediatech), or another appropriate medium, supplemented with 10% FBS (Atlantic Biologics, Atlanta, Ga., USA) and penicillin-streptomycin-glutamine (Mediatech). Cells are seeded in 96-well plates with 3000 cells/well in alpha-MEM medium supplemented with 10% FBS, penicillin-streptomycin-glutamine, 50 ng/ml RANKL, and 20 ng/ml M-CSF. The medium is changed every 3 days, exposed to anti-Siglec-7 antagonistic antibodies and the number of multinucleated (at least three nuclei) $TRACP^+$ osteoclasts are counted and scored by light microscopy. To determine complexity and size, osteoclasts are counted by number of nuclei (>10 or 3-10 nuclei). The surface area of osteoclasts is also measured by using Image J software (NIH). In addition, expression levels of osteoclasts genes are determined. Total RNA is extracted from osteoclastogenic cultures at different time points using TRIzol reagent (Invitrogen). After first-strand cDNA synthesis using a SuperScript III kit (Invitrogen), real-time quantitative PCR reactions are performed for Nfatc1, Acp5, Ctsk, Calcr, and CcndI. Relative quantification of target mRNA expression is calculated and normalized to the expression of cyclophilin and expressed as (mRNA of the target gene/mRNA of cyclophilin) $3\times10^6$. (J. OF BONE AND MINERAL RESEARCH (2006), 21, 237-245; J Immunol 2012; 188:2612-2621).

Alternatively, macrophages, neutrophils, or NK cells are seeded onto the plates in triplicate wells and treated with RANKL, M-CSF, and with an anti-Siglec-7 and/or Siglec-7 bispecific antibody, or an isotype-matched control monoclonal antibody. The medium is changed every 3 days until large multinucleated cells are visible. After 3 to 5 days in culture, cells are fixed with 3.7% formaldehyde in PBS for 10 min. Plates are then washed twice in PBS, incubated for 30 s in a solution of 50% acetone and 50% ethanol, and washed with PBS. Cells are stained for tartrate-resistant acid phosphatase (TRAP) with a kit from Sigma (product 435). Multinucleated (more than two nuclei), TRAP-positive cells are then counted by light microscopy, as described (e.g., Peng et al., (2010) Sci Signal., 3(122); ra38).

Example 18: In Vivo Protection from EAE and Cuprizone in a Whole Animal

Adult 7-9 week-old female C57BL/6 mice (obtained from Charles River Laboratories) are injected in the tail base bilaterally with 200 µl of an innoculum containing 100 µg of myelin oligodendrocyte glycoprotein peptide 35-55 (amino acids MEVGWYRSPFSRVVHLYRNGK (SEQ ID NO: 536); Seqlab) and 1 mg of *Mycobacterium tuberculosis* H37 Ra (Difco) in incomplete Freund adjuvant (Difco). Pertussis toxin (200 ng; List Bio-logical Laboratories) is injected at day 0 and at day 2 after immunization. Clinical signs are scored as follows: 0, no clinical signs; 1, complete limp tail; 2, complete limp tail and abnormal gait; 3, one hind-limb paraparesis; 4, complete hindlimb paraparesis; and 5, fore- and hind-limb paralysis or moribund. Only mice having disease onset (clinical score of 1 or more) at day 14 are used for experiments. Agonistic anti-Siglec-7 and/or Siglec-7 bispecific antibodies are injected intraperitoneally or intravenously in EAE-diseased mice at the day of the first clinical symptoms or at any other desired time (PLoS Med (2007) 4(4): e124).

Young or aged wild-type (WT) mice are fed a standard diet (Harlan) containing 0.2% cuprizone (CPZ) powdered oxalic bis(cyclohexylidenehydrazide) (Sigma-Aldrich) for 4, 6 or 12 weeks. For Histological and immunohistochemical analyses brains are removed after mouse perfusion with 4% paraformaldehyde (PFA), fixed in 4% PFA for 24 h, followed by immersion in 30% sucrose for 24-48 h. To evaluate myelin integrity and damage, as well as cell proliferation and inflammation sections or mouse brain are stained with anti-MBP (1:100; Abcam, ab7349), -dMBP (1:2000; Millipore, ab5864), -β APP (1:100; Invitrogen, 51-2700), -SMI-31 (1:1000; Covance, smi-31R), -Iba1 (1:600; Wako, 019-19741), -BrdU (1:250; Abcam, ab1893), -GFAP (1:200; Invitrogen, 13-0300), -iNOS (1:100; BD Pharmingen, 610329), -LPL (1:400, from Dr. G. Olivecrona) and -MHC II (1:100; BD Pharmingen, 553549). For behavioral effects of the antibodies, mice are analyzed for locomotor activity using transparent polystyrene enclosures and computerized photobeam instrumentation. General activity variables (total ambulations, vertical rearings), along with indices of emotionality including time spent, distance traveled and entries, are analyzed. A battery of sensorimotor tests is performed to assess balance (ledge and platform), strength (inverted screen), coordination (pole and inclined screens) and initiation of movement (walking initiation). Motor coordination and balance are studied using a rotarod protocol (Cantoni et al., Acta Neuropathol (2015)129(3): 429-47).

Example 19: Characterization of the Therapeutic Use of Antagonistic Siglec-7 Antibodies and/or Siglec-7 Bispecific Antibodies in Established Animal Models of Traumatic Brain Injury The therapeutic utility of antagonistic anti-Siglec-7 and/or Siglec-7 bispecific antibodies is tested in established animal models of traumatic brain injury (Tanaka, Y et al. (2013) Neuroscience 231 49-60). Either regular mice or mice that express the human Siglec-7 gene under a bacterial artificial chromosome or under a myeloid promoter can be used. For example, a model of traumatic brain injury that induces the activation of microglia and astrocytes is used. Eight or nine week-old male C57BL/6J WT mice are used (purchased from Charles River Laboratories or Jackson Laboratories). Mice are anesthetized by intraperitoneal administration of xylazine hydrochloride (8 mg/g) and chloral hydrate (300 mg/kg) dissolved in sterile saline, and subsequently placed in a stereotaxic apparatus (Narishige, Tokyo, Japan). An incision is made in the scalp and the cranium is exposed. The periosteum is cleaned from the skull, a hole is drilled over the right cerebral hemisphere with a dental drill, and the duramater is removed with a needle tip. A stainless steel cannula, with a 0.5 mm outer diameter, is used to make a longitudinal stab wound in the right hemisphere. The cannula is positioned at 1.3 mm lateral to the midline, and 1 mm posterior to bregma, and introduced into the brain until the tip reaches a depth of 2 mm. The cannula is then shifted 2 mm caudally (bregma 3 mm), and then shifts back 2 mm rostrally to its initial position. Finally, the cannula is removed from the brain, and the scalp wound is sutured. Mice are then treated with antagonistic anti-Siglec-7 and/or Siglec-7 bispecific antibodies according to standard procedures and then analyzed by histology and immunofluorescence staining and behavioral tests. Such experiment can be also conducted in in mice that express the human Siglec-7 gene from a bacterial artificial chromosome or from a cDNA driven by a myeloid promoter or in mice that were transduced with lenti or AAV virus containing hSiglec-7 cDNA.

Example 20: Characterization of Therapeutic Use of Antagonistic Siglec-7 Antibodies and/or Siglec-7 Bispecific Antibodies in a Model of Neuro-Inflammation and Neuron Loss Following Toxin-Induced Injury The therapeutic utility of agonistic anti-Siglec-7 and/or Siglec-7 bispecific antibodies is tested in a model of neuro-inflammation and neuron loss following toxin-induced injury (Martens, L H et al., (2012) The Journal of Clinical Investigation, 122, 3955). Three-month-old regular mice, are treated with 4 intraperitoneal injections of MPTP (1-methyl-4-phenyl-1,2,3,6-tetrahydropyridine) per day for 2 days (4 µg/g body weight) (Sigma-Aldrich) or PBS. Mice are treated with agonistic anti-Siglec-7 and/or Siglec-7 bispecific antibodies according to standard protocols and then analyzed using Stereological counting to quantify dopamine neurons and microglia in the substantia nigra pars compacta (SNpc), as described. Such experiment can be also conducted in in mice that express the human Siglec-7 gene from a bacterial artificial chromosome or from a cDNA driven by a myeloid promoter or in mice that were transduced with lenti or AAV virus containing hSiglec-7 cDNA.

Example 21: Characterization of the Therapeutic Use of Antagonistic Siglec-7 Antibodies and/or Siglec-7 Bispecific Antibodies in Animal Models of Aging, Seizures, Spinal Cord Injury, Retinal Dystrophy, Frontotemporal Dementia, and Alzheimer's Disease The therapeutic utility of antagonistic anti-Siglec-7 and/or Siglec-7 bispecific antibodies is tested in animal models for aging, seizures, spinal cord injury, retinal dystrophy, frontotemporal dementia, Huntington disease, Parkinson's disease amyotrophic lateral sclerosis and Alzheimer's disease, as previously described (e.g., Beattie, M S et al., (2002) Neuron 36, 375-386; Volosin, M et al., (2006) J. Neurosci. 26, 7756-7766; Nykjaer, A et al., (2005) Curr. Opin. Neurobiol. 15, 49-57; Jansen, P et al., (2007) Nat. Neurosci. 10, 1449-1457; Volosin, M et al., (2008) J. Neurosci. 28, 9870-9879; Fahnestock, M et al., (2001) Mol. Cell Neurosci. 18, 210-220; Nakamura, K et al., (2007) Cell Death. Differ. 14, 1552-1554; Yune, T et al., (2007) Brain Res. 1183, 32-42; Wei, Y et al., (2007) Neurosci. Lett. 429, 169-174; Provenzano, M J et al., (2008) Laryngoscope 118, 87-93; Nykjaer. A et al., (2004) Nature 427, 843-848; Harrington, A W et al., (2004) Proc. Natl. Acad. Sci. U.S.A. 101, 6226-6230; Teng. H K et al., (2005) J. Neurosci. 25, 5455-5463; Jansen, P et al., (2007) Nat. Neurosci. 10, 1449-1457; Volosin, M et al., (2008) J. Neurosci. 28, 9870-9879; Fan, Y J et al., (2008) Eur. J. Neurosci. 27, 2380-2390; Al-Shawi, R et al., (2008) Eur. J. Neurosci. 27, 2103-2114; and Yano, H et al., (2009) J. Neurosci. 29, 14790-14802). Such experiment can be also conducted in in mice that express the human Siglec-7 gene from a bacterial artificial chromosome or from a cDNA driven by a myeloid promoter or in mice that were transduced with *lenti* or AAV virus containing hSiglec-7 cDNA.

Example 22: Characterization of the Therapeutic Use of Antagonistic Siglec-7 Antibodies and/or Siglec-7 Bispecific Antibodies in a Model of Infection The therapeutic utility of antagonistic anti-Siglec-7 antibodies and/or Siglec-7 bispecific antibodies is tested in a model of infection. For example, *Listeria monocytogenes* or other infection in normal mice can be used, as previously described (e.g., Yin, F et al., (2009) J. Exp. Med, 207, 117-128). Either regular mice or mice that express the human Siglec-7 gene under a bacterial artificial chromosome or under a myeloid promoter can be used.

Example 23: Characterization of the Therapeutic Use of Antagonistic Siglec-7 Antibodies and/or Siglec-7 Bispecific Antibodies in a Model of Inflammatory Diseases The therapeutic utility of antagonistic anti-Siglec-7 and/or Siglec-7 bispecific antibodies is tested in a model of inflammatory diseases. For example rheumatoid arthritis or in an established model of another inflammatory disease (Mizoguchi (2012) Prog Mol Biol Transl Sci., 105:263-320; and Asquith et al., (2009) Eur J Immunol. 39:2040-4). Such experiment can be also conducted in in mice that express the human Siglec-7 gene from a bacterial artificial chromosome or from a cDNA driven by a myeloid promoter or in mice that were transduced with *lenti* or AAV virus containing hSiglec-7 cDNA.

Example 24: Screening for Anti-Siglec-7 Antibodies and/or Siglec-7 Bispecific Antibodies that Induce or Inhibit Phosphorylation of Siglec-7 and Downstream Signaling Molecules Cells (J774, RAW 264.7, BMM cells, human primary monocytes, macrophages, neutrophils, NK cells, dendritic cells, T cells, microglia, or osteoclasts) are removed from tissue culture dishes with PBS-EDTA, washed with PBS, and counted. Cells are incubated with an anti-Siglec-7 antibodies and/or Siglec-7 bispecific antibody or with an isotype-matched control antibody at 1 µg/$10^6$ cells for 20 min on ice or under other conditions. Cells are lysed in ice-cold radioimmunoprecipitation assay (RIPA) buffer for 20 min followed by centrifugation at 16,000 g for 10 min at 4° C. to remove insoluble materials. The resulting supernatant is subjected to immunoprecipitation reactions with the indicated antibodies (DAP12, ERK, or AKT) and protein A- or protein G-agarose (Sigma). The beads are extensively washed with RIPA buffer and the proteins are separated by SDS-polyacrylamide gel electrophoresis (SDS-PAGE). The proteins are then transferred to nitrocellulose membranes by Western blotting, incubated with the appropriate antibodies (antibodies that specifically recognize phosphorylated tyrosine or phosphorylated form of DAP12, ERK, Syk, LCK, FYN, C-Cbl, VAV, or AKT) and visualized with the enhanced chemiluminescence (ECL) system (Pierce), as described (e.g., Peng et al., (2010) Sci Signal., 3(122): ra38).

Example 25: Screening for Anti-Siglec-7 and/or Siglec-7 Bispecific Antibodies that Induce or Inhibit Calcium Flux BMM cells are washed twice with HEPES-containing buffer [20 mM HEPES (pH7.3), 120 mM NaCl, 1 mM CaCl, 1 mM MgCl, 5 mM KCl, glucose (1 mg/ml), bovine serum albumin (1 mg/ml)] followed by incubation in 0.05% Pluronic F-127 (Invitrogen) and 1 µM Indo-1 AM (Invitrogen) for 20 min at 37° C. Cells are washed twice with HEPES buffer and are then stimulated with an anti-Siglec-7 antibodies and/or Siglec-7 bispecific antibody (16 µg/ml) or with a control antibody (16 µg/ml) and monitored by spectrophotometer (PTL Photon Technology International). The Indo-1 fluorescence emission is converted to calcium ($Ca^{2+}$) according to manufacturer's instructions (e.g., Peng et al., (2010) Sci Signal., 3(122): ra38).

Example 26: Siglec-7 Increases the Survival of Macrophages, Neutrophils, NK Cells, and Dendritic Cells To evaluate the role of Siglec-7 in cell survival, human or mouse macrophages, neutrophils, NK cells, microglia, T cells, and dendritic cells are cultured in the presence of inflammatory mediators, and cell survival is measured.

Murine bone marrow precursor cells from Siglec-7-expressing or WT mice are obtained by flushing tibial and femoral marrow cells with cold PBS. After one wash with PBS, erythrocytes are lysed using ACK Lysing Buffer (Lonza), washed twice with PBS and suspended at $0.5 \times 10^6$ cells/ml in complete RPMI media (10% FCS, Pen/Strep, Gln, neAA) with the indicated amounts of 50 ng/ml M-CSF to produce macrophages, neutrophils, or NK cells, or 10 ng/ml GM-CSF to produce dendritic cells. For M2-type macrophages, 10 ng/ml IL-4 is added to the cultured cells. For M1-type macrophages, 50 ng/ml IFN is added. In some experiments LPS or zymosan is added to the cell culture at day 5 at a concentration range of 1 µg/ml-0.01 ng/ml. Recombinant cytokines are purchased from Peprotech.

To analyze viability of bone marrow-derived macrophages, neutrophils, or NK cells, cells are prepared as above and cultured in MCSF. Cells are either plated at $10^5$/200 µL in a 96-well plate (for viability analysis using a luciferase based-assay) or at $0.5 \times 10^6$/1 ml in a 6-well plate (for Tripan Blue exclusion cell count) in non-tissue culture treated plates. Media containing fresh M-CSF is added at day 3. At the indicated time points cells are gently detached from the plates with 3 mM EDTA and counted using a Burker chamber. For FACS analysis of live cells, macrophages are cultured either in 50 ng/ml MCSF for 6 days (+MCSF) or in 50 ng/ml MCSF for 4 days before MCSF is removed for an additional 36 hrs (−MCSF). Cells are stained using CD11b antibody and DAPI. For luciferase viability assays, cell viability is measured at day 5 of culture in graded concentrations of growth factors GMCSF (dendritic cells), MCSF (M1 macrophages), or MCSF+IL-4 (M2 macrophages). Cells are directly incubated with ToxGlo reagent (Promega) and luciferase activity (luminescence) is determined. For FACS analysis of viable macrophages cultured in the presence of inflammatory mediators IFN, LPS, or zymosan, cells are collected at day 5 and stained using CD11b antibody and DAPI.

Example 27: Siglec-7 Increases the Expression of Inflammatory Cell Surface Markers on Macrophages, Neutrophils, or NK Cells In order to determine the role of Siglec-7 in inflammatory marker expression, macrophages, neutrophils, and NK cells are cultured with various inflammatory mediators, and the expression of surface markers (e.g., CD86 and CD206) is measured in the presence or absence of Siglec-7 antibodies.

Macrophages, neutrophils, and NK cells are plated and allowed to adhere for 4 h at 37° C., and TLR agonists LPS (*Salmonella abortus equi*) and zymosan (*Saccharomyces cerevisiae*) are added at concentrations ranging from 0.01-100 ng/ml (LPS) or 0.01-10 µg/ml (zymosan). Alternatively, macrophages, neutrophils, and NK cells are cultured in the presence of the cytokines IL-4 (10 ng/ml) or IFN (0.5-50 ng/ml). FACS analysis of CD86 and CD206 is performed on a BD FACS Canto 48 hours later. Data analysis is performed with FlowJo (TreeStar) software version 10.0.7.

Example 28: Analysis of the Anti-Cancer Effect of Siglec-7 Antibodies and/or Bispecific Antibodies Groups of 10 C57Bl6/NTac mice at 8 weeks (+/−2 weeks) of age, either regular mice or mice that express the human Siglec-7 gene from a bacterial artificial chromosome or from a myeloid promoter, are challenged subcutaneously with tumor cells (e.g. $1 \times 10^6$ to $1 \times 10^6$ MC38, Lewis Lung, or B16 cells) suspended in 100 ul PBS. Animals are anesthetized with isoflurane prior to implant. Starting at day 2, groups of mice are injected i.p. every 3 days for 4 doses with 200 ug of each of antagonistic anti-Siglec-7 antibodies. Tumor growth is monitored with a caliper biweekly to measure tumor growth starting at day 4. The endpoint of the experiment is a tumor volume of 2000 mm$^3$ or 60 days. Tumor growth and % survival are the outcome measures. Reduced tumor take and growth rate, reduced number of tumor infiltrating immune suppressor macrophages, neutrophils, and/or NK cells, and increased effector T cell influx into the tumor indicate the anti-cancer effects of blocking anti-Siglec-7 antibodies.

Immunodeficient mice or immunodeficient transgenic mice that express human IL-3, human GM-CSF, human IL-6, human IL-2, and were seeded with human immune cells from human placenta, fetal liver, peripheral blood or another source can also be used for such studies (Ito M et al., (2008) Curr Top Microbiol Immunol.; 324:53-76; Ito R., et al., (2012) *Cellular & Molecular Immunology* 9, 208-214; Brehm et al., (2010) Curr Opin Endocrinol Diabetes Obes. 17(2): 120-125; Zhou et al., (2013) Cancer Letters. 344, 13-19). Such mice can be used in conjunction with either cell line tumors or patient-derived human tumor xenografts (Siolas et al., (2013) Cancer Res.; 73(17): 5315-5319).

Such experiment can be also conducted in in mice that express the human Siglec-7 gene from a bacterial artificial chromosome or from a cDNA driven by a myeloid promoter or in mice that were transduced with lenti or AAV virus containing hSiglec-7 cDNA.

Example 29: Analysis of Additive Anti-Tumor Effect of Combination Therapy that Combines Siglec-7 Antibodies and/or Bispecific Antibodies with Antibodies Against Inhibitory Checkpoint Proteins or Inhibitory Cytokines/Chemokines and their Receptors Groups of 15 C57Bl6/NTac mice at 8 weeks (+/−2 weeks) of age are challenged subcutaneously with tumor cells as described in Example 28. Animals are anesthetized with isoflurane prior to implant. Starting at day 2, mice are injected i.p. every 3 days for 4 doses with 200 ug anti-Siglec-7 antibodies alone or in combination with antibodies against checkpoint proteins (e.g. anti-PDL1 mAb clone 10F.9G2 and/or anti-CTLA4 mAb clone UC10-4F10-11) at day 3, 6, and 9. Treatment groups include anti-Siglec-7; anti-CTLA4; anti-PDL1; anti-Siglec-7+anti-CTLA4; anti-Siglec-7+anti-PDL1; and isotype control. Tumor growth is monitored with a caliper biweekly to measure tumor growth starting at day 4. The endpoint of the experiment is a tumor volume of 2000 mm$^3$ or 60 days. Tumor growth and % survival are the outcome measures. A decrease in tumor growth and an increase in % survival with combination therapy indicate that anti-Siglec-7 antibodies have additive or synergistic therapeutic effects with anti-checkpoint antibodies. Antagonistic antibodies against checkpoint molecules include antibodies against PDL1, PDL2, PD1, CTLA4, B7-H3, B7-H4, HVEM, BTLA, KIR, GAL9, TIM3, A2AR, LAG-3, and Phosphatidyl Serine. Antagonist antibodies against inhibitory cytokines include antibodies against CCL2, CSF-1, and IL-2. Immuno-deficient mice or immuno-deficient transgenic mice that express human IL-3, human GM CSF, human IL-6, human I12, and were seeded with human immune cells from human placenta, fatal liver, peripheral blood or another source can also be used for such studies (Ito M et al., (2008) Curr Top Microbiol Immunol.; 324:53-76; Ito R., et al., (2012) *Cellular & Molecular Immunology* 9, 208-214; Brehm et al., (2010) Curr Opin Endocrinol Diabetes Obes. 17(2): 120-125; Zhou et al., (2013) Cancer Letters. 344, 13-19). Such mice can be used in conjunction with either cell line tumors or Patient derived human tumors xenografts (Siolas et al., (2013) Cancer Res.; 73(17): 5315-5319).

Such experiment can be also conducted in in mice that express the human Siglec-7 gene from a bacterial artificial chromosome or from a cDNA driven by a myeloid promoter or in mice that were transduced with *lenti* or AAV virus containing hSiglec-7 cDNA.

Example 30: Analysis of Additive Anti-Tumor Effect of Combination Therapy that Combines Siglec-7 Antibodies and/or Bispecific Antibodies with Antibodies that Activate Stimulatory Checkpoint Proteins Groups of 15 C57Bl6/NTac mice at 8 weeks (+/−2 weeks) of age are challenged subcutaneously with tumor cells as described in Example 28. Animals are anesthetized with isoflurane prior to implant. Starting at day 2, mice are injected i.p. every 3 days for 4 doses with 200 µg anti-Siglec-7 antibodies alone or in combination with agonistic antibodies that activate stimulatory checkpoint proteins (e.g. OX40 or ICOS mAb) at day 3, 6, and 9. Tumor growth is monitored with a caliper biweekly to measure tumor growth starting at day 4. The endpoint of the experiment is a tumor volume of 2000 mm$^3$ or 60 days. Tumor growth and % survival are the outcome measures. A decrease in tumor growth and an increase in % survival with combination therapy indicate that anti-Siglec-7 antibodies have additive or synergistic therapeutic effects with stimulatory checkpoint antibodies. Stimulatory checkpoint antibodies include agonistic/stimulatory antibodies against CD28, ICOS, CD137, CD27, CD40, and GITR.

Immuno-deficient mice or immuno-deficient transgenic mice that express human IL-3, human GM CSF, human IL-6, human Il2, and were seeded with human immune cells from human placenta, fatal liver, peripheral blood or another source can also be used for such studies (Ito M et al., (2008) Curr Top Microbiol Immunol.; 324:53-76; Ito R., et al., (2012) *Cellular & Molecular Immunology* 9, 208-214; Brehm et al., (2010) Curr Opin Endocrinol Diabetes Obes. 17(2): 120-125; Zhou et al., (2013) Cancer Letters. 344, 13-19). Such mice can be used in conjunction with either cell line tumors or Patient derived human tumors xenografts (Siolas et al., (2013) Cancer Res.; 73(17): 5315-5319).

Such experiment can be also conducted in in mice that express the human Siglec-7 gene from a bacterial artificial chromosome or from a cDNA driven by a myeloid promoter or in mice that were transduced with lentivirus or AAV virus containing human Siglec-7 cDNA.

Example 31: Analysis of Additive Anti-Tumor Effect of Combination Therapy that Combines Siglec-7 Antibodies and/or Bispecific Antibodies with Stimulatory Cytokines Groups of 15 C57Bl6/NTac mice at 8 weeks (+1-2 weeks) of age are challenged subcutaneously with tumor cells as described in Example 28. Animals are anesthetized with isoflurane prior to implant. Starting at day 2, mice are injected i.p. every 3 days for 4 doses with 200 ug anti-Siglec-7 antibodies alone or in combination with stimulatory cytokines (e.g. IL-12, IFN-a). Tumor growth is monitored with a caliper biweekly to measure tumor growth starting at day 4. The endpoint of the experiment is a tumor volume of 2000 mm$^3$ or 60 days. Tumor growth and % survival are the outcome measures. A decrease in tumor growth and an increase in % survival with combination therapy indicate that anti-Siglec-7 antibodies have additive or synergistic therapeutic effects with immune-stimulatory cytokines. Stimulatory cytokines include IFN-a/b, IL-2, IL-12, IL-18, GM-CSF, and G-CSF.

Immuno-deficient mice or immuno-deficient transgenic mice that express human IL-3, human GM CSF, human IL-6, human Il2, and were seeded with human immune cells from human placenta, fatal liver, peripheral blood or another source can also be used for such studies (Ito M et al., (2008) Curr Top Microbiol Immunol.; 324:53-76; Ito R., et al., (2012) *Cellular & Molecular Immunology* 9, 208-214; Brehm et al., (2010) Curr Opin Endocrinol Diabetes Obes. 17(2): 120-125; Zhou et al., (2013) Cancer Letters. 344, 13-19). Such mice can be used in conjunction with either cell line tumors or Patient derived human tumors xenografts (Siolas et al., (2013) Cancer Res.; 73(17): 5315-5319).

Such experiment can be also conducted in in mice that express the human Siglec-7 gene from a bacterial artificial chromosome or from a cDNA driven by a myeloid promoter or in mice that were transduced with lenti or AAV virus containing hSiglec-7 cDNA.

Example 32: Analysis of Ability of Siglec-7 Antibody and/or Bispecific Antibody Fabs to Stimulate Viability of Innate Immune Cells The agonistic functionality of plate bound, cross-linked anti-Siglec-7 antibody Fab fragments is evaluated in innate immune cells (e.g., macrophages, neutrophils, and NK cells).

Macrophages, neutrophils, and NK cells are cultured in the presence of M-CSF and plate bound Siglec-7 antibody Fabs, and cell viability is measured.

Macrophages, neutrophils, NK cells, and DC derived from human monocytes, as well as T cells and human microglia derived from human monocytes are plated on non-tissue-culture-treated 96-well plates, pre-coated with either 12.5 nM or 100 nM of cross-linked Siglec-7 Fabs. Cells are cultured for 48 hours in the presence of 10 ng/ml M-CSF. Analysis of viability is performed using CellTiter-Glo® kit (Promega). Plates are read with a BioTek Synergy Microplate Reader using GEN5 2.04 software.

Example 33: Analysis of the Ability of Siglec-7 Antibodies and/or Bispecific Antibodies to Modulate NFAT-Dependent Genes The ability of antagonistic anti-Siglec-7 antibodies activate NFAT-dependent genes is evaluate using a luciferase reporter gene under the control of an NFAT (nuclear factor of activated T cells) promoter.

A cell line derived from mouse T lymphocytes BW5147.G.1.4 (ATCC® TIB48™) that express the ITAM motif containing co-receptor DAP12 and its ligand binding partner TREM2 is infected with human Siglec-7, and with Cignal Lenti NFAT-Luciferase virus (Qiagen). Luciferase signaling is activated by plate bound anti-TREM2 antibodies. Full-length and Fab fragment anti-Siglec-7 antibodies are either co-plated with the TREM2 antibodies or applied in solution. For plate binding, antibodies are applied at 10 µg/ml in DPBS on tissue-culture treated clear bottom white 96well plates (100 ul/well), overnight at 4° C. Wells are rinsed three times with DPBS and subsequently plated at 100,000 cells/well in media with 1% serum. As a positive control for signaling, PMA (0.05 ug/ml) and ionomycin (0.25 uM) are added together. Cells are incubated for 6 hours and luciferase activity is measured by adding ONE-Glo™ reagent (Promega) to each well and incubating 3 min at RT on a plate shaker. Luciferase signal is measured using a BioTek plate reader.

Example 34: Analysis of Anti-Stroke Effect of Siglec-7 Antibodies and/or Bispecific Antibodies Transient occlusion of the middle cerebral artery (MCAO)—a model that closely resembles human stroke is used to induce cerebral infarction in mice. Monofilament (70SPRe, Doccol Corp, USA) is introduced into the internal carotid artery through an incision of the right common carotid artery. The middle cerebral artery is occluded for 30 minutes with a range of reperfusion times (6 h, 12 h, 24 h, 2 d, 7 d and 28 d). The effect of surgery is controlled using sham animals at 12 h and at 7 d. Sham animals undergo the same surgical procedure without occlusion of the middle cerebral artery. MCAO animals treated with antagonistic anti-Siglec-7 antibodies or control antibodies are tested for infarct volumetry, acute inflammatory response (12 h reperfusion), transcription of pro-inflammatory cytokines TNFa, IL-1a, and IL-1b, microglial activity (CD68, Iba1), transcription of chemokines CCL2 (MCP1), CCL3 (MIP1a and the chemokine receptor CX3CR1 and invasion of CD3-positive T cells (Sieber et al. (2013) PLoS ONE 8(1): e52982. doi:10.1371/journal.pone.0052982.). Such experiment can be conducted in regular mice or alternatively in mice that express the human Siglec-7 gene from a bacterial artificial chromosome or from a cDNA driven by a myeloid promoter or in mice that were transduced with lenti or AAV virus containing hSiglec-7 cDNA.

Example 35: Analysis of Anti-Alzheimer's Disease Effect of Anti-Siglec-7 Antibodies and/or Bispecific Antibodies To evaluate the ability of antagonistic anti-Siglec-7 antibodies to delay, prevent, or reverse the development of Alzheimer's disease (AD), 5×FAD mice are used. 5×FAD mice overexpress mutant human APP (695) with the Swedish (K670N, M671L), Florida (I716V), and London (V717I) familial Alzheimer's disease (FAD) mutations, along with human PS1 harboring two FAD mutations, M146L and L286V. Both transgenes are regulated by the mouse Thy 1 promoter to drive over expression on the brain and recapitulate major features of AD. Mice treated with the agonistic anti-Siglec-7 antibodies or with control antibodies are tested for A beta plaque load with immunohistochemistry and by ELISA of tissue extracts. They are further tested for the number of microglia in the brain, and for reduction in cognitive deficit using Morris Water maze, a spatial learning and memory task. Radial Arm Water Maze, a spatial learning and memory task, Y Maze (quantifies spontaneous alternation as a measure of spatial cognition), novelty preference in an open field, operant learning to assess learning and memory, and fear conditioning (mousebiology.org website; Wang et al., (2015) Cell. pii: S0092-8674(15)00127-0). Such experiment can be also conducted in in mice that express the human Siglec-7 gene from a bacterial artificial chromosome or from a cDNA driven by a myeloid promoter or in mice that were transduced with lenti or AAV virus containing hSiglec-7 cDNA.

Example 36: Analysis of the Protective Effect of Siglec-7 Antibodies and/or Bispecific Antibodies in Respiratory Tract Infections To evaluate the ability of antagonist Siglec-7 antibodies to delay, prevent, or treat bacterial respiratory tract infections, a preclinical mouse model involving challenge of C57Bl6 mice with *Streptococcus pneumoniae* is used. This model involves intranasal (i.n.) administration of 105 CFU *S. pneumoniae* serotype 3 (ATCC 6303) as described (see, e.g., Sharif O et al. 2014 *PLoS Pathog.* 2014 June; 10(6): e1004167; and Schabbauer G et al. 2010 *J Immunol* 185: 468-476). In this model ~90% WT C57Bl6 mice succumb to infection within 6 days post infection.

Ten to fifteen mice/group are challenged with *S. pneumoniae* and concomitantly are treated with antagonist anti-Siglec-7 antibodies every other day starting from day 0. The first dose of anti-Siglec-7 antibodies is administered 3 hours prior to challenge with *S. pneumonia*. Mice are monitored daily for 15 days to check for death events. % of mice surviving bacteria challenge is determined.

In separate experiments, count of bacterial load and cytokine expression in the blood and in the lungs is also determined. 24 or 48 hours after infection blood is collected in EDTA-containing tubes and plated on agar plates to enumerate bacterial CFU in the plasma. Plasma is stored at −20° C. for cytokine analysis by ELISA. Lungs are harvested, homogenized and plated on agar plates to enumerate bacterial CFU, or incubated for 30 min in lysis buffer and supernatants analyzed for cytokine measurements.

In separate experiments, lungs are collected 40 hours post bacterial infection, fixed in 10% formalin, and embedded in paraffin for H&E pathology analysis.

Such experiment can be also conducted in in mice that express the human Siglec-7 gene from a bacterial artificial chromosome or from a cDNA driven by a myeloid promoter or in mice that were transduced with lenti or AAV virus containing hSiglec-7 cDNA.

Example 37: Analysis of the Protective Effect of Siglec-7 Antibodies and/or Bispecific Antibodies in Sepsis To evaluate the ability of antagonist Siglec-7 antibodies to delay, prevent, or treat sepsis, a preclinical mouse model involving systemic challenge of C57Bl6 mice with LPS is used. This model involves intraperitoneal (i.p.) administration of 37 mg/ml LPS as described (see, e.g., Gawish R et al. 2014 *FASEB J*). In this model >95% WT C57Bl6 mice succumb infection within 40 hours post LPS injection.

Cohorts of mice are challenged with LPS and concomitantly are treated with antagonist anti-Siglec-7 antibodies every day starting from day 0. The first dose of anti-Siglec-7 antibodies is administered 3 hours prior to challenge with LPS. Mice are monitored every ~4 hours during daytime, to check for death events. Percentage of mice surviving LPS challenge is determined.

In separate experiments, peritoneal lavage fluid (PLF) is collected. Supernatants are stored at −20° C. for cytokine analysis by ELISA; pelleted cells are counted to quantify inflammatory cells recruited in the peritoneal cavity. Similar studies can be conducted to test the efficacy of Siglec-7 antibodies in other models of infection (see, e.g., Sun et al., (2013) *Invest Ophthalmol Vis Sci.* 17; 54(5):3451-62).

Such experiment can be also conducted in in mice that express the human Siglec-7 gene from a bacterial artificial chromosome or from a cDNA driven by a myeloid promoter or in mice that were transduced with lenti or AAV virus containing hSiglec-7 cDNA.

Example 38: Analysis of the Protective Effect of Siglec-7 Antibodies and/or Bispecific Antibodies in Acute and Chronic Colitis To evaluate the ability of antagonist anti-Siglec-7 antibodies to delay, prevent, or treat colitis, preclinical mouse models of acute or chronic colitis are used. For DSS-induced colitis, mice receive 3% DSS in drinking water ad libitum for 8 days. For TNBS-induced colitis, mice are anesthetized and treated with an intra-rectal injection of 3 mg TNBS in 20% ethanol (vol/vol) or vehicle alone as a control. For the chronic colitis model, all mice are treated with 3 cycles of 2% DSS for 5 days, followed by a 10-day recovery period. For all models, weight loss, stool consistency, and presence of fecal occult blood are monitored daily and used to calculate the disease activity index, as described (see, e.g., Correale C, 2013, *Gastroenterology*, February 2013, pp. 346-356.e3).

Cohorts of mice are treated with antagonist anti-Siglec-7 antibodies every day starting from day 0 and subjected to DSS or TNBS administration. Mice are monitored every day, to check for weight loss, stool consistency, and presence of fecal occult blood were monitored daily and used to calculate the disease activity index, as described (see, e.g., S. Vetrano, *Gastroenterology*, 135 (2008), pp. 173-184).

In separate experiments, endoscopic and histological images of mucosal damage are collected to evaluate inflammatory cell infiltration and mucosal damage. Similar studies can be conducted to test the benefit of Siglec-7 antibodies in other models of autoimmunity including Crohn's disease, inflammatory bowel disease, and ulcerative colitis (see, e.g., Low et al., (2013) *Drug Des Devel Ther.;* 7: 1341-1357; and Sollid et al., (2008) *PLoS Med* 5(9); e198).

Such experiment can be also conducted in in mice that express the human Siglec-7 gene from a bacterial artificial chromosome or from a cDNA driven by a myeloid promoter or in mice that were transduced with lenti or AAV virus containing hSiglec-7 cDNA.

Example 39: Analysis of the Protective Effect of Siglec-7 Antibodies and/or Bispecific Antibodies in Wound Healing To evaluate the ability of agonistic anti-Siglec-7 antibodies to increase colonic wound repair following injury, a mouse model of biopsy injury in the colon is used. In this model, the endoscope with outer operating sheath is inserted to the mid-descending colon and the mucosa is surveyed to the ano-rectal junction. Then, a single full thickness area of the entire mucosa and submucosa is removed with flexible biopsy forceps with a diameter of 3 French, avoiding penetration of the muscularis propria. Each mouse is biopsy injured at 3-5 sites along the dorsal side of the colon (see, e.g., Seno H, 2008, *Proc Natl Acad Sci USA.* 2009 Jan. 6; 106(1): 256-261).

Cohorts of mice are treated with agonist anti-Siglec-7 antibodies 2 or 3 days after biopsy injury. Mice are monitored every day for 15 days, to check for weight loss and wound healing by measuring the surface area of lesions.

Such experiment can be also conducted in in mice that express the human Siglec-7 gene from a bacterial artificial chromosome or from a cDNA driven by a myeloid promoter or in mice that were transduced with lenti or AAV virus containing hSiglec-7 cDNA.

Example 40: Analysis of the Protective Effect of Siglec-7 Antibodies and/or Bispecific Antibodies in Retinal Degeneration AMD is a degenerative disease of the outer retina. It is thought that inflammation, particularly inflammatory cytokines and macrophages, neutrophils, and/or NK cells contribute to AMD disease progression.

The presence of macrophages, neutrophils, and NK cells in the proximity of AMD lesions is documented, in the drusen, Bruch's membrane, choroid and retina. Macrophages, neutrophils, and NK cells release tissue factor (TF) and vascular endothelial growth factor (VEGF), which triggers the expansion of new blood vessels formation in patients showing choroidal neovasulcarization.

The type of macrophage present in the macular choroid changes with age, displaying elevated levels of M2 macrophages, neutrophils, and NK cells in older eyes compared to younger eyes. However, advanced AMD maculae had higher M1 to M2 rations compared to normal autopsied eyes of similar age. (see, e.g., Cao X et al. (2011), *Pathol Int* 61(9): pp 528-35). This suggests a link between classical M1 macrophage activation in the eye in the late onset of AMD progression.

Retinal microglia cells are tissue-resident macrophages that are also normally present in the inner retina. In the event of damage, microglia can be activated and act as mediator of inflammation. Activated microglia has been detected in the AMD tissue samples and has been proposed as one potential contributor of inflammatory processed that lead to AMD pathogenesis (Gupta et al., (2003) *Exp Eye Res.,* 76(4):463-71). The ability of Siglec-7 antibodies to prevent, delay, or reverse AMD is tested in one or more of AMD models (see, e.g., Pennesi et al., (2012) *Mol Aspects Med.;* 33(4); 487-509).

Overall inflammatory macrophages, neutrophils, and NK cells (either M1 and/or activated microglia) are documented to correlate with AMD disease progression and therefore represent a therapeutic target for antagonist Siglec-7 antibodies. Similar therapeutic benefit can be achieved in glaucoma and genetic forms or retinal degeneration such as retinitis pigmentosa.

The ability of Siglec-7 antibodies to prevent, delay, or reverse retinal ganglion cell degeneration in glaucoma is tested in a glaucoma model (see, e.g., El-Danaf et al., (2015) *J Neurosci.* 11; 35(6):2329-43). Likewise, the therapeutic benefit of REM2 in genetically induced retinal degeneration and retinitis pigmentosa is tested as described in Chang et al., (2002) Vision Res.; 42(4):517-25, and in "Retinal Degeneration Rat Model Resource Availability of P23H and S334ter Mutant Rhodopsin Transgenic Rats and RCS Inbred and RCS Congenic Strains of Rats," MM LaVail, Jun. 30, 2011.

Such experiment can be also conducted in in mice that express the human Siglec-7 gene from a bacterial artificial chromosome or from a cDNA driven by a myeloid promoter or in mice that were transduced with lenti or AAV virus containing hSiglec-7 cDNA.

Example 41: Analysis of the Protective Effect of Siglec-7 Antibodies and/or Bispecific Antibodies in Adipogenesis and Diet-Induced Obesity To test the effect of Siglec-7 antibodies in adipogenesis and obesity, a mouse model of high-fat diet (HFD) is used (see, e.g., Park et al., (2015) *Diabetes.* 64(1):117-27).

Such experiment can be also conducted in in mice that express the human Siglec-7 gene from a bacterial artificial chromosome or from a cDNA driven by a myeloid promoter or in mice that were transduced with lenti or AAV virus containing hSiglec-7 cDNA.

Example 42: Analysis of the Protective Effect of Antagonist Siglec-7 Antibodies and/or Bispecific Antibodies in Osteoporosis Bone is a dynamic organ constantly remodeled to support calcium homeostasis and structural needs. The osteoclast is the cell responsible for removing both the organic and inorganic components of bone. The osteoclast is derived from hematopoietic progenitors in the macrophage lineage and differentiates in response to the tumor necrosis factor family cytokine receptor activators of NFκB ligand. Osteoclasts, the only bone-resorbing cells, are central to the pathogenesis of osteoporosis and osteoporosis (Novack et al., (2008) *Animal Rev Pathol.,* 3:457-84).

Osteoporosis is a progressive bone disease that is characterized by a decrease in bone mass and density which can lead to an increased risk of fracture. It is mostly manifested in the first years following menopause, when bone turnover is accelerated, with increased activity of both osteoclasts and osteoblasts. Owing to an imbalance in the processes of resorption and synthesis, however, the net effect is bone loss, which is largely trabecular. Thus, the most prevalent sites of fracture in osteoporosis are the wrist, femoral neck, and vertebral bodies, in which the trabecular structure is key to overall bone strength.

Reduced osteoclast function results in osteoporosis, with increased bone mass and elimination of bone marrow space, as observed in animal models lacking DAP12 ITAM signaling adapter and resulting in a significant defect in differentiation of osteoclast-like cells (Koga, et al., (2004) *Nature* 428: 758-763).

Thus, administering an antagonist anti-Siglec-7 antibody of the present disclosure can prevent, reduce the risk of, and/or treat osteoporosis. In some embodiments, administering an agonist anti-Siglec-7 antibody may induce one or more Siglec-7 activities in an individual having osteoporosis (e.g., DAP12 phosphorylation, Syk activation, and accelerated differentiation into osteoclasts) (Peng et al (2010). *Sci Signal.* 2010 18; 3 122; and Humphrey et al., (2006) *J Bone Miner Res.,* 21(2):237-45).

Such experiment can be also conducted in in mice that express the human Siglec-7 gene from a bacterial artificial chromosome or from a cDNA driven by a myeloid promoter or in mice that were transduced with lenti or AAV virus containing hSiglec-7 cDNA.

Example 43: Analysis of the Ability of Siglec-7 Antibodies and/or Bispecific Antibodies to Modulate Binding of Siglec-7 to SHP1, SHP2 and Other Signaling Molecules Human primary monocytes, macrophages, neutrophils, NK cells, dendritic cells, T cells, microglia or osteoclasts are removed from tissue culture dishes with PBS-EDTA, washed with PBS, and counted. Cells are incubated with an anti-Siglec-7 and/or Siglec-7 bispecific antibody or with an isotype-matched control antibody at 1 μg/$10^6$ cells for 20 min on ice or under other conditions. Cells are lysed in ice-cold radioimmunoprecipitation assay (RIPA) buffer for 20 min followed by centrifugation at 16,000 g for 10 min at 4° C. to remove insoluble materials. The resulting supernatant is subjected to immunoprecipitation reactions with the indicated antibodies (SHP1, SHP2, c-Cbl, Vav, Syk, LcK, Fyn, GRb2, PLC-gamma. Toll like receptor, DAMP receptors, pattern recognition receptor) and protein A- or protein G-agarose (Sigma). The beads are extensively washed with RIPA buffer and the proteins are separated by SDS-polyacrylamide gel electrophoresis (SDS-PAGE). The proteins are then transferred to nitrocellulose membranes by Western blotting, incubated with the appropriate Siglec-7 antibodies and visualized with the enhanced chemiluminescence (ECL) system (Pierce), as described (e.g., Peng et al., (2010) *Sci Signal.*, 3(122); ra38). Alternatively, the cells are incubated with an anti-Siglec-7 and/or Siglec-7 bispecific antibody or with an isotype-matched control antibody at 1 μg/$10^6$ cells for 20 min on ice or under other conditions. Cells are lysed in ice-cold radioimmunoprecipitation assay (RIPA) buffer for 20 min followed by centrifugation at 16,000 g for 10 min at 4° C. to remove insoluble materials. The resulting supernatant is subjected to immunoprecipitation reactions with a second Siglec-7 antibody. The proteins are then transferred to nitrocellulose membranes by Western blotting and incubated with the indicated antibodies (SHP1, SHP2, c-Cbl, Vav, Syk, LcK, Fyn, GRb2, PLC-gamma. Toll like receptor, DAMP receptors, pattern recognition receptor).

Example 44: In Vivo Effects of Anti-Siglec-7 and Anti-PD1 Antibody Combination Treatment A CTG-0202 patient-derived melanoma tumor was first passaged in pre-study animals prior to implantation to humanized mice. When tumors reached 1-1.5 $cm^3$ in stock animals, they were harvested for re-implantation into pre-study animals. Pre-study animals were implanted unilaterally on the left flank with tumor fragments. The CTG-0202 melanoma tumors were used at passage number 6.

Figure 16A:
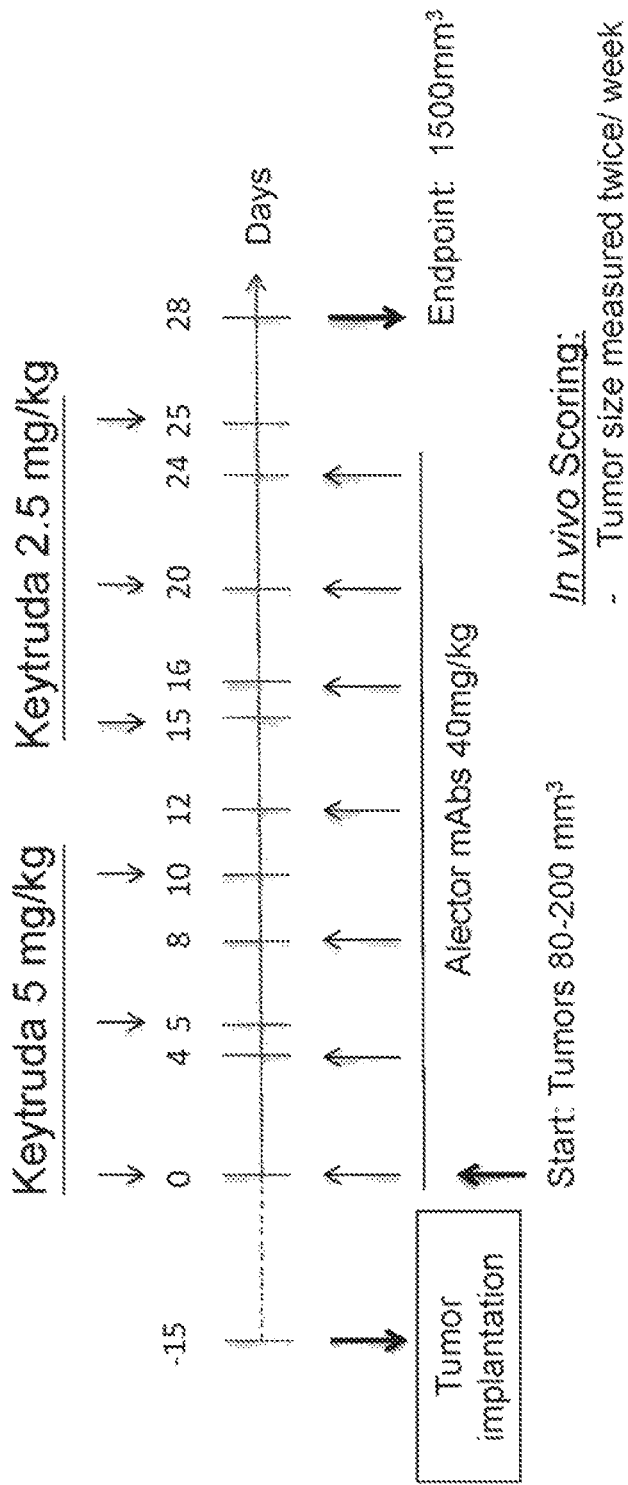
FIG. 16A depicts a PD-1/Siglec-7 combination antibody treatment protocol for a mouse model of patient-derived cancer in immunologically humanized mice.

Immunocompromised female mice (Taconic NOG) were humanized with fetal liver-derived $CD34^+$ hematopoietic cells. Mice were housed on irradiated papertwist-enriched ⅛" corncob bedding (Sheperd) in individual HEPA ventilated cages (Innocage® IVC, Innovive USA) on a 12-hour light-dark cycle at 68-74° F. (20-23° C.) and 30-70% humidity. Mice were fed water ad libitum (reverse osmosis, 2 ppm $Cl_2$) and an irradiated test rodent diet (Teklad 2919) consisting of 19% protein, 9% fat, and 4% fiber. 48 humanized mice were implanted, and pre-study tumor volumes were recorded for each experiment beginning seven to ten days after implantation. When tumors reached approximately 80-200 $mm^3$ in volume, mice were matched by tumor volume into treatment or control groups to be used for dosing, and dosing was initiated on Day 0. Test groups were administered anti-PD-1 antibody Keytruda® (pembrolizumab) in combination with a control monoclonal antibody (Group 1), or in combination with anti-Siglec-7 antibody 10B5 (Group 2). Table 11 and FIG. 16A depict the dosing schedule, dosing amounts, and route of administration.

TABLE 11

Antibody dosing schedule and route of administration for the in vivo cancer efficacy study of the Siglec-7 antibody 10B5

| Group | Antibody n Treatment | Dose Volume (mg/kg) | ROA | Schedule | Total # of Doses |
|---|---|---|---|---|---|
| 1 | 8 Keytruda | 5/2.5 | IP | q5d × 6 | 6 |
|  | Alector CTR mAb | 40 | IP | q5d × 6 | 6 |
| 2 | 8 Keytruda | 5/2.5 | IP | q5d × 6 | 6 |
|  | Alector 10B5 | 40 | IP | q5d × 6 | 6 |

In Table 11, "n" refers to the number of mice in each treatment group; "Alector CTR mAb" refers to an isotype control antibody: "Alector 10B5" refers to anti-Siglec-7 antibody 10B5; "ROA" refers to route of administration; "IP" refers to intraperitoneal; "q5dx6" refers to a dosing schedule of administration every five days for a total of six doses.

Beginning at Day 0, mice were observed daily and weighed twice weekly using a digital scale. Tumor dimensions were measured twice weekly by digital caliper and data including individual and mean estimated tumor volumes (Mean TV±SEM) was recorded for each group. Tumor volume was calculated using the formula (1): TV=width2× length×0.52. At study completion, percent tumor growth inhibition (% TGI) values were calculated and reported for each treatment group (T) versus control (C) using initial (i) and final (f) tumor measurements by the formula (2): % TGI=1−(Tf−Ti)/(Cf−Ci).

Individual mice reporting a tumor volume ≤50% of the Day 0 measurement for two consecutive measurements were considered partial responders (PR). Individual mice lacking palpable tumors (<4×4 $mm^2$ for two consecutive measurements) were classified as complete responders (CR); a CR that persisted until study completion was considered a tumor-free survivor (TFS). Tumor doubling time (DT) was determined for the vehicle treated groups using the formula DT=(Di−Df)*log 2/(log TVi−log TV)$_f$ where D=Day and TV=Tumor Volume. Statistical differences in tumor volume were determined using two-way ANOVA. The study was concluded when the mean tumor volume of the control group reached 1500 $mm^3$ at day 28.

At study termination harvested tumors were shipped overnight in media on ice packs and processed the following day. Whole blood samples were collected by cardiac puncture and shipped in sodium heparin and processed the following day upon delivery. Tumor samples were treated with collagenase for 30 min at 37° C. Samples were dissociated through a cell strainer and resuspended in 2% FBS in PBS. Red blood cells in whole blood samples were lysed using ACK lysing buffer and cells were then washed in 2% FBS in PBS twice. Cells were counted using a hemocytometer and one million cells were stained with fluorochrome-conjugated antibodies for 30 minutes on ice, then washed with 2% FBS in PBS. Cells were fixed with 4% paraformaldehyde in PBS. All the stained cells were analyzed on a FACS Canto (BD Biosciences) and the data analyzed with FlowJo software (TreeStar). To asses receptor downregulation, mouse (m) CD45, human (h) CD45, human (h) CD3, and human (h) CD14 antibodies were used to gate on the $CD14^+$ population. To identify tumor-infiltrating immune cells, hCD45, hCD3, hCD4, hCD8, and hCD14 antibodies were used to gate on populations according to standard procedure.

Figure 16B:
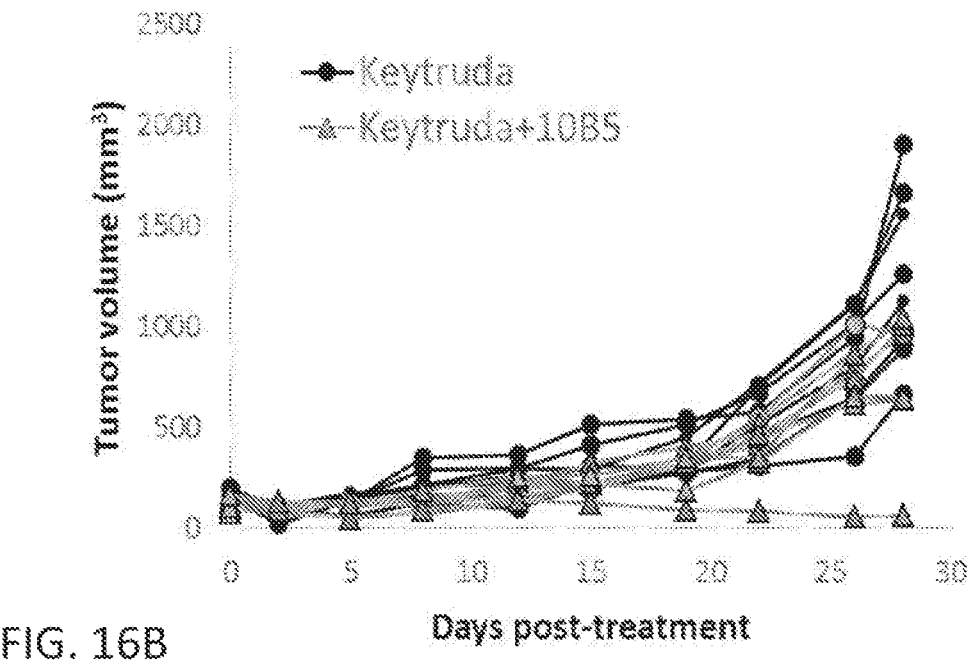
FIG. 16B depicts tumor volume after antibody treatment in individual mice that were engrafted with human immune stem cells. Mice were treated either with Keytruda® (pembrolizumab) anti-PD-1 antibody alone or in combination with anti-Siglec-7 antibody 10B5.
Figure 16C:
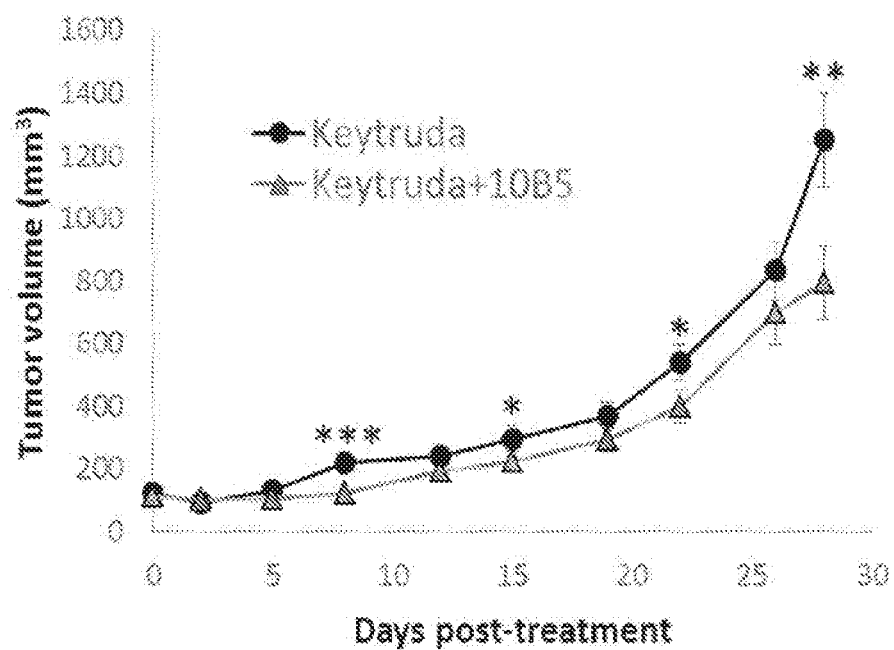
FIG. 16C depicts mean tumor volume after treatment for 28 days with Keytruda®® (pembrolizumab) anti-PD-1 antibody alone or in combination with anti-Siglec-7 antibody 10B5 in mice that were engrafted with human immune stem cells. *: $p<0.05$; : $p<0.01$; *: $p<0.001$ for Keytruda® (pembrolizumab)+10B5 vs Keytruda® (pembrolizumab). Means per treatment groups are presented. Error bars represent SEM.

As shown in FIGS. 16B and 16C, the combination treatment with Siglec-7 antibody 10B5 and the anti-PD-1 antibody Keytruda® (pembrolizumab) significantly inhibited tumor growth m vivo in the patient-derived melanoma tumor model in mice engrafted with human immune stem cells. Tumor volume at each time point was corrected for donor, tumor size at time 0 and mouse weight by multiple linear regression using R lm( ) function. At each time point, statistical significance was assessed by using R lm( ) function.

Figure 16D:
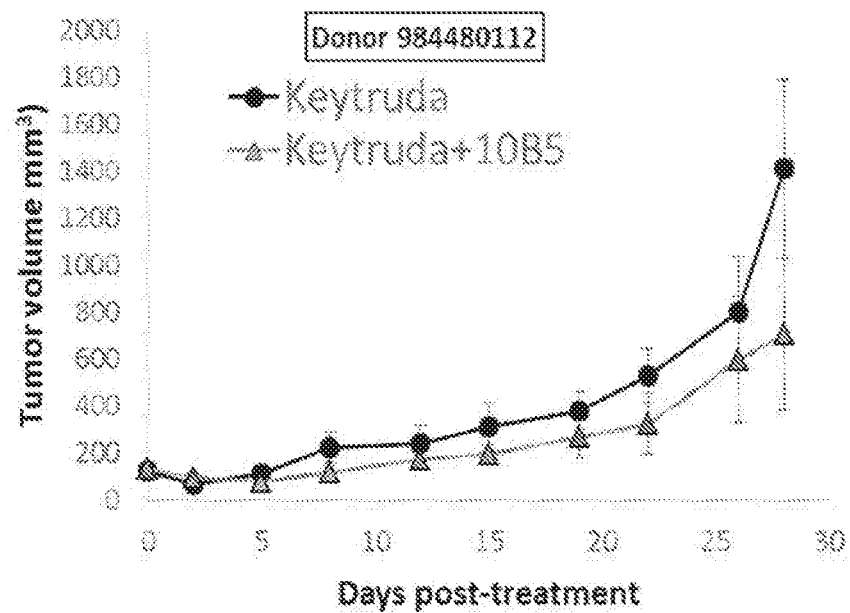
FIG. 16D depicts the mean tumor volume after treatment for 28 days with Keytruda® (pembrolizumab) anti-PD-1 antibody alone or in combination with anti-Siglec-7 antibody 10B5 in mice that were engrafted with human immune stem cells from the human donor 984480112. Means per treatment groups are presented. Error bars represent SEM.
Figure 16E:
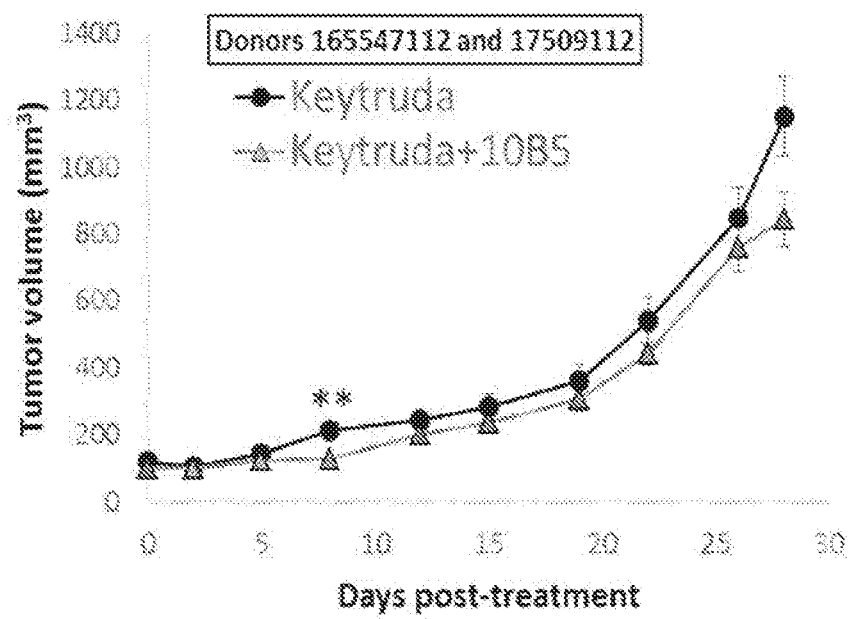
FIG. 16E depicts the mean tumor volume after treatment for 28 days with Keytruda® (pembrolizumab) anti-PD-1 antibody alone or in combination with anti-Siglec-7 antibody 10B5 in mice that were engrafted with human immune stem cells from either of the human donors 165547112 or 17509112. : $p<0.01$ for Keytruda® (pembrolizumab)+10B5 vs Keytruda® (pembrolizumab). Means per treatment groups are presented. Error bars represent SEM.

As shown in FIGS. 16D and 16E, the combination treatment with the Siglec-7 antibody 10B5 and the anti-PD-1 antibody Keytruda® (pembrolizumab) inhibited tumor growth in vivo in the patient-derived melanoma tumor model that was implanted in mice engrafted with human immune stem cells from different human donors (donor #: 984480112, 165547112, and 17509112). Tumor volume at each time point was corrected for donor, tumor size at time 0 and mouse weight by multiple linear regression using R lm( ) function. At each time point, statistical significance was assessed by using R lm( ) function.

FIG. 16B-E depict pre-clinical efficacy of the anti-Siglec-7 antibody 10B5 as a therapeutic for treating human cancer. The Siglec-7 antibody 10B5, when delivered in combination with the anti-PD1 antibody Keytruda® (pembrolizumab), significantly reduced tumor volume in melanoma tumors (FIG. 16B-E). Notably, Keytruda® (pembrolizumab) in combination with an isotype control (Alector CTR mAb) did not inhibit tumor growth (FIG. 16B-E).

Figure 16F:
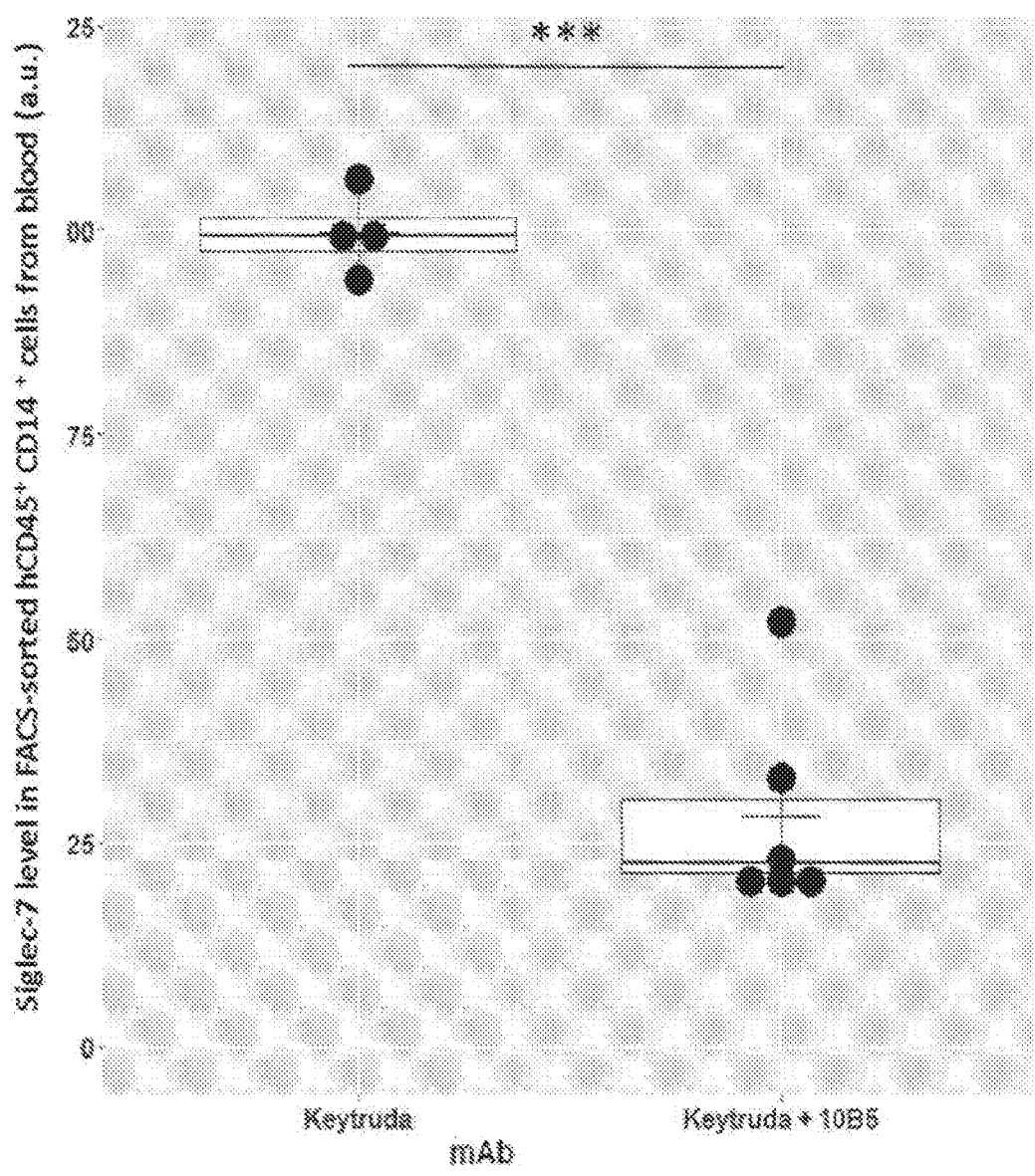
FIG. 16F depicts in vivo reduction in cell surface levels of Siglec-7 in peripheral blood human (h) $CD45^+$ $CD14^+$ myeloid cells from mice treated with Keytruda®® (pembrolizumab) anti-PD-1 antibody alone or in combination with anti-Siglec-7 antibody 10B5. *: $p<0.001$ for Keytruda® (pembrolizumab)+10B5 vs Keytruda® (pembrolizumab), correcting for donor and day of animal sacrifice. +: mean; boxplot midline: median; upper and lower boundaries of the boxes correspond to the first and third quartiles (25th and 75th percentiles).

As shown in FIG. 16F, the combination treatment with the Siglec-7 antibody 10B5 and the anti-PD-1 antibody Keytruda® (pembrolizumab) reduced cell surface levels of Siglec-7 in peripheral blood $hCD45^+$ $CD14^+$ myeloid cells from peripheral blood in a mouse tumor model that was engrafted with human immune stem cells and the patient-derived xenograft CTG-0202 melanoma tumors. Statistical significance was assessed by using the R lm( ) function.

Figure 16G:
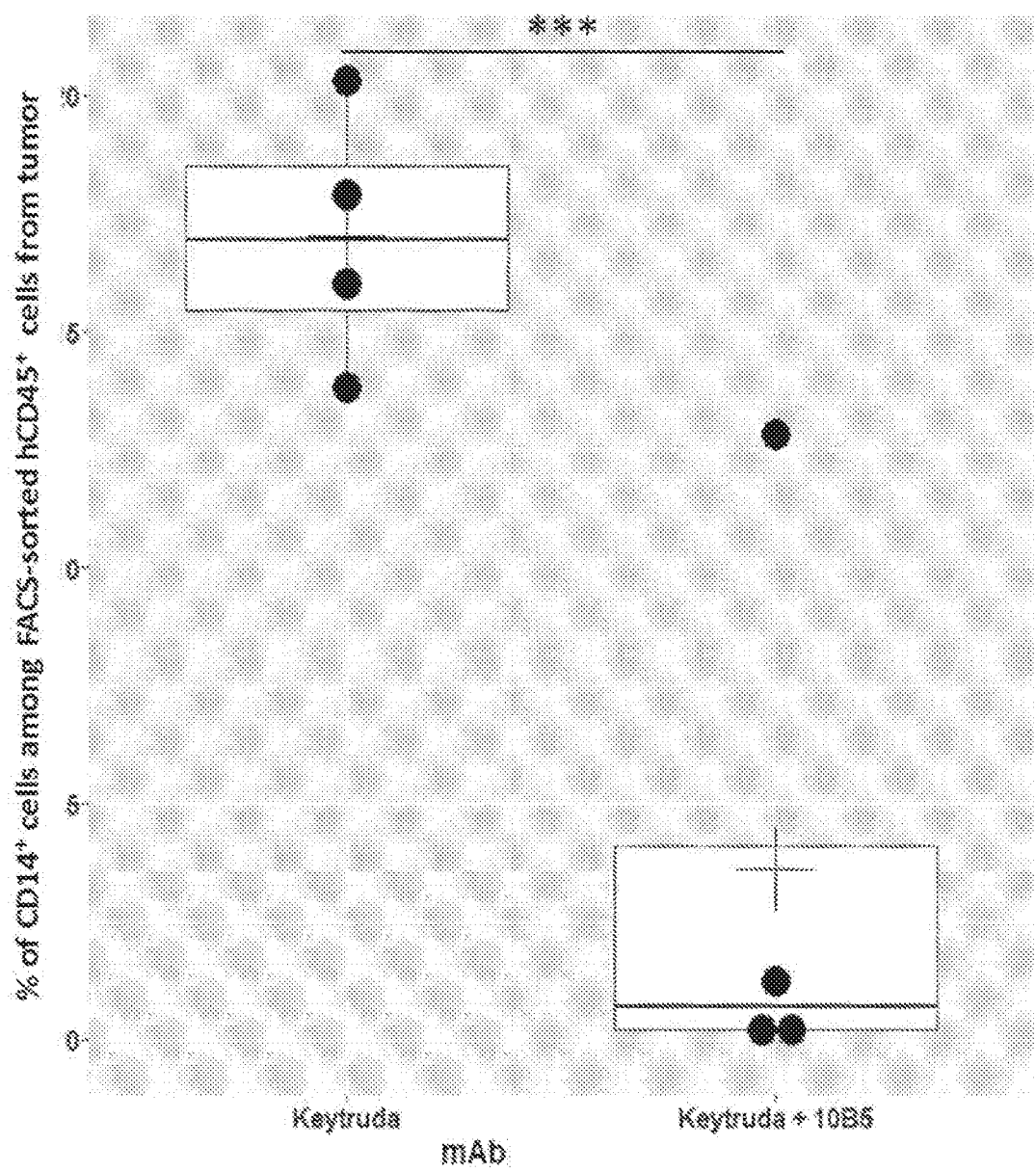
FIG. 16G depicts in vive reduction in tumor infiltrating human (h) $CD45^+$ $CD14^+$ myeloid cells from mice treated with Keytruda® (pembrolizumab) anti-PD-1 antibody alone or in combination with anti-Siglec-7 antibody 10B5. *: $p<0.001$ for Keytruda® (pembrolizumab)+10B5 vs Keytruda® (pembrolizumab), correcting for donor. +: mean; boxplot midline: median; upper and lower boundaries of the boxes correspond to the first and third quartiles (25th and 75th percentiles).

As shown in FIG. 16G, the combination treatment with the Siglec-7 antibody 10B5 and the anti-PD-1 antibody Keytruda® (pembrolizumab) reduced the number of tumor infiltrating $hCD45^+$ $CD14^+$ myeloid cells in a mouse tumor model that was engrafted with human immune stem cells and the patient-derived xenograft CTG-0202 melanoma tumors. Statistical significance was assessed by using the R lm( ) function.

Figure 16H:
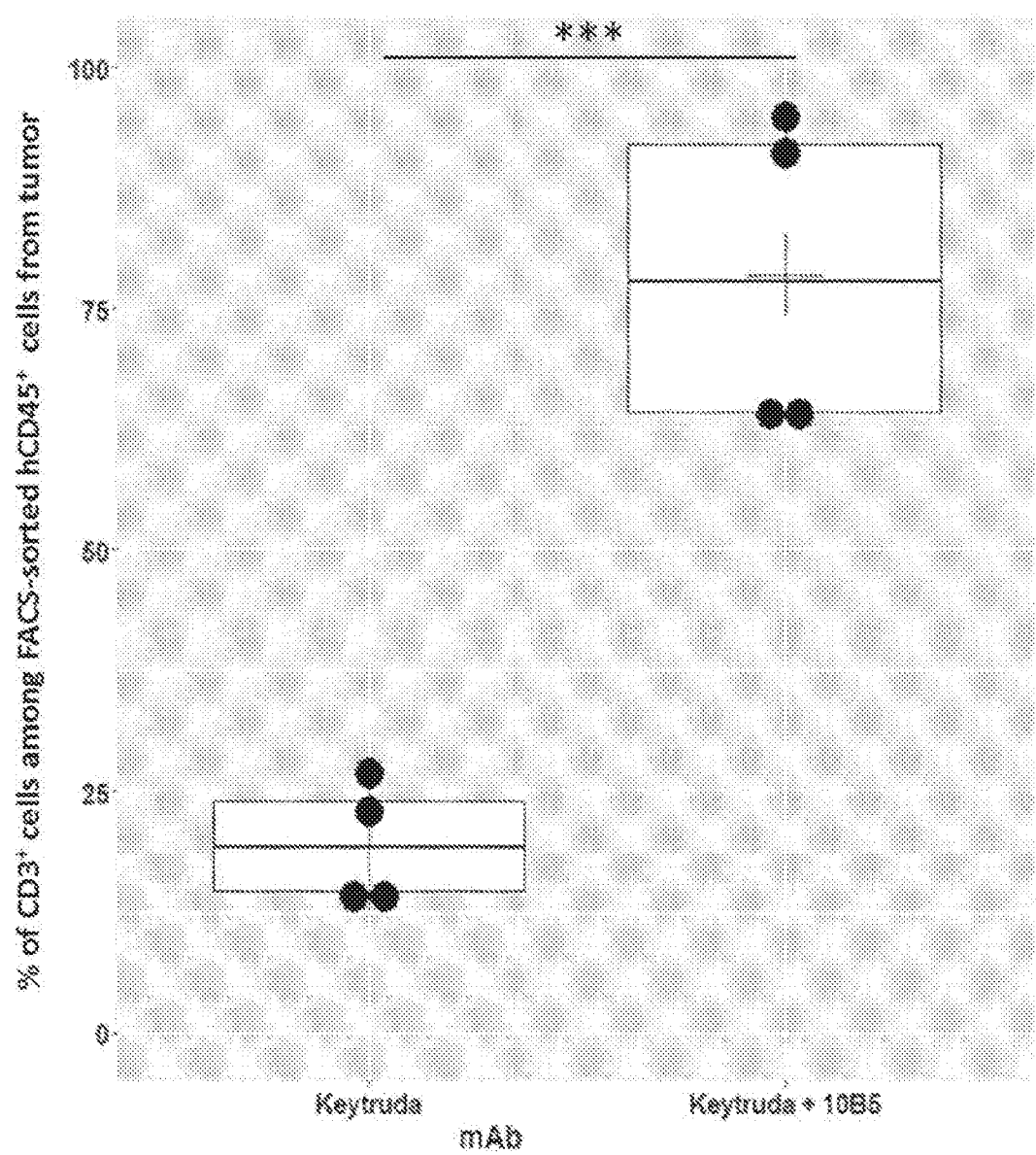
FIG. 16H depicts in vivo increase in tumor infiltrating human (h) $CD45^+$ $CD3^+$ T cells from mice treated with Keytruda® (pembrolizumab) anti-PD-1 antibody alone or in combination with anti-Siglec-7 antibody 10B5. *: $p<0.001$ for Keytruda® (pembrolizumab)+10B5 vs Keytruda® (pembrolizumab), correcting for donor. +: mean; boxplot midline: median; upper and lower boundaries of the boxes correspond to the first and third quartiles (25th and 75th percentiles).

As shown in FIG. 16H, the combination treatment with the Siglec-7 antibody 10B5 and the anti-PD-1 antibody Keytruda® (pembrolizumab) increased the number of tumor infiltrating $hCD45^+$ $CD3^+$ T cells in a mouse tumor model that was engrafted with human immune stem cells and the patient-derived xenograft CTG-0202 melanoma tumors. Statistical significance was assessed by using the R lm( ) function.

Figure 16I:
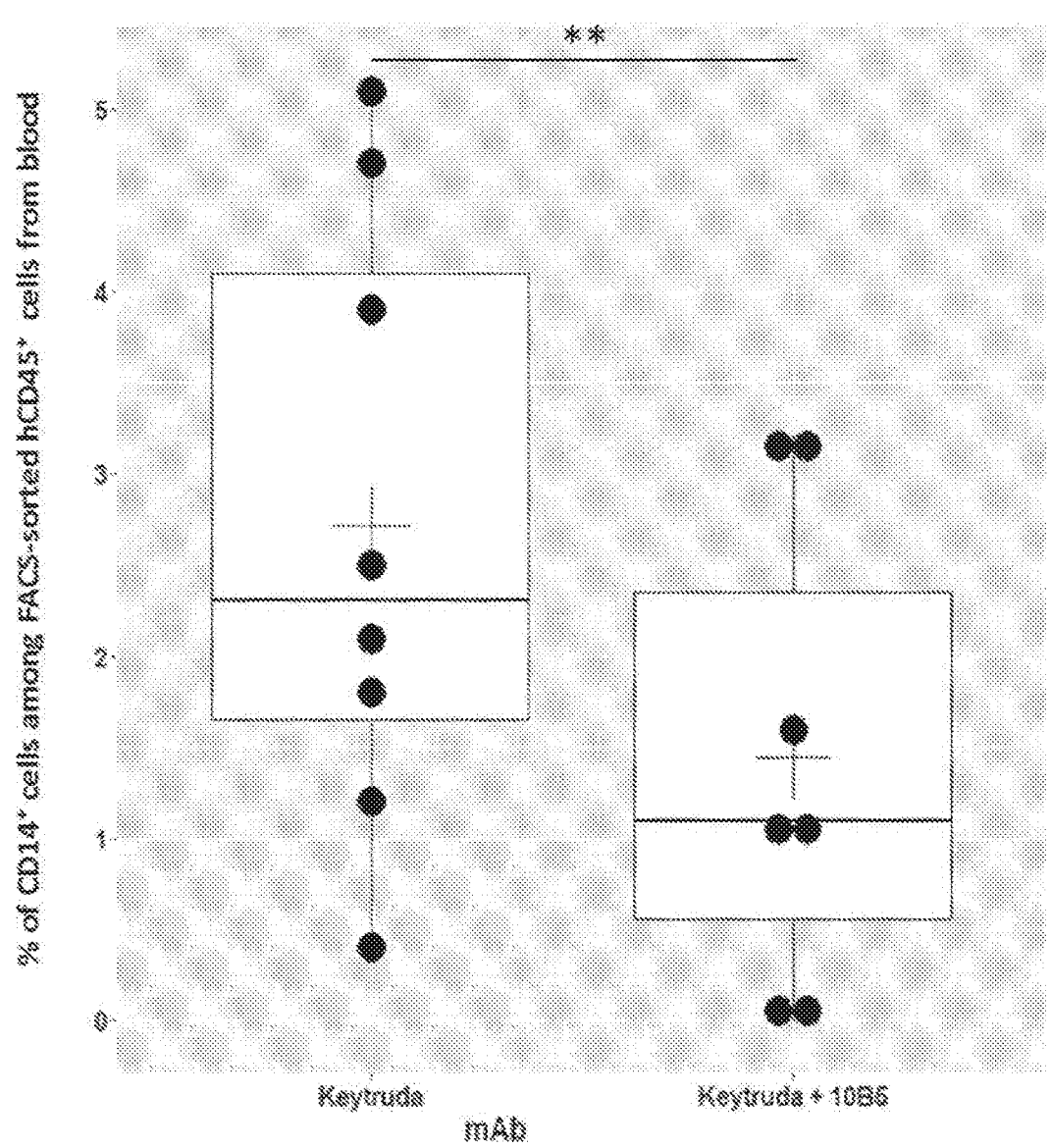
FIG. 16I depicts in vivo reduction in peripheral blood human (h) $CD45^+$ $CD14^+$ myeloid cells from mice treated with Keytruda® (pembrolizumab) anti-PD-1 antibody alone or in combination with anti-Siglec-7 antibody 10B5. **: $p<0.01$ for Keytruda® (pembrolizumab)+10B5 vs Keytruda® (pembrolizumab), correcting for donor. +: mean; boxplot midline: median; upper and lower boundaries of the boxes correspond to the first and third quartiles (25th and 75th percentiles).

As shown in FIG. 16I, the combination treatment with the Siglec-7 antibody 10B5 and the anti-PD-1 antibody Keytruda® (pembrolizumab) reduced the number of peripheral blood $hCD45^+$ $CD14^+$ myeloid cells in a mouse tumor model that was engrafted with human immune stem cells and the patient-derived xenograft CTG-0202 melanoma tumors. Statistical significance was assessed by using the R lm( ) function.

Importantly for the studies described herein, both the tumor and the immune system responding to the tumor were human. The immune system of the mouse was humanized using a method whereby the mouse immune system was genetically ablated and myeloablated with irradiation, then replaced with human donor $CD34^+$ hematopoietic stem and progenitor cells that repopulated and developed myeloid and lymphoid immune cells. The tumor was a patient-derived melanoma. The human-specific Siglec-7 antibody 10B5 displayed target specific engagement and downregulation of human Siglec-7. Receptor downregulation was significant on peripheral and tumor $CD14^+$ myeloid cells. Therefore any effects on tumor volume, tumor growth rate, increased tumor infiltration of $CD3^+$ T-cells, and reduced CD14+ cells were the result of 10B5 antibody-mediated downregulation of Siglec-7 on human myeloid immune cells.

The data presented above showed that the Siglec-7 antibody 10B5 was a potent and significant receptor-downregulating antibody on peripheral and tumor infiltrating myeloid cells. Analysis of the tumor infiltrating immune cell populations demonstrated a significant increase of $CD3^+$ T-cells. Additionally, myeloid cell populations were also affected by Siglec-7 antibody treatment. A significant decrease in $CD14^+$ myeloid cells was observed in tumors, as well as in peripheral blood cell populations. This data suggested that downregulation of Siglec-7 functionally altered tumor infiltrating immune cell populations. Taken together, these studies demonstrated the pre-clinical efficacy of anti-Siglec-7 antibodies as a therapeutic for treating human cancer.

Example 45: Effects of Siglec-7 Antibodies on Myeloid-Derived Suppressor Cells (MDSC)

Peripheral blood mononuclear cells (PBMCs) were separated from whole blood by ficoll centrifugation. After ACK lysis of red blood cells, human PBMCs were cultured in RPMI media supplemented 10% FBS (Hyclone), L-glutamine, Pen/Strep, non-essential amino acids, sodium pyruvate, and a suppressive cytokine cocktail containing: 10 ng/ml recombinant IL-6 (Sigma-Aldrich), IL-8 (R&D Systems), and GM-CSF (R&D Systems). In some experiments, human PBMCs were cultured with tumor conditioned media supplemented with 10 ng/ml GM-CSF. Tumor conditioned media was RPMI media with the supplements noted above, except IL-6 and IL-8, that had been harvested from tumor cell line cultures and sterile filtered with 0.2 μm membrane. Cytokines, antibodies (anti-Siglec-7 antibodies 4E3 or 10B, or isotype control antibodies), or rhGM-CSF spiked tumor supernatant were added to human PBMCs every 2-3 days for a week.

For FACS analysis, suspension and adherent cells were harvested and tested for expression of the indicated receptors by standard FACS procedure. Importantly, dead cells were gated out of the expression analysis, and all MFI values were derived from live cells. Plotted values were calculated as delta MFI compared to isotype treated conditions.

For T cell proliferation assays, myeloid-derived suppressor cells (MDSCs) were isolated by magnetic-based negative selection using a cocktail of antibodies to CD2, CD3, CD8, CD19, and CD56 (STEMCELL Technologies) after 7 days of culturing. Isolated MDSCs were plated at 50,000 cells per well in a flat-bottom 96-well non-TC plate and treated with the indicated antibodies prior to addition of T cells.

Non-autologous donor CD3 or CD8 T-cells were isolated from whole blood using RosetteSep selection technology (STEMCELL Technologies), labeled with CFSE (Life Technologies), and activated with 10 U/mL IL-2 and 1:1 ratio CD3/CD28 T-Activator Dynabeads (Life Technologies). MDSCs and T cells were co-cultured at a ratio of 1:2 or 50,000:100,000 cells per well. CFSE was detected on a FACS Canto (BD Biosciences) 3 days post co-culture. Data were analyzed with FlowJo version 10.1 (TreeStar) software.

Figure 17A:
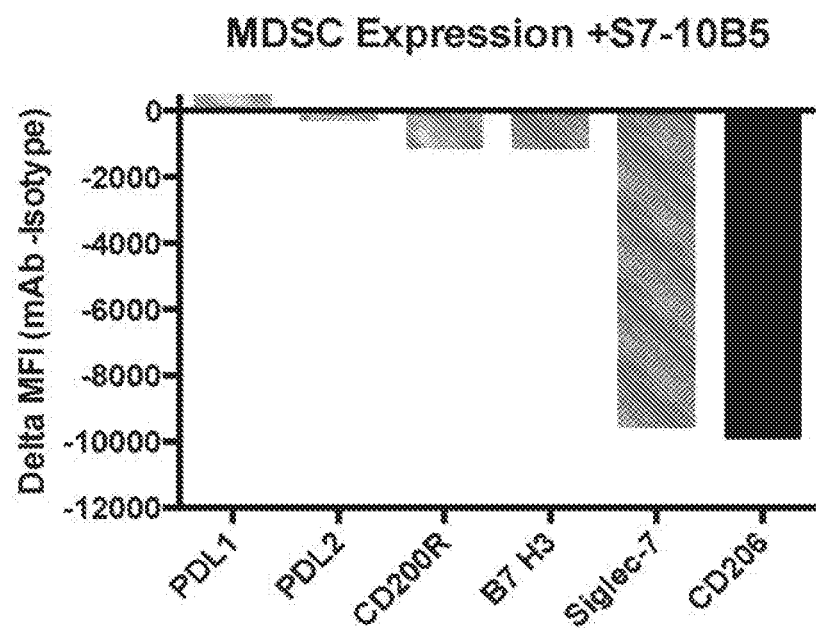
FIG. 17A depicts change in expression quantified by mean fluorescence intensity (MFI) of PD-L1, PD-L2, CD200R, B7-H3, Siglec-7, and CD206 between myeloid-derived suppressor cells (MDSCs) treated with isotype control antibody (mIgG1) compared to cells treated with anti-Siglec-7 antibody 10B5.
Figure 17B:
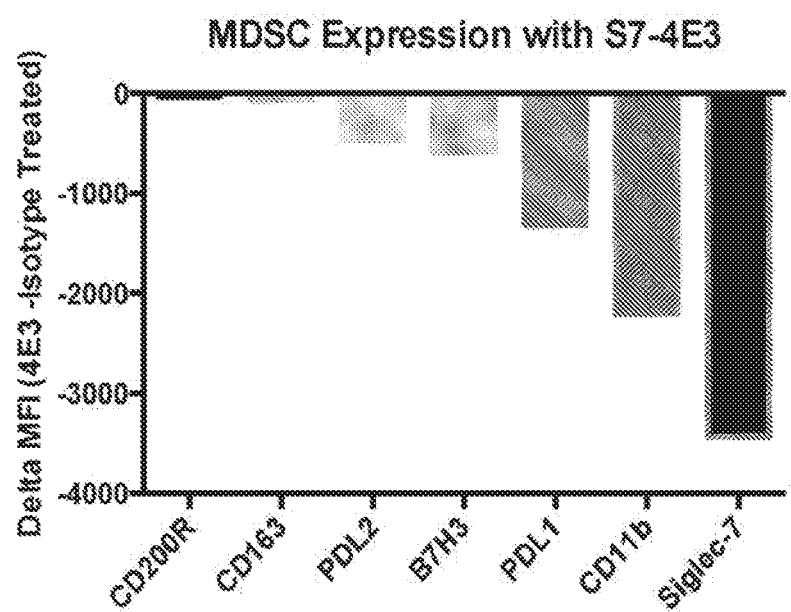
FIG. 17B depicts change in expression quantified by mean fluorescence intensity (MFI) of CD200R, CD163, PD-L2, B7-H3, PD-L1, CD11b, and Siglec-7 between myeloid-derived suppressor cells (MD-SCs) treated with isotype control antibody (mIgG1) compared to cells treated with anti-Siglec-7 antibody 4E3.

As shown in FIG. 17A and FIG. 17B, the anti-Siglec-7 antibodies 10B5 and 4E3 decreased expression of PD-L1 and PD-L2 (PD-1 ligands), B7-H3 (a potent T-cell check point inhibitor), CD200R (an inhibitory signaling receptor), and CD163 and CD206 (M2-type markers) on the surface of MDSCs. These results indicated that anti-Siglec-7 antibody-mediated target engagement, and subsequent downregulation of Siglec-7, led to phenotypic alterations on MDSCs, including reduced expression of suppressive ligands and receptors.

Figure 17C:
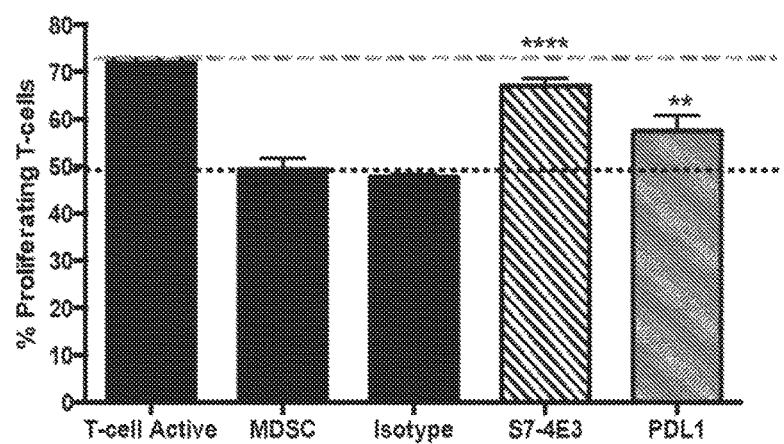
FIG. 17C depicts the percentage of activated T cell proliferation in the absence and presence of co-cultured myeloid-derived suppressor cells (MDSCs). Additionally, co-cultured T cells/MDSCs were left untreated, or were treated with anti-Siglec-7 antibody 4E3, a mouse isotype control antibody (mIgG1), or an anti-PD-L1 antibody (PDL1). **: $p<0.00001$.
Figure 17D:
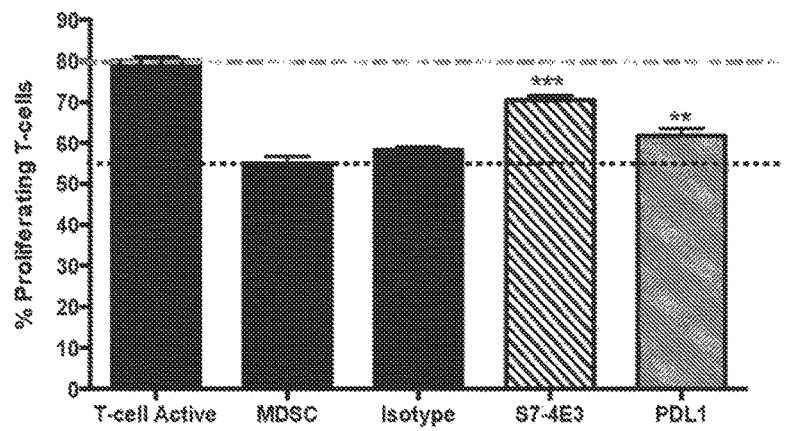
FIG. 17D depicts the percentage of activated T cell proliferation for T cells treated with glioblastoma-conditioned media, cultured in the absence and presence of co-cultured myeloid-derived suppressor cells (MDSCs). Additionally, co-cultured T cells/MDSCs were left untreated, or were treated with anti-Siglec-7 antibody 4E3, a mouse isotype control antibody (mIgG1), or an anti-PD-L1 antibody (PDL1). : $p<0.01$; ***: $p<0.001$.

As shown in FIG. 17C and FIG. 17D, the anti-Siglec-7 antibodies 10B5 and 4E3 increased T cell proliferation in the presence of MDSCs, allowing for the generation of more tumor-fighting T cells. MDSCs co-cultured with activated T cells suppressed T-cell proliferation by ~25%. In these studies, MDSCs treated with the Siglec-7 antibodies 10B5 or 4E3 induced less suppression of T-cell proliferation (FIG. 17C and FIG. 17D). An isotype control (mIgG1) antibody did not affect MDSC-dependent suppression of T cell proliferation. Treatment of MDSCs with Siglec-7-targeting antibodies was more effective in alleviating MDSC-mediated T-cell suppression than was a PD-L1 blocking antibody (FIG. 17C and FIG. 17D).

Finally, the ability of the anti-Siglec-7 antibodies to induce cell death of MDSCs was tested. Human peripheral blood cells were ficolled, red blood cells were lysed with ACK lysis buffer, and cells were washed 3 times before plating in RPMI with 10% FBS, Pen/Strep, 1 mM Glutamine, non-essential amino acids, and sodium pyruvate. Human PBMCs were cultured for one week at 37° C. in 5% $CO_2$ with the following cytokines: 10 ng/ml rhGM-CSF (R&D), 10 ng/ml rhIL-8 (R&D), and 10 ng/ml rhIL-6 (Sigma). To some flasks, mIgG1 (BioXcell) isotype antibody, or the Siglec-7 antibodies 4E3 or 10B5 were added. Every 2-3 days media, cytokines, and antibodies where noted were replenished. After 7 days of culture, cells were harvested by scraping and triterating, and resuspended in PBS with 2% FBS and 1 mM EDTA for FACS analysis. For assessment of live and dead cell populations, Live/Dead Fixable Aqua dead cell stain (Thermo Fisher) was diluted 1:500 in PBS with 2% FBS and 1 mM EDTA and incubated for 30 minutes on ice. Cells were washed 3 times in buffer and analyzed on a BD FACS Canto (BD Biosciences) for forward and side scatter and AmCyan fluorescence. Data were analyzed with FlowJo (Tree Star Software).

Figure 18:
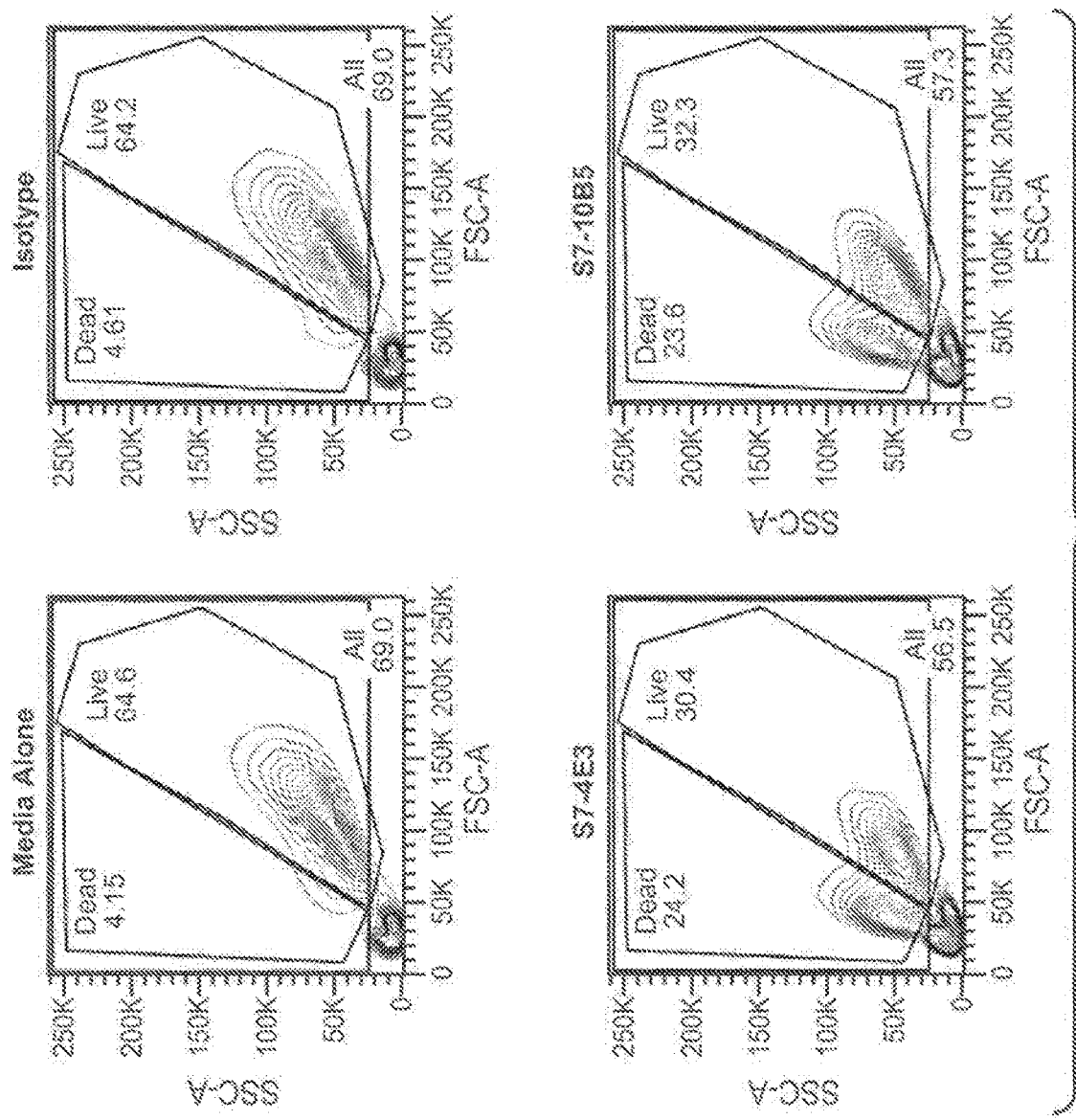
FIG. 18 depicts results showing anti-Siglec-7 antibodies 4E3 and 10B5 selectively kill a subset of myeloid-derived suppressor cells (MDSCs). Top row: Live/Dead Gates by cell morphology: increase in dead cell gate with S7-4E3 and S7-10B5. Middle row: Gating on Live/Dead cells using dye: Dye HIGH positive cells are DEAD, dye low cells are alive. Histograms: showing Live/Dead cell dye in histogram format.
Figure 18:
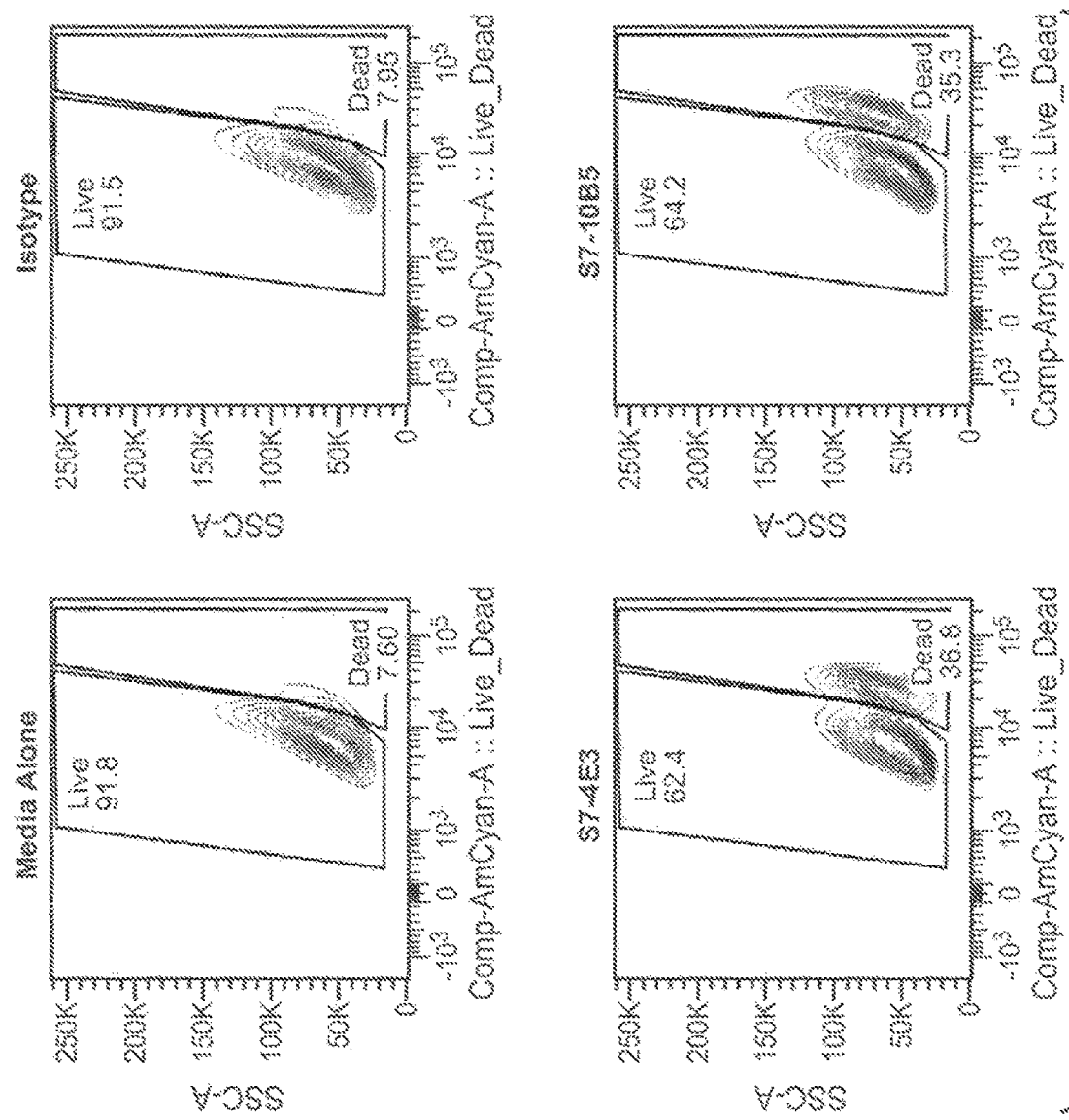
Figure 18:
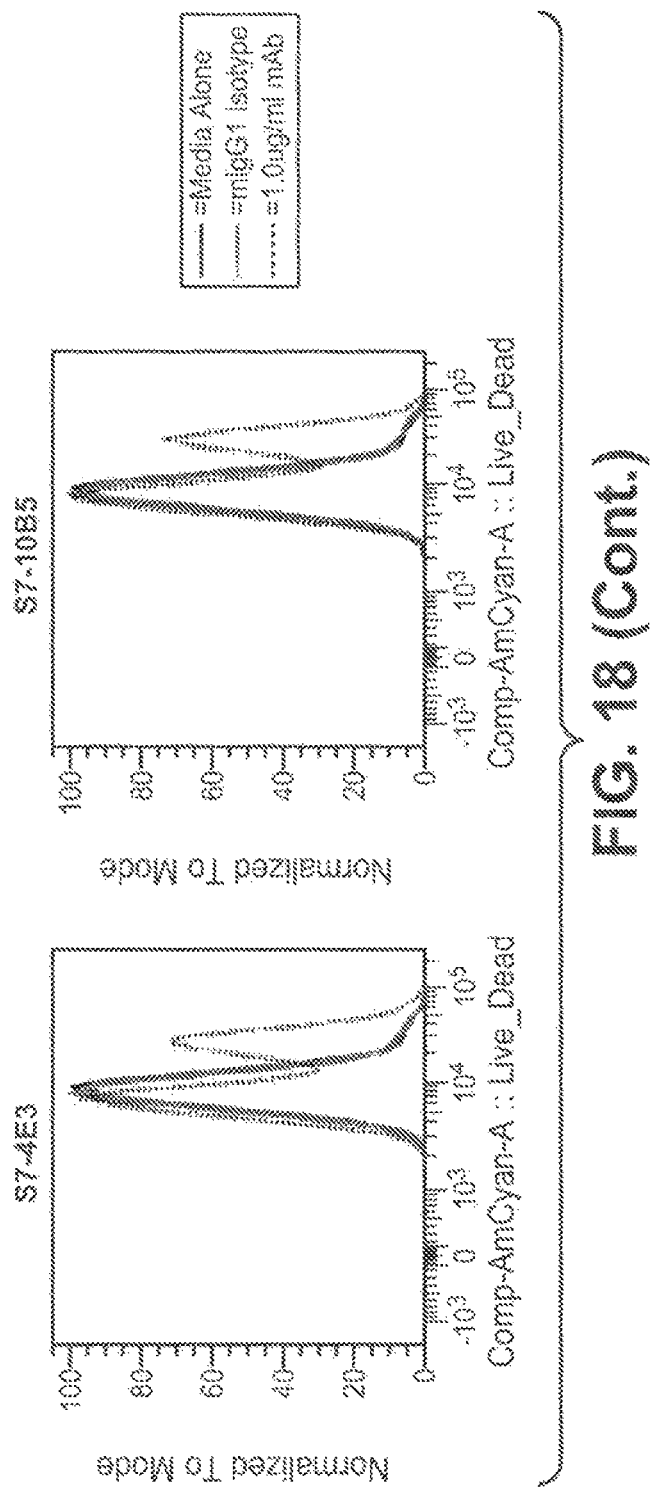

As shown in FIG. 18, the anti-Siglec-7 antibodies 4E3 and 10B5 were capable of inducing cell death in a subset of differentiating MDSCs. Both anti-Siglec-7 antibodies induced an approximately 30% increase in MDSC cell death (FIG. 18, middle row) relative to media alone, or isotype-treated cells.

Taken together, the above studies indicated that the anti-Siglec-7 antibodies 10B5 and 4E3 were capable of phenotypically altering MDSCs (e.g., by reducing expression of suppressive ligands and receptors), effecting downstream MDSC functions (e.g., reducing MDSC-dependent suppression of T-cell proliferation), and inducing cell death of a subset of MDSCs.

---

What is claimed is:

1. An isolated monoclonal anti-Siglec-7 antibody, wherein the anti-Siglec-7 antibody comprises a light chain variable domain comprising an HVR-L1, an HVR-L2, and an HVR-L3 and a heavy chain variable domain comprising an HVR-H1, an HVR-H2, and an HVR-H3, wherein
the HVR-L1 comprises the amino acid sequence of SEQ ID NO: 14 or an amino acid sequence with at least about 90% homology to SEQ ID NO: 14, the HVR-L2 comprises the amino acid sequence of SEQ ID NO: 27 or an amino acid sequence with at least about 90% homology to SEQ ID NO: 27, the HVR-L3 comprises the amino acid sequence of SEQ ID NO: 40 or an amino acid sequence with at least about 90% homology to SEQ ID NO: 40, the HVR-H1 comprises the amino acid sequence of SEQ ID NO: 53 or an amino acid sequence with at least about 90% homology to SEQ ID NO: 53, the HVR-H2 comprises the amino acid sequence of SEQ ID NO: 66 or an amino acid sequence with at least about 90% homology to SEQ ID NO: 66, and the HVR-H3 comprises the amino acid sequence of SEQ ID NO: 79 or an amino acid sequence with at least about 90% homology to SEQ ID NO: 79.

2. The anti-Siglec-7 antibody of claim 1, wherein the anti-Siglec-7 antibody decreases cell surface levels of Siglec-7 and inhibits interaction between Siglec-7 and one or more Siglec-7 ligands.

3. The anti-Siglec-7 antibody of claim 2, wherein the one or more Siglec-7 ligands are selected from the group consisting of Siglec-7 ligands expressed on red blood cells, Siglec-7 ligands expressed on bacterial cells, Siglec-7 ligands expressed on apoptotic cells, Siglec-7 ligands expressed on nerve cells, Siglec-7 ligands expressed on glial cells, Siglec-7 ligands expressed on microglia, Siglec-7 ligands expressed on astrocytes, Siglec-7 ligands expressed on tumor cells, Siglec-7 ligands expressed on viruses, Siglec-7 ligands expressed on dendritic cells, Siglec-7 ligands bound to beta amyloid plaques, Siglec-7 ligands bound to Tau tangles, Siglec-7 ligands on disease-causing proteins, Siglec-7 ligands on disease-causing peptides, Siglec-7 ligands expressed on macrophages, Siglec-7 ligands expressed on neutrophils, Siglec-7 ligands expressed on monocytes, Siglec-7 ligands expressed on natural killer cells, Siglec-7 ligands expressed on T cells, Siglec-7 ligands expressed on T helper cells, Siglec-7 ligands expressed on cytotoxic T cells, Siglec-7 ligands expressed on B cells, Siglec-7 ligands expressed on tumor-imbedded immunosuppressor dendritic cells, Siglec-7 ligands expressed on tumor-imbedded immunosuppressor macrophages, Siglec-7 ligands expressed on tumor-imbedded immunosuppressor neutrophils, Siglec-7 ligands expressed on tumor-imbedded immunosuppressor NK cells, Siglec-7 ligands expressed on myeloid-derived suppressor cells, Siglec-7 ligands expressed on regulatory T cells, secreted mucins, sialic acid, sialic acid-containing glycolipids, sialic acid-containing glycoproteins, alpha-2,8-disialyl containing glycolipids, branched alpha-2,6-linked sialic acid-containing glycoproteins, terminal alpha-2,6-linked sialic acid-containing glycolipids, terminal alpha-2,3-linked sialic acid-containing glycoproteins, and disialogangliosides.

4. The anti-Siglec-7 antibody of claim 2, wherein the cell surface levels of Siglec-7 are measured on primary cells selected from the group consisting of dendritic cells, bone marrow-derived dendritic cells, monocytes, microglia, macrophages, neutrophils, and NK cells, or on cell lines, and wherein the cell surface levels of Siglec-7 are measured utilizing an in vitro cell assay.

5. The anti-Siglec-7 antibody of claim 1, wherein the anti-Siglec-7 antibody inhibits one or more Siglec-7 activities.

6. The anti-Siglec-7 antibody of claim 1, wherein the anti-Siglec-7 antibody does not reduce TREM2 expression.

7. The anti-Siglec-7 antibody of claim 1, wherein the anti-Siglec-7 antibody binds to one or more amino acid residues selected from the group consisting of I72, W74, N81, and R124 of SEQ ID NO: 1, or one or more amino acid residues on a mammalian Siglec-7 protein corresponding to an amino acid residue selected from the group consisting of I72, W74, N81, and R124 of SEQ ID NO: 1.

8. The anti-Siglec-7 antibody of claim 1, wherein the anti-Siglec-7 antibody is of the IgG class, the IgM class, or the IgA class.

9. The anti-Siglec-7 antibody of claim 8, wherein the anti-Siglec-7 antibody has an IgG1, IgG2, IgG3, or IgG4 isotype.

10. The anti-Siglec-7 antibody of claim 9, wherein:
(a) the anti-Siglec-7 antibody has a human or mouse IgG1 isotype and comprises one or more amino acid substitutions in the Fc region at a residue position selected from the group consisting of: N297A, D265A, D270A, L234A, L235A, G237A, P238D, L328E, E233D, G237D, H268D, P271G, A330R, C226S, C229S, E233P, L234V, L234F, L235E, P331S, S267E, L328F, A330L, M252Y, S254T, T256E, N297Q, P238S, P238A, A327Q, A327G, P329A, K322A, T394D, and any combination thereof, wherein the numbering of the residues is according to EU numbering, or comprises an amino acid deletion in the Fc region at a position corresponding to glycine 236;
(b) the anti-Siglec-7 antibody has an IgG1 isotype and comprises an IgG2 isotype heavy chain constant domain 1(CH1) and hinge region, optionally wherein the IgG2 isotype CH1 and hinge region comprises the amino acid sequence of ASTKGPSVFP LAPCSRSTSE STAALGCLVK DYFPEPVTVS WNSGALT-SGVHTFPAVLQSS GLYSLSSVVT VPSSNFGTQT YTCNVDHKPS NTKVDKTVERKCCVECPPCP (SEQ ID NO: 475), and optionally wherein the antibody Fc region comprises a S267E amino acid substitution, a L328F amino acid substitution, or both, and/or a N297A or N297Q amino acid substitution, wherein the numbering of the residues is according to EU numbering;

(c) the anti-Siglec-7 antibody has an IgG2 isotype and comprises one or more amino acid substitutions in the Fc region at a residue position selected from the group consisting of: P238S, V234A, G237A, H268A, H268Q, V309L, A330S, P331S, C214S, C232S, C233S, S267E, L328F, M252Y, S254T, T256E, H268E, N297A, N297Q, A330L, and any combination thereof, wherein the numbering of the residues is according to EU numbering;

(d) the anti-Siglec-7 antibody has a human or mouse IgG4 isotype and comprises one or more amino acid substitutions in the Fc region at a residue position selected from the group consisting of: L235A, G237A, S228P, L236E, S267E, E318A, L328F, M252Y, S254T, T256E, E233P, F234V, L234A/F234A, S228P, S241P, L248E, T394D, N297A, N297Q, L235E, and any combination thereof, wherein the numbering of the residues is according to EU numbering; or (e) the anti-Siglec-7 antibody has a hybrid IgG2/4 isotype, and optionally wherein the antibody comprises an amino acid sequence comprising amino acids 118 to 260 of human IgG2 and amino acids 261 to 447 of human IgG4, wherein the numbering of the residues is according to EU or, Kabat numbering.

11. The anti-Siglec-7 antibody of claim 1, wherein Siglec-7 is a mammalian protein or a human protein.

12. The anti-Siglec-7 antibody of claim 1, wherein the anti-Siglec-7 antibody binds Siglec-7 in a pH dependent manner.

13. The anti-Siglec-7 antibody of claim 1, wherein the anti-Siglec-7 antibody is an antibody fragment that binds to an epitope comprising amino acid residues on human Siglec-7 or a mammalian Siglec-7 protein.

14. The anti-Siglec-7 antibody of claim 1, wherein the anti-Siglec-7 antibody is an Fab, Fab', Fab'-SH, F(ab')2, Fv, or scFv fragment.

15. The anti-Siglec-7 antibody of claim 1, wherein the anti-Siglec-7 antibody is a murine antibody, a humanized antibody, a bispecific antibody, a multivalent antibody, a conjugated antibody, or a chimeric antibody.

16. The anti-Siglec-7 antibody of claim 1, wherein the anti-Siglec-7 antibody has a dissociation constant ($K_D$) for human Siglec-7 that ranges from about 9.5 nM to about 17 pM, wherein the $K_D$ is determined at a temperature of approximately 25° C.

17. The anti-Siglec-7 antibody of claim 1, wherein the anti-Siglec-7 antibody binds to human dendritic cells with an $EC_{50}$ that ranges from 2 nM to 100 pM, wherein the $EC_{50}$ is determined at a temperature of approximately 4° C.

18. The anti-Siglec-7 antibody of claim 1, wherein the anti-Siglec-7 antibody decreases cell surface levels of Siglec-7 with an $EC_{50}$ that ranges from 500 pM to 18 pM, wherein the $EC_{50}$ is determined at a temperature of approximately 37° C.

19. The anti-Siglec-7 antibody of claim 1, wherein the light chain variable domain comprises an amino acid sequence selected from the group consisting of SEQ ID NOs: 259-268 and 484-486.

20. The anti-Siglec-7 antibody of claim 1, wherein the heavy chain variable domain comprises an amino acid sequence selected from the group consisting of SEQ ID NOs: 389-398 and 490-492.

21. The anti-Siglec-7 antibody of claim 1, wherein the light chain variable domain comprises one or more framework sequences selected from the group consisting of SEQ ID NOs: 92, 105, 118, and 131.

22. The anti-Siglec-7 antibody of claim 1, wherein the heavy chain variable domain comprises one or more framework sequences selected from the group consisting of SEQ ID NOs: 144, 157, 170, and 183.

23. A pharmaceutical composition comprising the anti-Siglec-7 antibody of claim 1, and a pharmaceutically acceptable carrier.

24. An isolated nucleic acid comprising a nucleic acid sequence encoding the anti-Siglec-7 antibody of claim 2.

25. A vector comprising the nucleic acid of claim 24.

26. An isolated host cell comprising the vector of claim 25.

27. A method of producing an anti-Siglec-7 antibody, comprising culturing the host cell of claim 26 so that the anti-Siglec-7 antibody is produced.

28. An isolated monoclonal anti-Siglec-7 antibody, wherein the anti-Siglec-7 antibody comprises a light chain variable domain and a heavy chain variable domain, wherein
the light chain variable domain comprises an HVR-L1 comprising the amino acid sequence of SEQ ID NO: 14 or the amino acid sequence of SEQ ID NO: 14 having one conservative amino acid substitution, an HVR-L2 comprising the amino acid sequence of SEQ ID NO: 27 or the amino acid sequence of SEQ ID NO: 27 having one conservative amino acid substitution, an HVR-L3 comprising the amino acid sequence of SEQ ID NO: 40 or the amino acid sequence of SEQ ID NO: 40 having one conservative amino acid substitution, and wherein the heavy chain variable domain comprises an HVR-H1 comprising the amino acid sequence of SEQ ID NO: 53 or the amino acid sequence of SEQ ID NO: 53 having one conservative amino acid substitution, an HVR-H2 comprising the amino acid sequence of SEQ ID NO: 66 or the amino acid sequence of SEQ ID NO: 66 having one conservative amino acid substitution, and an HVR-H3 comprising the amino acid sequence of SEQ ID NO: 79 or the amino acid sequence of SEQ ID NO: 79 having one conservative amino acid substitution.

29. An isolated monoclonal anti-Siglec-7 antibody, wherein the anti-Siglec-7 antibody comprises a light chain variable domain and a heavy chain variable domain, wherein the light chain variable domain comprises an amino acid sequence selected from the group consisting of SEQ ID NOs: 259-268 and 484-486.

30. An isolated monoclonal anti-Siglec-7 antibody, wherein the anti-Siglec-7 antibody comprises a light chain variable domain and a heavy chain variable domain, wherein the heavy chain variable domain comprises an amino acid sequence selected from the group consisting of SEQ ID NOs: 389-398 and 490-492.

* * * * *

UNITED STATES PATENT AND TRADEMARK OFFICE
CERTIFICATE OF CORRECTION

| | | |
|---|---|---|
| PATENT NO. | : 11,390,680 B2 | Page 1 of 1 |
| APPLICATION NO. | : 16/792040 | |
| DATED | : July 19, 2022 | |
| INVENTOR(S) | : Monroe et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 85 days.

Signed and Sealed this
Eleventh Day of February, 2025

Coke Morgan Stewart
*Acting Director of the United States Patent and Trademark Office*